US007998986B2

(12) United States Patent
Bayne et al.

(10) Patent No.: US 7,998,986 B2
(45) Date of Patent: Aug. 16, 2011

(54) MODULATORS OF LXR

(75) Inventors: Christopher D. Bayne, San Diego, CA (US); Alan T. Johnson, Poway, CA (US); Shao-Po Lu, San Diego, CA (US); Raju Mohan, Encinitas, CA (US); Ronald C. Griffith, Escondido, CA (US)

(73) Assignee: Exelixis Patent Company LLC, San Francisco, CA (US)

( * ) Notice: Subject to any disclaimer, the term of this patent is extended or adjusted under 35 U.S.C. 154(b) by 981 days.

(21) Appl. No.: 10/327,813

(22) Filed: Dec. 20, 2002

(65) Prior Publication Data

US 2003/0181420 A1 Sep. 25, 2003

Related U.S. Application Data

(60) Provisional application No. 60/342,707, filed on Dec. 21, 2001.

(51) Int. Cl.
*A61K 31/4412* (2006.01)
*C07D 213/64* (2006.01)

(52) U.S. Cl. ......... 514/345; 546/300; 546/301; 546/302

(58) Field of Classification Search .................. 546/300, 546/301, 302; 514/345
See application file for complete search history.

(56) References Cited

U.S. PATENT DOCUMENTS

| 72,073 | A | 6/1902 | Medina et al ................... 435/7.1 |
|---|---|---|---|
| 3,576,814 | A | 4/1971 | Seidel et al. |
| 3,710,795 | A | 1/1973 | Higuchi et al. ............... 128/260 |
| 3,951,982 | A | 4/1976 | Goel et al. ..................... 260/268 |
| RE28,819 | E | 5/1976 | Thompson .................... 424/243 |
| 3,954,734 | A | 5/1976 | Doub et al. ................. 260/239.1 |
| 4,028,084 | A | 6/1977 | McNulty et al. ................... 71/94 |
| 4,044,126 | A | 8/1977 | Cook et al. ..................... 424/243 |
| 4,053,470 | A | 10/1977 | Doub et al. ....................... 544/25 |
| 4,093,730 | A | 6/1978 | Butti et al. ..................... 424/270 |
| 4,108,630 | A | 8/1978 | Johnson et al. |
| 4,137,408 | A | 1/1979 | Kaltenbronn et al. ........... 544/28 |
| 4,159,202 | A | 6/1979 | Furrer et al. |
| 4,231,938 | A | 11/1980 | Monaghan et al. ........ 260/343.5 |
| 4,328,245 | A | 5/1982 | Yu et al. ........................ 424/305 |
| 4,346,227 | A | 8/1982 | Terahara et al. ............... 560/119 |
| 4,358,603 | A | 11/1982 | Yu ..................................... 560/2 |
| 4,364,923 | A | 12/1982 | Cook et al. ...................... 424/46 |
| 4,409,239 | A | 10/1983 | Yu ................................. 424/305 |
| 4,410,545 | A | 10/1983 | Yu et al. ......................... 424/305 |
| 4,414,209 | A | 11/1983 | Cook et al. ..................... 424/243 |
| 4,444,784 | A | 4/1984 | Hoffman et al. ............... 424/279 |
| 4,559,354 | A | 12/1985 | Fuhrer et al. |
| 4,585,894 | A | 4/1986 | Johnson et al. ................ 564/164 |
| 4,681,893 | A | 7/1987 | Roth |
| 5,033,252 | A | 7/1991 | Carter ............................... 53/425 |
| 5,052,558 | A | 10/1991 | Carter ............................ 206/439 |
| 5,070,012 | A | 12/1991 | Nolan et al. ....................... 435/6 |
| 5,071,773 | A | 12/1991 | Evans et al. .................... 436/501 |
| 5,112,839 | A | 5/1992 | Gericke et al. ................. 514/337 |
| 5,145,966 | A | 9/1992 | Aumueller et al. |
| 5,157,037 | A | 10/1992 | Schuetz et al. ................. 514/269 |
| 5,177,080 | A | 1/1993 | Angerbauer et al. .......... 514/277 |
| 5,194,438 | A | 3/1993 | Schuetz et al. ................. 514/269 |
| 5,221,623 | A | 6/1993 | Legocki et al. .............. 435/252.3 |
| 5,254,543 | A | 10/1993 | Hanko et al. ..................... 514/89 |
| 5,273,995 | A | 12/1993 | Roth .............................. 514/422 |
| 5,283,173 | A | 2/1994 | Fields et al. ........................ 435/6 |
| 5,298,429 | A | 3/1994 | Evans et al. .................... 436/501 |
| 5,323,907 | A | 6/1994 | Kalvelage ...................... 206/531 |
| 5,326,767 | A | 7/1994 | Schuetz et al. ................. 514/269 |
| 5,332,750 | A | 7/1994 | Mederski et al. .............. 514/340 |
| 5,332,833 | A | 7/1994 | Sekiya et al. ................. 548/338.5 |
| 5,354,772 | A | 10/1994 | Kathawala ..................... 514/414 |
| 5,356,911 | A | 10/1994 | Müller-Gliemann et al. 514/340 |
| 5,378,711 | A | 1/1995 | Schuetz et al. ................. 514/311 |
| 5,378,720 | A | 1/1995 | Hlasta et al. ................... 514/373 |
| 5,380,868 | A | 1/1995 | Gallenkamp et al. ....... 548/365.4 |
| 5,399,566 | A | 3/1995 | Katano et al. ................. 514/340 |
| 5,407,948 | A | 4/1995 | Fey et al. ....................... 514/333 |
| 5,410,066 | A | 4/1995 | Gallenkamp et al. ....... 548/375.1 |
| 5,439,927 | A | 8/1995 | Sekiya et al. .................. 514/399 |
| 5,466,233 | A | 11/1995 | Weiner et al. ................. 604/890.1 |
| 5,466,701 | A | 11/1995 | Hlasta et al. ................... 514/373 |
| 5,468,614 | A | 11/1995 | Fields et al. ........................ 435/6 |
| 5,484,890 | A | 1/1996 | Johnson et al. ................ 530/383 |
| 5,504,070 | A | 4/1996 | Bihovsky et al. ................ 514/15 |

(Continued)

FOREIGN PATENT DOCUMENTS

CA        1115278        12/1981

(Continued)

OTHER PUBLICATIONS

Accession No. 1994:557497. Elgemeie et al, CAPLUS abstract of "Synthesis of several N-substituted amino-2-pyridones." Organic Preparations & Procedures Int. (1994). vol. 26(4). pp. 465-468.*
Accession No. 2000:879315. Tonkikh et al, CAPLUS abstract of "4(3H)-Quinazolines containing a heterocyclic group in position 3." Chemistry of Het. Compounds (2000). vol. 36(7). pp. 822-829.*
Accession No. 1999:185916, Salman, Asmaa, abstract of "Synthesis and reaction of cyanopyridone derivatives and their potential biological activities," Pharmazie (1999), vol. 54 (No. 3), pp. 178-183.*
Accession No. 1995:468947, Attia, Adel et al, abstract of "Synthesis of some N-hexopyranosyl-2-pyridones and -2-pyridinethiones, " Carbohydrate Research (1995), vol. 268 (No. 2), pp. 295-300.*
Accession No. 1931. 3141, Basu, Umaprasanna, abstract of "B-Diketones in ring formation. III", J. Indian Chem. Soc. (1931), vol. 8, pp. 119-128.*
Vivekananda, S. A. et al, "Electron-impact Mass Spectral Study of 2-Allyloxy-6-phenyl-4-trifluoromethyl Pyridines and N-allyl-6-phenyl-4-trifluoromethyl-2-(1H)-pyridones," Rapid Comm. Mass Spec. (1998), vol. 12, pp. 651-657.*

(Continued)

*Primary Examiner* — Joseph K. McKane
*Assistant Examiner* — Janet L Coppins
(74) *Attorney, Agent, or Firm* — Fox Rothschild LLP; Gerard P. Norton

(57) ABSTRACT

Compounds, compositions and methods for modulating the activity of nuclear receptors are provided. In particular, heterocyclic compounds are provided for modulating the activity of nuclear receptors, including liver X receptor (LXR) and orphan nuclear receptors. In certain embodiments, the compounds are N-substituted pyridones.

119 Claims, 78 Drawing Sheets

U.S. PATENT DOCUMENTS

| | | | |
|---|---|---|---|
| 5,514,825 A | 5/1996 | Vuligonda et al. | 558/426 |
| 5,543,534 A | 8/1996 | Vuligonda et al. | 549/421 |
| 5,571,696 A | 11/1996 | Evans et al. | 435/69.1 |
| 5,591,858 A | 1/1997 | Vuligonda et al. | 546/322 |
| 5,598,269 A | 1/1997 | Kitaevich et al. | 356/399 |
| 5,599,823 A | 2/1997 | Müller-Gliemann et al. | 514/340 |
| 5,599,967 A | 2/1997 | Vuligonda et al. | 560/48 |
| 5,605,915 A | 2/1997 | Vuligonda et al. | 514/356 |
| 5,607,967 A | 3/1997 | Friedman et al. | 514/461 |
| 5,612,363 A | 3/1997 | Mohan et al. | 514/392 |
| 5,618,503 A | 4/1997 | Johnson et al. | 423/87 |
| 5,618,844 A | 4/1997 | Gowravaram et al. | 514/575 |
| 5,618,931 A | 4/1997 | Beard et al. | 544/224 |
| 5,618,943 A | 4/1997 | Vuligonda et al. | 546/342 |
| 5,624,922 A | 4/1997 | Johnson et al. | 514/220 |
| 5,625,041 A | 4/1997 | Johnson et al. | 530/416 |
| 5,648,503 A | 7/1997 | Vuligonda et al. | 549/13 |
| 5,648,514 A | 7/1997 | Johnson et al. | 560/102 |
| 5,650,289 A | 7/1997 | Wood | 435/8 |
| 5,654,469 A | 8/1997 | Vuligonda et al. | 560/56 |
| 5,659,042 A | 8/1997 | Gillett et al. | 546/318 |
| 5,667,973 A | 9/1997 | Fields et al. | 435/6 |
| 5,674,713 A | 10/1997 | McElroy et al. | 435/69.7 |
| 5,683,888 A | 11/1997 | Campbell | 435/8 |
| 5,684,022 A | 11/1997 | Shuto et al. | 514/335 |
| 5,693,641 A | 12/1997 | Buckman et al. | 514/249 |
| 5,696,233 A | 12/1997 | Evans et al. | 530/350 |
| 5,698,571 A | 12/1997 | Audia et al. | 514/323 |
| 5,710,004 A | 1/1998 | Evans et al. | 435/6 |
| 5,723,620 A | 3/1998 | Vuligonda et al. | 546/280.1 |
| 5,723,666 A | 3/1998 | Vuligonda et al. | 564/253 |
| 5,726,173 A | 3/1998 | Mohan et al. | 514/235.8 |
| 5,726,198 A | 3/1998 | Mohan et al. | 514/387 |
| 5,728,553 A | 3/1998 | Goodey et al. | 435/69.6 |
| 5,728,697 A | 3/1998 | Mohan et al. | 514/235.8 |
| 5,728,846 A | 3/1998 | Vuligonda et al. | 549/16 |
| 5,731,308 A | 3/1998 | Mohan et al. | 514/219 |
| 5,731,311 A | 3/1998 | Mohan et al. | 514/235.8 |
| 5,741,657 A | 4/1998 | Tsien et al. | 435/18 |
| 5,741,896 A | 4/1998 | Vuligonda et al. | 534/860 |
| 5,747,542 A | 5/1998 | Vuligonda et al. | 514/646 |
| 5,753,635 A | 5/1998 | Buckman et al. | 514/81 |
| 5,760,276 A | 6/1998 | Beard et al. | 560/102 |
| 5,763,635 A | 6/1998 | Vuligonda et al. | 556/442 |
| 5,773,594 A | 6/1998 | Johnson et al. | 534/298 |
| 5,808,083 A | 9/1998 | Johnson et al. | 546/348 |
| 5,808,124 A | 9/1998 | Beard et al. | 556/419 |
| 5,814,645 A | 9/1998 | Kanellakopulos et al. | 514/332 |
| 5,843,746 A | 12/1998 | Tatsumi et al. | 435/189 |
| 5,846,970 A | 12/1998 | Buckman et al. | 514/224.2 |
| 5,846,972 A | 12/1998 | Buckman et al. | 514/230.5 |
| 5,855,654 A | 1/1999 | Willingham et al. | 106/18.32 |
| 5,859,005 A | 1/1999 | Mohan et al. | 514/218 |
| 5,863,914 A | 1/1999 | Mohan et al. | 514/231.5 |
| 5,863,930 A | 1/1999 | Dressel et al. | 514/340 |
| 5,869,497 A | 2/1999 | Johnson et al. | 514/278 |
| 5,877,207 A | 3/1999 | Klein et al. | 514/456 |
| 5,883,255 A | 3/1999 | Berges et al. | 546/70 |
| 5,888,830 A | 3/1999 | Mohan et al. | 436/174 |
| 5,935,984 A | 8/1999 | Goldmann et al. | 514/399 |
| 5,945,340 A | 8/1999 | Francis et al. | 436/10 |
| 5,951,121 A | 9/1999 | Takahashi | 303/155 |
| 5,952,345 A | 9/1999 | Klein et al. | 514/341 |
| 5,955,108 A | 9/1999 | Sutton et al. | 424/489 |
| 5,955,604 A | 9/1999 | Tsien et al. | 540/222 |
| 5,958,954 A | 9/1999 | Klein et al. | 514/333 |
| 5,962,473 A | 10/1999 | Johnson et al. | 514/323 |
| 5,994,375 A | 11/1999 | Kochanny et al. | 514/341 |
| 5,998,471 A | 12/1999 | Johnson et al. | 514/510 |
| 5,998,655 A | 12/1999 | Vuligonda et al. | 560/100 |
| 6,008,204 A | 12/1999 | Klein et al. | 514/63 |
| 6,025,382 A | 2/2000 | Bastian et al. | 514/422 |
| 6,028,033 A | 2/2000 | Hill et al. | 504/244 |
| 6,051,731 A | 4/2000 | Vuligonda et al. | 560/56 |
| 6,054,470 A | 4/2000 | Betageri et al. | 514/349 |
| 6,071,912 A | 6/2000 | Kochanny et al. | 514/241 |
| 6,087,505 A | 7/2000 | Vuligonda et al. | 546/281.1 |
| 6,090,810 A | 7/2000 | Klein et al. | 514/253 |
| 6,117,987 A | 9/2000 | Johnson et al. | 534/798 |
| 6,156,784 A | 12/2000 | Betageri et al. | 514/426 |
| 6,166,088 A | 12/2000 | Kochanny et al. | 514/637 |
| 6,184,215 B1 | 2/2001 | Elias et al. | 514/182 |
| 6,187,814 B1 | 2/2001 | Elias et al. | 514/531 |
| 6,187,933 B1 | 2/2001 | Vuligonda et al. | 549/416 |
| 6,204,054 B1 | 3/2001 | Sutton et al. | 435/334 |
| 6,221,808 B1 | 4/2001 | Schmidt et al. | 504/117 |
| 6,228,848 B1 | 5/2001 | Klein et al. | 514/63 |
| 6,242,454 B1 | 6/2001 | Kochanny et al. | 514/269 |
| 6,251,921 B1 | 6/2001 | Bastian et al. | 514/337 |
| 6,252,090 B1 | 6/2001 | Vasudevan et al. | 549/23 |
| 6,255,330 B1 | 7/2001 | Goldmann et al. | 514/369 |
| 6,265,350 B1 | 7/2001 | Schnatterer et al. | 504/252 |
| 6,268,365 B1 | 7/2001 | Betageri et al. | 514/247 |
| 6,274,091 B1 | 8/2001 | Mohan et al. | 422/103 |
| 6,284,768 B1 | 9/2001 | Betageri et al. | 514/277 |
| 6,291,677 B1 | 9/2001 | Vasudevan et al. | 546/165 |
| 6,294,503 B1 | 9/2001 | Gupta et al. | 504/225 |
| 6,303,785 B1 | 10/2001 | Vasudevan et al. | 546/144 |
| 6,313,107 B1 | 11/2001 | Vasudevan et al. | 514/150 |
| 6,316,503 B1 | 11/2001 | Li et al. | 514/604 |
| 6,344,182 B1 | 2/2002 | Sutton et al. | 424/9.52 |
| 6,344,561 B2 | 2/2002 | Vuligonda et al. | 546/315 |
| 6,348,186 B1 | 2/2002 | Sutton et al. | 424/9.52 |
| 6,350,774 B1 | 2/2002 | Bach et al. | 514/422 |
| 6,355,806 B1 | 3/2002 | Johnson et al. | 546/348 |
| 6,359,135 B1 | 3/2002 | Vasudevan et al. | 546/18 |
| 6,369,225 B1 | 4/2002 | Vasudevan et al. | 544/238 |
| 6,369,261 B1 | 4/2002 | Johnson et al. | 560/59 |
| 6,380,201 B1 | 4/2002 | Johnson et al. | 514/255.05 |
| 6,380,256 B1 | 4/2002 | Vasudevan et al. | 514/567 |
| 6,378,919 B1 | 5/2002 | Davis et al. | |
| 6,387,892 B1 | 5/2002 | Vasudevan et al. | 514/150 |
| 6,387,919 B1 | 5/2002 | Davis et al. | |
| 6,387,951 B1 | 5/2002 | Vasudevan et al. | 514/543 |
| 6,391,901 B1 | 5/2002 | Chirgadze et al. | 514/376 |
| 6,399,774 B1 | 6/2002 | Vasudevan et al. | 544/230 |
| 6,416,957 B1 | 7/2002 | Evans et al. | 435/7.1 |
| 6,444,471 B1 | 9/2002 | Johnson | 436/10 |
| 6,465,663 B2 | 10/2002 | Vuligonda et al. | 549/60 |
| 6,469,028 B1 | 10/2002 | Klein et al. | 514/311 |
| 6,479,035 B1 | 11/2002 | Cripps et al. | 424/45 |
| 6,495,552 B2 | 12/2002 | Vasudevan et al. | 514/252.04 |
| 6,521,624 B1 | 2/2003 | Klein et al. | 514/253 |
| 6,531,599 B2 | 3/2003 | Vasudevan et al. | 544/230 |
| 6,538,149 B1 | 3/2003 | Vuligonda et al. | 560/5 |
| 6,555,690 B2 | 4/2003 | Johnson et al. | 546/309 |
| 6,603,019 B2 | 8/2003 | Vasudevan et al. | 548/341.5 |
| 7,482,366 B2 | 1/2009 | Bayne et al. | |
| 2003/0181420 A1 | 9/2003 | Bayne et al. | |
| 2005/0080111 A1 | 4/2005 | Bayne et al. | |
| 2008/0119488 A1 | 5/2008 | Bayne et al. | |

FOREIGN PATENT DOCUMENTS

| | | |
|---|---|---|
| CA | 2077412 | 3/1993 |
| CA | 2084857 | 6/1993 |
| CH | 00477475 A1 | 8/1969 |
| CN | 1289803 | 4/2001 |
| DD | 244341 A1 | 4/1987 |
| DE | 01189994 B1 | 4/1965 |
| DE | 2637477 A1 | 2/1978 |
| DE | 2824341 A1 | 12/1978 |
| DE | 4309552 A1 | 9/1994 |
| DE | 4313747 A1 | 11/1994 |
| DE | 4407488 A1 | 9/1995 |
| DE | 4414648 A1 | 11/1995 |
| DE | 19518739 A1 | 11/1996 |
| DE | 19627421 A1 | 1/1998 |
| DE | 19729061 A1 | 1/1999 |
| EP | 0018305 A1 | 10/1980 |
| EP | 0051813 B1 | 5/1982 |
| EP | 0140646 B1 | 5/1985 |
| EP | 0176064 A1 | 4/1986 |
| EP | 0294995 B1 | 12/1988 |
| EP | 0339105 A1 | 11/1989 |
| EP | 0350691 B2 | 1/1990 |
| EP | 0406656 B1 | 1/1991 |
| EP | 0 487 745 A | 6/1992 |

| | | | | | | |
|---|---|---|---|---|---|---|
| EP | 0500297 A1 * | 8/1992 | | WO | 9729067 A1 | 8/1997 |
| EP | 0530702 A1 | 3/1993 | | WO | 9731947 A1 | 9/1997 |
| EP | 0542059 B1 | 5/1993 | | WO | 9748672 A2 | 12/1997 |
| EP | 0546420 A1 | 6/1993 | | WO | 9800366 A1 | 1/1998 |
| EP | 0546420 B1 | 6/1993 | | WO | 9807723 A1 | 2/1998 |
| EP | 0547708 A1 | 6/1993 | | WO | 9807725 A1 | 2/1998 |
| EP | 0548680 A1 | 6/1993 | | WO | 9817115 A1 | 4/1998 |
| EP | 0551572 B1 | 7/1993 | | WO | 9825875 A1 | 6/1998 |
| EP | 0557843 A2 | 9/1993 | | WO | 9832444 A1 | 7/1998 |
| EP | 0594019 A1 | 4/1994 | | WO | 9839284 A1 | 9/1998 |
| EP | 0594022 A1 | 4/1994 | | WO | 9848804 A1 | 11/1998 |
| EP | 0624583 B1 | 11/1994 | | WO | 9858922 A1 | 12/1998 |
| EP | 0626378 A1 | 11/1994 | | WO | 9923075 A1 | 5/1999 |
| EP | 0705600 A1 | 4/1996 | | WO | 9931066 A1 | 6/1999 |
| EP | 0842934 A1 | 5/1996 | | WO | 9933821 A1 | 7/1999 |
| EP | 0733629 A1 | 9/1996 | | WO | 9940062 A1 | 8/1999 |
| EP | 0747049 A1 | 12/1996 | | WO | 9952893 A1 | 10/1999 |
| EP | 0747055 A2 | 12/1996 | | WO | 9955676 A1 | 11/1999 |
| EP | 0755934 A1 | 1/1997 | | WO | 9965901 A1 | 12/1999 |
| EP | 0797995 A2 | 10/1997 | | WO | 0002556 | 1/2000 |
| EP | 0802192 A1 | 10/1997 | | WO | 0017334 A2 | 3/2000 |
| EP | 0824917 A2 | 2/1998 | | WO | 0025134 A1 | 5/2000 |
| EP | 0832650 A2 | 4/1998 | | WO | 0037075 | 6/2000 |
| EP | 0838458 A1 | 4/1998 | | WO | 0037077 A1 | 6/2000 |
| EP | 0853610 B1 | 7/1998 | | WO | 0039102 | 7/2000 |
| EP | 0856255 A2 | 8/1998 | | WO | 0040965 A1 | 7/2000 |
| EP | 0859661 B1 | 8/1998 | | WO | 0049992 A2 | 8/2000 |
| EP | 0922045 B1 | 6/1999 | | WO | 0054759 | 9/2000 |
| EP | 0931786 A2 | 7/1999 | | WO | 0057915 A1 | 10/2000 |
| EP | 0948478 B1 | 10/1999 | | WO | 0066611 | 11/2000 |
| EP | 1006108 A1 | 6/2000 | | WO | 0073277 A1 | 12/2000 |
| EP | 1006112 A1 | 6/2000 | | WO | 0078972 A2 | 12/2000 |
| EP | 1031578 A2 | 8/2000 | | WO | 0103705 A1 | 1/2001 |
| EP | 1082958 A2 | 3/2001 | | WO | 0115676 A2 | 3/2001 |
| EP | 1226832 A2 | 7/2002 | | WO | 0119342 A2 | 3/2001 |
| EP | 1239672 A2 | 9/2002 | | WO | 0122964 A1 | 4/2001 |
| EP | 1300396 A1 | 4/2003 | | WO | 0137805 A1 | 5/2001 |
| GB | 2345058 | 6/2000 | | WO | 0142215 A1 | 6/2001 |
| JP | 51122075 | 10/1976 | | WO | 0147493 A1 | 7/2001 |
| JP | 53-025578 A | 3/1978 | | WO | 0160818 A1 | 8/2001 |
| JP | 53-050179 | 5/1978 | | WO | 0182917 A2 | 11/2001 |
| JP | 64-9979 | 1/1989 | | WO | WO 01/96308 A1 | 12/2001 |
| JP | 1261371 | 10/1989 | | WO | 0218361 A2 | 3/2002 |
| JP | 2124871 | 5/1990 | | WO | 0226727 A2 | 4/2002 |
| JP | 8208516 | 8/1996 | | WO | 0236581 A1 | 5/2002 |
| JP | 2001302637 | 10/2001 | | WO | 02083143 A1 | 10/2002 |
| WO | 9119697 A1 | 12/1991 | | WO | 02085397 A1 | 10/2002 |
| WO | 92/06085 | 4/1992 | | WO | 02089800 A2 | 11/2002 |
| WO | 9207856 A1 | 5/1992 | | WO | 02090355 A1 | 11/2002 |
| WO | 9310143 A1 | 5/1993 | | WO | 02098856 A2 | 12/2002 |
| WO | 9311154 A1 | 6/1993 | | WO | 03002559 A2 | 1/2003 |
| WO | 9316698 A1 | 9/1993 | | WO | 03002561 A1 | 1/2003 |
| WO | 9320818 A1 | 10/1993 | | WO | 03059884 | 7/2003 |
| WO | 9323040 A1 | 11/1993 | | WO | WO 2004/103974 A1 | 5/2004 |
| WO | 9323041 A1 | 11/1993 | | | | |
| WO | 9400494 A1 | 1/1994 | | | | |
| WO | 9421632 A1 | 9/1994 | | | | |
| WO | 9502596 A1 | 1/1995 | | | | |
| WO | 9503803 A1 | 2/1995 | | | | |
| WO | 9522966 A1 | 8/1995 | | | | |
| WO | 9527700 A1 | 10/1995 | | | | |
| WO | 9528984 A1 | 11/1995 | | | | |
| WO | 9603378 A1 | 2/1996 | | | | |
| WO | 9611000 A1 | 4/1996 | | | | |
| WO | 9611006 A1 | 4/1996 | | | | |
| WO | 9612181 A1 | 4/1996 | | | | |
| WO | 9612701 A1 | 5/1996 | | | | |
| WO | 9620930 A1 | 7/1996 | | | | |
| WO | 9622021 A1 | 7/1996 | | | | |
| WO | 9637481 A1 | 11/1996 | | | | |
| WO | 9637515 A1 | 11/1996 | | | | |
| WO | 9638421 A1 | 12/1996 | | | | |
| WO | 9640256 A1 | 12/1996 | | | | |
| WO | 9640257 A1 | 12/1996 | | | | |
| WO | 9640258 A2 | 12/1996 | | | | |
| WO | 9641639 A1 | 12/1996 | | | | |
| WO | 9709297 A2 | 3/1997 | | | | |
| WO | 9710896 A1 | 3/1997 | | | | |
| WO | 9725033 A1 | 7/1997 | | | | |

OTHER PUBLICATIONS

Abdel Hafez et al., "Synthesis of Azo-Sulfa Drugs Based on 2-Pyridinone and 2-Pyridinethione", *Journal of the Chinese Chemical Society*, 40:289-296 (1993).

Agarwal et al., "AGN193109 Is a Highly Effective Antagonist of Retinoid Action in Human Ectocervical Epithelial Cells", *J. Biol. Chem.*, 271(21):12209-12212 (1996).

Aggarwal et al., "Reaction of α-Ketoketene S, N-Acetals with Cyanoacetamide: A New General Method for Substituted and Fused 4-9N-Alkylamino-, N-Arylamino-, or N-Morpholino)-3-Cyano-2(1H)-Pyridones", *Synthesis*, (3):214-216 (1982).

Alajarin et al., "Nuevas Reacciones de las Aldiminas Derivadas de la 1-Amino-4,6-Difenil-2-Piridona", *Anales de Quimica*, 74(4): 625-7 (1978).

Alajarin et al., "1-Amino-4,6-Difenil-2-Pyridone in Organic Synthesis: Conversion of Benzylic Alcohols and Benzylamines into Benzonitril and Conversion of Aryl Methyl Ketones into Aroyl Cyanides", *Anales de Quimica*, 77:338-341 (1980).

Alajarin et al., "Preparation of Fused Meso-Ionic Compounds from 1-Amino-4,6-Diphenyl-2-Pyridone", *Tetrahedron Letters*, 21:4025-4026 (1980).

Alberti et al., "Structural characterisation of the mouse nuclear oxysterol receptor genes *LXRα* and *LXRβ*", *Gene*, 243:93-103 (2000).

Alejandre-Durán et al., "Study on the Mutagenicity of Nifurtimox and Eight Derivatives with the L-Arabinose Resistance Test of Salmonella Typhimurium", *Mutation Research*, 206:193-200 (1988).

Ali et al., "Action of Grignard Reagents on 2-Alkylthio-s-triazolo[1,5-*b*]isoquinolin-5(10H)-ones & Their Derivatives", *Indian Journal of Chemistry*, 13:1145-1148 (1975).

Ansel, H.C., Chapter 6, "Peroral Solids, Capsules, Tablets, and Controlled-Release Dosage Forms", Book: *Introduction to Pharmaceutical Dosage Forms*, Lea & Febiger, Philadelphia, 4th Ed., Lea & Febiger, Philadelphia, p. 126 (1985).

Aranyos et al., "Novel Electron-Rich Bulky Phosphine Ligands Facilitate the Palladium-Catalyzed Preparation of Diaryl Ethers", *J. Am. Chem. Soc.*, 121: 4369-4378 (1999).

Argues et al., "Some Synthetic Applications of 1-Amino-4,6-Diphenylpyridine-2-Thione", *Anales de Quimica*, 77:248-250 (1981).

Balicki et al., "Novel Pyrethroid Insecticides 111* Synthesis of Some N-(1-Pyridyl) Substituted Amides of Cyclopropanecarboxylic Acids", *Bulletin of the Polish Academy of Sciences Chemistry*, 37(7-8):269-275 (1986).

Bantick et al., "New Non-Peptide Angiotensin II Receptor Antagonists. 1: Structure-Activity Relationships of a Series of 2(1H)-Pyridinones", *Bioorganic & Medicinal Chemistry Letters*, 4(1):121-126 (1994).

Bapat et al., "Pyridines as Leaving Groups in Synthetic Transformations: Nucleophilic Displacements of Amino Groups, and Novel Preparations of Nitriles and Isocyanates", *Tetrahedron Letters*, 31:2691-2694 (1976).

Barrett-Connor, E., "Epidemiology, Obesity, and Non-Insulin-Dependent Diabetes Mellitus", *Epidemiol. Rev.*, 11:172-181 (1989).

Berger et al., "Secreted Placental alkaline phosphatase: a powerful new quantitative indicator of gene expression in eukaryotic cells", *Gene*, 66:1-10 (1988).

Bomika et al., "Alkylation of 3-Cyano-2-Oxopyridine Derivatives", *Khimiya Geterotsiklicheskikh Soediinenii*, 8:899-902 (1976).

Bronstein et al., "1,2-Dioxetanes: Novel Chemiluminescent Enzyme Substrates. Applications to Immunoassays", *J. Bioluminescence and Chemiluminescence*, 4:99-111 (1989).

Buckman et al., "Automated Parallel Solid-Phase Synthesis of Non-Peptide CCR1 Receptor Antagonists", *Combinatorial Chem. & High Throughput Screening*, 5:249-251 (2002).

Buckman et al., "Design, Synthesis, and Biological Activity of Novel Purine and Bicyclic Pyrimidine Factor Xa Inhibitors", *Bioorganic & Med. Chem. Ltrs*, 8:2235-2240 (1998).

Cade et al., Lack of Biological Activity of Preproendothelin [110-130] in Several Endothelin Assays, *Life Sciences*, 47(23):2079-2103 (1990).

Carpenter et al., "Configuring Radioligand Receptor Binding Assays for HTS Using Scintillation Proximity Assay Technology", *Meth. Mol. Biol.*, vol. 190, Book: High Throughput Screening: Methods and Protocols, Humana Press Inc., Totowa, New Jersey, pp. 31-49 (2002).

Database CAPLUS on ACS, AN 1987:458776, Gutcait, A. et al., "Synthesis, structure, and properties of 1-amino-6-phenyl-4-trifluoromethyl-3-cyano-2-pyridone", *Latvijas PSR Zinatnu Akademijas Vestis, Kimijas Serija*, M:607-12 (1986).

Database CAPLUS on ACS, AN 1988:167259, Jure, M. et al., "1-Methyl-6-phenyl-4-trifluoromethy1-3-cyano-2-pyridone and its properties", *Latvijas Psr Zinatnu Akademijas Vestis, Kimijas Serija*, (5):627-631 (1987).

Derwent Abstract for Japanese Patent Application JP1009979 (Emperor No. 649979), published Jan. 13, 1989, "Novel (hetero)aryl-oxazolidinone derivs. -useful as hypoglycaemic agents".

Derwent Abstract for Japanese Patent Application JP 51122075, published Oct. 25, 1976, "Isocarbostyril antispasmodics, tranquillisers, sedatives, antipyretics—prepd. by reacting 3-phenyl isocoumarin derivs. with corresp. acid hydrazides".

Derwent Abstract for Japanese Patent Application JP 1261371, published Oct. 18, 1989, "New nitrogen-contg. heterocyclic cpds.—useful for treating plant blight and as insecticides".

Derwent Abstract for Japanese Patent Application JP 2124871, published May 14, 1990, "1-Substd. heterocyclic-carboxylic acid amide derivs.—useful as anti-allergy agents and showing inhibition against 5-lipoxygenase".

Derwent Abstract for PCT Patent Application WO 200002556, published Jan. 20, 2000, "Compositions comprise a combination of indomethacin and an angiotensin II AT1 receptor antagonist, useful for treating chronic glomerulonephritis".

Derwent Abstract for PCT Patent Application WO 200037075, published Jun. 29, 2000, "Compositions containing an immunosuppressant and an AT1 angitensin II receptor antagonist, for prevention and treatment of vascular complications due to graft rejection".

Derwent Abstract for European Patent Application EP 594022, published Apr. 27, 1994, "New 1-biphenylylmethyl-2-pyridone derivs.—used as angiotensin II antagonists, esp. for treating hypertension or arteriosclerosis".

Derwent Abstract for German Patent Application DE 19627421, published Jan. 15, 1998, "Use of (carboxy- or tetrazolyl-biphenyl)methyl) pyridone compunds—to treat liver disease, especially necrosis and fibrosis".

Derwent Abstract for German Patent Application DE 19729061, published Jan. 14, 1999, "Colour photographic material sensitised without increased fogging—has computer emulsion containing unsaturated nitrogen-heterocyclic carbonyl or imino compund forming loose coupler complex to avoid residual leuco compound after processing".

Derwent Abstract for German Patent Application DE 2637477, published Feb. 23, 1978, "(1,2)-Dihydro-(2)-oxo-nicotinic acids—useful as hypolipidaemics and some as hypoglycaemics (NL 22.2.77)".

Derwent Abstract for German Patent Application DE 4313747, published Nov. 3, 1994, "Prodn. of antihypertensive biphenyl-tetrazole cpds.—from new 2-(tetrazol-5-yl)phenyl-boric acid by metal catalysed reaction with aryl halide or sulphonate".

Derwent Abstract for German Patent Application DE 4407488, published Sep. 14, 1995, "Use of biphenylyl-methyl or phenyl-pyridyl-methyl-pyridone pds.—for treating glaucoma and diabetic retinopathy and for increasing the mobility of vitreous humour".

Derwent Abstract for German Patent Application DE 4414648, published Nov. 2, 1995, "N-Aralkylation of 2-pyridone derivs. with aralkyl halide—afterdeprotonation with lithium cpd., esp. for prodn. of angiotensin II antagonists".

Derwent Abstract for PCT Patent Publication WO 9603378, published Feb. 8, 1996, "New phenylated-amide derivs. are ACAT inibitors for treating arteriosclerosis—e.g. N-pyrazolyl-phenyl-3-phenyl-octane amide derivs."

Derwent Abstract for Chinese Patent Application CN 1289803, published Apr. 4, 2001, "Temporarily water-soluble disperse dye containing carboxymethyl sulfonyl and its synthesis process".

Derwent Abstract for Japanese Patent Application JP 2001302637, published Oct. 31, 2003, "New yellow coloring matter for thermal transcription recording sheets, excelling in color concentration and light resistance".

Derwent Abstract for PCT Patent Publication WO 9637481, published Nov. 28, 1996, "Prepn. of 1H-tetrazole cpd. from carbo-nitrile and alkali metal azide—in presence of zinc chloride, giving prod. at lower cost without using toxic materials, used to produce e.g. biphenyl-heterocyclic derivs."

Chen et al., "Synthesis and Fluorescence Behaviour of Some 3-Cyano-4-Substituted-6-Pyrenyl-2-Pyridone Derivatives", *Dyes and Pigments*, 27(3):249-259 (1995).

Chiang et al., "Farnesoid X Receptor Responds to Bile Acids and Represses Cholesterol 7α-Hydroxylase Gene (*CYP7A1*) Transcription", *J. Biol. Chem.*, 275(15):10918-10924 (2000).

Chiasson et al., "The Efficacy of Acarbose in the Treatment of Patients with Non-Insulin-dependent Diabetes Mellitus", *Ann. Internal Med.*, 121:928-935 (1994).

Chiba et al., "Distinct Retinoid X Receptor-Retinoic Acid Receptor Heterodimers Are Differentially Involved in the Control of Expression of Retinoid Target Genes in F9 Embryonal Carcinoma Cells", *Mol. Cell. Biol.*, 17(6):3013-3020 (1997).

Coniff et al., "Acarbose: A Review of US Clinical Experience", *Clinical Therapeutics*, 19(1):16-26 (1997).

Coniff et al., "Multicenter, Placebo-Controlled Trial Comparing Acarbose (BAY g 5421) With Placebo, Tolbutamide, and Tolbutamide-Plus-Acarbose in Non-Insulin-Dependent Diabetes Mellitus", *Am. J. Med.*, 98:443-451 (1995).

DiSepio et al., "Identification of the AP1-Antagonism Domain of Retinoic Acid Receptors", *Mol. Cell Biol. Res. Comm.*, 1:7-13 (1999).

Ehm, "Über die Kondensation von N-Substituierten Acetessigsäureamiden zu α-Pyridonderivaten und über davon abgeleitete Verbindungen", *Liebigs Ann. Chem.*, (10):1642-1660 (1977).

El-Hashash et al., "Behaviour of 3-Nitrobenzal-p-Isopropyl or p-Chloro-aceptophenones Toward Oxygen and Carbon Nucleophiles and Some Studies with the Products", *J. Chem. Soc. Pak.*, 9(2):229-234 (1987).

El-Kholy et al., "Pyrone Series. Part XI. Reactivity of 4,6-Diaryl-2-Pyrones and Cyclo-Propane Derivatives Obtained from 2-Pyrazolines", *J. Chem. Soc. C*, (11):1578-1584 (1970).

El-Kholy et al., "Prone Series. IX. Some Reactions of 1-Amino-4,5,6-Triaryl-2-Pyridones", *J. Chem. Soc., C*, (6):974-978 (1969).

El-Kholy et al., "Prone Series. X. Reactivity of 4,5,6-Triaryl-2-Pyridones and the Corresponding Thio-Analogues", *J. Chem. Soc.,C*, (15):1950-1954 (1969).

El-Kholy et al., "Reactivity of 3-Amino-, 3-Halogeno-, and 3-Nitro-2-Pyrones and Thiopyrones", *J. Heterocycl. Chem.*, 12(1):129-133 (1975).

El-Mobayed et al., "Reactions with 6-Acetyl 3, 5-Diarylcyclohexen-1-Ones and 2-Hydroxy 4, 6-Diaryl Nicotinonitrile Synthesised by Michael Reactions from 3-Nitrobenzal-p-Isopropyl Acetophenones and some Studies with the Products", *Egypt. J. Pharm. Sci.*, 30 1-4 :329-337 (1989).

Elgemeie et al., "Synthesis of Several N-Substituted Amino-2-Pyridones", *Organic Preparations and Procedures*, 26(4):465-497 (1994).

Elgemeie et al., "Novel Synthesis of Pyridine-2(1H)Thiones, N-Amino-2-Pyridones and Pyridazine Derivatives", *Organic Preparations and Procedures Int.*, 23(5):645-650 (1991).

Elgemeie et al., "Reactions of Acylthiosemicarbazides with β-Diketones: Novel Synthesis of N-(1-Pyridyl)thiourea Derivatives", *J. Chem. Research*, (S):87 (1993).

Elmoghayar et al., "Activated Nitriles in Heterocyclic Synthesis. Part III [1]. Synthesis of N-Amino-2-Pyridone, Pyranopyrazole and Thiazolopyridine Derviatives", *J. Heterocyclic Chem.*, 21:1885-1887 (1984).

Evans et al., "Synthesis of Diaryl Ethers through the Copper-Promoted Arylation of Phenols with Arylboronic Acids. An Expedient Synthesis of Thyroxine", *Tetrahedron Ltrs.*, 39:2937-2940 (1998).

Evans, R.M., "The Steriod and Thyroid Hormone Receptor Superfamily", *Science*, 240:889-895 (1988).

Faid-Allah, "Synthesis of Pyridones and Dihydropyridines from Pyrylium Salts and Nitriles from Adimines", *Croatica Chemica ACTA*, 60(4):717-733 (1987).

Flier, J.S., "Insulin Receptors and Insulin Resistance", *Ann. Rev. Med.*, 34:145-160 (1983).

Furukawa et al., "Synthesis of 5-(Alkylaminocarbonyl)-4,6-Dimethyl-2-Pyridones from N-Alkyl-3-Oxobutanamides", *Synthesis*, 12:1715-1717 (1998).

Garcia et al., "Morbidity and Mortality in Diabetics in the Framingham Population: Sixteen Year Follow-up Study", *Diabetes*, 23(21):105-111 (1974).

Glass, C.K., "Differential Recognition of Target Genes by Nuclear Receptor Monomers, Dimers, and Heterodimers", *Endocrine Rev.*,15(3):391-407 (1994).

Glickman et al., "A Comparison of ALPHAScreen, TR-FRET, and TRF as Assay Methods for FXR Nuclear Receptors", *J. Biomol. Screening*, 7(1):3-10 (2002).

Gorman et al., "Recombinant Genomes Which Express Chloramphenicol Acetyltransferase in Mammalian Cells", *Mol. Cell. Biol.*, 2(9):1044-1051 (1982).

Gutcait et al., "Synthesis, structure and properties of 1-amino-6-phenyl-4-trifluoromethyl-3-cyano-2-pyridone," *Lativijas PSR Zinatnu Akademijas Vestis, Kimijas Serija* (5): 607-612 (1986).

Haffner, S.M., "Management of Dyslipidemia in Adults With Diabetes", *Diabetes Care*; 21(1):160-178 (1998).

Hayashi et al., "Syntheses and Anti-tumor Activity of N-Heterocyclic Compounds Having the Cyclic Hydrazide Structure", *Yakugaku Zasshi*, 98(11):1560-1565 (1978).

Hayashi et al., "2-Amino-3-Phyenylisocarbostyril", *Yakugaku Zasshi*, 94(10):1322-1327 (1974).

Heyman et al., "9-Cis Retinoic Acid Is a High Affinity Ligand for the Retinoid X Receptor", *Cell*, 68:397-406 (1992).

Howard et al., "Lipoprotein Composition in Diabetes Mellitus", *Atherosclerosis*, 30:153-162 (1978).

Issac, "Model Studies Related to Synthesis and 1,4-Dipolar Cycloaddition Reactions of Mesoionic Heterocycles", *Bull. Chem. Soc. Jpn.*, 72:503-509 (1999).

IUPAC-IUB Commission on Biochemical Nomenclature Abbreviated Nomenclature of Synthetic Polypeptides (Polymerized Amino Acids): Revised Recommendations, *Biochem.*, 11(5):942-944-(1972).

Iwamoto et al., "Effect of Combination Therapy of Troglitazone and Sulphonylureas in Patients with Type 2 Diabetes Who Were Poorly Controlled by Sulphonylurea Therapy Alone", *Diabetic Medicine*, 13:365-370 (1996).

Janowski et al., "An oxysterol signalling pathway mediated by the nuclear receptor LXRα", *Nature*, 383:728-731 (1996).

Johnson et al., "High Affinity Retinoic Acid Receptor Antagonists: Analogs of AGN 193109", *Bioorganic & Med. Chem. Ltrs*, 9:573-576 (1999).

Johnson et al., "Identification of Retinoic Acid Receptor β Subtype Specific Agonists", *J. Med. Chem.*, 39(26):5027-5030 (1996).

Johnson et al., "Synthesis and Characterization of a Highly Potent and Effective Antagonist of Retinoic Acid Receptors", *J. Med. Chem.*, 38:4764-4767 (1995).

Johnson et at, "Synthesis and Biological Activity of High-Affinity Retinoic Acid Receptor Antagonists", *Bioorganic & Med. Chem.*, 7:1321-1338 (1999).

Joslin, E.P., "Arteriosclerosis and Diabetes", *Ann. Clin. Med.*, 5(12):1061-1080 (1927).

Jurado et al., "Genetic Differences Between the Standard Ames Tester Strains TA100 and TA98", *Mutagenesis*, 8(6):527-532 (1993).

Jurado et al., "Role of Classical Nitroreductase and O-Acetyltransferase on the Mutagenicity of Nifurtimox and Eight Derivatives in Salmonella Typhimurium", *Environmental and Molecular Mutagenesis*, 26:86-93 (1995).

Jure, M. et al., "1-Methyl-6-phenyl-4-trifluoromethyl-3-cyano-2-pyridone and its properties", *Latvijas PSR Zinatnu Akademijas Vestis, Kimijas Serija*, (5):627-631 (1987).

Kain, S.R., "Use of Secreted Alkaline Phosphatase as a Reporter of Gene Expression in Mammalian Cells", Book: *Methods in Molecular Biology, vol. 63: Recombinant Protein Protocols: Detection and Isolation*, Humana Press Inc., Totowa, New Jersey, pp. 49-60 (1997).

Kaplan et al. (Eds.), "Chapter 10: Cardiovascular Diseases", Book: *Health and Human Behavior*, McGraw-Hill, Inc., pp. 206-242 (1993).

Katritzky et al., "Heterocycles in Organic Synthesis, Part 23. 1-Amino-4,6-diphenyl-2-pyridone: a New Reagent for the Conversion of Aldehydes into Nitriles", *J. Chem. Soc., Perkins Trans.*, 1(8):1957-1960 (1979).

Katritzky et al., "1-Chloromethyl-3,5-Dimethylpyrazole Hydrochloride. A Useful Synthetic Intermediate", *Can. J. Chem.*, 67:1144-1147 (1989).

Katritzky et al., "Preparation of Some Novel Pyridone Derivatives", *Pakistan J. Sci. Ind. Res.*, 21(1):1-4 (1978).

Katritzky et al., "α-(4,6-Diphenyl-2-oxo-1-pyridyl)benzyl-lithiums and their Reactions with Electrophiles", *J. Chem. Soc. Perkins* 1: 2851-2855 (1980).

Kislyi et al, "Investigation of the Regioselectivity of Alkylation of 3-Nitropyridin-2(1H)-ones", *Russian Chemical Bulletin, International Edition*, 50(3):460-463 (2001).

Klein et al., "Identification and Functional Separation of Retinoic Acid Receptor Neutral Antagonists and Inverse Agonists", *J. Biol. Chem.*, 271(37):22692-22696 (1996).

Knowler et al., "Obesity in the Pima Indians: its magnitude and relationship with diabetes", *Am J. Clin. Nutr.*, 53:1543S-1551S (1991).

Kochhar et al., "The use of a retinoid receptor antagonist in a new model to study vitamin A-dependent developmental events", *Int. J. Dev. Biol.*, 42:601-608 (1998).

Koller et al., "The Preparation of Substituted 1(2H)-Isoquinolinones From Polylithiated 2-(2-Methylphenyl)hydrazinecarboxylic Acid Esters", *Synthetic Communications*, 26(9):1763-1774 (1996).

Kosulina et al., "Synthesis and anthelmintic activity of new 2-pyridinone derivatives," *Khim. -farm. Zh.* 31(4).: 30-32 (1997).

Kumar et al., "Keten Dithioacetals Part II. Reaction of 3OCyano-4-Methylthio-2(1H)-Pyridones with Hydrazine and Guanidine: Synthesis of Novel Substituted and Fused Pyrazolo [4,3-c]Pyridone and Pyrido[4,3-d]Pyrimidine Derivatives", *J. Chem. Soc., Perkins Trans*, 1(8):857-862 (1978).

Kul'nevich, V. et al., "Synthesis and antiviral activity of N-alkyl-3-cyano-2-pyridones and 3-cyano-2-alkoxypyridines," *Khim. -Farm. Zh.*, 24(2): 132-4 (1990).

Kuthan et al., "Ome 3-Cyano-4, 6-Diaryl-2-Pyridones with Luminiscent Properties", *Collection Czechoslov. Chem. Commun.*, 44:2409-2416 (1979).

Kwiterovick, P.O., "State-of-the-Art Update and Review: Clinical Trials of Lipid-Lowering Agents", *Am. J. Cardiology*, 82(12A):3U-17U (1998).

Laakso et al., "Epidemiology of macrovascular disease in diabetes", *Diabetes Reviews*, 5(4):294-315 (1997).

Lehmann et al.,"Activation of the Nuclear Receptor LXR by Oxysterols Defines a New Hormone Response Pathway", *J. Biol. Chem.*, 272(6):3137-3140 (1997).

Levin et al., "9-*Cis* retinoic acid stereoisomer binds and activates the nuclear receptor RXRα", *Nature*, 355:359-361 (1992).

Lisovenko et al., "Intermolecular Cyclodimerization of Aroyl(Imidoyl)Ketenes Generated by Thermolysis of 5-Aryl-4-Imidoyl-2,3-Dihydro-2,3-Furandiones", *Chemistry of Heterocyclic Compounds*, 37 10 :1314-1316 (2001).

Lorenzo et al., "Reactividad de N,N'Biheterociclos Frente a Reactivos Nucleofilos", *Anales de Quimica*, 77:351-354 (1980).

Mahler et al., "Clinical Review 102: Type 2 Diabetes Mellitus: Update on Diagnosis, Pathophysiology, and Treatment", *J. Clin. Endocrin. & Metab.*, 84(4):1165-1171 (1999).

Mangelsdorf et al., "Characterization of three RXR genes that mediate the action of 9-*cis* retinoic acid", *Genes & Development*, 6:329-344 (1992).

Mangelsdorf et al., "The RXR Heterodimers and Orphan Receptors", *Cell*, 83:841-850 (1995).

Martínez Ortiz et al, "Contribución al Estudio Polarográfico de la 1-Bencilidenamino-4,6- Difenil-2-Piridona", *An. Univ. Murcia, Cienc.* vol. Date 1980-1982 39-40(1-4):147-157 (1983).

Martinez-Oritz et al., "Electrochemical Behavior of 1-(o-Nitrobenzylidene) Amino-4,6-Diphenyl-2-Pyridone" , *Port Electrochem Acta*, 3:147-159 (1985).

Martinez-Ortiz et al., "Electrochemical Behaviour of Aldimines Derived from 1-Amino-4,6-Diphenyl-2-Pyridone", *J. Electroanal. Chem.*, 154:193-203 (1983).

Mester et al., "NMR Studies in the Heterocyclic Series XXX-Carbon-13 NMR Study of 5-Nitrofurfural Derivatives", *Magn. Reson. Chem.*, 25(8):737-739 (1987).

Mester et al., "Activity Against Trypanosoma Cruzi of New Analogues of Nifurtimox", *Arch. Pharm.* (Weinheim), 320:115-120 (1987).

Mester et al., "Quantitative Structure Activity Relationships of 5-Nitrofuran Derivatives", *Chromatographia*, 30(3/4):191-194 (1990).

Mishnev et al., "Molecular and Crystal Strucuture of 1-(2-Hydroxybenzilidene)Amino-6-Phenyl-4-Trifluoromethyl-3-Cyano-2-Pyridone," *Latvijas PSR Zinatu akademijas Vestis. Kimijas Serija* (2:) 168-171 (1987).

Mohan et al., "Synthesis and Biological Activity of Angiotensin II Analogues Containing a Val-His Replacement Valψ[CH(CONH₂)NH]His", *J. Med. Chem.*, 34:2402-2410 (1991).

Mohan et al., "Solid Phase Synthesis of N-Substituted Amidinophenoxy Pyridines as Factor XA Inhibitors", *Bioorganic & Med. Chem. Ltrs*, 8:1877-1882 (1998).

Molina et al., "Fused Mesoionic Heterocycles", *Tetrahedron Letters*, 24(33):3523-3526 (1983).

Molina et al., "Reacciòn de 4,6-difenil-2-piridonas N-sustituidas con 1-fluoro-2, 4-dinitrobenceno", *An. Univ. Murcia Clinic, Ciene.*,vol. Date 1980-1982 39-40(1-4):227-236 (1983).

Molina et al., "Heterocyclization Reactions with Carbodiimides Synthesis of Fused 1,2,4-Triazoles", *Heterocycles*, 24(12):3363-3368 (1986).

Molina et al., "Influencia de la Temperature Sobre Ia Naturaleza de Los Productos de Termolisis de Los Derivados N-Acilados de Ia 1-Amino-4, 6-Difenil-2-Piridona", *Anales de Quimica*, 24:1125-1127 (1978).

Molina et al., "New Synthesis of Pyrazole and Isoxazole Derivatives", *J.Heterocyclic Chem.*, 21:461-464 (1984).

Molina et aL, "Preparation Y Propiedades de Aldiminas Derivadas de la 1-Amino-4,6-Difenil-2-Piridona Y Benzaldehidos Orto-Sustituidos", *Anales de Quimica*, 75(9-10):739-44.

Molina et al., "Fused Mesoionic Heterocycles: Synthesis of 1,3,4-Oxadiazolo[3,3-a]-Pyridine and 1,3,4-Thiadiazolo[3,2-a]Pyridine Derivatives", *J. Chem. Soc. Perkins Trans*, 1(2):351-355 (1982).

Molina et al., "Fused Mesoionic Heterocycles: Synthesis of 1,3,4-Triazolo[3,2-a]Pyridine Derivatives", *J. Chem. Soc. Perkin Trans.*, 1(8):1891-1897 (1984).

Moraga et al., "Genotoxicity Testing of Antiparasitic Nitrofurans in the *Drosophila* Wing Somatic Mutation and Recombination Test", *Metagenesis*, 4(2):105-110 (1989).

Mukherjee et al., "Ligand and coactivator recruitment preferences of peroxisome proliferator activated receptor α", *J. Steroid Biochem. Mol. Biol.*, 81:217-225 (2002).

Nagpal et al., "Tazarotene-Induced Gene 1 (TIG1), a Novel Retinoic Acid Receptor-Responsive Gene in Skin", *J. Invest. Dermatol.*, 106(2):269-274 (1996).

Nakib et al., "A Novel Synthetic Route to 2,3,4-Trisubstituted 6-Pheynl-Pyridines", *J. Chem. Research*, S:146-147 (1988).

Ng et al., "Design, Synthesis, and Biological Activity of Novel Factor Xa Inhibitors: 4-Aryloxy Substituents of 2,6-Diphenoxypyridines", *Bioorganic & Med. Chem.*, 10:657-666 (2002).

Nogrady, T., "Pro-Drugs and Soft Drugs", *Medicinal Chemistry: A Biochemical Approach*, Oxford University Press, New York, pp. 388-394 (1985).

O'Malley (Ed.), "Editorial: Did Eucaryotic Steroid Receptors Evolve from Intracrine Gene Regulators?", *Endocrinology*, 125(3):1119-1120 (1989).

Owicki, J.C., "Fluroescence Polarization and Anisotrophy in High Throughput Screening: Perspectives and Primer", *J. Biomol. Screening*, 5(5):297-306 (2000).

Peet et al., "The LXRs: a new class of oxysterol receptors", *Curr. Opin. Genetics Develop.*, 8:571-575 (1998).

Peet et al., "Cholesterol and Bile Acid Metabolism Are Impaired in Mice Lacking the Nuclear Oxysterol Receptor LXRα", *Cell*, 93:693-704 (1998).

Phillips et al., "Design, Synthesis, and Activity of a Novel Series of Factor Xa Inhibitors: Optimization of Arylamidine Groups", *J. Med. Chem.*, 45:2484-2493 (2002).

Phillips et al., "Discovery of *N*-[2-[5-Amino(imino)methyl]-2-hydroxyphenoxyl]-3,5-difluoro-6-[3-(4,5-dihydro-1-methyl-1*H*-imidazol-2-yl)phenoxylpyridfin-4-yl]-*N*methylglycine(ZK-807834): A Potent, Selective, and Orally Active Inhibitor of the Blood Coagulation Enzyme Factor Xa", *J. Med. Chem.*, 41:3557-3562 (1998).

Physicians' Desk Reference: PDR, Oradell, N.J.:Medical Economics Co. "Hormones", p. 216 (2000).

Pierce et al., "Preparation and Antiinflammatory Activity of 2- and 4-Pyridones", *J. Med. Chem.*, 25:131-136 (1982).

Rastogi et al., "Keten SS-Acetals. Part 10. Reaction of α-Oxoketen SS-Acetals with N-Alkylcyanoacetamides: a New General Method for Substituted and Fused 2,7-Dialky1-8-amino-5-cyano-2,7-napthyridine-1,6(2H,7H)-Diones", *J. Chem. Soc., Perkin Trans*, 1(6):554-558 (1978).

Reaven et al., "Insulin Resistance and Human Disease: A Short History", *J. Basic and Clin. Phys. and Pharm.*, 9:387-406 (1998).

Reaven, G.M., "Pathophysiology of Insulin Resistance in Human Disease", *Physiol. Reviews*, 75(3):473-486 (1995).

Rees et al., "An N-Aminopyridone-Pyridazine Rearrangement; A New Decarbonylation Reaction", *J. Chem. Soc. D, Chemical Communications*, (8):377 (1969).

Rees et al., "Reactive Intermediates. Part XVIII. An N-Aminopyridone-to-Pyridazine Rearrangement; a New Decarbonylation Reaction", *J. Chem. Sco. Perkin Trans.*, 1(6):77-82 (1972).

Ried et al, "Über Struktur und Reaktionen von Phenylcyclobutendion-Enamin-1:1-Addukten", *Liebigs Ann. Chem.*, 762:1-12 (1972).

Ried et al., "3-Hydroxy-Pyridone-(2) aus Phenylcyclobutendion und Enaminen", *Liebigs Ann. Chem.*, 725:230-233 (1969).

Salman, "New Heterocyclic Synthesis from Cyanopyridine Derivatives", *Comman. Fac. Sci. Univ. Ank. Series B*, 44:57-66 (1998).

Salman, "Synthesis and Reaction of Cyanopyridone Derivatives and their Potential Biological Activities", *Pharmazie*, 54:178-183 (1999).

Saunders et al., "Expression of oestrogen receptor beta (ERβ1) protein in human breast cancer biopsies", *British J. Cancer*, 86(2):250-256 (2002).

Shiba et al., "NOvs. O-(S-) PTC Alkylation of 3-Cyano-4, 6-Dimethyl-2-Oxo (Thioxo)-1, 2-Dihydropyridine", *Phosphorus, Sulfur, and Silicon*, 158:91-95 (2000).

Siddiq, "The Effect of the Substituents on the Carbonyl Absorptions of 2H-Pyrid-2-Ones and 2H-Thiopyran-2-Ones", *Pakistan J. Sci. Ind. Res.*, 31(1):6-10 (1988).

Sinai et al., "Targeted Disruption of the Nuclear Receptor FXR/BAR Impairs Bile Acid and Lipid Homeostasis", *Cell*, 102:731-744 (2000).

Soliman et at, "Synthesis of Some Substituted Pyridones from Chalcones", *J. Serb. Chem. Soc.*, 56(7):377-381 (1991).

Song et al., "Ubiquitous Receptor: Structures, Immunocytochemical Localization, and Modulation of Gene Activation by Receptors for Retinoic Acids and Thyroid Hormones", *Ann. New York Acad. of Sciences*, 761:38-49 (1995).

Standeven et al., "Specific Antagonist of Retinoid Toxicity in Mice", *Toxicology Appl. Pharm.*, 138:169-175 (1996).

Standeven et al., "Retinoid-Induced Epiphyseal Plate Closure in Guinea Pigs", *Fundamental Appl. Toxicology*, 34:91-98 (1996).

Standeven et at, "Retinoid-Induced Hypertriglyceridemia in Rats Is Mediated by Retinoic Acid Receptors", *Fundamental Appl. Toxicology*, 33:264-271 (1996).

STN Abstract 1990:400185, Document No. 113:185 for Kul'nevich, V. et al, "Synthesis and antiviral activity of N-alkyl-3-cyano-2-pyridones and 3-cyano-2-alkoxypyridines," *Khim. -Farm. Zh.*, 24(2): 132-4 (1990).

STN Abstract 1985:45743, Document No. 102:45743 for Tsoi et al., "Synthesis of 1-Alkyl-4, 6-Dimethyl-2-Oxo: Micotinonitriles", *Farm, Inst, Perm, USSR Deposited Doc.*, VINITI:3802-3883 (1983).

STN Abstract 1998:100985, Document No. 128:192569 for Kosulina et al., "Synthesis and anthelmintic activity of new 2-pyridinone derivatives," *Khim. -farm. Zh.* 31(4): 30-32 (1997).

Teng et al., "Identification of Highly Potent Retinoic Acid Receptor α-Selective Antagonists", *J. Med. Chem.*, 40:2245-2451 (1997).

Tominaga et al., "Synthesis and Reactions of 6-Aryl- and 6-Styryl-3-cyano-4-methylthio-2H-pyran-2-ones", *Chem. Pharm. Bull.*, 32191:3384-3395 (1984).

Tomkins, G.M., "The Metabolic Code", *Science*, 189:760-763 (1975).

Tonkikh et al., "4(3H)-Quinazolinones Containing Heterocyclic Group in Position", *Chemistry of Heterocyclic Compounds*, 36(7):822-829 (2000).

Tsien, R.Y., "The Green Fluorescent Protein", *Annu. Rev. Biochem.*, 67:509-544 (1998).

Tsoi et al., "Synthesis of 1-Alkyl-4, 6-Dimethyl-2-Oxo: Micotinonitriles", *Farm, Inst, Perm, USSR Deposited Doc.*, VINITI:3802-3883 (1983).

Turner et al., "Insulin resistance, impaired glucose tolerance and non-insulin-dependent diabetes, pathologic mechanisms and treatment: Current status and therapeutic possibilities", *Progress in Drug Research*, 51:3-94 (1998).

Urizar et al., "The Farnesoid X-activated Receptor Mediates Bile Acid Activation of Phospholipid Transfer Protein Gene Expression", *J. Biol. Chem.*, 275(50):39313-39317 (2000).

VanAllan et al., "Reactions of Some 4-Methylene-4H-Pyran Derivatives with Primary and Secondary Amines", *J. Heterocycl. Chem.*, 7(3):495-507 (1970).

Wan et al., "Hepatocyte-Specific Mutation Establishes Retinoid X Receptor α as a Heterodimeric Integrator of Multiple Physiological Processes in the Liver", *Mol. Cell. Biol.*, 20(12):4436-4444 (2000).

Whitlow et al., "Crystallographic analysis of potent and selective factor Xa inhibitors complexed to bovine trypsin", *Acta Cryst.*, D55:1395-1404 (1999).

Willy et al., "LXR, a nuclear receptor that defines a distinct retinoid response pathway", *Genes & Development*, 9:1033-1045 (1995).

Wright et al., "UKPDS 28: A Randomized Trial of Efficacy of Early Addition of Metformin in Sulfonylurea-Treated Type 2 Diabetes", *Diabetes Care*, 21(1):87-92 (1998).

Xu et al., "Polymer Supported Bases in Solution-Phase Synthesis. 2. A Convenient Method for N-Alkylation Reactions of Weakly Acidic Heterocycles", *Biooroganic & Med. Chem. Ltrs.*, 8:1089-1092 (1998).

Yalpani, M., "Cholesterol-lowering drugs", *Chemistry & Industry*, pp. 85-89 (1996).

Zapata et al., "Estudio Cinetico de la Hidrolisis Acida de la 1-Bencilidenamino-4,6-Difenil-2-Piridona", *Hidroeists*, 80:526-530 (1984).

Zayed et al., "Synthesis of Some new N'-Substituted N-Aminopyridine Derivatives", *Pharmazie*, 40:725-726 (1985).

Zhang et al., "AT, Receptor Blockers Prevent Sympathetic Hyperactivity and Hypertension by Chronic Ouabain and Hypertonic Saline", *Am. J. Physiol. Heart Circ. Physiol.*, 280:H1318-H1323 (2001).

Zhou, et al., "Nuclear Receptors Have Distinct Affinities for Coactivators: Characterization by Fluorescence Resonance Energy Transfer", *Mol. Endocrinol.*, 12(10):1594-1604 (1998).

N.T.A. Dawood: "Synthesis of Some Pyridone Derivatives.", Bolletino Chimico Farmaceutico, vol. 140, No. 3, 2001, pp. 149-154.

Morissette et al., "High-throughput crystallization: polymorphs, salts, co-crystals and solvates of pharmaceutical solids", Advanced Drug Delivery Reviews, 2004, 56, 275-300.

Borch, R. F. et al., "New synthesis of substituted 2(1H)-pyridones. Synthesis of a potential camptothecin intermediate", J. Org. Chem., 37(8), 1972, 1141-1145.

Buysens, K. J. et al., "Intramolecular Diels-Alder Reactions of 2(1H)-Pyrazinones: Synthesis of New Furo/Pyrano-pyridinones and -pyridines", Tetrahedron, 51(45), 1995, 12463-12478.

Office Action dated Dec. 16, 2009 in the corresponding Canadian Application No. 2,469,435, listing CAS registry numbers.

STN Columbus printout generated on Jun. 25, 2010, pp. 1-172.

Heinz Hoberg et al.: "Nickel(0)-katalysierte [2+2+2]-Cycloaddition von Alkynen mit Isocyanaten zu 2-Oxo-1,2- dihydrophyridinen," Synthesis, 1982, No. 4, pp. 324-325.

Masayuki Kuzuya et al.: "The Structure-Reactivity-Chemoselectivity Relationship on the Reactions of 1-Unsubstituted Tautomeric 2-Pyridones with Benzyne," Bulletin of the Chemical Society of Japan, 1985, vol. 58, No. 4, pp. 1149-1155.

Helena Sladowska: "Investigations on the Synthesis and Properties of Some N-Arylpiperazinylalkyl Derivatives of Imides of 3, 4-Pyridinedicarboxylic Acids," Farmaco, 1963, vol. 48, No. 1, pp. 85-94.

H. Jahine et al.: "Reactions with 3-Chloro & 3-Hydrazino-4-benzyl-6-phenylpyridazines," Indian Journal of Chemistry, Section B: Organic Chemistry Including Medicianl Chemistry, 1977, vol. 15B, No. 4, pp. 352-355.

M.C. Hobhkob et al., Zhurnal Organicheskoi Khimii, 1996, vol. 32, No. 5, pp. 667-674.

Carlo Musante e Silvana Fatutta—Sul furoil-piruvato di etile: composti eterociclici contenenti il nucleo del furano (*),: Gazzetta Chimica Italiana, 1958, vol. 88, pp. 879-898.

Silvana Fatutta: "Benzofuroll-2-piruvato di etile ealcuni soul prodotti di condensazlone," Gazzetta Chimica Italiana, 1959, vol. 89, pp. 964-978.

V. Ariegnn et al.: "Cercetari asupra unor N.R.-x-piridone, Nota II. Derivati sulfonamidlici ai x-piridonei," Farmacia, 1971, vol. 19, No. 3, pp. 129-133.

Helena Sladowska, "Badania Nadsynteza I Wlasciwosciamio-I N-Arylopiperazyny-Lopropylowych Pochodnych Estru Etylowego Kwasu 3-Cyja-No-2-Hydroksy-6-Metylopirydyno-4-karboksylowego," Acta Poloniae Pharmaceutca, 1992, vol. 49, No. 1-2, pp. 61-65.

Office Action mailed on Nov. 14, 2008 in U.S. Appl. No. 10/327,813.

Final Office Action mailed on May 1, 2008 in U.S. Appl. No. 10/327,813.

Office Action mailed on Oct. 17, 2007 in U.S. Appl. No. 10/327,813.

Final Office Action mailed on Mar. 26, 2007 in U.S. Appl. No. 10/327,813.

Office Action mailed on Aug. 15, 2006 in U.S. Appl. No. 10/327,813.
Office Action mailed on Feb. 7, 2006 in U.S. Appl. No. 10/327,813.
Office Action mailed on Jul. 5, 2005 in U.S. Appl. No. 10/327,813.
Office Action mailed on Sep. 2, 2004 in U.S. Appl. No. 10/327,813.

Kurihara, Takushi, et al., "Synthesis of C-nor-4,6-Secocamptothecin and Related Compounds," Journal of Heterocyclic Chemistry, 1993, vol. 30, No. 3, pp. 643-652.

Noguchi, Michihiko, et al., "Reaction of 1, 3, 6-Trimethylpyrimidine-2, 4 (1H, 3H)-Dione-5-Carbaldehype with Aldimines," Chemistry Express, 1989, vol. 4, No. 8, pp. 503-506.

Van Allan, J.A., et al., "Reactions of Some Pyranylidene Esters with Amines," Journal of Heterocyclic Chemistry, 1971, vol. 8, No. 5, pp. 803-807.

Katritzky et al., "2- and 4-Pyrdiones by Oxidative Demethylation of 2- and 4-Methyl-pyridinium Cations," Journal of the Chemical Society Perkin Transactions I, 9:1888-1889 (1980).

Katritzky et al., "Oxidative Demthylation of α- and γ-Methyl-N-heterocyclonium Salts: a New Method for Preparation of N-Substituted-α- and-γ-oxo-N-heterocycles," Journal of the Chemical Society Chemical Communication, 9:552 (1983).

Katritzky et al., "Elimination Reactions of Pyridinium Cations," Arab Gulf Journal of Scientific Research, 1(1):85-97 (1983).

Katritzky et al., "Products from Metallation and Attempted Metallation of 1-Alkyl-4, 6-Diphenyl-2-Pyridones and Subsequent Reaction with Electrophiles," Tetrahedron Letters, 12(46):4451-4454 (1980).

Von J Faust et al., "Zur Chemie des 4,6-Diphenyl-2H-thiopyranthions-(2)," Journal fur Praktische Chemie, 311 (1):61-70 (1969).

Katritzky et al., "Heterocycle Stabilized Carbanions, Two Series of Anomalous Products from 1-Alkyl-4,6-diphenyl-2-pyridones," Journal of the Chemical Society Perkin Transactions I, No. 1:143-151 (1982).

Bennett, D. J. et al., "An update on non-steroidal liver X receptor agonists and their potential use in the treatment of atherosclerosis", Expert Opin. Ther. Patents, 2006, 16(12), 1673-1699.

Horig, H. et al., "From bench to clinic and back: Perspective on the 1st IQPC translational research conference", Journal of Transitional Medicine, 2004, 2(44), 8 pages.

Michael, L.F. et al., "The Pharmacology of LXR", Mini-Reviews in Medicinal Chemistry, 2005, 5(8), 729-740.

Schafer, S. et al., "Failure is an option: learning from unsuccessful proof-of-concept trials", Drug Discovery Today, 2008, 13(21/22), 913-916.

Zhao, C. et al., "Liver x receptor in cholesterol metabolism", Journal of Endocrinology, 2010, vol. 204, 233-240.

Gong, H. et al., "Orphan nuclear receptors, PXR and LXR: new ligands and therapeutic potential", Expert Opin. Ther. Targets, 2004, 8(1), 49-54.

Office Action issued Jul. 22, 2010 for Canadian Application No. 2,469,435.

CAS Registry Numbers cited in the Office Action issued Jul. 22, 2010 for Canadian Application No. 2,469,435.

Pelton et al., "Nuclear Receptors as Potential Targets for Modulation Reverse Cholesterol Transport," Current Topics in Medicinal Chemistry, 5:265-282 (2005).

Sokolovskaya et al., "DI- and TRI(2-DPRON-6-YL) Arenes," Chemistry of Heterocyclic Compounds, 13(7):723-727 (1977) (translated from Khimiya Geterotsiklicheskikh Soedinenii, 7:897-901 (1977)).

BYRN et al., Chapter 11 Hydrates and Solvates in Solid-State Chemistry of Drugs (2nd Ed.), 233-247 (1999).

Rouhi, A.M., Chemistry & Engineering News., 81(8):32-35 (Feb. 24, 2003).

* cited by examiner

| Serial No. | Structure | Ki(a) | Ki(b) | EC50(a) | %Eff(a) | EC50(b) | %Eff(b) |
|---|---|---|---|---|---|---|---|
| 1 | (3-cyano-4-trifluoromethyl-2-oxo-6-(4-chlorophenyl)-1-(2,4-dimethylbenzyl)pyridine) | B1 | B1 | III | B | III | B |
| 2 | (3-cyano-4-trifluoromethyl-2-oxo-6-phenyl-1-(4-isopropylbenzyl)pyridine) | D1 | D1 | IV | A | IV | B |
| 3 | (3-cyano-4-trifluoromethyl-2-oxo-6-phenyl-1-(4-tert-butylbenzyl)pyridine) | NC | NC | NC | A | NC | A |
| 4 | (3-cyano-4-trifluoromethyl-2-oxo-6-phenyl-1-(2,4,5-trifluorobenzyl)pyridine) | A1 | A1 | III | B | III | B |
| 5 | (3-cyano-4-trifluoromethyl-2-oxo-6-phenyl-1-(naphthalen-1-ylmethyl)pyridine) | B1 | B1 | IV | A | IV | B |

FIG. 1A

| | | | | | | | |
|---|---|---|---|---|---|---|---|
| 6 | (structure) | NC | NC | NC | NC | NC | NC |
| 7 | (structure) | B1 | B1 | III | B | III | B |
| 8 | (structure) | D1 | D1 | III | A | IV | A |
| 9 | (structure) | NC | NC | NC | NC | NC | NC |
| 10 | (structure) | A1 | A1 | III | B | III | B |

FIG. 1B

| | | | | | | | |
|---|---|---|---|---|---|---|---|
| 11 | 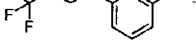 | B1 | B1 | III | B | IV | B |
| 12 |  | B1 | A1 | III | B | III | B |
| 13-1 |  | A1 | A1 | III | B | III | B |
| 13-2 | | A1 | A1 | III | B | III | C |
| 14 |  | C1 | B1 | III | B | III | B |
| 15 |  | B1 | B1 | IV | B | IV | B |
| 16 |  | NC | NC | NC | NC | NC | NC |
FIG.1C

| | | | | | | | |
|---|---|---|---|---|---|---|---|
| 17 | (structure: 3-cyano-6-methyl-4-benzyl-1-piperidinyl-pyridin-2-one) | D1 | NC | NC | NC | NC | NC |
| 18 | (structure: 3-cyano-4-trifluoromethyl-6-phenyl-1-(4-acetylbenzyl)-pyridin-2-one) | C1 | B1 | IV | B | IV | B |
| 19 | (structure: 3-cyano-4-trifluoromethyl-6-phenyl-1-((2,2-dimethyl-1,3-dioxolan-4-yl)methyl)-pyridin-2-one) | NC | D1 | III | A | NC | B |
| 20 | (structure: 3-cyano-4-trifluoromethyl-6-phenyl-1-(2,3-dihydroxypropyl)-pyridin-2-one) | NC | NC | NC | NC | NC | NC |
| 21 | (structure: 6-(4-methoxyphenyl)-1-(4-methylbenzyl)-pyridin-2-one) | NC | NC | NC | NC | NC | NC |

FIG. 1D

| | | | | | | | |
|---|---|---|---|---|---|---|---|
| 22 | (structure: 1-(4-methylbenzyl)-6-(3-methoxyphenyl)pyridin-2(1H)-one) | NC | NC | NC | NC | NC | NC |
| 23 | (structure: 1-(4-methylbenzyl)-6-(biphenyl-4-yl)pyridin-2(1H)-one) | NC | NC | NC | NC | NC | NC |
| 24 | (structure: 1-(4-methylbenzyl)-6-(3-trifluoromethylphenyl)pyridin-2(1H)-one) | NC | NC | NC | NC | NC | NC |
| 25 | (structure: 1-(4-methylbenzyl)-6-(3-carboxyphenyl)pyridin-2(1H)-one) | NC | NC | NC | NC | NC | NC |

FIG. 1E

| # | Structure | | | | | | |
|---|---|---|---|---|---|---|---|
| 26 | (4-methylbenzyl pyridinone-thiophene) | NC | NC | NC | NC | NC | NC |
| 27 | (benzyl cyano CF3 pyridinone phenyl NHCOCF3) | B1 | B1 | IV | B | IV | C |
| 28 | (benzyl cyano CF3 pyridinone thiazole) | C1 | B1 | IV | A | IV | A |
| 29 | (4-methylbenzyl cyano CF3 pyridinone thiazole) | B1 | A1 | III | B | III | C |
| 30-1 | (2,4-dimethylbenzyl cyano CF3 pyridinone thiazole) | B1 | A1 | III | B | III | D |
| 30-2 | | B1 | A1 | III | B | III | C |
| 31 | (4-methylbenzyl cyano CF3 pyridinone furan) | B1 | B1 | III | B | IV | C |

FIG. 1F

| | | | | | | | |
|---|---|---|---|---|---|---|---|
| 32-1 | (structure) | B1 | B1 | III | A | III | B |
| 32-2 | | B1 | A1 | III | B | III | B |
| 33 | (structure) | C1 | B1 | NC | B | IV | C |
| 34 | (structure) | B1 | A1 | III | B | IV | B |
| 35 | (structure) | D1 | B1 | IV | B | IV | B |
| 36 | (structure) | B1 | B1 | IV | B | IV | B |

FIG. 1G

| # | Structure | | | | | | |
|---|---|---|---|---|---|---|---|
| 37 | (3-cyano-4-(chlorodifluoromethyl)-1-benzyl-6-(m-tolyl)pyridin-2(1H)-one) | B1 | A1 | III | B | III | C |
| 38 | (3-cyano-4-(1-methoxy-1-methyl-fluoroethyl)-1-benzyl-6-(m-tolyl)pyridin-2(1H)-one) | D1 | C1 | IV | A | NC | B |
| 39 | (3-cyano-4-(trifluoromethyl)-1-(2,4-dimethylbenzyl)-6-(m-tolyl)pyridin-2(1H)-one) | A1 | A1 | III | A | III | B |
| 40 | (3-cyano-4-(heptafluoropropyl)-1-(2,4-dimethylbenzyl)-6-phenylpyridin-2(1H)-one) | B1 | B1 | III | B | III | B |
| 41 | (3-cyano-4-(heptafluoropropyl)-1-(2,4-dimethylbenzyl)-6-(m-tolyl)pyridin-2(1H)-one) | B1 | B1 | III | B | III | B |

FIG. 1H

| 42 | 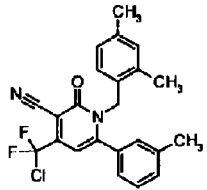 | A1 | A1 | III | B | III | B |
| 43 | 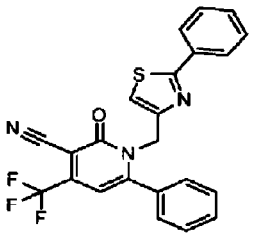 | NC | NC | IV | A | IV | A |
| 44 | 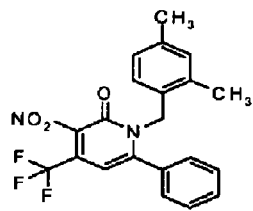 | NC | NC | NC | NC | NC | NC |
| 45 | 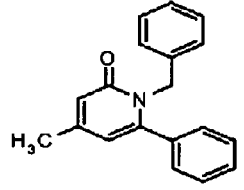 | NC | NC | NC | NC | NC | NC |
| 46 | 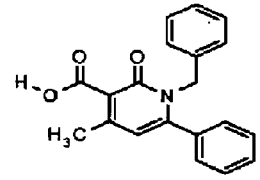 | NC | NC | NC | NC | NC | NC |
FIG. 1I

| # | Structure | | | | | | |
|---|---|---|---|---|---|---|---|
| 47 | (structure) | B1 | B1 | IV | C | IV | C |
| 48 | (structure) | B1 | B1 | IV | A | IV | B |
| 49 | (structure) | NC | NC | NC | NC | NC | NC |
| 50 | (structure) | NC | D1 | NC | NC | IV | A |

FIG. 1J

| | | | | | | | |
|---|---|---|---|---|---|---|---|
| 51 | 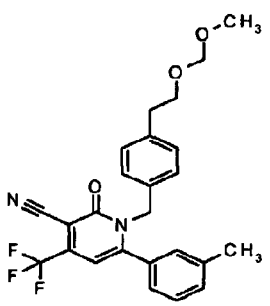 | NC | NC | NC | NC | IV | A |
| 52 | 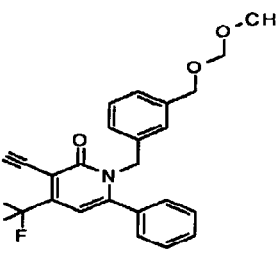 | NC | NC | NC | NC | NC | NC |
| 53 | 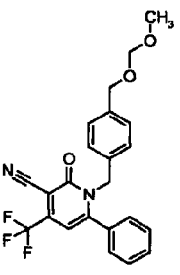 | D1 | D1 | NC | NC | NC | NC |
| 54 | 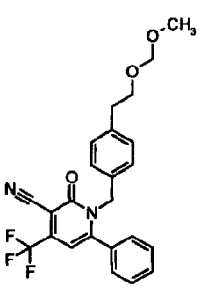 | NC | NC | NC | NC | NC | NC |
FIG. 1K

| | | | | | | | |
|---|---|---|---|---|---|---|---|
| 55 | (structure) | D1 | D1 | IV | A | IV | A |
| 56 | (structure) | C1 | B1 | NC | A | NC | B |
| 57 | (structure) | D1 | D1 | NC | A | NC | A |
| 58 | (structure) | C1 | B1 | IV | B | IV | B |
| 59 | (structure) | NC | IV | NC | NC | NC | NC |

FIG. 1L

| | | | | | | | |
|---|---|---|---|---|---|---|---|
| 60 | 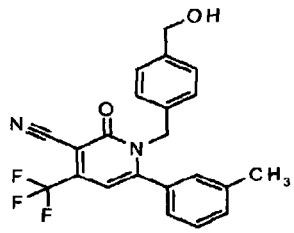 | D1 | D1 | NC | B | IV | B |
| 61 | 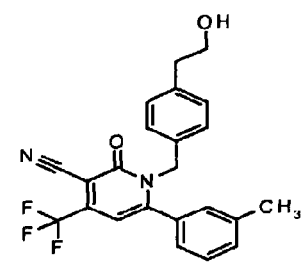 | NC | NC | NC | NC | NC | NC |
| 62 | 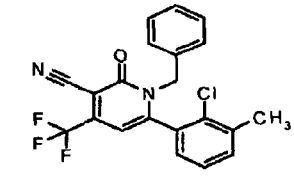 | B1 | A1 | III | C | III | C |
| 63 | 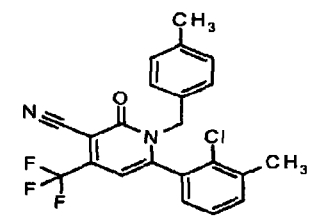 | A1 | A1 | III | C | III | B |
| 64 | 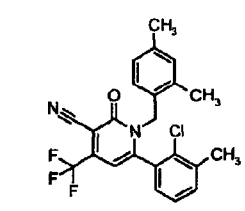 | B1 | A1 | III | B | III | B |
FIG. 1M

| | | | | | | | |
|---|---|---|---|---|---|---|---|
| 65 | 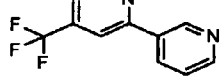 | NC | D1 | IV | A | IV | A |
| 66 |  | D1 | B1 | IV | B | IV | B |
| 67 |  | A1 | A1 | III | B | III | C |
| 68 | 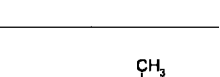 | D1 | B1 | IV | A | IV | B |
| 69 | 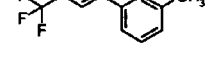 | B1 | B1 | IV | B | III | B |
FIG. 1N

| | | | | | | | |
|---|---|---|---|---|---|---|---|
| 70 | 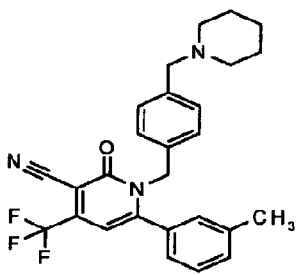 | D1 | D1 | NC | NC | NC | NC |
| 71 | 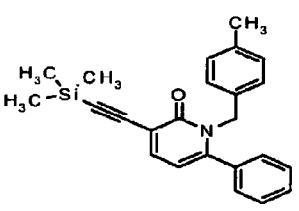 | NC | NC | NC | NC | NC | NC |
| 72 | 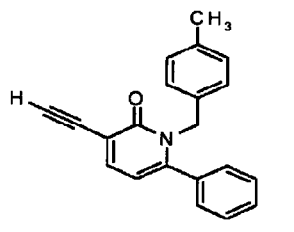 | NC | NC | NC | NC | NC | NC |
| 73 | 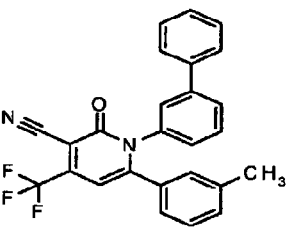 | D1 | B1 | IV | A | IV | B |
| 74 | 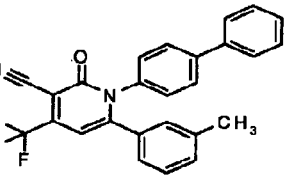 | D1 | D1 | NC | NC | IV | A |
FIG. 10

| # | Structure | | | | | | |
|---|---|---|---|---|---|---|---|
| 75 | (structure) | D1 | D1 | IV | A | IV | B |
| 76 | (structure) | B1 | B1 | IV | C | IV | C |
| 77 | (structure) | B1 | A1 | III | C | IV | C |
| 78 | (structure) | B1 | B1 | IV | B | IV | B |
| 79 | (structure) | D1 | B1 | IV | B | IV | B |

FIG. 1P

| 80 | (structure) | NC | D1 | IV | A | IV | A |
| 81 | (structure) | NC | NC | NC | NC | IV | A |
| 82 | (structure) | C1 | B1 | IV | B | IV | B |
| 83 | (structure) | B1 | B1 | IV | B | IV | B |
| 84 | (structure) | D1 | C1 | IV | B | NC | B |

FIG. 1Q

| # | Structure | | | | | | |
|---|---|---|---|---|---|---|---|
| 85 | 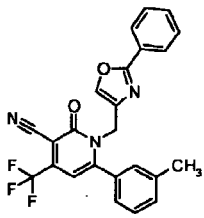 | NC | D1 | IV | A | IV | A |
| 86 | 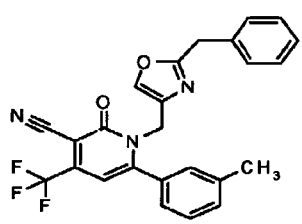 | NC | D1 | NC | NC | NC | NC |
| 87 | 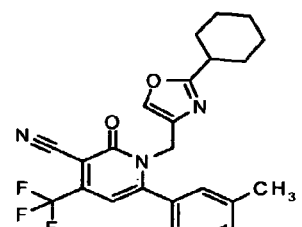 | NC | NC | NC | NC | NC | A |
| 88 | 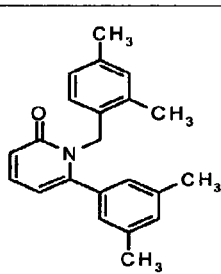 | NC | NC | NC | NC | NC | NC |
| 89 | 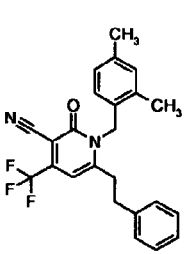 | C1 | B1 | IV | A | IV | B |
FIG. 1R

| | | | | | | | |
|---|---|---|---|---|---|---|---|
| 90 | 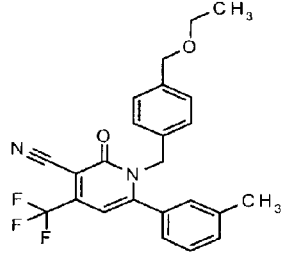 | NC | D1 | IV | A | IV | B |
| 91 | 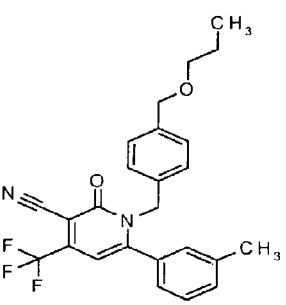 | D1 | D1 | NC | NC | IV | A |
| 92 | 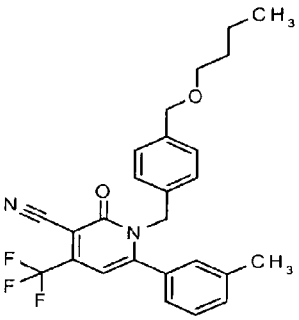 | D1 | D1 | IV | A | III | A |
| 93 | 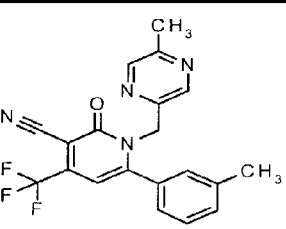 | B1 | B1 | IV | C | IV | C |
FIG. 1S

| # | Structure | | | | | | |
|---|---|---|---|---|---|---|---|
| 94 | (structure) | D1 | C1 | IV | A | IV | B |
| 95 | (structure) | D1 | D1 | NC | NC | NC | NC |
| 96 | (structure) | D1 | D1 | NC | NC | NC | NC |
| 97 | (structure) | NC | D1 | NC | NC | NC | NC |
| 98 | (structure) | D1 | D1 | IV | A | IV | B |
| 99 | (structure) | D1 | D1 | NC | NC | NC | NC |

FIG. 1T

| | | | | | | | |
|---|---|---|---|---|---|---|---|
| 100 | (structure) | NC | NC | NC | NC | NC | NC |
| 101 | (structure) | D1 | B1 | IV | A | IV | B |
| 102 | (structure) | NC | NC | NC | NC | NC | NC |
| 103 | (structure) | NC | D1 | NC | NC | NC | NC |
| 104 | (structure) | D1 | C1 | IV | A | IV | B |
| 105 | (structure) | D1 | C1 | IV | A | IV | B |

FIG. 1U

| | | | | | | | |
|---|---|---|---|---|---|---|---|
| 106 | (structure) | D1 | B1 | IV | B | IV | C |
| 107 | (structure) | D1 | D1 | IV | B | IV | B |
| 108 | (structure) | D1 | D1 | NC | B | NC | B |
| 109-1 | (structure) | B1 | B1 | III | B | III | C |
| 109-2 | | C1 | B1 | III | B | III | B |
| 110-1 | (structure) | B1 | B1 | III | B | III | C |
| 110-2 | | B1 | A1 | III | B | III | C |

FIG. 1V

| 111 | 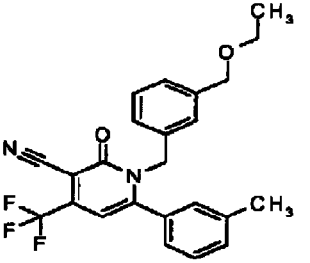 | NC | NC | NC | NC | NC | NC |
|---|---|---|---|---|---|---|---|
| 112 | 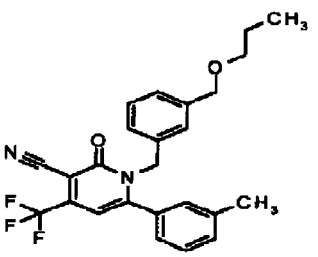 | D1 | D1 | NC | NC | NC | NC |
| 113 | 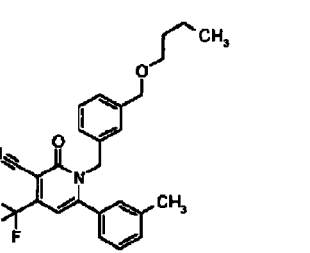 | D1 | D1 | NC | NC | NC | NC |
| 114 | 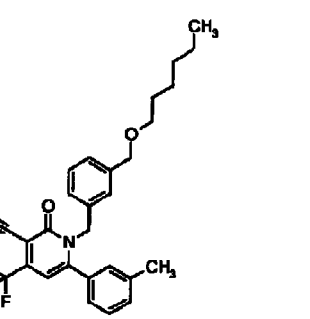 | NC | NC | NC | NC | NC | NC |
FIG. 1W

| | | | | | | | |
|---|---|---|---|---|---|---|---|
| 115 | 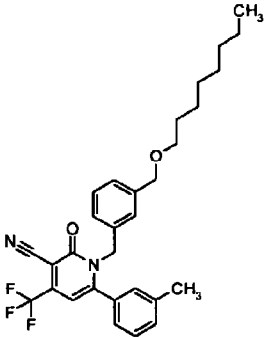 | NC | NC | NC | NC | NC | NC |
| 116 | 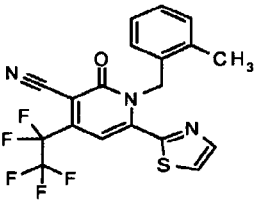 | B1 | A1 | III | B | III | C |
| 117 | 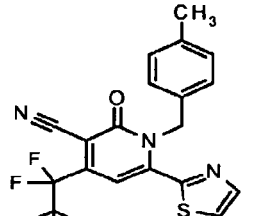 | B1 | B1 | III | B | III | C |
| 118 | 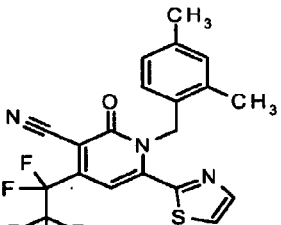 | B1 | A1 | III | B | III | C |
| 119 | 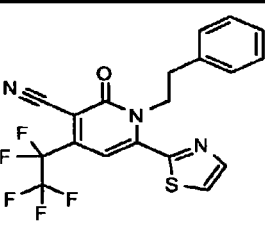 | D1 | D1 | IV | B | IV | C |
FIG. 1X

| # | Structure | | | | | | |
|---|---|---|---|---|---|---|---|
| 120 | (structure) | D1 | D1 | NC | NC | NC | NC |
| 121 | (structure) | B1 | A1 | IV | B | IV | C |
| 122 | (structure) | B1 | B1 | IV | B | IV | C |
| 123-1 | (structure) | B1 | A1 | III | B | III | C |
| 123-2 |  | A1 | A1 | III | B | III | C |
| 124 | (structure) | D1 | D1 | NC | B | IV | B |
| 125 | (structure) | C | B1 | IV | B | IV | B |

FIG. 1Y

| | | | | | | | |
|---|---|---|---|---|---|---|---|
| 126 | 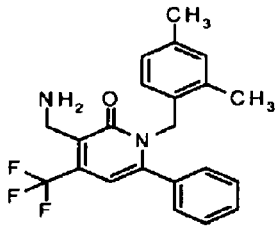 | C | B1 | IV | B | IV | C |
| 127 | 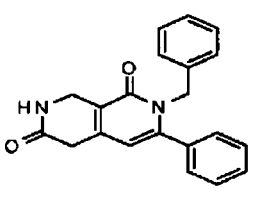 | NC | NC | NC | NC | NC | NC |
| 128 | 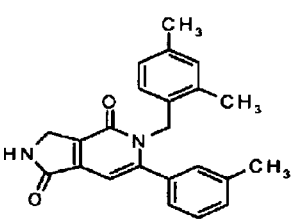 | NC | NC | NC | NC | NC | NC |
| 129 | 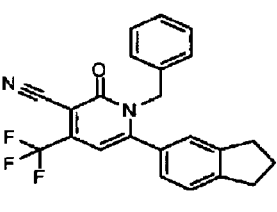 | B1 | B1 | III | B | III | B |
| 130 | 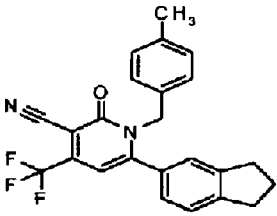 | B1 | A1 | III | B | III | C |
FIG. 1Z

| | | | | | | | |
|---|---|---|---|---|---|---|---|
| 131 | (structure) | B1 | A1 | III | C | III | C |
| 132 | (structure) | C | B1 | III | A | III | A |
| 133 | (structure) | B1 | A1 | III | C | II | C |
| 134 | (structure) | B1 | A1 | III | B | III | B |
| 135 | (structure) | B1 | B1 | IV | B | III | C |

FIG. 1AA

| 136 | [structure] | D1 | D1 | IV | A | NC | A |
| 137 | [structure] | A1 | A1 | II | B | II | C |
| 138 | [structure] | D1 | D1 | IV | A | IV | B |
| 139 | [structure] | D1 | D1 | IV | A | NC | NC |
| 140 | [structure] | D1 | D1 | IV | B | IV | B |

FIG. 1AB

| # | Structure | | | | | | |
|---|---|---|---|---|---|---|---|
| 141 | (ethyl carbamate derivative) | NC | D1 | NC | NC | IV | A |
| 142 | (acetamide derivative) | NC | NC | NC | NC | IV | A |
| 143 | (propionamide derivative) | D1 | NC | NC | NC | IV | A |
| 144 | (isobutyramide derivative) | NC | D1 | NC | NC | IV | A |
| 145 | (butyramide derivative) | NC | NC | NC | NC | NC | NC |
| 146 | (benzamide derivative) | D1 | D1 | NC | NC | NC | NC |

FIG. 1AC

| 147 | 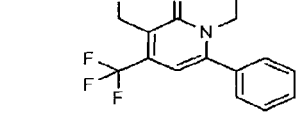 | D1 | D1 | NC | NC | IV | A |
| --- | --- | --- | --- | --- | --- | --- | --- |
| 148 | 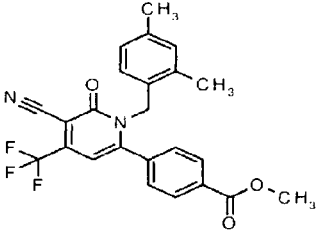 | B1 | B1 | IV | B | IV | B |
| 149 | 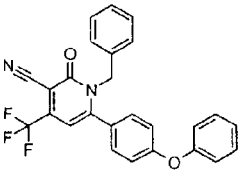 | A1 | A1 | III | B | II | C |
| 150 | 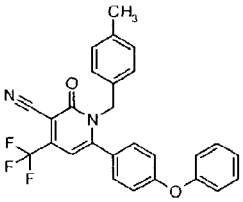 | NC | NC | II | C | II | C |
| 151 | 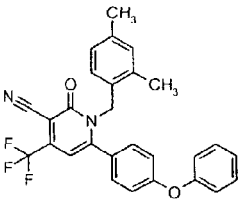 | A1 | A1 | II | C | II | C |
FIG. 1AD

| | | | | | | | |
|---|---|---|---|---|---|---|---|
| 152 | (structure) | C | C1 | IV | A | IV | A |
| 153 | (structure) | B1 | B1 | III | B | III | B |
| 154 | (structure) | B1 | B1 | III | B | III | B |
| 155 | (structure) | D1 | C | IV | B | IV | B |
| 156 | (structure) | B1 | A1 | III | B | III | C |

FIG. 1AE

| | | | | | | | |
|---|---|---|---|---|---|---|---|
| 157 | (structure) | A1 | A1 | III | B | III | C |
| 158 | (structure) | D1 | D1 | IV | A | IV | B |
| 159 | (structure) | B1 | B1 | IV | B | IV | C |
| 160 | (structure) | B1 | A1 | III | B | III | C |
| 161 | (structure) | B1 | B1 | III | B | III | A |

FIG. 1AF

| | | | | | | | |
|---|---|---|---|---|---|---|---|
| 162 | 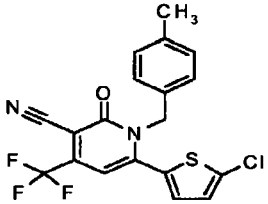 | B1 | B1 | III | C | III | B |
| 163 | 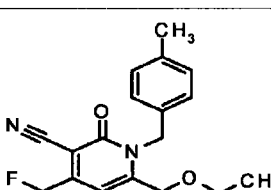 | B1 | A1 | III | B | III | B |
| 164 | 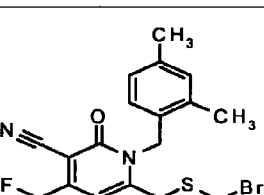 | D1 | D1 | III | B | III | B |
| 165 | 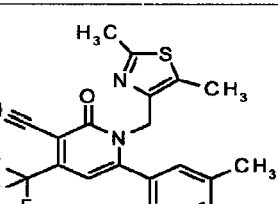 | B1 | A1 | III | B | III | B |
| 166 | 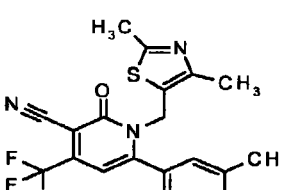 | C1 | C1 | IV | B | IV | A |
| 167 | 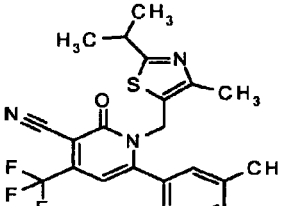 | D1 | D1 | IV | A | NC | NC |
FIG. 1AG

| # | Structure | | | | | | |
|---|---|---|---|---|---|---|---|
| 168 | (2-ethyl-4-methylthiazol-5-yl)methyl pyridinone with CN, CF3, m-tolyl | C1 | C1 | IV | B | IV | A |
| 169 | (2-isopropyl-5-methylthiazol-4-yl)methyl pyridinone with CN, CF3, m-tolyl | B1 | B1 | III | B | III | B |
| 170 | (2-ethyl-5-methylthiazol-4-yl)methyl pyridinone with CN, CF3, m-tolyl | B1 | A1 | III | B | III | B |
| 171 | 2,4-dimethylbenzyl pyridinone with dimethylaminomethyl, CF3, phenyl | B1 | B1 | III | B | III | B |
| 172 | 2,4-dimethylbenzyl pyridinone with CN, dimethoxymethyl, m-tolyl | A1 | A1 | III | B | III | B |

FIG. 1AH

| 173 | 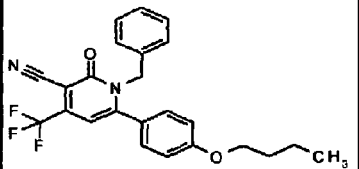 | C | B1 | III | B | III | B |
| 174 | 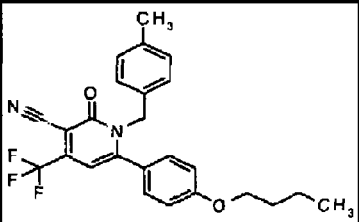 | B1 | B1 | III | B | III | B |
| 175 | 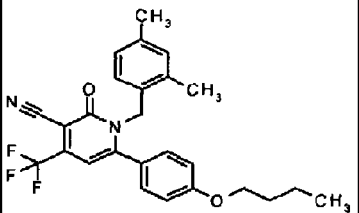 | B1 | A1 | III | B | II | B |
| 176 | 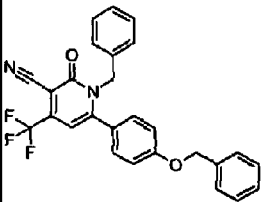 | C1 | B1 | II | A | III | B |
| 177 | 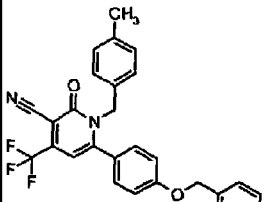 | B1 | B1 | III | B | III | B |
FIG. 1AI

| | | | | | | | |
|---|---|---|---|---|---|---|---|
| 178 | *(structure)* | B1 | A1 | III | B | III | B |
| 179 | *(structure)* | A1 | A1 | II | B | III | C |
| 180 | *(structure)* | A1 | A1 | II | C | IV | C |
| 181 | *(structure)* | A1 | A1 | II | B | II | C |
| 182 | *(structure)* | A1 | A1 | II | B | II | C |

FIG. 1AJ

| | | | | | | | |
|---|---|---|---|---|---|---|---|
| 183-1 | 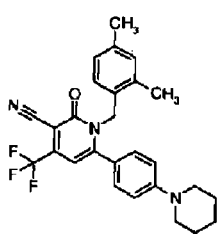 | A1 | A1 | II | B | II | C |
| 183-2 | | A1 | A1 | II | B | II | C |
| 184 | 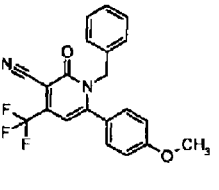 | C1 | B1 | IV | B | IV | C |
| 185 | 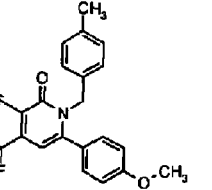 | B1 | A1 | III | B | III | C |
| 186 | 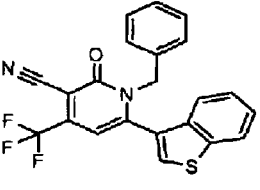 | C1 | B1 | III | B | III | B |
| 187 | 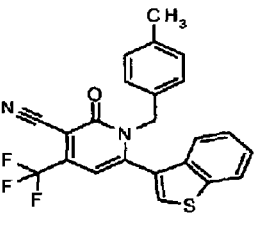 | B1 | A1 | III | B | III | C |
FIG. 1AK

| 188 | 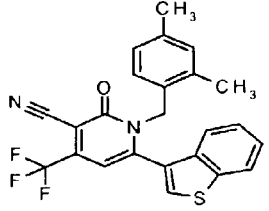 | B1 | A1 | III | B | III | C |
|---|---|---|---|---|---|---|---|
| 189 | 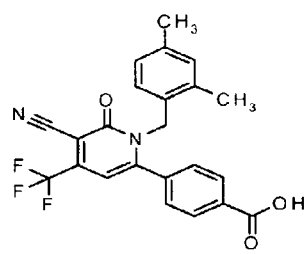 | D1 | D1 | NC | B | NC | NC |
| 190 | 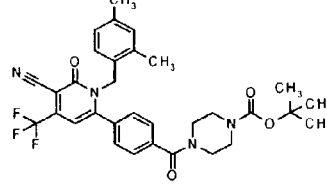 | B1 | B1 | III | B | IV | D |
| 191 | 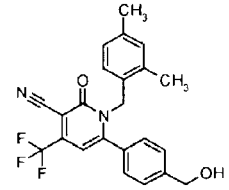 | B1 | A1 | III | B | III | C |
| 192 | 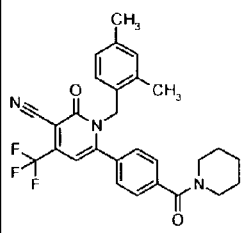 | B1 | B1 | III | B | IV | D |
FIG. 1AL

| | | | | | | | |
|---|---|---|---|---|---|---|---|
| 193 | (structure) | C1 | B1 | III | B | III | C |
| 194 | (structure) | C1 | B1 | III | B | III | C |
| 195 | (structure) | B1 | B1 | III | B | III | C |
| 196 | (structure) | B1 | A1 | III | C | III | D |
| 197 | (structure) | D1 | B1 | III | B | III | C |

FIG. 1AM

| # | Structure | | | | | | |
|---|---|---|---|---|---|---|---|
| 198 | (structure) | D1 | D1 | IV | B | IV | B |
| 199 | (structure) | A1 | A1 | III | B | III | C |
| 200 | (structure) | D1 | C1 | IV | A | III | A |
| 201 | (structure) | B1 | B1 | III | B | III | B |
| 202 | (structure) | B1 | A1 | III | B | III | C |

FIG. 1AN

| # | Structure | | | | | | |
|---|---|---|---|---|---|---|---|
| 203 | (structure) | D1 | D1 | IV | A | NC | NC |
| 204 | (structure) | D1 | D1 | IV | B | IV | B |
| 205 | (structure) | C1 | C1 | III | B | IV | B |
| 206 | (structure) | C1 | B1 | IV | C | NC | D |
| 207 | (structure) | C1 | B1 | IV | B | IV | C |

FIG. 1AO

| # | Structure | | | | | | |
|---|---|---|---|---|---|---|---|
| 208 | (structure) | B1 | B1 | III | A | III | B |
| 209 | (structure) | B1 | A1 | III | B | III | C |
| 210 | (structure) | B1 | B1 | III | B | III | C |
| 211 | (structure) | B1 | B1 | III | C | III | C |
| 212 | (structure) | B1 | A1 | III | C | III | C |
| 213 | (structure) | B1 | A1 | II | C | II | D |

FIG. 1AP

| 214 | 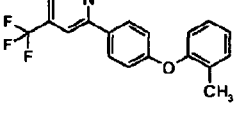 | A1 | A1 | II | B | II | C |
| 215 | 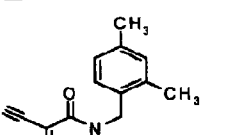 | A1 | A1 | II | C | II | D |
| 216 | 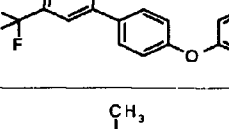 | A1 | A1 | III | C | II | C |
| 217 | 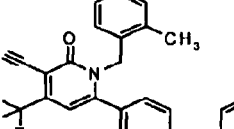 | A1 | A1 | II | C | II | C |
| 218 | 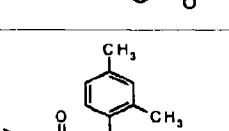 | B1 | B1 | IV | B | IV | B |
| 219 | 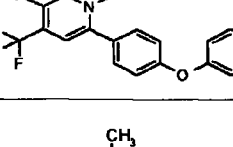 | B1 | B1 | II | B | II | B |
FIG. 1AQ

| # | Structure | | | | | | |
|---|---|---|---|---|---|---|---|
| 220 | 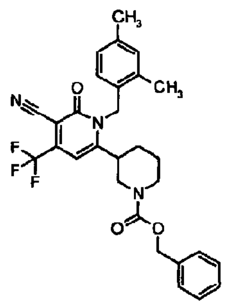 | B1 | A1 | III | B | III | B |
| 221 | 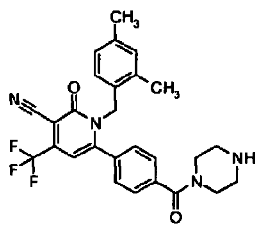 | D1 | D1 | NC | B | IV | B |
| 222 | 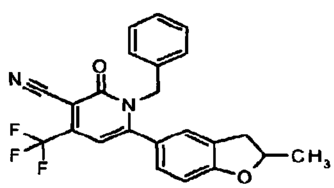 | C1 | B1 | III | A | NC | C |
| 223 | 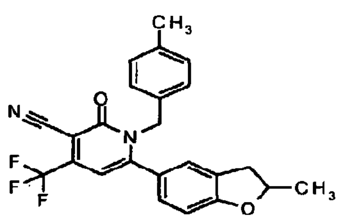 | B1 | A1 | III | B | III | B |
| 224 | 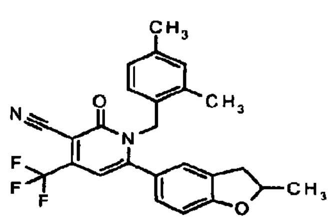 | A1 | A1 | III | B | III | B |

FIG. 1AR

| | | | | | | | |
|---|---|---|---|---|---|---|---|
| 225 | 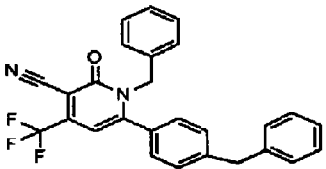 | D1 | B1 | IV | A | III | B |
| 226 | 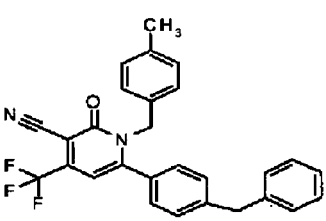 | B1 | B1 | III | B | III | B |
| 227 | 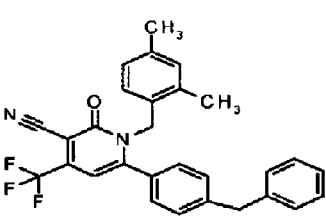 | B1 | A1 | III | B | III | B |
| 228 | 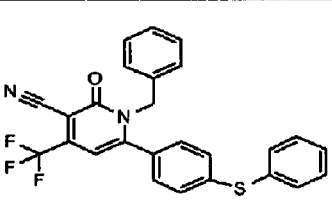 | C1 | B1 | IV | B | III | B |
| 229 | 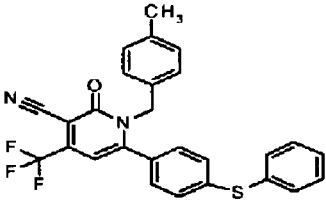 | B1 | B1 | III | B | III | C |
FIG. 1AS

| 230 | 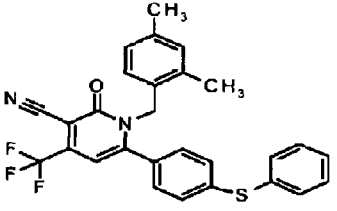 | B1 | A1 | III | B | III | C |
| 231 | 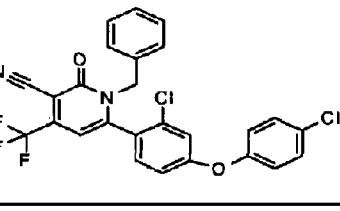 | B1 | B1 | III | B | III | C |
| 232 | 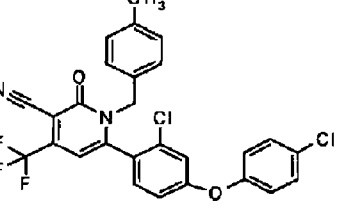 | A1 | A1 | III | B | III | C |
| 233 | 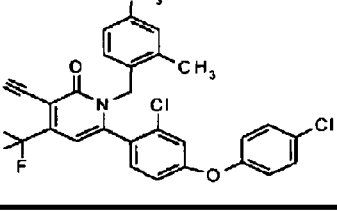 | B1 | A1 | II | B | II | C |
| 234 | 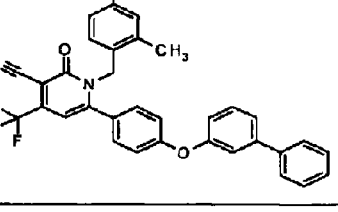 | B1 | A1 | III | B | NC | C |
FIG. 1AT

| | | | | | | | |
|---|---|---|---|---|---|---|---|
| 235 | (structure) | D1 | D1 | IV | A | NC | A |
| 236 | (structure) | NC | NC | NC | NC | NC | NC |
| 237-1 | (structure) | D1 | D1 | IV | A | IV | B |
| 237-2 | | D1 | C1 | IV | A | IV | B |
| 238 | (structure) | NC | NC | NC | A | NC | B |
| 239 | (structure) | B1 | B1 | III | B | III | B |

FIG. 1AU

| # | Structure | | | | | | |
|---|---|---|---|---|---|---|---|
| 240 | (2-ethyl-5-methyl-thiazol-4-ylmethyl pyridinone with CF3 and 4-phenoxyphenyl) | B1 | B1 | III | B | III | C |
| 241 | (2-isopropyl-5-methyl-thiazol-4-ylmethyl pyridinone with CF3 and 4-phenoxyphenyl) | D1 | C1 | III | B | IV | B |
| 242 | (2,4-dimethylbenzyl pyridinone with CF3 and 1-(3-methylbenzyl)piperidin-4-yl) | B1 | B1 | NC | B | III | B |
| 243 | (2,4-dimethylbenzyl pyridinone with CF3 and 4-(4-hydroxy-3-methylphenoxy)phenyl) | A1 | A1 | II | B | II | C |
| 244 | (2,4-dimethylbenzyl pyridinone with CF3 and 4-(3-methyl-4-hydroxyphenoxy)phenyl) | A1 | A1 | I | B | I | C |

FIG. 1AV

| # | Structure | | | | | | |
|---|---|---|---|---|---|---|---|
| 245 | (structure) | A1 | A1 | II | B | II | C |
| 246 | (structure) | B1 | A1 | III | B | III | C |
| 247 | (structure) | NC | NC | NC | NC | IV | A |
| 248 | (structure) | A1 | A1 | I | B | II | C |
| 249 | (structure) | A1 | A1 | II | C | II | C |
| 250 | (structure) | A1 | A1 | II | C | II | C |

FIG. 1AW

| # | Structure | | | | | | |
|---|---|---|---|---|---|---|---|
| 251 | 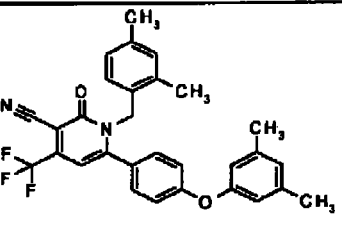 | A1 | A1 | I | C | I | D |
| 252 | 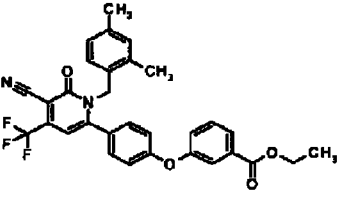 | A1 | A1 | II | B | II | C |
| 253 | 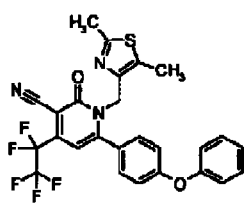 | B1 | B1 | III | B | III | C |
| 254 | 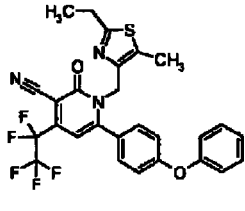 | B1 | B1 | III | B | III | C |
| 255 | 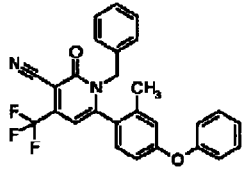 | B1 | A1 | II | B | II | B |
| 256 | 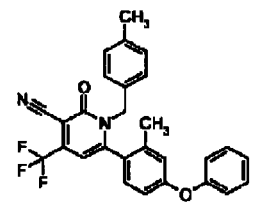 | A1 | A1 | II | B | II | D |
FIG. 1AX

| | | | | | | | |
|---|---|---|---|---|---|---|---|
| 257 | 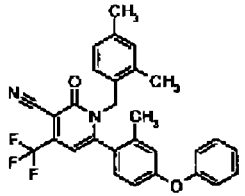 | A1 | A1 | II | B | II | C |
| 258 | 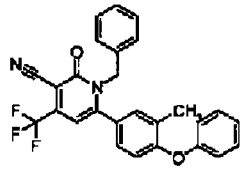 | B1 | B1 | III | B | III | C |
| 259 | 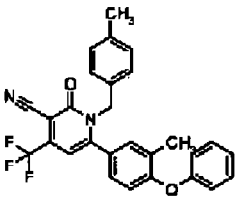 | A1 | A1 | II | B | II | C |
| 260 | 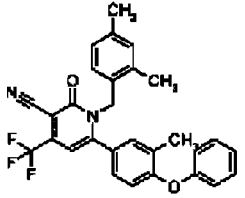 | A1 | A1 | II | C | II | C |
| 261 | 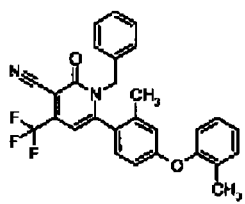 | A1 | A1 | II | C | II | C |
FIG. 1AY

| | | | | | | | |
|---|---|---|---|---|---|---|---|
| 262 | 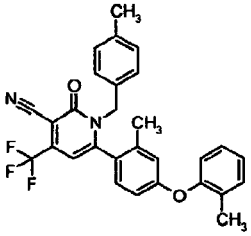 | A1 | A1 | II | B | II | C |
| 263 | 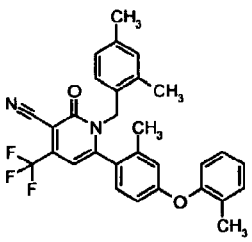 | B1 | A1 | II | B | II | C |
| 264 | 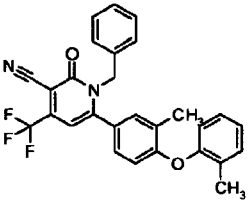 | A1 | A1 | II | B | II | B |
| 265 | 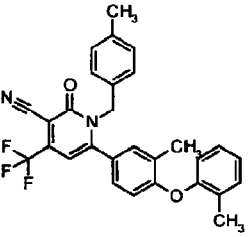 | B1 | A1 | II | B | II | B |
| 266 | 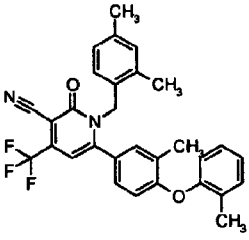 | A1 | A1 | II | B | II | B |
FIG. 1AZ

| 267 | 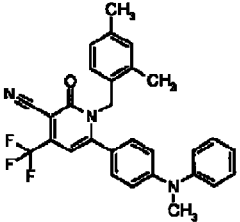 | B1 | A1 | III | B | III | B |
| 268 | 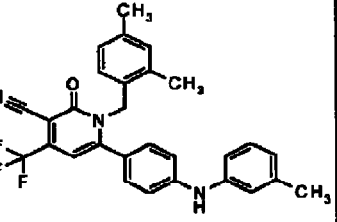 | A1 | A1 | II | C | II | C |
| 269 | 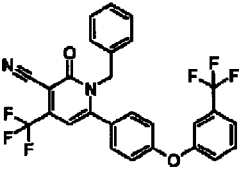 | B1 | A1 | III | B | II | C |
| 270 | 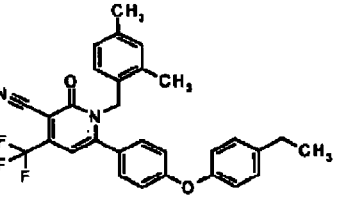 | A1 | A1 | II | C | II | C |
| 271 | 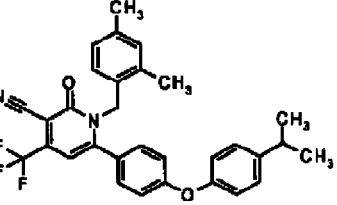 | B1 | A1 | II | C | II | C |
| 272 | 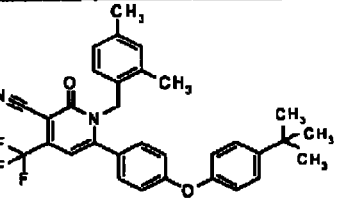 | B1 | B1 | III | B | III | C |
FIG. 1BA

| | | | | | | | |
|---|---|---|---|---|---|---|---|
| 273 | 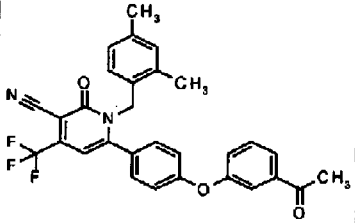 | A1 | A1 | II | B | II | C |
| 274 | 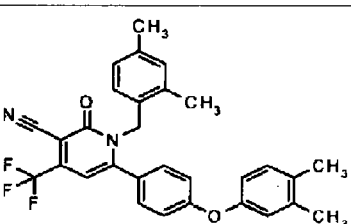 | A1 | A1 | II | B | II | C |
| 275 | 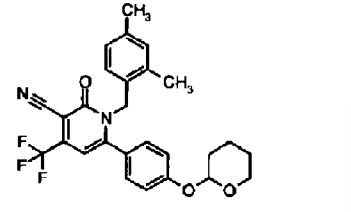 | A1 | B1 | II | B | III | B |
| 276 | 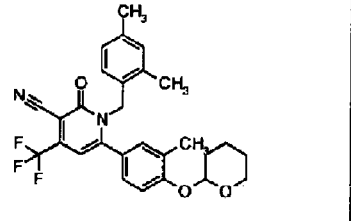 | A1 | A1 | III | B | III | B |
| 277 | 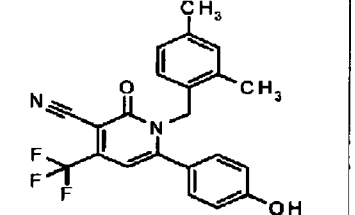 | B1 | A1 | III | B | III | B |
FIG. 1BB

| | | | | | | | |
|---|---|---|---|---|---|---|---|
| 278 | 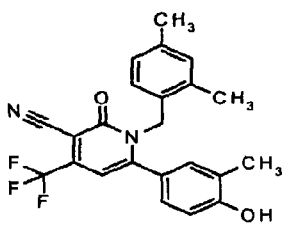 | B1 | B1 | III | B | III | B |
| 279 | 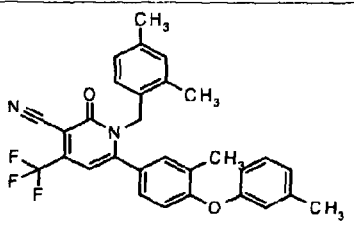 | A1 | A1 | II | B | II | B |
| 280 | 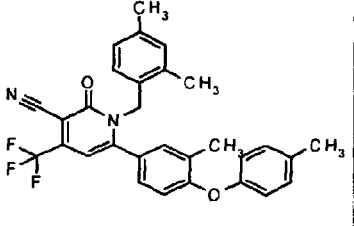 | B1 | B1 | III | B | III | B |
| 281 | 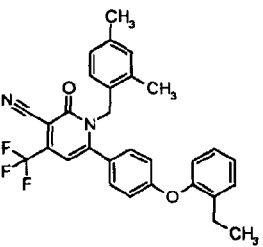 | A1 | A1 | II | B | II | B |
| 282 | 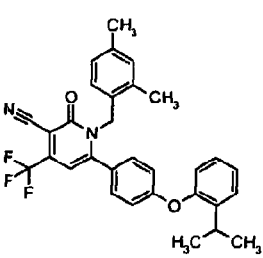 | A1 | A1 | II | B | II | B |
FIG. 1BC

| | | | | | | | |
|---|---|---|---|---|---|---|---|
| 283 | 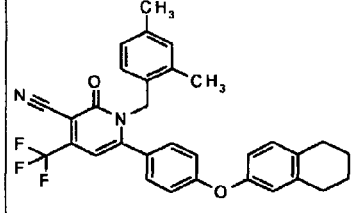 | A1 | A1 | II | B | II | B |
| 284 | 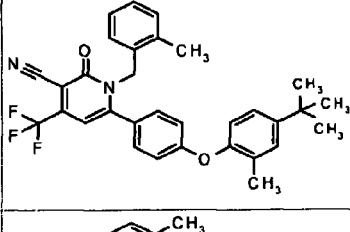 | B1 | B1 | III | B | III | C |
| 285 | 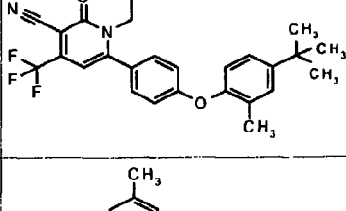 | B1 | B1 | III | B | III | B |
| 286 | 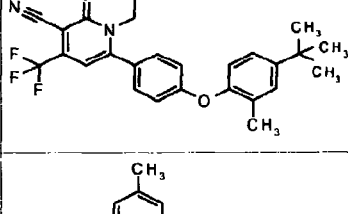 | B1 | A1 | III | B | III | C |
| 287 | 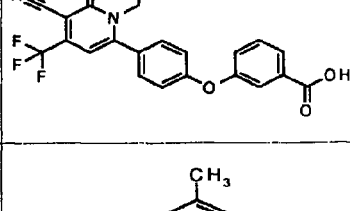 | A1 | A1 | III | B | III | B |
| 288 | 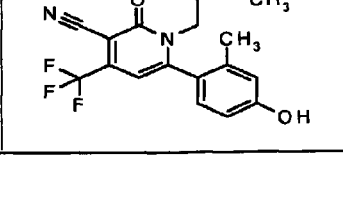 | A1 | A1 | III | B | III | B |
FIG. 1BD

| | | | | | | | |
|---|---|---|---|---|---|---|---|
| 289 | 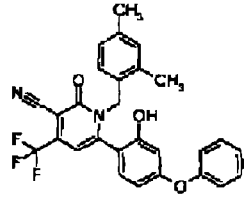 | A1 | B1 | III | B | III | B |
| 290 | 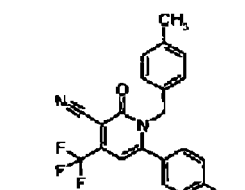 | B1 | B1 | III | B | III | B |
| 291 | 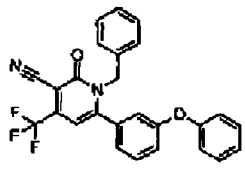 | B1 | A1 | III | B | III | B |
| 292 | 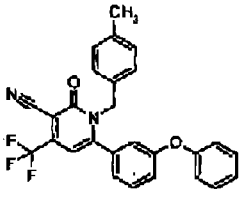 | B1 | A1 | III | B | III | B |
| 293 | 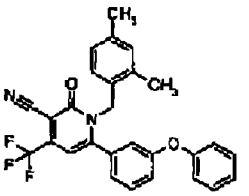 | A1 | A1 | II | B | II | B |
FIG. 1BE

| 294 | 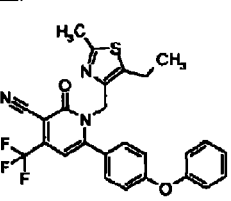 | B1 | B1 | III | B | III | B |
| 295 | 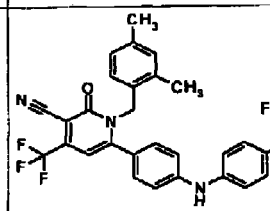 | D1 | C1 | II | B | II | B |
| 296 | 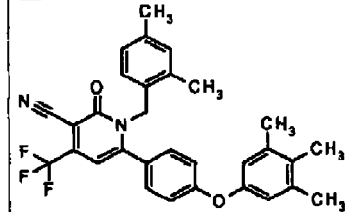 | A1 | A1 | II | B | II | C |
| 297 | 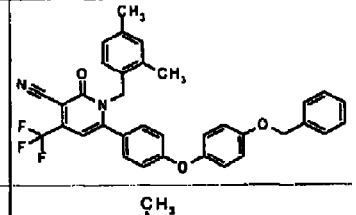 | B1 | B1 | II | C | II | C |
| 298 | 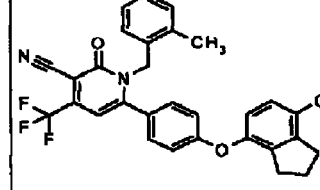 | A1 | A1 | II | B | II | C |
| 299 | 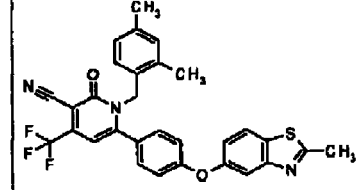 | A1 | B1 | II | B | II | B |
FIG. 1BF

| | | | | | | | |
|---|---|---|---|---|---|---|---|
| 300 | (structure) | B1 | B1 | II | B | II | B |
| 301 | (structure) | A1 | A1 | II | B | II | C |
| 302 | (structure) | B1 | B1 | III | B | III | B |
| 303 | (structure) | A1 | A1 | II | B | II | B |
| 304 | (structure) | D1 | B1 | III | B | III | C |
| 305 | (structure) | B1 | A1 | II | B | II | C |

FIG. 1BG

| # | Structure | | | | | | |
|---|---|---|---|---|---|---|---|
| 306 | (structure) | A1 | A1 | II | B | II | C |
| 307 | (structure) | A1 | A1 | III | B | III | C |
| 308 | (structure) | A1 | A1 | III | B | III | C |
| 309 | (structure) | B1 | A1 | III | B | III | C |
| 310 | (structure) | B1 | B1 | III | B | III | C |
| 311 | (structure) | B1 | A1 | III | B | II | C |

FIG. 1BH

| | | | | | | | |
|---|---|---|---|---|---|---|---|
| 312 | ![structure] | D1 | C1 | II | C | II | D |
| 313 | ![structure] | D1 | C1 | III | B | III | C |
| 314 | ![structure] | B1 | A1 | III | B | II | C |
| 315 | ![structure] | A1 | A1 | II | B | II | C |
| 316 | ![structure] | B1 | B1 | III | B | III | B |

FIG. 1BI

| # | Structure | | | | | | |
|---|---|---|---|---|---|---|---|
| 317 | (structure) | A1 | A1 | II | B | II | C |
| 318 | (structure) | A1 | A1 | II | B | II | C |
| 319 | (structure) | A1 | A1 | II | B | II | C |
| 320 | (structure) | A1 | A1 | II | B | II | C |
| 321 | (structure) | A1 | A1 | II | B | II | D |

FIG. 1BJ

| # | Structure | | | | | | |
|---|---|---|---|---|---|---|---|
| 322 | (structure) | A1 | A1 | III | B | III | C |
| 323 | (structure) | B1 | B1 | II | B | II | C |
| 324 | (structure) | A1 | A1 | II | B | II | D |
| 325 | (structure) | B1 | B1 | III | B | III | C |
| 326 | (structure) | A1 | A1 | II | B | II | C |
| 327 | (structure) | B1 | A1 | II | B | II | D |

FIG. 1BK

| # | Structure | | | | | | |
|---|---|---|---|---|---|---|---|
| 328 | (structure) | A1 | A1 | II | B | II | C |
| 329 | (structure) | A1 | A1 | II | B | II | C |
| 330 | (structure) | A1 | A1 | I | C | I | D |
| 331 | (structure) | A1 | A1 | II | B | II | B |
| 332 | (structure) | B1 | A1 | II | C | II | C |
| 333 | (structure) | A1 | A1 | II | B | II | C |

FIG. 1BL

| # | Structure | | | | | | |
|---|---|---|---|---|---|---|---|
| 335 | 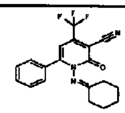 | B1 | B1 | IV | B | IV | NC |
| 336 | 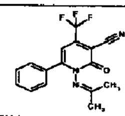 | D1 | D1 | NC | A | NC | NC |
| 337 | 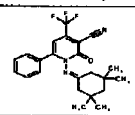 | NC | NC | NC | A | NC | NC |
| 338 | 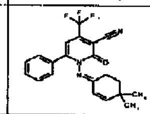 | NC | NC | NC | A | NC | NC |
| 339 | 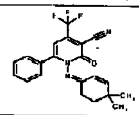 | NC | NC | NC | A | NC | NC |
| 340 | 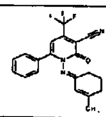 | NC | D1 | NC | A | NC | NC |
| 341 | 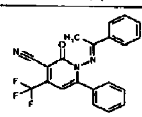 | D1 | D1 | NC | A | NC | NC |
| 342 | 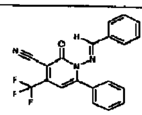 | NC | NC | NC | A | NC | NC |
| 343 | 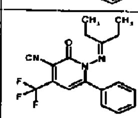 | D1 | D1 | IV | B | NC | NC |
| 344 | 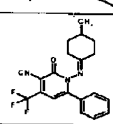 | D1 | D1 | IV | A | NC | NC |
| 345 | 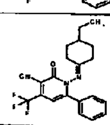 | D1 | D1 | IV | A | NC | NC |
| 346 | 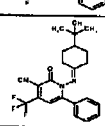 | NC | NC | NC | A | NC | NC |
| 347 | 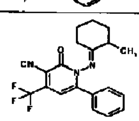 | D1 | B1 | IV | B | NC | NC |
| 348 | 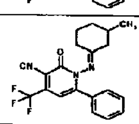 | D1 | D1 | IV | A | NC | NC |

FIG. 1BN

| # | Structure | | | | | | |
|---|---|---|---|---|---|---|---|
| 349 | 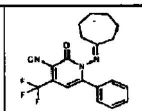 | D1 | B1 | IV | B | NC | NC |
| 350 | 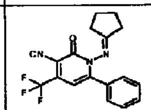 | D1 | D1 | NC | A | NC | NC |
| 351 | 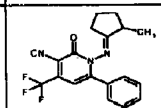 | D1 | C1 | IV | B | NC | NC |
| 352 | 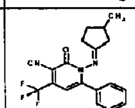 | D1 | D1 | IV | A | NC | NC |
| 353 | 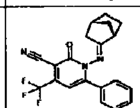 | D1 | D1 | IV | B | NC | NC |
| 354 | 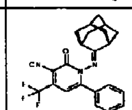 | D1 | D1 | NC | A | NC | NC |
| 355 | 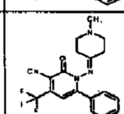 | NC | D1 | NC | A | NC | NC |
| 356 | 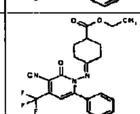 | NC | NC | NC | A | NC | NC |
| 357 | 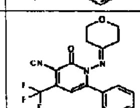 | D1 | D1 | NC | A | NC | NC |
| 358 | 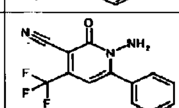 | NC | NC | NC | A | NC | NC |
| 359 | 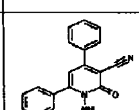 | NC | NC | NC | A | NC | NC |
| 360 | 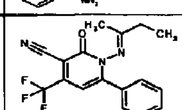 | D1 | D1 | IV | A | NC | NC |
| 361 | 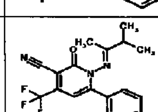 | C1 | B1 | IV | B | NC | NC |
| 362 | 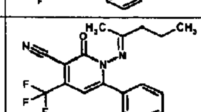 | D1 | D1 | NC | B | NC | NC |

FIG. 1BO

| 363 | 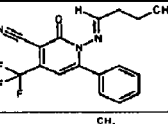 | NC | D1 | NC | A | NC | NC |
| --- | --- | --- | --- | --- | --- | --- | --- |
| 364 | 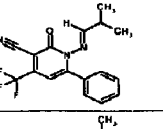 | D1 | D1 | NC | A | NC | NC |
| 365 | 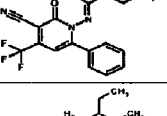 | D1 | D1 | NC | A | NC | NC |
| 366 | 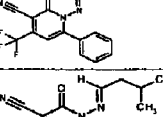 | NC | NC | NC | A | NC | NC |
| 367 | 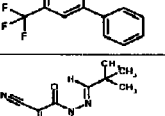 | D1 | D1 | NC | A | NC | NC |
| 368 | 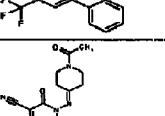 | NC | NC | NC | A | NC | NC |
| 369 | 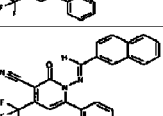 | NC | NC | NC | A | NC | NC |
| 370 | 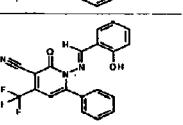 | NC | D1 | NC | A | NC | NC |
| 371 | 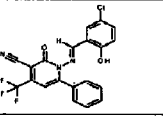 | NC | D1 | NC | A | NC | NC |
| 372 | 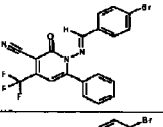 | NC | NC | NC | A | NC | NC |
| 373 | 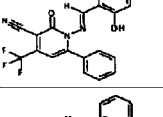 | NC | D1 | NC | A | NC | NC |
| 374 | 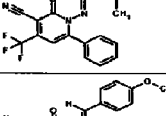 | NC | NC | NC | A | NC | NC |
| 375 | 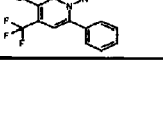 | NC | NC | NC | A | NC | NC |
| 376 |  | NC | NC | NC | A | NC | NC |
FIG. 1BP

| # | Structure | | | | | | |
|---|---|---|---|---|---|---|---|
| 377 | 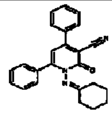 | NC | NC | NC | A | NC | NC |
| 378 | 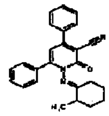 | NC | NC | NC | A | NC | NC |
| 379 | 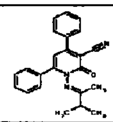 | NC | NC | NC | A | NC | NC |
| 380 | 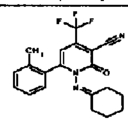 | C1 | D1 | IV | A | NC | NC |
| 381 | 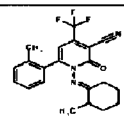 | D1 | C1 | NC | A | NC | NC |
| 382 | 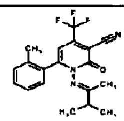 | D1 | D1 | IV | A | NC | NC |
| 383 | 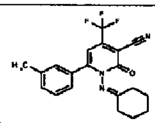 | B1 | B1 | IV | B | NC | NC |
| 384 | 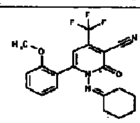 | C1 | D1 | IV | A | NC | NC |
| 385 | 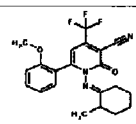 | D1 | D1 | NC | A | NC | NC |
| 386 | 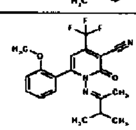 | D1 | D1 | IV | A | NC | NC |
| 387 | 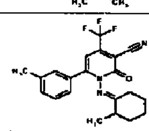 | B1 | B1 | IV | A | NC | NC |
| 388 | 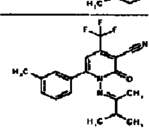 | B1 | B1 | IV | B | NC | NC |
| 389 | 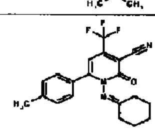 | B1 | B1 | IV | B | NC | NC |
| 390 | 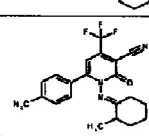 | C1 | B1 | IV | A | NC | NC |

FIG. 1BQ

| # | Structure | | | | | | |
|---|---|---|---|---|---|---|---|
| 391 | 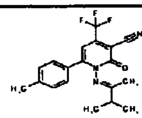 | C1 | C1 | IV | A | NC | NC |
| 392 | 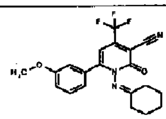 | B1 | B1 | IV | B | NC | NC |
| 393 | 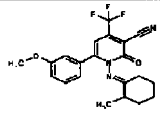 | D1 | B1 | IV | B | III | B |
| 394 | 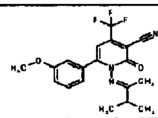 | C1 | B1 | IV | B | NC | NC |
| 395 | 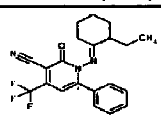 | D1 | D1 | IV | A | NC | NC |
| 396 | 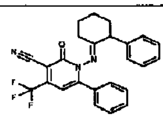 | NC | NC | NC | A | NC | NC |
| 397 | 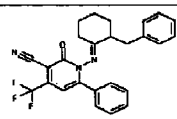 | NC | NC | NC | A | NC | NC |
| 398 | 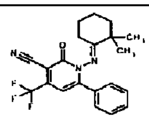 | D1 | C1 | IV | A | IV | NC |
| 399 | 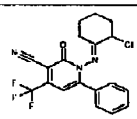 | C1 | B1 | III | B | IV | NC |
| 400 | 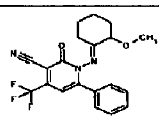 | NC | NC | NC | A | NC | A |
| 401 | 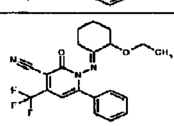 | NC | NC | NC | A | NC | NC |
| 402 | 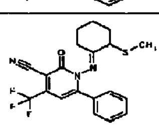 | NC | D1 | IV | A | NC | NC |
| 403 | 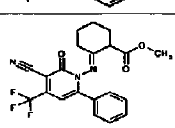 | NC | NC | NC | A | NC | NC |
| 404 | 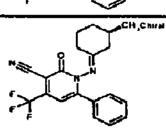 | NC | D1 | IV | A | NC | NC |

FIG. 1BR

| # | Structure | | | | | | |
|---|---|---|---|---|---|---|---|
| 405 | 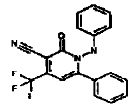 | NC | D1 | NC | A | NC | NC |
| 406 | 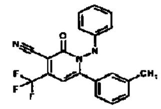 | NC | D1 | IV | A | NC | NC |
| 407 | 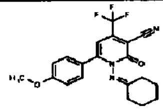 | D1 | C1 | IV | C | IV | NC |
| 408 | 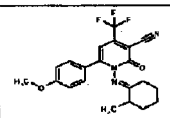 | D1 | C1 | IV | B | IV | NC |
| 409 | 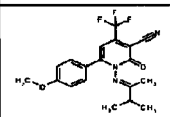 | D1 | D1 | IV | B | IV | NC |
| 410 | 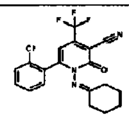 | B1 | B1 | III | B | IV | NC |
| 411 | 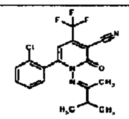 | B1 | B1 | III | B | IV | NC |
| 412 | 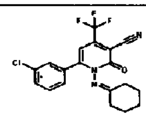 | C1 | B1 | III | B | IV | NC |
| 413 | 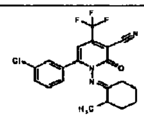 | C1 | B1 | III | A | IV | NC |
| 414 | 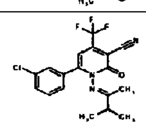 | C1 | B1 | IV | B | IV | NC |
| 415 | 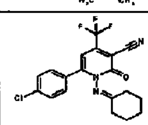 | C1 | C1 | IV | B | IV | NC |
| 416 | 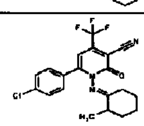 | NC | D1 | IV | A | IV | NC |
| 417 | 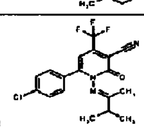 | D1 | D1 | IV | B | IV | NC |
| 418 | 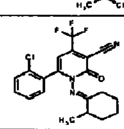 | C1 | B1 | IV | A | IV | B |

FIG. 1BS

| # | Structure | | | | | | |
|---|---|---|---|---|---|---|---|
| 419 | 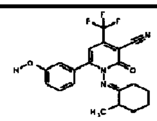 | D1 | C1 | IV | A | IV | B |
| 420 | 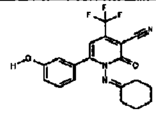 | D1 | C1 | IV | A | IV | B |
| 421 | 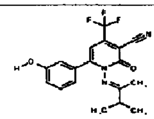 | D1 | D1 | IV | A | NC | NC |
| 422 | 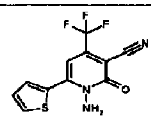 | NC | NC | NC | A | NC | NC |
| 423 | 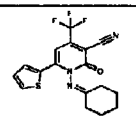 | D1 | D1 | IV | A | NC | NC |
| 424 | 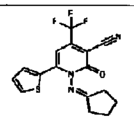 | NC | NC | NC | A | NC | NC |
| 425 | 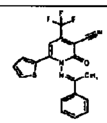 | NC | NC | NC | A | NC | NC |
| 426 | 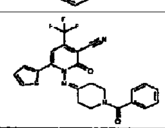 | NC | NC | NC | A | NC | NC |
| 427 | 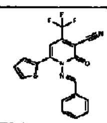 | NC | NC | III | A | NC | NC |
| 428 | 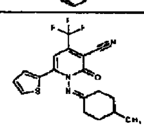 | D1 | D1 | NC | A | NC | NC |
| 429 | 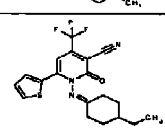 | D1 | D1 | NC | A | NC | NC |
| 430 | 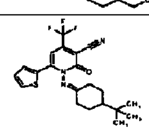 | NC | NC | NC | NC | NC | NC |
| 431 | 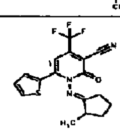 | D1 | D1 | NC | NC | NC | NC |
| 432 | 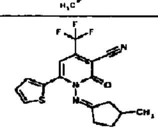 | NC | NC | NC | NC | NC | NC |

FIG. 1BT

| | | | | | | | |
|---|---|---|---|---|---|---|---|
| 433 |  | D1 | D1 | III | A | NC | NC |
| 434 |  | B1 | B1 | IV | B | IV | B |
| 435 |  | D1 | C1 | IV | A | NC | NC |
| 436 |  | B1 | A1 | IV | B | III | B |
| 437 |  | B1 | A1 | III | A | III | B |
| 438 |  | B1 | A1 | III | C | III | B |
| 439 |  | B1 | B1 | IV | B | III | B |
| 440 |  | B1 | B1 | III | B | III | B |
| 441 |  | B1 | A1 | III | B | III | B |
| 442 |  | B1 | B1 | III | B | III | B |
| 443 |  | B1 | A1 | III | C | III | B |
| 444 |  | B1 | B1 | IV | B | IV | A |
| 445 |  | NC | D1 | NC | A | NC | NC |
| 446 |  | D1 | B1 | IV | A | NC | NC |
FIG. 1BU

| # | Structure | | | | | | |
|---|---|---|---|---|---|---|---|
| 447 | 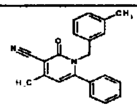 | D1 | D1 | NC | NC | NC | A |
| 448 | 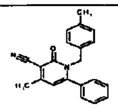 | D1 | B1 | IV | B | NC | NC |
| 449 | 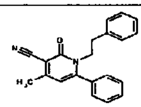 | D1 | D1 | NC | NC | NC | A |
| 450 | 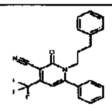 | D1 | C1 | IV | B | IV | B |
| 451 | 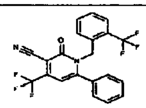 | B1 | B1 | IV | B | IV | B |
| 452 | 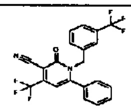 | C1 | B1 | IV | B | IV | B |
| 453 | 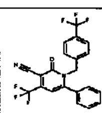 | D1 | C1 | IV | A | IV | B |
| 454 | 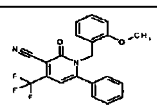 | B1 | B1 | IV | B | IV | B |
| 455 | 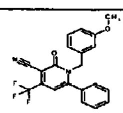 | B1 | B1 | IV | B | IV | B |
| 456 | 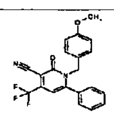 | B1 | B1 | IV | B | IV | B |
| 457 | 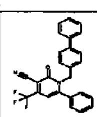 | NC | NC | NC | A | NC | A |
| 458 | 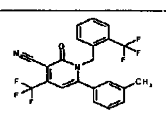 | B1 | B1 | III | B | III | B |
| 459 | 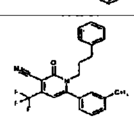 | D1 | D1 | IV | A | IV | A |

FIG. 1BV

| 460 | | C1 | B1 | III | B | III | B |
|---|---|---|---|---|---|---|---|
| 461 | | D1 | D1 | IV | A | IV | B |
| 462 | | B1 | B1 | III | B | IV | B |
| 463 | | B1 | B1 | III | B | III | B |
| 464 | | B1 | B1 | III | B | III | C |
| 465 | | D1 | NC | NC | A | IV | A |
| 466 | | B1 | B1 | IV | B | III | B |
| 467 | | B1 | B1 | III | B | III | B |
| 468 | | B1 | A1 | III | B | III | B |
| 469 | | D1 | C1 | IV | A | IV | B |
| 470 | | D1 | C1 | IV | A | IV | B |
| 471 | | D1 | B1 | IV | B | IV | B |
| 472 | | B1 | B1 | IV | B | IV | B |

FIG. 1BW

| # | Structure | | | | | | |
|---|---|---|---|---|---|---|---|
| 473 | 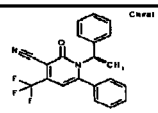 | D1 | C1 | IV | A | IV | B |
| 474 | 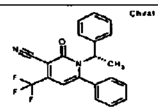 | D1 | C1 | IV | B | IV | B |
| 475 | 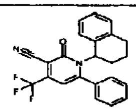 | D1 | C1 | IV | A | IV | B |
| 476 | 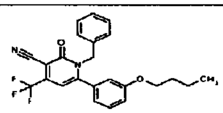 | D1 | C1 | IV | A | III | A |
| 477 | 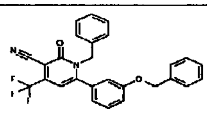 | B1 | B1 | III | A | III | B |
| 478 | 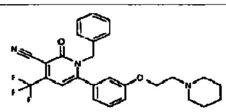 | NC | D1 | NC | A | NC | A |
| 479 | 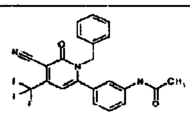 | D1 | B1 | IV | B | IV | C |
| 480 | 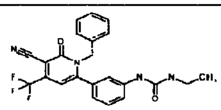 | D1 | D1 | NC | A | IV | B |
| 481 | 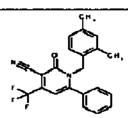 | B1 | A1 | III | C | III | B |
| 482 | 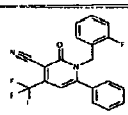 | B1 | A1 | III | B | III | B |
| 483 | 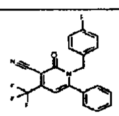 | B1 | B1 | IV | C | III | B |
| 484 | 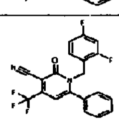 | B1 | A1 | III | B | III | B |
| 485 | 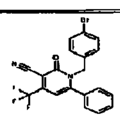 | B1 | B1 | III | B | III | B |

FIG. 1BX

| # | Structure | | | | | | |
|---|---|---|---|---|---|---|---|
| 486 | 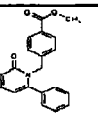 | C1 | B1 | IV | B | IV | B |
| 487 | 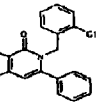 | B1 | B1 | III | C | III | C |
| 488 | 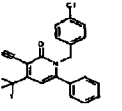 | B1 | A1 | III | B | III | B |
| 489 | 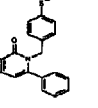 | C1 | B1 | IV | B | III | B |
| 490 | 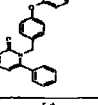 | NC | D1 | NC | A | NC | A |
| 491 | 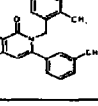 | A1 | A1 | III | C | II | B |
| 492 | 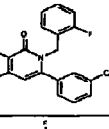 | B1 | A1 | III | B | III | B |
| 493 | 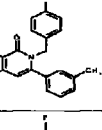 | B1 | A1 | III | B | III | B |
| 494 | 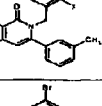 | B1 | A1 | III | B | III | B |
| 495 | 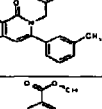 | B1 | B1 | III | C | III | B |
| 496 | 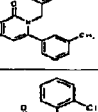 | B1 | B1 | III | C | III | B |
| 497 | 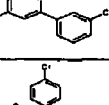 | B1 | A1 | III | B | III | B |
| 498 | 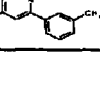 | B1 | A1 | III | C | III | B |
FIG. 1BY

| # | Structure | | | | | | |
|---|---|---|---|---|---|---|---|
| 499 | 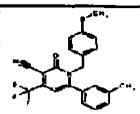 | B1 | B1 | III | B | III | B |
| 500 | 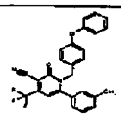 | NC | NC | NC | A | NC | A |
| 501 | 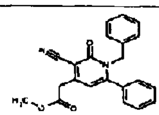 | NC | NC | NC | A | NC | A |
| 502 | 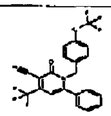 | D1 | D1 | IV | A | III | A |
| 503 | 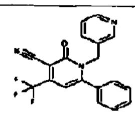 | NC | D1 | IV | A | IV | B |
| 504 | 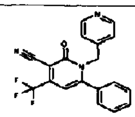 | NC | NC | NC | A | NC | A |
| 505 | 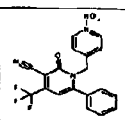 | B1 | A1 | III | B | III | C |
| 506 | 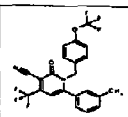 | D1 | D1 | IV | A | III | B |
| 507 | 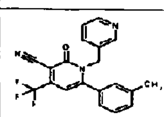 | D1 | D1 | III | B | III | B |
| 508 | 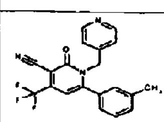 | NC | NC | NC | A | NC | A |

FIG. 1BZ

SEQUENCE LISTING

```
<160> NUMBER OF SEQ ID NOS: 18

<210> SEQ ID NO 1
<211> LENGTH: 1528
<212> TYPE: DNA
<213> ORGANISM: Homo Sapien
<220> FEATURE:
<221> NAME/KEY: CDS
<222> LOCATION: (36)...(1379)
<300> PUBLICATION INFORMATION:
<308> DATABASE ACCESSION NUMBER: GeneBank Nm_005693
<309> DATABASE ENTRY DATE: 2002-05-14

<400> SEQUENCE: 1
cagtgccttg gtaatgacca gggctccaga aagag atg tcc ttg tgg ctg ggg         53
                                      Met Ser Leu Trp Leu Gly
                                       1               5 gcc cct gtg cct gac att cct cct gac tct gcg gtg gag ctg tgg aag      101
Ala Pro Val Pro Asp Ile Pro Pro Asp Ser Ala Val Glu Leu Trp Lys
         10                  15                  20 cca ggc gca cag gat gca agc agc cag gcc cag gga ggc agc agc tgc      149
```

```
Pro Gly Ala Gln Asp Ala Ser Ser Gln Ala Gln Gly Gly Ser Ser Cys
         25                  30                  35 atc ctc aga gag gaa gcc agg atg ccc cac tct gct ggg ggt act gca      197
Ile Leu Arg Glu Glu Ala Arg Met Pro His Ser Ala Gly Gly Thr Ala
         40                  45                  50 ggg gtg ggg ctg gag gct gca gag ccc aca gcc ctg ctc acc agg gca      245
Gly Val Gly Leu Glu Ala Ala Glu Pro Thr Ala Leu Leu Thr Arg Ala
 55                  60                  65                  70 gag ccc cct tca gaa ccc aca gag atc cgt cca caa aag cgg aaa aag      293
Glu Pro Pro Ser Glu Pro Thr Glu Ile Arg Pro Gln Lys Arg Lys Lys
                 75                  80                  85 ggg cca gcc ccc aaa atg ctg ggg aac gag cta tgc agc gtg tgt ggg      341
Gly Pro Ala Pro Lys Met Leu Gly Asn Glu Leu Cys Ser Val Cys Gly
                 90                  95                 100 gac aag gcc tcg ggc ttc cac tac aat gtt ctg agc tgc gag ggc tgc      389
Asp Lys Ala Ser Gly Phe His Tyr Asn Val Leu Ser Cys Glu Gly Cys
             105                 110                 115 aag gga ttc ttc cgc cgc agc gtc atc aag gga gcg cac tac atc tgc      437
Lys Gly Phe Phe Arg Arg Ser Val Ile Lys Gly Ala His Tyr Ile Cys
    120                 125                 130 cac agt ggc ggc cac tgc ccc atg gac acc tac atg cgt cgc aag tgc      485
His Ser Gly Gly His Cys Pro Met Asp Thr Tyr Met Arg Arg Lys Cys
135                 140                 145                 150 cag gag tgt cgg ctt cgc aaa tgc cgt cag gct ggc atg cgg gag gag      533
Gln Glu Cys Arg Leu Arg Lys Cys Arg Gln Ala Gly Met Arg Glu Glu
                155                 160                 165 tgt gtc ctg tca gaa gaa cag atc cgc ctg aag aaa ctg aag cgg caa      581
Cys Val Leu Ser Glu Glu Gln Ile Arg Leu Lys Lys Leu Lys Arg Gln
            170                 175                 180 gag gag gaa cag gct cat gcc aca tcc ttg ccc ccc agg cgt tcc tca      629
Glu Glu Glu Gln Ala His Ala Thr Ser Leu Pro Pro Arg Arg Ser Ser
        185                 190                 195 ccc ccc caa atc ctg ccc cag ctc agc ccg gaa caa ctg ggc atg atc      677
Pro Pro Gln Ile Leu Pro Gln Leu Ser Pro Glu Gln Leu Gly Met Ile
    200                 205                 210 gag aag ctc gtc gct gcc cag caa cag tgt aac cgg cgc tcc ttt tct      725
Glu Lys Leu Val Ala Ala Gln Gln Gln Cys Asn Arg Arg Ser Phe Ser
215                 220                 225                 230 gac cgg ctt cga gtc acg cct tgg ccc atg gca cca gat ccc cat agc      773
Asp Arg Leu Arg Val Thr Pro Trp Pro Met Ala Pro Asp Pro His Ser
                235                 240                 245 cgg gag gcc cgt cag cag cgc ttt gcc cac ttc act gag ctg gcc atc      821
Arg Glu Ala Arg Gln Gln Arg Phe Ala His Phe Thr Glu Leu Ala Ile
            250                 255                 260 gtc tct gtg cag gag ata gtt gac ttt gct aaa cag cta ccc ggc ttc      869
Val Ser Val Gln Glu Ile Val Asp Phe Ala Lys Gln Leu Pro Gly Phe
        265                 270                 275 ctg cag ctc agc cgg gag gac cag att gcc ctg ctg aag acc tct gcg      917
Leu Gln Leu Ser Arg Glu Asp Gln Ile Ala Leu Leu Lys Thr Ser Ala
    280                 285                 290 atc gag gtg atg ctt ctg gag aca tct cgg agg tac aac cct ggg agt      965
Ile Glu Val Met Leu Leu Glu Thr Ser Arg Arg Tyr Asn Pro Gly Ser
295                 300                 305                 310 gag agt atc acc ttc ctc aag gat ttc agt tat aac cgg gaa gac ttt     1013
Glu Ser Ile Thr Phe Leu Lys Asp Phe Ser Tyr Asn Arg Glu Asp Phe
                315                 320                 325 gcc aaa gca ggg ctg caa gtg gaa ttc atc aac ccc atc ttc gag ttc     1061
Ala Lys Ala Gly Leu Gln Val Glu Phe Ile Asn Pro Ile Phe Glu Phe
            330                 335                 340 tcc agg gcc atg aat gag ctg caa ctc aat gat gcc gag ttt gcc ttg     1109
```

```
Ser Arg Ala Met Asn Glu Leu Gln Leu Asn Asp Ala Glu Phe Ala Leu
        345                 350                 355 ctc att gct atc agc atc ttc tct gca gac cgg ccc aac gtg cag gac    1157
Leu Ile Ala Ile Ser Ile Phe Ser Ala Asp Arg Pro Asn Val Gln Asp
    360                 365                 370 cag ctc cag gtg gag agg ctg cag cac aca tat gtg gaa gcc ctg cat    1205
Gln Leu Gln Val Glu Arg Leu Gln His Thr Tyr Val Glu Ala Leu His
375                 380                 385                 390 gcc tac gtc tcc atc cac cat ccc cat gac cga ctg atg ttc cca cgg    1253
Ala Tyr Val Ser Ile His His Pro His Asp Arg Leu Met Phe Pro Arg
                395                 400                 405 atg cta atg aaa ctg gtg agc ctc cgg acc ctg agc agc gtc cac tca    1301
Met Leu Met Lys Leu Val Ser Leu Arg Thr Leu Ser Ser Val His Ser
            410                 415                 420 gag caa gtg ttt gca ctc cgt ctg cag gac aaa aag ctc cca ccg ctg    1349
Glu Gln Val Phe Ala Leu Arg Leu Gln Asp Lys Lys Leu Pro Pro Leu
        425                 430                 435 ctc tct gag atc tgg gat gtg cac gaa tga ctgttctgtc cccatatttt      1399
Leu Ser Glu Ile Trp Asp Val His Glu *
    440                 445 ctgttttctt ggccggatgg ctgaggcctg gtggctgcct cctagaagtg gaacagactg   1459
agaagggcaa acattcctgg gagctgggca aggagatcct cccgtggcat taaagagag    1519 tcaaagggt                                                          1528

<210> SEQ ID NO 2
<211> LENGTH: 447
<212> TYPE: PRT
<213> ORGANISM: Homo Sapien

<400> SEQUENCE: 2

Met Ser Leu Trp Leu Gly Ala Pro Val Pro Asp Ile Pro Pro Asp Ser
1               5                   10                  15

Ala Val Glu Leu Trp Lys Pro Gly Ala Gln Asp Ala Ser Ser Gln Ala
            20                  25                  30

Gln Gly Gly Ser Ser Cys Ile Leu Arg Glu Glu Ala Arg Met Pro His
        35                  40                  45

Ser Ala Gly Gly Thr Ala Gly Val Gly Leu Glu Ala Ala Glu Pro Thr
    50                  55                  60

Ala Leu Leu Thr Arg Ala Glu Pro Pro Ser Glu Pro Thr Glu Ile Arg
65                  70                  75                  80

Pro Gln Lys Arg Lys Lys Gly Pro Ala Pro Lys Met Leu Gly Asn Glu
                85                  90                  95

Leu Cys Ser Val Cys Gly Asp Lys Ala Ser Gly Phe His Tyr Asn Val
            100                 105                 110

Leu Ser Cys Glu Gly Cys Lys Gly Phe Phe Arg Arg Ser Val Ile Lys
        115                 120                 125

Gly Ala His Tyr Ile Cys His Ser Gly Gly His Cys Pro Met Asp Thr
    130                 135                 140

Tyr Met Arg Arg Lys Cys Gln Glu Cys Arg Leu Arg Lys Cys Arg Gln
145                 150                 155                 160

Ala Gly Met Arg Glu Glu Cys Val Leu Ser Glu Glu Gln Ile Arg Leu
                165                 170                 175

Lys Lys Leu Lys Arg Gln Glu Glu Glu Gln Ala His Ala Thr Ser Leu
            180                 185                 190

Pro Pro Arg Arg Ser Ser Pro Pro Gln Ile Leu Pro Gln Leu Ser Pro
        195                 200                 205
```

```
Glu Gln Leu Gly Met Ile Glu Lys Leu Val Ala Ala Gln Gln Gln Cys
    210                 215                 220

Asn Arg Arg Ser Phe Ser Asp Arg Leu Arg Val Thr Pro Trp Pro Met
225                 230                 235                 240

Ala Pro Asp Pro His Ser Arg Glu Ala Arg Gln Gln Arg Phe Ala His
                245                 250                 255

Phe Thr Glu Leu Ala Ile Val Ser Val Gln Glu Ile Val Asp Phe Ala
            260                 265                 270

Lys Gln Leu Pro Gly Phe Leu Gln Leu Ser Arg Glu Asp Gln Ile Ala
        275                 280                 285

Leu Leu Lys Thr Ser Ala Ile Glu Val Met Leu Leu Glu Thr Ser Arg
    290                 295                 300

Arg Tyr Asn Pro Gly Ser Glu Ser Ile Thr Phe Leu Lys Asp Phe Ser
305                 310                 315                 320

Tyr Asn Arg Glu Asp Phe Ala Lys Ala Gly Leu Gln Val Glu Phe Ile
                325                 330                 335

Asn Pro Ile Phe Glu Phe Ser Arg Ala Met Asn Glu Leu Gln Leu Asn
            340                 345                 350

Asp Ala Glu Phe Ala Leu Leu Ile Ala Ile Ser Ile Phe Ser Ala Asp
        355                 360                 365

Arg Pro Asn Val Gln Asp Gln Leu Gln Val Glu Arg Leu Gln His Thr
    370                 375                 380

Tyr Val Glu Ala Leu His Ala Tyr Val Ser Ile His His Pro His Asp
385                 390                 395                 400

Arg Leu Met Phe Pro Arg Met Leu Met Lys Leu Val Ser Leu Arg Thr
                405                 410                 415

Leu Ser Ser Val His Ser Glu Gln Val Phe Ala Leu Arg Leu Gln Asp
            420                 425                 430

Lys Lys Leu Pro Pro Leu Leu Ser Glu Ile Trp Asp Val His Glu
        435                 440                 445

<210> SEQ ID NO 3
<211> LENGTH: 1815
<212> TYPE: DNA
<213> ORGANISM: Homo Sapien
<220> FEATURE:
<221> NAME/KEY: CDS
<222> LOCATION: (56)...(1438)
<300> PUBLICATION INFORMATION:
<308> DATABASE ACCESSION NUMBER: GeneBank XM_046419
<309> DATABASE ENTRY DATE: 2002-08-01

<400> SEQUENCE: 3
cgctgttgct tggagagggg cgggacctgg agagaggctg ctccgtgacc ccacc atg      58
                                                              Met
                                                              1 tcc tct cct acc acg agt tcc ctg gat acc ccc ctg cct gga aat ggc     106
Ser Ser Pro Thr Thr Ser Ser Leu Asp Thr Pro Leu Pro Gly Asn Gly
        5                   10                  15 ccc cct cag cct ggc gcc cct tct tct tca ccc act gta aag gag gag     154
Pro Pro Gln Pro Gly Ala Pro Ser Ser Ser Pro Thr Val Lys Glu Glu
    20                  25                  30 ggt ccg gag ccg tgg ccc ggg gtt ccg gac cct gat gtc cca ggc act     202
Gly Pro Glu Pro Trp Pro Gly Gly Pro Asp Pro Asp Val Pro Gly Thr
35                  40                  45 gat gag gcc agc tca gcc tgc agc aca gac tgg gtc atc cca gat ccc     250
Asp Glu Ala Ser Ser Ala Cys Ser Thr Asp Trp Val Ile Pro Asp Pro
50                  55                  60                  65 gaa gag gaa cca gag cgc aag cga aag aag ggc cca gcc ccg aag atg     298
```

-continued

```
              Glu Glu Glu Pro Glu Arg Lys Arg Lys Lys Gly Pro Ala Pro Lys Met
                              70                  75                  80 ctg ggc cac gag ctt tgc cgt gtc tgt ggg gac aag gcc tcc ggc ttc          346
Leu Gly His Glu Leu Cys Arg Val Cys Gly Asp Lys Ala Ser Gly Phe
            85                  90                  95 cac tac aac gtg ctc agc tgc gaa ggc tgc aag ggc ttc ttc cgg cgc          394
His Tyr Asn Val Leu Ser Cys Glu Gly Cys Lys Gly Phe Phe Arg Arg
            100                 105                 110 agt gtg gtc cgt ggt ggg gcc agg cgc tat gcc tgc cgg ggt ggc gga          442
Ser Val Val Arg Gly Gly Ala Arg Arg Tyr Ala Cys Arg Gly Gly Gly
        115                 120                 125 acc tgc cag atg gac gct ttc atg cgg cgc aag tgc cag cag tgc cgg          490
Thr Cys Gln Met Asp Ala Phe Met Arg Arg Lys Cys Gln Gln Cys Arg
130                 135                 140                 145 ctg cgc aag tgc aag gag gca ggg atg agg gag cag tgc gtc ctt tct          538
Leu Arg Lys Cys Lys Glu Ala Gly Met Arg Glu Gln Cys Val Leu Ser
                150                 155                 160 gaa gaa cag atc cgg aag aag aag att cgg aaa cag cag cag gag tca          586
Glu Glu Gln Ile Arg Lys Lys Lys Ile Arg Lys Gln Gln Gln Glu Ser
                165                 170                 175 cag tca cag tcg cag tca cct gtg ggg ccg cag ggc agc agc agc tca          634
Gln Ser Gln Ser Gln Ser Pro Val Gly Pro Gln Gly Ser Ser Ser Ser
                180                 185                 190 gcc tct ggg cct ggg gct tcc cct ggt gga tct gag gca ggc agc cag          682
Ala Ser Gly Pro Gly Ala Ser Pro Gly Gly Ser Glu Ala Gly Ser Gln
    195                 200                 205 ggc tcc ggg gaa ggc gag ggt gtc cag cta aca gcg gct caa gaa cta          730
Gly Ser Gly Glu Gly Glu Gly Val Gln Leu Thr Ala Ala Gln Glu Leu
210                 215                 220                 225 atg atc cag cag ttg gtg gcg gcc caa ctg cag tgc aac aaa cgc tcc          778
Met Ile Gln Gln Leu Val Ala Ala Gln Leu Gln Cys Asn Lys Arg Ser
                230                 235                 240 ttc tcc gac cag ccc aaa gtc acg ccc tgg ccc ctg ggc gca gac ccc          826
Phe Ser Asp Gln Pro Lys Val Thr Pro Trp Pro Leu Gly Ala Asp Pro
                245                 250                 255 cag tcc cga gat gcc cgc cag caa cgc ttt gcc cac ttc acg gag ctg          874
Gln Ser Arg Asp Ala Arg Gln Gln Arg Phe Ala His Phe Thr Glu Leu
                260                 265                 270 gcc atc atc tca gtc cag gag atc gtg gac ttc gct aag caa gtg cct          922
Ala Ile Ile Ser Val Gln Glu Ile Val Asp Phe Ala Lys Gln Val Pro
275                 280                 285 ggt ttc ctg cag ctg ggc cgg gag gac cag atc gcc ctc ctg aag gca          970
Gly Phe Leu Gln Leu Gly Arg Glu Asp Gln Ile Ala Leu Leu Lys Ala
290                 295                 300                 305 tcc act atc gag atc atg ctg cta gag aca gcc agg cgc tac aac cac         1018
Ser Thr Ile Glu Ile Met Leu Leu Glu Thr Ala Arg Arg Tyr Asn His
                310                 315                 320 gag aca gag tgt atc acc ttc ttg aag gac ttc acc tac agc aag gac         1066
Glu Thr Glu Cys Ile Thr Phe Leu Lys Asp Phe Thr Tyr Ser Lys Asp
            325                 330                 335 gac ttc cac cgt gca ggc ctg cag gtg gag ttc atc aac ccc atc ttc         1114
Asp Phe His Arg Ala Gly Leu Gln Val Glu Phe Ile Asn Pro Ile Phe
            340                 345                 350 gag ttc tcg cgg gcc atg cgg cgg ctg ggc ctg gac gac gct gag tac         1162
Glu Phe Ser Arg Ala Met Arg Arg Leu Gly Leu Asp Asp Ala Glu Tyr
    355                 360                 365 gcc ctc ctc atc gcc atc aac atc ttc tcg gcc gac cgg ccc aac gtg         1210
Ala Leu Leu Ile Ala Ile Asn Ile Phe Ser Ala Asp Arg Pro Asn Val
370                 375                 380                 385 cag gag ccg ggc cgc gtg gag gcg ttg cag cag ccc tac gtg gag gcg         1258
```

-continued

```
Gln Glu Pro Gly Arg Val Glu Ala Leu Gln Gln Pro Tyr Val Glu Ala
            390                 395                 400 ctg ctg tcc tac acg cgc atc aag agg ccg cag gac cag ctg cgc ttc    1306
Leu Leu Ser Tyr Thr Arg Ile Lys Arg Pro Gln Asp Gln Leu Arg Phe
            405                 410                 415 ccg cgc atg ctc atg aag ctg gtg agc ctg cgc acg ctg agc tct gtg    1354
Pro Arg Met Leu Met Lys Leu Val Ser Leu Arg Thr Leu Ser Ser Val
            420                 425                 430 cac tcg gag cag gtc ttc gcc ttg cgg ctc cag gac aag aag ctg ccg    1402
His Ser Glu Gln Val Phe Ala Leu Arg Leu Gln Asp Lys Lys Leu Pro
            435                 440                 445 cct ctg ctg tcg gag atc tgg gac gtc cac gag tga ggggctggcc         1448
Pro Leu Leu Ser Glu Ile Trp Asp Val His Glu *
450                 455                 460 acccagcccc acagccttgc ctgaccaccc tccagcagat agacgccggc acccttcct   1508 cttcctaggg tggaaggggc cctgggccga gcctgtagac ctatcggctc tcatcccttg   1568
ggataagccc cagtccaggt ccaggaggct ccctccctgc ccagcgagtc ttccagaagg   1628
ggtgaaaggg ttgcaggtcc cgaccactga cccttcccgg ctgccctccc tccccagctt   1688
acacctcaag cccagcacgc agtgcacctt gaacagaggg aggggaggac ccatggctct   1748
cccccctagc ccgggagacc agggccttcc tcttcctctg cttttattta ataaaaacta   1808
aaaacag                                                             1815

<210> SEQ ID NO 4
<211> LENGTH: 460
<212> TYPE: PRT
<213> ORGANISM: Homo Sapien

<400> SEQUENCE: 4

Met Ser Ser Pro Thr Thr Ser Ser Leu Asp Thr Pro Leu Pro Gly Asn
 1               5                  10                  15

Gly Pro Pro Gln Pro Gly Ala Pro Ser Ser Ser Pro Thr Val Lys Glu
            20                  25                  30

Glu Gly Pro Glu Pro Trp Pro Gly Gly Pro Asp Pro Asp Val Pro Gly
        35                  40                  45

Thr Asp Glu Ala Ser Ser Ala Cys Ser Thr Asp Trp Val Ile Pro Asp
    50                  55                  60

Pro Glu Glu Glu Pro Glu Arg Lys Arg Lys Lys Gly Pro Ala Pro Lys
65                  70                  75                  80

Met Leu Gly His Glu Leu Cys Arg Val Cys Gly Asp Lys Ala Ser Gly
                85                  90                  95

Phe His Tyr Asn Val Leu Ser Cys Glu Gly Cys Lys Gly Phe Phe Arg
            100                 105                 110

Arg Ser Val Val Arg Gly Gly Ala Arg Arg Tyr Ala Cys Arg Gly Gly
        115                 120                 125

Gly Thr Cys Gln Met Asp Ala Phe Met Arg Arg Lys Cys Gln Gln Cys
    130                 135                 140

Arg Leu Arg Lys Cys Lys Glu Ala Gly Met Arg Glu Gln Cys Val Leu
145                 150                 155                 160

Ser Glu Glu Gln Ile Arg Lys Lys Lys Ile Arg Lys Gln Gln Gln Glu
                165                 170                 175

Ser Gln Ser Gln Ser Gln Ser Pro Val Gly Pro Gln Gly Ser Ser Ser
            180                 185                 190

Ser Ala Ser Gly Pro Gly Ala Ser Pro Gly Gly Ser Glu Ala Gly Ser
        195                 200                 205
```

```
Gln Gly Ser Gly Glu Gly Glu Gly Val Gln Leu Thr Ala Ala Gln Glu
    210                 215                 220
Leu Met Ile Gln Gln Leu Val Ala Ala Gln Leu Gln Cys Asn Lys Arg
225                 230                 235                 240
Ser Phe Ser Asp Gln Pro Lys Val Thr Pro Trp Pro Leu Gly Ala Asp
                245                 250                 255
Pro Gln Ser Arg Asp Ala Arg Gln Gln Arg Phe Ala His Phe Thr Glu
            260                 265                 270
Leu Ala Ile Ile Ser Val Gln Glu Ile Val Asp Phe Ala Lys Gln Val
        275                 280                 285
Pro Gly Phe Leu Gln Leu Gly Arg Glu Asp Gln Ile Ala Leu Leu Lys
    290                 295                 300
Ala Ser Thr Ile Glu Ile Met Leu Leu Glu Thr Ala Arg Arg Tyr Asn
305                 310                 315                 320
His Glu Thr Glu Cys Ile Thr Phe Leu Lys Asp Phe Thr Tyr Ser Lys
                325                 330                 335
Asp Asp Phe His Arg Ala Gly Leu Gln Val Glu Phe Ile Asn Pro Ile
            340                 345                 350
Phe Glu Phe Ser Arg Ala Met Arg Arg Leu Gly Leu Asp Asp Ala Glu
        355                 360                 365
Tyr Ala Leu Leu Ile Ala Ile Asn Ile Phe Ser Ala Asp Arg Pro Asn
    370                 375                 380
Val Gln Glu Pro Gly Arg Val Glu Ala Leu Gln Gln Pro Tyr Val Glu
385                 390                 395                 400
Ala Leu Leu Ser Tyr Thr Arg Ile Lys Arg Pro Gln Asp Gln Leu Arg
                405                 410                 415
Phe Pro Arg Met Leu Met Lys Leu Val Ser Leu Arg Thr Leu Ser Ser
            420                 425                 430
Val His Ser Glu Gln Val Phe Ala Leu Arg Leu Gln Asp Lys Lys Leu
        435                 440                 445
Pro Pro Leu Leu Ser Glu Ile Trp Asp Val His Glu
    450                 455                 460

<210> SEQ ID NO 5
<211> LENGTH: 2070
<212> TYPE: DNA
<213> ORGANISM: Rattus norvegicus
<220> FEATURE:
<221> NAME/KEY: CDS
<222> LOCATION: (172)...(1581)
<300> PUBLICATION INFORMATION:
<308> DATABASE ACCESSION NUMBER: GeneBank U18374
<309> DATABASE ENTRY DATE: 1995-06-21

<400> SEQUENCE: 5
ctgagttctg agcgtctaca gcgaaagtgc tgggctttgg aaaggagacc tgggctccga      60
atcctctcag ggccttggac gtctctgacc caaaacaatc caaggttctt atttgaagac     120
caccatccca gaagcacatt ctcgagttga aaagttggag tggtgttcga a atg aat     177
                                                        Met Asn
                                                          1 ctg att ggg ccc tcc cat tta caa gcc acg gac gag ttt gct ctt tct     225
Leu Ile Gly Pro Ser His Leu Gln Ala Thr Asp Glu Phe Ala Leu Ser
      5                  10                  15 gaa aac tta ttt gga gtg cta aca gag cac gcg gca ggt cct ctg ggg     273
Glu Asn Leu Phe Gly Val Leu Thr Glu His Ala Ala Gly Pro Leu Gly
 20                  25                  30 cag aat ctg gac ttg gaa tcg tac tcc cca tac aac aat gtg cag ttt     321
Gln Asn Leu Asp Leu Glu Ser Tyr Ser Pro Tyr Asn Asn Val Gln Phe
```

```
               35                  40                  45                  50
cct caa gtt cag cca cag atc tcc tcc tcg tcc tat tat tcc aac ctg       369
Pro Gln Val Gln Pro Gln Ile Ser Ser Ser Ser Tyr Tyr Ser Asn Leu
                    55                  60                  65 ggt ttc tac ccg caa caa ccg gaa gac tgg tac tct cct gga ctc tat       417
Gly Phe Tyr Pro Gln Gln Pro Glu Asp Trp Tyr Ser Pro Gly Leu Tyr
        70                  75                  80 gaa ctc agg cga atg ccc act gag agt gta tac cag gga gag act gag       465
Glu Leu Arg Arg Met Pro Thr Glu Ser Val Tyr Gln Gly Glu Thr Glu
            85                  90                  95 gta tcc gag atg cct gtg aca aag aag ccg cga atg gcc gcc tca tcg       513
Val Ser Glu Met Pro Val Thr Lys Lys Pro Arg Met Ala Ala Ser Ser
100                 105                 110 gcg gga aga ata aaa ggg gat gag ctg tgt gtg gtc tgc gga gac agg       561
Ala Gly Arg Ile Lys Gly Asp Glu Leu Cys Val Val Cys Gly Asp Arg
115                 120                 125                 130 gcc tct ggg tac cat tac aac gcg ctc acc tgc gag ggc tgc aaa ggt       609
Ala Ser Gly Tyr His Tyr Asn Ala Leu Thr Cys Glu Gly Cys Lys Gly
                135                 140                 145 ttc ttc cga aga agc atc acc aaa aac gcc gtg tac aag tgt aag aac       657
Phe Phe Arg Arg Ser Ile Thr Lys Asn Ala Val Tyr Lys Cys Lys Asn
            150                 155                 160 ggg ggc aac tgc gtg atg gat atg tac atg cgt cgg aag tgc cag gat       705
Gly Gly Asn Cys Val Met Asp Met Tyr Met Arg Arg Lys Cys Gln Asp
        165                 170                 175 tgc cgg cta agg aag tgc aga gag atg gga atg ttg gct gaa tgt ttg       753
Cys Arg Leu Arg Lys Cys Arg Glu Met Gly Met Leu Ala Glu Cys Leu
    180                 185                 190 tta act gaa att cag tgt aaa tct aaa cgg cta agg aaa aat gtg aag       801
Leu Thr Glu Ile Gln Cys Lys Ser Lys Arg Leu Arg Lys Asn Val Lys
195                 200                 205                 210 cag cat gcg gat cag aca gtg aat gag gac agc gaa ggg cgt gac ttg       849
Gln His Ala Asp Gln Thr Val Asn Glu Asp Ser Glu Gly Arg Asp Leu
                215                 220                 225 cgg caa gtg acc tcc acg acc aag cta tgc agg gag aaa act gaa ctc       897
Arg Gln Val Thr Ser Thr Thr Lys Leu Cys Arg Glu Lys Thr Glu Leu
            230                 235                 240 act gta gac cag cag acc ctc ctg gat tat att atg gac tca tac agc       945
Thr Val Asp Gln Gln Thr Leu Leu Asp Tyr Ile Met Asp Ser Tyr Ser
        245                 250                 255 aaa cag aga atg cca cag gag atc aca aat aaa atc tta aaa gaa gaa       993
Lys Gln Arg Met Pro Gln Glu Ile Thr Asn Lys Ile Leu Lys Glu Glu
    260                 265                 270 ttt agt gca gaa gaa aat ttt ctc ata tta aca gaa atg gct acc agt      1041
Phe Ser Ala Glu Glu Asn Phe Leu Ile Leu Thr Glu Met Ala Thr Ser
275                 280                 285                 290 cac gta cag att ctc gta gaa ttc aca aaa aga ctt cca ggg ttt cag      1089
His Val Gln Ile Leu Val Glu Phe Thr Lys Arg Leu Pro Gly Phe Gln
                295                 300                 305 aca ctg gac cac gaa gac cag att gct ttg ctc aaa ggg tcc gca gtc      1137
Thr Leu Asp His Glu Asp Gln Ile Ala Leu Leu Lys Gly Ser Ala Val
            310                 315                 320 gag gcc atg ttc ctt cgt tca gcg gag att ttc aat aag aaa ctt cct      1185
Glu Ala Met Phe Leu Arg Ser Ala Glu Ile Phe Asn Lys Lys Leu Pro
        325                 330                 335 gcc gga cac gca gac ctg ttg gaa gaa aga att cga aag agc ggc atc      1233
Ala Gly His Ala Asp Leu Leu Glu Glu Arg Ile Arg Lys Ser Gly Ile
    340                 345                 350 tcc gat gag tac ata acc ccg atg ttt agt ttc tat aaa agt gtc ggg      1281
Ser Asp Glu Tyr Ile Thr Pro Met Phe Ser Phe Tyr Lys Ser Val Gly
```

```
                355                 360                 365                 370
gag ctg aaa atg acc cag gaa gag tac gct ctg ctc aca gca att gtc    1329
Glu Leu Lys Met Thr Gln Glu Glu Tyr Ala Leu Leu Thr Ala Ile Val
                375                 380                 385 atc ctc tct cca gac aga caa tac ata aag gat aga gag gca gtg gag    1377
Ile Leu Ser Pro Asp Arg Gln Tyr Ile Lys Asp Arg Glu Ala Val Glu
            390                 395                 400 aag ctt cag gag cct ctg ctc gat gtc cta caa aaa ctc tgc aag atc    1425
Lys Leu Gln Glu Pro Leu Leu Asp Val Leu Gln Lys Leu Cys Lys Ile
        405                 410                 415 tac cag ccc gag aac cct cag cat ttc gcc tgc ctc ctg ggt cgc ctg    1473
Tyr Gln Pro Glu Asn Pro Gln His Phe Ala Cys Leu Leu Gly Arg Leu
    420                 425                 430 aca gaa ctc cgg aca ttc aac cat cac cac gct gag atg ctg atg tct    1521
Thr Glu Leu Arg Thr Phe Asn His His His Ala Glu Met Leu Met Ser
435                 440                 445                 450 tgg agg gtg aat gac cac aag ttc acc ccg ctc ctc tgt gag atc tgg    1569
Trp Arg Val Asn Asp His Lys Phe Thr Pro Leu Leu Cys Glu Ile Trp
                455                 460                 465 gat gtg cag tga aggacacggg gagaggctag ctccttgtcc tcctcagagc        1621
Asp Val Gln *
agcaacctgg tattggactt cccttctttt catttgtacc aggtctcact caagaatctc  1681
aatgaatatt tatgtggcaa ttatacaatt cccacaactg taaatacagg ctccatagaa  1741
ttgcttcccc tacactgtat tttacaaggc ttcgggaaac cccactgaca cgcccttttt  1801
gcctcattaa atcaattgtt acttcaattt tgtcaactga gctagggacc gcctcgtttt  1861
atcctccatg cggcaacatt atatatatat atattttatc aaatagctgt tttctcttcc  1921
tttttttttt tttttttttt cggagctggg gactgaaccc agggccttgc gcttgctagg  1981
caagcgctct accactgagc taaatcccca accccctatta aatagctgtt ttcaactgag  2041
acaataaact gaacgtaatg ccaagagaa                                    2070

<210> SEQ ID NO 6
<211> LENGTH: 469
<212> TYPE: PRT
<213> ORGANISM: Rattus norvegicus

<400> SEQUENCE: 6

Met Asn Leu Ile Gly Pro Ser His Leu Gln Ala Thr Asp Glu Phe Ala
1               5                   10                  15

Leu Ser Glu Asn Leu Phe Gly Val Leu Thr Glu His Ala Ala Gly Pro
            20                  25                  30

Leu Gly Gln Asn Leu Asp Leu Glu Ser Tyr Ser Pro Tyr Asn Asn Val
        35                  40                  45

Gln Phe Pro Gln Val Gln Pro Gln Ile Ser Ser Ser Tyr Tyr Ser
    50                  55                  60

Asn Leu Gly Phe Tyr Pro Gln Gln Pro Glu Asp Trp Tyr Ser Pro Gly
65                  70                  75                  80

Leu Tyr Glu Leu Arg Arg Met Pro Thr Glu Ser Val Tyr Gln Gly Glu
                85                  90                  95

Thr Glu Val Ser Glu Met Pro Val Thr Lys Lys Pro Arg Met Ala Ala
            100                 105                 110

Ser Ser Ala Gly Arg Ile Lys Gly Asp Glu Leu Cys Val Val Cys Gly
        115                 120                 125

Asp Arg Ala Ser Gly Tyr His Tyr Asn Ala Leu Thr Cys Glu Gly Cys
    130                 135                 140

Lys Gly Phe Phe Arg Arg Ser Ile Thr Lys Asn Ala Val Tyr Lys Cys
```

```
            145                 150                 155                 160
Lys Asn Gly Gly Asn Cys Val Met Asp Met Tyr Met Arg Arg Lys Cys
                    165                 170                 175

Gln Asp Cys Arg Leu Arg Lys Cys Arg Glu Met Gly Met Leu Ala Glu
            180                 185                 190

Cys Leu Leu Thr Glu Ile Gln Cys Lys Ser Lys Arg Leu Arg Lys Asn
            195                 200                 205

Val Lys Gln His Ala Asp Gln Thr Val Asn Glu Asp Ser Glu Gly Arg
    210                 215                 220

Asp Leu Arg Gln Val Thr Ser Thr Thr Lys Leu Cys Arg Glu Lys Thr
225                 230                 235                 240

Glu Leu Thr Val Asp Gln Gln Thr Leu Leu Asp Tyr Ile Met Asp Ser
            245                 250                 255

Tyr Ser Lys Gln Arg Met Pro Gln Glu Ile Thr Asn Lys Ile Leu Lys
            260                 265                 270

Glu Glu Phe Ser Ala Glu Glu Asn Phe Leu Ile Leu Thr Glu Met Ala
            275                 280                 285

Thr Ser His Val Gln Ile Leu Val Glu Phe Thr Lys Arg Leu Pro Gly
            290                 295                 300

Phe Gln Thr Leu Asp His Glu Asp Gln Ile Ala Leu Leu Lys Gly Ser
305                 310                 315                 320

Ala Val Glu Ala Met Phe Leu Arg Ser Ala Glu Ile Phe Asn Lys Lys
            325                 330                 335

Leu Pro Ala Gly His Ala Asp Leu Leu Glu Glu Arg Ile Arg Lys Ser
            340                 345                 350

Gly Ile Ser Asp Glu Tyr Ile Thr Pro Met Phe Ser Phe Tyr Lys Ser
            355                 360                 365

Val Gly Glu Leu Lys Met Thr Gln Glu Glu Tyr Ala Leu Leu Thr Ala
    370                 375                 380

Ile Val Ile Leu Ser Pro Asp Arg Gln Tyr Ile Lys Asp Arg Glu Ala
385                 390                 395                 400

Val Glu Lys Leu Gln Glu Pro Leu Leu Asp Val Leu Gln Lys Leu Cys
            405                 410                 415

Lys Ile Tyr Gln Pro Glu Asn Pro Gln His Phe Ala Cys Leu Leu Gly
            420                 425                 430

Arg Leu Thr Glu Leu Arg Thr Phe Asn His His Ala Glu Met Leu
            435                 440                 445

Met Ser Trp Arg Val Asn Asp His Lys Phe Thr Pro Leu Leu Cys Glu
450                 455                 460

Ile Trp Asp Val Gln
465

<210> SEQ ID NO 7
<211> LENGTH: 2218
<212> TYPE: DNA
<213> ORGANISM: Homo Sapien
<220> FEATURE:
<221> NAME/KEY: CDS
<222> LOCATION: (354)...(1772)
<300> PUBLICATION INFORMATION:
<308> DATABASE ACCESSION NUMBER: GeneBank NM_005123
<309> DATABASE ENTRY DATE: 2002-11-05

<400> SEQUENCE: 7
acgagactct ctcctcctcc tcacctcatt gtctccccga cttatcctaa tgcgaaattg      60
gattctgagc atttgtagca aaatcgctgg gatctgagga ggaagactca gtccagaatc     120
```

-continued

```
ctcccagggc cttgaaagtc catctctgac ccaaaacaat ccaaggaggt agaagacatc    180
gtagaaggag tgaaagaaga aaagaagact tagaaacata gctcaaagtg aacactgctt    240
ctcttagttt cctggatttc ttctggacat ttcctcaaga tgaaacttca gacactttgg    300 agttttttt gaagaccacc ataaagaaag tgcatttcaa ttgaaaaatt tgg atg       356
                                                          Met
                                                          1 gga tca aaa atg aat ctc att gaa cat tcc cat tta cct acc aca gat    404
Gly Ser Lys Met Asn Leu Ile Glu His Ser His Leu Pro Thr Thr Asp
        5                  10                 15 gaa ttt tct ttt tct gaa aat tta ttt ggt gtt tta aca gaa caa gtg    452
Glu Phe Ser Phe Ser Glu Asn Leu Phe Gly Val Leu Thr Glu Gln Val
         20                  25                 30 gca ggt cct ctg gga cag aac ctg gaa gtg gaa cca tac tcg caa tac    500
Ala Gly Pro Leu Gly Gln Asn Leu Glu Val Glu Pro Tyr Ser Gln Tyr
 35                  40                 45 agc aat gtt cag ttt ccc caa gtt caa cca cag att tcc tcg tca tcc    548
Ser Asn Val Gln Phe Pro Gln Val Gln Pro Gln Ile Ser Ser Ser Ser
 50                  55                 60                 65 tat tat tcc aac ctg ggt ttc tac ccc cag cag cct gaa gag tgg tac    596
Tyr Tyr Ser Asn Leu Gly Phe Tyr Pro Gln Gln Pro Glu Glu Trp Tyr
                 70                 75                 80 tct cct gga ata tat gaa ctc agg cgt atg cca gct gag act ctc tac    644
Ser Pro Gly Ile Tyr Glu Leu Arg Arg Met Pro Ala Glu Thr Leu Tyr
             85                 90                 95 cag gga gaa act gag gta gca gag atg cct gta aca aag aag ccc cgc    692
Gln Gly Glu Thr Glu Val Ala Glu Met Pro Val Thr Lys Lys Pro Arg
         100                105                110 atg ggc gcg tca gca ggg agg atc aaa ggg gat gag ctg tgt gtt gtt    740
Met Gly Ala Ser Ala Gly Arg Ile Lys Gly Asp Glu Leu Cys Val Val
 115                 120                125 tgt gga gac aga gcc tct gga tac cac tat aat gca ctg acc tgt gag    788
Cys Gly Asp Arg Ala Ser Gly Tyr His Tyr Asn Ala Leu Thr Cys Glu
130                 135                140                 145 ggg tgt aaa ggt ttc ttc agg aga agc att acc aaa aac gct gtg tac    836
Gly Cys Lys Gly Phe Phe Arg Arg Ser Ile Thr Lys Asn Ala Val Tyr
                 150                155                160 aag tgt aaa aac ggg ggc aac tgt gtg atg gat atg tac atg cga aga    884
Lys Cys Lys Asn Gly Gly Asn Cys Val Met Asp Met Tyr Met Arg Arg
             165                170                175 aag tgt caa gag tgt cga cta agg aaa tgc aaa gag atg gga atg ttg    932
Lys Cys Gln Glu Cys Arg Leu Arg Lys Cys Lys Glu Met Gly Met Leu
         180                185                190 gct gaa tgc ttg tta act gaa att cag tgt aaa tct aag cga ctg aga    980
Ala Glu Cys Leu Leu Thr Glu Ile Gln Cys Lys Ser Lys Arg Leu Arg
 195                 200                205 aaa aat gtg aag cag cat gca gat cag acc gtg aat gaa gac agt gaa   1028
Lys Asn Val Lys Gln His Ala Asp Gln Thr Val Asn Glu Asp Ser Glu
210                 215                220                 225 ggt cgt gac ttg cga caa gtg acc tcg aca aca aag tca tgc agg gag   1076
Gly Arg Asp Leu Arg Gln Val Thr Ser Thr Thr Lys Ser Cys Arg Glu
                 230                235                240 aaa act gaa ctc acc cca gat caa cag act ctt cta cat ttt att atg   1124
Lys Thr Glu Leu Thr Pro Asp Gln Gln Thr Leu Leu His Phe Ile Met
             245                250                255 gat tca tat aac aaa cag agg atg cct cag gaa ata aca aat aaa att   1172
Asp Ser Tyr Asn Lys Gln Arg Met Pro Gln Glu Ile Thr Asn Lys Ile
         260                265                270 tta aaa gaa gaa ttc agt gca gaa gaa aat ttt ctc att ttg acg gaa   1220
Leu Lys Glu Glu Phe Ser Ala Glu Glu Asn Phe Leu Ile Leu Thr Glu
```

```
                                275                     280                     285
atg gca acc aat cat gta cag gtt ctt gta gaa ttc aca aaa aag cta           1268
Met Ala Thr Asn His Val Gln Val Leu Val Glu Phe Thr Lys Lys Leu
290                     295                     300                     305 cca gga ttt cag act ttg gac cat gaa gac cag att gct ttg ctg aaa           1316
Pro Gly Phe Gln Thr Leu Asp His Glu Asp Gln Ile Ala Leu Leu Lys
                        310                     315                     320 ggg tct gcg gtt gaa gct atg ttc ctt cgt tca gct gag att ttc aat           1364
Gly Ser Ala Val Glu Ala Met Phe Leu Arg Ser Ala Glu Ile Phe Asn
                    325                     330                     335 aag aaa ctt ccg tct ggg cat tct gac cta ttg gaa gaa aga att cga           1412
Lys Lys Leu Pro Ser Gly His Ser Asp Leu Leu Glu Glu Arg Ile Arg
                340                     345                     350 aat agt ggt atc tct gat gaa tat ata aca cct atg ttt agt ttt tat           1460
Asn Ser Gly Ile Ser Asp Glu Tyr Ile Thr Pro Met Phe Ser Phe Tyr
355                     360                     365 aaa agt att ggg gaa ctg aaa atg act caa gag gag tat gct ctg ctt           1508
Lys Ser Ile Gly Glu Leu Lys Met Thr Gln Glu Glu Tyr Ala Leu Leu
370                     375                     380                     385 aca gca att gtt atc ctg tct cca gat aga caa tac ata aag gat aga           1556
Thr Ala Ile Val Ile Leu Ser Pro Asp Arg Gln Tyr Ile Lys Asp Arg
                        390                     395                     400 gag gca gta gag aag ctt cag gag cca ctt ctt gat gtg cta caa aag           1604
Glu Ala Val Glu Lys Leu Gln Glu Pro Leu Leu Asp Val Leu Gln Lys
                    405                     410                     415 ttg tgt aag att cac cag cct gaa aat cct caa cac ttt gcc tgt ctc           1652
Leu Cys Lys Ile His Gln Pro Glu Asn Pro Gln His Phe Ala Cys Leu
                420                     425                     430 ctg ggt cgc ctg act gaa tta cgg aca ttc aat cat cac cac gct gag           1700
Leu Gly Arg Leu Thr Glu Leu Arg Thr Phe Asn His His His Ala Glu
435                     440                     445 atg ctg atg tca tgg aga gta aac gac cac aag ttt acc cca ctt ctc           1748
Met Leu Met Ser Trp Arg Val Asn Asp His Lys Phe Thr Pro Leu Leu
450                     455                     460                     465 tgt gaa atc tgg gac gtg cag tga tggggattac aggggagggg tctagctcct          1802
Cys Glu Ile Trp Asp Val Gln  *
                        470 ttttctctct catattaatc tgatgtataa ctttcctttta tttcacttgt acccagtttc        1862 actcaagaaa tcttgatgaa tatttatgtt gtaattacat gtgtaacttc cacaactgta        1922 aatattgggc tagatagaac aactttctct acattgtgtt ttaaaaggct ccagggaatc        1982 ctgcattcta attggcaagc cctgtttgcc taattaaatt gattgttact tcaattctat        2042 ctgttgaact agggaaaatc tcattttgct catcttacca tattgcatat attttattaa        2102 agagttgtat tcaatcttgg caataaagca aacataatgg caacagaaaa aaaaaaaaaa        2162 aaaaaaaaaa aaaaaaaaaa aaaaaaaaaa aaaaaaaaaa aaaaaaaaaa aaaaaa           2218

<210> SEQ ID NO 8
<211> LENGTH: 472
<212> TYPE: PRT
<213> ORGANISM: Homo Sapien

<400> SEQUENCE: 8

Met Gly Ser Lys Met Asn Leu Ile Glu His Ser His Leu Pro Thr Thr
1                   5                   10                  15

Asp Glu Phe Ser Phe Ser Glu Asn Leu Phe Gly Val Leu Thr Glu Gln
                20                  25                  30

Val Ala Gly Pro Leu Gly Gln Asn Leu Glu Val Glu Pro Tyr Ser Gln
            35                  40                  45
```

-continued

```
Tyr Ser Asn Val Gln Phe Pro Gln Val Gln Pro Gln Ile Ser Ser Ser
 50                  55                  60

Ser Tyr Tyr Ser Asn Leu Gly Phe Tyr Pro Gln Gln Pro Glu Glu Trp
 65                  70                  75                  80

Tyr Ser Pro Gly Ile Tyr Glu Leu Arg Arg Met Pro Ala Glu Thr Leu
                 85                  90                  95

Tyr Gln Gly Glu Thr Glu Val Ala Glu Met Pro Val Thr Lys Lys Pro
            100                 105                 110

Arg Met Gly Ala Ser Ala Gly Arg Ile Lys Gly Asp Glu Leu Cys Val
            115                 120                 125

Val Cys Gly Asp Arg Ala Ser Gly Tyr His Tyr Asn Ala Leu Thr Cys
            130                 135                 140

Glu Gly Cys Lys Gly Phe Phe Arg Arg Ser Ile Thr Lys Asn Ala Val
145                 150                 155                 160

Tyr Lys Cys Lys Asn Gly Gly Asn Cys Val Met Asp Met Tyr Met Arg
                165                 170                 175

Arg Lys Cys Gln Glu Cys Arg Leu Arg Lys Cys Lys Glu Met Gly Met
            180                 185                 190

Leu Ala Glu Cys Leu Leu Thr Glu Ile Gln Cys Lys Ser Lys Arg Leu
            195                 200                 205

Arg Lys Asn Val Lys Gln His Ala Asp Gln Thr Val Asn Glu Asp Ser
210                 215                 220

Glu Gly Arg Asp Leu Arg Gln Val Thr Ser Thr Thr Lys Ser Cys Arg
225                 230                 235                 240

Glu Lys Thr Glu Leu Thr Pro Asp Gln Gln Thr Leu Leu His Phe Ile
                245                 250                 255

Met Asp Ser Tyr Asn Lys Gln Arg Met Pro Gln Glu Ile Thr Asn Lys
            260                 265                 270

Ile Leu Lys Glu Glu Phe Ser Ala Glu Asn Phe Leu Ile Leu Thr
            275                 280                 285

Glu Met Ala Thr Asn His Val Gln Val Leu Val Glu Phe Thr Lys Lys
290                 295                 300

Leu Pro Gly Phe Gln Thr Leu Asp His Glu Asp Gln Ile Ala Leu Leu
305                 310                 315                 320

Lys Gly Ser Ala Val Glu Ala Met Phe Leu Arg Ser Ala Glu Ile Phe
                325                 330                 335

Asn Lys Lys Leu Pro Ser Gly His Ser Asp Leu Leu Glu Glu Arg Ile
            340                 345                 350

Arg Asn Ser Gly Ile Ser Asp Glu Tyr Ile Thr Pro Met Phe Ser Phe
            355                 360                 365

Tyr Lys Ser Ile Gly Glu Leu Lys Met Thr Gln Glu Glu Tyr Ala Leu
            370                 375                 380

Leu Thr Ala Ile Val Ile Leu Ser Pro Asp Arg Gln Tyr Ile Lys Asp
385                 390                 395                 400

Arg Glu Ala Val Glu Lys Leu Gln Glu Pro Leu Leu Asp Val Leu Gln
                405                 410                 415

Lys Leu Cys Lys Ile His Gln Pro Glu Asn Pro Gln His Phe Ala Cys
            420                 425                 430

Leu Leu Gly Arg Leu Thr Glu Leu Arg Thr Phe Asn His His His Ala
            435                 440                 445

Glu Met Leu Met Ser Trp Arg Val Asn Asp His Lys Phe Thr Pro Leu
450                 455                 460

Leu Cys Glu Ile Trp Asp Val Gln
```

```
<210> SEQ ID NO 9
<211> LENGTH: 5449
<212> TYPE: DNA
<213> ORGANISM: Homo Sapien
<220> FEATURE:
<221> NAME/KEY: CDS
<222> LOCATION: (69)...(1457)
<300> PUBLICATION INFORMATION:
<308> DATABASE ACCESSION NUMBER: GeneBank NM_002957
<309> DATABASE ENTRY DATE: 2002-06-21

<400> SEQUENCE: 9
```

| | | |
|---|---|---|
| gcgccggggg ccgccgcgcc cgccgcccgc tgcctgcgcc gccggccggg catgagttag | | 60 |

| gtg aac tcc tcc ctc acc tcc ccg acg ggg cga ggc tcc atg gct gcc | | 158 |
|---|---|---|
| Val Asn Ser Ser Leu Thr Ser Pro Thr Gly Arg Gly Ser Met Ala Ala | | |
| 15 20 25 30 | | |

| tcgcagac atg gac acc aaa cat ttc ctg ccg ctc gat ttc tcc acc cag | | 110 |
|---|---|---|
| Met Asp Thr Lys His Phe Leu Pro Leu Asp Phe Ser Thr Gln | | |
| 1 5 10 | | |

| ccc tcg ctg cac ccg tcc ctg ggg cct ggc atc ggc tcc ccg gga cag | | 206 |
|---|---|---|
| Pro Ser Leu His Pro Ser Leu Gly Pro Gly Ile Gly Ser Pro Gly Gln | | |
| 35 40 45 | | |

| ctg cat tct ccc atc agc acc ctg agc tcc ccc atc aac ggc atg ggc | | 254 |
|---|---|---|
| Leu His Ser Pro Ile Ser Thr Leu Ser Ser Pro Ile Asn Gly Met Gly | | |
| 50 55 60 | | |

| ccg cct ttc tcg gtc atc agc tcc ccc atg ggc ccc cac tcc atg tcg | | 302 |
|---|---|---|
| Pro Pro Phe Ser Val Ile Ser Ser Pro Met Gly Pro His Ser Met Ser | | |
| 65 70 75 | | |

| gtg ccc acc aca ccc acc ctg ggc ttc agc act ggc agc ccc cag ctc | | 350 |
|---|---|---|
| Val Pro Thr Thr Pro Thr Leu Gly Phe Ser Thr Gly Ser Pro Gln Leu | | |
| 80 85 90 | | |

| agc tca cct atg aac ccc gtc agc agc agc gag gac atc aag ccc ccc | | 398 |
|---|---|---|
| Ser Ser Pro Met Asn Pro Val Ser Ser Ser Glu Asp Ile Lys Pro Pro | | |
| 95 100 105 110 | | |

| ctg ggc ctc aat ggc gtc ctc aag gtc ccc gcc cac cct tca gga aac | | 446 |
|---|---|---|
| Leu Gly Leu Asn Gly Val Leu Lys Val Pro Ala His Pro Ser Gly Asn | | |
| 115 120 125 | | |

| atg gct tcc ttc acc aag cac atc tgc gcc atc tgc ggg gac cgc tcc | | 494 |
|---|---|---|
| Met Ala Ser Phe Thr Lys His Ile Cys Ala Ile Cys Gly Asp Arg Ser | | |
| 130 135 140 | | |

| tca ggc aag cac tat gga gtg tac agc tgc gag ggg tgc aag ggc ttc | | 542 |
|---|---|---|
| Ser Gly Lys His Tyr Gly Val Tyr Ser Cys Glu Gly Cys Lys Gly Phe | | |
| 145 150 155 | | |

| ttc aag cgg acg gtg cgc aag gac ctg acc tac acc tgc cgc gac aac | | 590 |
|---|---|---|
| Phe Lys Arg Thr Val Arg Lys Asp Leu Thr Tyr Thr Cys Arg Asp Asn | | |
| 160 165 170 | | |

| aag gac tgc ctg att gac aag cgg cag cgg aac cgg tgc cag tac tgc | | 638 |
|---|---|---|
| Lys Asp Cys Leu Ile Asp Lys Arg Gln Arg Asn Arg Cys Gln Tyr Cys | | |
| 175 180 185 190 | | |

| cgc tac cag aag tgc ctg gcc atg ggc atg aag cgg gaa gcc gtg cag | | 686 |
|---|---|---|
| Arg Tyr Gln Lys Cys Leu Ala Met Gly Met Lys Arg Glu Ala Val Gln | | |
| 195 200 205 | | |

| gag gag cgg cag cgt ggc aag gac cgg aac gag aat gag gtg gag tcg | | 734 |
|---|---|---|
| Glu Glu Arg Gln Arg Gly Lys Asp Arg Asn Glu Asn Glu Val Glu Ser | | |
| 210 215 220 | | |

| acc agc agc gcc aac gag gac atg ccg gtg gag agg atc ctg gag gct | | 782 |
|---|---|---|
| Thr Ser Ser Ala Asn Glu Asp Met Pro Val Glu Arg Ile Leu Glu Ala | | |
| 225 230 235 | | |

| gag ctg gcc gtg gag ccc aag acc gag acc tac gtg gag gca aac atg | | 830 |
|---|---|---|
| Glu Leu Ala Val Glu Pro Lys Thr Glu Thr Tyr Val Glu Ala Asn Met | | |

```
                        240                 245                 250
ggg ctg aac ccc agc tcg ccg aac gac cct gtc acc aac att tgc caa    878
Gly Leu Asn Pro Ser Ser Pro Asn Asp Pro Val Thr Asn Ile Cys Gln
255                 260                 265                 270 gca gcc gac aaa cag ctt ttc acc ctg gtg gag tgg gcc aag cgg atc    926
Ala Ala Asp Lys Gln Leu Phe Thr Leu Val Glu Trp Ala Lys Arg Ile
                275                 280                 285 cca cac ttc tca gag ctg ccc ctg gac gac cag gtc atc ctg ctg cgg    974
Pro His Phe Ser Glu Leu Pro Leu Asp Asp Gln Val Ile Leu Leu Arg
            290                 295                 300 gca ggc tgg aat gag ctg ctc atc gcc tcc ttc tcc cac cgc tcc atc   1022
Ala Gly Trp Asn Glu Leu Leu Ile Ala Ser Phe Ser His Arg Ser Ile
        305                 310                 315 gcc gtg aag gac ggg atc ctc ctg gcc acc ggg ctg cac gtc cac cgg   1070
Ala Val Lys Asp Gly Ile Leu Leu Ala Thr Gly Leu His Val His Arg
    320                 325                 330 aac agc gcc cac agc gca ggg gtg ggc gcc atc ttt gac agg gtg ctg   1118
Asn Ser Ala His Ser Ala Gly Val Gly Ala Ile Phe Asp Arg Val Leu
335                 340                 345                 350 acg gag ctt gtg tcc aag atg cgg gac atg cag atg gac aag acg gag   1166
Thr Glu Leu Val Ser Lys Met Arg Asp Met Gln Met Asp Lys Thr Glu
                355                 360                 365 ctg ggc tgc ctg cgc gcc atc gtc ctc ttt aac cct gac tcc aag ggg   1214
Leu Gly Cys Leu Arg Ala Ile Val Leu Phe Asn Pro Asp Ser Lys Gly
            370                 375                 380 ctc tcg aac ccg gcc gag gtg gag gcg ctg agg gag aag gtc tat gcg   1262
Leu Ser Asn Pro Ala Glu Val Glu Ala Leu Arg Glu Lys Val Tyr Ala
        385                 390                 395 tcc ttg gag gcc tac tgc aag cac aag tac cca gag cag ccg gga agg   1310
Ser Leu Glu Ala Tyr Cys Lys His Lys Tyr Pro Glu Gln Pro Gly Arg
    400                 405                 410 ttc gct aag ctc ttg ctc cgc ctg ccg gct ctg cgc tcc atc ggg ctc   1358
Phe Ala Lys Leu Leu Leu Arg Leu Pro Ala Leu Arg Ser Ile Gly Leu
415                 420                 425                 430 aaa tgc ctg gaa cat ctc ttc ttc aag ctc atc ggg gac aca ccc       1406
Lys Cys Leu Glu His Leu Phe Phe Lys Leu Ile Gly Asp Thr Pro
                435                 440                 445 att gac acc ttc ctt atg gag atg ctg gag gcg ccg cac caa atg act   1454
Ile Asp Thr Phe Leu Met Glu Met Leu Glu Ala Pro His Gln Met Thr
            450                 455                 460 tag gcctgcgggc ccatcctttg tgcccacccg ttctggccac cctgcctgga        1507
* cgccagctgt tcttctcagc ctgagccctg tccctgccct tctctgcctg gcctgtttgg  1567
actttggggc acagcctgtc actgctctgc ctaagagatg tgttgtcacc ctccttattt  1627
ctgttactac ttgtctgtgg cccagggcag tggctttcct gaggcagcag ccttcgtggc  1687
aagaactagc gtgagcccag ccaggcgcct ccccaccggg ctctcaggac accctgccac  1747
accccacggg gcttgggcga ctacagggtc ttcgggcccc agccctggag ctgcaggagt  1807
tgggaacggg gcttttgttt ccgttgctgt ttatcgatgc tggttttcag aattcctgtg  1867
tggccctcct gtctggagtg acatcttcat ctgctctgaa tactggtgcc cagccagccc  1927
gtgacagctt ccccctaatc aggaggggac agctggggc gcaagctggt gtgtcatcag   1987
caaagacctc agccgcctcg gggatgagag gggactcgtg gggcaagcaa gctgccctgt  2047
gctctgagtg aggggggaagg tagccccttt ttccaaagat aactcacagt tttgccctcg 2107 agccaatgag aacatgagct gccctctgtg caaggtttcg gggccacctc caggctgcag  2167
gggcgggtca ctcacccccc tgtttctct ctgccttggt gttctggttt cagactcccg   2227
```

```
actccccgtt cagaccagag tgccccggcc cctccccagc ctgagtcttc tccttgctct    2287
gcggggtggg ctgaggcttg tccttgtttc ctgcagggct ggccctggct cgggcagggt    2347
ggggcatcac cacctcactg gccttgctgg aggcacaggg ctctgcggac ctgcagccat    2407
ctgtgaggcc cgcggggatg ggaggggagg agggtggcct gttggtttcc ctcagagggg    2467
gcaggtggcc tggagagaga ggggctcagg aactgggagc ctcgtgggtg gggcagatgc    2527
tccgcggcct ggagtggctc tgccggggca ttggtgggac ccctgctcag gccttctctc    2587
tggctgccag ttgtgtctaa aagactcttg gaatctgaga acccgagtc gcagcgccct     2647 cgggcctggg ccacacgcag gccctggtgg gaccacccag cctggtattg tccacggaca    2707
gcgttgttca cccagagcct tacttgggag cctcactgaa cgcctgctct ggttgaaggt    2767
ggggtggggg cggggcttgg ggcctccctg gctcagccca gtgcggcctg cgctcctcc    2827 cgcaggctct gcccccgggc tccggtggtg cggggccctc tcaggttgaa ctcgcctctt    2887
ttgcactgga aggccctccc tttggcctga gtacttttcc cgttcacgcc tcagtcccgt    2947
ggacccagcc tttgtcagtg gcaggtgcct gaacagaggg tggatggggg ggataccgga    3007
gggggtcttg tcttcccagc cgcagtctag gaatgatgcg gggggggtgga cgccttctcc    3067 atagtctttc cccacctgga gcaggggctt cctcagtggt gaggggagct gcctacaggt    3127
tggaccggga ggcagtggct tggagaggca gctttccagc cttggtgggg aagaaagtgt    3187
ccattctttg ccttcctgga gctcccagcc agagctgagc ttaggcaccc gagtggagcc    3247
tgcagctgag tctgtgcccg agacaggctg tcagagattc cagaagcctc tcctccccgc    3307
cgccctccac ccctgccttt cagcgttgtg gatccctaga ggtggccccc tgcccgatcc    3367
accgtcctga ggcagagtgt tgagcctcat acctgtacca ggtcccccggc cagctgggcc    3427 cctcccaggc actgccagga agcccagct gcccctggcg ggtgtggtgg aaatggcagg    3487
agggtgcagg tactcttggg gccccagcgg tgggagtgca aaagacccaa cgccaacacc    3547
tggtgccttt tgcagccagc gcccacccat ccgtgcccgg acccttggga atgcccgcgg    3607
ctccagagga aaaagcccag ggacggggcc tccgttgcgg ggggtcggct gcttcttggg    3667
aactttgtcg tttccggcgc tggctggctg gctggctgta aagcactgaa gccccccggc    3727
cgccaacccc tgaaagcaga acctggcctc cctggccaca gcagccttac ccaccgctct    3787
acgtgtcccg ggcacttccc gcagccttcc cgtcccttc tcatcggcct tgtagttgta    3847
cagtgctgtt ggtttgaaaa ggtgatgtgt ggggagtgcg gctcatcact gagtagagag    3907
gtagaatttc tatttaacca gacctgtagt agtattacca atccagttca attaaggtga    3967 tttttttgtaa ttattattat tttggtggga caatctttaa ttttctaaag atagcactaa    4027
catcagctca ttagccacct gtgcctgtcc ccgccttggc ccggctggat gaagcggctt    4087
ccccgcaggg ccccccacttc ccagtggctg cttcctgggg acccagggca ccccggcacc    4147
ttcaggcacg ctcctcagct ggtcacctcc cggctttgcc gttcagatgg ggctcctgag    4207
gctcaggagt gaagatgcca cagagccggg ctccctagg ctgcgtcggg catgcttgga    4267
agctggcctg ccaggacctt ccaccctggg gcctgtgtca gccgccggcc ctcccgcaccc    4327 tggaagcaca cggcctctgg gaaggacagc cctgaccttc ggttttccga gcacggtgtt    4387
tcccaagaat tctgggctgg cggcctggtg gcagtgctgg agatgacccc gagcccctcc    4447
ccgtggggca cccaggaggg ccctgccgga atgtgcagcc tgtgggtagt cggctggtgt    4507
ccctgtcgtg gagctggggt gcgtgatctg gtgctcgtcc acgcaggtgt gtggtgtaaa    4567
catgtatgtg ctgtacagag agacgcgtgt ggagagagcc gcacaccagc gccacccagg    4627
```

```
aaaggcggag cggttaccag tgttttgtgt ttattttaa tcaagacgtt tccctgttt    4687 tcctataaat ttgcttcgtg taagcaagta cataaggacc ctcctttggt gaaatccggg    4747
ttcgaatgaa tatctcaagg caggagatgc atctatttta agatgctttg gagcagacag    4807
ctttagccgt tcccaatcct tagcaatgcc ttagctggga cgcatagcta atactttaga    4867
gaggatgaca gatccataaa gagagtaaag ataagagaaa atgtctaaag catctggaaa    4927
ggtaaaaaaa aaaaatctat ttttgtacaa atgtaatttt atccctcatg tatacttgga    4987
tatggcgggg ggagggctgg gactgtttcg tttctgcttc tagagattga ggtgaaagct    5047
tcgtccgaga aacgccagga cagacgatgg cagaggagag ggctcctgtg acggcggcga    5107
ggcttgggag gaaaccgccg caatgggggt gtcttccctc ggggcaggag ggtgggcctg    5167
aggctttcaa gggttttctt cccttcgag taattttaa agccttgctc tgttgtgtcc    5227
tgttgccggc tctggccttc ctgtgactga ctgtgaagtg gcttctccgt acgattgtct    5287
ctgaaacatc gtggcctcag gtgccagggt ttgatggaca gtagcattag aattgtggaa    5347
aaggaacacg caaagggaga agtgtgagag gagaaacaaa atatgagcgt ttaaaataca    5407
tcgccattca gttcgttaaa aaaaaaaaaa aaaaaaaaa aa                        5449

<210> SEQ ID NO 10
<211> LENGTH: 462
<212> TYPE: PRT
<213> ORGANISM: Homo Sapien

<400> SEQUENCE: 10

Met Asp Thr Lys His Phe Leu Pro Leu Asp Phe Ser Thr Gln Val Asn
 1               5                   10                  15

Ser Ser Leu Thr Ser Pro Thr Gly Arg Gly Ser Met Ala Ala Pro Ser
            20                  25                  30

Leu His Pro Ser Leu Gly Pro Gly Ile Gly Ser Pro Gly Gln Leu His
        35                  40                  45

Ser Pro Ile Ser Thr Leu Ser Ser Pro Ile Asn Gly Met Gly Pro Pro
    50                  55                  60

Phe Ser Val Ile Ser Ser Pro Met Gly Pro His Ser Met Ser Val Pro
65                  70                  75                  80

Thr Thr Pro Thr Leu Gly Phe Ser Thr Gly Ser Pro Gln Leu Ser Ser
                85                  90                  95

Pro Met Asn Pro Val Ser Ser Ser Glu Asp Ile Lys Pro Pro Leu Gly
            100                 105                 110

Leu Asn Gly Val Leu Lys Val Pro Ala His Pro Ser Gly Asn Met Ala
        115                 120                 125

Ser Phe Thr Lys His Ile Cys Ala Ile Cys Gly Asp Arg Ser Ser Gly
    130                 135                 140

Lys His Tyr Gly Val Tyr Ser Cys Glu Gly Cys Lys Gly Phe Phe Lys
145                 150                 155                 160

Arg Thr Val Arg Lys Asp Leu Thr Tyr Thr Cys Arg Asp Asn Lys Asp
                165                 170                 175

Cys Leu Ile Asp Lys Arg Gln Arg Asn Arg Cys Gln Tyr Cys Arg Tyr
            180                 185                 190

Gln Lys Cys Leu Ala Met Gly Met Lys Arg Glu Ala Val Gln Glu Glu
        195                 200                 205

Arg Gln Arg Gly Lys Asp Arg Asn Glu Asn Glu Val Glu Ser Thr Ser
    210                 215                 220

Ser Ala Asn Glu Asp Met Pro Val Glu Arg Ile Leu Glu Ala Glu Leu
```

-continued

```
            225                 230                 235                 240
Ala Val Glu Pro Lys Thr Glu Thr Tyr Val Glu Ala Asn Met Gly Leu
                    245                 250                 255

Asn Pro Ser Ser Pro Asn Asp Pro Val Thr Asn Ile Cys Gln Ala Ala
            260                 265                 270

Asp Lys Gln Leu Phe Thr Leu Val Glu Trp Ala Lys Arg Ile Pro His
        275                 280                 285

Phe Ser Glu Leu Pro Leu Asp Asp Gln Val Ile Leu Leu Arg Ala Gly
    290                 295                 300

Trp Asn Glu Leu Leu Ile Ala Ser Phe Ser His Arg Ser Ile Ala Val
305                 310                 315                 320

Lys Asp Gly Ile Leu Leu Ala Thr Gly Leu His Val His Arg Asn Ser
                325                 330                 335

Ala His Ser Ala Gly Val Gly Ala Ile Phe Asp Arg Val Leu Thr Glu
            340                 345                 350

Leu Val Ser Lys Met Arg Asp Met Gln Met Asp Lys Thr Glu Leu Gly
        355                 360                 365

Cys Leu Arg Ala Ile Val Leu Phe Asn Pro Asp Ser Lys Gly Leu Ser
    370                 375                 380

Asn Pro Ala Glu Val Glu Ala Leu Arg Glu Lys Val Tyr Ala Ser Leu
385                 390                 395                 400

Glu Ala Tyr Cys Lys His Lys Tyr Pro Glu Gln Pro Gly Arg Phe Ala
                405                 410                 415

Lys Leu Leu Leu Arg Leu Pro Ala Leu Arg Ser Ile Gly Leu Lys Cys
            420                 425                 430

Leu Glu His Leu Phe Phe Phe Lys Leu Ile Gly Asp Thr Pro Ile Asp
        435                 440                 445

Thr Phe Leu Met Glu Met Leu Glu Ala Pro His Gln Met Thr
    450                 455                 460
```

<210> SEQ ID NO 11
<211> LENGTH: 2081
<212> TYPE: DNA
<213> ORGANISM: Mus musculus
<220> FEATURE:
<221> NAME/KEY: CDS
<222> LOCATION: (167)...(1573)
<300> PUBLICATION INFORMATION:
<308> DATABASE ACCESSION NUMBER: GeneBank X57638
<309> DATABASE ENTRY DATE: 1991-03-19

<400> SEQUENCE: 11

```
gtcacagcct aggctttgct ggggacctga gaaacgctgc cgccaagttg aagttcaagg      60
ccctgccttc cctgtgaact gacgtttgtg gctggtcaag ttcgggaaca agacgttgtc     120
atcacagctt agcgctctgt ggcctgcctg ccacatcca tccaac atg gtg gac         175
                                                  Met Val Asp
                                                    1 aca gag agc ccc atc tgt cct ctc tcc cca ctg gag gca gat gac ctg       223
Thr Glu Ser Pro Ile Cys Pro Leu Ser Pro Leu Glu Ala Asp Asp Leu
    5                  10                   15 gaa agt ccc tta tct gaa gaa ttc tta caa gaa atg gga aac att caa       271
Glu Ser Pro Leu Ser Glu Glu Phe Leu Gln Glu Met Gly Asn Ile Gln
20                  25                   30                  35 gag att tct cag tcc atc ggt gag gag agc tct gga agc ttt ggt ttt       319
Glu Ile Ser Gln Ser Ile Gly Glu Glu Ser Ser Gly Ser Phe Gly Phe
            40                   45                  50 gca gac tac cag tac tta gga agc tgt ccg ggc tcc gag ggc tct gtc       367
Ala Asp Tyr Gln Tyr Leu Gly Ser Cys Pro Gly Ser Glu Gly Ser Val
```

-continued

```
                   55                  60                  65
atc aca gac acc ctc tct cca cgt tcc agc cct tcc tca gtc agc tgc       415
Ile Thr Asp Thr Leu Ser Pro Arg Ser Ser Pro Ser Ser Val Ser Cys
        70                  75                  80 ccc gtg atc ccc gcc agc acg gac gag tcc ccc ggc agt gcc ctg aac       463
Pro Val Ile Pro Ala Ser Thr Asp Glu Ser Pro Gly Ser Ala Leu Asn
    85                  90                  95 atc gag tgt cga ata tgt ggg gac aag gcc tca ggg tac cac tac gga       511
Ile Glu Cys Arg Ile Cys Gly Asp Lys Ala Ser Gly Tyr His Tyr Gly
100                 105                 110                 115 gtt cac gca tgt gaa ggc tgt aag ggc ttc ttt cgg cga act att cgg       559
Val His Ala Cys Glu Gly Cys Lys Gly Phe Phe Arg Arg Thr Ile Arg
                120                 125                 130 ctg aag ctg gtg tac gac aag tgt gat cgg agc tgc aag att cag aag       607
Leu Lys Leu Val Tyr Asp Lys Cys Asp Arg Ser Cys Lys Ile Gln Lys
            135                 140                 145 aag aac cgg aac aaa tgc cag tac tgc cgt ttt cac aag tgc ctg tct       655
Lys Asn Arg Asn Lys Cys Gln Tyr Cys Arg Phe His Lys Cys Leu Ser
        150                 155                 160 gtc ggg atg tca cac aat gca att cgc ttt gga aga atg cca aga tct       703
Val Gly Met Ser His Asn Ala Ile Arg Phe Gly Arg Met Pro Arg Ser
    165                 170                 175 gaa aaa gca aaa ctg aaa gca gaa att ctt acc tgt gaa cac gac ctg       751
Glu Lys Ala Lys Leu Lys Ala Glu Ile Leu Thr Cys Glu His Asp Leu
180                 185                 190                 195 aaa gat tcg gaa act gca gac ctc aaa tct ctg ggc aag aga atc cac       799
Lys Asp Ser Glu Thr Ala Asp Leu Lys Ser Leu Gly Lys Arg Ile His
                200                 205                 210 gaa gcc tac ctg aag aac ttc aac atg aac aag gtc aag gcc cgg gtc       847
Glu Ala Tyr Leu Lys Asn Phe Asn Met Asn Lys Val Lys Ala Arg Val
            215                 220                 225 ata ctc gcg gga aag acc agc aac aac ccg cct ttt gtc ata cat gac       895
Ile Leu Ala Gly Lys Thr Ser Asn Asn Pro Pro Phe Val Ile His Asp
        230                 235                 240 atg gag acc ttg tgt atg gcc gag aag acg ctt gtg gcc aag atg gtg       943
Met Glu Thr Leu Cys Met Ala Glu Lys Thr Leu Val Ala Lys Met Val
    245                 250                 255 gcc aac ggc gtc gaa gac aaa gag gca gag gtc cga ttc ttc cac tgc       991
Ala Asn Gly Val Glu Asp Lys Glu Ala Glu Val Arg Phe Phe His Cys
260                 265                 270                 275 tgc cag tgc atg tcc gtg gag acc gtc acg gag ctc aca gaa ttt gcc      1039
Cys Gln Cys Met Ser Val Glu Thr Val Thr Glu Leu Thr Glu Phe Ala
                280                 285                 290 aag gct atc cca ggc ttt gca aac ttg gac ttg aac gac caa gtc acc      1087
Lys Ala Ile Pro Gly Phe Ala Asn Leu Asp Leu Asn Asp Gln Val Thr
            295                 300                 305 ttg cta aag tac ggt gtg tat gaa gcc atc ttc acg atg ctg tcc tcc      1135
Leu Leu Lys Tyr Gly Val Tyr Glu Ala Ile Phe Thr Met Leu Ser Ser
        310                 315                 320 ttg atg aac aaa gac ggg atg ctg atc gcg tac ggc aat ggc ttt atc      1183
Leu Met Asn Lys Asp Gly Met Leu Ile Ala Tyr Gly Asn Gly Phe Ile
    325                 330                 335 aca cgc gag ttc ctt aag aac ctg agg aag ccg ttc tgt gac atc atg      1231
Thr Arg Glu Phe Leu Lys Asn Leu Arg Lys Pro Phe Cys Asp Ile Met
340                 345                 350                 355 gaa ccc aag ttt gac ttc gct atg aag ttc aat gcc tta gaa ctg gat      1279
Glu Pro Lys Phe Asp Phe Ala Met Lys Phe Asn Ala Leu Glu Leu Asp
                360                 365                 370 gac agt gac att tcc ctg ttt gtg gct gct ata att tgc tgt gga gat      1327
Asp Ser Asp Ile Ser Leu Phe Val Ala Ala Ile Ile Cys Cys Gly Asp
```

```
                    375                 380                 385
cgg cct ggc ctt cta aac ata ggc tac att gag aag ttg cag gag ggg    1375
Arg Pro Gly Leu Leu Asn Ile Gly Tyr Ile Glu Lys Leu Gln Glu Gly
        390                 395                 400 att gtg cac gtg ctt aag ctc cac ctg cag agc aac cat cca gat gac    1423
Ile Val His Val Leu Lys Leu His Leu Gln Ser Asn His Pro Asp Asp
405                 410                 415 acc ttc ctc ttc cca aag ctc ctt caa aaa atg gtg gac ctt cgg cag    1471
Thr Phe Leu Phe Pro Lys Leu Leu Gln Lys Met Val Asp Leu Arg Gln
420                 425                 430                 435 ctg gtc acg gag cat gcg cag ctc gta cag gtc atc aag aag acc gag    1519
Leu Val Thr Glu His Ala Gln Leu Val Gln Val Ile Lys Lys Thr Glu
            440                 445                 450 tcc gac gca gcg ctg cac cca ctg ttg caa gag atc tac aga gac atg    1567
Ser Asp Ala Ala Leu His Pro Leu Leu Gln Glu Ile Tyr Arg Asp Met
                455                 460                 465 tac tga tctttcctga gatggcaggc cattaccact gttcagggac ctccgaggcc    1623
Tyr *
tgcggcccca tacaggagag cagggatttg cacagagggc ctccctccta cgcttggga    1683 tgaagagggc tgagcgtagg taatgcgggc tctccccaca tcctttctga atggcactt    1743 ctaagactac ctgctaccga aatggggtg atcggaggct aataggattc agacagtgac    1803
agacaacggc agtccccagt ctggtcttaa ccggcccaat gttaatcaat gcacagcact    1863
ctacgttgcg tttataattc gccattaatt aacgggtaac ctcgaagtct gagcggtctg    1923
ttcccttcct gccacccttc tggctatgtg cactctctta aatccctgaa actaatctg    1983 cactttttaa cctttgaaaa cctacaagtc aaggtgtggc ccaaggttag ccatttaaat    2043
gtggcaaaaa aaaaaaaaa aaaaaaaaaa aaaaaaa                              2081

<210> SEQ ID NO 12
<211> LENGTH: 468
<212> TYPE: PRT
<213> ORGANISM: Mus musculus

<400> SEQUENCE: 12

Met Val Asp Thr Glu Ser Pro Ile Cys Pro Leu Ser Pro Leu Glu Ala
1               5                   10                  15

Asp Asp Leu Glu Ser Pro Leu Ser Glu Glu Phe Leu Gln Glu Met Gly
            20                  25                  30

Asn Ile Gln Glu Ile Ser Gln Ser Ile Gly Glu Glu Ser Gly Ser
        35                  40                  45

Phe Gly Phe Ala Asp Tyr Gln Tyr Leu Gly Ser Cys Pro Gly Ser Glu
    50                  55                  60

Gly Ser Val Ile Thr Asp Thr Leu Ser Pro Arg Ser Ser Pro Ser Ser
65                  70                  75                  80

Val Ser Cys Pro Val Ile Pro Ala Ser Thr Asp Glu Ser Pro Gly Ser
                85                  90                  95

Ala Leu Asn Ile Glu Cys Arg Ile Cys Gly Asp Lys Ala Ser Gly Tyr
            100                 105                 110

His Tyr Gly Val His Ala Cys Glu Gly Cys Lys Gly Phe Phe Arg Arg
        115                 120                 125

Thr Ile Arg Leu Lys Leu Val Tyr Asp Lys Cys Asp Arg Ser Cys Lys
    130                 135                 140

Ile Gln Lys Lys Asn Arg Asn Lys Cys Gln Tyr Cys Arg Phe His Lys
145                 150                 155                 160

Cys Leu Ser Val Gly Met Ser His Asn Ala Ile Arg Phe Gly Arg Met
                165                 170                 175
```

```
Pro Arg Ser Glu Lys Ala Lys Leu Lys Ala Glu Ile Leu Thr Cys Glu
            180                 185                 190

His Asp Leu Lys Asp Ser Glu Thr Ala Asp Leu Lys Ser Leu Gly Lys
            195                 200                 205

Arg Ile His Glu Ala Tyr Leu Lys Asn Phe Asn Met Asn Lys Val Lys
        210                 215                 220

Ala Arg Val Ile Leu Ala Gly Lys Thr Ser Asn Asn Pro Pro Phe Val
225                 230                 235                 240

Ile His Asp Met Glu Thr Leu Cys Met Ala Glu Lys Thr Leu Val Ala
                245                 250                 255

Lys Met Val Ala Asn Gly Val Glu Asp Lys Glu Ala Glu Val Arg Phe
            260                 265                 270

Phe His Cys Cys Gln Cys Met Ser Val Glu Thr Val Thr Glu Leu Thr
        275                 280                 285

Glu Phe Ala Lys Ala Ile Pro Gly Phe Ala Asn Leu Asp Leu Asn Asp
290                 295                 300

Gln Val Thr Leu Leu Lys Tyr Gly Val Tyr Glu Ala Ile Phe Thr Met
305                 310                 315                 320

Leu Ser Ser Leu Met Asn Lys Asp Gly Met Leu Ile Ala Tyr Gly Asn
                325                 330                 335

Gly Phe Ile Thr Arg Glu Phe Leu Lys Asn Leu Arg Lys Pro Phe Cys
            340                 345                 350

Asp Ile Met Glu Pro Lys Phe Asp Phe Ala Met Lys Phe Asn Ala Leu
        355                 360                 365

Glu Leu Asp Asp Ser Asp Ile Ser Leu Phe Val Ala Ala Ile Ile Cys
370                 375                 380

Cys Gly Asp Arg Pro Gly Leu Leu Asn Ile Gly Tyr Ile Glu Lys Leu
385                 390                 395                 400

Gln Glu Gly Ile Val His Val Leu Lys Leu His Leu Gln Ser Asn His
                405                 410                 415

Pro Asp Asp Thr Phe Leu Phe Pro Lys Leu Leu Gln Lys Met Val Asp
            420                 425                 430

Leu Arg Gln Leu Val Thr Glu His Ala Gln Leu Val Gln Val Ile Lys
        435                 440                 445

Lys Thr Glu Ser Asp Ala Ala Leu His Pro Leu Leu Gln Glu Ile Tyr
450                 455                 460

Arg Asp Met Tyr
465

<210> SEQ ID NO 13
<211> LENGTH: 1323
<212> TYPE: DNA
<213> ORGANISM: Mus musculus
<220> FEATURE:
<221> NAME/KEY: CDS
<222> LOCATION: (1)...(1323)
<300> PUBLICATION INFORMATION:
<308> DATABASE ACCESSION NUMBER: GeneBank U10375
<309> DATABASE ENTRY DATE: 1994-07-22

<400> SEQUENCE: 13 atg gaa cag cca cag gag gag acc cct gag gcc cgg gaa gag gag aaa      48
Met Glu Gln Pro Gln Glu Glu Thr Pro Glu Ala Arg Glu Glu Glu Lys
 1               5                  10                  15 gag gaa gtg gcc atg ggt gac gga gcc ccg gag ctc aat ggg gga cca      96
Glu Glu Val Ala Met Gly Asp Gly Ala Pro Glu Leu Asn Gly Gly Pro
            20                  25                  30
```

| | |
|---|---:|
| gaa cac acg ctt cct tcc agc agc tgt gca gac ctc tcc cag aat tcc<br>Glu His Thr Leu Pro Ser Ser Ser Cys Ala Asp Leu Ser Gln Asn Ser<br>     35                     40                  45 | 144 |
| tcc cct tcc tcc ctg ctg gac cag ctg cag atg ggc tgt gat ggg gcc<br>Ser Pro Ser Ser Leu Leu Asp Gln Leu Gln Met Gly Cys Asp Gly Ala<br> 50                    55                  60 | 192 |
| tca ggc ggc agc ctc aac atg gaa tgt cgg gtg tgc ggg gac aag gcc<br>Ser Gly Gly Ser Leu Asn Met Glu Cys Arg Val Cys Gly Asp Lys Ala<br>65                70                 75                 80 | 240 |
| tcg ggc ttc cac tac ggg gtc cac gcg tgc gag ggg tgc aag ggc ttc<br>Ser Gly Phe His Tyr Gly Val His Ala Cys Glu Gly Cys Lys Gly Phe<br>                85                  90                 95 | 288 |
| ttc cgc cgg aca atc cgc atg aag ctc gag tat gag aag tgc gat cgg<br>Phe Arg Arg Thr Ile Arg Met Lys Leu Glu Tyr Glu Lys Cys Asp Arg<br>            100                 105               110 | 336 |
| atc tgc aag atc cag aag aag aac cgc aac aag tgt cag tac tgc cgc<br>Ile Cys Lys Ile Gln Lys Lys Asn Arg Asn Lys Cys Gln Tyr Cys Arg<br>        115                 120               125 | 384 |
| ttc cag aag tgc ctg gca ctc ggc atg tcg cac aac gct atc cgc ttt<br>Phe Gln Lys Cys Leu Ala Leu Gly Met Ser His Asn Ala Ile Arg Phe<br>130                  135               140 | 432 |
| gga cgg atg ccg gac ggc gag aag agg aag ctg gtg gcg ggg ctg act<br>Gly Arg Met Pro Asp Gly Glu Lys Arg Lys Leu Val Ala Gly Leu Thr<br>145                  150               155               160 | 480 |
| gcc agc gag ggg tgc cag cac aac ccc cag ctg gcc gac ctg aag gcc<br>Ala Ser Glu Gly Cys Gln His Asn Pro Gln Leu Ala Asp Leu Lys Ala<br>                165               170               175 | 528 |
| ttc tct aag cac atc tac aac gcc tac ctg aaa aac ttc aac atg acc<br>Phe Ser Lys His Ile Tyr Asn Ala Tyr Leu Lys Asn Phe Asn Met Thr<br>            180                 185               190 | 576 |
| aaa aag aag gcc cgg agc atc ctc acc ggc aag tcc agc cac aac gca<br>Lys Lys Lys Ala Arg Ser Ile Leu Thr Gly Lys Ser Ser His Asn Ala<br>        195                 200               205 | 624 |
| ccc ttt gtc atc cac gac atc gag aca ctg tgg cag gca gag aag ggc<br>Pro Phe Val Ile His Asp Ile Glu Thr Leu Trp Gln Ala Glu Lys Gly<br>210                  215               220 | 672 |
| ctg gtg tgg aaa cag ctg gtg aac ggg ctg ccg ccc tac aac gag atc<br>Leu Val Trp Lys Gln Leu Val Asn Gly Leu Pro Pro Tyr Asn Glu Ile<br>225                  230               235               240 | 720 |
| agt gtg cac gtg ttc tac cgc tgc cag tcc acc aca gtg gag aca gtc<br>Ser Val His Val Phe Tyr Arg Cys Gln Ser Thr Thr Val Glu Thr Val<br>                245               250               255 | 768 |
| cga gag ctc acc gag ttc gcc aag aac atc ccc aac ttc agc agc ctc<br>Arg Glu Leu Thr Glu Phe Ala Lys Asn Ile Pro Asn Phe Ser Ser Leu<br>        260                 265               270 | 816 |
| ttc ctc aat gac cag gtg acc ctc ctc aag tat ggc gtg cac gag gcc<br>Phe Leu Asn Asp Gln Val Thr Leu Leu Lys Tyr Gly Val His Glu Ala<br>275                  280               285 | 864 |
| atc ttt gcc atg ctg gcc tcc atc gtc aac aaa gac ggg ctg ctg gtg<br>Ile Phe Ala Met Leu Ala Ser Ile Val Asn Lys Asp Gly Leu Leu Val<br>        290                 295               300 | 912 |
| gcc aac ggc agt ggc ttc gtc acc cac gag ttc ttg cga agt ctc cgc<br>Ala Asn Gly Ser Gly Phe Val Thr His Glu Phe Leu Arg Ser Leu Arg<br>305                  310               315               320 | 960 |
| aag ccc ttc agt gac atc att gag ccc aag ttc gag ttt gct gtc aag<br>Lys Pro Phe Ser Asp Ile Ile Glu Pro Lys Phe Glu Phe Ala Val Lys<br>                325               330               335 | 1008 |
| ttc aat gcg ctg gag ctc gat gac agt gac ctg gcg ctc ttc atc gcg<br>Phe Asn Ala Leu Glu Leu Asp Asp Ser Asp Leu Ala Leu Phe Ile Ala<br>            340                 345               350 | 1056 |

```
gcc atc att ctg tgt gga gac cgg cca ggc ctc atg aat gtg ccc cag      1104
Ala Ile Ile Leu Cys Gly Asp Arg Pro Gly Leu Met Asn Val Pro Gln
            355                 360                 365 gta gaa gcc atc cag gac acc att ctg cgg gct cta gaa ttc cat ctg      1152
Val Glu Ala Ile Gln Asp Thr Ile Leu Arg Ala Leu Glu Phe His Leu
        370                 375                 380 cag gtc aac cac cct gac agc cag tac ctc ttc ccc aag ctg ctg cag      1200
Gln Val Asn His Pro Asp Ser Gln Tyr Leu Phe Pro Lys Leu Leu Gln
385                 390                 395                 400 aag atg gca gac ctg cgg cag ctg gtc act gag cat gcc cag atg atg      1248
Lys Met Ala Asp Leu Arg Gln Leu Val Thr Glu His Ala Gln Met Met
                405                 410                 415 cag tgg cta aag aag acg gag agt gag acc ttg ctg cac ccc ctg ctc      1296
Gln Trp Leu Lys Lys Thr Glu Ser Glu Thr Leu Leu His Pro Leu Leu
            420                 425                 430 cag gaa atc tac aag gac atg tac taa                                  1323
Gln Glu Ile Tyr Lys Asp Met Tyr *
                435                 440

<210> SEQ ID NO 14
<211> LENGTH: 440
<212> TYPE: PRT
<213> ORGANISM: Mus musculus

<400> SEQUENCE: 14

Met Glu Gln Pro Gln Glu Glu Thr Pro Glu Ala Arg Glu Glu Lys
  1               5                  10                  15

Glu Glu Val Ala Met Gly Asp Gly Ala Pro Glu Leu Asn Gly Gly Pro
            20                  25                  30

Glu His Thr Leu Pro Ser Ser Ser Cys Ala Asp Leu Ser Gln Asn Ser
        35                  40                  45

Ser Pro Ser Ser Leu Leu Asp Gln Leu Gln Met Gly Cys Asp Gly Ala
    50                  55                  60

Ser Gly Gly Ser Leu Asn Met Glu Cys Arg Val Cys Gly Asp Lys Ala
65                  70                  75                  80

Ser Gly Phe His Tyr Gly Val His Ala Cys Glu Gly Cys Lys Gly Phe
                85                  90                  95

Phe Arg Arg Thr Ile Arg Met Lys Leu Glu Tyr Glu Lys Cys Asp Arg
            100                 105                 110

Ile Cys Lys Ile Gln Lys Lys Asn Arg Asn Lys Cys Gln Tyr Cys Arg
        115                 120                 125

Phe Gln Lys Cys Leu Ala Leu Gly Met Ser His Asn Ala Ile Arg Phe
    130                 135                 140

Gly Arg Met Pro Asp Gly Glu Lys Arg Lys Leu Val Ala Gly Leu Thr
145                 150                 155                 160

Ala Ser Glu Gly Cys Gln His Asn Pro Gln Leu Ala Asp Leu Lys Ala
                165                 170                 175

Phe Ser Lys His Ile Tyr Asn Ala Tyr Leu Lys Asn Phe Asn Met Thr
            180                 185                 190

Lys Lys Lys Ala Arg Ser Ile Leu Thr Gly Lys Ser Ser His Asn Ala
        195                 200                 205

Pro Phe Val Ile His Asp Ile Glu Thr Leu Trp Gln Ala Glu Lys Gly
    210                 215                 220

Leu Val Trp Lys Gln Leu Val Asn Gly Leu Pro Pro Tyr Asn Glu Ile
225                 230                 235                 240

Ser Val His Val Phe Tyr Arg Cys Gln Ser Thr Thr Val Glu Thr Val
                245                 250                 255
```

```
Arg Glu Leu Thr Glu Phe Ala Lys Asn Ile Pro Asn Phe Ser Ser Leu
        260                 265                 270

Phe Leu Asn Asp Gln Val Thr Leu Leu Lys Tyr Gly Val His Glu Ala
            275                 280                 285

Ile Phe Ala Met Leu Ala Ser Ile Val Asn Lys Asp Gly Leu Leu Val
        290                 295                 300

Ala Asn Gly Ser Gly Phe Val Thr His Glu Phe Leu Arg Ser Leu Arg
305                 310                 315                 320

Lys Pro Phe Ser Asp Ile Ile Glu Pro Lys Phe Glu Phe Ala Val Lys
                325                 330                 335

Phe Asn Ala Leu Glu Leu Asp Asp Ser Asp Leu Ala Leu Phe Ile Ala
            340                 345                 350

Ala Ile Ile Leu Cys Gly Asp Arg Pro Gly Leu Met Asn Val Pro Gln
        355                 360                 365

Val Glu Ala Ile Gln Asp Thr Ile Leu Arg Ala Leu Glu Phe His Leu
    370                 375                 380

Gln Val Asn His Pro Asp Ser Gln Tyr Leu Phe Pro Lys Leu Leu Gln
385                 390                 395                 400

Lys Met Ala Asp Leu Arg Gln Leu Val Thr Glu His Ala Gln Met Met
                405                 410                 415

Gln Trp Leu Lys Lys Thr Glu Ser Glu Thr Leu Leu His Pro Leu Leu
            420                 425                 430

Gln Glu Ile Tyr Lys Asp Met Tyr
        435                 440

<210> SEQ ID NO 15
<211> LENGTH: 1827
<212> TYPE: DNA
<213> ORGANISM: Homo Sapien
<220> FEATURE:
<221> NAME/KEY: CDS
<222> LOCATION: (292)...(1683)
<300> PUBLICATION INFORMATION:
<308> DATABASE ACCESSION NUMBER: GeneBank XM_053680
<309> DATABASE ENTRY DATE: 2002-05-08

<400> SEQUENCE: 15
gtagcggtga cggcggcggc ggcggcggcg gcagcattat gcgtgattac tgacaggcac       60
cagctgctgc cgccacagcc gtctcaaacg cactatgtgg actctccgat ctagaggcag      120
attcctgact aatcccagag ggctggccca gcctgtgctc cccgggctgc taggaagcga      180
tgaccactct tgttagccca agttgaagaa agccgggctg tgcctgggag ccagagaggg      240
cggtaatatt tagaagctgc acaggagagg aacatgaact gacgagtaaa c atg tat      297
                                                          Met Tyr
                                                            1 gga aat tat tct cac ttc atg aag ttt ccc gca ggc tat gga ggc tcc      345
Gly Asn Tyr Ser His Phe Met Lys Phe Pro Ala Gly Tyr Gly Gly Ser
        5                   10                  15 cct ggc cac act ggc tct aca tcc atg agc cca tca gca gcc ttg tcc      393
Pro Gly His Thr Gly Ser Thr Ser Met Ser Pro Ser Ala Ala Leu Ser
    20                  25                  30 aca ggg aag cca atg gac agc cac ccc agc tac aca gat acc cca gtg      441
Thr Gly Lys Pro Met Asp Ser His Pro Ser Tyr Thr Asp Thr Pro Val
35                  40                  45                  50 agt gcc cca cgg act ctg agt gca gtg ggg acc ccc ctc aat gcc ctg      489
Ser Ala Pro Arg Thr Leu Ser Ala Val Gly Thr Pro Leu Asn Ala Leu
                55                  60                  65 ggc tct cca tat cga gtc atc acc tct gcc atg ggc cca ccc tca gga      537
Gly Ser Pro Tyr Arg Val Ile Thr Ser Ala Met Gly Pro Pro Ser Gly
```

-continued

```
                     70                      75                       80
gca ctt gca gcg cct cca gga atc aac ttg gtt gcc cca ccc agc tct       585
Ala Leu Ala Ala Pro Pro Gly Ile Asn Leu Val Ala Pro Pro Ser Ser
             85                      90                      95 cag cta aat gtg gtc aac agt gtc agc agt tca gag gac atc aag ccc       633
Gln Leu Asn Val Val Asn Ser Val Ser Ser Glu Asp Ile Lys Pro
        100                     105                     110 tta cca ggg ctt ccc ggg att gga aac atg aac tac cca tcc acc agc       681
Leu Pro Gly Leu Pro Gly Ile Gly Asn Met Asn Tyr Pro Ser Thr Ser
115                     120                     125                 130 ccc gga tct ctg gtt aaa cac atc tgt gcc atc tgt gga gac aga tcc       729
Pro Gly Ser Leu Val Lys His Ile Cys Ala Ile Cys Gly Asp Arg Ser
                135                     140                     145 tca gga aag cac tac ggg gta tac agt tgt gaa ggc tgc aaa ggg ttc       777
Ser Gly Lys His Tyr Gly Val Tyr Ser Cys Glu Gly Cys Lys Gly Phe
            150                     155                     160 ttc aag agg acg ata agg aag gac ctc atc tac acg tgt cgg gat aat       825
Phe Lys Arg Thr Ile Arg Lys Asp Leu Ile Tyr Thr Cys Arg Asp Asn
        165                     170                     175 aaa gac tgc ctc att gac aag cgt cag cgc aac cgc tgc cag tac tgt       873
Lys Asp Cys Leu Ile Asp Lys Arg Gln Arg Asn Arg Cys Gln Tyr Cys
180                     185                     190 cgc tat cag aag tgc ctt gtc atg ggc atg aag agg gaa gct gtg caa       921
Arg Tyr Gln Lys Cys Leu Val Met Gly Met Lys Arg Glu Ala Val Gln
195                     200                     205                 210 gaa gaa aga cag agg agc cga gag cga gct gag agt gag gca gaa tgt       969
Glu Glu Arg Gln Arg Ser Arg Glu Arg Ala Glu Ser Glu Ala Glu Cys
            215                     220                     225 gct acc agt ggt cat gaa gac atg cct gtg gag agg att cta gaa gct      1017
Ala Thr Ser Gly His Glu Asp Met Pro Val Glu Arg Ile Leu Glu Ala
        230                     235                     240 gaa ctt gct gtt gaa cca aag aca gaa tcc tat ggt gac atg aat atg      1065
Glu Leu Ala Val Glu Pro Lys Thr Glu Ser Tyr Gly Asp Met Asn Met
            245                     250                     255 gag aac tcg aca aat gac cct gtt acc aac ata tgt cat gct gct gac      1113
Glu Asn Ser Thr Asn Asp Pro Val Thr Asn Ile Cys His Ala Ala Asp
        260                     265                     270 aag cag ctt ttc acc ctc gtt gaa tgg gcc aag cgt att ccc cac ttc      1161
Lys Gln Leu Phe Thr Leu Val Glu Trp Ala Lys Arg Ile Pro His Phe
275                     280                     285                 290 tct gac ctc acc ttg gag gac cag gtc att ttg ctt cgg gca ggg tgg      1209
Ser Asp Leu Thr Leu Glu Asp Gln Val Ile Leu Leu Arg Ala Gly Trp
            295                     300                     305 aat gaa ttg ctg att gcc tct ttc tcc cac cgc tca gtt tcc gtg cag      1257
Asn Glu Leu Leu Ile Ala Ser Phe Ser His Arg Ser Val Ser Val Gln
        310                     315                     320 gat ggc atc ctt ctg gcc acg ggt tta cat gtc cac cgg agc agt gcc      1305
Asp Gly Ile Leu Leu Ala Thr Gly Leu His Val His Arg Ser Ser Ala
            325                     330                     335 cac agt gct ggg gtc ggc tcc atc ttt gac aga gtc cta act gag ctg      1353
His Ser Ala Gly Val Gly Ser Ile Phe Asp Arg Val Leu Thr Glu Leu
        340                     345                     350 gtt tcc aaa atg aaa gac atg cag atg gac aag tcg gaa ctg gga tgc      1401
Val Ser Lys Met Lys Asp Met Gln Met Asp Lys Ser Glu Leu Gly Cys
355                     360                     365                 370 ctg cga gcc att gta ctc ttt aac cca gat gcc aag ggc ctg tcc aac      1449
Leu Arg Ala Ile Val Leu Phe Asn Pro Asp Ala Lys Gly Leu Ser Asn
            375                     380                     385 ccc tct gag gtg gag act ctg cga gag aag gtt tat gcc acc ctt gag      1497
Pro Ser Glu Val Glu Thr Leu Arg Glu Lys Val Tyr Ala Thr Leu Glu
```

```
                       390                 395                 400
gcc tac acc aag cag aag tat ccg gaa cag cca ggc agg ttt gcc aag         1545
Ala Tyr Thr Lys Gln Lys Tyr Pro Glu Gln Pro Gly Arg Phe Ala Lys
            405                 410                 415 ctg ctg ctg cgc ctc cca gct ctg cgt tcc att ggc ttg aaa tgc ctg         1593
Leu Leu Leu Arg Leu Pro Ala Leu Arg Ser Ile Gly Leu Lys Cys Leu
420                 425                 430 gag cac ctc ttc ttc ttc aag ctc atc ggg gac acc ccc att gac acc         1641
Glu His Leu Phe Phe Phe Lys Leu Ile Gly Asp Thr Pro Ile Asp Thr
435                 440                 445                 450 ttc ctc atg gag atg ttg gag acc ccg ctg cag atc acc tga                 1683
Phe Leu Met Glu Met Leu Glu Thr Pro Leu Gln Ile Thr  *
                455                 460 gccccaccag ccacagcctc cccacccagg atgaccctg ggcaggtgtg tgtggacccc        1743
caccctgcac tttcctccac ctcccaccct gaccccttc ctgtcccaa aatgtgatgc         1803 ttataataaa gaaaaccttt ctac                                              1827

<210> SEQ ID NO 16
<211> LENGTH: 463
<212> TYPE: PRT
<213> ORGANISM: Homo Sapien

<400> SEQUENCE: 16

Met Tyr Gly Asn Tyr Ser His Phe Met Lys Phe Pro Ala Gly Tyr Gly
1               5                   10                  15

Gly Ser Pro Gly His Thr Gly Ser Thr Ser Met Ser Pro Ser Ala Ala
            20                  25                  30

Leu Ser Thr Gly Lys Pro Met Asp Ser His Pro Ser Tyr Thr Asp Thr
        35                  40                  45

Pro Val Ser Ala Pro Arg Thr Leu Ser Ala Val Gly Thr Pro Leu Asn
    50                  55                  60

Ala Leu Gly Ser Pro Tyr Arg Val Ile Thr Ser Ala Met Gly Pro Pro
65                  70                  75                  80

Ser Gly Ala Leu Ala Ala Pro Gly Ile Asn Leu Val Ala Pro Pro
            85                  90                  95

Ser Ser Gln Leu Asn Val Val Asn Ser Val Ser Ser Ser Glu Asp Ile
            100                 105                 110

Lys Pro Leu Pro Gly Leu Pro Gly Ile Gly Asn Met Asn Tyr Pro Ser
        115                 120                 125

Thr Ser Pro Gly Ser Leu Val Lys His Ile Cys Ala Ile Cys Gly Asp
130                 135                 140

Arg Ser Ser Gly Lys His Tyr Gly Val Tyr Ser Cys Glu Gly Cys Lys
145                 150                 155                 160

Gly Phe Phe Lys Arg Thr Ile Arg Lys Asp Leu Ile Tyr Thr Cys Arg
                165                 170                 175

Asp Asn Lys Asp Cys Leu Ile Asp Lys Arg Gln Arg Asn Arg Cys Gln
            180                 185                 190

Tyr Cys Arg Tyr Gln Lys Cys Leu Val Met Gly Met Lys Arg Glu Ala
        195                 200                 205

Val Gln Glu Glu Arg Gln Arg Ser Arg Glu Arg Ala Glu Ser Glu Ala
    210                 215                 220

Glu Cys Ala Thr Ser Gly His Glu Asp Met Pro Val Glu Arg Ile Leu
225                 230                 235                 240

Glu Ala Glu Leu Ala Val Glu Pro Lys Thr Glu Ser Tyr Gly Asp Met
                245                 250                 255
```

```
Asn Met Glu Asn Ser Thr Asn Asp Pro Val Thr Asn Ile Cys His Ala
            260                 265                 270

Ala Asp Lys Gln Leu Phe Thr Leu Val Glu Trp Ala Lys Arg Ile Pro
        275                 280                 285

His Phe Ser Asp Leu Thr Leu Glu Asp Gln Val Ile Leu Leu Arg Ala
    290                 295                 300

Gly Trp Asn Glu Leu Leu Ile Ala Ser Phe Ser His Arg Ser Val Ser
305                 310                 315                 320

Val Gln Asp Gly Ile Leu Leu Ala Thr Gly Leu His Val His Arg Ser
                325                 330                 335

Ser Ala His Ser Ala Gly Val Gly Ser Ile Phe Asp Arg Val Leu Thr
            340                 345                 350

Glu Leu Val Ser Lys Met Lys Asp Met Gln Met Asp Lys Ser Glu Leu
        355                 360                 365

Gly Cys Leu Arg Ala Ile Val Leu Phe Asn Pro Asp Ala Lys Gly Leu
    370                 375                 380

Ser Asn Pro Ser Glu Val Glu Thr Leu Arg Glu Lys Val Tyr Ala Thr
385                 390                 395                 400

Leu Glu Ala Tyr Thr Lys Gln Lys Tyr Pro Glu Gln Pro Gly Arg Phe
                405                 410                 415

Ala Lys Leu Leu Leu Arg Leu Pro Ala Leu Arg Ser Ile Gly Leu Lys
            420                 425                 430

Cys Leu Glu His Leu Phe Phe Phe Lys Leu Ile Gly Asp Thr Pro Ile
        435                 440                 445

Asp Thr Phe Leu Met Glu Met Leu Glu Thr Pro Leu Gln Ile Thr
    450                 455                 460

<210> SEQ ID NO 17
<211> LENGTH: 1330
<212> TYPE: DNA
<213> ORGANISM: Homo Sapien
<220> FEATURE:
<221> NAME/KEY: CDS
<222> LOCATION: (97)...(837)
<300> PUBLICATION INFORMATION:
<308> DATABASE ACCESSION NUMBER: GeneBank XM_042579
<309> DATABASE ENTRY DATE: 2002-02-06

<400> SEQUENCE: 17
ttggggttgt gctccaggga tggcctttca catagactgc agtgtaaatg acagcctctg      60
gaatgtgcat tgcagggcct tgcttagtgg taggga atg att tcc atc act tct     114
                                       Met Ile Ser Ile Thr Ser
                                         1               5 gtg aca ttc tgc ttc cca ata agt ctt cct gtg act tcc cta ttt ccc      162
Val Thr Phe Cys Phe Pro Ile Ser Leu Pro Val Thr Ser Leu Phe Pro
             10                  15                  20 cca tcc cag att aac tca aca gtg tca ctc cct ggg ggt ggg tct ggc      210
Pro Ser Gln Ile Asn Ser Thr Val Ser Leu Pro Gly Gly Gly Ser Gly
         25                  30                  35 ccc cct gaa gat gtg aag cca cca gtc tta ggg gtc cgg ggc ctg cac      258
Pro Pro Glu Asp Val Lys Pro Pro Val Leu Gly Val Arg Gly Leu His
 40                  45                  50 tgt cca ccc cct cca ggt ggc cct ggg gct ggc aaa cgg cta tgt gca      306
Cys Pro Pro Pro Pro Gly Gly Pro Gly Ala Gly Lys Arg Leu Cys Ala
 55                  60                  65                  70 atc tgc ggg gac aga agc tca ggc aaa cac tac ggg gtt tac agc tgt      354
Ile Cys Gly Asp Arg Ser Ser Gly Lys His Tyr Gly Val Tyr Ser Cys
             75                  80                  85 gag ggt tgc aag ggc ttc ttc aaa cgc acc atc cgc aaa gac ctt aca      402
```

```
                Glu Gly Cys Lys Gly Phe Phe Lys Arg Thr Ile Arg Lys Asp Leu Thr
                             90                  95                 100 tac tct tgc cgg gac aac aaa gac tgc aca gtg gac aag cgc cag cgg      450
Tyr Ser Cys Arg Asp Asn Lys Asp Cys Thr Val Asp Lys Arg Gln Arg
            105                 110                 115 aac cgc tgt cag tac tgc cgc tat cag aag tgc ctg gcc act ggc atg      498
Asn Arg Cys Gln Tyr Cys Arg Tyr Gln Lys Cys Leu Ala Thr Gly Met
        120                 125                 130 aag agg gag gcg gta cag gag gag cgt cag cgg gga aag gac aag gat      546
Lys Arg Glu Ala Val Gln Glu Glu Arg Gln Arg Gly Lys Asp Lys Asp
135                 140                 145                 150 ggg gat ggg gag ggg gct ggg gga gcc ccc gag gag atg cct gtg gac      594
Gly Asp Gly Glu Gly Ala Gly Gly Ala Pro Glu Glu Met Pro Val Asp
                155                 160                 165 agg atc ctg gag gca gag ctt gct gtg gaa cag aag agt gac cag ggc      642
Arg Ile Leu Glu Ala Glu Leu Ala Val Glu Gln Lys Ser Asp Gln Gly
            170                 175                 180 gtt gag ggt cct ggg gga acc ggg ggt agc ggc agc agc gtg agt gtt      690
Val Glu Gly Pro Gly Gly Thr Gly Gly Ser Gly Ser Ser Val Ser Val
        185                 190                 195 ggg gtc aat cca ctc tcc ttc gtg atg ggg gtt ggg gga ggt agt cta      738
Gly Val Asn Pro Leu Ser Phe Val Met Gly Val Gly Gly Gly Ser Leu
200                 205                 210 ggt ctg ttc tac atc ccc tcc ccc tcc ttt ccc ctc ata acc ttc cta      786
Gly Leu Phe Tyr Ile Pro Ser Pro Ser Phe Pro Leu Ile Thr Phe Leu
215                 220                 225                 230 aca cta ctt ggg act gga ggt gct gcc aaa caa ggt ctt tca aac atc      834
Thr Leu Leu Gly Thr Gly Gly Ala Ala Lys Gln Gly Leu Ser Asn Ile
                235                 240                 245 tga ggtggatgtg atagctcctt ctgtctccac tccccaaaca acccactggc           887
* agaaccatag gcatgtccca aataaataat tgtttgcact aatgccagaa gagaagactc    947
acttacaggg attggtttgg atggggctca caggaagact atatgtaagg aggggtgtc    1007 aaaagcctct tacaaggggg ctcccagcat atctcaaaat cttccataac tcttacccc    1067 gtcccctgca gccaaatgac cctgtgacta acatctgtca ggcagctgac aaacagctat   1127
tcacgcttgt tgagtgggcg aagaggatcc cacactttc ctccttgcct ctggatgatc    1187
aggtcatatt gctgcgggca ggtcagtgac cttggatccc tttgacttct tgacatttga   1247
cccctctttg acttcccgat ctttagtgac cccagtggcc ttaccttgcg tacccaggga   1307
gccaaacttg ctgacctcgc cac                                           1330

<210> SEQ ID NO 18
<211> LENGTH: 246
<212> TYPE: PRT
<213> ORGANISM: Homo Sapien

<400> SEQUENCE: 18

Met Ile Ser Ile Thr Ser Val Thr Phe Cys Phe Pro Ile Ser Leu Pro
1               5                   10                  15

Val Thr Ser Leu Phe Pro Pro Ser Gln Ile Asn Ser Thr Val Ser Leu
            20                  25                  30

Pro Gly Gly Gly Ser Gly Pro Pro Glu Asp Val Lys Pro Pro Val Leu
        35                  40                  45

Gly Val Arg Gly Leu His Cys Pro Pro Pro Gly Gly Pro Gly Ala
    50                  55                  60

Gly Lys Arg Leu Cys Ala Ile Cys Gly Asp Arg Ser Ser Gly Lys His
65                  70                  75                  80
```

```
Tyr Gly Val Tyr Ser Cys Glu Gly Cys Lys Gly Phe Phe Lys Arg Thr
                85              90              95
Ile Arg Lys Asp Leu Thr Tyr Ser Cys Arg Asp Asn Lys Asp Cys Thr
            100             105             110
Val Asp Lys Arg Gln Arg Asn Arg Cys Gln Tyr Cys Arg Tyr Gln Lys
            115             120             125
Cys Leu Ala Thr Gly Met Lys Arg Glu Ala Val Gln Glu Glu Arg Gln
    130             135             140
Arg Gly Lys Asp Lys Asp Gly Asp Gly Glu Gly Ala Gly Gly Ala Pro
145             150             155             160
Glu Glu Met Pro Val Asp Arg Ile Leu Glu Ala Glu Leu Ala Val Glu
                165             170             175
Gln Lys Ser Asp Gln Gly Val Glu Gly Pro Gly Gly Thr Gly Gly Ser
            180             185             190
Gly Ser Ser Val Ser Val Gly Val Asn Pro Leu Ser Phe Val Met Gly
        195             200             205
Val Gly Gly Gly Ser Leu Gly Leu Phe Tyr Ile Pro Ser Pro Ser Phe
    210             215             220
Pro Leu Ile Thr Phe Leu Thr Leu Leu Gly Thr Gly Gly Ala Ala Lys
225             230             235             240
Gln Gly Leu Ser Asn Ile
            245
```

MODULATORS OF LXR

RELATED APPLICATIONS

Benefit of priority under 35 U.S.C. 119(e) is claimed herein to U.S. provisional patent application No. 60/342,707, filed Dec. 21, 2001, to Bayne et al., entitled "MODULATORS OF LXR". The disclosure of the above-referenced application is incorporated by reference herein in its entirety.

FIELD OF THE INVENTION

Compounds, compositions and methods for modulating the activity of liver X receptors (LXRs) are provided. In particular, pyridone derivatives are provided for modulating the activity of LXRs.

BACKGROUND OF THE INVENTION

Nuclear Receptors

Nuclear receptors are a superfamily of regulatory proteins that are structurally and functionally related and are receptors for, e.g., steroids, retinoids, vitamin D and thyroid hormones (see, e.g., Evans (1988) *Science* 240:889-895). These proteins bind to cis-acting elements in the promoters of their target genes and modulate gene expression in response to ligands for the receptors.

Nuclear receptors can be classified based on their DNA binding properties (see, e.g., Evans, supra and Glass (1994) *Endocr. Rev.* 15:391-407). For example, one class of nuclear receptors includes the glucocorticoid, estrogen, androgen, progestin and mineralocorticoid receptors which bind as homodimers to hormone response elements (HREs) organized as inverted repeats (see, e.g., Glass, supra). A second class of receptors, including those activated by retinoic acid, thyroid hormone, vitamin $D_3$, fatty acids/peroxisome proliferators (i.e., peroxisome proliferator activated receptors or PPARs) and ecdysone, bind to HREs as heterodimers with a common partner, the retinoid X receptors (i.e., RXRs, also known as the 9-cis retinoic acid receptors; see, e.g., Levin et al. (1992) *Nature* 355:359-361 and Heyman et al. (1992) *Cell* 68:397-406).

RXRs are unique among the nuclear receptors in that they bind DNA as a homodimer and are required as a heterodimeric partner for a number of additional nuclear receptors to bind DNA (see, e.g., Mangelsdorf et al. (1995) *Cell* 83:841-850). The latter receptors, termed the class II nuclear receptor subfamily, include many which are established or implicated as important regulators of gene expression. There are three RXR genes (see, e.g., Mangelsdorf et al. (1992) *Genes Dev.* 6:329-344), coding for RXRα, -β, and -γ, all of which are able to heterodimerize with any of the class II receptors, although there appear to be preferences for distinct RXR subtypes by partner receptors in vivo (see, e.g., Chiba et al. (1997) *Mol. Cell. Biol.* 17:3013-3020). In the adult liver, RXRα is the most abundant of the three RXRs (see, e.g., Mangelsdorf et al. (1992) *Genes Dev.* 6:329-344), suggesting that it might have a prominent role in hepatic functions that involve regulation by class II nuclear receptors. See also, Wan et al. (2000) *Mol. Cell. Biol.* 20:4436-4444.

Orphan Nuclear Receptors

Included in the nuclear receptor superfamily of regulatory proteins are nuclear receptors for whom the ligand is known and those which lack known ligands. Nuclear receptors falling in the latter category are referred to as orphan nuclear receptors. The search for activators for orphan receptors has led to the discovery of previously unknown signaling pathways (see, e.g., Levin et al., (1992), supra and Heyman et al., (1992), supra). For example, it has been reported that bile acids, which are involved in physiological processes such as cholesterol catabolism, are ligands for farnesoid X receptor (FXR).

Since it is known that products of intermediary metabolism act as transcriptional regulators in bacteria and yeast, such molecules may serve similar functions in higher organisms (see, e.g., Tomkins (1975) *Science* 189:760-763 and O'Malley (1989) *Endocrinology* 125:1119-1120). For example, one biosynthetic pathway in higher eukaryotes is the mevalonate pathway, which leads to the synthesis of cholesterol, bile acids, porphyrin, dolichol, ubiquinone, carotenoids, retinoids, vitamin D, steroid hormones and farnesylated proteins.

LXRα and LXRβ

LXRα is found predominantly in the liver, with lower levels found in kidney, intestine, spleen and adrenal tissue (see, e.g., Willy, et al. (1995) *Gene Dev.* 9(9):1033-1045). LXRβ is ubiquitous in mammals and was found in nearly all tissues examined. LXRs are activated by certain naturally occurring, oxidized derivatives of cholesterol (see, e.g., Lehmann, et al. (1997) *J. Biol. Chem.* 272(6):3137-3140). LXRα is activated by oxycholesterol and promotes cholesterol metabolism (Peet et al. (1998) *Cell* 93:693-704). Thus, LXRs appear to play a role in, e.g., cholesterol metabolism (see, e.g., Janowski, et al. (1996) *Nature* 383:728-731).

Nuclear Receptors and Disease

Nuclear receptor activity has been implicated in a variety of diseases and disorders, including, but not limited to, hypercholesterolemia (see, e.g., International Patent Application Publication No. WO 00/57915), osteoporosis and vitamin deficiency (see, e.g., U.S. Pat. No. 6,316,5103), hyperlipoproteinemia (see, e.g., International Patent Application Publication No. WO 01/60818), hypertriglyceridemia, lipodystrophy, hyperglycemia and diabetes mellitus (see, e.g., International Patent Application Publication No. WO 01/82917), atherosclerosis and gallstones (see, e.g., International Patent Application Publication No. WO 00/37077), disorders of the skin and mucous membranes (see, e.g., U.S. Pat. Nos. 6,184,215 and 6,187,814, and International Patent Application Publication No. WO 98/32444), acne (see, e.g., International Patent Application Publication No. WO 00/49992), and cancer, Parkinson's disease and Alzheimer's disease (see, e.g., International Patent Application Publication No. WO 00/17334). Activity of nuclear receptors, including LXRs, FXR and PPAR, and orphan nuclear receptors, has been implicated in physiological processes including, but not limited to, bile acid biosynthesis, cholesterol metabolism or catabolism, and modulation of cholesterol 7α-hydroxylase gene (CYP7A1) transcription (see, e.g., Chiang et al. (2000) *J. Biol. Chem.* 275:10918-10924), HDL metabolism (see, e.g., Urizar et al. (2000) *J. Biol. Chem.* 275:39313-39317 and International Patent Application Publication No. WO 01/03705), and increased cholesterol efflux and increased expression of ATP binding cassette transporter protein (ABC1) (see, e.g., International Patent Application Publication No. WO 00/78972).

Thus, there is a need for compounds, compositions and methods of modulating the activity of nuclear receptors, including LXRs, FXR, PPAR and orphan nuclear receptors. Such compounds are useful in the treatment, prevention, or amelioration of one or more symptoms of diseases or disorders in which nuclear receptor activity is implicated.

SUMMARY OF THE INVENTION

Compounds for use in compositions and methods for modulating the activity of nuclear receptors are provided. In particular, compounds for use in compositions and methods for modulating liver X receptors (LXRα and LXRβ), FXR, PPAR and/or orphan nuclear receptors are provided. In certain embodiments, the compounds are N-substituted pyridone compounds. In one embodiment, the compounds provided herein are agonists of LXR. In another embodiment, the compounds provided herein are antagonists of LXR. Agonists that exhibit low efficacy are, in certain embodiments, antagonists.

In one embodiment, the compounds for use in the compositions and methods provided herein have formula I:

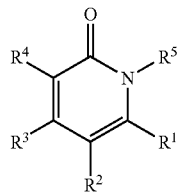

where, $R^1$ is selected from substituted or unsubstituted alkyl, substituted or unsubstituted alkenyl, substituted or unsubstituted alkynyl, substituted or unsubstituted aryl, substituted or unsubstituted heteroaryl, substituted or unsubstituted aralkyl, substituted or unsubstituted heteroaralkyl, substituted or unsubstituted cycloalkyl, substituted or unsubstituted cycloalkenyl, substituted or unsubstituted cycloalkynyl, substituted or, unsubstituted heterocyclyl, substituted or unsubstituted cycloalkylalkyl and substituted or unsubstituted heterocyclylalkyl;

$R^2$ is hydrogen, substituted or unsubstituted alkyl, substituted or unsubstituted alkenyl, substituted or unsubstituted alkynyl, substituted or unsubstituted aryl;

$R^3$ and $R^4$ are selected from (i), (ii), (iii) or (iv) as follows:
  (i) $R^3$ is substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocyclyl, substituted or unsubstituted alkylaryl, substituted or unsubstituted aryl, substituted or unsubstituted heteroaryl, $C(J)OR^{30}$ or $C(J)NR^{31}R^{32}$; and $R^4$ is hydrogen, substituted or unsubstituted alkyl, substituted or unsubstituted alkenyl, substituted or unsubstituted alkynyl, halide, pseudohalide, $C(J)R^{30}$, $C(J)OR^{30}$, $C(J)NR^{31}R^{32}$, $CH_2NR^{31}R^{32}$, $CH_2OR^{31}$, $CR^{30}=CR^{31}R^{32}$, $NO_2$ or $NR^{31}R^{32}$;
  (ii) $R^3$ and $R^4$, together with the atoms to which they are attached, form a substituted or unsubstituted heterocyclic ring;
  (iii) $R^3$ and $R^4$, together with the atoms to which they are attached, form a substituted or unsubstituted heterocyclic ring with the proviso that the nitrogen atom in the heterocyclic ring is not substituted with a phenyl ring; or
  (iv) $R^3$ and $R^4$, together with the atoms to which they are attached, form a substituted or unsubstituted heterocyclic ring with the proviso that the heterocyclic ring does not have more than one oxo substituent;

$R^5$ is substituted or unsubstituted alkyl, substituted or unsubstituted alkenyl, substituted or unsubstituted alkynyl, substituted or unsubstituted heterocyclyl, substituted or unsubstituted aryl, substituted or unsubstituted heteroaryl, substituted or unsubstituted aralkyl, substituted or unsubstituted aralkenyl, substituted or unsubstituted aralkynyl, substituted or unsubstituted heteroaralkyl, substituted or unsubstituted heteroaralkenyl, substituted or unsubstituted heteroaralkynyl, $-N=CR^6R^7$ or $-NR^9R^{10}$;

$R^6$ and $R^7$ are each independently hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted aryl, substituted or unsubstituted heteroaryl, substituted or unsubstituted aralkyl, or substituted or unsubstituted heteroaralkyl; or together form substituted or unsubstituted alkylene, substituted or unsubstituted alkenylene, substituted or unsubstituted alkynylene, or $-(CH_2)_xX(CH_2)_y$— where x and y are each independently 1, 2 or 3, and X is O, S or $NR^8$;

$R^8$ is substituted or unsubstituted alkyl, substituted or unsubstituted alkenyl, substituted or unsubstituted alkynyl, substituted or unsubstituted alkylcarbonyl, substituted or unsubstituted arylcarbonyl, or substituted or unsubstituted heteroarylcarbonyl;

$R^9$ and $R^{10}$ are each independently hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted aralkyl, or substituted or unsubstituted heteroaralkyl;

$R^{30}$ is hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, or substituted or unsubstituted heteroaralkyl;

$R^{31}$ and $R^{32}$ are each independently hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, $C(J)R^{35}$; or $R^{31}$ and $R^{32}$, together with the atoms to which they are attached, form substituted or unsubstituted cycloalkyl ring, a substituted or unsubstituted heterocyclic ring or a substituted or unsubstituted heteroaryl ring;

J is O, S or $NR^{40}$;

$R^{35}$ is hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted aryl, substituted or unsubstituted heteroaryl, substituted or unsubstituted alkoxy, substituted or unsubstituted aralkoxy, substituted or unsubstituted alkylamino, substituted or unsubstituted dialkylamino, substituted or unsubstituted arylalkylamino, or substituted or unsubstituted diarylamino;

$R^{40}$ is hydrogen, substituted or unsubstituted alkyl, substituted or unsubstituted aryl, or substituted or unsubstituted heteroaryl;

where the alkyl, alkenyl, alkynyl, cycloalkyl, heterocyclyl, alkylene, alkenylene, alkynylene, aryl, heteroaryl, aralkyl, aralkenyl, aralkynyl, heteroaralkyl, heteroaralkenyl and heteroaralkynyl moieties of $R^1$, $R^2$, $R^3$, $R^5$, $R^6$, $R^7$, $R^8$, $R^9$ and $R^{10}$ are unsubstituted or substituted with one or more substituents, in one embodiment, one to three or four substituents, each independently selected from $Q^1$, where $Q^1$ is halo, pseudohalo, hydroxy, oxo, thia, nitrile, nitro, formyl, mercapto, amino, hydroxyalkyl, hydroxyalkylaryloxy, hydroxyaryl, hydroxyalkylaryl, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, diaryl, hydroxyaryl, alkylaryl, heteroaryl, aralkyl, aralkenyl, aralkynyl, alkylaralkyl, heteroarylalkyl, trialkylsilyl, dialkylarylsilyl, alkyldiarylsilyl, triarylsilyl, alkylidene, arylalkylidene, alkylcarbonyl, alkylarylcarbonyl, arylcarbonyl, heterocyclylcarbonyl, heteroarylcarbonyl, alkoxycarbonyl, alkoxycarbonylalkyl, alkoxycarbonylaryloxy, aryloxycarbonyl, aryloxycarbonylalkyl, heterocyclylcarbonylalkylaryl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, haloalkoxy, alkoxyaryloxy, alkylaryloxy, diaryloxy, alkylaryloxyalkyl, alkyldiaryloxy, perfluoroalkoxy, alkenyloxy, alkynyloxy, aryloxyalkaoxy, aralkoxyaryloxy, alkylarylcycloalkyloxy, heterocycloxy, alkoxyalkyl, alkoxyalkoxyalkyl, alkylheteroaryloxy, alkylcycloalkoxy, cycloalkyloxy, heterocyclyloxy, aralkoxy, haloaryloxy, heteroaryloxy, alkylheteroaryloxy, alkoxycarbonylheterocycloxy, alkylcarbonylaryloxy, alkylcarbonyloxy, arylcarbonyloxy, aralkylcarbonyloxy, alkoxycarbonyloxy, aryloxycarbonyloxy, alkoxyaryloxy, aralkoxycarbonyloxy, ureido, alkylureido, arylureido, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, haloalkylarylamino, arylamino, diarylamino, alkylarylamino, aralkylamino, alkylcarbonylamino, aralkylcarbonylamino, haloalkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylenedioxyalkyl, dialkylalkylenedioxyalkyl, alkylsulfonylamino, arylsulfonylamino, azido, dialkylphosphonyl, alkylarylphosphonyl, diarylphosphonyl, alkylthio, arylthio, perfluoroalkylthio, hydroxycarbonylalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl, arylaminosulfonyl, diarylaminosulfonyl or alkylarylaminosulfonyl; or two $Q^1$ groups, which substitute atoms in a 1,2 or 1,3 arrangement, together form alkylenedioxy (i.e., —O—(CH$_2$)$_z$—O—), thioalkylenoxy (i.e., —S—(CH$_2$)$_z$—O—) or alkylenedithioxy (i.e., —S—(CH$_2$)$_z$—S—) where z is 1 or 2; and each $Q^1$ is independently unsubstituted or substituted with one or more substituents, in one embodiment, one to three or four substituents, each independently selected from $Q^2$, where $Q^2$ is halo, pseudohalo, hydroxy, oxo, thia, nitrile, nitro, formyl, mercapto, amino, hydroxyalkyl, hydroxyaryl, hydroxycarbonyl, alkyl, haloalkyl, polyhaloalkyl, aminoalkyl, diaminoalkyl, alkenyl containing 1 to 2 double bonds, alkynyl containing 1 to 2 triple bonds, cycloalkyl, heterocyclyl, aryl, heteroaryl, aralkyl, aralkenyl, aralkynyl, alkoxycarbonyl, aryloxycarbonyl, aralkoxycarbonyl, arylcarbonylalkyl, aminocarbonyl, alkoxy, aryloxy, aralkoxy, alkylenedioxy, amino, aminoalkyl, dialkylamino, arylamino, diarylamino, alkylamino, dialkylamino, haloalkylamino, arylamino, diarylamino, alkylarylamino, aralkylamino, alkoxycarbonylamino, arylcarbonylamino, alkylthio or arylthio.

In another embodiment, the compounds for use in the compositions and methods provided herein have formula I:

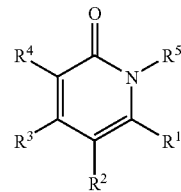

where $R^1$ is substituted or unsubstituted aryl, substituted or unsubstituted heteroaryl, substituted or unsubstituted aralkyl, substituted or unsubstituted heteroaralkyl, substituted or unsubstituted cycloalkyl, substituted or unsubstituted heterocyclyl, substituted or unsubstituted cycloalkylalkyl, or substituted or unsubstituted heterocyclylalkyl; $R^2$ is hydrogen, substituted or unsubstituted alkyl, or substituted or unsubstituted aryl; $R^3$ is substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted aryl, or substituted or unsubstituted heteroaryl; $R^4$ is halide, pseudohalide, $C(J)R^{30}$, $C(J)OR^{30}$, $C(J)NR^{31}R^{32}$, $CH_2NR^{31}R^{32}$, $CH_2OR^{31}$, $CR^{30}=CR^{31}R^{32}$, $NO_2$ or $NR^{31}R^{32}$; an $R^5$ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted aralkyl, substituted or unsubstituted aralkenyl, substituted or unsubstituted aralkynyl, substituted or unsubstituted heteroaralkyl, substituted or unsubstituted heteroaralkenyl, substituted or unsubstituted heteroaralkynyl, —N=CR$^6$R$^7$ or —NR$^9$R$^{10}$;

where $R^6$ and $R^7$ are each independently hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted aryl, substituted or unsubstituted heteroaryl, substituted or unsubstituted aralkyl, or substituted or unsubstituted heteroaralkyl; or together form substituted or unsubstituted alkylene, substituted or unsubstituted alkenylene, substituted or unsubstituted alkynylene, or —(CH$_2$)$_x$X(CH$_2$)$_y$— where x and y are each independently 1, 2 or 3, and X is O, S or NR$^8$;

$R^8$ is substituted or unsubstituted alkyl, substituted or unsubstituted alkenyl, substituted or unsubstituted alkynyl, substituted or unsubstituted alkylcarbonyl, substituted or unsubstituted arylcarbonyl, or substituted or unsubstituted heteroarylcarbonyl;

$R^9$ and $R^{10}$ are each independently hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted aralkyl, or substituted or unsubstituted heteroaralkyl;

$R^{30}$ is hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, or substituted or unsubstituted heteroaralkyl;

$R^{31}$ and $R^{32}$ are each independently hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, or $C(J)R^{35}$;

J is O, S or $NR^{40}$;

$R^{35}$ is hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted aryl, substituted or unsubstituted heteroaryl, substituted or unsubstituted alkoxy, substituted or unsubstituted aralkoxy, substituted or unsubstituted alkylamino, substituted or unsubstituted dialkylamino, substituted or unsubstituted arylalkylamino, or substituted or unsubstituted diarylamino;

$R^{40}$ is hydrogen, substituted or unsubstituted alkyl, substituted or unsubstituted aryl, or substituted or unsubstituted heteroaryl;

where the alkyl, alkenyl, alkynyl, cycloalkyl, heterocyclyl, alkylene, alkenylene, alkynylene, aryl, heteroaryl, aralkyl, aralkenyl, aralkynyl, heteroaralkyl, heteroaralkenyl and heteroaralkynyl moieties of $R^1$, $R^2$, $R^3$, $R^5$, $R^6$, $R^7$, $R^8$, $R^9$ and $R^{10}$ are unsubstituted or substituted with one or more substituents, in one embodiment, one to three or four substituents, each independently selected from $Q^1$, where $Q^1$ is halo, pseudohalo, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, ureido, alkylureido, arylureido, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, azido, dialkylphosphonyl, alkylarylphosphonyl, diarylphosphonyl, alkylthio, arylthio, perfluoroalkylthio, hydroxycarbonylalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl, arylaminosulfonyl, diarylaminosulfonyl or alkylarylaminosulfonyl; or two $Q^1$ groups, which substitute atoms in a 1,2 or 1,3 arrangement, together form alkylenedioxy (i.e., —O—$(CH_2)_z$—O—), thioalkylenoxy (i.e., —S—$(CH_2)_z$—O—) or alkylenedithioxy (i.e., —S—$(CH_2)_z$—S—) where z is 1 or 2; and the aryl and heteroaryl groups of $Q^1$ are unsubstituted or substituted with one or more substituents, in one embodiment, one to three or four substituents, each independently selected from $Q^2$, where $Q^2$ is alkyl, halo, pseudohalo, alkoxy, aryloxy or alkylenedioxy.

In certain embodiments, $R^2$ is hydrogen, or is substituted or unsubstituted alkyl. In other embodiments, $R^2$ is hydrogen.

In another embodiment, $R^3$ is substituted or unsubstituted alkyl, substituted or unsubstituted alkenyl, or substituted or unsubstituted alkynyl. In another embodiment, $R^3$ is substituted or unsubstituted alkyl. In another embodiment, $R^3$ is haloalkyl. In other embodiments, $R^3$ is lower haloalkyl. In another embodiment, $R^3$ is lower perfluoroalkyl. In another embodiment, $R^3$ is trifluoromethyl or pentafluoroethyl. In another embodiment, $R^3$ is trifluoromethyl.

In other embodiments, $R^4$ is pseudohalide. In another embodiment, $R^4$ is cyano.

In another embodiment, $R^6$ and $R^7$ are selected with the proviso that (i) they are not both methyl; and (ii) they do not together form pentylene (i e., —$(CH_2)_5$—).

The groups $R^1$, $R^2$, $R^3$, $R^4$, $R^5$, $R^6$, $R^7$, $R^8$, $R^9$, $R^{10}$, $Q^1$ and $Q^2$ are selected such that the resulting compound has nuclear receptor modulation activity, such as in at least one assay described herein, including LXR or orphan nuclear receptor modulation activity, such as LXR antagonist or agonist activity. In certain embodiments, the compounds provided herein have an $IC_{50}$ and/or $EC_{50}$ of less than about 100 μM in a LXRα or LXRβ binding or co-transfection assay. The LXRα or LXRβ $IC_{50}$ and/or $EC_{50}$ values for the compounds provided herein are, in certain embodiments, less than about 50 μM, 25 μM, 10 μM, 1 μM, 100 nM, 10 nM or 1 nM in binding or co-transfection assays. In certain of these embodiments, the compounds provided herein are LXR agonists. In other of these embodiments, the compounds provided herein are LXR antagonists. In other embodiments, the compounds provided herein exhibit a % efficacy relative to standard (N-(3-((4-fluorophenyl)-(naphthalene-2-sulfonyl)amino)propyl)-2,2-dimethylpropionamide) of greater than about 50%, 60%, 70%, 80%, 90%, 100%, 110%, 120%, 130%, 140% or more in a co-transfection assay.

Also of interest are any pharmaceutically-acceptable derivatives, including salts, esters, enol ethers, enol esters, solvates, hydrates and prodrugs of the compounds described herein. Pharmaceutically-acceptable salts, include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chloro-benzyl-2-pyrrolidin-1'-ylmethylbenzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc, aluminum, and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates.

Pharmaceutical compositions formulated for administration by an appropriate route and means containing effective concentrations of one or more of the compounds provided herein, or pharmaceutically acceptable derivatives thereof, that deliver amounts effective for the treatment, prevention, or amelioration of one or more symptoms of diseases or disorders that are modulated or otherwise affected by nuclear receptor activity, including LXR and/or orphan nuclear receptor activity, or in which nuclear receptor activity, including LXR and/or orphan nuclear receptor activity, is implicated, are also provided. The effective amounts and concentrations are effective for ameliorating any of the symptoms of any of the diseases or disorders.

Methods for treatment, prevention, or amelioration of one or more symptoms of diseases or disorders mediated by or in which nuclear receptor activity, including LXR and/or orphan nuclear receptor activity, is implicated, are provided. Such methods include methods of treatment, prevention and amelioration of one or more symptoms of hypercholesterolemia, hyperlipoproteinemia, hypertriglyceridemia, lipodystrophy, hyperglycemia, diabetes mellitus, dyslipidemia, atherosclerosis, gallstone disease, acne vulgaris, acneiform skin conditions, diabetes, Parkinson's disease, cancer, Alzheimer's disease, inflammation, immunological disorders, lipid disorders, obesity, conditions characterized by a perturbed epidermal barrier function, conditions of disturbed differentiation or excess proliferation of the epidermis or mucous membrane, or cardiovascular disorders, using one or more of the compounds provided herein, or pharmaceutically acceptable derivatives thereof.

Methods of modulating the activity of nuclear receptors, including LXR and/or orphan nuclear receptors, using the compounds and compositions provided herein are also provided. The compounds and compositions provided herein are active in assays, such as the assays provided herein, that measure the activity of nuclear receptors, including LXR and/or orphan nuclear receptors. These methods include inhibiting and up-regulating the activity of nuclear receptors, including LXR and/or orphan nuclear receptors.

Methods of reducing cholesterol levels in a subject in need thereof by administration of one or more compounds or compositions provided herein are also provided.

Methods of modulating cholesterol metabolism using the compounds and compositions provided herein are provided.

Methods of treating, preventing, or ameliorating one or more symptoms of diseases or disorders which are affected by cholesterol, triglyceride, or bile acid levels by administration of one or more of the compounds and compositions provided herein are also provided.

Methods of raising the plasma level of high density lipoprotein (HDL) by administration of one or more compounds and compositions provided herein are also provided.

In practicing the methods, effective amounts of the compounds or compositions containing therapeutically effective concentrations of the compounds, which are formulated for systemic delivery, including parenteral, oral, or intravenous delivery, or for local or topical application, for the treatment of nuclear receptor, including LXR and/or orphan nuclear receptor, mediated diseases or disorders, or diseases or disorders in which nuclear receptor activity, including LXR and/or orphan nuclear receptor activity, is implicated, including, but not limited to, hypercholesterolemia, hyperlipoproteinemia, hypertriglyceridemia, lipodystrophy, hyperglycemia, diabetes mellitus, dyslipidemia, atherosclerosis, gallstone disease, acne vulgaris, acneiform skin conditions, diabetes, Parkinson's disease, cancer, Alzheimer's disease, inflammation, immunological disorders, lipid disorders, obesity, conditions characterized by a perturbed epidermal barrier function, conditions of disturbed differentiation or excess proliferation of the epidermis or mucous membrane, or cardiovascular disorders, are administered to an individual exhibiting the symptoms of these diseases or disorders. The amounts are effective to ameliorate or eliminate one or more symptoms of the diseases or disorders.

Articles of manufacture containing packaging material, a compound or composition, or pharmaceutically acceptable derivative thereof, provided herein, which is effective for modulating the activity of nuclear receptors, including LXR and/or orphan nuclear receptors, or for treatment, prevention or amelioration of one or more symptoms of nuclear receptor, including LXR and/or orphan nuclear receptor, mediated diseases or disorders, or diseases or disorders in which nuclear receptor activity, including LXR and/or orphan nuclear receptor activity, is implicated, within the packaging material, and a label that indicates that the compound or composition, or pharmaceutically acceptable derivative thereof, is used for modulating the activity of nuclear receptors, including LXR and/or orphan nuclear receptors, or for treatment, prevention or amelioration of one or more symptoms of nuclear receptor, including LXR and/or orphan nuclear receptor, mediated diseases or disorders, or diseases or disorders in which nuclear receptor activity, including LXR and/or orphan nuclear receptor activity, is implicated, are provided.

DETAILED DESCRIPTION OF PREFERRED EMBODIMENTS

A. Definitions

Figure 1B:
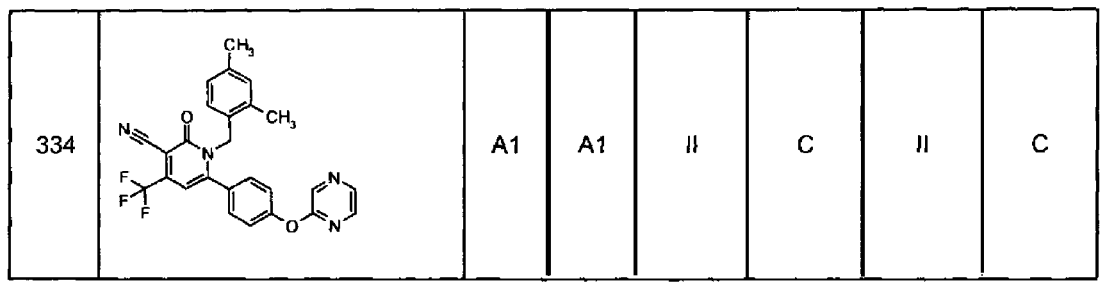
FIG. 1 provides in vitro data for the compounds whose synthesis is described in the Examples. Data is provided for LXRα and LXRβ receptors. Average $EC_{50}$ ("EC50_AVG") for LXR agonism is provided as follows: I=0.0001-0.01 µM, II=0.01-0.1 µM, III=0.1-1.0 µM, IV=1.0-10.0 µM and NC=Not Calculated. Average percent efficacy ("EFF_AVG") for LXR agonism relative to control (N-(3-((4-fluoro-phenyl)-(naphthalene-2-sulfonyl)-amino)propyl)-2,2-dimethyl-propionamide) is provided as follows: A=0-50%, B=50-100%, C=100-150%, D>150% and NC=Not Calculated. Average Ki is provided as follows: A1=0.0001-0.1 µM, B1=0.1-1 µM, C1=1-2 µM, D1=>2 µM.

Unless defined otherwise, all technical and scientific terms used herein have the same meaning as is commonly understood by one of ordinary skill in the art to which this invention belongs. All patents, applications, published applications and other publications are incorporated by reference in their entirety. In the event that there are a plurality of definitions for a term herein, those in this section prevail unless stated otherwise.

As used herein, a nuclear receptor is a member of a superfamily of regulatory proteins that are receptors for, e.g., steroids, retinoids, vitamin D and thyroid hormones. These proteins bind to cis-acting elements in the promoters of their target genes and modulate gene expression in response to a ligand therefor. Nuclear receptors may be classified based on their DNA binding properties. For example, the glucocorticoid, estrogen, androgen, progestin and mineralocorticoid receptors bind as homodimers to hormone response elements (HREs) organized as inverted repeats. Another example are receptors, including those activated by retinoic acid, thyroid hormone, vitamin $D_3$, fatty acids/peroxisome proliferators and ecdysone, that bind to HREs as heterodimers with a common partner, the retinoid X receptor (RXR). Among the latter receptors is LXR.

As used herein, an orphan nuclear receptor is a nuclear receptor for which the natural ligand is unknown.

As used herein, liver X receptor or LXR refers to a nuclear receptor implicated in cholesterol biosynthesis. As used herein, the term LXR refers to both $LXR\alpha$ and $LXR\beta$, two forms of the protein found in mammals. Liver X receptor-$\alpha$ or $LXR\alpha$ refers to the receptor described in U.S. Pat. Nos. 5,571,696, 5,696,233 and 5,710,004, and Willy et al. (1995) *Gene Dev.* 9(9):1033-1045. Liver X receptor-$\beta$ or $LXR\beta$ refers to the receptor described in Peet et al. (1998) *Curr. Opin. Genet. Dev.* 8(5):571-575; Song et al. (1995) *Ann. N.Y. Acad. Sci.* 761:38-49; Alberti et al. (2000) *Gene* 243(1-2):93-103; and references cited therein; and in U.S. Pat. Nos. 5,571,696, 5,696,233 and 5,710,004.

Diabetes mellitus, commonly called diabetes, refers to a disease process derived from multiple causative factors and characterized by elevated levels of plasma glucose, referred to as hyperglycemia. See, e.g., LeRoith, D. et al., (eds.), DIABETES MELLITUS (Lippincott-Raven Publishers, Philadelphia, Pa. U.S.A. 1996). According to the American Diabetes Association, diabetes mellitus is estimated to affect approximately 6% of the world population. Uncontrolled hyperglycemia is associated with increased and premature mortality due to an increased risk for macrovascular and macrovascular diseases, including nephropathy, neuropathy, retinopathy, hypertension, cerebrovascular disease and coronary heart disease. Therefore, control of glucose homeostasis is a critically important approach for the treatment of diabetes.

There are two major forms of diabetes: type 1 diabetes (formerly referred to as insulin-dependent diabetes or IDEM); and type 2 diabetes (formerly referred to as noninsulin dependent diabetes or NIDDM).

Type 2 diabetes is a disease characterized by insulin resistance accompanied by relative, rather than absolute, insulin deficiency. Type 2 diabetes can range from predominant insulin resistance with relative insulin deficiency to predominant insulin deficiency with some insulin resistance. Insulin resistance is the diminished ability of insulin to exert its biological action across a broad range of concentrations. In insulin resistant individuals, the body secretes abnormally high amounts of insulin to compensate for this defect. When inadequate amounts of insulin are present to compensate for insulin resistance and adequate control of glucose, a state of impaired glucose tolerance develops. In a significant number of individuals, insulin secretion declines further and the plasma glucose level rises, resulting in the clinical state of diabetes. Type 2 diabetes can be due to a profound resistance to insulin stimulating regulatory effects on glucose and lipid metabolism in the main insulin-sensitive tissues: muscle, liver and adipose tissue. This resistance to insulin responsiveness results in insufficient insulin activation of glucose uptake, oxidation and storage in muscle and inadequate insulin repression of lipolysis in adipose tissue and of glucose production and secretion in liver. In Type 2 diabetes, free fatty acid levels are often elevated in obese and some non-obese patients and lipid oxidation is increased.

Premature development of atherosclerosis and increased rate of cardiovascular and peripheral vascular diseases are characteristic features of patients with diabetes. Hyperlipidemia is an important precipitating factor for these diseases. Hyperlipidemia is a condition generally characterized by an abnormal increase in serum lipids in the bloodstream and is an important risk factor in developing atherosclerosis and heart disease. For a review of disorders of lipid metabolism, see, e.g., Wilson, J. et al., (ed.), Disorders of Lipid Metabolism, Chapter 23, Textbook of Endocrinology, 9th Edition, (W. B. Sanders Company, Philadelphia, Pa. U.S.A. 1998). Hyperlipidemia is usually classified as primary or secondary hyperlipidemia. Primary hyperlipidemia is generally caused by genetic defects, while secondary hyperlipidemia is generally caused by other factors, such as various disease states, drugs, and dietary factors. Alternatively, hyperlipidemia can result from both a combination of primary and secondary causes of hyperlipidemia. Elevated cholesterol levels are associated with a number of disease states, including coronary artery disease, angina pectoris, carotid artery disease, strokes, cerebral arteriosclerosis, and xanthoma.

Dyslipidemia, or abnormal levels of lipoproteins in blood plasma, is a frequent occurrence among diabetics, and has been shown to be one of the main contributors to the increased incidence of coronary events and deaths among diabetic subjects (see, e.g., Joslin, E. Ann. Chim. Med. (1927) 5: 1061-1079). Epidemiological studies since then have confirmed the association and have shown a several-fold increase in coronary deaths among diabetic subjects when compared with nondiabetic subjects (see, e.g., Garcia, M. J. et al., Diabetes (1974) 23: 105-11 (1974); and Laakso, M. and Lehto, S., Diabetes Reviews (1997) 5(4): 294-315). Several lipoprotein abnormalities have been described among diabetic subjects (Howard B., et al., Arteriosclerosis (1978) 30: 153-162).

The term "insulin resistance" can be defined generally as a disorder of glucose metabolism. More specifically, insulin resistance can be defined as the diminished ability of insulin to exert its biological action across a broad range of concentrations producing less than the expected biologic effect. (see, e.g., Reaven, G. M., J. Basic & Clin. Phys. & Pharm. (1998) 9: 387-406 and Flier, J. Ann Rev. Med. (1983) 34:145-60). Insulin resistant persons have a diminished ability to properly metabolize glucose and respond poorly, if at all, to insulin therapy. Manifestations of insulin resistance include insufficient insulin activation of glucose uptake, oxidation and storage in muscle and inadequate insulin repression of lipolysis in adipose tissue and of glucose production and secretion in liver. Insulin resistance can cause or contribute to polycystic ovarian syndrome, Impaired Glucose Tolerance (IGT), gestational diabetes, hypertension, obesity, atherosclerosis and a variety of other disorders. Eventually, the insulin resistant individuals can progress to a point where a diabetic state is reached. The association of insulin resistance with glucose intolerance, an increase in plasma triglyceride and a decrease in high-density lipoprotein cholesterol concentrations, high blood pressure, hyperuricemia, smaller denser low-density lipoprotein particles, and higher circulating levels of plasminogen activator inhibitor-1), has been referred to as "Syndrome X" (see, e.g., Reaven, G. M., Physiol. Rev. (1995) 75: 473-486).

The term "diabetes mellitus" or "diabetes" means a disease or condition that is generally characterized by metabolic defects in production and utilization of glucose which result in the failure to maintain appropriate blood sugar levels in the body. The result of these defects is elevated blood glucose, referred to as "hyperglycemia." Type 2 diabetes often occurs in the face of normal, or even elevated, levels of insulin and can result from the inability of tissues to respond appropriately to insulin. Most type 2 diabetic patients are insulin resistant and have a relative deficiency of insulin, in that insulin secretion can not compensate for the resistance of peripheral tissues to respond to insulin. In addition, many type 2 diabetics are obese. Other types of disorders of glucose homeostasis include Impaired Glucose Tolerance, which is a metabolic stage intermediate between normal glucose homeostasis and diabetes, and Gestational Diabetes Mellitus, which is glucose intolerance in pregnancy in women with no previous history of type 1 or type 2 diabetes.

The term "complication" of diabetes includes, but is not limited to, microvascular complications and macrovascular complications. Microvascular complications are those complications which generally result in small blood vessel damage. These complications include, e.g., retinopathy (the impairment or loss of vision due to blood vessel damage in the eyes); neuropathy (nerve damage and foot problems due to blood vessel damage to the nervous system); and nephropathy (kidney disease due to blood vessel damage in the kidneys). macrovascular complications are those complications which generally result from large blood vessel damage. These complications include, e.g., cardiovascular disease and peripheral vascular disease. Cardiovascular disease refers to diseases of blood vessels of the heart. See. e.g., Kaplan, R. M., et al., "Cardiovascular diseases" in HEALTH AND HUMAN BEHAVIOR, pp. 206-242 (McGraw-Hill, New York 1993). Cardiovascular disease is generally one of several forms, including, e.g., hypertension (also referred to as high blood pressure), coronary heart disease, stroke, and rheumatic heart disease. Peripheral vascular disease refers to diseases of any of the blood vessels outside of the heart. It is often a narrowing of the blood vessels that carry blood to leg and arm muscles.

The term "hyperlipidemia" refers to the presence of an abnormally elevated level of lipids in the blood. Hyperlipidemia can appear in at least three forms: (1) hypercholesterolemia, i.e., an elevated cholesterol level; (2) hypertriglyceridemia, i.e., an elevated triglyceride level; and (3) combined hyperlipidemia, i.e., a combination of hypercholesterolemia and hypertriglyceridemia.

The term "dyslipidemia" refers to abnormal levels of lipoproteins in blood plasma including both depressed and/or elevated levels of lipoproteins (e.g., elevated levels of LDL, VLDL and depressed levels of HDL).

Exemplary Primary Hyperlipidemia include, but are not limited to, the following: (1) Familial Hyperchylomicronemia, a rare genetic disorder which causes a deficiency in an enzyme, LP lipase, that breaks down fat molecules. The LP lipase deficiency can cause the accumulation of large quantities of fat or lipoproteins in the blood;

(2) Familial Hypercholesterolemia, a relatively common genetic disorder caused where the underlying defect is a series of mutations in the LDL receptor gene that result in malfunctioning LDL receptors and/or absence of the LDL receptors. This brings about ineffective clearance of LDL by the LDL receptors resulting in elevated LDL and total cholesterol levels in the plasma;

(3) Familial Combined Hyperlipidemia, also known as multiple lipoprotein-type hyperlipidemia; an inherited disorder where patients and their affected first-degree relatives can at various times manifest high cholesterol and high triglycerides. Levels of HDL cholesterol are often moderately decreased;

(4) Familial Defective Apolipoprotein B-100 is a relatively common autosomal dominant genetic abnormality. The defect is caused by a single nucleotide mutation that produces a substitution of glutamine for arginine which can cause reduced affinity of LDL particles for the LDL receptor. Consequently, this can cause high plasma LDL and total cholesterol levels;

(5) Familial Dysbetaliproteinemia, also referred to as Type III Hyperlipoproteinemia, is an uncommon inherited disorder resulting in moderate to severe elevations of serum TG and cholesterol levels with abnormal apolipoprotein E function. HDL levels are usually normal; and (6) Familial Hypertriglyceridemia, is a common inherited disorder in which the concentration of plasma VLDL is elevated. This can cause mild to moderately elevated triglyceride levels (and usually not cholesterol levels) and can often be associated with low plasma HDL levels.

Risk factors in exemplary Secondary Hyperlipidemia include, but are not limited to, the following: (1) disease risk factors, such as a history of type 1 diabetes, type 2 diabetes, Cushing's syndrome, hypothyroidism and certain types of renal failure; (2) drug risk factors, which include, birth control pills; hormones, such as estrogen, and corticosteroids; certain diuretics; and various β-blockers; (3) dietary risk factors include dietary fat intake per total calories greater than 40%; saturated fat intake per total calories greater than 10%; cholesterol intake greater than 300 mg per day; habitual and excessive alcohol use; and obesity; and (4) non-genetic dyslipidemias.

The terms "obese" and "obesity" refers to, according to the World Health Organization, a Body Mass Index (BMI) greater than 27.8 kg/m$^2$ for men and 27.3 kg/m$^2$ for women (BMI equals weight (kg)/height (m$^2$). Obesity is linked to a variety of medical conditions including diabetes and hyperlipidemia. Obesity is also a known risk factor for the development of type 2 diabetes (See, e.g., Barrett-Conner, E., Epidemol. Rev. (1989) 11: 172-181; and Knowler, et al., Am. J Clin. Nutr. (1991) 53:1543-1551).

As used herein, pharmaceutically acceptable derivatives of a compound include salts, esters, enol ethers, enol esters, acetals, ketals, hemiacetals, hemiketals, acids, bases, solvates, hydrates or prodrug thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxy-methyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C═C(OR) where R is hydrogen, alkyl, alkenyl, alkynyl, aryl, heteroaryl, aralkyl, heteroaralkyl, cycloalkyl or heterocyclyl. Pharmaceutically acceptable enol esters include, but are not limited to, derivatives of formula C═C(OC(O)R) where R is hydrogen, alkyl, alkenyl, alkynyl, aryl, heteroaryl, aralkyl, heteroaralkyl, cycloalkyl or heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, treatment means any manner in which one or more of the symptoms of a disease or disorder are ameliorated or otherwise beneficially altered. Treatment also encompasses any pharmaceutical use of the compositions herein, such as use for treating a nuclear receptor, including LXR and/or orphan nuclear receptor, mediated diseases or disorders, or diseases or disorders in which nuclear receptor activity, including LXR and/or orphan nuclear receptor activity, is implicated.

As used herein, amelioration of the symptoms of a particular disorder by administration of a particular compound or pharmaceutical composition refers to any lessening, whether permanent or temporary, lasting or transient that can be attributed to or associated with administration of the composition.

The term "modulate" refers to the treating, prevention, suppression, enhancement or induction of a function or condition. For example, the compounds claimed herein, can modulate hyperlipidemia by lowering cholesterol in a human, thereby suppressing hyperlipidemia.

As used herein, the $IC_{50}$ refers to an amount, concentration or dosage of a particular test compound that achieves a 50% inhibition of a maximal response, such as modulation of LXR activity, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

The term "cholesterol" refers to a steroid alcohol that is an essential component of cell membranes and myelin sheaths and, as used herein, incorporates its common usage. Cholesterol also serves as a precursor for steroid hormones and bile acids.

The term "triglyceride(s)" ("TGs"), as used herein, incorporates its common usage. TGs consist of three fatty acid molecules esterified to a glycerol molecule and serve to store fatty acids which are used by muscle cells for energy production or are taken up and stored in adipose tissue.

As used herein, a prodrug is a compound that, upon in vivo administration, is metabolized by one more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388-392).

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. The compounds provided herein include all possible isomers, as well as, their racemic and optically pure forms. Optically active (+) and (−), (r)- and (S)-, or (D)- and (L)-isomers may be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included. In the case of amino acid residues, such residues may be of either the L- or D-form. The configuration for naturally occurring amino acid residues is generally L. When not specified the residue is the L form. As used herein, the term "amino acid" refers to α-amino acids which are racemic, or of either the D- or L-configuration. The designation "d" preceding an amino acid designation (e.g., dAla, dSer, dVal, etc.) refers to the D-isomer of the amino acid. The designation "dl" preceding an amino acid designation (e.g., dlPip) refers to a mixture of the L- and D-isomers of the amino acid. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

As used herein, substantially pure means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, the nomenclature alkyl, alkoxy, carbonyl, etc. is used as is generally understood by those of skill in this art.

As used herein, alkyl, alkenyl and alkynyl carbon chains, if not specified, contain from 1 to 20 carbons, or 1 to 16 carbons, and are straight or branched. Alkenyl carbon chains of from 2 to 20 carbons, in certain embodiments, contain 1 to 8 double bonds, and the alkenyl carbon chains of 2 to 16 carbons, in certain embodiments, contain 1 to 5 double bonds. Alkynyl carbon chains of from 2 to 20 carbons, in certain embodiments, contain 1 to 8 triple bonds, and the alkynyl carbon chains of 2 to 16 carbons, in certain embodiments, contain 1 to 5 triple bonds. Exemplary alkyl, alkenyl and alkynyl groups herein include, but are not limited to, methyl, ethyl, propyl, isopropyl, isobutyl, n-butyl, sec-butyl, tert-butyl, isopentyl, neopentyl, tert-penytyl and isohexyl. As used herein, lower alkyl, lower alkenyl, and lower alkynyl refer to carbon chains having less than about 6 carbons. As used herein, "alk(en)(yn)yl" refers to an alkyl group containing at least one double bond and at least one triple bond.

As used herein, "cycloalkyl" refers to a saturated mono- or multicyclic ring system, in certain embodiments of 3 to 10 carbon atoms, in other embodiments of 3 to 6 carbon atoms; cycloalkenyl and cycloalkynyl refer to mono- or multicyclic ring systems that respectively include at least one double bond and at least one triple bond. Cycloalkenyl and cycloalkynyl groups may, in certain embodiments, contain 3 to 10 carbon atoms, with cycloalkenyl groups, in further embodiments, containing 4 to 7 carbon atoms and cycloalkynyl groups, in further embodiments, containing 8 to 10 carbon atoms. The ring systems of the cycloalkyl, cycloalkenyl and cycloalkynyl groups may be composed of one ring or two or more rings which may be joined together in a fused, bridged or spiro-connected fashion. "Cycloalk(en)(yn)yl" refers to a cycloalkyl group containing at least one double bond and at least one triple bond.

As used herein, "substituted alkyl," "substituted alkenyl," "substituted alkynyl," "substituted cycloalkyl," "substituted cycloalkenyl," and "substitued cycloalkynyl" refer to alkyl, alkenyl, alkynyl, cycloalkyl, cycloalkenyl and cycloalkynyl groups, respectively, that are substituted with one or more substituents, in certain embodiments one to three substituents.

As used herein, "aryl" refers to aromatic monocyclic or multicyclic groups containing from 6 to 19 carbon atoms. Aryl groups include, but are not limited to groups such as fluorenyl, substituted fluorenyl, phenyl, substituted phenyl, naphthyl and substituted naphthyl.

As used herein, "heteroaryl" refers to a monocyclic or multicyclic aromatic ring system, in certain embodiments, of about 5 to about 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrrolidinyl, pyrimidinyl, tetrazolyl, thienyl, pyridyl, pyrrolyl, N-methylpyrrolyl, quinolinyl and isoquinolinyl.

As used herein, a "heteroarylium" group is a heteroaryl group that is positively charged on one or more of the heteroatoms.

As used herein, "heterocyclyl" refers to a monocyclic or multicyclic non-aromatic ring system, in one embodiment of 3 to 10 members, in another embodiment of 4 to 7 members, in a further embodiment of 5 to 6 members, where one or more, in certain embodiments, 1 to 3, of the atoms in the ring system is a heteroatom, that is, an element other than carbon, including but not limited to, nitrogen, oxygen or sulfur.

As used herein, "substituted aryl," "substituted heteroaryl" and "substituted heterocyclyl" refer to aryl, heteroaryl and heterocyclyl groups, respectively, that are substituted with one or more substituents, in certain embodiments one to three substituents.

As used herein, "aralkyl" refers to an alkyl group in which one of the hydrogen atoms of the alkyl is replaced by an aryl group.

As used herein, "heteroaralkyl" refers to an alkyl group in which one of the hydrogen atoms of the alkyl is replaced by a heteroaryl group.

As used herein, "halo", "halogen" or "halide" refers to F, Cl, Br or I.

As used herein, pseudohalides or pseudohalo groups are groups that behave substantially similar to halides. Such compounds can be used in the same manner and treated in the same manner as halides. Pseudohalides include, but are not limited to, cyanide, cyanate, thiocyanate, selenocyanate, trifluoromethoxy, and azide.

As used herein, "haloalkyl" refers to an alkyl group in which one or more of the hydrogen atoms are replaced by halogen. Such groups include, but are not limited to, chloromethyl, trifluoromethyl and 1-chloro-2-fluoroethyl.

As used herein, "haloalkoxy" refers to RO— in which R is a haloalkyl group.

As used herein, "sulfinyl" or "thionyl" refers to —S(O)—.
As used herein, "sulfonyl" or "sulfuryl" refers to —S(O)$_2$—.
As used herein, "sulfo" refers to —S(O)$_2$O—.
As used herein, "carboxy" refers to a divalent radical, —C(O)O—.
As used herein, "aminocarbonyl" refers to —C(O)NH$_2$.
As used herein, "alkylaminocarbonyl" refers to —C(O)NHR in which R is alkyl, including lower alkyl. As used herein, "dialkylaminocarbonyl" refers to —C(O)NR'R in which R' and R are independently alkyl, including lower alkyl; "carboxamide" refers to groups of formula —NR'COR in which R' and R are independently alkyl, including lower alkyl.

As used herein, "diarylaminocarbonyl" refers to —C(O)NRR' in which R and R' are independently selected from aryl, including lower aryl, such as phenyl.

As used herein, "arylalkylaminocarbonyl" refers to —C(O)NRR' in which one of R and R' is aryl, including lower aryl, such as phenyl, and the other of R and R' is alkyl, including lower alkyl.

As used herein, "arylaminocarbonyl" refers to —C(O)NHR in which R is aryl, including lower aryl, such as phenyl.

As used herein, "hydroxycarbonyl" refers to —COOH.
As used herein, "alkoxycarbonyl" refers to —C(O)OR in which R is alkyl, including lower alkyl.
As used herein, "aryloxycarbonyl" refers to —C(O)OR in which R is aryl, including lower aryl, such as phenyl.
As used herein, "alkoxy" and "alkylthio" refer to RO— and RS—, in which R is alkyl, including lower alkyl.
As used herein, "aryloxy" and "arylthio" refer to RO— and RS—, in which R is aryl, including lower aryl, such as phenyl.

As used herein, "alkylene" refers to a straight, branched or cyclic, in certain embodiments straight or branched, divalent aliphatic hydrocarbon group, in one embodiment having from 1 to about 20 carbon atoms, in another embodiment having from 1 to 12 carbons. In a further embodiment alkylene includes lower alkylene. There may be optionally inserted along the alkylene group one or more oxygen, sulphur or substituted or unsubstituted nitrogen atoms, where the nitrogen substituent is alkyl. Alkylene groups include, but are not limited to, methylene (—CH$_2$—), ethylene (—CH$_2$CH$_2$—), propylene (—(CH$_2$)$_3$—), methylenedioxy (—O—CH$_2$—O—) and ethylenedioxy (—O—(CH$_2$)$_2$—O—). The term "lower alkylene" refers to alkylene groups having 1 to 6 carbons. In certain embodiments, alkylene groups are lower alkylene, including alkylene of 1 to 3 carbon atoms.

As used herein, "azaalkylene" refers to —(CRR)$_n$—NR—(CRR)$_m$—, where n and m are each independently an integer from 0 to 4. As used herein, "oxaalkylene" refers to —(CRR)$_n$—O—(CRR)$_m$—, where n and m are each independently an integer from 0 to 4. As used herein, "thiaalkylene" refers to —(CRR)$_n$—S—(CRR)$_m$—, where n and m are each independently an integer from 0 to 4.

As used herein, "alkenylene" refers to a straight, branched or cyclic, in one embodiment straight or branched, divalent aliphatic hydrocarbon group, in certain embodiments having from 2 to about 20 carbon atoms and at least one double bond, in other embodiments 1 to 12 carbons. In further embodiments, alkenylene groups include lower alkenylene. There may be optionally inserted along the alkenylene group one or more oxygen, sulphur or substituted or unsubstituted nitrogen atoms, where the nitrogen substituent is alkyl. Alkenylene groups include, but are not limited to, —CH=CH—CH=CH— and —CH=CH—CH$_2$—. The term "lower alkenylene" refers to alkenylene groups having 2 to 6 carbons. In certain embodiments, alkenylene groups are lower alkenylene, including alkenylene of 3 to 4 carbon atoms. As used herein, "1,3-diaza-1,3-butadienylene" refers to —N═CH—N═CH—. As used herein, "1,2-diaza-1,3-butadienylene" refers to —N═N—CH═CH—. As used herein, "2,3-diaza-1,3-butadienylene" refers to —CH═N—N═CH—.

As used herein, "azaalkenylene" refers to —NR—(CR═CR)$_n$—, where n is 1 or 2; and also refers to —CR═CR—NR—CR═CR—. As used herein, "oxaalkenylene" refers to —O—(CR═CR)$_n$—, where n is 1 or 2; and also refers to —CR═CR—O—CR═CR—. As used herein, "thiaalkenylene" refers to —S—(CR═CR)$_n$—, where n is 1 or 2; and also refers to —CR═CR—S—CR═CR—.

As used herein, "alkynylene" refers to a straight, branched or cyclic, in certain embodiments straight or branched, divalent aliphatic hydrocarbon group, in one embodiment having from 2 to about 20 carbon atoms and at least one triple bond, in another embodiment 1 to 12 carbons. In a further embodiment, alkynylene includes lower alkynylene. There may be optionally inserted along the alkynylene group one or more oxygen, sulphur or substituted or unsubstituted nitrogen atoms, where the nitrogen substituent is alkyl. Alkynylene groups include, but are not limited to, —C≡C—C≡C—, —C≡C— and —C≡C—CH$_2$—. The term "lower alkynylene" refers to alkynylene groups having 2 to 6 carbons. In certain embodiments, alkynylene groups are lower alkynylene, including alkynylene of 3 to 4 carbon atoms.

As used herein, "alk(en)(yn)ylene" refers to a straight, branched or cyclic, in certain embodiments straight or branched, divalent aliphatic hydrocarbon group, in one embodiment having from 2 to about 20 carbon atoms and at least one triple bond, and at least one double bond; in another embodiment 1 to 12 carbons. In further embodiments, alk(en)(yn)ylene includes lower alk(en)(yn)ylene. There may be optionally inserted along the alkynylene group one or more oxygen, sulphur or substituted or unsubstituted nitrogen atoms, where the nitrogen substituent is alkyl. Alk(en)(yn)ylene groups include, but are not limited to, —C═C—(CH$_2$)$_n$—C≡C—, where n is 1 or 2. The term "lower alk(en)(yn)ylene" refers to alk(en)(yn)ylene groups having up to 6 carbons. In certain embodiments, alk(en)(yn)ylene groups have about 4 carbon atoms.

As used herein, "cycloalkylene" refers to a divalent saturated mono- or multicyclic ring system, in certain embodiments of 3 to 10 carbon atoms, in other embodiments 3 to 6 carbon atoms; cycloalkenylene and cycloalkynylene refer to divalent mono- or multicyclic ring systems that respectively include at least one double bond and at least one triple bond. Cycloalkenylene and cycloalkynylene groups may, in certain embodiments, contain 3 to 10 carbon atoms, with cycloalkenylene groups in certain embodiments containing 4 to 7 carbon atoms and cycloalkynylene groups in certain embodiments containing 8 to 10 carbon atoms. The ring systems of the cycloalkylene, cycloalkenylene and cycloalkynylene groups may be composed of one ring or two or more rings which may be joined together in a fused, bridged or spiro-connected fashion. "Cycloalk(en)(yn)ylene" refers to a cycloalkylene group containing at least one double bond and at least one triple bond.

As used herein, "substituted alkylene," "substituted alkenylene," "substituted alkynylene," "substituted cycloalkylene," "substituted cycloalkenylene," and "substitued cycloalkynylene" refer to alkylene, alkenylene, alkynylene, cycloalkylene, cycloalkenylene and cycloalkynylene groups, respectively, that are substituted with one or more substituents, in certain embodiments one to three substituents.

As used herein, "arylene" refers to a monocyclic or polycyclic, in certain embodiments monocyclic, divalent aromatic group, in one embodiment having from 5 to about 20 carbon atoms and at least one aromatic ring, in another embodiment 5 to 12 carbons. In further embodiments, arylene includes lower arylene. Arylene groups include, but are not limited to, 1,2-, 1,3- and 1,4-phenylene. The term "lower arylene" refers to arylene groups having 5 or 6 carbons.

As used herein, "heteroarylene" refers to a divalent monocyclic or multicyclic aromatic ring system, in one embodiment of about 5 to about 15 members where one or more, in certain embodiments 1 to 3, of the atoms in the ring system is a heteroatom, that is, an element other than carbon, including but not limited to, nitrogen, oxygen or sulfur.

As used herein, "heterocyclylene" refers to a divalent monocyclic or multicyclic non-aromatic ring system, in certain embodiments of 3 to 10 members, in one embodiment 4 to 7 members, in another embodiment 5 to 6 members, where one or more, including 1 to 3, of the atoms in the ring system is a heteroatom, that is, an element other than carbon, including but not limited to, nitrogen, oxygen or sulfur.

As used herein, "substituted arylene," "substituted heteroarylene" and "substituted heterocyclylene" refer to arylene, heteroarylene and heterocyclylene groups, respectively, that are substituted with one or more substituents, in certain embodiments one to three substituents.

As used herein, "alkylidene" refers to a divalent group, such as ═CR'R", which is attached to one atom of another group, forming a double bond. Alkylidene groups include, but are not limited to, methylidene (═CH$_2$) and ethylidene (═CHCH$_3$). As used herein, "arylalkylidene" refers to an alkylidene group in which either R' or R" is an aryl group. "Cycloalkylidene" groups are those where R' and R" are linked to form a carbocyclic ring. "Heterocyclylidene" groups are those where at least one of R' and R" contain a heteroatom in the chain, and R' and R" are linked to form a heterocyclic ring.

As used herein, "amido" refers to the divalent group —C(O)NH—. "Thioamido" refers to the divalent group —C(S)NH—. "Oxyamido" refers to the divalent group —OC(O)NH—. "Thiaamido" refers to the divalent group —SC(O)NH—. "Dithiaamido" refers to the divalent group —SC(S)NH—. "Ureido" refers to the divalent group —HNC(O)NH—. "Thioureido" refers to the divalent group —HNC(S)NH—.

As used herein, "semicarbazide" refers to —NHC(O)NHNH—. "Carbazate" refers to the divalent group —OC(O)NHNH—. "Isothiocarbazate" refers to the divalent group —SC(O)NHNH—. "Thiocarbazate" refers to the divalent group —OC(S)NHNH—. "Sulfonylhydrazide" refers to the group —SO$_2$NHNH—. "Hydrazide" refers to the divalent group —C(O)NHNH—. "Azo" refers to the divalent group —N═N—. "Hydrazinyl" refers to the divalent group —NH—NH—.

Where the number of any given substituent is not specified (e.g., "haloalkyl"), there may be one or more substituents present. For example, "haloalkyl" may include one or more of the same or different halogens. As another example, "C$_{1-3}$alkoxyphenyl" may include one or more of the same or different alkoxy groups containing one, two or three carbons.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942-944).

B. Heterocyclic Modulators of Nuclear Receptors

Compounds for use in compositions and methods for modulating the activity of nuclear receptors are provided. In particular, compounds for use in compositions and methods for modulating liver X receptors (LXRα and LXRβ), either selectively or in combination, and/or orphan nuclear receptors are provided.

In one embodiment, the compounds have formula I:

$$\text{I}$$

where, $R^2$ is substituted or unsubstituted alkyl or hydrogen, where the substituents are selected from one or more $Q^1$; and $R^1$, $R^3$, $R^4$ and $R^5$ are selected above. In another embodiment, $R^2$ is lower alkyl or hydrogen. In another embodiment, $R^2$ is hydrogen.

In another embodiment, $R^1$ is selected from substituted or unsubstituted alkyl, substituted or unsubstituted aryl, substituted or unsubstituted heteroaryl, substituted or unsubstituted aralkyl, substituted or unsubstituted heteroaralkyl, substituted or unsubstituted cycloalkyl, substituted or unsubstituted cycloalkenyl and substituted or unsubstituted heterocyclyl, where the substituents are selected from one or more $Q^1$.

In another embodiment, $R^1$ is substituted or unsubstituted aryl, where the substituents are selected from one or more $Q^1$.

In another embodiment, $R^1$ is substituted or unsubstituted heteroaryl, where the substituents are selected from one or more $Q^1$.

In another embodiment, $R^1$ is substituted or unsubstituted heterocyclyl, where the substituents are selected from one or more $Q^1$.

In other embodiments, $R^1$ is substituted or unsubstituted methyl, substituted or unsubstituted cyclohexyl, substituted or unsubstituted cyclopentenyl, substituted or unsubstituted phenyl, substituted or unsubstituted benzyl, substituted or unsubstituted naphthyl, substituted or unsubstituted furyl, substituted or unsubstituted thienyl, substituted or unsubstituted pyrrolyl, substituted or unsubstituted pyrazolyl, substituted or unsubstituted thiazolyl, substituted or unsubstituted piperidinyl, substituted or unsubstituted pyridinyl, substituted or unsubstituted pyrazinyl, substituted or unsubstituted indanyl, substituted or unsubstituted benzofuryl, substituted or unsubstituted thianaphthyl or substituted or unsubstituted indolyl, where the substituents are selected from one or more $Q^1$.

In other embodiments, $R^1$ is substituted or unsubstituted phenyl, substituted or unsubstituted naphthyl, substituted or unsubstituted furyl, substituted or unsubstituted thienyl, or substituted or unsubstituted pyrrolyl, where the substituents are selected from one or more $Q^1$.

In another embodiment, $R^1$ is substituted or unsubstituted phenyl, substituted or unsubstituted naphthyl, or substituted or unsubstituted thienyl, where the substituents are selected from one or more $Q^1$.

In other embodiments, $R^1$ is substituted or unsubstituted furyl, substituted or unsubstituted thienyl, substituted or unsubstituted pyrrolyl, substituted or unsubstituted pyrazolyl, substituted or unsubstituted thiazolyl, substituted or unsubstituted piperidinyl or substituted or unsubstituted pyridinyl, substituted or unsubstituted pyrazinyl, substituted or unsubstituted benzofuryl, substituted or unsubstituted thianaphthyl or substituted or unsubstituted indolyl, where the substituents are selected from one or more $Q^1$.

In another embodiment, $R^1$ is substituted or unsubstituted phenyl.

In another embodiment, $R^1$ is substituted or unsubstituted thienyl.

In certain embodiments, $R^1$ is unsubstituted or substituted with one or more $Q^1$, in one embodiment, one to three or five substituents, in another embodiment, one or two substituents, each independently selected from $Q^1$, where $Q^1$ is halo, pseudohalo, nitro, hydroxy, amino, hydroxyalkyl, hydroxyalkylaryloxy, hydroxyaryl, hydroxyalkylaryl, hydroxycarbonyl, haloalkyl, alkyl, heterocyclyl, heterocyclylalkyl, aryl, heteroaryl, aralkyl, heteroaralkyl, alkylaralkyl, alkylarylcarbonyl, heterocyclylcarbonyl, alkoxycarbonyl, alkoxycarbonylaryloxy, aryloxycarbonyl, heterocyclylcarbonylalkylaryl, aralkoxycarbonyl, alkoxy, aryloxy, heteroaryloxy, aralkoxy, alkylaryloxy, alkylaryloxyalkyl, alkyldiaryloxy, aryloxyalkoxy, aralkoxyaryloxy, alkylarylcycloalkyloxy, alkylheteroaryloxy, cycloalkyloxy, heterocyclylalkoxy, heterocyclyloxy, haloaryloxy, alkylcarbonylaryloxy, arylamino, alkylarylamino, aralkylamino, alkylcarbonylamino, alkylaminocarbonyl, haloalkylcarbonylamino and arylthio; and each $Q^1$ is unsubstituted or further substituted with $Q^2$, which is hydrogen, alkyl, aryl, alkoxy, hydroxycarbonyl, alkoxycarbonyl, pseudohalide, halo, aryloxy, aralkoxy, haloalkyl, alkylthio, alkylamino, dialkylamino or hydroxy.

In another embodiment, $R^1$ is substituted with $Q^1$, which is selected from alkoxycarbonylaryloxy, aryloxy, alkylaryloxy, alkylaryloxyalkyl, alkyldiaryloxy, aryloxyalkoxy, aralkoxyaryloxy, alkylarylcycloalkyloxy, alkylheteroaryloxy, cycloalkyloxy, heterocyclylalkoxy, heterocyclyloxy, heteroaryloxy, haloaryloxy, alkoxycarbonylheterocycloxy, alkylcarbonylaryloxy, dialkylaminoaryloxy, alkoxyaryloxy, cyanoaryloxy, aryloxyaryloxy, dialkylaryloxy, haloalkylaryloxy, alkylthioaryloxy, alkylarylamino, hydroxyaryloxy, arylamino, alkylamino, aralkylamino and arylthio.

In another embodiment, $R^1$ is substituted with $Q^1$, which is selected from alkyl, alkoxy, halo, pseudohalo, haloalkyl, nitro, hydroxy, alkoxy, aralkoxy, heterocyclylalkoxy, alkylcarbonylamino and alkylaminocarbonylamino.

In another embodiment, $R^1$ is substituted with $Q^1$, which is selected from methyl, ethyl, trifluoromethyl, nitro, hydroxy, n-butyloxy, 3-(2-piperidinyl)ethoxy, methylcarbonylamino, ethylaminocarbonylamino, chloro, bromo, benzylamino, methylphenoxymethyl, trifluoromethylcarbonylamino, methoxycarbonyl, phenoxy, cyano, n-butoxy, benzoxy, 1-piperidinyl, methoxy, hydroxycarbonyl, tert-butoxycarbonylpiperazinylcarbonyl, hydroxymethyl, 1-piperidinylcarbonyl, phenyl, methylphenyl, dimethylamino, methylcarbonylamino, methoxyphenoxy, methylphenoxy, piperidinylmethyl, biphenoxy, benzoxycarbonyl, piperazinylcarbonyl, benzyl, phenylthio, chlorophenoxy, methylbenzyl, hydroxymethylphenoxy, ethoxycarbonylphenoxy, tert-butylmethylphenoxy, tertbutylbiphenoxy, ethylphenoxy, isopropylphenoxy, tertbutylphenoxy, N,N-dimethylphenoxy, N,N-phenylmethylamino, 3-methylphenyl-1-amino, trifluoromethylphenoxy, ethylphenoxy, methylcarbonylphenoxy, tetrahydropyranyloxy, tetrahydronaphthoxy, hydroxycarbonylphenoxy, 1,3-hexafluoro-2-hydroxypropylphenylamino, benzoxyphenoxy, cyclohexyloxy, alkylindanyloxy, methoxycarbonylphenoxy, isopropylphenoxy, tert-butylphenoxy, N,N-dimethylaminophenoxy, methoxyphenoxy, methoxycarbonylphenoxy, cyanophenoxy, fluorophenoxy, benzoxyphenoxy, trifluoromethylphenoxy, bromophenoxy, 3,5-ditrifluoromethylphenoxy, methylthiophenoxy, indolyl, tertbutoxycarbonyl-piperidinyloxy, hydroxyphenoxy, pyrimidinoxy and pyrazinoxy.

In another embodiment, R¹ is substituted with Q¹, which is selected from methyl, methoxy, chloro, ethyl, trifluoromethyl, nitro, hydroxy, n-butoxy, 3-(2-piperidinyl)ethoxy, methylcarbonylamino or ethylaminocarbonylamino.

In another embodiment, R¹ has formula IA:

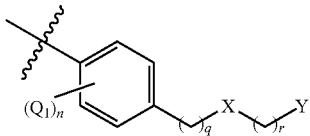

where, n is an integer from 0 to 4, in one embodiment, from 0 to 2, in another embodiment, 0 or 1; q and r are each independently selected from 0 to 5, in one embodiment 0 to 3, in another embodiment 0 or 1; X is O, S or NR', where R' is alkyl, aryl or hydrogen; Y is substituted or unsubstituted alkyl, substituted or unsubstituted aryl, substituted or unsubstituted heteroaryl, substituted or unsubstituted heterocyclyl or substituted or unsubstituted cycloalkyl, where the substituents, when present are selected from one or more Q¹ as above. In another embodiment, Q¹ is selected from halo, hydroxy, alkyl, alkoxy, alkoxycarbonyl, haloalkyl, alkylcarbonyl, hydroxycarbonyl, hydroxyhaloalkyl, aryl, aralkoxy and heteroaryl. In another embodiment, X is O. In another embodiment X is S. In another embodiment, X is NR'. In another embodiment, R' is lower alkyl or hydrogen. In another embodiment, R' is hydrogen. In another embodiment, Y is substituted or unsubstituted aryl. In another embodiment, Y is substituted or unsubstituted heteroaryl. In another embodiment, Y is substituted or unsubstituted phenyl.

In another embodiment, R¹ is methyl, cyclohexyl, 1-cyclopentenyl, 5-indanyl, phenyl, 1-naphthyl, 2-naphthyl, 3-methylphenyl, 2-chlorophenyl, 4-chlorophenyl, 3-ethylphenyl, 3-trifluoromethylphenyl, 3-nitrophenyl, 3-hydroxyphenyl, 3-n-butoxyphenyl, 3-benzyloxyphenyl, 3-(2-piperidinyl)ethoxyphenyl, 3-methylcarbonylaminophenyl, 3-ethylaminocarbonylaminophenyl, 2-methylphenyl, 2-methoxyphenyl, 4-methylphenyl, 3-methoxyphenyl, 4-methoxyphenyl, 3-chlorophenyl, 4-chlorophenyl, 3-benzylaminophenyl, 3-(3-methyl)phenoxymethylphenyl, benzyl, 3-trifluoromethylcarbonylaminophenyl, 3,5-dimethylphenyl, 2-chloro-3-methylphenyl, phenylethyl, 4-butoxyphenyl, 4-methoxycarbonylphenyl, 4-phenoxyphenyl, 4-cyanophenyl, 4-benzoxyphenyl, 4-(1-piperidinyl)phenyl, 4-hydroxycarbonylphenyl, 4-(4-tert-butoxycarbonylpiperazin-1-ylcarbonyl) phenyl, 4-hydroxymethylphenyl, 4-(1-piperidinylcarbonyl) phenyl, 4-dimethylaminophenyl, 4-methylcarbonylaminophenyl, 4-nitrophenyl, 6-(1,2,3,4-tetrahydro)naphthyl, 4-(4-methoxyphenoxy)phenyl, 4-(2-methylphenoxy)phenyl, 4-(3-methylphenoxy)phenyl, 4-(4-methylphenoxy)phenyl, 4-(3-methoxyphenoxy)phenyl, 4-(1-piperidinylmethyl)phenyl, 4-(4-biphenoxy)phenyl, 3-(1-benzoxycarbonyl)-piperidinyl, 4-(1-piperazinylcarbonyl)phenyl, 5-(2-methyl-2,3-dihydro)benzofuryl, 4-benzylphenyl, 4-phenylthiophenyl, 4-(4-chlorophenoxy)-2-chlorophenyl, 4-(3-biphenoxy)phenyl, 4-(1-benzoxycarbonyl)-piperidinyl, 4-piperidinyl, 4-(1-(3-methylbenzyl))-piperidinyl, 4-(3-methyl-4-hydroxyphen-1-oxy)phenyl, 4-(2-methyl-4-hydroxyphenoxy)phenyl, 4-(4-ethoxycarbonylphenoxy)phenyl, 4-(2-methyl-4-tertbutylphenoxy)phenyl, 4-(2-phenyl-4-tertbutylphenoxy) phenyl, 4-(3-ethylphenoxy)phenyl, 4-(3-isopropylphenoxy) phenyl, 4-(3-tertbutylphenoxy)phenyl, 4-(3,5-dimethylphenoxy)phenyl, 4-phenoxy-2-methylphenyl, 4-(2-methylphenoxy)-2-methylphenyl, 4-(2-methylphenoxy)-3-methylphenyl, 4-N-methyl-N-phenylaminophenyl, 4-(3-trifluoromethylphenoxy)phenyl, 4-(4-ethylphenoxy)phenyl, 4-(4-isopropylphenoxy)phenyl, 4-(4-tertbutylphenoxy)phenyl, 4-(3-methylcarbonylphenoxy)phenyl, 4-(3,4-dimethylphenoxy)phenyl, 4-(2-tetrahydropyranyloxy)phenyl, 4-(2-tetrahydropyranyloxy)-3-methylphenyl, 4-hydroxyphenyl, 3-methyl-4-hydroxyphenyl, 4-(4-methylphenoxy)-3-methylphenyl, 4-(2-ethylphenoxy)phenyl, 4-(2-isopropylphenoxy)phenyl, 4-(5,6,7,8-tetrahydronaphthyloxy)phenyl, 4-(3-hydroxycarbonylphenoxy)phenyl, 2-methyl-4-hydroxyphenyl, 4-phenoxy-2-hydroxyphenyl, 3-phenoxyphenyl, 4-(4-(1,3-hexafluoro-2-hydroxypropyl)phenylamino)phenyl, 4-(2,3,4-trimethylphenoxy)phenyl, 4-(4-benzyloxyphenoxy)phenyl, 4-(3-(methyl-3-indanyloxy)phenyl, 4-(2-methyl-5-benzothiazoloxy)phenyl, 4-cyclohexyloxyphenyl, 4-(3-methoxycarbonylphenoxy)phenyl, 4-(3-isopropylphenoxy)-3-methylphenyl, 4-tert-butyl-phenoxy-3-methylphenyl, 4-N,N-dimethylaminophenoxy-3-methylphenyl, 4-methoxy-phenoxy-3-methylphenyl, 3-methoxy-phenoxy-3-methylphenyl, 4-(3-methoxycarbonyl-phenoxy)-3-methylphenyl, 4-(3-cyanophenoxy)-3-methylphenyl, 4-(4-fluorophenoxy)-3-methylphenyl, 4-(4-benzoxy-phenoxy)-3-methylphenyl, 4-(3-benzoxy-phenoxy)-3-methylphenyl, 4-(2,5-dimethylphenoxy)-3-methylphenyl, 4-(2-chlorophenoxy)-3-methylphenyl, 4-(3-chlorophenoxy)-3-methylphenyl, 4-(2-trifluoromethylphenoxy)-3-methylphenyl, 4-(3-trifluoromethylphenoxy)-2-methylphenyl, 4-(3-bromophenoxy)-phenyl, 4-(4-bromophenoxy)-phenyl, 4-(3-benzyloxy-phenoxy)-phenyl, 4-(3-cyanophenoxy)-phenyl, 4-(4-cyanophenoxy)phenyl, 4-(2,4-dimethylphenoxy)-phenyl, 4-(3,5-trifluoromethylphenoxy)phenyl, 4-(4-methylthio-phenoxy)-phenyl, 4-(4-N,N-dimethylamino-phenoxy)-phenyl, 5-indolyloxyphenyl, 4-(1-tert-butoxycarbonyl-piperidin-4-oxy)-phenyl, 4-(4-hydroxyphenoxy)-phenyl, 4-(2-pyrimidinoxy)-phenyl, 4-(2-pyrazinoxy)-phenyl, 2-thienyl, 2-(5-chloro)thienyl, 2-(5-bromo)thienyl, 2-(5-phenyl)thienyl, 3-thianaphthyl, 3-methyl-2-thianaphthyl, 2-(5-(3-methylphenyl))-thienyl, 3-pyridinyl, 2-pyrazinyl, 4-(1-phenyl-5-methyl)pyrazolyl, 2-(1-methyl)pyrrolyl, 3-(1-methyl)indolyl, 3-(1-benzyloxycarbonyl)-piperidinyl, 4-(1-benzyloxyarbonyl)-piperidinyl, 4-piperidinyl, 4-(1-(3-methylbenzyl))-piperidinyl, 2-furyl, 2-(5-methyl)-furyl, 3-(2,5-dimethyl)-furyl, benzofuryl, 3-(2,4-dimethyl)-furyl, 2-thiazolyl or 5-(2,4-dimethyl)thiazolyl.

In another embodiment, R¹ is phenyl, 1-naphthyl, 2-naphthyl, 3-methylphenyl, 3-methoxyphenyl, 2-chlorophenyl, 3-ethylphenyl, 3-trifluoromethylphenyl, 3-nitrophenyl, 3-hydroxyphenyl, 3-n-butoxyphenyl, 3-benzyloxyphenyl, 3-(2-piperidinyl)ethoxyphenyl, 3-methylcarbonyl-aminophenyl, 3-ethylaminocarbonylaminophenyl, 2-methylphenyl, 2-methoxyphenyl, 4-methylphenyl, 3-methoxyphenyl, 4-methoxyphenyl, 3-chlorophenyl or 4-chlorophenyl.

In another embodiment, R¹ is 3-(3-methyl)phenoxymethylphenyl, 4-phenoxyphenyl, 4-benzoxyphenyl, 4-(4-methoxyphenoxy)phenyl, 4-(2-methylphenoxy)phenyl, 4-(3-methylphenoxy)phenyl, 4-(4-methylphenoxy)phenyl, 4-(3-methoxyphenoxy)phenyl, 4-(4-biphenoxy)phenyl, 4-(4-chlorophenoxy)-2-chlorophenyl, 4-(3-biphenoxy)phenyl, 4-(3-methyl-4-hydroxyphenoxy)phenyl, 4-(2-methyl-4-hydroxyphenoxy)phenyl, 4-(4-ethoxycarbonylphenoxy)phenyl, 4-(2-methyl-4-tertbutylphenoxy)phenyl, 4-(2-phenyl-4-tertbutylphenoxy)phenyl, 4-(3-ethylphenoxy)phenyl, 4-(3-isopropylphenoxy)phenyl, 4-(3-tertbutylphenoxy)phenyl, 4-(3,5-dimethylphenoxy)phenyl, 4-phenoxy-2-methylphenyl, 4-(2-methylphenoxy)-2-methylphenyl, 4-(2-methylphenoxy)-3-methylphenyl, 4-(3-trifluoromethylphenoxy)phenyl, 4-(4-ethylphenoxy)phenyl, 4-(4-isopropylphenoxy)phenyl, 4-(4-tertbutylphenoxy)phenyl, 4-(3-methylcarbonylphenoxy)phenyl, 4-(3,4-dimethylphenoxy)phenyl, 4-(4-methylphenoxy)-3-methylphenyl, 4-(2-ethylphenoxy)phenyl, 4-(2-isopropylphenoxy)phenyl, 4-(5,6,7,8-tetrahydronaphthyloxy)phenyl, 4-(3-hydroxycarbonylphenoxy)phenyl, 2-methyl-4-hydroxyphenyl, 4-phenoxy-2-hydroxyphenyl, 3-phenoxyphenyl, 4-(2,3,4-trimethylphenoxy)phenyl, 4-(4-benzyloxyphenoxy)phenyl, 4-(3-methoxycarbonylphenoxy)phenyl, 4-(3-isopropylphenoxy)-3-methylphenyl, 4-tert-butyl-phenoxy-3-methylphenyl, 4-N,N-dimethylaminophenoxy-3-methylphenyl, 4-methoxy-phenoxy-3-methylphenyl, 3-methoxy-phenoxy-3-methylphenyl, 4-(3-methoxycarbonyl-phenoxy)-3-methylphenyl, 4-(3-cyanophenoxy)-3-methylphenyl, 4-(4-fluorophenoxy)-3-methylphenyl, 4-(4-benzoxy-phenoxy)-3-methylphenyl, 4-(3-benzoxy-phenoxy)-3-methylphenyl, 4-(2,5-dimethylphenoxy)-3-methylphenyl, 4-(2-chlorophenoxy)-3-methylphenyl, 4-(3-chlorophenoxy)-3-methylphenyl, 4-(2-trifluoromethylphenoxy)-3-methylphenyl, 4-(3-trifluoromethylphenoxy)-2-methylphenyl, 4-(3-bromophenoxy)-3-methylphenyl, 4-(3-bromophenoxy)-phenyl, 4-(3-benzyloxy-phenoxy)-phenyl, 4-(3-cyanophenoxy)-phenyl, 4-(4-cyanophenoxy)phenyl, 4-(2,4-dimethylphenoxy)-phenyl, 4-(3,5-trifluoromethylphenoxy)phenyl, 4-(4-methylthio-phenoxy)-phenyl or 4-(4-N,N-dimethylamino-phenoxy)-phenyl.

In another embodiment, $R^1$ is 4-N-methyl-N-phenylaminophenyl, 4-(4-(1,3-hexafluoro-2-hydroxypropyl)phenyl-1-amino)phenyl or 4-phenylthiophenyl.

In another embodiment, $R^1$ is 2-thienyl, 2-(5-chloro)thienyl, 2-(5-bromo)thienyl, 2-(5-phenyl)thienyl, 3-thianaphthyl, 3-methyl-2-thianaphthyl or 2-(5-(3-methylphenyl))-thienyl. In another embodiment, $R^1$ is thienyl. In another embodiment, $R^1$ is 2-thienyl.

In another embodiment, $R^1$ is 3-pyridinyl, 2-pyrazinyl, 4-(1-phenyl-5-methyl)pyrazolyl, 2-(1-methyl)pyrrolyl, 3-(1-methyl)indolyl, 3-(1-benzyloxycarbonyl)-piperidinyl, 4-(1-benzyloxycarbonyl)-piperidinyl, 4-piperidinyl or 4-(1-(3-methylbenzyl)-piperidinyl.

In another embodiment, $R^1$ is 2-furyl, 2-(5-methyl)-furyl, 3-(2,5-dimethyl)-furyl, benzofuryl or 3-(2,4-dimethyl)-furyl.

In another embodiment, $R^1$ is 2-thiazolyl or 5-(2,4-dimethyl)thiazolyl.

In another embodiment, $R^3$ is substituted or unsubstituted alkyl, substituted or unsubstituted alkylaryl, substituted or unsubstituted aryl, substituted or unsubstituted alkoxycarbonyl or substituted or unsubstituted alkylaminocarbonyl, where the substituents are selected from one or more $Q^1$. In another embodiment, $R^3$ is substituted or unsubstituted alkyl or substituted or unsubstituted aryl. In another embodiment, $R^3$ is substituted or unsubstituted alkoxycarbonyl. In another embodiment, $R^3$ is substituted or unsubstituted alkyl. In another embodiment, $R^3$ is haloalkyl. In certain embodiments, $R^3$ is substituted with $Q^1$, which is halo, pseudohalo, alkyl, alkoxy, alkoxycarbonyl or aryloxycarbonyl. In another embodiments, $R^3$ is substituted with $Q^1$, which is halo. In further embodiments, $R^3$ is substituted with $Q^1$, which is fluoro, chloro, phenyl, methyl, methoxy or methylamino.

In further embodiments, $R^3$ is substituted or unsubstituted methyl, or substituted or unsubstituted phenyl. In another embodiments, $R^3$ is methyl, trifluoromethyl, pentafluoroethyl, heptafluoropropyl, chlorodifluoromethyl, 1-(1-methoxy-1-fluoro)ethyl, methoxycarbonyl, ethoxycarbonyl, methylaminocarbonyl, dimethoxymethyl, methoxycarbonylmethyl or phenyl. In another embodiment, $R^3$ is trifluoromethyl, methyl, methoxycarbonylmethyl or phenyl.

In another embodiment, $R^4$ is hydrogen, substituted or unsubstituted alkyl, substituted or unsubstituted alkynyl, pseudohalide, hydroxycarbonyl, $CH_2NR^{31}R^{32}$ or $NO_2$; where the substituents are each independently selected from one or more $Q^1$. In another embodiment, $R^4$ is pseudohalide. In another embodiment, $R^4$ is substituted or unsubstituted methyl, substituted or unsubstituted acetyl. In another embodiment, $R^4$ is substituted or unsubstituted acetyl, where the substitutent is trialkylsilyl. In further embodiments, $R^4$ is substituted with $Q^1$, which is trialkylsilyl, alkylcarbonylamino, arylcarbonylamino, aralkylcarbonylamino, alkoxycarbonylamino, dialkylamino, alkylamino or amino.

In another embodiment, $R^4$ is alkylcarbonylaminoalkyl, alkoxycarbonylaminoalkyl, aralkoxycarbonylaminoalkyl or aryloxycarbonylaminoalkyl. In another embodiment, $R^4$ is hydrogen, cyano, nitro, hydroxycarbonyl, trimethylsilylacetyl, acetyl, methylcarbonylaminomethyl, ethylcarbonylaminomethyl, n-propylcarbonylaminomethyl, isopropylcarbonylaminomethyl, n-octylcarbonylaminomethyl, phenylcarbonylaminomethyl, benzylcarbonylaminomethyl, phenylethylcarbonylaminomethyl, ethoxycabonylaminomethyl dimethylaminomethyl or aminomethyl. In another embodiment, $R^4$ is cyano.

In certain embodiments, $R^3$ and $R^4$, together with the atoms to which they are attached, form substituted or unsubstituted heterocyclic ring. In certain embodiments, $R^3$ and $R^4$, together with the atoms to which they are attached, form substituted or unsubstituted heterocyclic ring, with the proviso that the nitrogen atom in the heterocyclic ring is not substituted with a phenyl group. In certain embodiments, $R^3$ and $R^4$, together with the atoms to which they are attached, form substituted or unsubstituted heterocyclic ring, with the proviso that the heterocyclic ring does not have more than one oxo substitutent. In another embodiment, $R^3$ and $R^4$ together with the atoms to which they are attached form 2-oxotetrahydropyridine or 2-oxo-3-pyrroline.

In another embodiment, $R^5$ is substituted or unsubstituted alkyl, substituted or unsubstituted aralkyl, substituted or unsubstituted aryl, substituted or unsubstituted heterocyclyl, substituted or unsubstituted heterocyclylalkyl, substituted or unsubstituted heteroaryl, substituted or unsubstituted heteroaralkyl, $—N=CR^6R^7$ or $—NR^9R^{10}$. In another embodiment, $R^5$ is substituted or unsubstituted aryl, substituted or unsubstituted heteroaryl, substituted or unsubstituted aralkyl, substituted or unsubstituted heteroaralkyl, $—N=CR^6R^7$ or $—NR^9R^{10}$. In another embodiment, $R^5$ is substituted or unsubstituted aryl, substituted or unsubstituted aralkyl, $—N=CR^6R^7$ or $—NR^9R^{10}$. In further embodiments, $R^5$ is substituted or unsubstituted aralkyl, or $—N=CR^6R^7$. In another embodiment, $R^5$ is substituted or unsubstituted aralkyl. In another embodiment, $R^5$ is substituted or unsubstituted heterocyclylalkyl. In another embodiment, $R^5$ is substituted or unsubstituted heteroaralkyl. In another embodiment, $R^5$ is $—N=CR^6R^7$. In another embodiment, $R^5$ is substituted or unsubstituted heterocyclyl.

In another embodiment, $R^5$ is substituted or unsubstituted methyl, substituted or unsubstituted ethyl, substituted or unsubstituted propyl, substituted or unsubstituted phenyl, substituted or unsubstituted piperidinyl, substituted or unsubstituted benzyl, substituted or unsubstituted 2-phenethyl, substituted or unsubstituted 1-phenethyl, substituted or unsubstituted 3-phenylpropyl, substituted or unsubstituted 1,2,3,4-tetrahydro-1-naphthyl, substituted or unsubstituted 3-pyridylmethyl, substituted or unsubstituted 4-pyridylmethyl, substituted or unsubstituted 2-pyrazinyl, substituted or unsubstituted thiazolylmethyl, substituted or unsubstituted oxazolylmethyl.

In another embodiment, $R^5$ is substituted or unsubstituted phenyl, substituted or unsubstituted benzyl, substituted or unsubstituted 2-phenethyl, substituted or unsubstituted 1-phenethyl, substituted or unsubstituted 3-phenylpropyl, substituted or unsubstituted 1,2,3,4-tetrahydro-1-naphthyl, substituted or unsubstituted 3-pyridylmethyl, substituted or unsubstituted 4-pyridylmethyl, —N=$CR^6R^7$ or —$NR^9R^{10}$.

In another embodiment, $R^5$ is substituted or unsubstituted piperidinyl, substituted or unsubstituted 3-pyridylmethyl, substituted or unsubstituted 4-pyridylmethyl, substituted or unsubstituted 2-pyrazinyl, substituted or unsubstituted thiazolylmethyl, or substituted or unsubstituted oxazolylmethyl.

In another embodiment, $R^5$ is substituted or unsubstituted benzyl.

In certain embodiments, $R^5$ is unsubstituted or substituted with one or more, in one embodiment, one, two or three $Q^1$ groups, where $Q^1$ is alkyl, haloalkyl, halohydroxyalkyl, alkoxy, alkoxyalkoxyalkyl, alkoxyalkyl, aryl, halo, alkoxycarbonyl, alkylthio, aryloxy, haloalkoxy, aralkyl, heteroaryl, hydroxy, hydroxyalkyl, heterocyclyl, heterocyclylalkyl, alkylcarbonyl, arylcarbonyl, alkylalkelenedioxy or dialkylalkelenedioxy. In other embodiments, $R^5$ is unsubstituted or substituted with one or more $Q^1$ groups, where $Q^1$ is alkyl, haloalkyl, alkoxy, aryl, halo, alkoxycarbonyl, alkylthio, aryloxy, haloalkoxy, aralkyl, heteroaryl, hydroxy, alkylcarbonyl or arylcarbonyl.

In other embodiments, $R^5$ is unsubstituted or substituted with one or more, in one embodiment one, two or three, $Q^1$ groups, where $Q^1$ is methyl, isopropyl, trifluoromethyl, methoxy, fluoro, bromo, methoxycarbonyl, chloro, methylthio, phenoxy, trifluoromethoxy, 3-pyridyl, 4-pyridyl, 2-pyridyl, ethyl, n-propyl, cyclohexyl, n-propyloxymethyl, n-pentyloxymethyl, n-octyloxymethyl, ethoxymethyl, n-butoxymethyl, n-hexyloxymethyl, n-octyloxymethyl, tert-butyl, ethoxycarbonyl, methylcarbonyl, hydroxy, phenyl, benzyl, n-butyl, ethoxy, phenylcarbonyl, 2-(2-methyl)-methylenedioxy, 1-piperidinyl, 5-(2,2-dimethyl)-methylenedioxy, methoxymethoxymethyl, hydroxymethyl, hydroxyethyl, methoxymethyl, 1-piperidinylmethyl or 1,3-trifluoro-2-hydroxypropyl.

In another embodiment, $Q^1$ is methyl, trifluoromethyl, methoxy, fluoro, bromo, methoxycarbonyl, chloro, methylthio, phenoxy, trifluoromethoxy, 3-pyridyl, 4-pyridyl, 2-pyridyl, ethyl, tert-butyl, ethoxycarbonyl, methylcarbonyl, hydroxy, phenyl, benzyl, n-butyl, ethoxy or phenylcarbonyl.

In another embodiment, $R^5$ is 2,4-dimethylbenzyl, 4-isopropylbenzyl, 4-tert-butylbenzyl, 2,4,5-trifluorobenzyl, 1-naphthylmethyl, 4-(2-(2-methyl)-1,3-dioxymethylene) benzyl, 4-methylbenzyl, 4-ethylbenzyl, 1-piperidinyl, 4-methylcarbonylbenzyl, 5-(2,2-dimethyl)-1,3-dioxymethelenemethyl, 1,2-dihydroxypropanyl, benzyl, 4-(2-methyl)-thiazolylmethyl, 4-(2-phenyl)thiazolylmethyl, 3-methoxymethoxymethylbenzyl, 3-hydroxymethylbenzyl, 4-hydroxymethylbenzyl, 4-hydroxyethylbenzyl, 4-methoxymethylbenzyl, 4-(1-piperidinylmethyl)benzyl, 3-biphenyl, 4-biphenyl, 4-(1,3-trifluoro-2-hydroxypropyl)phenyl, 4-(2-ethyl)thiazolylmethyl, 4-(2-isopropyl)thiazolylmethyl, 4-(2-propyl)thiazolylmethyl, 4-(2-benzyl)thiazolylmethyl, 4-(2-methyl)oxazolylmethyl, 4-(2-ethyl)oxazolylmethyl, 4-(2-propyl)oxazolylmethyl, 4-(2-phenyl)oxazolylmethyl, 4-(2-benzyl)oxazolylmethyl, 4-(2-cyclohexyl)oxazolylmethyl, 4-n-propyloxymethylbenzyl, 2-(5-methyl)pyrazinylmethyl, 4-n-pentyloxymethylbenzyl, 4-n-octyloxymethylbenzyl, 3-ethoxymethylbenzyl, 3-n-butoxymethylbenzyl, 3-n-hexyloxymethylbenzyl, 3-n-octyloxymethylbenzyl, 2-methylbenzyl, 4-methylbenzyl, 3-methylbenzyl, phenylethyl, 4-(2,5-dimethyl)thiazolylmethyl, 4-(2-isopropyl-5-methyl)thiazolylmethyl, 4-(2-ethyl-5-methyl)thiazolylmethyl, 4-(2-methyl-5-ethyl)thiazolylmethyl, 4-(2,5-diethyl)thiazolylmethyl, phenyl, 2-phenylethyl, 3-phenylpropyl, benzyl, 3-methylbenzyl, 2-trifluoromethylbenzyl, 3-trifluoromethylbenzyl, 4-trifluoromethylbenzyl, 2-methoxybenzyl, 3-methoxybenzyl, 4-methoxybenzyl, 4-phenylbenzyl, 1-phenylethyl, 1,2,3,4-tetrahydro-1-naphthyl, 2-fluorobenzyl, 4-fluorobenzyl, 2,4-difluorobenzyl, 4-bromobenzyl, 4-methoxycarbonylbenzyl, 2-chlorobenzyl, 4-chorobenzyl, 4-methylthiobenzyl, 4-phenoxybenzyl, 4-trifluoromethoxybenzyl, 3-pyridylmethyl or 4-pyridylmethyl.

In another embodiment, $R^5$ is 4-(2-(2-methyl)-1,3-dioxymethylene)benzyl, 1-piperidinyl, 5-(2,2-dimethyl)-1,3-dioxymethelenemethyl, 4-(2-methyl)-thiazolylmethyl, 4-(2-phenyl)thiazolylmethyl, 4-(1-piperidinylmethyl)benzyl, 4-(2-ethyl)thiazolylmethyl, 4-(2-isopropyl)thiazolylmethyl, 4-(2-propyl)thiazolylmethyl, 4-(2-benzyl)thiazolylmethyl, 4-(2-methyl)oxazolylmethyl, 4-(2-ethyl)oxazolylmethyl, 4-(2-propyl)oxazolylmethyl, 4-(2-phenyl)oxazolylmethyl, 4-(2-benzyl)oxazolylmethyl, 4-(2-cyclohexyl)oxazolylmethyl, 2-(5-methyl)pyrazinylmethyl, 4-(2,5-dimethyl)thiazolylmethyl, 4-(2-isopropyl-5-methyl)thiazolylmethyl, 4-(2-ethyl-5-methyl)thiazolylmethyl, 4-(2-methyl-5-ethyl)thiazolylmethyl, 4-(2,5-diethyl)thiazolylmethyl, 3-pyridylmethyl or 4-pyridylmethyl.

In another embodiment, $R^5$ is phenyl, 2-phenylethyl, 3-phenyl-propyl, benzyl, 2-methylbenzyl, 3-methylbenzyl, 4-methylbenzyl, 2-trifluoromethylbenzyl, 3-trifluoromethylbenzyl, 4-trifluoromethylbenzyl, 2-methoxybenzyl, 3-methoxybenzyl, 4-methoxybenzyl, 4-phenylbenzyl, 1-phenylethyl, 2,4-dimethylbenzyl, 2-fluorobenzyl, 4-fluorobenzyl, 2,4-difluorobenzyl, 4-bromobenzyl, 4-methoxycarbonylbenzyl, 2-chlorobenzyl, 4-chorobenzyl, 4-methylthiobenzyl, 4-phenoxybenzyl, 4-trifluoromethoxybenzyl, 3-pyridylmethyl, or 4-pyridylmethyl.

In another embodiment, $R^5$ is —N=$CR^6R^7$ where $R^6$ and $R^7$ are each independently hydrogen, substituted or unsubstituted alkyl, or substituted or unsubstituted aryl; or together form substituted or unsubstituted alkylene, substituted or unsubstituted alkenylene, or —$(CH_2)_xX(CH_2)_y$— where x and y are each 2, and X is O or $NR^8$; where $R^8$ is substituted or unsubstituted alkyl, substituted or unsubstituted alkylcarbonyl, or substituted or unsubstituted arylcarbonyl.

In other embodiments, $R^6$ and $R^7$ are each independently hydrogen, substituted or unsubstituted methyl, substituted or unsubstituted ethyl, substituted or unsubstituted n-propyl, substituted or unsubstituted i-propyl, substituted or unsubstituted i-butyl, substituted or unsubstituted tert-butyl, substituted or unsubstituted phenyl, substituted or unsubstituted s-butyl, substituted or unsubstituted 3-pentyl, or substituted or unsubstituted naphthyl; where the substituents are selected from one or more $Q^1$. In another embodiment, $R^6$ and $R^7$ are unsubstituted or substituted with one or more, in one embodiment one or two, $Q^1$ groups, where $Q^1$ is hydroxy, halo, alkyl or alkoxy. In another embodiment, $R^6$ and $R^7$ are unsubstituted or substituted with one or more, in one embodiment one or two, $Q^1$ groups, where $Q^1$ is hydroxy, chloro, bromo, methyl or methoxy.

In other embodiments, $R^6$ and $R^7$ are each independently hydrogen, methyl, phenyl, ethyl, isopropyl, n-propyl, s-butyl, 3-pentyl, isobutyl, t-butyl, 2-naphthyl, 2-hydroxyphenyl, 2-hydroxy-5-chlorophenyl, 4-bromophenyl, 2-hydroxy-4-bromophenyl, 2-methylphenyl or 4-methoxyphenyl. In other embodiments, $R^6$ and $R^7$ are each independently hydrogen, methyl, ethyl, isopropyl, n-propyl, s-butyl, 3-pentyl, isobutyl or t-butyl.

In another embodiment, $R^6$ and $R^7$ together form substituted or unsubstituted alkylene, substituted or unsubstituted alkenylene, or —$(CH_2)_xX(CH_2)_y$— where x and y are each 2, and X is O or $NR^8$, where the substituents are selected from one or more $Q^1$. In other embodiments, $R^6$ and $R^7$ together form substituted or unsubstituted butylene, substituted or unsubstituted pentylene, substituted or unsubstituted hexylene, or substituted or unsubstituted pentenylene, where the substituents are selected from one or more $Q^1$. In other embodiments, $R^6$ and $R^7$ are unsubstituted or substituted with one or more, in one embodiment one or two, substituents selected from $Q^1$, which is alkyl, alkoxycarbonyl, aryl, aralkyl, halo, alkoxy and alkylthio. In other embodiments, $R^6$ and $R^7$ are unsubstituted or substituted with one or more, in one embodiment one or two, substituents selected from $Q^1$, which is methyl, ethyl, tert-butyl, ethoxycarbonyl, ethyl, phenyl, benzyl, n-butyl, chloro, methoxy, ethoxy, methylthio and methoxycarbonyl.

In another embodiment, $R^6$ and $R^7$ together form —$(CH_2)_x$ $X(CH_2)_y$— where x and y are each 2, and X is O or $NR^8$, where $R^8$ is substituted or unsubstituted alkyl, substituted or unsubstituted alkylcarbonyl, or substituted or unsubstituted arylcarbonyl, and the substituents are selected from one or more $Q^1$. In other embodiments, $R^8$ is alkyl, alkylcarbonyl or arylcarbonyl. In another embodiment, $R^8$ is methyl, methylcarbonyl or phenylcarbonyl.

In other embodiments, $R^6$ and $R^7$ together form pentylene, 2,2,4,4-tetramethylpentylene, 3,3-dimethyl-1-pentenylene, 2-methyl-1-pentenylene, 3-methylpentylene, 3-ethylpentylene, 3-tert-butylpentylene, 1-methylpentylene, 2-methylpentylene, hexylene, butylene, 1-methylbutylene, 2-methylbutylene, 1,3-ethylenebutylene, 3-ethoxycarbonylpentylene, 1-ethylpentylene, 1-phenylpentylene, 1-benzylpentylene, 1-n-butylpentylene, 1,1-dimethylpentylene, 1-chloropentylene, 1-methoxypentylene, 1-ethoxypentylene, 1-methylthiopentylene or 1-methoxycarbonylpentylene.

In another embodiment, $R^5$ is —$NR^9R^{10}$, where $R^9$ and $R^{10}$ are each independently hydrogen, or substituted or unsubstituted aryl. In another embodiment, $R^9$ and $R^{10}$ are each independently hydrogen, or substituted or unsubstituted phenyl. In another embodiment, $R^9$ and $R^{10}$ are each independently hydrogen or phenyl.

In another embodiment, the compounds for use in the compositions and methods provided herein have formula I, where $R^1$ is substituted or unsubstituted aryl, substituted or unsubstituted aralkyl, substituted or unsubstituted heteroaryl, or substituted or unsubstituted heteroaralkyl; $R^2$ is hydrogen, or substituted or unsubstituted alkyl; $R^3$ is haloalkyl; $R^4$ is cyano; and $R^5$ is substituted or unsubstituted aryl, substituted or unsubstituted aralkyl, substituted or unsubstituted heterocyclyl, or —$N=CR^6R^7$; where $R^6$ and $R^7$ are each independently hydrogen or substituted or unsubstituted alkyl;

where the alkyl, heterocyclyl, aryl, heteroaryl, aralkyl and heteroaralkyl moieties of $R^1$, $R^2$, $R^3$, $R^5$, $R^6$ and $R^7$ are unsubstituted or substituted with one or more substituents, in one embodiment one to three or four substituents, each independently selected from $Q^1$, as defined above.

In another embodiment, the compounds for use in the compositions and methods have formula II:

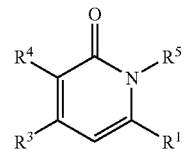

where $R^1$, $R^3$, $R^4$ and $R^5$ are selected as above.

In another embodiment, the compounds for use in the compositions and methods have formula III:

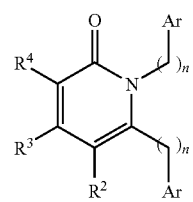

where $R^2$, $R^3$ and $R^4$ are selected as above; each Ar is independently substituted or unsubstituted aryl, substituted or unsubstituted cycloalkyl; substituted or unsubstituted heteroaryl, or substituted or unsubstituted heterocyclyl, where there are 0 to 5 substituents, in one embodiment 0, 1, 2 or 3 substituents, each independently selected from $Q^1$; and each n is independently an integer from 0 to 6, in one embodiment 0 to 3, in another embodiment 0 or 1.

In another embodiment, the compounds are of formula III where $R^2$ is hydrogen. In another embodiment, the compounds have formula III where $R^3$ is haloalkyl. In another embodiment, the compounds have formula III where $R^3$ is perfluoroalkyl. In another embodiment, the compounds have formula III where $R^3$ is trifluoromethyl or pentafluoroethyl. In another embodiment, the compounds have formula III where $R^3$ is trifluoromethyl. In another embodiment, the compounds have formula III where $R^4$ is cyano. In another embodiment, the compounds have formula III where Ar is substituted or unsubstituted aryl, substituted or unsubstituted heteroaryl, or substituted or unsubstituted heterocyclyl. In another embodiment, the compounds have formula III where Ar is N-pyrrolidinyl.

In another embodiment, the compounds for use in the compositions and methods provided herein have formula IV:

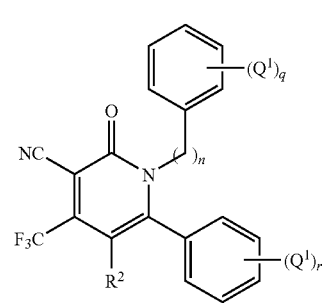

where $R^2$, $Q^1$ and n are selected as above; and q and r are each independently an integer from 0 to 5, or from 0 to 3, or 0 or 1.

In another embodiment, the compounds for use in the compositions and methods provided herein have formula V:

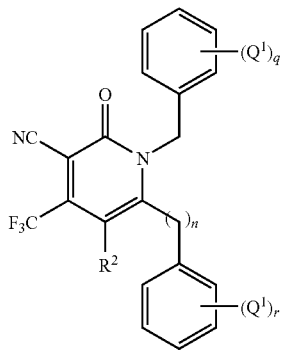

where $R^2$, $Q^1$, q, r and n are selected as above.

In another embodiment, the compounds for use in the compositions and methods provided herein have formula VI:

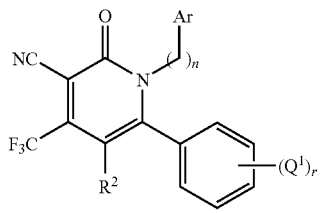

where Ar, $R^2$, $Q^1$, r and n are selected as above. In another embodiment, the compounds have formula VI where Ar is substituted or unsubstituted heteroaryl.

In another embodiment, the compounds for use in the compositions and methods provided herein have formula VII:

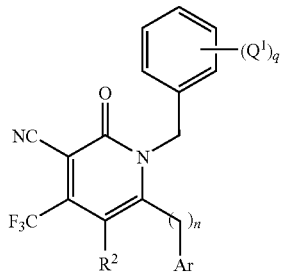

where Ar, $R^2$, $Q^1$, q and n are selected as above.

In another embodiment, the compounds for use in the compositions and methods provided herein have formula VIII:

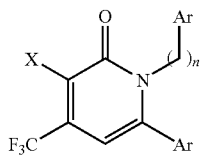

where each Ar is independently selected as above; n is selected as above; and X is cyano, nitro or $NR^{31}R^{32}$, where $R^{31}$ and $R^{32}$ are selected as above.

In another embodiment, the compounds for use in the compositions and methods provided herein have formula IX:

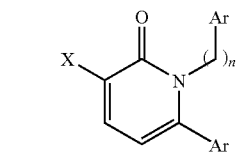

where each Ar is independently selected as above; n is selected as above; and X is bromo, CHO, $COOR^{30}$ or $CONR^{31}R^{32}$, where $R^{30}$, $R^{31}$ and $R^{32}$ are selected as above.

In another embodiment, the compounds for use in the compositions and methods provided herein have formula X:

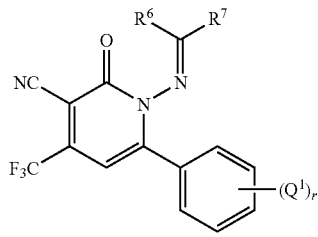

where $Q^1$, r, $R^6$ and $R^7$ are selected as above.

In another embodiment, the compounds for use in the compositions and methods provided herein have formula XI:

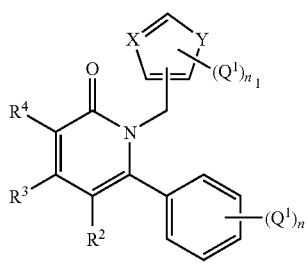

wherein n is an integer from 0 to 5; $n_1$ is an integer from 0 to 2; Y is selected from O, S and NR', where R' is hydrogen, alkyl or aryl; X is N; $Q^1$, $R^2$, $R^3$ and $R^4$ are selected as above.

In another embodiment, the compounds for use in the compositions and methods provided herein have formula XII:

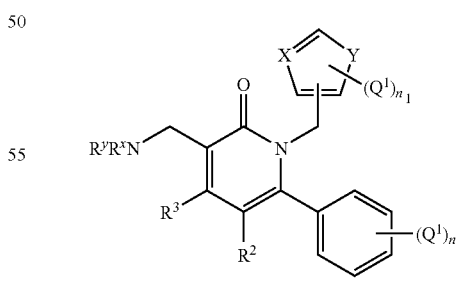

wherein n is an integer from 0 to 5; $n_1$ is an integer from 0 to 2; Y is selected from O, S and NR', where R' is hydrogen, alkyl or aryl; X is N; $R^x$ and $R^y$ are each independently selected from hydrogen, alkyl, alkylcarbonyl, aryl, arylcarbonyl, aralkylcarbonyl, alkoxycarbonyl, aryloxycarbonyl and aralkoxycarbonyl; $Q^1$, $R^2$, $R^3$ and $R^4$ are selected as above.

In another embodiment, the compounds for use in the compositions and methods provided herein have formula XIII:

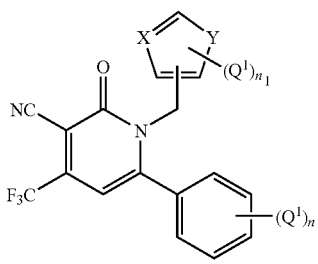

wherein the variables are as defined above.

In another embodiment, the compounds for use in the compositions and methods provided herein have formula XIV:

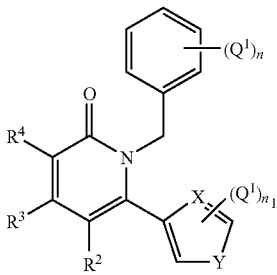

wherein the variables are as defined above.

In another embodiment, the compounds for use in the compositions and methods provided herein have formula XV:

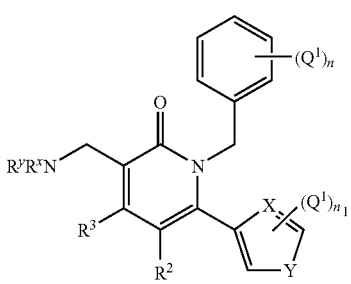

wherein the variables are as defined above.

In another embodiment, the compounds for use in the compositions and methods provided herein have formula XVI:

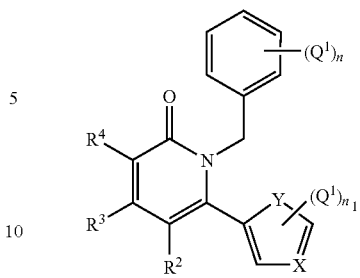

wherein the variables are as defined above.

In another embodiment, the compounds for use in the compositions and methods provided herein have formula XVI1:

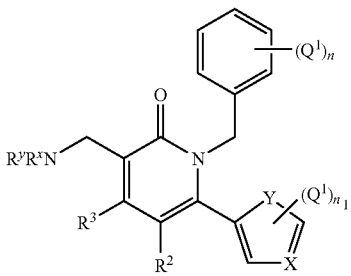

wherein the variables are as defined above.

In another embodiment, the compounds for use in the compositions and methods provided herein have formula XVII:

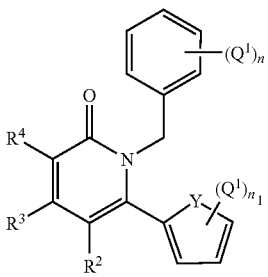

wherein the variables are as defined above.

In another embodiment, the compounds for use in the compositions and methods provided herein have formula XVIII:

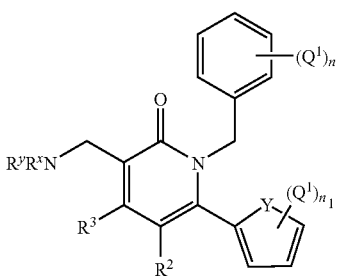

wherein the variables are as defined above.

In another embodiment, the compounds for use in the compositions and methods provided herein have formula XIX:

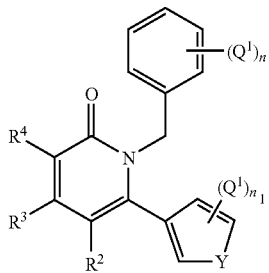

wherein the variables are as defined above.

In another embodiment, the compounds for use in the compositions and methods provided herein have formula XX:

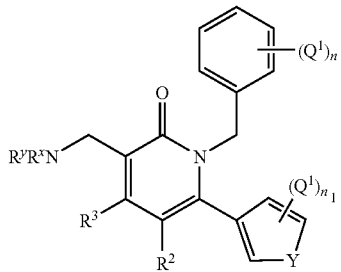

wherein the variables are as defined above.

In another embodiment, the compounds for use in the compositions and methods provided herein are selected from FIG. 1.

In another embodiment, the compounds for use in the compositions and methods provided herein are selected from:
1-Cyclohexylideneamino-2-oxo-6-phenyl-4-trifluoromethyl-1,2-dihydropyridine-3-carbonitrile;
1-Isopropylideneamino-2-oxo-6-phenyl-4-trifluoromethyl-1,2-dihydropyridine-3-carbonitrile;
2-Oxo-6-phenyl-1-(3,3,5,5-tetramethyl-cyclohexylideneamino)-4-trifluoromethyl-1,2-dihydropyridine-3-carbonitrile;
1-(4,4-Dimethyl-cyclohex-2-enylideneamino)-2-oxo-6-phenyl-4-trifluoromethyl-1,2-dihydropyridine-3-carbonitrile (isomer 1);
1-(4,4-Dimethyl-cyclohex-2-enylideneamino)-2-oxo-6-phenyl-4-trifluoromethyl-1,2-dihydropyridine-3-carbonitrile (isomer 2);
1-(3-Methyl-cyclohex-2-enylideneamino)-2-oxo-6-phenyl-4-trifluoromethyl-1,2-dihydropyridine-3-carbonitrile;
2-Oxo-6-phenyl-1-(1-phenyl-ethylideneamino)-4-trifluoromethyl-1,2-dihydropyridine-3-carbonitrile;
1-(Benzylidene-amino)-2-oxo-6-phenyl-4-trifluoromethyl-1,2-dihydropyridine-3-carbonitrile;
1-(1-Ethyl-propylideneamino)-2-oxo-6-phenyl-4-trifluoromethyl-1,2-dihydropyridine-3-carbonitrile;
1-(4-Methyl-cyclohexylideneamino)-2-oxo-6-phenyl-4-trifluoromethyl-1,2-dihydropyridine-3-carbonitrile;
1-(4-Ethyl-cyclohexylideneamino)-2-oxo-6-phenyl-4-trifluoromethyl-1,2-dihydropyridine-3-carbonitrile;
1-(4-tert-Butyl-cyclohexylideneamino)-2-oxo-6-phenyl-4-trifluoromethyl-1,2-dihydropyridine-3-carbonitrile;
1-(2-Methyl-cyclohexylideneamino)-2-oxo-6-phenyl-4-trifluoromethyl-1,2-dihydropyridine-3-carbonitrile;
1-Cycloheptylideneamino-2-oxo-6-phenyl-4-trifluoromethyl-1,2-dihydropyridine-3-carbonitrile;
1-Cyclopentylideneamino-2-oxo-6-phenyl-4-trifluoromethyl-1,2-dihydropyridine-3-carbonitrile;
1-(2-Methyl-cyclopentylideneamino)-2-oxo-6-phenyl-4-trifluoromethyl-1,2-dihydropyridine-3-carbonitrile;
1-(3-Methyl-cyclopentylideneamino)-2-oxo-6-phenyl-4-trifluoromethyl-1,2-dihydropyridine-3-carbonitrile;
1-(Bicyclo[2.2.1]hept-2-ylideneamino)-2-oxo-6-phenyl-4-trifluoromethyl-1,2-dihydropyridine-3-carbonitrile;
1-(Adamantan-2-ylideneamino)-2-oxo-6-phenyl-4-trifluoromethyl-1,2-dihydropyridine-3-carbonitrile;
1-(1-Methyl-piperidin-4-ylideneamino)-2-oxo-6-phenyl-4-trifluoromethyl-1,2-dihydropyridine-3-carbonitrile;
4-(3-Cyano-2-oxo-6-phenyl-4-trifluoromethyl-2H-pyridin-1-ylimino)-cyclohexanecarboxylic acid ethyl ester;
2-Oxo-6-phenyl-1-(tetrahydro-pyran-4-ylideneamino)-4-trifluoromethyl-1,2-dihydropyridine-3-carbonitrile;
1-Amino-2-oxo-6-phenyl-4-trifluoromethyl-1,2-dihydropyridine-3-carbonitrile;
1-Amino-2-oxo-4,6-diphenyl-1,2-dihydropyridine-3-carbonitrile;
1-sec-Butylideneamino-2-oxo-6-phenyl-4-trifluoromethyl-1,2-dihydropyridine-3-carbonitrile;
1-(1,2-Dimethyl-propylideneamino)-2-oxo-6-phenyl-4-trifluoromethyl-1,2-dihydropyridine-3-carbonitrile;
1-(1-Methyl-butylideneamino)-2-oxo-6-phenyl-4-trifluoromethyl-1,2-dihydropyridine-3-carbonitrile;
1-Butylideneamino-2-oxo-6-phenyl-4-trifluoromethyl-1,2-dihydropyridine-3-carbonitrile;
1-Isobutylideneamino-2-oxo-6-phenyl-4-trifluoromethyl-1,2-dihydropyridine-3-carbonitrile;
1-(2-Methyl-butylideneamino)-2-oxo-6-phenyl-4-trifluoromethyl-1,2-dihydropyridine-3-carbonitrile;
1-(2-Ethyl-butylideneamino)-2-oxo-6-phenyl-4-trifluoromethyl-1,2-dihydropyridine-3-carbonitrile;
1-(3-Methyl-butylideneamino)-2-oxo-6-phenyl-4-trifluoromethyl-1,2-dihydropyridine-3-carbonitrile;
1-(2,2-Dimethyl-propylideneamino)-2-oxo-6-phenyl-4-trifluoromethyl-1,2-dihydropyridine-3-carbonitrile;
1-(1-Acetyl-piperidin-4-ylideneamino)-2-oxo-6-phenyl-4-trifluoromethyl-1,2-dihydropyridine-3-carbonitrile;
1-[(Naphthalen-2-ylmethylene)-amino]-2-oxo-6-phenyl-4-trifluoromethyl-1,2-dihydropyridine-3-carbonitrile;
1-[(2-Hydroxy-benzylidene)-amino]-2-oxo-6-phenyl-4-trifluoromethyl-1,2-dihydropyridine-3-carbonitrile;
1-[(2-Hydroxy-5-chloro-benzylidene)-amino]-2-oxo-6-phenyl-4-trifluoromethyl-1,2-dihydropyridine-3-carbonitrile;
1-[(4-Bromo-benzylidene)-amino]-2-oxo-6-phenyl-4-trifluoromethyl-1,2-dihydropyridine-3-carbonitrile;
1-[(2-Hydroxy-4-bromo-benzylidene)-amino]-2-oxo-6-phenyl-4-trifluoromethyl-1,2-dihydropyridine-3-carbonitrile;
1-[(2-Methyl-benzylidene)-amino]-2-oxo-6-phenyl-4-trifluoromethyl-1,2-dihydropyridine-3-carbonitrile;
1-[(4-Methoxy-benzylidene)-amino]-2-oxo-6-phenyl-4-trifluoromethyl-1,2-dihydropyridine-3-carbonitrile;
1-Cyclohexylideneamino-2-oxo-6-phenyl-4-trifluoromethyl-1,2-dihydropyridine-3-carbonitrile;
1-Cyclohexylideneamino-2-oxo-4,6-diphenyl-1,2-dihydropyridine-3-carbonitrile;
1-(2-Methyl-cyclohexylideneamino)-2-oxo-4,6-diphenyl-1,2-dihydropyridine-3-carbonitrile;
1-(1,2-Dimethyl-propylideneamino)-2-oxo-4,6-diphenyl-1,2-dihydropyridine-3-carbonitrile;

1-Cyclohexylideneamino-2-oxo-6-o-tolyl-4-trifluoromethyl-1,2-dihydropyridine-3-carbonitrile;
1-(2-Methyl-cyclohexylideneamino)-2-oxo-6-o-tolyl-4-trifluoromethyl-1,2-dihydropyridine-3-carbonitrile;
1-(1,2-Dimethyl-propylideneamino)-2-oxo-6-o-tolyl-4-trifluoromethyl-1,2-dihydropyridine-3-carbonitrile;
1-Cyclohexylideneamino-2-oxo-6-m-tolyl-4-trifluoromethyl-1,2-dihydropyridine-3-carbonitrile;
1-Cyclohexylideneamino-6-(2-methoxy-phenyl)-2-oxo-4-trifluoromethyl-1,2-dihydropyridine-3-carbonitrile;
1-(2-Methyl-cyclohexylideneamino)-6-(2-methoxy-phenyl)-2-oxo-4-trifluoromethyl-1,2-dihydropyridine-3-carbonitrile;
1-(1,2-Dimethyl-propylideneamino)-6-(2-methoxy-phenyl)-2-oxo-4-trifluoromethyl-1,2-dihydropyridine-3-carbonitrile;
1-(2-Methyl-cyclohexylideneamino)-2-oxo-6-m-tolyl-4-trifluoromethyl-1,2-dihydropyridine-3-carbonitrile;
1-(1,2-Dimethyl-propylideneamino)-2-oxo-6-m-tolyl-4-trifluoromethyl-1,2-dihydropyridine-3-carbonitrile;
1-Cyclohexylideneamino-2-oxo-6-p-tolyl-4-trifluoromethyl-1,2-dihydropyridine-3-carbonitrile;
1-(2-Methyl-cyclohexylideneamino)-2-oxo-6-p-tolyl-4-trifluoromethyl-1,2-dihydropyridine-3-carbonitrile;
1-(1,2-Dimethyl-propylideneamino)-2-oxo-6-p-tolyl-4-trifluoromethyl-1,2-dihydropyridine-3-carbonitrile;
1-Cyclohexylideneamino-6-(3-methoxy-phenyl)-2-oxo-4-trifluoromethyl-1,2-dihydro-pyridine-3-carbonitrile;
1-(2-Methyl-cyclohexylideneamino)-6-(3-methoxy-phenyl)-2-oxo-4-trifluoromethyl-1,2-dihydro-pyridine-3-carbonitrile;
1-(1,2-Dimethyl-propylideneamino)-6-(3-methoxy-phenyl)-2-oxo-4-trifluoromethyl-1,2-dihydro-pyridine-3-carbonitrile;
1-(2-Ethyl-cyclohexylideneamino)-2-oxo-6-phenyl-4-trifluoromethyl-1,2-dihydropyridine-3-carbonitrile;
2-Oxo-6-phenyl-1-(2-phenyl-cyclohexylideneamino)-4-trifluoromethyl-1,2-dihydropyridine-3-carbonitrile;
1-(2-Benzyl-cyclohexylideneamino)-2-oxo-6-phenyl-4-trifluoromethyl-1,2-dihydropyridine-3-carbonitrile;
1-(2,2-Dimethyl-cyclohexylideneamino)-2-oxo-6-phenyl-4-trifluoromethyl-1,2-dihydropyridine-3-carbonitrile;
1-(2-Chloro-cyclohexylideneamino)-2-oxo-6-phenyl-4-trifluoromethyl-1,2-dihydropyridine-3-carbonitrile;
1-(2-Methoxy-cyclohexylideneamino)-2-oxo-6-phenyl-4-trifluoromethyl-1,2-dihydropyridine-3-carbonitrile;
1-(2-Ethoxy-cyclohexylideneamino)-2-oxo-6-phenyl-4-trifluoromethyl-1,2-dihydropyridine-3-carbonitrile;
1-(2-Methlythio-cyclohexylideneamino)-2-oxo-6-phenyl-4-trifluoromethyl-1,2-dihydropyridine-3-carbonitrile;
2-(3-Cyano-2-oxo-6-phenyl-4-trifluoromethyl-2H-pyridin-1-ylimino)-cyclohexanecarboxylic acid methyl ester;
(3R)-1-(3-Methyl-cyclohexylideneamino)-2-oxo-6-phenyl-4-trifluoromethyl-1,2-dihydropyridine-3-carbonitrile;
2-Oxo-6-phenyl-1-phenylamino-4-trifluoromethyl-1,2-dihydropyridine-3-carbonitrile;
2-Oxo-1-phenylamino-6-m-tolyl-4-trifluoromethyl-1,2-dihydropyridine-3-carbonitrile;
1-Cyclohexylideneamino-6-(4-methoxy-phenyl)-2-oxo-4-trifluoromethyl-1,2-dihydropyridine-3-carbonitrile;
1-(2-Methyl-cyclohexylideneamino)-6-(4-methoxy-phenyl)-2-oxo-4-trifluoromethyl-1,2-dihydropyridine-3-carbonitrile;
1-(1,2-Dimethyl-propylideneamino)-6-(4-methoxy-phenyl)-2-oxo-4-trifluoromethyl-1,2-dihydropyridine-3-carbonitrile;
6-(2-Chloro-phenyl)-1-cyclohexylideneamino-2-oxo-4-trifluoromethyl-1,2-dihydro-pyridine-3-carbonitrile;
6-(2-Chloro-phenyl)-1-(1,2-dimethyl-propylideneamino)-2-oxo-4-trifluoromethyl-1,2-dihydro-pyridine-3-carbonitrile;
6-(3-Chloro-phenyl)-1-cyclohexylideneamino-2-oxo-4-trifluoromethyl-1,2-dihydro-pyridine-3-carbonitrile;
6-(3-Chloro-phenyl)-1-(2-methyl-cyclohexylideneamino)-2-oxo-4-trifluoromethyl-1,2-dihydro-pyridine-3-carbonitrile;
6-(3-Chloro-phenyl)-1-(1,2-dimethyl-propylideneamino)-2-oxo-4-trifluoromethyl-1,2-dihydro-pyridine-3-carbonitrile;
6-(4-Chloro-phenyl)-1-cyclohexylideneamino-2-oxo-4-trifluoromethyl-1,2-dihydro-pyridine-3-carbonitrile;
6-(4-Chloro-phenyl)-1-(2-methyl-cyclohexylideneamino)-2-oxo-4-trifluoromethyl-1,2-dihydro-pyridine-3-carbonitrile;
6-(4-Chloro-phenyl)-1-(1,2-dimethyl-propylideneamino)-2-oxo-4-trifluoromethyl-1,2-dihydro-pyridine-3-carbonitrile;
6-(2-Chloro-phenyl)-1-(2-methyl-cyclohexylideneamino)-2-oxo-4-trifluoromethyl-1,2-dihydro-pyridine-3-carbonitrile;
6-(3-Methoxy-phenyl)-1-(2-methyl-cyclohexylideneamino)-2-oxo-4-trifluoromethyl-1,2-dihydro-pyridine-3-carbonitrile;
1-Cyclohexylideneamino-6-(3-hydroxy-phenyl)-2-oxo-4-trifluoromethyl-1,2-dihydro-pyridine-3-carbonitrile;
1-(1,2-Dimethyl-propylideneamino)-6-(3-hydroxy-phenyl)-2-oxo-4-trifluoromethyl-1,2-dihydro-pyridine-3-carbonitrile;
2-Oxo-6-phenyl-4-trifluoromethyl-3',4',5',6'-tetrahydro-2H,2'H-[1,1']bipyridinyl-3-carbonitrile;
2-Oxo-6-phenyl-1-pyrrolidin-1-yl-4-trifluoromethyl-1,2-dihydro-pyridine-3-carbonitrile;
1-(3-Cyano-2-oxo-6-phenyl-4-trifluoromethyl-2H-pyridin-1-yl)-3-phenyl-urea;
2-Oxo-6-m-tolyl-4-trifluoromethyl-3',4',5',6'-tetrahydro-2H,2'H-[1,1']bipyridinyl-3-carbonitrile;
2-Oxo-1-pyrrolidin-1-yl-6-m-tolyl-4-trifluoromethyl-1,2-dihydro-pyridine-3-carbonitrile;
1-Amino-2-oxo-6-thiophen-2-yl-4-trifluoromethyl-1,2-dihydro-pyridine-3-carbonitrile;
1-Cyclohexylideneamino-2-oxo-6-thiophen-2-yl-4-trifluoromethyl-1,2-dihydro-pyridine-3-carbonitrile;
1-Cyclopentylideneamino-2-oxo-6-thiophen-2-yl-4-trifluoromethyl-1,2-dihydro-pyridine-3-carbonitrile;
2-Oxo-1-(1-phenyl-ethylideneamino)-6-thiophen-2-yl-4-trifluoromethyl-1,2-dihydro-pyridine-3-carbonitrile;
1-(1-Benzoyl-piperidin-4-ylideneamino)-2-oxo-6-thiophen-2-yl-4-trifluoromethyl-1,2-dihydro-pyridine-3-carbonitrile;
1-(Benzylidene-amino)-2-oxo-6-thiophen-2-yl-4-trifluoromethyl-1,2-dihydro-pyridine-3-carbonitrile;
1-(4-Methyl-cyclohexylideneamino)-2-oxo-6-thiophen-2-yl-4-trifluoromethyl-1,2-dihydro-pyridine-3-carbonitrile;
1-(4-Ethyl-cyclohexylideneamino)-2-oxo-6-thiophen-2-yl-4-trifluoromethyl-1,2-dihydro-pyridine-3-carbonitrile;
1-(4-tert-Butyl-cyclohexylideneamino)-2-oxo-6-thiophen-2-yl-4-trifluoromethyl-1,2-dihydro-pyridine-3-carbonitrile;
1-(2-Methyl-cyclopentylideneamino)-2-oxo-6-thiophen-2-yl-4-trifluoromethyl-1,2-dihydro-pyridine-3-carbonitrile;
1-(3-Methyl-cyclopentylideneamino)-2-oxo-6-thiophen-2-yl-4-trifluoromethyl-1,2-dihydro-pyridine-3-carbonitrile;

1-(2-Methyl-cyclohexylideneamino)-2-oxo-6-thiophen-2-yl-4-trifluoromethyl-1,2-dihydro-pyridine-3-carbonitrile;
1-Benzyl-2-oxo-6-phenyl-4-trifluoromethyl-1,2-dihydro-pyridine-3-carbonitrile;
1-Benzyl-6-naphthalen-2-yl-2-oxo-4-trifluoromethyl-1,2-dihydro-pyridine-3-carbonitrile;
1-(2-Methyl-benzyl)-2-oxo-6-phenyl-4-trifluoromethyl-1,2-dihydro-pyridine-3-carbonitrile;
1-(3-Methyl-benzyl)-2-oxo-6-phenyl-4-trifluoromethyl-1,2-dihydro-pyridine-3-carbonitrile;
1-(4-Methyl-benzyl)-2-oxo-6-phenyl-4-trifluoromethyl-1,2-dihydro-pyridine-3-carbonitrile;
2-Oxo-1-phenethyl-6-phenyl-4-trifluoromethyl-1,2-dihydro-pyridine-3-carbonitrile;
1-Benzyl-2-oxo-6-m-tolyl-4-trifluoromethyl-1,2-dihydro-pyridine-3-carbonitrile;
1-(2-Methyl-benzyl)-2-oxo-6-m-tolyl-4-trifluoromethyl-1,2-dihydro-pyridine-3-carbonitrile;
1-(3-Methyl-benzyl)-2-oxo-6-m-tolyl-4-trifluoromethyl-1,2-dihydro-pyridine-3-carbonitrile;
1-(4-Methyl-benzyl)-2-oxo-6-m-tolyl-4-trifluoromethyl-1,2-dihydro-pyridine-3-carbonitrile;
2-Oxo-1-phenethyl-6-m-tolyl-4-trifluoromethyl-1,2-dihydro-pyridine-3-carbonitrile;
1-Benzyl-4-methyl-2-oxo-6-phenyl-1,2-dihydro-pyridine-3-carbonitrile;
1-(2-Methyl-benzyl)-4-methyl-2-oxo-6-phenyl-1,2-dihydro-pyridine-3-carbonitrile;
1-(3-Methyl-benzyl)-4-methyl-2-oxo-6-phenyl-1,2-dihydro-pyridine-3-carbonitrile;
1-(4-Methyl-benzyl)-4-methyl-2-oxo-6-phenyl-1,2-dihydro-pyridine-3-carbonitrile;
4-Methyl-2-oxo-1-phenethyl-6-phenyl-1,2-dihydro-pyridine-3-carbonitrile;
2-Oxo-6-phenyl-1-(3-phenyl-propyl)-4-trifluoromethyl-1,2-dihydro-pyridine-3-carbonitrile;
2-Oxo-6-phenyl-4-trifluoromethyl-1-(2-trifluoromethyl-benzyl)-1,2-dihydro-pyridine-3-carbonitrile;
2-Oxo-6-phenyl-4-trifluoromethyl-1-(3-trifluoromethyl-benzyl)-1,2-dihydro-pyridine-3-carbonitrile;
2-Oxo-6-phenyl-4-trifluoromethyl-1-(4-trifluoromethyl-benzyl)-1,2-dihydro-pyridine-3-carbonitrile;
1-(2-Methoxy-benzyl)-2-oxo-6-phenyl-4-trifluoromethyl-1,2-dihydro-pyridine-3-carbonitrile;
1-(3-Methoxy-benzyl)-2-oxo-6-phenyl-4-trifluoromethyl-1,2-dihydro-pyridine-3-carbonitrile;
1-(4-Methoxy-benzyl)-2-oxo-6-phenyl-4-trifluoromethyl-1,2-dihydro-pyridine-3-carbonitrile;
1-Biphenyl-4-ylmethyl-2-oxo-6-phenyl-4-trifluoromethyl-1,2-dihydro-pyridine-3-carbonitrile;
2-Oxo-6-m-tolyl-4-trifluoromethyl-1-(2-trifluoromethyl-benzyl)-1,2-dihydro-pyridine-3-carbonitrile;
2-Oxo-1-(3-phenyl-propyl)-6-m-tolyl-4-trifluoromethyl-1,2-dihydro-pyridine-3-carbonitrile;
2-Oxo-6-m-tolyl-4-trifluoromethyl-1-(3-trifluoromethyl-benzyl)-1,2-dihydro-pyridine-3-carbonitrile;
2-Oxo-6-m-tolyl-4-trifluoromethyl-1-(4-trifluoromethyl-benzyl)-1,2-dihydro-pyridine-3-carbonitrile;
1-(2-Methoxy-benzyl)-2-oxo-6-m-tolyl-4-trifluoromethyl-1,2-dihydro-pyridine-3-carbonitrile;
1-(3-Methoxy-benzyl)-2-oxo-6-m-tolyl-4-trifluoromethyl-1,2-dihydro-pyridine-3-carbonitrile;
1-(4-Methoxy-benzyl)-2-oxo-6-m-tolyl-4-trifluoromethyl-1,2-dihydro-pyridine-3-carbonitrile;
1-Biphenyl-4-ylmethyl-2-oxo-6-m-tolyl-4-trifluoromethyl-1,2-dihydro-pyridine-3-carbonitrile;
1-Benzyl-6-(3-methoxy-phenyl)-2-oxo-4-trifluoromethyl-1,2-dihydro-pyridine-3-carbonitrile;
1-Benzyl-6-(2-chloro-phenyl)-2-oxo-4-trifluoromethyl-1,2-dihydro-pyridine-3-carbonitrile;
1-Benzyl-6-(3-ethyl-phenyl)-2-oxo-4-trifluoromethyl-1,2-dihydro-pyridine-3-carbonitrile;
1-Benzyl-6-(3-trifluoromethyl-phenyl)-2-oxo-4-trifluoromethyl-1,2-dihydro-pyridine-3-carbonitrile;
1-Benzyl-6-(3-nitro-phenyl)-2-oxo-4-trifluoromethyl-1,2-dihydro-pyridine-3-carbonitrile;
1-Benzyl-6-(3-hydroxy-phenyl)-2-oxo-4-trifluoromethyl-1,2-dihydro-pyridine-3-carbonitrile;
2-Oxo-1,6-diphenyl-4-trifluoromethyl-1,2-dihydro-pyridine-3-carbonitrile;
(1R)-2-Oxo-6-phenyl-1-(1-phenyl-ethyl)-4-trifluoromethyl-1,2-dihydro-pyridine-3-carbonitrile;
(1S)-2-Oxo-6-phenyl-1-(1-phenyl-ethyl)-4-trifluoromethyl-1,2-dihydro-pyridine-3-carbonitrile;
2-Oxo-6-phenyl-1-(1,2,3,4-tetrahydro-naphthalen-1-yl)-4-trifluoromethyl-1,2-dihydro-pyridine-3-carbonitrile;
1-Benzyl-6-(3-butoxy-phenyl)-2-oxo-4-trifluoromethyl-1,2-dihydro-pyridine-3-carbonitrile;
1-Benzyl-6-(3-benzyloxy-phenyl)-2-oxo-4-trifluoromethyl-1,2-dihydro-pyridine-3-carbonitrile;
1-Benzyl-2-oxo-6-[3-(2-piperidin-1-yl-ethoxy)-phenyl]-4-trifluoromethyl-1,2-dihydro-pyridine-3-carbonitrile;
N-[3-(1-Benzyl-5-cyano-6-oxo-4-trifluoromethyl-1,6-dihydro-pyridin-2-yl)-phenyl]-acetamide;
1-[3-(1-Benzyl-5-cyano-6-oxo-4-trifluoromethyl-1,6-dihydro-pyridin-2-yl)-phenyl]-3-ethyl-urea;
1-(2,4-Dimethyl-benzyl)-2-oxo-6-phenyl-4-trifluoromethyl-1,2-dihydro-pyridine-3-carbonitrile;
1-(2-Fluoro-benzyl)-2-oxo-6-phenyl-4-trifluoromethyl-1,2-dihydro-pyridine-3-carbonitrile;
1-(4-Fluoro-benzyl)-2-oxo-6-phenyl-4-trifluoromethyl-1,2-dihydro-pyridine-3-carbonitrile;
1-(2,4-Difluoro-benzyl)-2-oxo-6-phenyl-4-trifluoromethyl-1,2-dihydro-pyridine-3-carbonitrile;
1-(4-Bromo-benzyl)-2-oxo-6-phenyl-4-trifluoromethyl-1,2-dihydro-pyridine-3-carbonitrile;
4-(3-Cyano-2-oxo-6-phenyl-4-trifluoromethyl-2H-pyridin-1-ylmethyl)-benzoic acid methyl ester;
1-(2-Chloro-benzyl)-2-oxo-6-phenyl-4-trifluoromethyl-1,2-dihydro-pyridine-3-carbonitrile;
1-(4-Chloro-benzyl)-2-oxo-6-phenyl-4-trifluoromethyl-1,2-dihydro-pyridine-3-carbonitrile;
1-(4-Methylthio-benzyl)-2-oxo-6-phenyl-4-trifluoromethyl-1,2-dihydro-pyridine-3-carbonitrile;
2-Oxo-1-(4-phenoxy-benzyl)-6-phenyl-4-trifluoromethyl-1,2-dihydro-pyridine-3-carbonitrile;
1-(2,4-Dimethyl-benzyl)-2-oxo-6-m-tolyl-4-trifluoromethyl-1,2-dihydro-pyridine-3-carbonitrile;
1-(2-Fluoro-benzyl)-2-oxo-6-m-tolyl-4-trifluoromethyl-1,2-dihydro-pyridine-3-carbonitrile;
1-(4-Fluoro-benzyl)-2-oxo-6-m-tolyl-4-trifluoromethyl-1,2-dihydro-pyridine-3-carbonitrile;
1-(2,4-Difluoro-benzyl)-2-oxo-6-m-tolyl-4-trifluoromethyl-1,2-dihydro-pyridine-3-carbonitrile;
1-(4-Bromo-benzyl)-2-oxo-6-m-tolyl-4-trifluoromethyl-1,2-dihydro-pyridine-3-carbonitrile;
4-(3-Cyano-2-oxo-6-m-tolyl-4-trifluoromethyl-2H-pyridin-1-ylmethyl)-benzoic acid methyl ester;
1-(2-Chloro-benzyl)-2-oxo-6-m-tolyl-4-trifluoromethyl-1,2-dihydro-pyridine-3-carbonitrile;
1-(4-Chloro-benzyl)-2-oxo-6-m-tolyl-4-trifluoromethyl-1,2-dihydro-pyridine-3-carbonitrile;

1-(4-Methylthio-benzyl)-2-oxo-6-m-tolyl-4-trifluoromethyl-1,2-dihydro-pyridine-3-carbonitrile;
2-Oxo-1-(4-phenoxy-benzyl)-6-m-tolyl-4-trifluoromethyl-1,2-dihydro-pyridine-3-carbonitrile;
(1-Benzyl-3-cyano-2-oxo-6-phenyl-1,2-dihydro-pyridin-4-yl)-acetic acid methyl ester;
2-Oxo-6-phenyl-1-(4-trifluoromethoxy-benzyl)-4-trifluoromethyl-1,2-dihydro-pyridine-3-carbonitrile;
2-Oxo-6-phenyl-1-pyridin-3-ylmethyl-4-trifluoromethyl-1,2-dihydro-pyridine-3-carbonitrile;
2-Oxo-6-phenyl-1-pyridin-4-ylmethyl-4-trifluoromethyl-1,2-dihydro-pyridine-3-carbonitrile;
1-(4-Nitro-benzyl)-2-oxo-6-phenyl-4-trifluoromethyl-1,2-dihydro-pyridine-3-carbonitrile;
2-Oxo-6-m-tolyl-1-(4-trifluoromethoxy-benzyl)-4-trifluoromethyl-1,2-dihydro-pyridine-3-carbonitrile;
2-Oxo-1-pyridin-3-ylmethyl-6-m-tolyl-4-trifluoromethyl-1,2-dihydro-pyridine-3-carbonitrile;
2-Oxo-1-pyridin-4-ylmethyl-6-m-tolyl-4-trifluoromethyl-1,2-dihydro-pyridine-3-carbonitrile;
1-(4-Nitro-benzyl)-2-oxo-6-m-tolyl-4-trifluoromethyl-1,2-dihydro-pyridine-3-carbonitrile;
1-(4-Morpholin-4-yl-benzyl)-2-oxo-6-phenyl-4-trifluoromethyl-1,2-dihydro-pyridine-3-carbonitrile;
[3-(1-Benzyl-5-cyano-6-oxo-4-trifluoromethyl-1,6-dihydro-pyridin-2-yl)-phenyl]-urea;
1-Benzyl-2-oxo-6-(3-phenethyloxy-phenyl)-4-trifluoromethyl-1,2-dihydro-pyridine-3-carbonitrile;
1-Benzyl-2-oxo-6-[3-(2,2,2-trifluoro-ethoxy)-phenyl]-4-trifluoromethyl-1,2-dihydro-pyridine-3-carbonitrile;
1-Benzyl-6-[3-(3-methyl-butoxy)-phenyl]-2-oxo-4-trifluoromethyl-1,2-dihydro-pyridine-3-carbonitrile;
[3-(1-Benzyl-5-cyano-6-oxo-4-trifluoromethyl-1,6-dihydro-pyridin-2-yl)-phenoxy]-acetic acid methyl ester;
4-[3-(1-Benzyl-5-cyano-6-oxo-4-trifluoromethyl-1,6-dihydro-pyridin-2-yl)-phenoxy]-butyric acid methyl ester;
1-Benzyl-6-[3-(3-hydroxy-propoxy)-phenyl]-2-oxo-4-trifluoromethyl-1,2-dihydro-pyridine-3-carbonitrile;
1-Benzyl-5-methyl-2-oxo-6-phenyl-4-trifluoromethyl-1,2-dihydro-pyridine-3-carbonitrile;
1-Benzyl-2-oxo-4,6-diphenyl-1,2-dihydro-pyridine-3-carbonitrile;
4-(3-Cyano-2-oxo-6-phenyl-4-trifluoromethyl-2H-pyridin-1-ylmethyl)-benzoic acid;
Ethyl-carbamic acid 3-(1-benzyl-5-cyano-6-oxo-4-trifluoromethyl-1,6-dihydro-pyridin-2-yl)-phenyl ester;
Butyl-carbamic acid 3-(1-benzyl-5-cyano-6-oxo-4-trifluoromethyl-1,6-dihydro-pyridin-2-yl)-phenyl ester;
1-Benzyl-6-[3-(2-methyl-benzyloxy)-phenyl]-2-oxo-4-trifluoromethyl-1,2-dihydro-pyridine-3-carbonitrile;
1-Benzyl-6-[3-(3-methyl-benzyloxy)-phenyl]-2-oxo-4-trifluoromethyl-1,2-dihydro-pyridine-3-carbonitrile;
1-Benzyl-6-[3-(4-methyl-benzyloxy)-phenyl]-2-oxo-4-trifluoromethyl-1,2-dihydro-pyridine-3-carbonitrile;
4-[3-(1-Benzyl-5-cyano-6-oxo-4-trifluoromethyl-1,6-dihydro-pyridin-2-yl)-phenoxymethyl]-benzoic acid methyl ester;
3-[3-(1-Benzyl-5-cyano-6-oxo-4-trifluoromethyl-1,6-dihydro-pyridin-2-yl)-phenoxymethyl]-benzoic acid methyl ester;
[3-(1-Benzyl-5-cyano-6-oxo-4-trifluoromethyl-1,6-dihydro-pyridin-2-yl)-phenoxy]-acetic acid;
4-[3-(1-Benzyl-5-cyano-6-oxo-4-trifluoromethyl-1,6-dihydro-pyridin-2-yl)-phenoxy]-butyric acid;
N-[3-(1-Benzyl-5-cyano-6-oxo-4-trifluoromethyl-1,6-dihydro-pyridin-2-yl)-phenyl]-butyramide;
Cyclohexanecarboxylic acid [3-(1-benzyl-5-cyano-6-oxo-4-trifluoromethyl-1,6-dihydro-pyridin-2-yl)-phenyl]-amide;
N-[3-(1-Benzyl-5-cyano-6-oxo-4-trifluoromethyl-1,6-dihydro-pyridin-2-yl)-phenyl]-benzamide;
[3-(1-Benzyl-5-cyano-6-oxo-4-trifluoromethyl-1,6-dihydro-pyridin-2-yl)-phenyl]-carbamic acid methyl ester;
[3-(1-Benzyl-5-cyano-6-oxo-4-trifluoromethyl-1,6-dihydro-pyridin-2-yl)-phenyl]-carbamic acid ethyl ester;
[3-(1-Benzyl-5-cyano-6-oxo-4-trifluoromethyl-1,6-dihydro-pyridin-2-yl)-phenyl]-carbamic acid phenyl ester;
6-(3-Amino-phenyl)-1-benzyl-2-oxo-4-trifluoromethyl-1,2-dihydro-pyridine-3-carbonitrile;
1-Cyclohexylmethyl-2-oxo-6-phenyl-4-trifluoromethyl-1,2-dihydro-pyridine-3-carbonitrile;
2-Oxo-6-phenyl-1-thiophen-2-ylmethyl-4-trifluoromethyl-1,2-dihydro-pyridine-3-carbonitrile;
1-(5-Methyl-furan-2-ylmethyl)-2-oxo-6-phenyl-4-trifluoromethyl-1,2-dihydro-pyridine-3-carbonitrile;
2-Oxo-6-phenyl-1-(2,3,5-trifluoro-benzyl)-4-trifluoromethyl-1,2-dihydro-pyridine-3-carbonitrile;
1-(4-Chloro-2-methyl-benzyl)-2-oxo-6-phenyl-4-trifluoromethyl-1,2-dihydro-pyridine-3-carbonitrile;
1-(3,4-Dichloro-benzyl)-2-oxo-6-phenyl-4-trifluoromethyl-1,2-dihydro-pyridine-3-carbonitrile;
1-(3-Fluoro-benzyl)-2-oxo-6-phenyl-4-trifluoromethyl-1,2-dihydro-pyridine-3-carbonitrile;
1-(4-Methyl-benzyl)-6-m-tolyl-1H-pyridin-2-one;
1-(4-Methyl-benzyl)-6-phenyl-1H-pyridin-2-one;
1-Benzyl-6-m-tolyl-1H-pyridin-2-one;
1-Benzyl-6-phenyl-1H-pyridin-2-one;
2-Oxo-6-phenyl-1-(2,3,4-trifluoro-benzyl)-4-trifluoromethyl-1,2-dihydro-pyridine-3-carbonitrile;
1-Cyclohexylmethyl-2-oxo-6-m-tolyl-4-trifluoromethyl-1,2-dihydro-pyridine-3-carbonitrile;
2-Oxo-1-thiophen-2-ylmethyl-6-m-tolyl-4-trifluoromethyl-1,2-dihydro-pyridine-3-carbonitrile;
2-Oxo-6-m-tolyl-1-(2,3,5-trifluoro-benzyl)-4-trifluoromethyl-1,2-dihydro-pyridine-3-carbonitrile;
1-(4-Chloro-2-methyl-benzyl)-2-oxo-6-m-tolyl-4-trifluoromethyl-1,2-dihydro-pyridine-3-carbonitrile;
1-(3,4-Dichloro-benzyl)-2-oxo-6-m-tolyl-4-trifluoromethyl-1,2-dihydro-pyridine-3-carbonitrile;
1-(3-Fluoro-benzyl)-2-oxo-6-m-tolyl-4-trifluoromethyl-1,2-dihydro-pyridine-3-carbonitrile;
1-(3,4-Difluoro-benzyl)-2-oxo-6-phenyl-4-trifluoromethyl-1,2-dihydro-pyridine-3-carbonitrile;
1-(2,5-Difluoro-benzyl)-2-oxo-6-phenyl-4-trifluoromethyl-1,2-dihydro-pyridine-3-carbonitrile;
1-(2,4-Dichloro-benzyl)-2-oxo-6-phenyl-4-trifluoromethyl-1,2-dihydro-pyridine-3-carbonitrile;
1-(2,3-Dimethyl-benzyl)-2-oxo-6-phenyl-4-trifluoromethyl-1,2-dihydro-pyridine-3-carbonitrile;
1-(2,5-Dimethyl-benzyl)-2-oxo-6-phenyl-4-trifluoromethyl-1,2-dihydro-pyridine-3-carbonitrile;
1-(3,4-Dimethyl-benzyl)-2-oxo-6-phenyl-4-trifluoromethyl-1,2-dihydro-pyridine-3-carbonitrile;
1-(2,3-Difluoro-benzyl)-2-oxo-6-phenyl-4-trifluoromethyl-1,2-dihydro-pyridine-3-carbonitrile;
1-(2-Bromo-benzyl)-2-oxo-6-phenyl-4-trifluoromethyl-1,2-dihydro-pyridine-3-carbonitrile;
1-(3-Bromo-benzyl)-2-oxo-6-phenyl-4-trifluoromethyl-1,2-dihydro-pyridine-3-carbonitrile;
1-(3,4-Difluoro-benzyl)-2-oxo-6-m-tolyl-4-trifluoromethyl-1,2-dihydro-pyridine-3-carbonitrile;
1-(2,5-Difluoro-benzyl)-2-oxo-6-m-tolyl-4-trifluoromethyl-1,2-dihydro-pyridine-3-carbonitrile;

1-(2,4-Dichloro-benzyl)-2-oxo-6-m-tolyl-4-trifluoromethyl-1,2-dihydro-pyridine-3-carbonitrile;
1-(2,3-Dimethyl-benzyl)-2-oxo-6-m-tolyl-4-trifluoromethyl-1,2-dihydro-pyridine-3-carbonitrile;
1-(2,5-Dimethyl-benzyl)-2-oxo-6-m-tolyl-4-trifluoromethyl-1,2-dihydro-pyridine-3-carbonitrile;
1-(3,4-Dimethyl-benzyl)-2-oxo-6-m-tolyl-4-trifluoromethyl-1,2-dihydro-pyridine-3-carbonitrile;
1-(2,3-Difluorol-benzyl)-2-oxo-6-m-tolyl-4-trifluoromethyl-1,2-dihydro-pyridine-3-carbonitrile;
1-(2-Bromo-benzyl)-2-oxo-6-m-tolyl-4-trifluoromethyl-1,2-dihydro-pyridine-3-carbonitrile;
1-(3-Bromo-benzyl)-2-oxo-6-m-tolyl-4-trifluoromethyl-1,2-dihydro-pyridine-3-carbonitrile;
N-[3-(1-Benzyl-5-cyano-6-oxo-4-trifluoromethyl-1,6-dihydro-pyridin-2-yl)-phenyl]-methanesulfonamide;
6-(3-Ethyl-phenyl)-1-(4-methyl-benzyl)-2-oxo-4-trifluoromethyl-1,2-dihydro-pyridine-3-carbonitrile;
1-(4-Methyl-benzyl)-2-oxo-6-p-tolyl-4-trifluoromethyl-1,2-dihydro-pyridine-3-carbonitrile;
6-(2-Chloro-phenyl)-1-(4-methyl-benzyl)-2-oxo-4-trifluoromethyl-1,2-dihydro-pyridine-3-carbonitrile;
6-(3-Chloro-phenyl)-1-(4-methyl-benzyl)-2-oxo-4-trifluoromethyl-1,2-dihydro-pyridine-3-carbonitrile;
6-(4-Chloro-phenyl)-1-(4-methyl-benzyl)-2-oxo-4-trifluoromethyl-1,2-dihydro-pyridine-3-carbonitrile;
3-[5-Cyano-1-benzyl-6-oxo-4-trifluoromethyl-1,6-dihydro-pyridin-2-yl]-benzoic acid;
3-[5-Cyano-1-benzyl-6-oxo-4-trifluoromethyl-1,6-dihydro-pyridin-2-yl]-benzoic acid tert-butyl ester;
1-Benzyl-6-(3-bromomethyl-phenyl)-2-oxo-4-trifluoromethyl-1,2-dihydro-pyridine-3-carbonitrile;
2-Oxo-6-phenyl-1-(2,2,2-trifluoro-ethyl)-4-trifluoromethyl-1,2-dihydro-pyridine-3-carbonitrile;
1-Benzyl-3-bromo-6-phenyl-1H-pyridin-2-one;
1-Biphenyl-4-ylmethyl-6-phenyl-1H-pyridin-2-one;
1-Benzyl-2-oxo-6-phenyl-1,2-dihydro-pyridine-3-carbonitrile;
3-(1-Benzyl-5-cyano-6-oxo-4-trifluoromethyl-1,6-dihydro-pyridin-2-yl)-N,N-diethyl-benzamide;
1-Benzyl-2-oxo-6-(3-phenoxymethyl-phenyl)-4-trifluoromethyl-1,2-dihydro-pyridine-3-carbonitrile;
1-Benzyl-6-(3-diethylaminomethyl-phenyl)-2-oxo-4-trifluoromethyl-1,2-dihydro-pyridine-3-carbonitrile;
1-Benzyl-2-oxo-4-pentafluoroethyl-6-phenyl-1,2-dihydro-pyridine-3-carbonitrile;
1-(4-Methyl-benzyl)-2-oxo-4-pentafluoroethyl-6-phenyl-1,2-dihydro-pyridine-3-carbonitrile;
1-(2,4-Dimethyl-benzyl)-2-oxo-4-pentafluoroethyl-6-phenyl-1,2-dihydro-pyridine-3-carbonitrile;
1-(2,4-Dimethyl-benzyl)-6-(3,5-dimethyl-phenyl)-2-oxo-4-trifluoromethyl-1,2-dihydro-pyridine-3-carbonitrile;
1-(2,4-Dimethyl-benzyl)-2-oxo-6-(5,5,8,8-tetramethyl-5,6,7,8-tetrahydro-naphthalen-2-yl)-4-trifluoromethyl-1,2-dihydro-pyridine-3-carbonitrile;
1-(2,4-Dimethyl-benzyl)-6-(3-ethyl-phenyl)-2-oxo-4-trifluoromethyl-1,2-dihydro-pyridine-3-carbonitrile;
1-(2,4-Dimethyl-benzyl)-2-oxo-6-p-tolyl-4-trifluoromethyl-1,2-dihydro-pyridine-3-carbonitrile;
1-(2,4-Dimethyl-benzyl)-6-(3-methoxy-phenyl)-2-oxo-4-trifluoromethyl-1,2-dihydro-pyridine-3-carbonitrile;
1-(2,4-Dimethyl-benzyl)-6-(4-methoxy-phenyl)-2-oxo-4-trifluoromethyl-1,2-dihydro-pyridine-3-carbonitrile;
1-(2,4-Dimethyl-benzyl)-6-(2-chloro-phenyl)-2-oxo-4-trifluoromethyl-1,2-dihydro-pyridine-3-carbonitrile;
1-(2,4-Dimethyl-benzyl)-6-(3-chloro-phenyl)-2-oxo-4-trifluoromethyl-1,2-dihydro-pyridine-3-carbonitrile;
1-(2,4-Dimethyl-benzyl)-6-(4-chloro-phenyl)-2-oxo-4-trifluoromethyl-1,2-dihydro-pyridine-3-carbonitrile; and
1-Benzyl-2-oxo-6-thiophen-2-yl-4-trifluoromethyl-1,2-dihydro-pyridine-3-carbonitrile.

C. Preparation of the Compounds

The compounds provided herein can be prepared using readily available starting materials or known intermediates. Schemes 1, 2 and 3 (infra) provide a summary of the synthetic routes utilized in producing the compounds provided herein.

Scheme 1, below, details the synthetic strategy utilized for the construction of N-amino-2-pyridone derivatives v. Such hydrazones can be readily obtained via the condensation of N-aminopyridones iii with aldehydes ($R^c$=H) and ketones (as iv) in the presence of acids in various solvents. The N-amino-2-pyridone itself is produced by a cyclocondensation reaction between 1,3-diketones i and cyanoacetohydrazide ii in the presence of various bases (see, e.g., Elgemeie et al. (1994) Org. Prep. Proc. Int. 26:465-468). The requisite 1,3-dicarbonyl compounds i can be obtained from the corresponding esters and methyl ketones using strong bases.

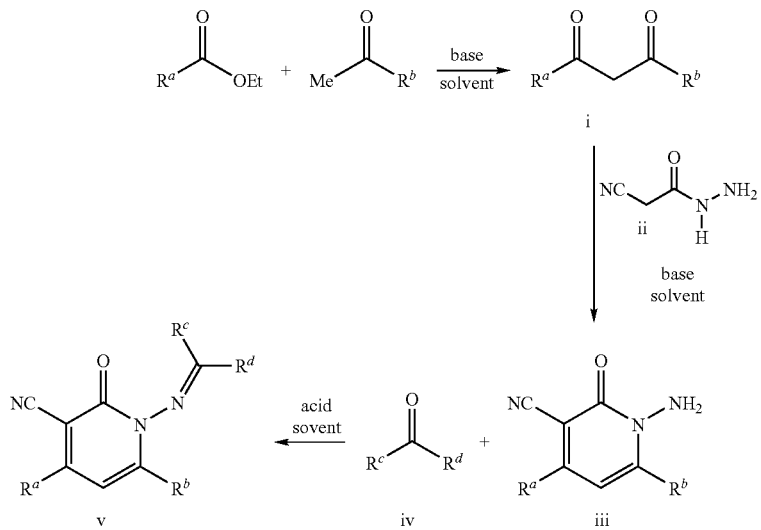

Scheme 2, below, details the synthetic strategy utilized in constructing the N-benzyl-2-pyridone ix compounds. These compounds are formed from an analogous cyclocondensation reaction to that used to form the N-aminopyridones. Reaction of cyanoacetamides viii with 1,2-diketones i using various bases produces N-benzyl-2-pyridones. The requisite cyanoacetamides viii are formed from either cyanoacetic acid vi or methyl cyanoactate vii. Cyanoacetic acid is first activated to its acid chloride using the reagent α,α-dichloromethyl methyl ether. The resultant acid chloride is reacted in situ with various amines to affect acylation. Direct conversion of methyl cyanoacetate vii to the corresponding cyanoacetamides viii is carried out with amines and in the presence of the acylation catalyst 4-(dimethylamino)pyridine (DMAP).

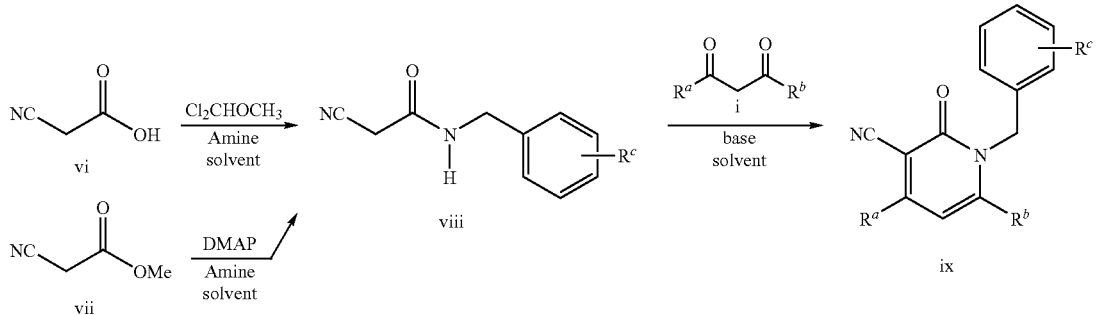

Scheme 3, below, details the synthetic strategy utilized to construct N-benzyl-2-pyridones containing a methoxycarbonylmethyl moiety at the C4-position of the pyridone ring. Compound xiii is obtained directly from the diester compound xii by reaction with benzylamines (for the conversion of pyrones to N-benzyl 2-pyridones, see, e.g., Katrizky et al. (1980) *J. Chem. Soc., Perkin Trans. 1*:2851-2855). Both pyridone formation and the ester cleavage (via decarboxylation) occur in this single step. The malonate substituted pyrone xii derives from the 4-methylsulfide variant xi via base-induced substitution with dimethylmalonate (see, e.g., Tominaga et al. (1984) *Chem. Pharm. Bull.* 32:3384-3395). Compound xi is readily obtained via the cyclocondensation reaction between the commercially available dithiane x and methyl ketones.

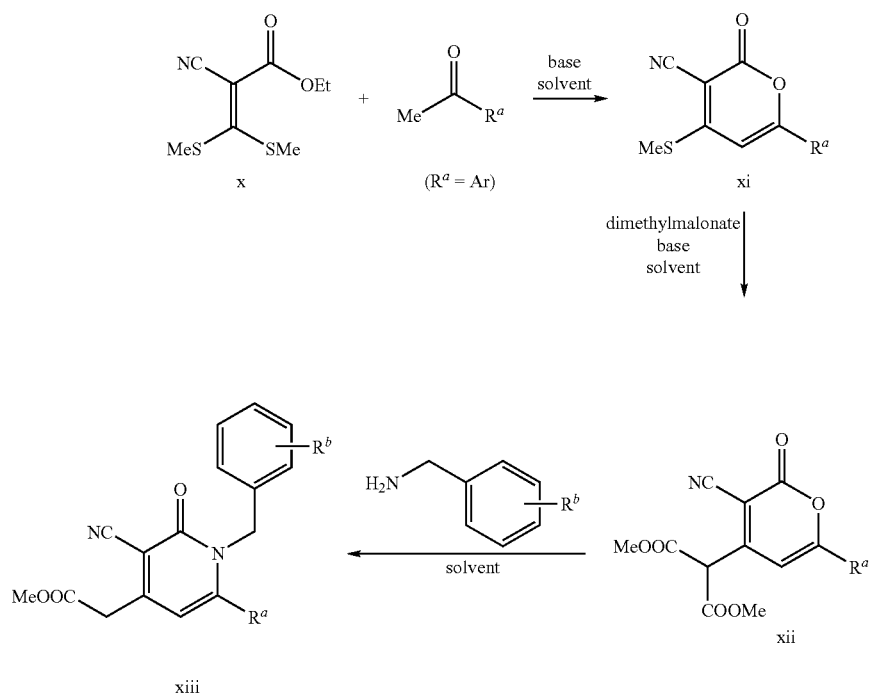

Other methods for the preparation of the compounds provided herein are shown in the Schemes below.
Scheme 4:
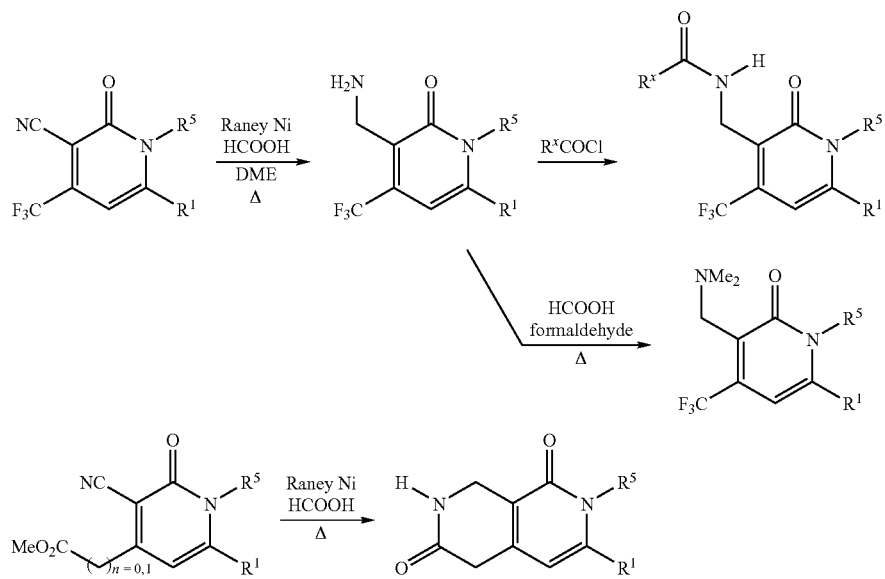
Scheme 5:
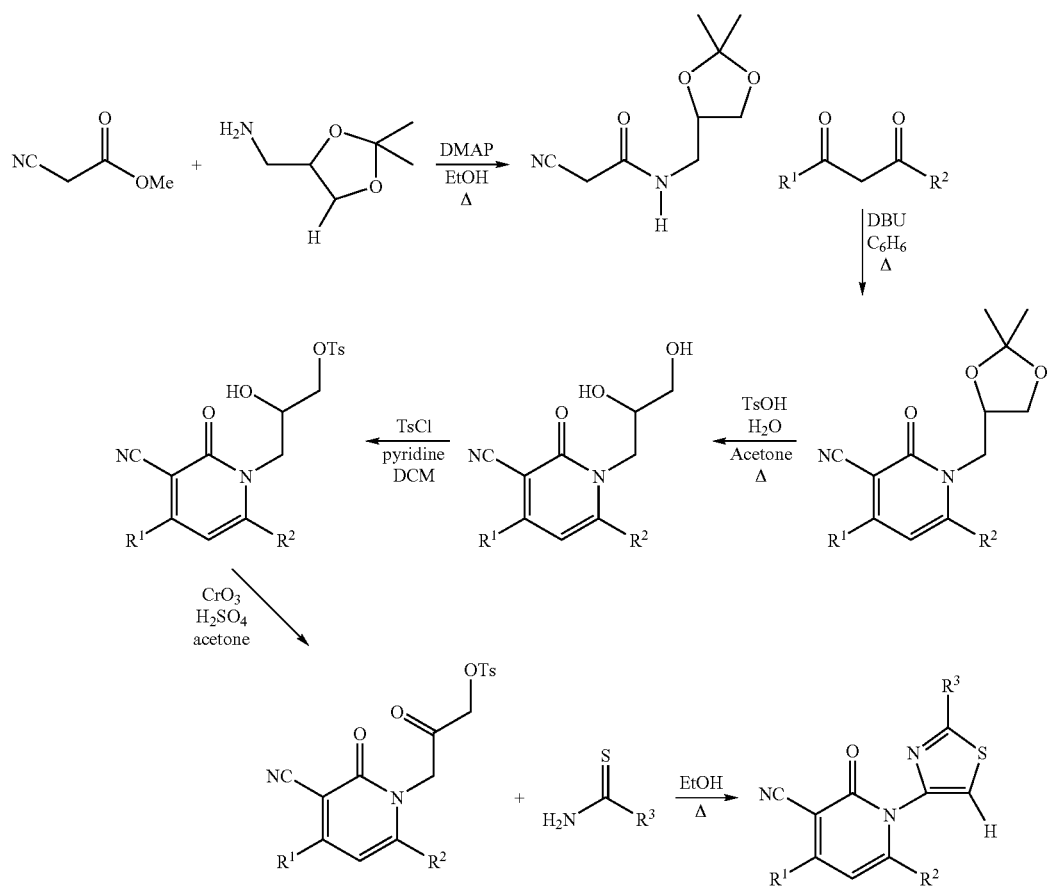

Scheme 6:
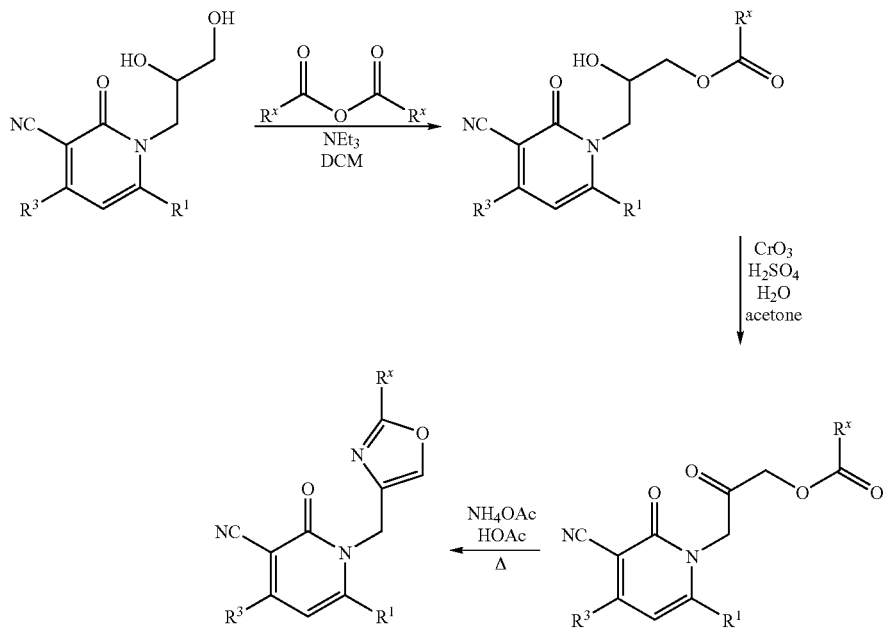
Scheme 7:
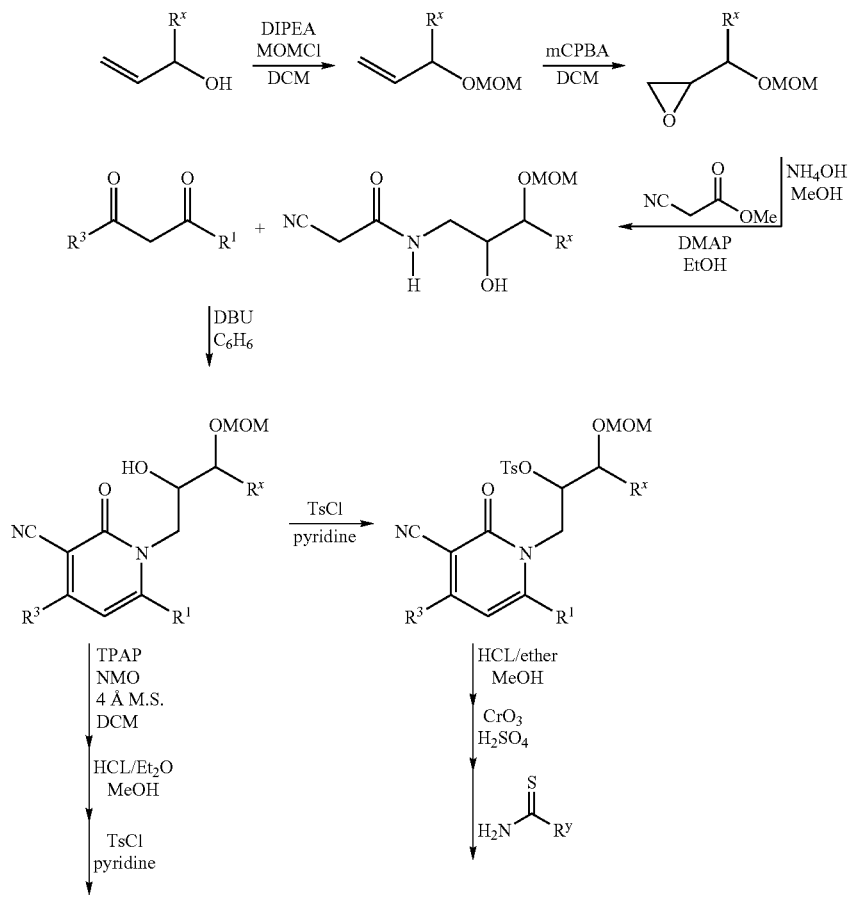

-continued
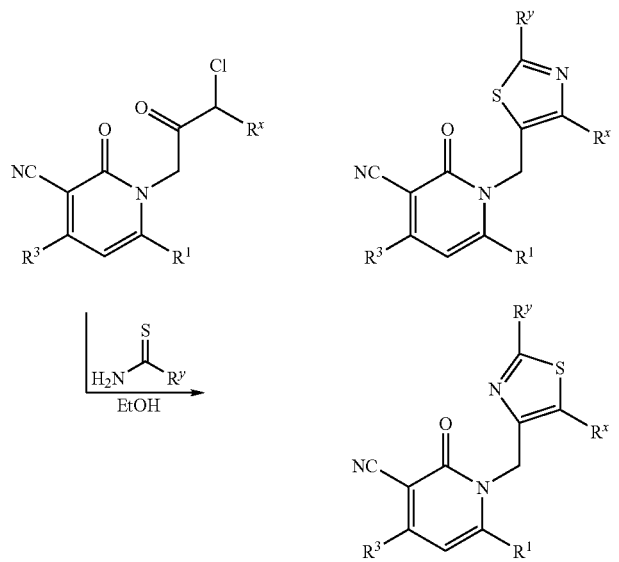
Scheme 8:
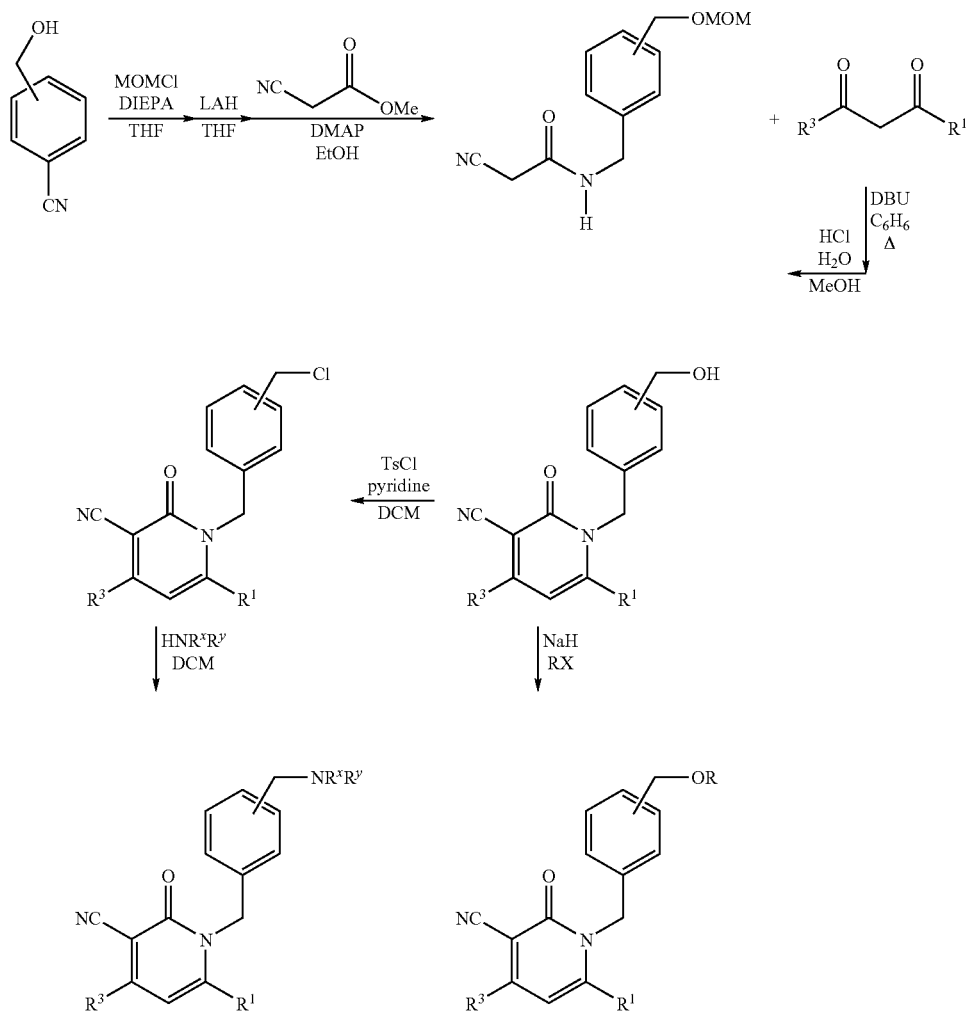

Scheme 9:
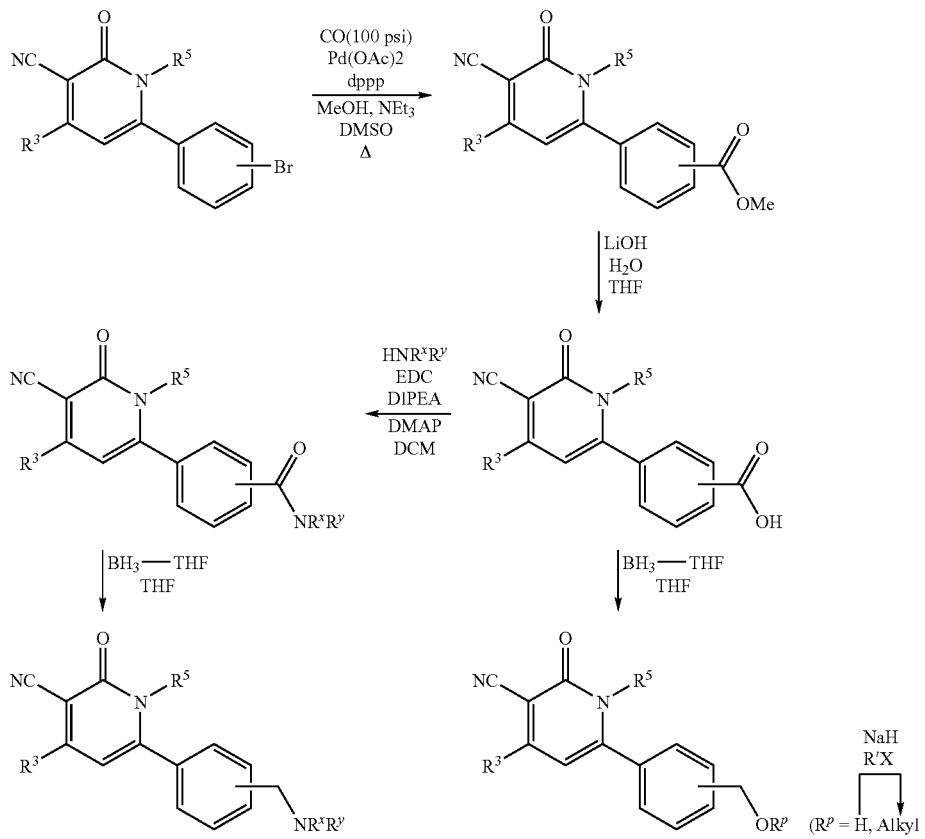
Scheme 10:
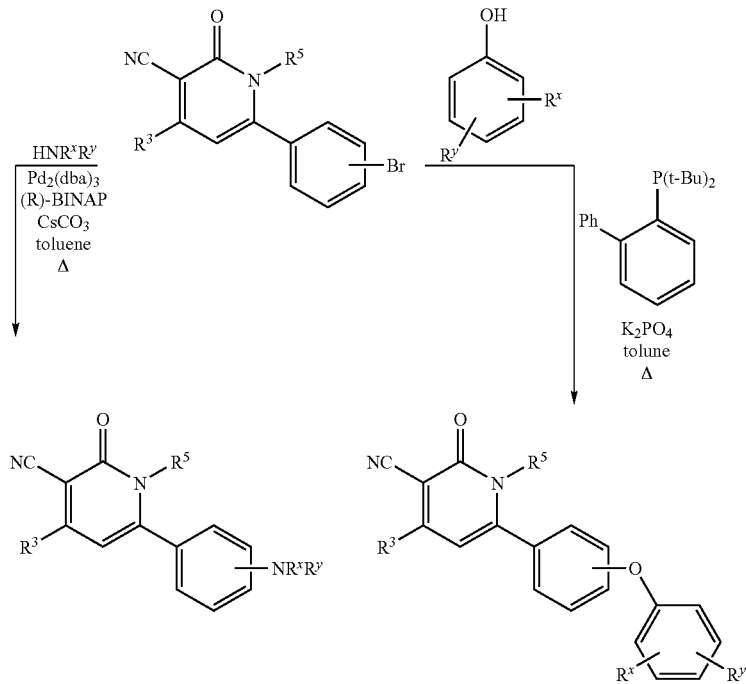

Scheme 11:
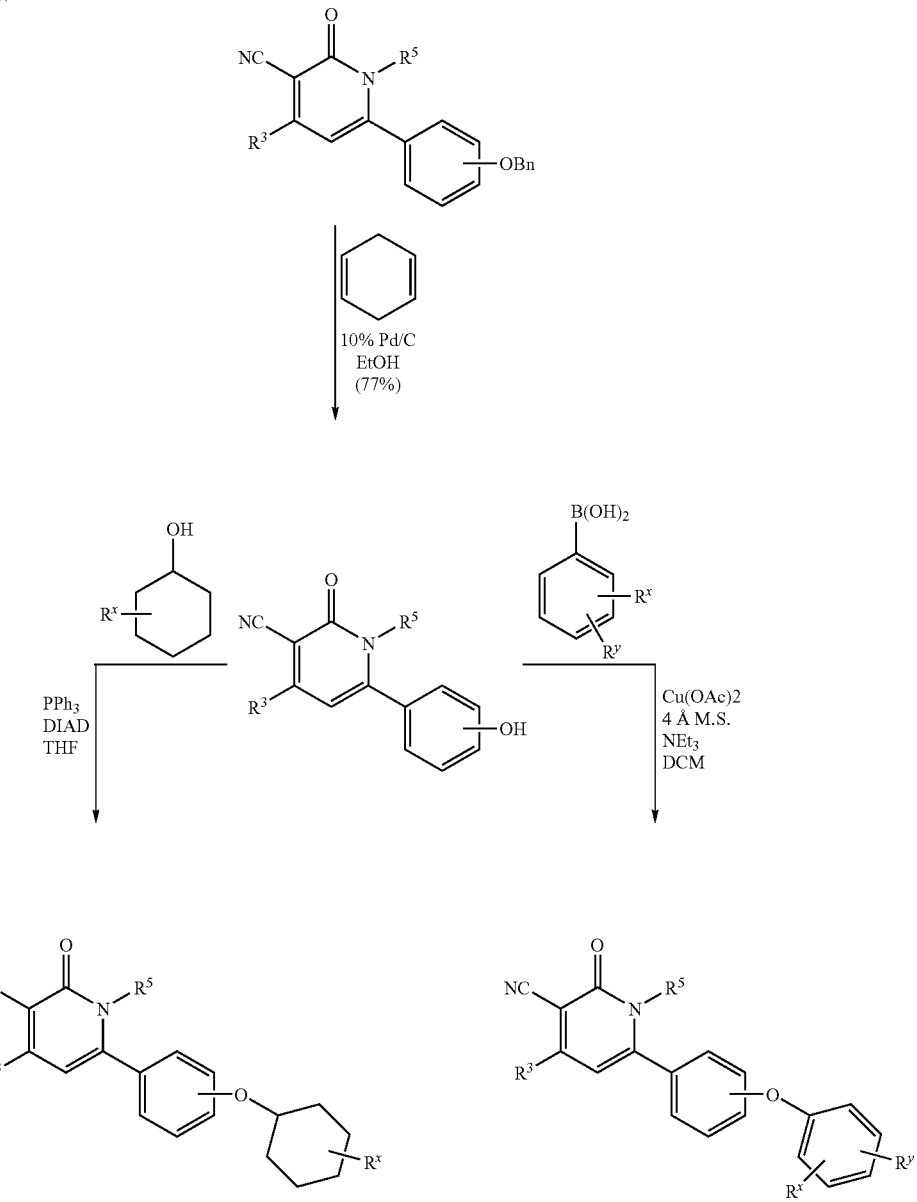
Scheme 12:
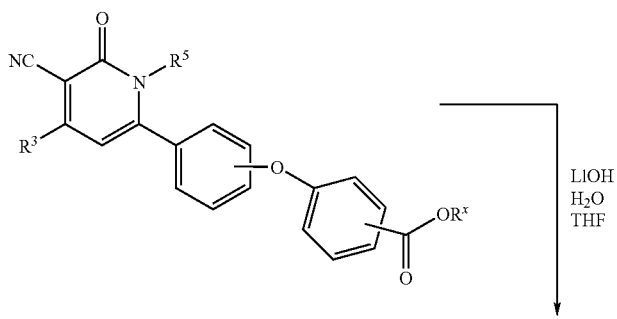

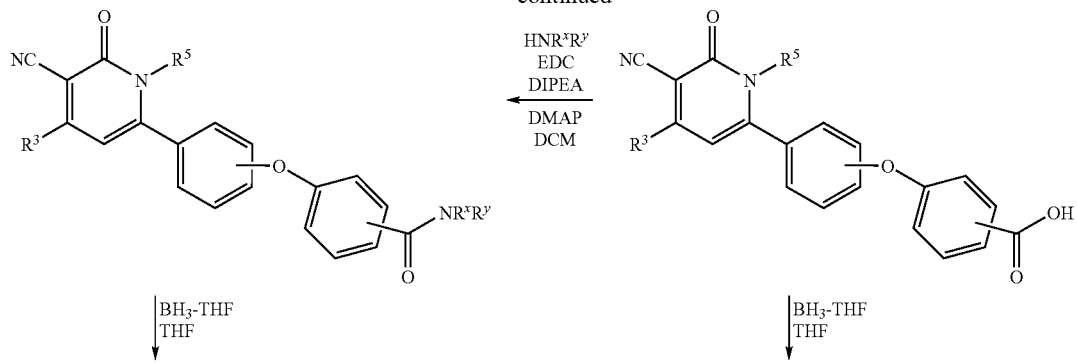
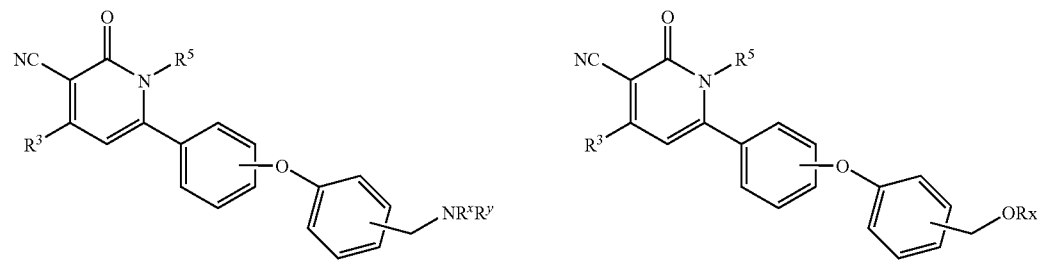
Scheme 13:
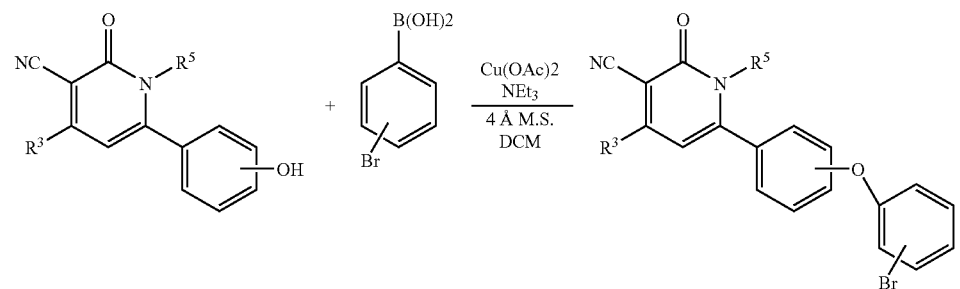
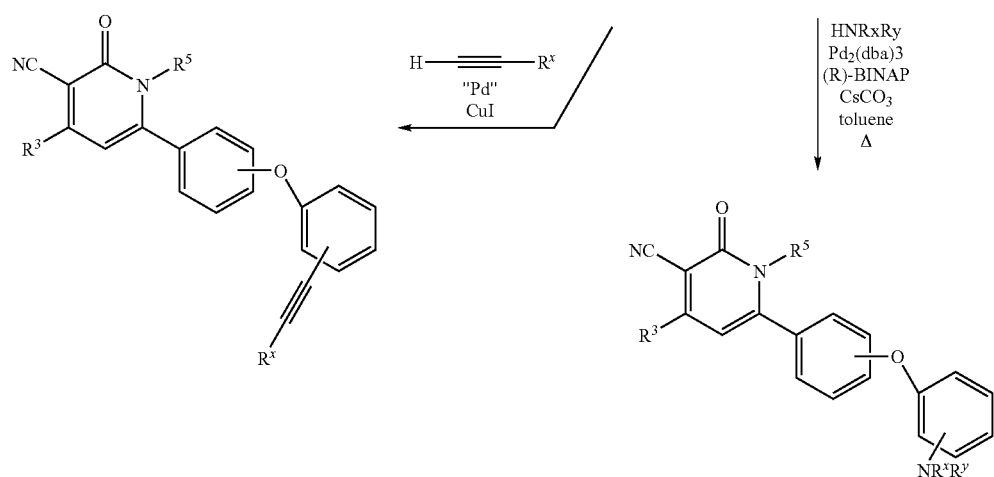

Scheme 14:
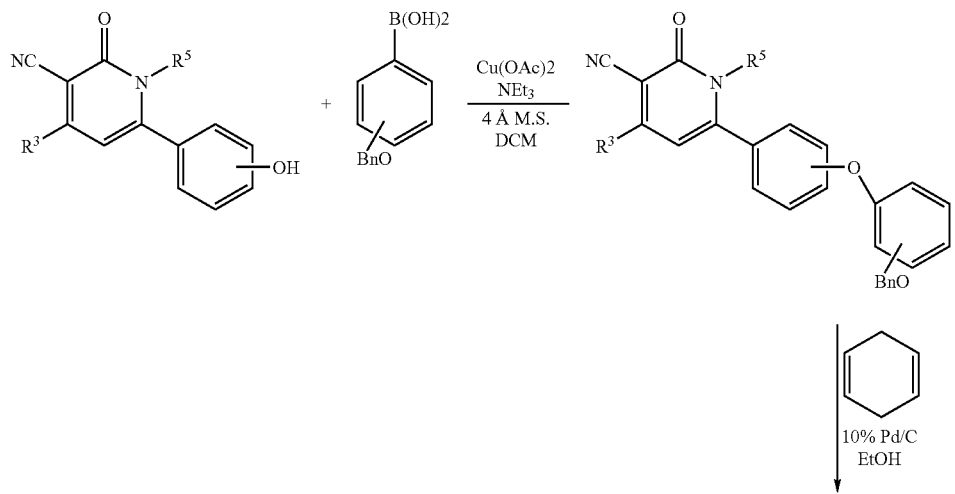
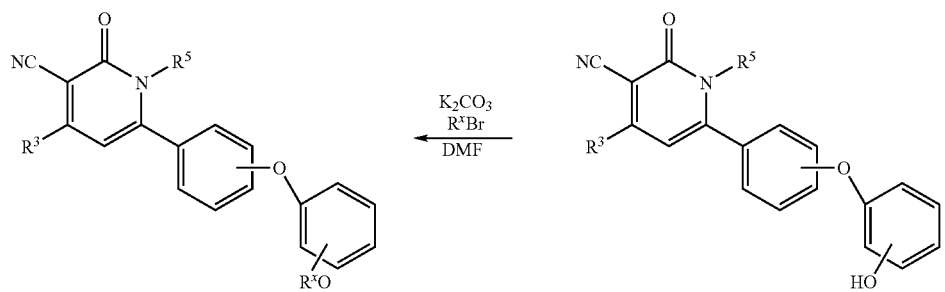
Scheme 15 (see, e.g., Attila et al. (1999) J. Am. Chem. Soc. 121:4369-4378):
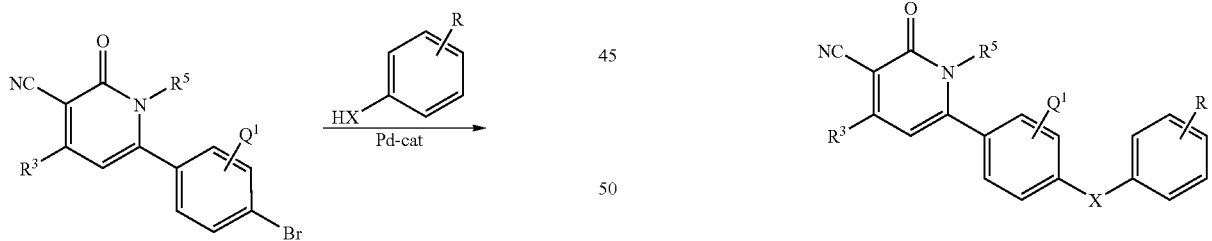
Scheme 16 (see, e.g., Evans et al. (1998) Tetrahedron Lett. 39:2937-2940):
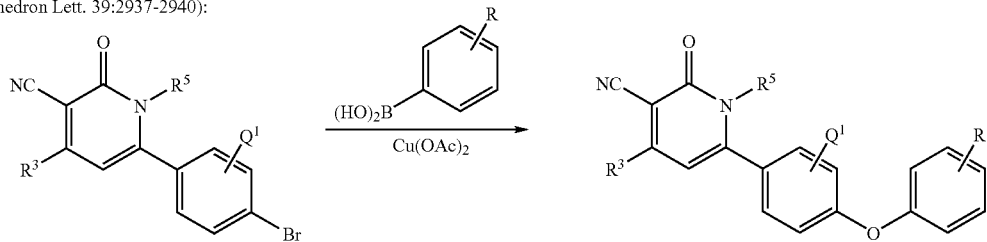

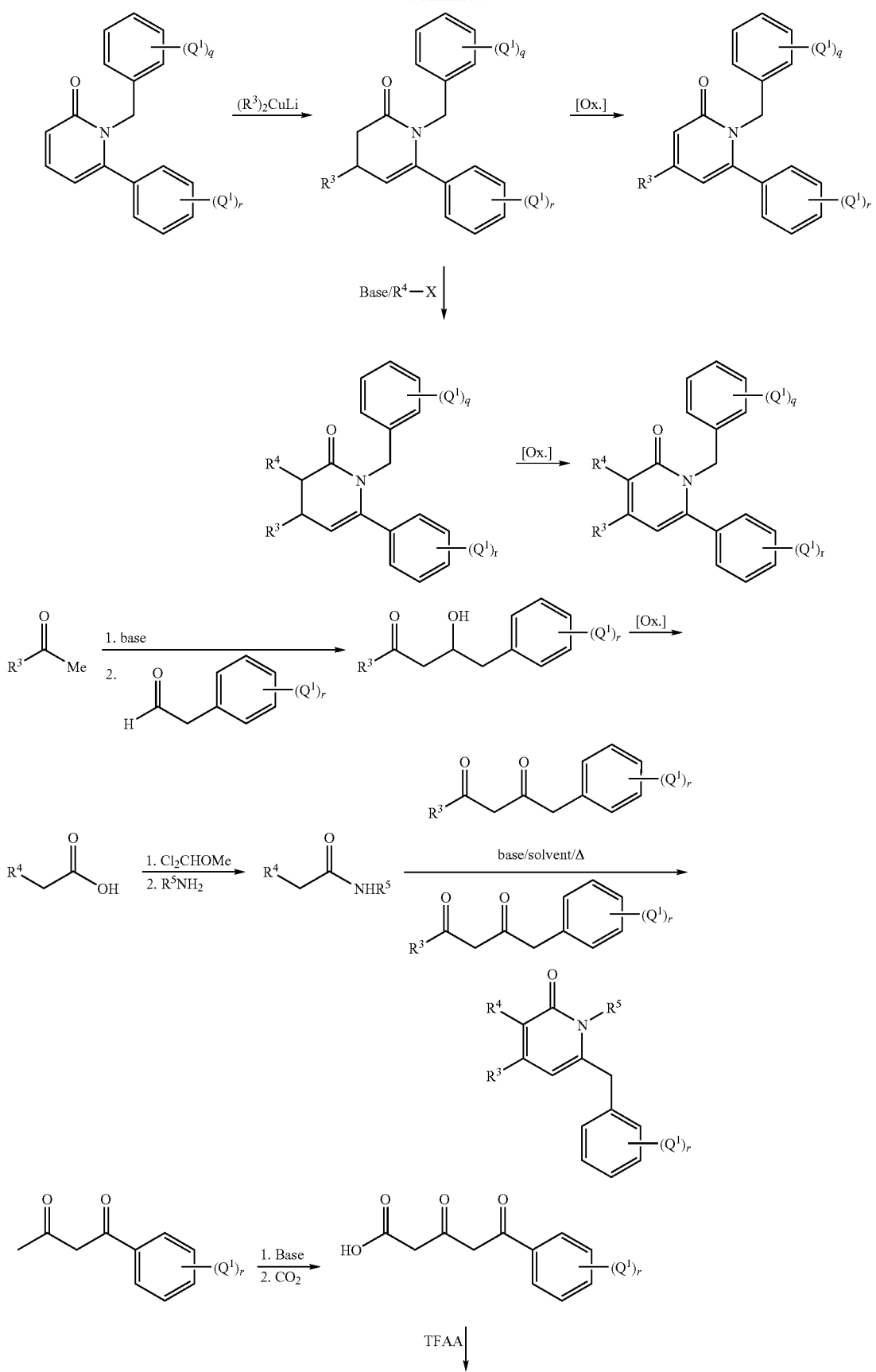

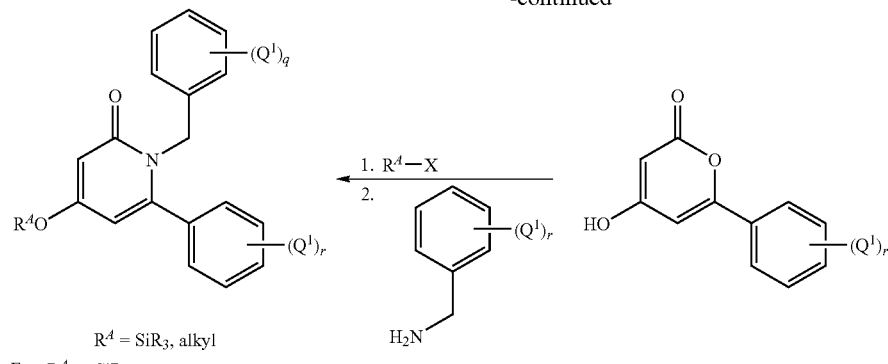

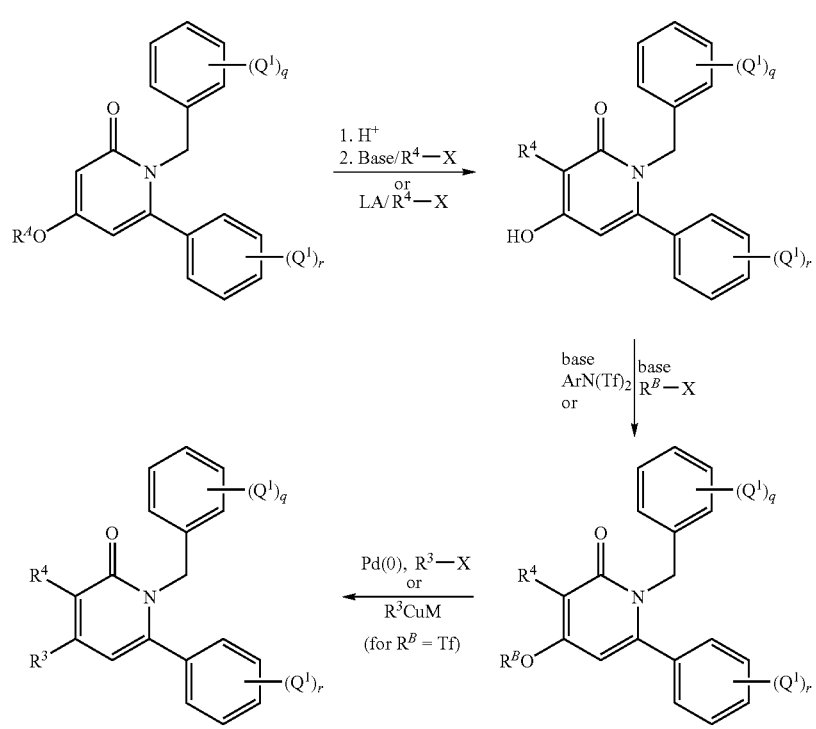

Starting materials in the synthesis examples provided herein are either available from commercial sources or via literature procedures. All commercially available compounds were used without further purification unless otherwise indicated. $CDCl_3$ (99.8% D, Cambridge Isotope Laboratories) was used in all experiments as indicated. $^1H$ NMR spectra were recorded on a Bruker Avance 400 MHz NMR spectrometer. Significant peaks are tabulated and typically include: number of protons, multiplicity (s, singlet; d, double; t, triplet; q, quartet; m, multiplet; br s, broad singlet) and coupling constant(s) in Hertz. Chemical shifts are reported as parts per million (δ) relative to tetramethylsilane. Mass spectra were recorded on a Perkin-Elmer SCIEX HPLC/MS instrument using reverse-phase conditions (acetonitrile/water, 0.05% trifluoroacetic acid) and electrospray (ES) ionization. Abbreviations used in the examples below have their accepted meanings in the chemical literature. For example, $CH_2Cl_2$ (dichloromethane), $C_6H_6$ (benzene), TFA (trifluoroacetic acid), EtOAc (Ethyl Acetate), $Et_2O$ (diethyl ether), DMAP (4-dimethylaminopyridine), DMF (N,N-dimethylformamide) and THF (tetrahydrofuran). Flash chromatography was performed using Merck Silica Gel 60 (230-400 mesh).

D. Formulation of Pharmaceutical Compositions

The pharmaceutical compositions provided herein contain therapeutically effective amounts of one or more of the nuclear receptor activity modulators provided herein that are useful in the prevention, treatment, or amelioration of one or more of the symptoms of diseases or disorders associated with nuclear receptor activity, including LXR and/or orphan nuclear receptor activity. Such diseases or disorders include, but are not limited to, hypercholesterolemia, hyperlipoproteinemia, hypertriglyceridemia, lipodystrophy, hyperglycemia, diabetes mellitus, dyslipidemia, atherosclerosis, gallstone disease, acne vulgaris, acneiform skin conditions, diabetes, Parkinson's disease, cancer, Alzheimer's disease, inflammation, immunological disorders, lipid disorders, obesity, conditions characterized by a perturbed epidermal barrier function, conditions of disturbed differentiation or excess proliferation of the epidermis or mucous membrane, and cardiovascular disorders.

The compositions contain one or more compounds provided herein. The compounds are preferably formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. Typically the compounds described above are formulated into pharmaceutical compositions using techniques and procedures well known in the art (see, e.g., *Ansel Introduction to Pharmaceutical Dosage Forms, Fourth Edition* 1985, 126).

In the compositions, effective concentrations of one or more compounds or pharmaceutically acceptable derivatives is (are) mixed with a suitable pharmaceutical carrier or vehicle. The compounds may be derivatized as the corresponding salts, esters, enol ethers or esters, acids, bases, solvates, hydrates or prodrugs prior to formulation, as described above. The concentrations of the compounds in the compositions are effective for delivery of an amount, upon administration, that treats, prevents, or ameliorates one or more of the symptoms of diseases or disorders associated with nuclear receptor activity or in which nuclear receptor activity is implicated. Such diseases or disorders include, but are not limited to, hypercholesterolemia, hyperlipopriteinemia, hypertriglyceridemia, lipodystrophy, hyperglycemia, diabetes mellitus, dyslipidemia, atherosclerosis, gallstone disease, acne vulgaris, acneiform skin conditions, diabetes, Parkinson's disease, cancer, Alzheimer's disease, inflammation, immunological disorders, lipid disorders, obesity, conditions characterized by a perturbed epidermal barrier function, conditions of disturbed differentiation or excess proliferation of the epidermis or mucous membrane, and cardiovascular disorders.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulted compound, pelleted by centrifugation, and then resuspended in PBS.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and in International Patent Application Publication Nos. 99/27365 and 00/25134 (see, e.g., EXAMPLES 13 and 14) and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders associated with nuclear receptor activity or in which nuclear receptor activity is implicated, as described herein.

Typically a therapeutically effective dosage should produce a serum concentration of active ingredient of from about 0.1 ng/ml to about 50-100 μg/ml. The pharmaceutical compositions typically should provide a dosage of from about 0.001 mg to about 2000 mg of compound per kilogram of body weight per day. Pharmaceutical dosage unit forms are prepared to provide from about 1 mg to about 1000 mg and preferably from about 10 to about 500 mg of the essential active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Pharmaceutically acceptable derivatives include acids, bases, enol ethers and esters, salts, esters, hydrates, solvates and prodrug forms. The derivative is selected such that its pharmacokinetic properties are superior to the corresponding neutral compound.

Thus, effective concentrations or amounts of one or more of the compounds described herein or pharmaceutically acceptable derivatives thereof are mixed with a suitable pharmaceutical carrier or vehicle for systemic, topical or local administration to form pharmaceutical compositions. Compounds are included in an amount effective for ameliorating one or more symptoms of, or for treating or preventing diseases or disorders associated with nuclear receptor activity or in which nuclear receptor activity is implicated, as described herein. The concentration of active compound in the composition will depend on absorption, inactivation, excretion rates of the active compound, the dosage schedule, amount administered, particular formulation as well as other factors known to those of skill in the art.

The compositions are intended to be administered by a suitable route, including orally, parenterally, rectally, topically and locally. For oral administration, capsules and tablets are presently preferred. The compositions are in liquid, semi-liquid or solid form and are formulated in a manner suitable for each route of administration. Preferred modes of administration include parenteral and oral modes of administration. Oral administration is presently most preferred.

Solutions or suspensions used for parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate. Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are typically formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

The composition can contain along with the active ingredient: a diluent such as lactose, sucrose, dicalcium phosphate, or carboxymethyl-cellulose; a lubricant, such as magnesium stearate, calcium stearate and talc; and a binder such as starch, natural gums, such as gum acacia-gelatin, glucose, molasses, polvinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound in an amount sufficient to alleviate the symptoms of the treated subject.

Dosage forms or compositions containing active ingredient in the range of 0.005% to 100% with the balance made up from non-toxic carrier may be prepared. For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain 0.001%-100% active ingredient, preferably 0.1-85%, typically 75-95%.

The active compounds or pharmaceutically acceptable derivatives may be prepared with carriers that protect the compound against rapid elimination from the body, such as time release formulations or coatings.

The compositions may include other active compounds to obtain desired combinations of properties. The compounds provided herein, or pharmaceutically acceptable derivatives thereof as described herein, may also be advantageously administered for therapeutic or prophylactic purposes together with another pharmacological agent known in the general art to be of value in treating one or more of the diseases or medical conditions referred to hereinabove, such as diseases or disorders associated with nuclear receptor activity or in which nuclear receptor activity is implicated. It is to be understood that such combination therapy constitutes a further aspect of the compositions and methods of treatment provided herein.

1. Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms, preferably capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the compound could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

Pharmaceutically acceptable carriers included in tablets are binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic adds include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. Re 28,819 and 4,358, 603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

2. Injectables, Solutions and Emulsions

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polyporpoylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses throught the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. Typically a therapeutically effective dosage is formulated to contain a concentration of at least about 0.1% w/w up to about 90% w/w or more, preferably more than 1% w/w of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

3. Lyophilized Powders

Of interest herein are also lyophilized powders, which can be reconstituted for administration as solutions, emulsions and other mixtures. They may also be reconsitituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (10-1000 mg, preferably 100-500 mg) or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, preferably 5-35 mg, more preferably about 9-30 mg of lyophilized powder, is added per mL of sterile water or other suitable carrier. The precise amount depends upon the selected compound. Such amount can be empirically determined.

4. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, preferably less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

5. Compositions for Other Routes of Administration

Other routes of administration, such as topical application, transdermal patches, and rectal administration are also contemplated herein.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm.

Tablets and capsules for rectal administration are manufactured using the same pharmaceutically acceptable substance and by the same methods as for formulations for oral administration.

6. Articles of Manufacture

The compounds or pharmaceutically acceptable derivatives may be packaged as articles of manufacture containing
  i) packaging material,
  ii) a compound or pharmaceutically acceptable derivative thereof provided herein, which is effective for modulating the activity of nuclear receptors, including LXR and/or orphan nuclear receptors, or for treatment, prevention or amelioration of one or more symptoms of nuclear receptor, including LXR and/or orphan nuclear receptor, mediated diseases or disorders, or diseases or disorders in which nuclear receptor activity, including LXR and/or orphan nuclear receptor activity is implicated, within the packaging material, and
  iii) a label that indicates that the compound or composition, or pharmaceutically acceptable derivative thereof, is used for modulating the activity of nuclear receptors, including LXR and/or orphan nuclear receptors, or for treatment, prevention or amelioration of one or more symptoms of nuclear receptor, including LXR and/or orphan nuclear receptor, mediated diseases or disorders, or diseases or disorders in which nuclear receptor activity, including LXR and/or orphan nuclear receptor activity is implicated.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease or disorder in which nuclear receptor activity, including LXR and/or orphan nuclear receptor activity, is implicated as a mediator or contributor to the symptoms or cause.

E. Evaluation of the Utility of the Compounds

Standard physiological, pharmacological and biochemical procedures are available for testing the compounds to identify those that possess biological activities that modulate the activity or nuclear receptors, including the LXRs (LXRα and LXRβ). Such assays include, for example, biochemical assays such as binding assays, fluorescence polarization assays, FRET based coactivator recruitment assays (see generally Glickman et al., J. Biomolecular Screening, 7 No. 1 3-10 (2002), as well as cell based assays including the co-transfection assay, the use of LBD-Gal 4 chimeras and protein-protein interaction assays, (see, Lehmann. et al., J. Biol Chem., 272(6) 3137-3140 (1997).

High throughput screening systems are commercially available (see, e.g., Zymark Corp., Hopkinton, Mass.; Air Technical Industries, Mentor, Ohio; Beckman Instruments Inc., Fullerton, Calif.; Precision Systems, Inc., Natick, Mass.) that enable these assays to be run in a high throughput mode. These systems typically automate entire procedures, including all sample and reagent pipetting, liquid dispensing timed incubations, and final readings of the microplate in detector(s) appropriate for the assay. These configurable systems provide high throughput and rapid start up as well as a high degree of flexibility and customization. The manufacturers of such systems provide detailed protocols for various high throughput systems. Thus, for example, Zymark Corp. provides technical bulletins describing screening systems for detecting the modulation of gene transcription, ligand binding, and the like.

Assays that do not require washing or liquid separation steps are preferred for such high throughput screening systems and include biochemical assays such as fluorescence polarization assays (see for example, Owicki, J., Biomol Screen October 2000; 5(5):297) scintillation proximity assays (SPA) (see for example, Carpenter et al., Methods Mol Biol 2002; 190:31-49) and fluorescence resonance energy transfer (FRET) or time resolved FRET based coactivator recruitment assays (Mukherjee et al., J Steroid Biochem Mol Biol July 2002; 81 (3):217-25; (Zhou et al., Mol Endocrinol. October 1998; 12(10):1594-604). Generally such assays can be preformed using either the full length receptor, or isolated ligand binding domain (LBD). In the case of LXRα the LBD comprises amino acids 188-447, for LXRβ the LDB comprises amino acids 198-461, and for FXR, the LBD comprises amino acids 244 to 472 of the full length sequence.

If a fluorescently labeled ligand is available, fluorescence polarization assays provide a way of detecting binding of compounds to the nuclear receptor of interest by measuring changes in fluorescence polarization that occur as a result of the displacement of a trace amount of the label ligand by the compound. Additionally this approach can also be used to monitor the ligand dependent association of a fluorescently labeled coactivator peptide to the nuclear receptor of interest to detect ligand binding to the nuclear receptor of interest.

The ability of a compound to bind to a receptor, or heterodimer complex with RXR, can also be measured in a homogeneous assay format by assessing the degree to which the compound can compete off a radiolabelled ligand with known affinity for the receptor using a scintillation proximity assay (SPA). In this approach, the radioactivity emitted by a radiolabelled compound (for example, [$^3$H] 24,25 Epoxycholesterol) generates an optical signal when it is brought into close proximity to a scintillant such as a Ysi-copper containing bead, to which the nuclear receptor is bound. If the radiolabelled compound is displaced from the nuclear receptor the amount of light emitted from the nuclear receptor bound scintillant decreases, and this can be readily detected using standard microplate liquid scintillation plate readers such as, for example, a Wallac MicroBeta reader.

The heterodimerization of LXR with RXRα can also be measured by fluorescence resonance energy transfer (FRET), or time resolved FRET, to monitor the ability of the compounds provided herein to bind to LXR or other nuclear receptors. Both approaches rely upon the fact that energy transfer from a donor molecule to an acceptor molecule only occurs when donor and acceptor are in close proximity. Typically the purified LBD of the nuclear receptor of interest is labeled with biotin then mixed with stoichiometric amounts of europium labeled streptavidin (Wallac Inc.), and the purified LBD of RXRα is labeled with a suitable fluorophore such as CY5™. Equimolar amounts of each modified LBD are mixed together and allowed to equilibrate for at least 1 hour prior to addition to either variable or constant concentrations of the sample for which the affinity is to be determined. After equilibration, the time-resolved fluorescent signal is quantitated using a fluorescent plate reader. The affinity of the compound can then be estimated from a plot of fluorescence versus concentration of compound added.

This approach can also be exploited to measure the ligand dependent interaction of a co-activator peptide with a nuclear receptor in order to characterize the agonist or antagonist activity of the compounds disclosed herein. Typically the assay in this case involves the use a recombinant Glutathione-S-transferase (GST)-nuclear receptor ligand binding domain (LBD) fusion protein and a synthetic biotinylated peptide sequence derived from the receptor interacting domain of a co-activator peptide such as the steroid receptor coactivator 1 (SRC-1). Typically GST-LBD is labeled with a europium chelate (donor) via a europium-tagged anti-GST antibody, and the coactivator peptide is labeled with allophycocyanin via a streptavidin-biotin linkage.

In the presence of an agonist for the nuclear receptor, the peptide is recruited to the GST-LBD bringing europium and allophycocyanin into close proximity to enable energy transfer from the europium chelate to the allophycocyanin. Upon excitation of the complex with light at 340 nm excitation energy absorbed by the europium chelate is transmitted to the allophycocyanin moiety resulting in emission at 665 nm. If the europium chelate is not brought into close proximity to the allophycocyanin moiety there is little or no energy transfer and excitation of the europium chelate results in emission at 615 nm. Thus the intensity of light emitted at 665 nm gives an indication of the strength of the protein-protein interaction. The activity of a nuclear receptor antagonist can be measured by determining the ability of a compound to competitively inhibit (i.e., $IC_{50}$) the activity of an agonist for the nuclear receptor.

In addition a variety of cell based assay methodologies may be successfully used in screening assays to identify and profile the specificity of compounds claimed herein. These approaches include the co-transfection assay, translocation assays, complementation assays and the use of gene activation technologies to over express endogenous nuclear receptors.

Three basic variants of the co-transfection assay strategy exist, co-transfection assays using full-length nuclear receptor, co transfection assays using chimeric nuclear receptors comprising the ligand binding domain of the nuclear receptor of interest fused to a heterologous DNA binding domain, and assays based around the use of the mammalian two hybrid assay system.

The basic co-transfection assay is based on the co-transfection into the cell of an expression plasmid to express the nuclear receptor of interest in the cell with a reporter plasmid comprising a reporter gene whose expression is under the control of DNA sequence that is capable of interacting with that nuclear receptor. (See for example U.S. Pat. Nos. 5,071,773; 5,298,429 and 6,416,957). Treatment of the transfected cells with an agonist for the nuclear receptor increases the transcriptional activity of that receptor which is reflected by an increase in expression of the reporter gene, which may be measured by a variety of standard procedures.

For those receptors that function as heterodimers with RXR, such as the LXRs, the co-transfection assay typically includes the use of expression plasmids for both the nuclear receptor of interest and RXR. Typical co-transfection assays require access to the full length nuclear receptor and suitable response elements that provide sufficient screening sensitivity and specificity to the nuclear receptor of interest.

Genes encoding the following full-length previously described proteins, which are suitable for use in the co-transfection studies and profiling the compounds described herein, include human LXRα (SEQ ID 1), human LXRβ (SEQ ID 3), rat FXR (SEQ ID 5), human FXR (SEQ ID 7), human RXRα (SEQ ID 9), human RXRβ (SEQ ID 17), human RXRγ (SEQ ID 15), human PPARα (SEQ ID 11) and human PPARδ (SEQ ID 13). All accession numbers in this application refer to GenBank accession numbers.

Reporter plasmids may be constructed using standard molecular biological techniques by placing cDNA encoding for the reporter gene downstream from a suitable minimal promoter. For example luciferase reporter plasmids may be constructed by placing cDNA encoding firefly luciferase immediately down stream from the herpes virus thymidine kinase promoter (located at nucleotides residues −105 to +51 of the thymidine kinase nucleotide sequence) which is linked in turn to the various response elements.

Numerous methods of co-transfecting the expression and reporter plasmids are known to those of skill in the art and may be used for the co-transfection assay to introduce the plasmids into a suitable cell type. Typically such a cell will not endogenously express nuclear receptors that interact with the response elements used in the reporter plasmid.

Numerous reporter gene systems are known in the art and include, for example, alkaline phosphatase Berger, J., et al. (1988) Gene 66 1-10; Kain, S. R. (1997) Methods. Mol. Biol. 63 49-60), β-galactosidase (See, U.S. Pat. No. 5,070,012, issued Dec. 3, 1991 to Nolan et al., and Bronstein, I., et al., (1989) J. Chemilum. Biolum. 4 99-111), chloramphenicol acetyltransferase (See Gorman et al., Mol Cell Biol. (1982) 2 1044-51), β-glucuronidase, peroxidase, β-lactamase (U.S. Pat. Nos. 5,741,657 and 5,955,604), catalytic antibodies, luciferases (U.S. Pat. Nos. 5,221,623; 5,683,888; 5,674,713; 5,650,289; 5,843,746) and naturally fluorescent proteins (Tsien, R. Y. (1998) Annu. Rev. Biochem. 67 509-44).

The use of chimeras comprising the ligand binding domain (LBD) of the nuclear receptor of interest fused to a heterologous DNA binding domain (DBD) expands the versatility of cell based assays by directing activation of the nuclear receptor in question to defined DNA binding elements recognized by defined DNA binding domain (see WO95/18380). This assay expands the utility of cell based co-transfection assays in cases where the biological response or screening window using the native DNA binding domain is not satisfactory.

In general the methodology is similar to that used with the basic co-transfection assay, except that a chimeric construct is used in place of the full length nuclear receptor. As with the full length nuclear receptor, treatment of the transfected cells with an agonist for the nuclear receptor LBD increases the transcriptional activity of the heterologous DNA binding domain which is reflected by an increase in expression of the reporter gene as described above. Typically for such chimeric constructs, the DNA binding domains from defined nuclear receptors, or from yeast or bacterially derived transcriptional regulators such as members of the GAL 4 and Lex A/Umud super families are used.

A third cell based assay of utility for screening compounds claimed herein is a mammalian two-hybrid assay that measures the ability of the nuclear hormone receptor to interact with a cofactor in the presence of a ligand. (See for example, U.S. Pat. Nos. 5,667,973, 5,283,173 and 5,468,614). The basic approach is to create three plasmid constructs that enable the interaction of the nuclear receptor with the interacting protein to be coupled to a transcriptional readout within a living cell. The first construct is an expression plasmid for expressing a fusion protein comprising the interacting protein, or a portion of that protein containing the interacting domain, fused to a GAL4 DNA binding domain. The second expression plasmid comprises DNA encoding the nuclear receptor of interest fused to a strong transcription activation domain such as VP16, and the third construct comprises the reporter plasmid comprising a reporter gene with a minimal promoter and GAL4 upstream activating sequences.

Once all three plasmids are introduced into a cell, the GAL4 DNA binding domain encoded in the first construct allows for specific binding of the fusion protein to GAL4 sites upstream of a minimal promoter. However because the GAL4 DNA binding domain typically has no strong transcriptional activation properties in isolation, expression of the reporter gene occurs only at a low level. In the presence of a ligand, the nuclear receptor-VP16 fusion protein can bind to the GAL4-interacting protein fusion protein bringing the strong transcriptional activator VP16 in close proximity to the GAL4 binding sites and minimal promoter region of the reporter gene. This interaction significantly enhances the transcription of the reporter gene, which can be measured for various reporter genes as described above. Transcription of the reporter gene is thus driven by the interaction of the interacting protein and nuclear receptor of interest in a ligand dependent fashion.

Any compound which is a candidate for activation of LXRα or LXRβ may be tested by these methods. Generally, compounds are tested at several different concentrations to optimize the chances that activation of the receptor will be detected and recognized if present. Typically assays are performed in triplicate and vary within experimental error by less than 15%. Each experiment is typically repeated three or more times with similar results.

Activity of the reporter gene can be conveniently normalized to the internal control and the data plotted as fold activation relative to untreated cells. A positive control compound (agonist) may be included along with DMSO as high and low controls for normalization of the assay data. Similarly, antagonist activity can be measured by determining the ability of a compound to competitively inhibit the activity of an agonist.

Additionally the compounds and compositions can be evaluated for their ability to increase or decrease the expression of genes known to be modulated by LXRα or β and other nuclear receptors in vivo, using Northern-blot, RT PCR or oligonucleotide microarray analysis to analyze RNA levels.

Western-blot analysis can be used to measure expression of proteins encoded by LXR target genes. Genes that are known to be regulated by the LXRs include the ATP binding cassette transporters ABCA1, ABCG1, ABCG5, ABCG8, the sterol response element binding protein 1c (SREBP1c) gene, stearoyl CoA desaturase 1 (SCD-1) and the apolipoprotein apoE gene (ApoE).

Established animal models exist for a number of diseases of direct relevance to the claimed compounds and these can be used to further profile and characterize the claimed compounds. These model systems include diabetic dislipidemia using Zucker (fa/fa) rats or (db/db) mice, spontaneous hyperlipidemia using apolipoprotein E deficient mice (ApoE$^{-/-}$), diet-induced hyperlipidemia, using low density lipoprotein receptor deficient mice (LDR$^{-/-}$) and atherosclerosis using both the Apo E($^{-/-}$) and LDL($^{-/-}$) mice fed a western diet. (21% fat, 0.05% cholesterol). Additionally LXR or FXR animal models (e.g., knockout mice) can be used to further evaluate the present compounds and compositions in vivo (see, for example, Peet, et al., *Cell,* 93:693-704 (1998), Sinal, et al., *Cell,* 102: 731-744 (2000)).

F. Methods of Use of the Compounds and Compositions

Methods and compounds for selectively regulating LXRα or LXRβ are also provided. In one embodiment, such compounds exhibit at least a 10 fold difference in IC$_{50}$, or EC$_{50}$ for LXRα compared to LXRβ.

F. Methods of Use of the Compounds and Compositions

Methods of use of the compounds and compositions provided herein are also provided. The methods involve both in vitro and in vivo uses of the compounds and compositions for altering nuclear receptor activity, including LXR and/or orphan nuclear receptor activity, and for treatment, prevention, or amelioration of one or more symptoms of diseases or disorder that are modulated by nuclear receptor activity, including LXR and/or orphan nuclear receptor activity, or in which nuclear receptor activity, including LXR and/or orphan nuclear receptor activity, is implicated.

Methods of reducing cholesterol levels and of modulating cholesterol metabolism are provided. As described above, LXR is implicated in modulated cholesteral metabolism and catabolism. See, e.g., International Patent Application Publication No. 00/40965.

Method of altering nuclear receptor activity, including liver X receptor (LXR) and/or orphan nuclear receptor activity, by contacting the receptor with one or more compounds or compositions provided herein, are provided.

Methods of treatment, prevention, or amelioration of one or more symptoms of a disease or disorder which is affected by cholesterol, triglyceride, or bile acid levels are provided.

Methods of treatment, prevention, or amelioration of one or more symptoms of hypercholesterolemia (see, e.g., International Patent Application Publication No. WO 00/57915); hyperlipoproteinemia (see, e.g., International Patent Application Publication No. WO 01/60818); hypertriglyceridemia, lipodystrophy, hyperglycemia or diabetes mellitus (see, e.g., International Patent Application Publication No. WO 01/82917); dyslipidemia, obesity, atherosclerosis, lipid disorders, cardiovascular disorders, or gallstone disease (see, e.g., International Patent Applciation Publication No. WO 00/37077); acne vulgaris or acneiform skin conditions (see, e.g., International Patent Application Publication No. WO 00/49992); atherosclerosis, diabetes, Parkinson's disease, inflammation, immunological disorders, obesity, cancer or Alzheimer's disease (see, e.g., International Patent Application Publication No. WO 00/17334); conditions characterized by a perturbed epidermal barrier function or conditions of disturbed differentiation or excess proliferation of the epidermis or mucous membrane (see, e.g., U.S. Pat. Nos. 6,184,215 and 6,187,814, and International Patent Application Publication No. Wo 98/32444) are provided.

Methods of increasing cholesterol efflux from mammalian cells using the compounds and compositions provided herein are provided (see, e.g., International Patent Application Publication No. WO 00/78972).

Methods of increasing the expression of ATP-Binding Cassette (ABC1) in mammalian cells using the compounds and compositions provided herein are provided (see, e.g., International Patent Application Publication No. WO 00/78972).

Methods of treating, preventing, or ameliorating one or more symptoms of hypocholesterolemia using the compounds and compositions provided herein are also provided.

Methods of post-myocardial infarction therapy using the compounds and compositions provided herein are also provided (see, e.g., International Patent Application Publication No. WO 01/03705).

Methods and compounds for selectively regulating LXRα or LXRβ are also provided. In one embodiment, such compounds exhibit at least a 10 fold difference in IC$_{50}$, or EC$_{50}$ for LXRα compared to LXRβ.

G. Combination Therapy

Also contemplated herein is combination therapy using a compound provided herein, or a pharmaceutically acceptable derivative thereof, in combination with one or more of the following: antihyperlipidemic agents, plasma HDL-raising agents, antihypercholesterolemic agents, cholesterol biosynthesis inhibitors (such as HMG CoA reductase inhibitors, such as lovastatin, simvastatin, pravastatin, fluvastatin, atorvastatin and rivastatin), acyl-coenzyme A:cholesterol acyltransferase (ACAT) inhibitors, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin B$_6$, vitamin B$_{12}$, antioxidant vitamins, β-blockers, anti-diabetes agents, angiotensin II antagonists, angiotensin converting enzyme inhibitors, platelet aggregation inhibitors, fibrinogen receptor antagonists, aspirin or fibric acid derivatives. The compound provided herein, or pharmaceutically acceptable derivative thereof, is administered simultaneously with, prior to, or after administration of one or more of the above agents. Pharmaceutical compositions containing a compound provided herein and one or more of the above agents are also provided.

Combination therapy includes administration of a single pharmaceutical dosage formulation which contains a LXR selective compound and one or more additional active agents, as well as administration of the LXR selective compound and each active agent in its own separate pharmaceutical dosage formulation. For example, a LXR agonist or antagonist claimed herein and an HMG-CoA reductase inhibitor can be administered to the patient together in a single oral dosage composition such as a tablet or capsule, or each agent administered in separate oral dosage formulations. Where separate dosage formulations are used, the compounds described herein and one or more additional active agents can be administered at essentially the same time, i.e., concurrently, or at separately staggered times, i.e., sequentially; combination therapy is understood to include all these regimens.

The compound is, in one embodiment, administered with a cholesterol biosynthesis inhibitor, particularly an HMG-CoA reductase inhibitor. The term HMG-CoA reductase inhibitor is intended to include all pharmaceutically acceptable salts, esters, free acids and lactone forms of compounds which have HMG-CoA reductase inhibitory activity and, therefore, the use of such salts, esters, free acids and lactone forms is included within the scope the compounds claimed herein. Compounds which have inhibitory activity for HMG-CoA reductase can be readily identified using assays well-known in the art. For instance, suitable assays are described or disclosed in U.S. Pat. No. 4,231,938 and WO 84/02131. Examples of suitable HMG-CoA reductase inhibitors include, but are not limited to, lovastatin (MEVACOR®; see, U.S. Pat. No. 4,231,938); simvastatin (ZOCOR®; see, U.S. Pat. No. 4,444,784); pravastatin sodium (PRAVACHOL®; see, U.S. Pat. No. 4,346,227); fluvastatin sodium (LESCOL®; see, U.S. Pat. No. 5,354,772); atorvastatin calcium (LIPITOR®; see, U.S. Pat. No. 5,273,995) and rivastatin (also known as cerivastatin; see, U.S. Pat. No. 5,177,080). The structural formulas of these and additional HMG-CoA reductase inhibitors that can be used in the methods claimed herein are described at page 87 of M. Yalpani, "Cholesterol Lowering Drugs," *Chemistry & Industry*, pp. 85-89 (Feb. 5, 1996). In one embodiments, the HMG-CoA reductase inhibitor is selected from lovastatin and simvastatin.

Dosage information for HMG-CoA reductase inhibitors is well known in the art, since several HMG-CoA reductase inhibitors are marketed in the U.S. In particular, the daily dosage amounts of the HMG-CoA reductase inhibitor may be the same or similar to those amounts which are employed for anti-hypercholesterolemic treatment and which are described in the *Physicians' Desk Reference* (PDR). For example, see the 50th Ed. of the PDR, 1996 (Medical Economics Co); in particular, see at page 216 the heading "Hypolipidemics," sub-heading "HMG-CoA Reductase Inhibitors," and the reference pages cited therein. In one embodiment, the oral dosage amount of HMG-CoA reductase inhibitor is from about 1 to 200 mg/day and, in another embodiment, from about 5 to 160 mg/day. However, dosage amounts will vary depending on the potency of the specific HMG-CoA reductase inhibitor used as well as other factors as noted above. An HMG-CoA reductase inhibitor which has sufficiently greater potency may be given in sub-milligram daily dosages.

As examples, the daily dosage amount for simvastatin may be selected from 5 mg, 10 mg, 20 mg, 40 mg, 80 mg and 160 mg; for lovastatin, 10 mg, 20 mg, 40 mg and 80 mg; for fluvastatin sodium, 20 mg, 40 mg and 80 mg; and for pravastatin sodium, 10 mg, 20 mg, and 40 mg. The daily dosage amount for atorvastatin calcium may be in the range of, in one embodiment, from 1 mg to 160 mg and, in another embodiment, from 5 mg to 80 mg. Oral administration may be in a single or divided doses of two, three, or four times daily, although a single daily dose of the HMG-CoA reductase inhibitor is preferred.

The compounds claimed herein can be utilized in methods for decreasing hyperglycemia and insulin resistance or for methods of treating type II diabetes. The compounds can be identified, formulated, and administered as described above.

The methods claimed herein can be used effectively in combination with one or more additional active diabetes agents depending on the desired target therapy (see, e.g., Turner, N. et al. Prog. Drug Res. (1998) 51: 33-94; Haffner, S. Diabetes Care (1998) 21: 160-178; and DeFronzo, R. et al. (eds.), Diabetes Reviews (1997) Vol. 5 No. 4). A number of studies have investigated the benefits of combination therapies with oral agents (see, e.g., Mahler, R., J. Clin. Endocrinol. Metab. (1999) 84: 1165-71; United Kingdom Prospective Diabetes Study Group: UKPDS 28, Diabetes Care (1998) 21: 87-92; Bardin, C. W., (ed.), CURRENT THERAPY IN ENDOCRINOLOGY AND METABOLISM, 6th Edition (Mosby—Year Book, Inc., St. Louis, Mo. 1997); Chiasson, J. et al., Ann. Intern. Med. (1994) 121: 928-935; Coniff, R. et al., Clin. Ther. (1997) 19: 16-26; Coniff, R. et al., Am. J. Med. (1995) 98: 443-451; and Iwamoto, Y. et al, Diabet. Med. (1996) 13 365-370; Kwiterovich, P. Am. J. Cardiol (1998) 82(12A): 3U-17U). These studies indicate that diabetes and hyperlipidemia modulation can be further improved by the addition of a second agent to the therapeutic regimen.

An example of combination therapy that modulates (prevents the onset of the symptoms or complications associated) atherosclerosis, is administered with one or more of the following active agents: an antihyperlipidemic agent; a plasma HDL-raising agent; an antihypercholesterolemic agent, such as a cholesterol biosynthesis inhibitor, e.g., an hydroxymethylglutaryl (HMG) CoA reductase inhibitor (also referred to as statins, such as lovastatin, simvastatin, pravastatin, fluvastatin, and atorvastatin), an HMG-CoA synthase inhibitor, a squalene epoxidase inhibitor, or a squalene synthetase inhibitor (also known as squalene synthase inhibitor); an acyl-coenzyme A cholesterol acyltransferase (ACAT) inhibitor, such as melinamide; probucol; nicotinic acid and the salts thereof and niacinamide; a cholesterol absorption inhibitor, such as β-sitosterol; a bile acid sequestrant anion exchange resin, such as cholestyramine, colestipol or dialkylaminoalkyl derivatives of a cross-linked dextran; an LDL (low density lipoprotein) receptor inducer; fibrates, such as clofibrate, bezafibrate, fenofibrate, and gemfibrizol; vitamin $B_6$ (also known as pyridoxine) and the pharmaceutically acceptable salts thereof, such as the HCl salt; vitamin $B_{12}$ (also known as cyanocobalamin); vitamin $B_3$ (also known as nicotinic acid and niacinamide, supra); anti-oxidant vitamins, such as vitamin C and E and beta carotene; a beta-blocker; an angiotensin II antagonist; an angiotensin converting enzyme inhibitor; and a platelet aggregation inhibitor, such as fibrinogen receptor antagonists (i.e., glycoprotein IIb/IIIa fibrinogen receptor antagonists) and aspirin.

Still another example of combination therapy can be seen in modulating diabetes (or treating diabetes and its related symptoms, complications, and disorders) with, for example, sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone); and related insulin sensitizers, such as selective and non-selective activators of PPARα, PPARβ and PPARγ; dehydroepiandrosterone (also referred to as DHEA or its conjugated sulphate ester, DHEA-$SO_4$); anti-glucocorticoids; TNFαinhibitors; α-glucosidase inhibitors (such as acarbose, miglitol, and voglibose), pramlintide (a synthetic analog of the human hormone amylin), other insulin secretagogues (such as repaglinide, gliquidone, and nateglinide), insulin, as well as the active agents discussed above for treating atherosclerosis.

Further provided herein are methods for treating obesity, as well as treating the complications of obesity, by administering a compound claimed herein. The antagonists can be identified, formulated, and administered similarly to the information described above. A LXR selective antagonist includes a partial agonist/antagonist or antagonist that exhibits about a two to about a ten-fold preference for LXRα or β compared to another nuclear receptor such as, for example FXR with respect to potency (IC$_{50}$, the concentration of compound that achieves 50% of the maximum reduction in the transcription activity achieved by the compound of interest observed in the presence of a sub-maximal concentration of LXR agonist) and/or efficacy (the maximum percent inhibition of transcription observed with the compound in question).

Another example of combination therapy can be seen in treating obesity or obesity-related disorders, wherein the methods can be effectively used in combination with, for example, phenylpropanolamine, phentermine, diethylpropion, mazindol; fenfluramine, dexfenfluramine, phentiramine, β$_3$ adrenoceptor agonist agents; sibutramine, gastrointestinal lipase inhibitors (such as orlistat), and leptins. Other agents used in treating obesity or obesity-related disorders include neuropeptide Y, enterostatin, cholecytokinin, bombesin, amylin, histamine H$_3$ receptors, dopamine D$_2$ receptors, melanocyte stimulating hormone, corticotrophin releasing factor, galanin and gamma amino butyric acid (GABA).

The following examples are offered by way of illustration and not by way of limitation.

Starting materials in the synthesis examples below are either available from commercial sources or via literature procedures. All commercially available compounds were used without further purification unless otherwise indicated. CDCl$_3$ (99.8% D, Cambridge Isotope Laboratories) was used in all experiments as indicated. $^1$H NMR spectra were recorded on a Bruker Avance 400 MHz NMR spectrometer. Significant peaks are tabulated and typically include: number of protons, multiplicity (s, singlet; d, double; t, triplet; q, quartet; m, multiplet; br s, broad singlet) and coupling constant(s) in Hertz. Chemical shifts are reported as parts per million (δ) relative to tetramethylsilane. Electron Ionization (EI) mass spectra were recorded on a Perkin-Elmer SCIEX HPLC/MS instrument using reverse-phase conditions (acetonitrile/water, 0.05% trifluoroacetic acid). Abbreviations used in the examples below have their accepted meanings in the chemical literature. For example, CH$_2$Cl$_2$ (dichloromethane), C$_6$H$_6$ (benzene), TFA (trifloroacetic acid), EtOAc (Ethyl Acetate), Et$_2$O (diethyl ether), DMAP (4-dimethylaminopyridine), DMF (N,N-dimethylformamide) and THF (tetrahydrofuran). Flash chromatography was performed using Merck Silica Gel 60 (230-400 mesh) according to Still et. al.[1]

Example 1

This example illustrates the preparation of compound 1.

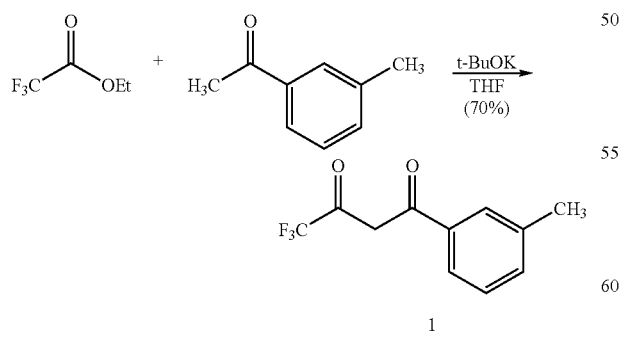

1

Potassium tert-butoxide (3.3 g, 28 mmoles, 95% powder) was slowly added to a solution of 3-methylacetophenone (3.2 mL, 23.5 mmoles) in anhydrous THF at 0° C. under nitrogen. The vigorously stirred mixture was allowed to warm to ambient temperature and was stirred at this temperature for 15 min. After this period the mix was chilled to 0° C. and to it was added ethyl trifluoroacetate (3.4 mL, 28.6 mmoles). The stirring mixture was next allowed the warm to ambient temp and was stirred for 12 hours. After this period the reaction was evaporated in vacuo (-THF) and the resulting residue was combined with 30 mL of water. 10% sulfuric acid was carefully added to the stirring mixture to adjust the to pH 6-7 (as indicated using EM Science colorpHast indicator strips, pH 0-14). The mixture was then extracted with Et$_2$O (3×15 mL). The combined ether layer was next washed with water (2×15 mL) and brine (15 mL). After drying the ether layer over anhydrous Na$_2$SO$_4$ the solution was evaporated in vacuo to yield the crude product as a yellow liquid. The product was purified via vacuum fractional distillation to yield 3.7 g (70% yield) of product as a clear liquid. B.P. 64° C. @ 0.05 mmHg.

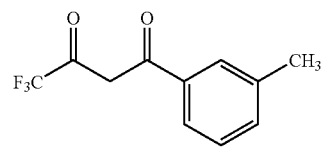

1

4,4,4-Trifluoro-1-m-tolyl-butane-1,3-dione $^1$H-NMR (CDCl$_3$): δ15.16 (bs, 1H), 7.76 (s, 1H), 7.74 (d, J=7.2 Hz, 1H), 7.45-7.38 (m, 2H), 6.56 (s, 1H), 2.44 (s, 3H).

The following compounds were prepared in a manner similar to that described above.

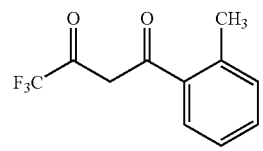

1.1

$^1$H-NMR (CDCl$_3$): δ15.0 (br, 1H), 7.60 (m, 1H), 7.47 (m, 1H), 7.33 (m, 2H), 6.36 (s, 1H), 2.57 (s, 3H).

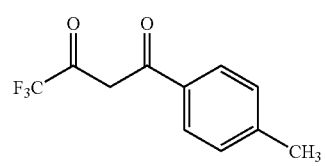

1.2

$^1$H-NMR (CDCl$_3$): δ15.1 (br, 1H), 7.83 (d, J=8.2 Hz, 2H), 7.29 (d, J=8.2 Hz, 2H), 6.52 (s, 1H), 2.43 (s, 3H).

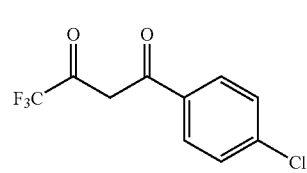

1.3

¹H-NMR (CDCl₃): δ14.8 (br, 1H), 7.71 (d, J=8.6 Hz, 2H), 7.33 (d, J=8.6 Hz, 2H), 6.30 (s, 1H).

1.4

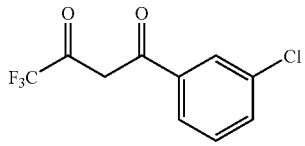

¹H-NMR (CDCl₃): δ14.7 (br, 1H), 7.90 (m, 1H), 7.80 (d, J=8.0 Hz, 1H), 7.57 (d, J=8.0 Hz, 1H), 7.44 (m, 1H), 6.52 (s, 1H).

1.5

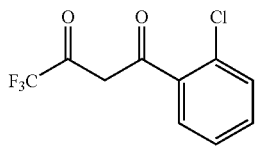

¹H-NMR (CDCl₃): δ14.4 (br, 1H), 7.68 (m, 1H), 7.48 (m, 1H), 7.47 (m, 1H), 7.39 (m, 1H), 6.56 (s, 1H).

1.6

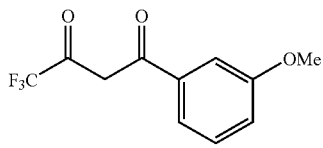

¹H-NMR (CDCl₃): δ15.09 (br, 1H), 7.51 (m, 1H), 7.46 (m, 1H), 7.41 (m, 1H), 7.16 (m, 1H), 6.56 (s, 1H), 3.88 (s, 3H).

1.7

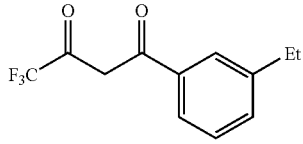

¹H-NMR (CDCl₃): δ15.18 (br, 1H), 7.77 (m, 1H), 7.75 (m, 1H), 7.46 (m, 1H), 7.43 (m, 1H), 6.57 (s, 1H), 2.73 (q, J=7.7 Hz, 2H), 1.28 (t, J=7.7 Hz, 3H).

1.8

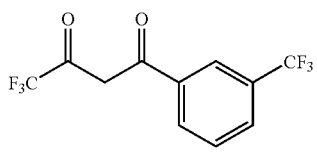

¹H-NMR (CDCl₃): δ14.89 (br, 1H), 8.19 (s, 1H), 8.13 (d, J=8.1, 1H), 7.88 (d, J=8.3 Hz, 1H), 7.67 (m, 1H), 6.60 (s, 1H).

1.9

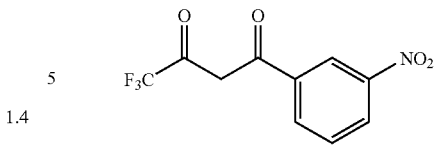

¹H-NMR (CDCl₃): δ14.75 (br, 1H), 8.78 (m, 1H), 8.48 (m, 1H), 8.29 (m, 1H), 7.76 (t, J=8 Hz, 1H), 6.66 (s, 1H).

1.10

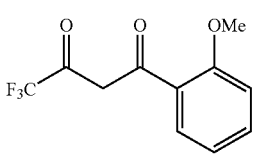

¹H-NMR (CDCl₃): δ15.25 (br, 1H), 8.0 (m, 1H), 7.56 (m, 1H), 7.10 (m, 1H), 7.02 (m, 1H), 3.98 (s, 3H).

1.11

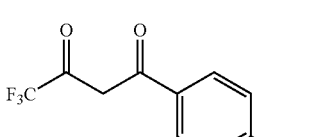

¹H-NMR (CDCl₃): δ15.4 (br, 1H), 7.92 (d, J=8.8 Hz, 2H), 6.97 (d, J=8.8 Hz, 2H), 6.48 (s, 1H), 3.89 (s, 3H).

1.12

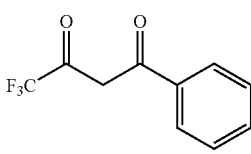

1-(4-Bromo-phenyl)-4,4,4-trifluoro-butane-1,3-dione

³¹H-NMR (CDCl₃): δ15.0 (s, 1H), 7.82 (d, J=8.6 Hz, 2H), 7.66 (d, J=8.6 Hz, 2H), 6.54 (s, 1H).

1.13

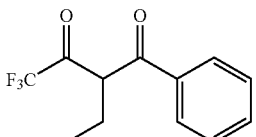

2-Ethyl-4,4,4-trifluoro-1-phenyl-butane-1,3-dione

¹H-NMR (CDCl₃): δ8.05 (bd, J'=8.1 Hz, 2H), 7.55 (tt, J'=7.6 Hz, J"=1.3 Hz, 1H), 7.45 (bt, J=7.3 hz, 2H), 4.38 (q, J=7.1 Hz, 2H), 1.4 (t, J=7.1 Hz, 3H).

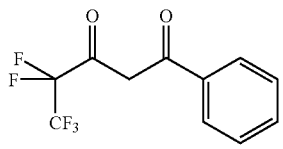

1.14

4,4,5,5,5-Pentafluoro-1-phenyl-pentane-1,3-dione $^1$H-NMR (CDCl$_3$): δ15.32 (bs, 1H), 7.99-7.94 (m, 2H), 7.64 (m, 1H), 7.55-7.48 (m, 2H), 6.64 (s, 1H).

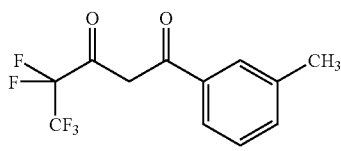

1.15

4,4,5,5,5-Pentafluoro-1-m-tolyl-pentane-1,3-dione $^1$H-NMR (CDCl$_3$): δ15.35 (bs, 1H), 7.79-7.73 (m, 2H), 7.47-7.36 (m, 2H), 6.63 (s, 1H), 2.44 (s, 3H).

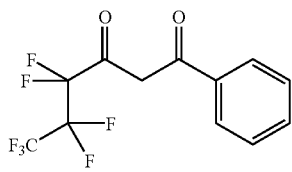

1.16

4,4,5,5,6,6,6-Heptafluoro-1-phenyl-hexane-1,3-dione $^1$H-NMR (CDCl$_3$): δ15.33 (bs, 1H), 7.99-7.94 (m, 2H), 7.67-7.61 (m, 1H), 7.55-7.50 (m, 2H), 6.62 (s, 1H),

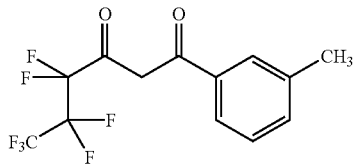

1.17

4,4,5,5,6,6,6-Heptafluoro-1-m-tolyl-hexane-1,3-dione $^1$H-NMR (CDCl$_3$): δ15.33 (bs, 1H), 7.79-7.73 (m, 2H), 7.47-7.36 (m, 2H), 6.61 (s, 1H), 2.45 (s, 3H).

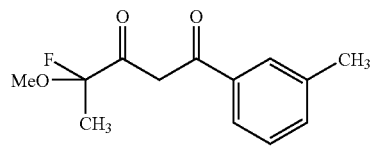

1.18

4-Fluoro-4-methoxy-1-m-tolyl-pentane-1,3-dione $^1$H-NMR (CDCl$_3$): δ15.65 (s, 1H), 7.79-7.74 (m, 2H), 7.45-7.36 (m, 2H), 6.68 (d, J=2.0 Hz, 1H), 3.61 (s, 3H), 2.44 (s, 3H).

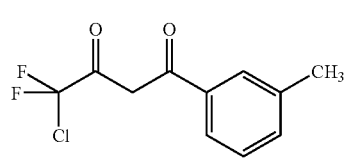

1.19

4-Chloro-4,4-difluoro-1-m-tolyl-butane-1,3-dione $^1$H-NMR (CDCl$_3$): δ14.95 (s, 1H), 7.76-7.71 (m, 2H), 7.45-7.36 (m, 2H), 6.52 (s, 1H), 2.44 (s, 3H).

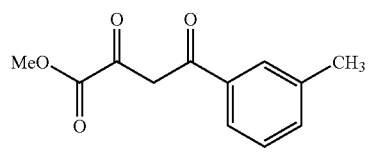

1.20

2,4-Dioxo-4-m-tolyl-butyric Acid Methyl Ester $^1$H-NMR (CDCl$_3$): δ15.3 (s, 1H), 7.83-7.78 (m, 2H), 7.45-7.36 (m, 2H), 7.08 (s, 1H) 3.95 (s, 3H), 2.44 (s, 3H).

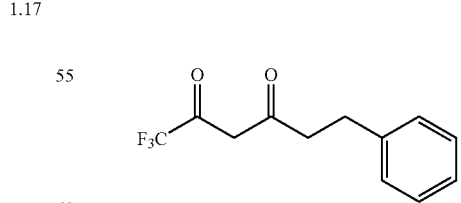

1.21

1,1,1-Trifluoro-6-phenyl-hexane-2,4-dione $^1$H-NMR (CDCl$_3$): δ14.3 (s, 1H), 7.34-7.15 (m, 5H), 5.89 (s, 1H), 2.98 (t, 8.1 Hz, 2H), 2.76 (t, J=7.6 Hz, 2H).

89

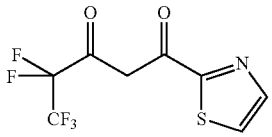

1.22

4,4,5,5,5-Pentafluoro-1-thiazol-2-yl-pentane-1,3-dione $^1$H-NMR (CDCl$_3$): δ14.3 (bs, 1H), 8.09 (d, J=3.0 Hz, 1H), 7.80 (d, J=3.0 Hz, 1H), 7.04 (bs, 1H).

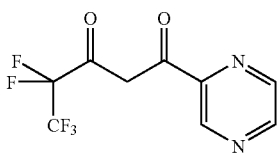

1.23

4,4,5,5,5-Pentafluoro-1-pyrazin-2-yl-pentane-1,3-dione $^1$H-NMR (CDCl$_3$): δ14.5 (bs, 1H), 9.34 (d, J=1.3 Hz, 1H), 8.81 (d, J=2.3 Hz, 1H), 8.71 (dd, J'=2.3 Hz, J"=1.3 Hz, 1H), 7.32 (s, 1H).

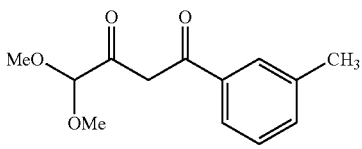

1.24

4,4-Dimethoxy-1-m-tolyl-butane-1,3-dione $^1$H-NMR (CDCl$_3$): δ15.8 (s, 1H), 7.75 (s, 2H), 7.36 (m, 3H), 6.56 (s, 1H), 4.83 (s, 1H), 3.45 (s, 3H).

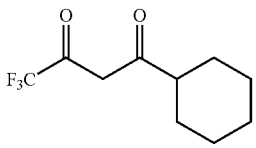

1.27

1-Cyclohexyl-4,4,4-trifluoro-butane-1,3-dione $^1$H-NMR (CDCl$_3$): δ5.92 (s, 1H), 2.33 (tt, J'=3.3 Hz, J"=11.4 Hz, 1H), 1.94-1.63 (m, 5H), 1.47-1.16 (m, 5H).

90

Example 2

This example illustrates the preparation of compound 2.

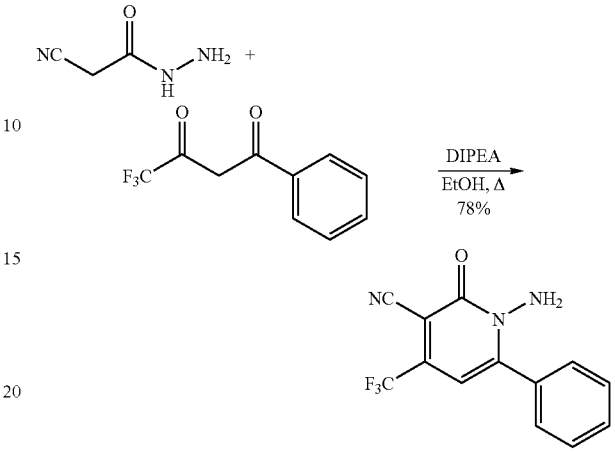

4,4,4-Trifluoro-1-phenyl-1,3-butanedione (2.0 g, 9.25 mmoles) and cyanoacetohydrazide (0.92 g, 9.28 mmoles) were combined within a round-bottom flask.

The mixture was dissolved into 30 mL of ethanol and the flask was equipped with a reflux condensor. To the stirring solution was added diisopropylethylamine (0.81 mL, 4.7 mmoles) and the mixture was stirred at 80° C. for 3 hours. After this period the mixture was evaporated and the resulting crude mixture was purified directly by flash silica chromatography using 30% EtOAc/Hexane to yield product 2.01 g (78% yield) as a yellow solid.

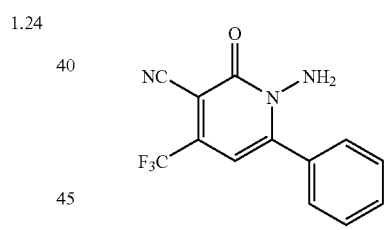

2

1-Amino-2-oxo-6-phenyl-4-trifluoromethyl-1,2-dihydro-pyridine-3-carbonitrile $^1$H-NMR (CDCl$_3$): δ7.63-7.54 (m, 5H), 6.53 (s, 1H), 5.68 (s, 2H). MS (ES+): 280.0 (M+H).

The following compounds were prepared in a manner similar to that described above.

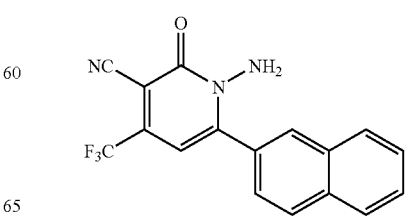

2.1

1-Amino-6-naphthalen-2-yl-2-oxo-4-trifluoromethyl-1,2-dihydro-pyridine-3-carbonitrile $^1$H-NMR (CDCl$_3$): δ8.03 (s, 1H), 7.93 (d, J=8.6 Hz, 1H), 7.89-7.85 (m, 2H), 7.62-7.52 (m, 3H), 6.56 (s, 1H), 5.67 (s, 2H).

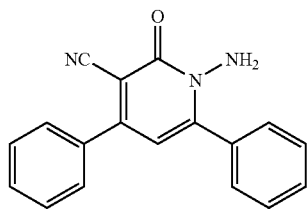

1-Amino-2-oxo-4,6-diphenyl-1,2-dihydro-pyridine-3-carbonitrile $^1$H-NMR (CDCl$_3$): δ7.65-7.58 (m, 4H), 7.56-7.46 (m, 6H), 6.38 (s, 1H), 5.40 (s, 2H). MS (ES+):288.0 (M+H)

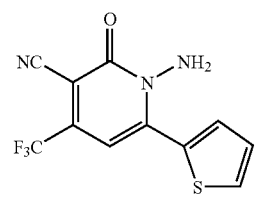

1-Amino-2-oxo-6-thiophen-2-yl-4-trifluoromethyl-1,2-dihydro-pyridine-3-carbonitrile $^1$H-NMR (CDCl$_3$): δ7.95 (m, 1H), 7.79 (m, 1H), 7.26 (m, 1H), 6.91 (s, 1H), 5.47 (s, 2H). MS (ES+):286.0 (M+H)

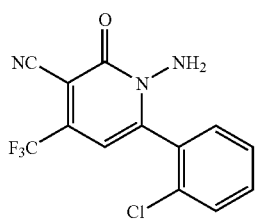

$^1$H-NMR (CDCl$_3$): δ7.57 (m, 1H), 7.56 (m, 1H), 7.49 (m, 1H), 7.39 (m, 1H), 6.50 (s, 1H), 5.54 (s, 2H).

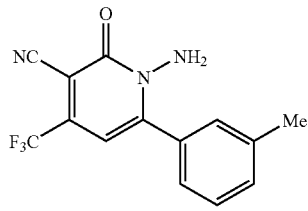

$^1$H-NMR (CDCl$_3$): δ7.46-7.37 (m, 4H), 6.52 (s, 1H), 5.81 (s, 2H), 2.45 (s, 3H).

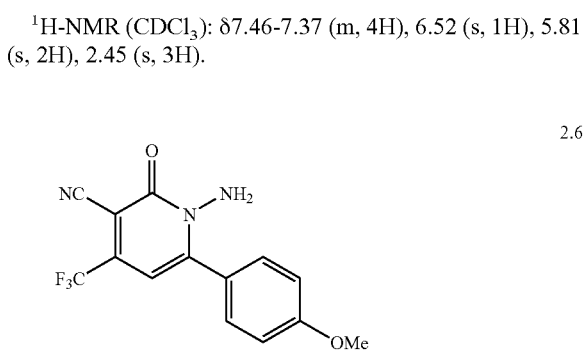

$^1$H-NMR (CDCl$_3$): δ7.64 (d, J=9.0 Hz, 2H), 7.05 (d, J=9.0 Hz, 2H), 6.51 (s, 1H), 5.78 (s, 2H), 3.90 (s, 3H).

Example 3

This example illustrates the preparation of compound 3.

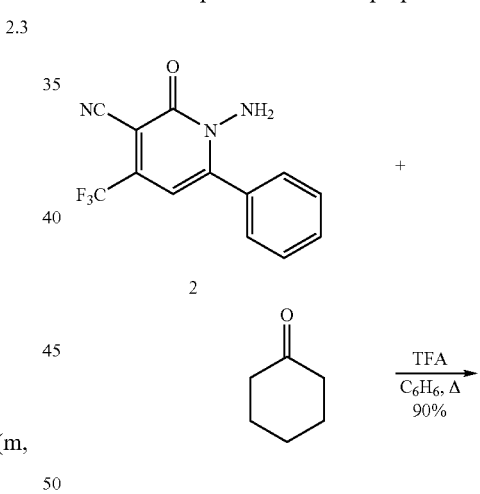

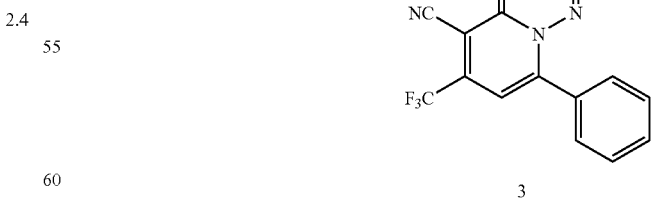

N-Aminopyridone 2 (70 mg, 0.25 mmoles) was dissolved into 3.0 mL of benzene within a screw capped vial. To this solution was added cyclohexanone 0.4 mL, 3.9 mmoles) and 2 μL of trifluoroacetic acid. The sealed reaction was then shaken at 85° C. for 2 hours. After this period the reaction mixture was evaporated in vacuo and the resulting residue was combined with DCM. The DCM solution was washed with saturated NaHCO₃ (2×10 mL), dried over anhydrous Na₂SO₄, and was evaporated to yield the crude product. The crude product was purified using flash silica chromatography (30% EtOAc/Hexane) to yield 82 mg (90% yield) of product as a yellow residue.

(*—DCM may be used as an alternative with heating at 50° C.)

3

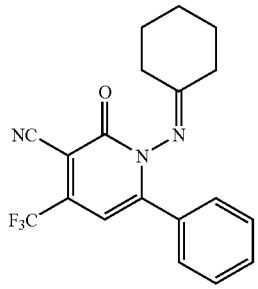

$^1$H-NMR (CDCl₃): δ7.53-7.45 (m, 3H), 7.41-7.39 (m, 2H), 6.50 (s, 1H), 2.47-2.44 (m, 1H), 2.39-2.34 (m, 1H), 2.20-2.14 (m, 1H), 2.07-2.02 (m, 1H), 1.88-1.85 (m, 2H), 1.60-1.55 (m, 2H), 1.44-1.42 (m, 1H), 1.35-1.31 (m, 1H). MS (ES+): 360.0 (M+H)

The following compounds were prepared in a manner similar to that described above.

3.1

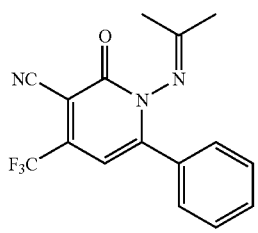

$^1$H-NMR (CDCl₃): δ7.52-7.47 (m, 3H), 7.40-7.37 (m, 2H), 6.50 (s, 1H), 2.12 (s, 3H), 1.85 (s, 3H). MS (ES+): 320.0 (M+H).

3.2

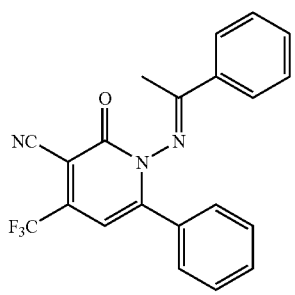

$^1$H-NMR (CDCl₃): δ7.68 (dd, J'=8.4 Hz, J"=1.2 Hz, 2H), 7.49-7.43 (m, 6H), 7.38 (t, J=8 Hz, 2H), 6.58 (s, 1H), 2.27 (s, 3H). MS (ES+): 382.0 (M+H).

3.3

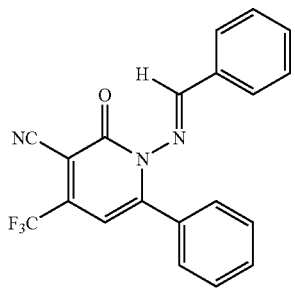

1-(Benzylidene-amino)-2-oxo-6-phenyl-4-trifluoromethyl-1,2-dihydro-pyridine-3-carbonitrile $^1$H-NMR (CDCl₃): δ8.97 (s, 1H), 7.66 (dd, J'=7.6 Hz, J"=0.8 Hz, 2H), 7.54-7.41 (m, 8H), 6.57 (s, 1H). MS (ES+): 368.0 (M+H).

3.4

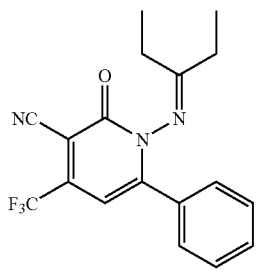

1-(1-Ethyl-propylideneamino)-2-oxo-6-phenyl-4-trifluoromethyl-1,2-dihydro-pyridine-3-carbonitrile $^1$H-NMR (CDCl₃): δ7.52-7.41 (m, 5H), 6.49 (s, 1H), 2.52-2.44 (m, 1H), 2.38-2.31 (m, 1H), 2.18-2.10 (m, 1H), 2.01-1.92 (m, 1H), 1.02-0.97 (m, 6H). MS (ES+): 348.0 (M+H).

3.5

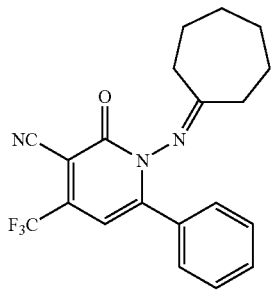

1-Cycloheptylideneamino-2-oxo-6-phenyl-4-trifluoromethyl-1,2-dihydro-pyridine-3-carbonitrile $^1$H-NMR (CDCl₃): δ7.54-7.44 (m, 5H), 6.49 (s, 1H), 2.62-2.54 (m, 2h), 2.45-2.39 (m, 1H), 2.08-2.00 (m, 1H), 1.75-1.45 (m, 6H), 1.12-1.06 (m, 2H). MS (ES+): 374.0 (M+H).

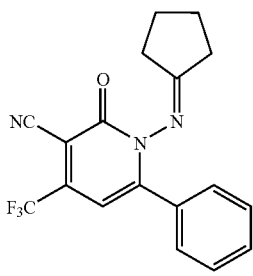

1-Cyclopentylideneamino-2-oxo-6-phenyl-4-trifluoromethyl-1,2-dihydro-pyridine-3-carbonitrile ¹H-NMR (CDCl₃): δ7.54-7.45 (m, 3H), 7.40 (dd, J'=8 Hz, J"=1.2 Hz, 2H), 2.85-2.0 (m, 8H). MS (ES+): 346.0 (M+H).

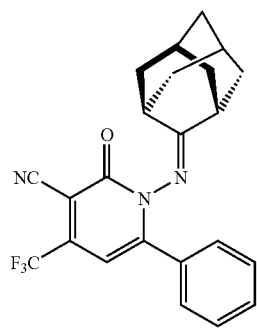

1-(Adamantan-2-ylideneamino)-2-oxo-6-phenyl-4-trifluoromethyl-1,2-dihydro-pyridine-3-carbonitrile ¹H-NMR (CDCl₃): δ7.53-7.45 (m, 5H), 6.49 (s, 1H), 2.82 (bs, 1H), 2.37 (bs, 1H), 2.21 (d, J=12.5 Hz, 1H), 2.14 (d, J=12.8 Hz, 1H), 2.03-1.99 (m, 2H), 1.90-1.76 (m, 6H), 1.25 (d, J=12.8 Hz, 1H), 1.08 (d, J=12.5 Hz, 1H). MS (ES+): 412.2 (M+H).

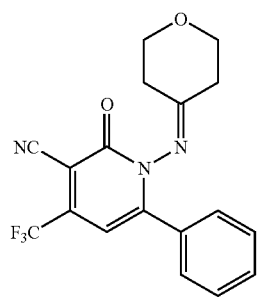

¹H-NMR (CDCl₃): δ7.56-7.47 (m, 3H), 7.40-7.37 (m, 2H), 6.52 (s, 1H), 3.95-3.89 (m, 2H), 3.69-3.65 (m, 1H), 3.58-3.54 (m, 1H), 2.68-2.63 (m, 1H), 2.47-2.35 (m, 2H), 2.16-2.12 (m, 1H). MS (ES+): 261.8 (M+H).

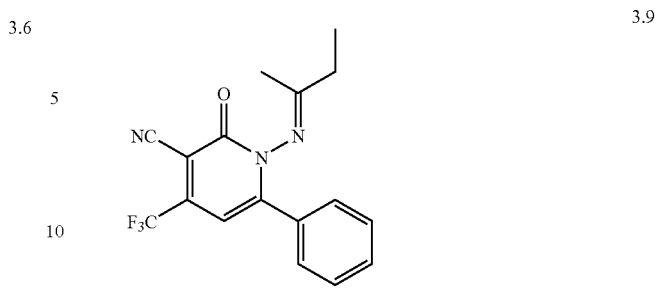

¹H-NMR (CDCl₃): δ7.51-7.44 (m, 3H), 7.42-7.38 (2H), 6.50 (s, 1H), 2.55-2.45 (m, 1H), 2.40-2.25 (m, 1H), 1.81 (s, 3H), 1.01 (t, J=7.6 Hz, 3H). MS (ES+): 334.2 (M+H).

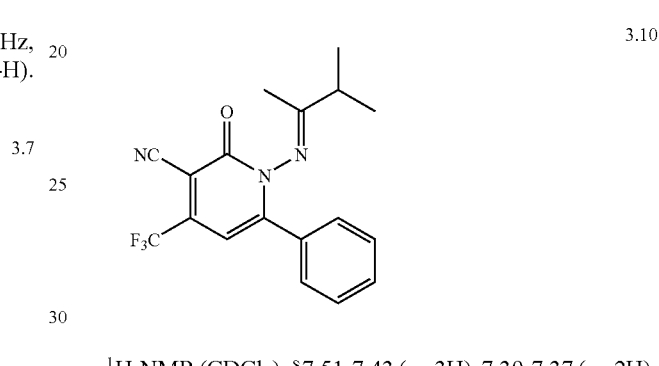

¹H-NMR (CDCl₃): δ7.51-7.43 (m, 3H), 7.39-7.37 (m, 2H), 6.50 (s, 1H), 2.63 (m, J=6.9 Hz, 1H), 1.78 (s, 3H), 1.04 (d, J=6.9 Hz, 3H), 1.00 (d, J=6.9 Hz, 3H).

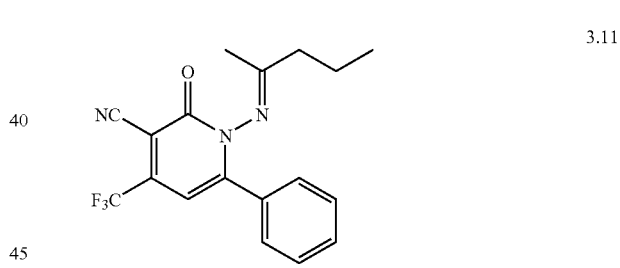

¹H-NMR (CDCl₃): δ7.52-7.44 (m, 3H), 7.40-7.37 (m, 2H), 6.50 (s, 1H), 2.40-2.30 (m, 2H), 1.81 (s, 3H), 1.53-1.45 (m, 2H), 0.80 (t, J=7.4 hz, 3H).

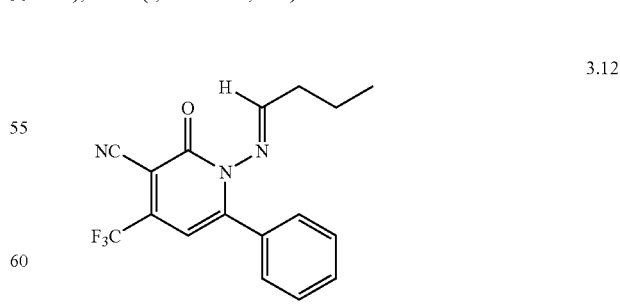

¹H-NMR (CDCl₃): δ8.16 (t, J=5.4 Hz, 1H), 7.53-7.45 (m, 3H), 7.42-7.38 (m, 2H), 6.48 (s, 1H), 2.47-2.42 (m, 2H), 1.61-1.52 (m, 2H), 0.89 (t, J=7.4 Hz, 3H). MS (ES+): 334.2 (M+H).

3.13

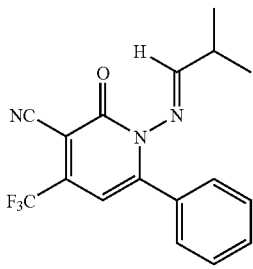

¹H-NMR (CDCl₃): δ8.07 (d, J=5.2 Hz, 1H), 7.51-7.45 (m, 3H), 7.41-7.38 (m, 2H), 6.49 (s, 1H), 2.78-2.65 (m, 1H), 1.09 (d, J=6.8 Hz, 6H).

3.14

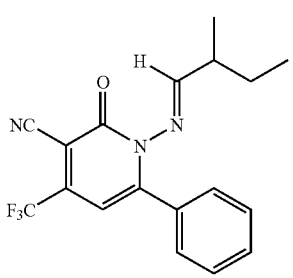

1-(2-Methyl-butylideneamino)-2-oxo-6-phenyl-4-trifluoromethyl-1,2-dihydro-pyridine-3-carbonitrile ¹H-NMR (CDCl₃): δ8.01 (d, J=6.2 Hz, 1H), 7.53-7.44 (m, 3H), 7.42-7.39 (m, 2H), 6.48 (s, 1H), 2.53-2.44 (m, J=6.8 Hz, 1H), 1.53-1.40 (m, 2H), 1.06 (d, J=6.8 Hz, 3H), 0.86 (t, J=7.5 Hz, 3H).

3.15

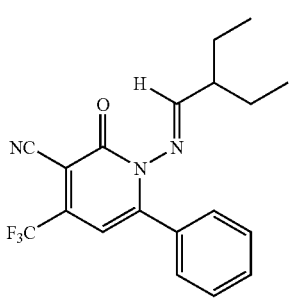

1-(2-Ethyl-butylideneamino)-2-oxo-6-phenyl-4-trifluoromethyl-1,2-dihydro-pyridine-3-carbonitrile ¹H-NMR (CDCl₃): δ7.92 (d, J=7.4 Hz, 1H), 7.52-7.40 (m, 5H), 6.47 (s, 1H), 2.29-2.23 (m, 1H), 1.57-1.44 (m, 4H), 0.81 (t, J=7.4, 6H). MS (ES+): 362.0 (M+H).

3.16

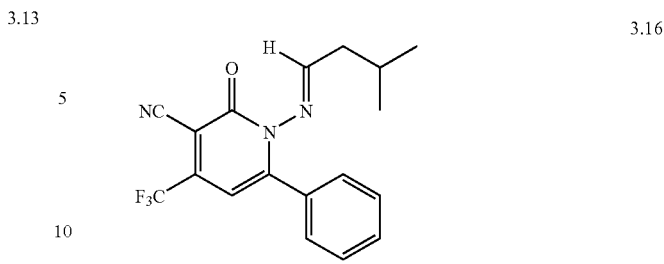

1-(3-Methyl-butylideneamino)-2-oxo-6-phenyl-4-trifluoromethyl-1,2-dihydro-pyridine-3-carbonitrile ¹H-NMR (CDCl₃): δ8.15 (t, J=5.9 Hz, 1H), 7.53-7.44 (m, 3H), 7.42-7.39 (m, 2H), 6.48 (s, 1H), 2.34 (t, J=5.9 Hz, 2H), 1.96 (m, J=6.7 Hz, 1H), 0.91 (d, J=6.7 Hz, 6H).

3.17

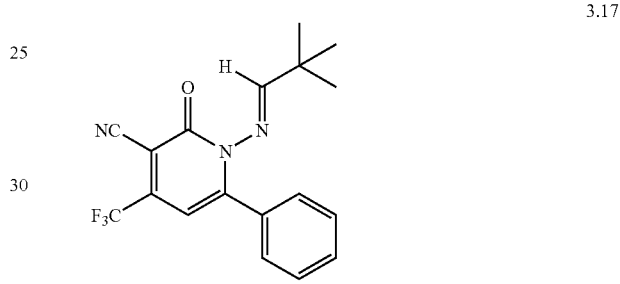

1-(2,2-Dimethyl-propylideneamino)-2-oxo-6-phenyl-4-trifluoromethyl-1,2-dihydro-pyridine-3-carbonitrile ¹H-NMR (CDCl₃): δ8.03 (s, 1H), 7.51-7.44 (m, 3H), 7.40-7.38 (m, 2H), 6.49 (s, 1H), 1.08 (s, 9H). MS (ES+): 348.0 (M+H).

3.18

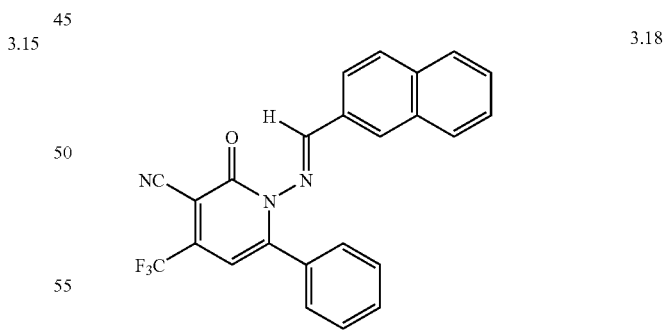

1-[(Naphthalen-2-ylmethylene)-amino]-2-oxo-6-phenyl-4-trifluoromethyl-1,2-dihydro-pyridine-3-carbonitrile ¹H-NMR (CDCl₃): δ9.12 (s, 1H), 8.09 (s, 1H), 7.91-7.74 (m, 4H), 7.62-7.44 (m, 7H), 6.59 (s, 1H). MS (ES+): 418.0 (M+H).

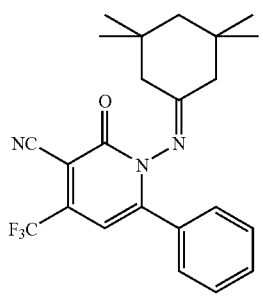

2-Oxo-6-phenyl-1-(3,3,5,5-tetramethyl-cyclohexylideneamino)-4-trifluoromethyl-1,2-dihydro-pyridine-3-carbonitrile

MS(ES+): 416.0 (M+H)

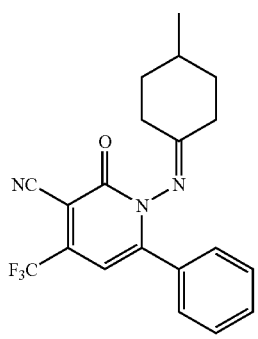

1-(4-Methyl-cyclohexylideneamino)-2-oxo-6-phenyl-4-trifluoromethyl-1,2-dihydro-pyridine-3-carbonitrile

MS(ES+): 374.0 (M+H)

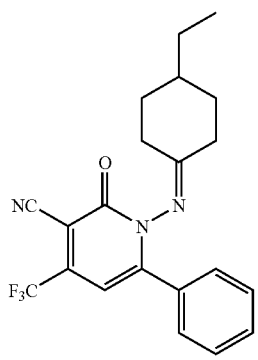

1-(4-Ethyl-cyclohexylideneamino)-2-oxo-6-phenyl-4-trifluoromethyl-1,2-dihydro-pyridine-3-carbonitrile

MS(ES+): 388.0 (M+H)

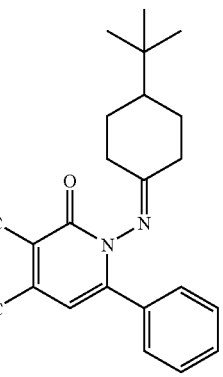

1-(4-tert-Butyl-cyclohexylideneamino)-2-oxo-6-phenyl-4-trifluoromethyl-1,2-dihydro-pyridine-3-carbonitrile

MS(ES+): 416.2 (M+H)

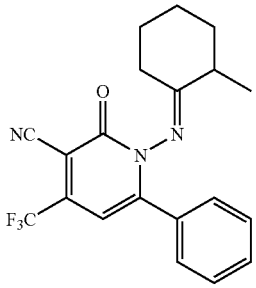

1-(2-Methyl-cyclohexylideneamino)-2-oxo-6-phenyl-4-trifluoromethyl-1,2-dihydro-pyridine-3-carbonitrile

MS(ES+): 374.0 (M+H)

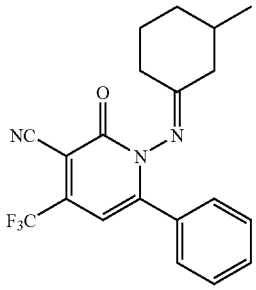

101

1-(3-Methyl-cyclohexylideneamino)-2-oxo-6-phenyl-4-trifluoromethyl-1,2-dihydro-pyridine-3-carbonitrile

MS(ES+): 374.0 (M+H)

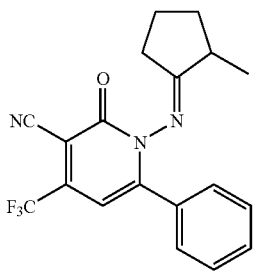

3.26

1-(2-Methyl-cyclopentylideneamino)-2-oxo-6-phenyl-4-trifluoromethyl-1,2-dihydro-pyridine-3-carbonitrile

MS(ES+): 30.0 (M+H)

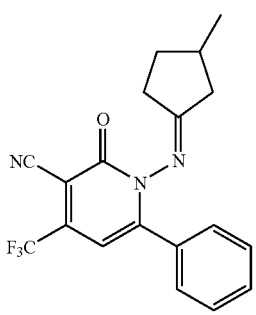

3.27

1-(3-Methyl-cyclopentylideneamino)-2-oxo-6-phenyl-4-trifluoromethyl-1,2-dihydro-pyridine-3-carbonitrile

MS(ES+): 360.0 (M+H)

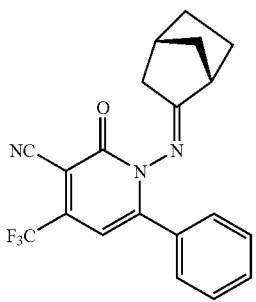

3.28

102

1-(Bicyclo[2.2.1]hept-2-ylideneamino)-2-oxo-6-phenyl-4-trifluoromethyl-1,2-dihydro-pyridine-3-carbonitrile

MS(ES+): 372.0 (M+H)

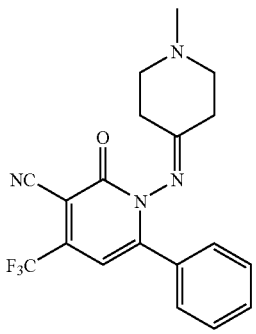

3.29

1-(1-Methyl-piperidin-4-ylideneamino)-2-oxo-6-phenyl-4-trifluoromethyl-1,2-dihydro-pyridine-3-carbonitrile

MS(ES+): 375.0 (M+H)

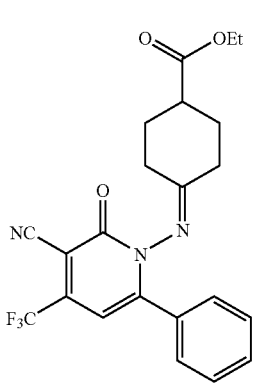

3.30

4-(3-Cyano-2-oxo-6-phenyl-4-trifluoromethyl-2H-pyridin-1-ylimino)-cyclohexanecarboxylic Acid Ethyl Ester

MS(ES+): 432.2 (M+H)

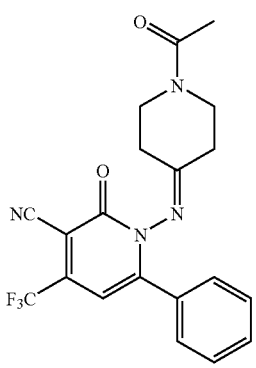

3.32

103

1-(1-Acetyl-piperidin-4-ylideneamino)-2-oxo-6-phenyl-4-trifluoromethyl-1,2-dihydro-pyridine-3-carbonitrile

MS(ES+): 403.0 (M+H)

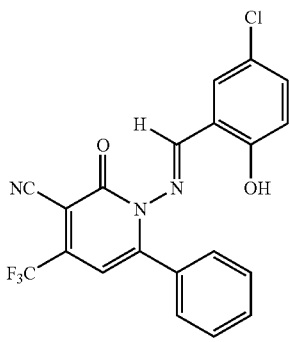

1-[(5-Chloro-2-hydroxy-benzylidene)-amino]-2-oxo-6-phenyl-4-trifluoromethyl-1,2-dihydro-pyridine-3-carbonitrile

MS(ES+): 418.0 (M+H)

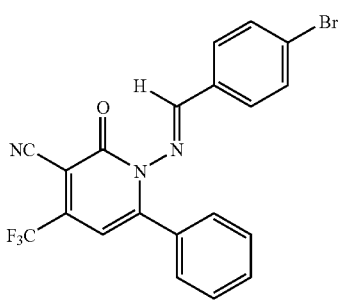

1-[(4-Bromo-benzylidene)-amino]-2-oxo-6-phenyl-4-trifluoromethyl-1,2-dihydro-pyridine-3-carbonitrile

MS(ES+): 446.0 (M+H)

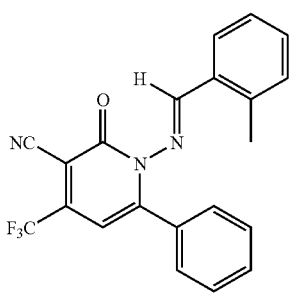

104

1-[(2-Methyl-benzylidene)-amino]-2-oxo-6-phenyl-4-trifluoromethyl-1,2-dihydro-pyridine-3-carbonitrile

MS(ES+): 382.2 (M+H)

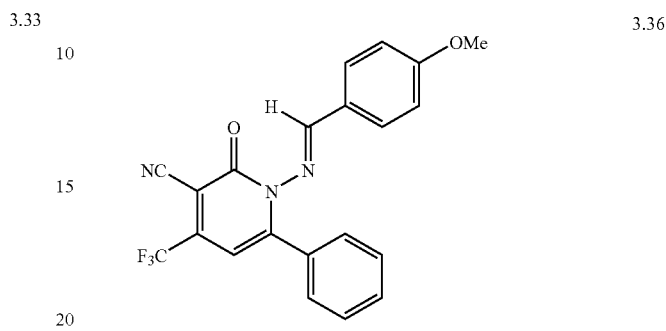

1-[(4-Methoxy-benzylidene)-amino]-2-oxo-6-phenyl-4-trifluoromethyl-1,2-dihydro-pyridine-3-carbonitrile

MS(ES+): 398.0 (M+H)

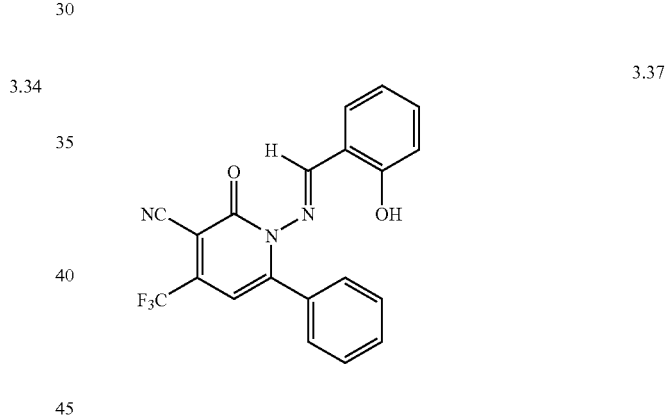

1-[(2-Hydroxy-benzylidene)-amino]-2-oxo-6-phenyl-4-trifluoromethyl-1,2-dihydro-pyridine-3-carbonitrile

MS(ES+): 384.0 (M+H)

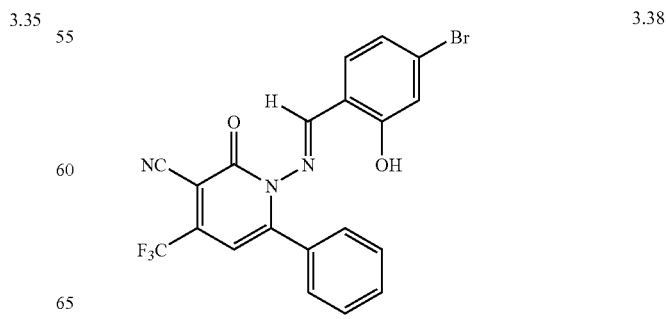

105

1-[(4-Bromo-2-hydroxy-benzylidene)-amino]-2-oxo-6-phenyl-4-trifluoromethyl-1,2-dihydro-pyridine-3-carbonitrile

MS(ES+): 462.0 (M+H)

3.39

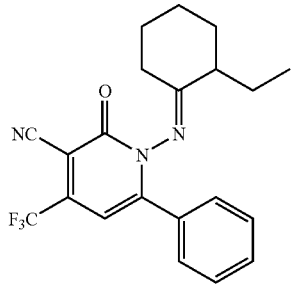

1-(2-Ethyl-cyclohexylideneamino)-2-oxo-6-phenyl-4-trifluoromethyl-1,2-dihydro-pyridine-3-carbonitrile

MS(ES+): 388.0 (M+H)

3.40

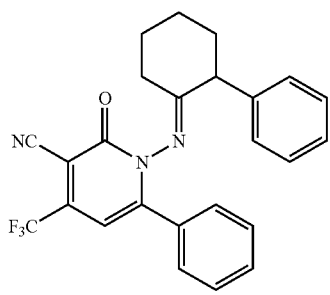

2-Oxo-6-phenyl-1-(2-phenyl-cyclohexylidene-amino)-4-trifluoromethyl-1,2-dihydro-pyridine-3-carbonitrile

MS(ES+): 436.2 (M+H)

3.41

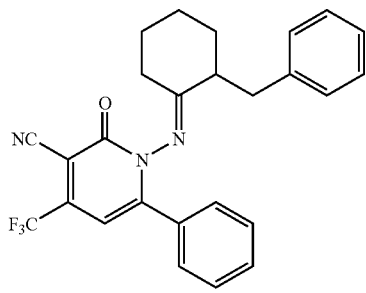

106

1-(2-Benzyl-cyclohexylideneamino)-2-oxo-6-phenyl-4-trifluoromethyl-1,2-dihydro-pyridine-3-carbonitrile

MS(ES+): 450.2 (M+H)

3.42

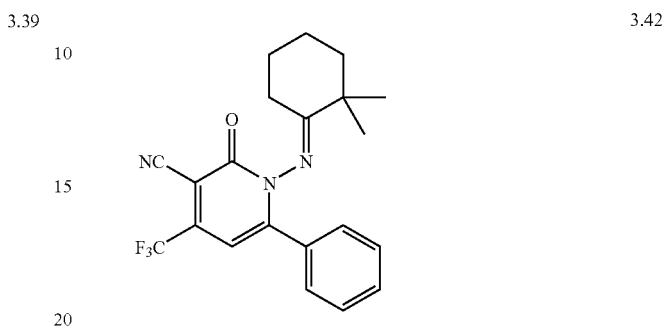

1-(2,2-Dimethyl-cyclohexylideneamino)-2-oxo-6-phenyl-4-trifluoromethyl-1,2-dihydro-pyridine-3-carbonitrile

MS(ES+): 388.0 (M+H)

3.43

1-(2-Chloro-cyclohexylideneamino)-2-oxo-6-phenyl-4-trifluoromethyl-1,2-dihydro-pyridine-3-carbonitrile

MS(ES+): 393.8 (M+H)

3.44

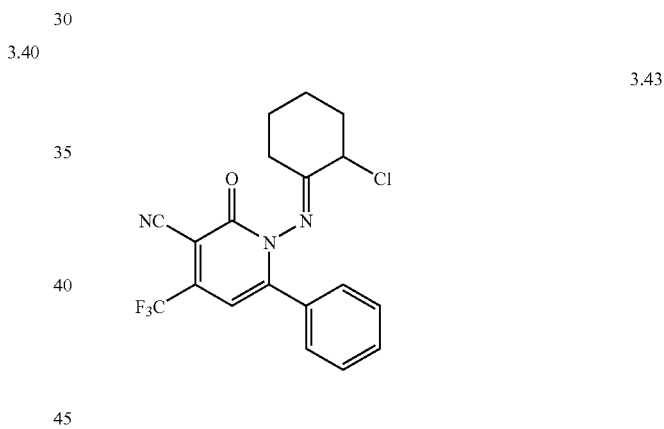

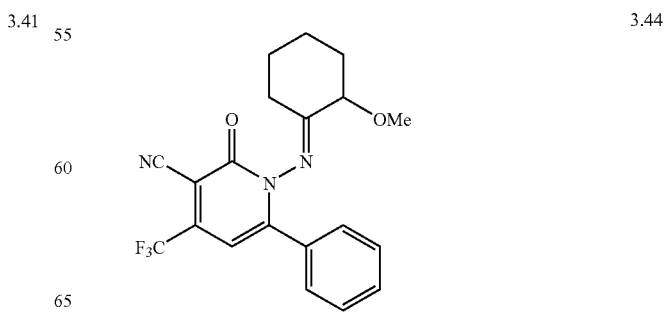

107

1-(2-Methoxy-cyclohexylideneamino)-2-oxo-6-phenyl-4-trifluoromethyl-1,2-dihydro-pyridine-3-carbonitrile

MS(ES+): 390.2 (M+H)

3.45

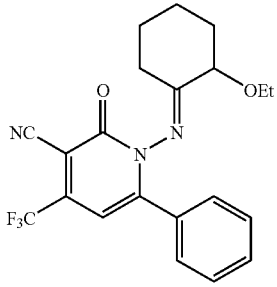

1-(2-Ethoxy-cyclohexylideneamino)-2-oxo-6-phenyl-4-trifluoromethyl-1,2-dihydro-pyridine-3-carbonitrile

MS(ES+): 404.0 (M+H)

3.46

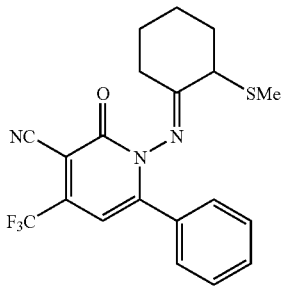

1-(2-Methylsulfanyl-cyclohexylideneamino)-2-oxo-6-phenyl-4-trifluoromethyl-1,2-dihydro-pyridine-3-carbonitrile

MS(ES+): 406.2 (M+H)

3.47

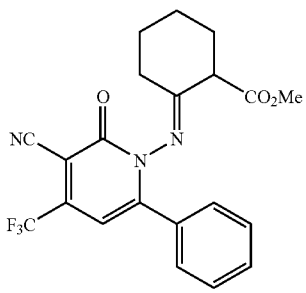

108

2-(3-Cyano-2-oxo-6-phenyl-4-trifluoromethyl-2H-pyridin-1-ylimino)-cyclohexanecarboxylic Acid Methyl Ester

MS(ES+): 418.0 (M+H)

3.48

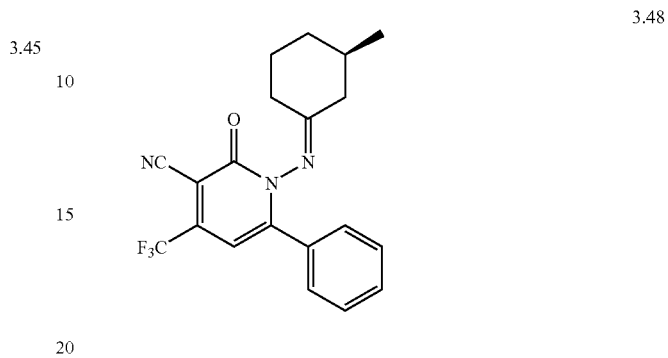

1-(3-Methyl-cyclohexylideneamino)-2-oxo-6-phenyl-4-trifluoromethyl-1,2-dihydro-pyridine-3-carbonitrile

MS(ES+): 374.0 (M+H)

3.49

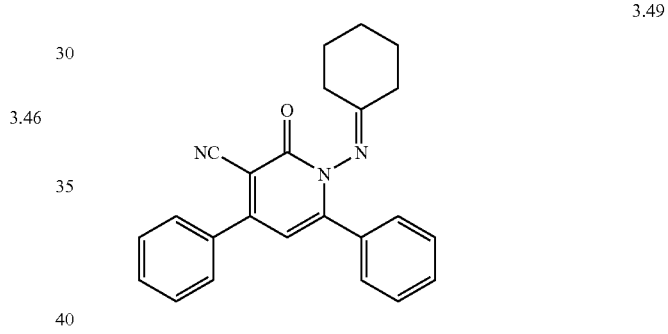

$^1$H-NMR (CDCl$_3$): δ7.60 (m, 2H), 7.44 (m, 4H), 7.36 (m, 4H), 6.30 (s, 1H), 2.40 (m, 1H), 2.30 (m, 1H), 2.16 (m, 1H), 2.10 (m, 1H), 1.80 (m, 2H), 1.63 (m, 1H), 1.53 (m, 1H), 1.32 (m, 1H).

3.50

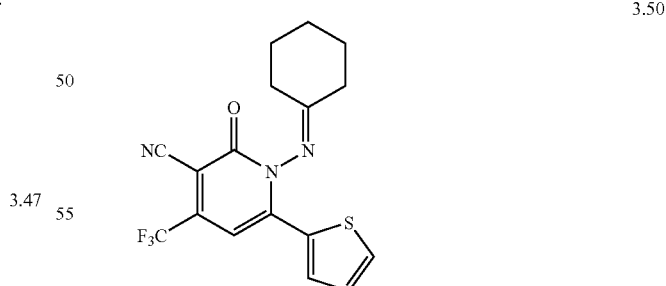

1-Cyclohexylideneamino-2-oxo-6-thiophen-2-yl-4-trifluoromethyl-1,2-dihydro-pyridine-3-carbonitrile

MS (ES+): 366.2 (M+H)

$^1$H-NMR (CDCl$_3$): δ7.77 (m, 2H), 7.74 (m, 1H), 7.21 (m, 1H), 6.89 (s, 1H), 2.72 (m, 2H), 2.23 (m, 1H), 2.10 (m, 1H), 2.03 (m, 1H), 1.87 (m, 2H), 1.68 (m, 2H), 1.44 (m, 1H).

3.51
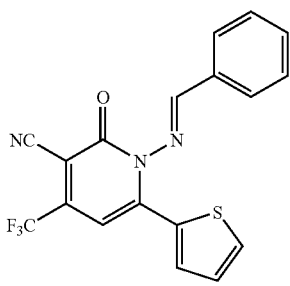
¹H-NMR (CDCl₃): δ8.89 (s, 1H), 7.88 (m, 1H), 7.86 (m, 1H), 7.74 (m, 1H), 7.66 (m, 1H), 7.56 (m, 1H), 7.46 (m, 2H), 7.12 (m, 1H), 6.89 (s, 1H).
3.52
¹H-NMR (CDCl₃): δ7.35 (m, 1H), 7.32 (m, 1H), 7.20 (m, 1H), 7.19 (m, 1H), 6.49 (s, 1H), 2.48 (m, 1H), 2.41 (s, 3H), 2.38 (m, 1H), 2.20 (m, 1H), 2.07 (m, 1H), 1.88 (m, 2H), 1.61 (m, 2H), 1.46 (m, 1H), 1.37 (m, 1H).
3.53
¹H-NMR (CDCl₃): δ7.33 (m, 1H), 7.31 (m, 1H), 7.19 (m, 1H), 7.17 (m, 1H), 6.49 (s, 1H), 2.64 (m, J=6.8 Hz, 1H), 2.40 (s, 3H), 1.79 (s, 3H), 1.06 (d, J=6.8 Hz, 3H), 1.02 (d, J=6.8 Hz, 3H).
3.54
¹H-NMR (CDCl₃): δ7.39 (m, 1H), 7.29 (m, 1H), 7.23 (m, 1H), 6.96 (m, 1H), 6.43 (s, 1H), 2.37 (m, 1H), 2.29 (s, 3H), 2.19 (m, 1H), 2.15 (m, 1H), 2.10 (m, 1H), 1.96 (m, 1H), 1.80 (m, 2H), 1.53 (m, 1H), 1.36 (m, 1H), 1.24 (m, 1H).
3.55
¹H-NMR (CDCl₃): δ7.33-7.24 (m, 4H), 6.48 (s, 1H), 2.49 (m, 1H), 2.42 (s, 3H), 2.38 (m, 1H), 2.19 (m, 1H), 2.04 (m, 1H), 1.87 (m, 2H), 1.59 (m, 2H), 1.49 (m, 1H), 1.36 (m, 1H).
3.56
¹H-NMR (CDCl₃): δ7.47 (m, 1H), 7.16 (m, 1H), 7.05 (m, 1H), 6.95 (m, 1H), 6.45 (s, 1H), 3.79 (s, 3H), 2.40 (m, 1H), 2.22 (m, 2H), 2.06 (m, 1H), 1.91 (m, 1H), 1.81 (m, 1H), 1.58 (m, 2H), 1.46 (m, 2H).

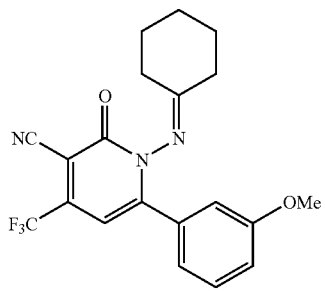
3.57
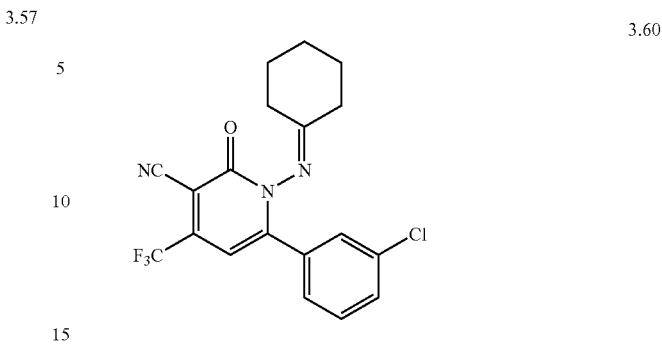
3.60
¹H-NMR (CDCl₃): δ7.37 (m, 1H), 7.03 (m, 1H), 6.95 (m, 1H), 6.93 (m, 1H), 6.50 (s, 1H), 3.84 (s, 3H), 2.49 (m, 1H), 2.38 (m, 1H), 2.18 (m, 1H), 2.05 (m, 1H), 1.86 (m, 2H), 1.60 (m, 2H), 1.49 (m, 1H), 1.37 (m, 1H).
¹H-NMR (CDCl₃): δ 7.50 (m, 1H), 7.43 (m, 1H), 7.37 (m, 1H), 7.31 (m, 1H), 6.49 (s, 1H), 2.48 (m, 1H), 2.40 (m, 1H), 2.22 (m, 1H), 2.11 (m, 1H), 1.92 (m, 2H), 1.63 (m, 2H), 1.51 (m, 1H), 1.42 (m, 1H).
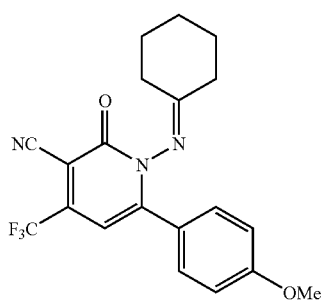
3.58
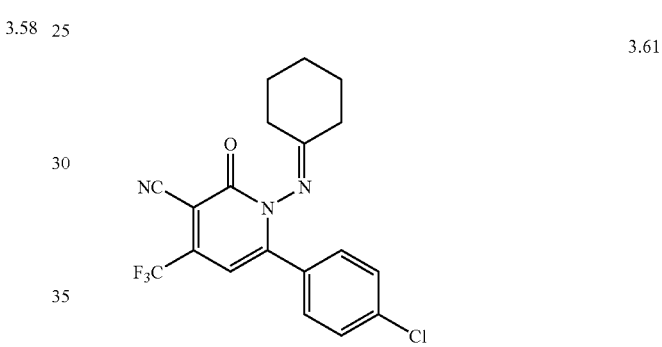
3.61
¹H-NMR (CDCl₃): δ7.39 (d, J=9.0 Hz, 2H), 6.96 (d, J=9.0 Hz, 2H), 6.48 (s, 1H), 3.87 (s, 3H), 2.52 (m, 1H), 2.41 (m, 1H), 2.18 (m, 1H), 2.02 (m, 1H), 1.87 (m, 2H), 1.60 (m, 2H), 1.52 (m, 1H), 1.34 (m, 1H).
1H-NMR (CDCl₃): δ 7.46 (d, J=8.3 Hz, 2H), 7.36 (d, J=8.3 Hz, 2H), 6.47 (s, 1H), 2.49 (m, 1H), 2.38 (m, 1H), 2.19 (m, 1H), 2.02 (m, 1H), 1.88 (m, 2H), 1.61 (m, 2H), 1.51 (m, 1H), 1.37 (m, 1H).
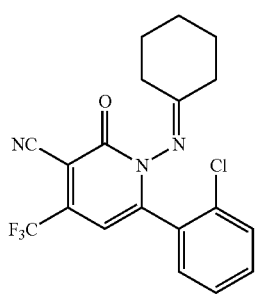
3.59
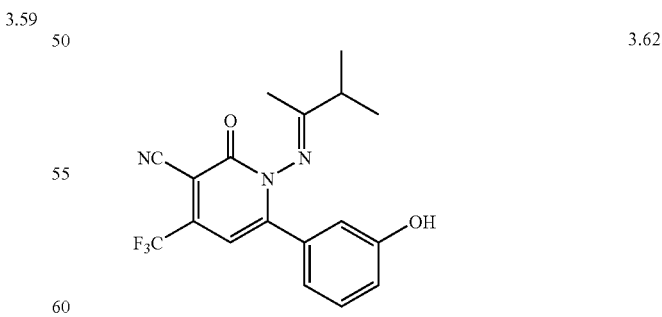
3.62
¹H-NMR (CDCl₃): δ7.57-7.30 (m, 4H), 6.46 (s, 1H), 2.37 (m, 1H), 2.23 (m, 2H), 2.05 (m, 1H), 1.91 (m, 1H), 1.83 (m, 1H), 1.60 (m, 2H), 1.54 (m, 1H), 1.44 (m, 1H).
¹H-NMR (CDCl₃): δ 7.31 (m, 1H), 6.98 (m, 1H), 6.95 (m, 1H), 2.08 (m, 1H), 6.53 (s, 1H), 2.62 (m, J=7.0 Hz, 1H), 1.76 (s, 3H), 1.03 (d, J=7.0 Hz, 3H), 0.99 (d, J=7.0 Hz, 3H).

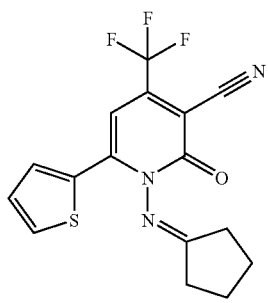

1-Cyclopentylideneamino-2-oxo-6-thiophen-2-yl-4-trifluoromethyl-1,2-dihydro-pyridine-3-carbonitrile
MS (ES+):352.2 (M+H)

3.63

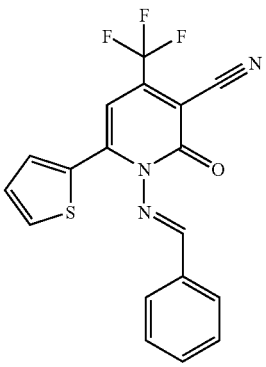

1-(Benzylidene-amino)-2-oxo-6-thiophen-2-yl-4-trifluoromethyl-1,2-dihydro-pyridine-3-carbonitrile
MS (ES+):374.1 (M+H)

3.66

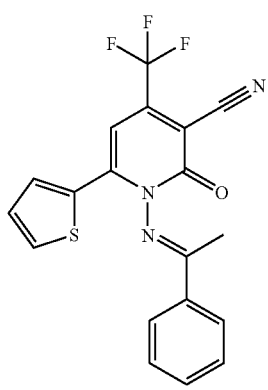

2-Oxo-1-(1-phenyl-ethylideneamino)-6-thiophen-2-yl-4-trifluoromethyl-1,2-dihydro-pyridine-3-carbonitrile
MS (ES+):388.0 (M+H)

3.64

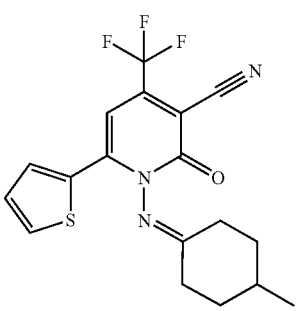

1-(4-Methyl-cyclohexylideneamino)-2-oxo-6-thiophen-2-yl-4-trifluoromethyl-1,2-dihydro-pyridine-3-carbonitrile
MS (ES+):380.1 (M+H)

3.67

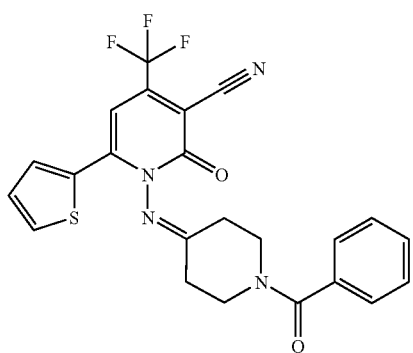

1-(1-Benzoyl-piperidin-4-ylideneamino)-2-oxo-6-thiophen-2-yl-4-trifluoromethyl-1,2-dihydro-pyridine-3-carbonitrile
MS (ES+):471.3 (M+H)

3.65

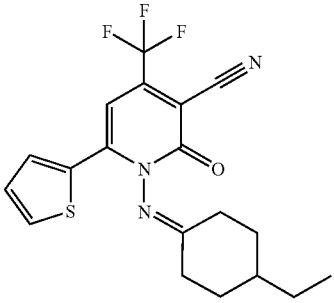

1-(4-Ethyl-cyclohexylideneamino)-2-oxo-6-thiophen-2-yl-4-trifluoromethyl-1,2-dihydro-pyridine-3-carbonitrile
MS (ES+):394.0 (M+H)

3.68

3.69

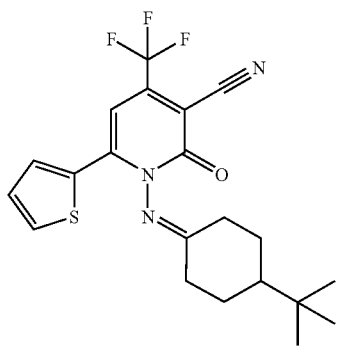

1-(4-tert-Butyl-cyclohexylideneamino)-2-oxo-6-thiophen-2-yl-4-trifluoromethyl-1,2-dihydro-pyridine-3-carbonitrile
MS (ES+):422.0 (M+H)

3.70

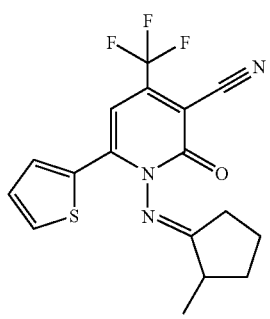

1-(2-Methyl-cyclopentylideneamino)-2-oxo-6-thiophen-2-yl-4-trifluoromethyl-1,2-dihydro-pyridine-3-carbonitrile
MS (ES+):366.1 (M+H)

3.71

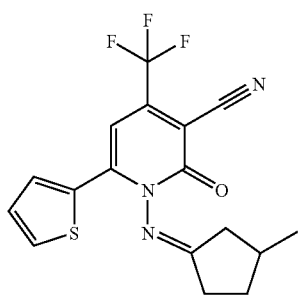

1-(3-Methyl-cyclopentylideneamino)-2-oxo-6-thiophen-2-yl-4-trifluoromethyl-1,2-dihydro-pyridine-3-carbonitrile
MS (ES+):366.2 (M+H)

3.72

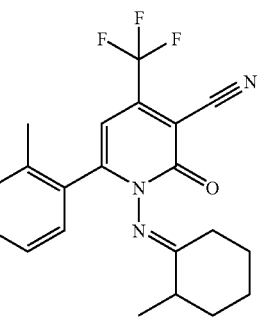

1-(2-Methyl-cyclohexylideneamino)-2-oxo-6-thiophen-2-yl-4-trifluoromethyl-1,2-dihydro-pyridine-3-carbonitrile
MS (ES+):380.3 (M+H)

3.73

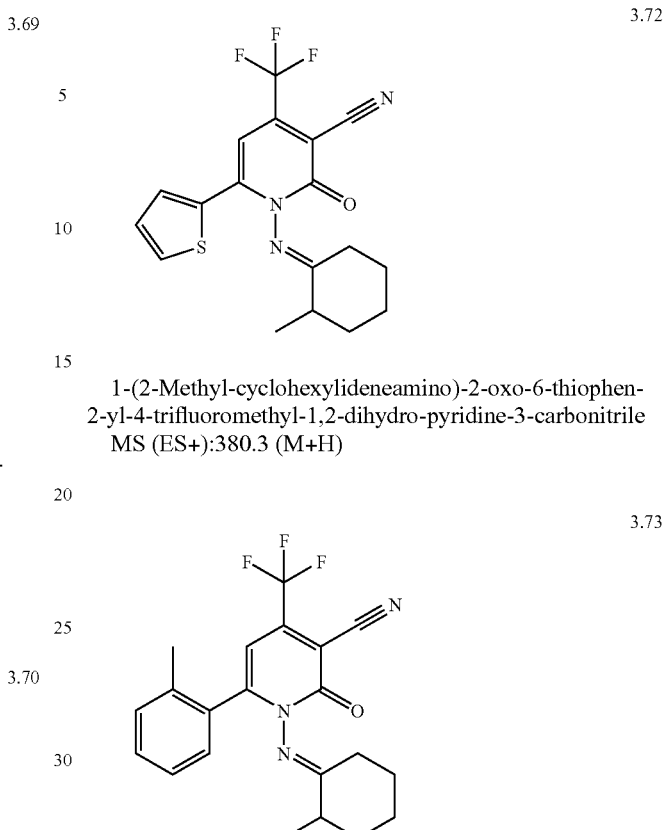

1-(2-Methyl-cyclohexylideneamino)-2-oxo-6-o-tolyl-4-trifluoromethyl-1,2-dihydro-pyridine-3-carbonitrile
MS (ES+):388.2 (M+H)

Example 4

This example illustrates the preparation of compound 4.

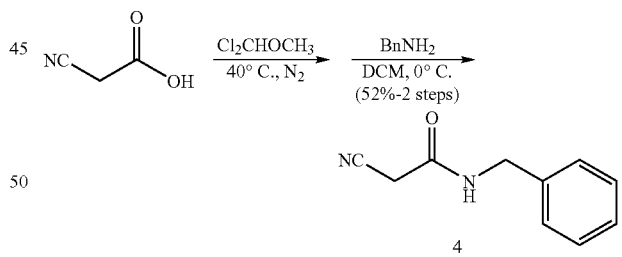

Cyanoacetic acid (8.0 g, 94.1 mmoles) and α,α-dichloromethyl methyl ether were measured out into a 30 mL round-bottom flask equipped with a magnetic stirbar. The flask was sealed with a septum, and the vessel was continuously flushed with dry $N_2$ gas. The temperature was carefully raised to 40° C. at which temperature the mixture began to liquify and bubble. Nitrogen flushing was maintained throughout this period with adequate venting to atmosphere to permit the release of gases formed during the reaction. The temperature was maintained at 40° C. for 45 minutes while adequate stirring was maintained by vigilant monitoring. After this period the nitrogen line was submerged into the stirring reaction mixture to facilitate the purging of gases (HCl) from the solution. The nitrogen purge was carried out for 30 min. After this period the reaction was cooled to 0° C. and was dissolved into 100 mL of anhydrous DCM. To the stirring acid chloride solution at 0° C. was slowly added benzylamine (21 mL, 192.2 mmoles) and the resulting mixture was stirred at ambient temperature for 30 min. After this period the reaction mixture was washed with 1N HCl (2×20 mL), sat'd NaHCO₃ (2×20 mL) and brine. The DCM solution was dried over anhydrous Na₂SO₄ and was evaporated in vacuo to yield the crude product as a yellowish solid. The crude material was purified by recrystallization in DCM/Hexane to yield 8.5 g (52% yield) of product as yellow, needlelike crystals. (Alternatively, the product can be purified using flash silica chromatography in 60% EtOAc/Hexane).

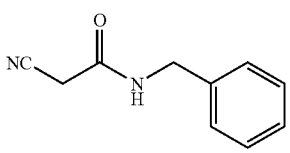

4

¹H-NMR (CDCl₃): δ7.39-7.28 (m, 5H), 6.39 (bs, 1H), 4.48 (d, J=5.7 Hz, 2H), 3.40 (s, 2H).

The following compounds were prepared in a manner similar to that described above.

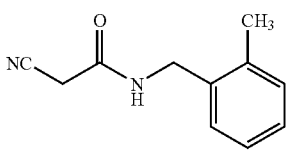

4.1

¹H-NMR (CDCl₃): δ7.25-7.19 (m, 4H), 6.15 (bs, 1H), 4.49 (d, J=5.4 Hz, 2H), 3.41 (s, 2H), 2.34 (s, 3H).

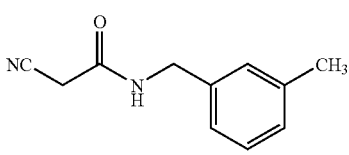

4.2

¹H-NMR (CDCl₃): δ7.27-7.23 (m, 1H), 7.14-7.07 (m, 3H), 6.29 (bs, 1H), 4.45 (d, J=5.6 Hz, 2H), 3.41 (s, 2H), 2.36 (s, 3H).

An alternative procedure utilizing commercially available methyl cyanoacetate illustrates the preparation of compound 4.

Example 5

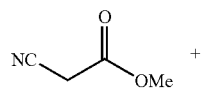 +

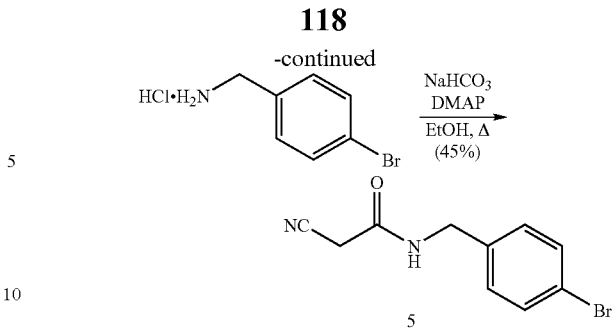

Methyl cyanoacetate (0.8 mL, 9.1 mmoles) and 4-Bromobenzylammonium chloride (0.97 g, 4.4 mmoles) were mixed with 10 mL of anhydrous ethanol within a round-bottom flask. To the stirring mixture at room temp was added sodium bicarbonate (0.55 g, 6.5 mmoles) and 4-(dimethylamino)pyridine (0.25 g, 2.0 mmoles). The mixture was then stirred at 80° C. for 5 hours. After this period the reaction was evaporated in vacuo, combined with DCM, and was washed with 1N HCl (2×15 mL), sat'd NaHCO₃ (2×15 mL) and brine. The DCM solution was dried over anhydrous Na₂SO₄ and was evaporated in vacuo to yield the crude product residue. The crude residue was purified using flash silica chromatography (60% EtOAc/Hexane) to yield 0.49 g (45% yield) of product as a yellow solid.

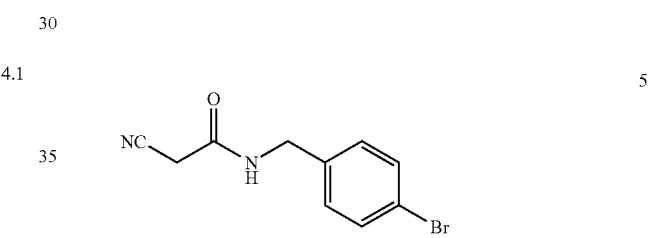

5

¹H-NMR (CDCl₃): δ7.49 (d, J=8.3 Hz, 2H), 7.17 (d, J=8.3 Hz, 2H), 6.38 (bs, 1H), 4.44 (d, J=5.8 Hz, 2H), 3.42 (s, 2H).

The following compounds were prepared in a manner similar to that described above.

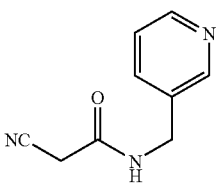

5.1

2-Cyano-N-pyridin-3-ylmethyl-acetamide

¹H-NMR (CDCl₃): δ8.53-8.48 (m, 2H), 7.65 (dt, J'=7.8 Hz, J''=1.8 Hz, 1H), 7.29 (dd, J'=7.8 hz, J''=4.8 Hz, 1H), 7.25 (bs, 1H), 4.47 (d, J=5.8 Hz, 2H), 3.43 (s, 2H).

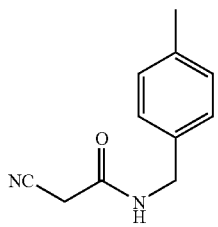

2-Cyano-N-(4-methyl-benzyl)-acetamide $^1$H-NMR (CDCl$_3$): δ7.18 (m, 4H), 6.27 (bs, 1H), 4.44 (d, J=5.6 Hz, 2H), 3.40 (s, 2H), 2.35 (s, 3H).

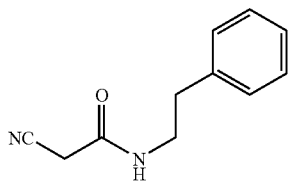

2-Cyano-N-phenethyl-acetamide $^1$H-NMR (CDCl$_3$): δ7.34 (m, 2H), 7.29-7.16 (m, 3H), 6.06 (bs, 1H), 3.58 (m, 2H), 3.32 (s, 2H), 2.86 (t, J=7.1 Hz, 2H).

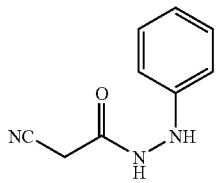

Cyano-acetic acid N'-phenyl-hydrazide $^1$H-NMR (CDCl$_3$): {rotamers} δ7.93 (bs, 0.36H), 7.53-7.39 (m, 1.1H), 7.36-7.20 (m, 3.4H), 7.11-6.91 (m, 1.4H), 6.89-6.76 (m, 1.7H), 6.08 (m, 0.40H), 5.92 (m, 0.50H), 4.88 (m, 0.25H), 4.44 (m, 0.33H), 3.90 (s, 0.50H), 3.60 (s, 1H), 3.48 (s, 1H), 3.33 (s, 0.25H).

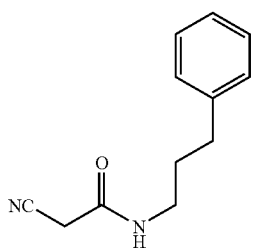

2-Cyano-N-(3-phenyl-propyl)-acetamide $^1$H-NMR (CDCl$_3$): δ7.34-7.27 (m, 2H), 7.24-7.14 (m, 3H), 6.07 (bs, 1H), 3.34 (bq, J=5.1 Hz, 2H), 3.30 (s, 2H), 2.68 (bt, J=7.5 Hz, 2H), 1.90 (m, J=7.5 Hz, 2H).

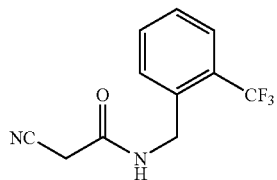

2-Cyano-N-(2-trifluoromethyl-benzyl)-acetamide $^1$H-NMR (CDCl$_3$): δ7.69 (bd, J=7.8 Hz, 1H), 7.59-7.53 (m, 2H), 7.48-7.41 (m, 1H), 6.40 (bs, 1H), 4.67 (d, J=6.1 Hz, 2H), 3.40 (s, 2H).

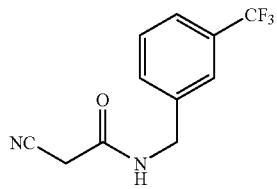

2-Cyano-N-(3-trifluoromethyl-benzyl)-acetamide $^1$H-NMR (CDCl$_3$): δ7.62-7.47 (m, 4H), 6.49 (bs, 1H), 4.55 (d, J=5.8 Hz, 2H), 3.44 (s, 2H).

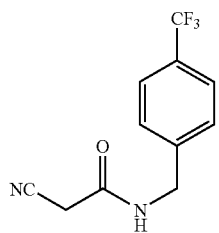

2-Cyano-N-(4-trifluoromethyl-benzyl)-acetamide $^1$H-NMR (CDCl$_3$): δ7.62 (d, J=8.1 Hz, 2H), 7.42 (d, J=8.1 Hz, 2H), 6.48 (bs, 1H), 4.55 (d, J=6.1 Hz, 2H), 3.44 (s, 2H).

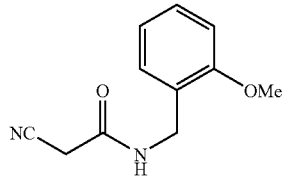

2-Cyano-N-(2-methoxy-benzyl)-acetamide

¹H-NMR (CDCl₃): δ7.35-7.23 (m, 2H), 6.97-6.89 (m, 2H), 6.80 (bs, 1H), 4.48 (d, J=5.8 Hz, 2H), 3.89 (s, 3H), 3.34 (s, 2H).

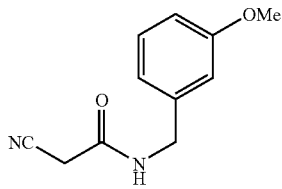

5.10

2-Cyano-N-(3-methoxy-benzyl)-acetamide

¹H-NMR (CDCl₃): δ7.30-7.25 (m, 1H), 6.89-6.81 (m, 3H), 6.36 (bs, 1H), 4.45 (d, J=5.8 Hz, 2H), 3.81 (s, 3H), 3.40 (s, 2H).

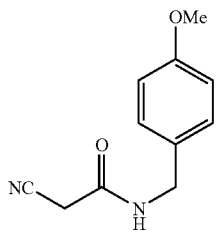

5.11

¹H-NMR (CDCl₃): δ7.22 (d, J=8.6 Hz, 2H), 6.89 (d, J=8.6 Hz, 2H), 6.26 (bs, 1H), 4.42 (d, J=5.3 Hz, 2H), 3.81 (s, 3H), 3.40 (s, 2H).

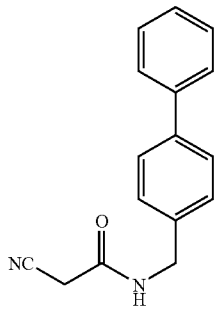

5.12

N-Biphenyl-4-ylmethyl-2-cyano-acetamide

¹H-NMR (CDCl₃): δ7.62-7.55 (m, 4H), 7.48-7.42 (m, 2H), 7.40-7.33 (m, 3H), 6.40 (bs, 1H), 4.53 (d, J=5.8 Hz, 2H), 3.43 (s, 2H).

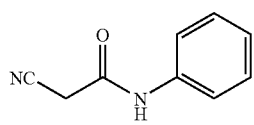

5.13

2-Cyano-N-phenyl-acetamide

¹H-NMR (CDCl₃): δ7.66 (bs, 1H), 7.53-7.48 (m, 2H), 7.41-7.35 (m, 2H), 7.23-7.18 (m, 1H), 3.57 (s, 2H).

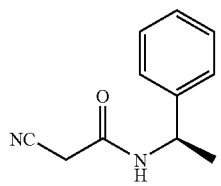

5.14

2-Cyano-N-(1-phenyl-ethyl)-acetamide

¹H-NMR (CDCl₃): δ7.41-7.23 (m, 5H), 6.24 (bs, 1H), 5.12 (m, 1H), 3.37 (m, 2H), 1.55 (d, J=7.1 Hz, 3H).

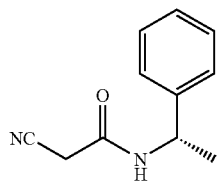

5.15

2-Cyano-N-(1-phenyl-ethyl)-acetamide

¹H-NMR (CDCl₃): δ7.41-7.23 (m, 5H), 6.24 (bs, 1H), 5.12 (m, 1H), 3.37 (m, 2H), 1.55 (d, J=7.1 Hz, 3H).

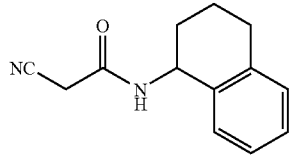

5.16

2-Cyano-N-(1,2,3,4-tetrahydro-naphthalen-1-yl)-acetamide

¹H-NMR (CDCl₃): δ7.28-7.09 (m, 4H), 6.26 (bs, 2H), 5.22-5.14 (m, 1H), 3.40 (s, 2H), 2.90-2.71 (m, 2H), 2.12-2.00 (m, 1H), 1.93-1.77 (m, 3H).

5.17

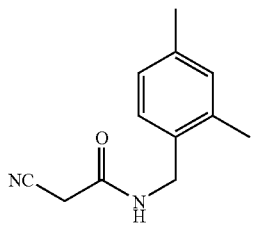

2-Cyano-N-(2,4-dimethyl-benzyl)-acetamide $^1$H-NMR (CDCl$_3$): δ7.14-7.08 (m, 1H), 7.05-6.98 (m, 2H), 6.13 (bs, 1H), 4.44 (d, J=5.3 Hz, 2H), 3.38 (s, 2H), 2.32 (s, 3H), 2.30 (s, 3H).

5.18

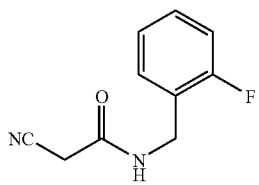

2-Cyano-N-(2-fluoro-benzyl)-acetamide $^1$H-NMR (CDCl$_3$): δ7.40-7.27 (m, 2H), 7.16-7.05 (m, 2H), 6.45 (bs, 1H), 4.54 (d, J=5.8 Hz, 2H), 3.39 (s, 2H).

5.19

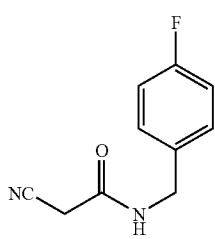

2-Cyano-N-(4-fluoro-benzyl)-acetamide $^1$H-NMR (CDCl$_3$): δ7.30-7.23 (m, 2H), 7.08-7.00 (m, 2H), 6.40 (bs, 1H), 4.45 (d, J=5.8 Hz, 2H), 3.41 (s, 2H).

5.20

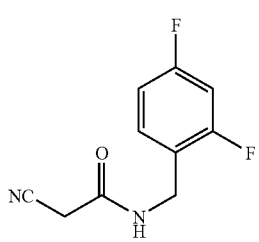

2-Cyano-N-(2,4-difluoro-benzyl)-acetamide $^1$H-NMR (CDCl$_3$): δ7.38-7.29 (m, 1H), 6.90-6.80 (m, 2H), 6.51 (bs, 1H), 4.48 (d, J=6.1 Hz, 2H), 3.39 (s, 2H).

5.21

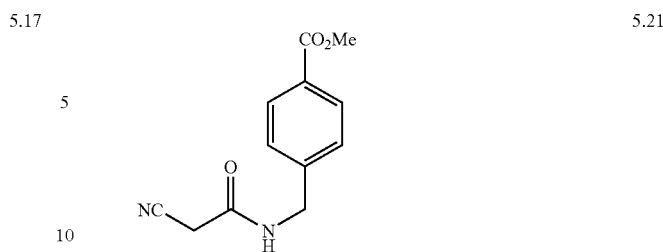

4-[(2-Cyano-acetylamino)-methyl]-benzoic Acid Methyl Ester $^1$H-NMR (CDCl$_3$): δ8.03 (d, J=8.1 Hz, 2H), 7.36 (d, J=8.1 Hz, 2H), 6.46 (bs, 1H), 4.55 (d, J=5.8 Hz, 2H), 3.92 (s, 3H), 3.45 (s, 2H).

5.22

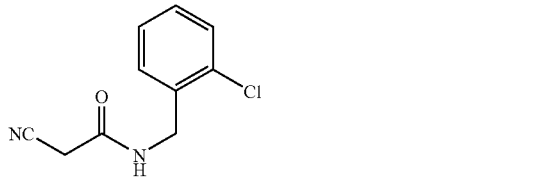

N-(2-Chloro-benzyl)-2-cyano-acetamide $^1$H-NMR (CDCl$_3$): δ7.43-7.36 (m, 2H), 7.31-7.23 (m, 2H), 6.53 (bs, 1H), 4.58 (d, J=5.8 Hz, 2H), 3.40 (s, 2H).

5.23

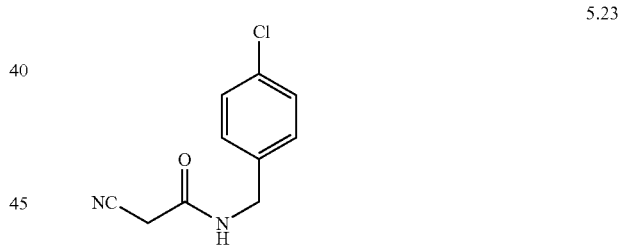

N-(4-Chloro-benzyl)-2-cyano-acetamide $^1$H-NMR (CDCl$_3$): δ7.36-7.30 (d, J=8.6 Hz, 2H), 7.25-7.20 (d, J=8.6 Hz, 2H), 6.43 (bs, 1H), 4.45 (d, J=5.81 Hz, 2H), 3.42 (s, 2H).

5.24

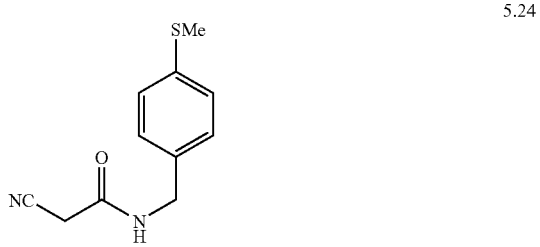

2-Cyano-N-(4-methylsulfanyl-benzyl)-acetamide

¹H-NMR (CDCl₃): δ7.26-7.18 (m, 4H), 6.34 (bs, 1H), 4.43 (d, J=5.6 Hz, 2H), 3.40 (s, 2H), 2.48 (s, 3H).

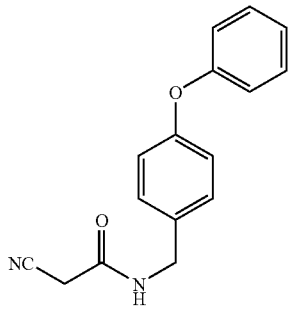

2-Cyano-N-(4-phenoxy-benzyl)-acetamide

¹H-NMR (CDCl₃): δ7.38-7.32 (m, 2H), 7.28-7.23 (m, 3H), 7.16-7.09 (m, 1H), 7.04-6.96 (m, 4H), 6.35 (bs, 1H), 4.45 (d, J=5.6 Hz, 2H), 3.42 (s, 2H).

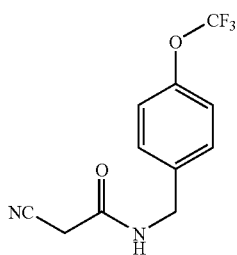

2-Cyano-N-(4-trifluoromethoxy-benzyl)-acetamide

¹H-NMR (CDCl₃): δ7.36-7.29 (m, 2H), 7.23-7.17 (m, 2H), 6.46 (bs, 1H), 4.48 (d, J=5.8 Hz, 2H), 3.42 (s, 2H).

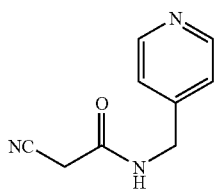

2-Cyano-N-pyridin-4-ylmethyl-acetamide

¹H-NMR (CDCl₃): δ8.61-8.51 (m, 2H), 7.24-7.18 (m, 2H), 6.99 (bs, 1H), 4.49 (d, J=5.8 Hz, 2H), 3.48 (s, 2H).

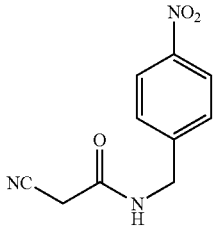

2-Cyano-N-(4-nitro-benzyl)-acetamide

¹H-NMR (CDCl₃): δ8.23 (d, J=8.6 Hz, 2H), 7.47 (d, J=8.6 Hz, 2H), 6.55 (bs, 1H), 4.60 (d, J=6.1 Hz, 2H), 3.47 (s, 2H).

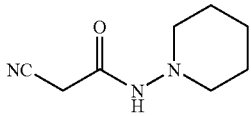

2-Cyano-N-piperidin-1-yl-acetamide

¹H-NMR (CDCl₃): δ6.51 (bs, 1H), 3.54 (s, 2H), 3.16-3.04 (m, 2H), 2.43-2.29 (m, 2H) 1.81-1.54 (m, 6H).

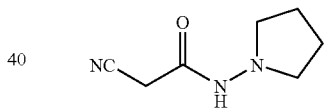

2-Cyano-N-pyrrolidin-1-yl-acetamide

¹H-NMR (CDCl₃): δ6.85 (bs, 1H), 3.59 (s, 2H), 3.46-3.03 (bm, 2H), 2.78-2.22 (bm, 2H), 1.96-1.78 (m, 4H).

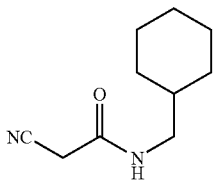

2-Cyano-N-cyclohexylmethyl-acetamide

¹H-NMR (CDCl₃): δ6.20 (bs, 1H), 3.38 (s, 2H), 3.15 (bt, J=6.3 Hz, 2H), 1.79-1.68 (m, 5H), 1.58-1.44 (m, 1H), 1.36-1.09 (m, 3H), 1.02-0.86 (m, 2H).

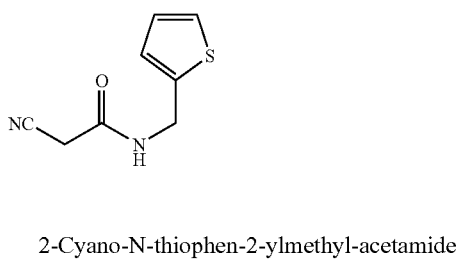

2-Cyano-N-thiophen-2-ylmethyl-acetamide $^1$H-NMR (CDCl$_3$): δ7.26 (dd, J'=5.1 Hz, J"=1.3 Hz, 1H), 7.03-6.99 (m, 1H), 6.99-6.95 (m, 1H), 6.57 (bs, 1H), 4.64 (d, J=5.6 Hz, 2H), 3.39 (s, 2H).

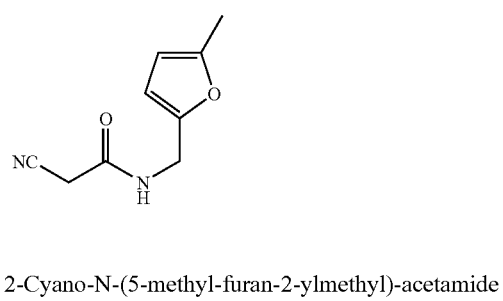

2-Cyano-N-(5-methyl-furan-2-ylmethyl)-acetamide $^1$H-NMR (CDCl$_3$): δ6.52 (bs, 1H), 6.14 (d, J=3.0 Hz, 1H), 5.93-5.88 (m, 1H), 4.40 (d, J=5.3 Hz, 2H), 3.39 (s, 2H), 2.27 (s, 3H).

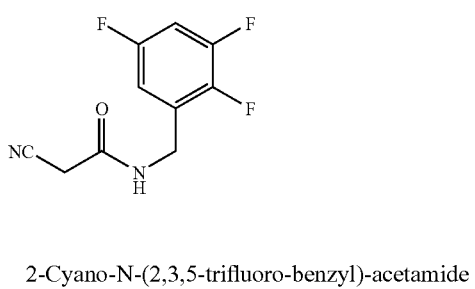

2-Cyano-N-(2,3,5-trifluoro-benzyl)-acetamide $^1$H-NMR (CDCl$_3$): δ6.94-6.83 (m, 2H), 6.66 (bs, 1H), 4.53 (bd, J=6.1 Hz, 2H), 3.44 (s, 2H).

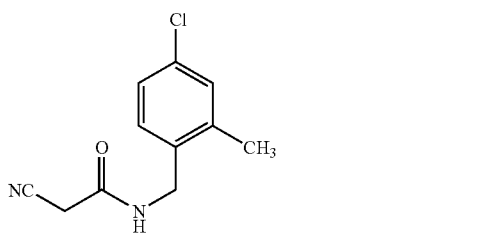

N-(4-Chloro-2-methyl-benzyl)-2-cyano-acetamide $^1$H-NMR (CDCl$_3$): δ7.22-7.13 (m, 3H), 6.28 (bs, 1H), 4.43 (d, J=5.6 Hz, 2H), 3.40 (s, 2H), 2.31 (s, 3H).

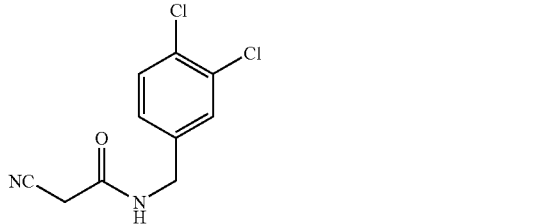

2-Cyano-N-(3,4-dichloro-benzyl)-acetamide $^1$H-NMR (CDCl$_3$): δ8.37 (bs, 1H), 7.14-7.09 (m, 2H), 6.87 (dd, J'=8.1 Hz, J"=2.0 Hz, 1H), 4.02 (d, J=5.8 Hz, 2H), 3.20 (s, 2H).

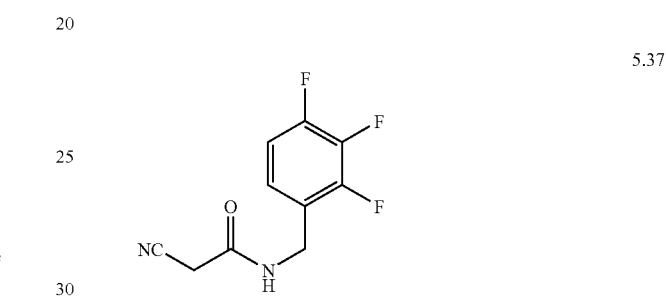

2-Cyano-N-(2,3,4-trifluoro-benzyl)-acetamide $^1$H-NMR (CDCl$_3$): δ7.14-7.06 (m, 1H), 7.01-6.90 (m, 1H), 6.54 (bs, 1H), 4.51 (d, J=5.8 Hz, 2H), 3.41 (s, 2H).

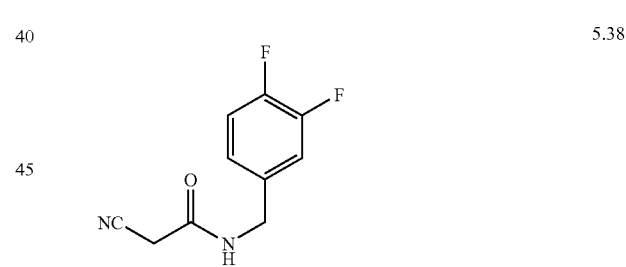

2-Cyano-N-(3,4-difluoro-benzyl)-acetamide $^1$H-NMR (CDCl$_3$): δ7.19-7.08 (m, 2H), 7.06-6.98 (m, 1H), 6.46 (bs, 1H), 4.44 (d, J=5.8 Hz, 2H), 3.43 (s, 2H).

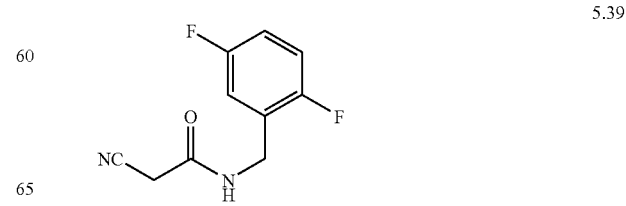

2-Cyano-N-(2,5-difluoro-benzyl)-acetamide

¹H-NMR (CDCl₃): δ7.09-6.94 (m, 3H), 6.58 (bs, 1H), 4.50 (d, J=6.1 Hz, 2H), 3.42 (s, 2H).

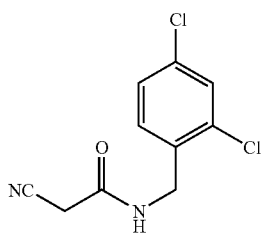

5.40

2-Cyano-N-(2,4-dichloro-benzyl)-acetamide

¹H-NMR (CDCl₃): δ7.42 (d, J=2.0 Hz, 1H), 7.35-7.23 (m, 2H), 6.58 (bs, 1H), 4.53 (d, J=6.1 Hz, 2H), 3.40 (s, 2H).

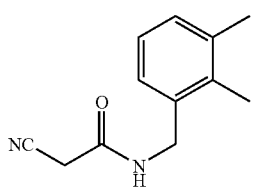

5.41

2-Cyano-N-(2,3-dimethyl-benzyl)-acetamide

¹H-NMR (CDCl₃): δ7.18-7.06 (m, 3H), 6.18 (bs, 1H), 4.49 (d, J=5.3 Hz, 2H), 3.37 (s, 2H), 2.30 (s, 3H), 2.22 (s, 3H).

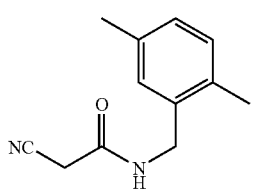

5.42

2-Cyano-N-(2,5-dimethyl-benzyl)-acetamide

¹H-NMR (CDCl₃): δ7.11-7.01 (m, 3H), 6.16 (bs, 1H), 4.44 (d, J=5.3 Hz, 2H), 3.40 (d, 2H), 2.32 (s, 3H), 2.29 (s, 3H).

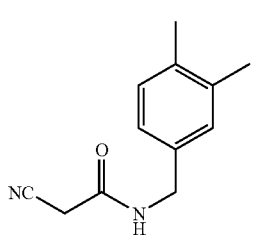

5.43

2-Cyano-N-(3,4-dimethyl-benzyl)-acetamide

¹H-NMR (CDCl₃): δ7.12 (d, J=7.6 Hz, 1H), 7.05 (bs, 1H), 7.01 (dd, J'=7.6 Hz, J''=1.3 Hz, 1H), 6.34 (bs, 1H), 4.40 (d, J=5.8 Hz, 2H), 3.38 (d, 2H), 2.26 (s, 3H), 2.25 (s, 3H).

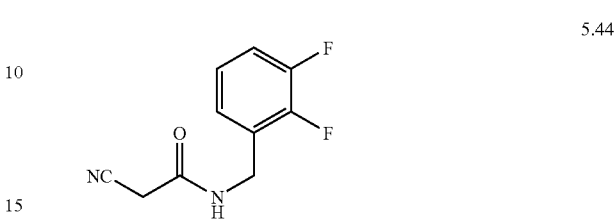

5.44

2-Cyano-N-(2,3-difluoro-benzyl)-acetamide

¹H-NMR (CDCl₃): δ7.19-7.0 (m, 3H), 6.46 (bs, 1H), 4.56 (dd, J'=6.1 Hz, J''=0.8 Hz, 2H), 3.41 (s, 2H).

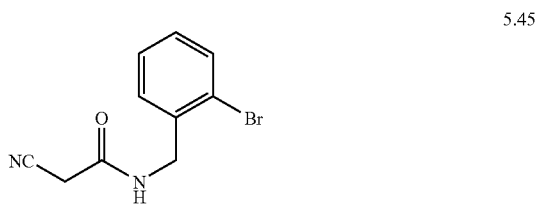

5.45

N-(2-Bromo-benzyl)-2-cyano-acetamide

¹H-NMR (CDCl₃): δ7.48-7.41 (m, 2H), 7.25-7.19 (m, 2H), 6.45 (bs, 1H), 4.45 (d, J=5.8 Hz, 2H), 3.43 (s, 2H).

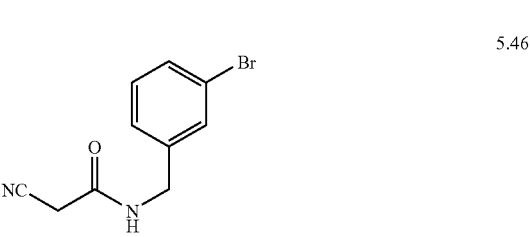

5.46

N-(3-Bromo-benzyl)-2-cyano-acetamide

¹H-NMR (CDCl₃): δ7.58 (dd, J'=8.1 Hz, J''=1.0 Hz, 1H), 7.39 (dd, J'=7.8 Hz, J''=1.5 Hz, 1H), 7.31 (dt, J'=7.6 Hz, J''=1.0 Hz, 1H), 7.20 (dt, J'=7.6 Hz, J''=1.5 Hz, 1H), 6.59 (bs, 1H), 4.56 (d, J=5.8 Hz, 2H), 3.39 (s, 2H).

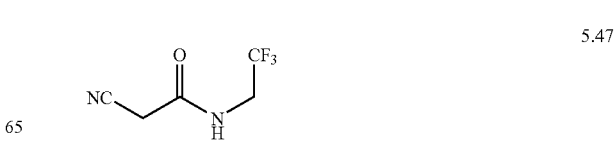

5.47

2-Cyano-N-(2,2,2-trifluoro-ethyl)-acetamide $^1$H-NMR (CDCl$_3$): δ6.38 (bs, 1H), 3.98 (m, 2H), 3.48 (s, 2H).

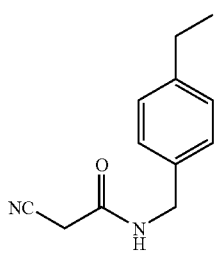

2-Cyano-N-(4-ethyl-benzyl)-acetamide $^1$H-NMR (CDCl$_3$): δ7.23-7.16 (m, 4H), 6.47 (bs, 1H), 4.42 (d, J=5.6 Hz, 2H), 3.36 (s, 2H), 2.64 (q, J=7.6 Hz, 2H), 1.23 (t, J=7.6 Hz, 3H).

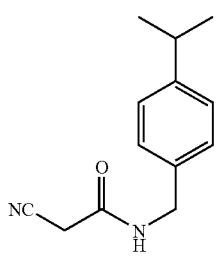

2-Cyano-N-(4-isopropyl-benzyl)-acetamide $^1$H-NMR (CDCl$_3$): δ7.23-7.16 (m, 4H), 6.65 (bs, 1H), 4.39 (d, J=5.6 Hz, 2H), 3.33 (s, 2H), 2.90 (m, J=6.8 Hz, 1H), 1.24 (d, J=6.8 Hz, 6H).

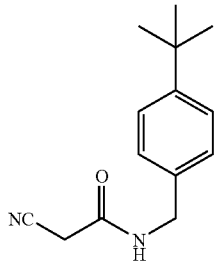

N-(4-tert-Butyl-benzyl)-2-cyano-acetamide $^1$H-NMR (CDCl$_3$): δ7.37 (d, J=8.3 Hz, 2H), 7.21 (d, J=8.3 hz, 2H), 6.59 (bs, 1H), 4.40 (d, J=5.6 hz, 2H), 3.33 (s, 2H), 1.31 (s, 9H).

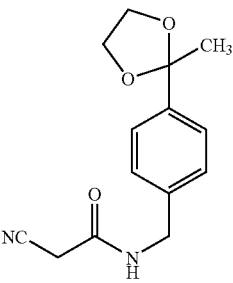

2-Cyano-N-[4-(2-methyl-[1,3]dioxolan-2-yl)-benzyl]-acetamide $^1$H-NMR (CDCl$_3$): δ7.48 (d, J=8.1 Hz, 2H), 7.27 (d, J=8.1 Hz, 2H), 6.37 (bs, 1H), 4.47 (d, J=5.6 Hz, 2H), 4.04 (m, 2H), 3.77 (m, 2H), 3.41 (s, 2H), 1.65 (s, 3H).

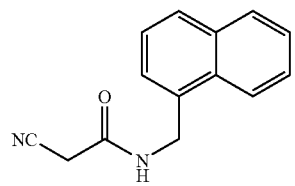

2-Cyano-N-naphthalen-1-ylmethyl-acetamide $^1$H-NMR (CDCl$_3$): δ7.98-7.83 (m, 3H), 7.61-7.50 (m, 2H), 7.48-7.41 (m, 2H), 6.27 (bs, 1H), 4.94 (d, J=5.3 Hz, 2H), 3.39 (s, 2H).

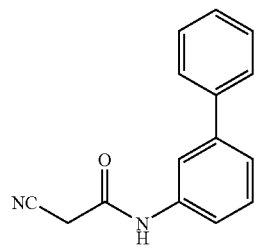

N-Biphenyl-3-yl-2-cyano-acetamide $^1$H-NMR (CDCl$_3$): δ7.75-7.33 (m, 10H), 3.59 (s, 2H).

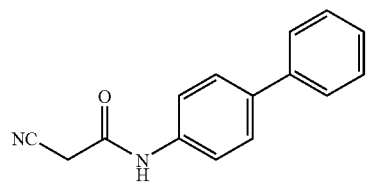

N-Biphenyl-4-yl-2-cyano-acetamide $^1$H-NMR (CDCl$_3$): δ7.74-7.67 (bs, 1H), 7.63-7.55 (m, 6H), 7.44 (t, J=7.3 Hz, 2H), 7.38-7.32 (m, 1H), 3.59 (s, 2H).

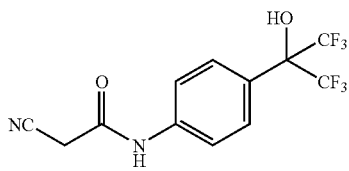

2-Cyano-N-[4-(2,2,2-trifluoro-1-hydroxy-1-trifluoromethyl-ethyl)-phenyl]-acetamide $^1$H-NMR (CDCl$_3$): δ9.59 (bs, 1H), 7.68-7.55 (m, 4H), 3.75 (s, 2H).

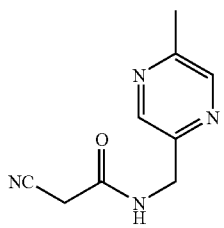

2-Cyano-N-(5-methyl-pyrazin-2-ylmethyl)-acetamide $^1$H-NMR (CDCl$_3$): δ8.48 (s, 1H), 8.42 (s, 1H), 7.16 (bs, 1H), 4.61 (d, J=5.1 Hz, 2H), 3.45 (s, 2H), 2.58 (s, 3H).

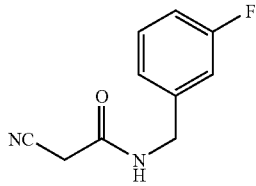

2-Cyano-N-(3-fluoro-benzyl)-acetamide $^1$H-NMR (CDCl$_3$): δ7.36-7.29 (m, 1H), 7.10-6.97 (m, 3H), 6.54 (bs, 1H), 4.47 (d, J=5.8 Hz, 2H), 3.43 (s, 2H).

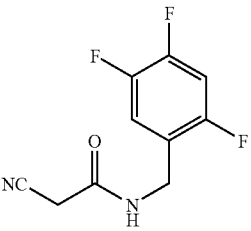

2-Cyano-N-(2,4,5-trifluoro-benzyl)-acetamide $^1$H-NMR (CDCl$_3$): 7.25-7.17 (m, 1H), 7.00-6.92 (m, 1H), 6.50 (bs, 1H), 4.47 (d, J=6.1 Hz, 2H), 3.41 (s, 2H).

Example 6

This example illustrates the preparation of compound 6.

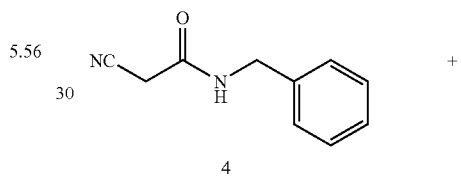

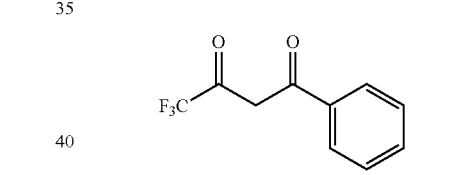

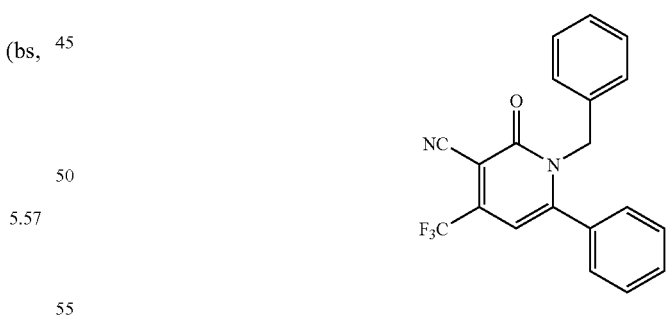

Benzyl cyanoacetamide (0.2 g, 1.2 mmoles) was combined with 4,4,4-trifluoro-1-phenyl-1,3-butanedione (0.24 g, 1.2 mmoles) and 1,8-diazabicyclo[5.4.0]undec-7-ene (90 μL, 0.6 mmoles) in 2.5 mL of benzene. The mixture was stirred at 90° C. for 12 hours. After this period the reaction mixture was evaporated in vacuo and the residue was purified directly using flask silica chromatography (20% EtOAc/Hexane) to yield 289 mg (68% yield) of product 6 as a white solid.

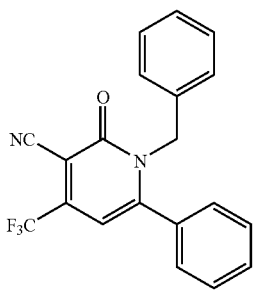

1-Benzyl-2-oxo-6-phenyl-4-trifluoromethyl-1,2-dihydro-pyridine-3-carbonitrile $^1$H-NMR (CDCl$_3$): δ7.54 (t, J=7.6 Hz, 1H), 7.45 (t, J=8 Hz, 2H), 7.25-7.17 (m, 5H), 6.88 (dd, J'=6.9 Hz, J''=1.5 Hz, 2H), 6.39 (s, 1H), 5.26 (s, 2H). MS (ES+): 355.2 (M+H).

The following compounds were prepared in a manner similar to that described above.

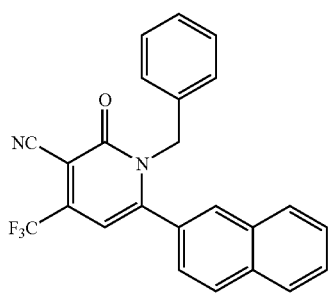

1-Benzyl-6-naphthalen-2-yl-2-oxo-4-trifluoromethyl-1,2-dihydro-pyridine-3-carbonitrile $^1$H-NMR (CDCl$_3$): δ7.92 (d, J=8.3 Hz, 2H), 7.77 (d, J=8.2 Hz, 1H), 7.65-7.57 (m, 3H), 7.24-7.18 (m, 4H), 6.88 (d, J=8.2 Hz, 2H), 6.49 (s, 1H), 5.29 (s, 2H).

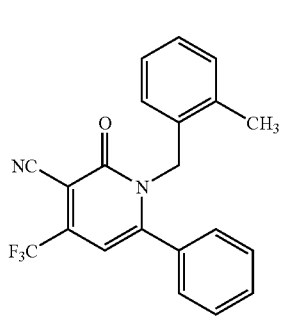

1-(2-Methyl-benzyl)-2-oxo-6-phenyl-4-trifluoromethyl-1,2-dihydro-pyridine-3-carbonitrile $^1$H-NMR (CDCl$_3$): δ7.49 (t, J=7.4 Hz, 1H), 7.36 (t, J=7.8 Hz, 2H), 7.16-7.05 (m, 5H), 6.74-6.72 (m, 1H), 6.45 (s, 1H), 5.15 (s, 2H), 1.93 (s, 3H). MS(ES+): 369.0 (M+H)

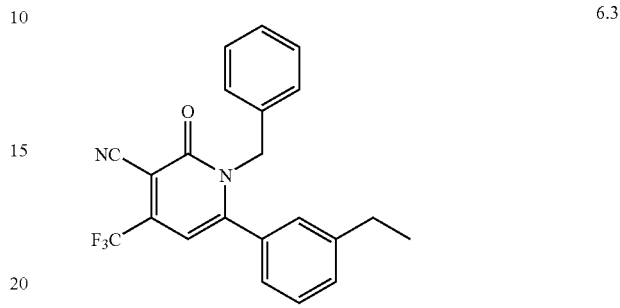

$^1$H-NMR (CDCl$_3$): δ7.36 (m, 2H), 7.24 (m, 3H), 7.03 (m, 1H), 6.92 (m, 1H), 6.90 (m, 1H), 6.88 (m, 1H), 6.40 (s, 1H), 5.25 (s, 2H), 2.60 (q, J=7.7 Hz, 2H), 1.15 (t, J=7.7 Hz, 3H).

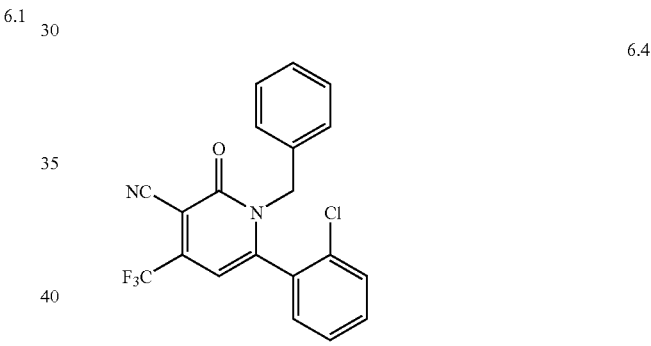

$^1$H-NMR (CDCl$_3$): δ7.53 (m, 1H), 7.50 (m, 1H), 7.28 (m, 1H), 7.21 (m, 1H), 7.18 (m, 2H), 6.97 (m, 1H), 6.84 (m, 1H), 6.82 (m, 1H), 6.35 (s, 1H), 5.68 (d, J=14.6 Hz, 2H), 4.68 (d, J=14.6 Hz, 2H).

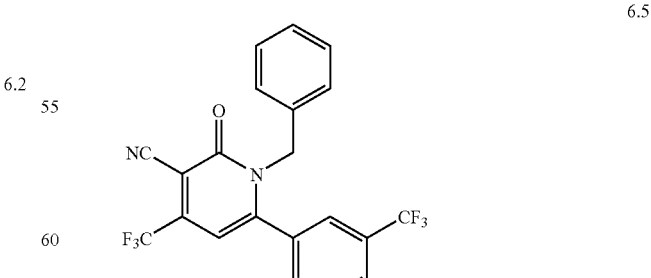

$^1$H-NMR (CDCl$_3$): δ7.80 (m, 1H), 7.60 (m, 1H), 7.38 (m, 1H), 7.32 (s, 1H), 7.24 (m, 3H), 6.81 (m, 2H), 6.39 (s, 1H), 5.21 (s, 2H).

6.6

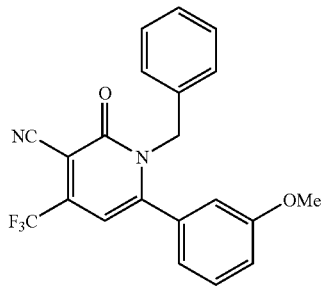

¹H-NMR (CDCl₃): δ7.36 (m, 1H), 7.25 (m, 3H), 7.05 (m, 1H), 6.92 (m, 2H), 6.79 (m, 1H), 6.60 (m, 1H), 6.42 (s, 1H), 5.25 (s, 2H), 3.64 (s, 3H).

6.7

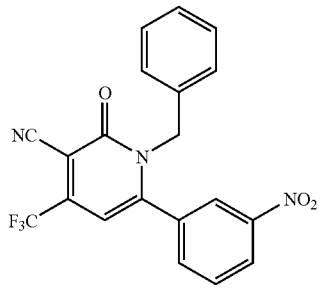

¹H-NMR (CDCl₃): δ8.38 (m, 1H), 7.97 (m, 1H), 7.65 (m, 1H), 7.48 (m, 1H), 7.25 (m, 3H), 6.81 (m, 2H), 6.40 (s, 1H), 5.23 (s, 2H).

6.8

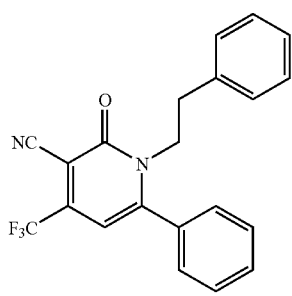

2-Oxo-1-phenethyl-6-phenyl-4-trifluoromethyl-1,2-dihydro-pyridine-3-carbonitrile ¹H-NMR (CDCl₃): δ7.60-7.54 (m, 1H), 7.53-7.47 (m, 2H), 7.23-7.18 (m, 3H), 7.16-7.11 (m, 2H), 6.88-6.82 (m, 2H), 6.33 (s, 1H), 4.22-4.16 (m, 2H), 2.95-2.89 (m, 2H). MS(ES+): 368.7 (M+H)

6.9

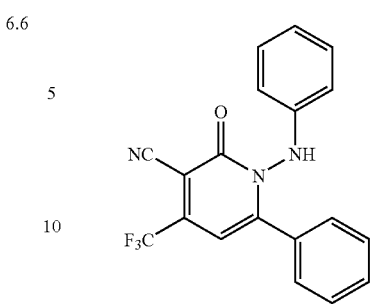

2-Oxo-6-phenyl-1-phenylamino-4-trifluoromethyl-1,2-dihydro-pyridine-3-carbonitrile ¹H-NMR (CDCl₃): δ7.59-7.54 (m, 2H), 7.53 (bs, 1H), 7.5-7.44 (m, H), 7.43-7.38 (m, 2H), 7.21-7.15 (m, 2H), 7.01-6.96 (m, 1H), 6.60 (d, J=7.1 Hz, 2H), 6.59 (s, 1H). MS(ES+): 356.0 (M+H)

6.10

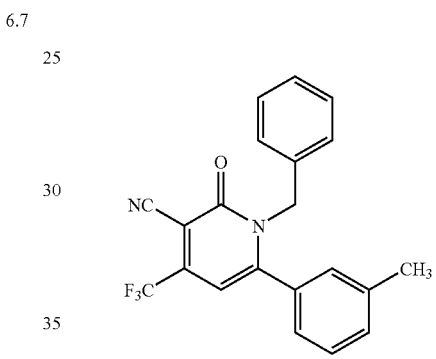

1-Benzyl-2-oxo-6-m-tolyl-4-trifluoromethyl-1,2-dihydro-pyridine-3-carbonitrile

¹H-NMR (CDCl₃): δ7.34 (d, J=5.1 Hz, 2H), 7.25-7.22 (m, 4H), 7.02-6.96 (m, 1H), 6.92-6.87 (m, 3H), 6.39 (s, 1H), 5.24 (bs, 2H), 2.32 (s, 3H). MS(ES+): 368.9 (M+H)

6.11

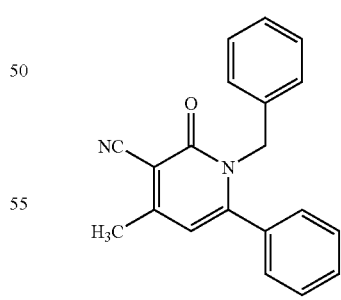

1-Benzyl-4-methyl-2-oxo-6-phenyl-1,2-dihydro-pyridine-3-carbonitrile

¹H-NMR (CDCl₃): δ7.50-7.44 (m, 1H), 7.38 (t, J=8.1 Hz, 2H), 7.24-7.17 (m, 3H), 7.11 (d, J=7.3 Hz, 2H), 6.91-6.83 (m, 2H), 6.08 (s, 1H), 5.17 (bs, 2H), 2.47 (s, 3H).

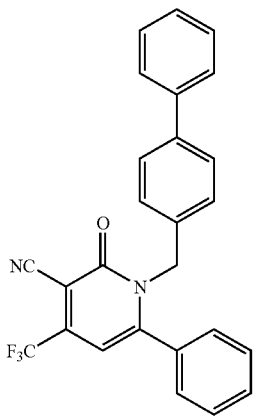

6.12

1-Biphenyl-4-ylmethyl-2-oxo-6-phenyl-4-trifluo-
romethyl-1,2-dihydro-pyridine-3-carbonitrile $^1$H-NMR (CDCl$_3$): δ7.59-7.51 (m, 3H), 7.51-7.40 (m, 6H), 7.38-7.32 (m, 1H), 7.23 (d, J=6.8 Hz, 2H), 6.97 (d, J=8.1 Hz, 2H), 6.42 (s, 1H), 5.30 (s, 2H). MS (ES+): 453.0 (M+Na).

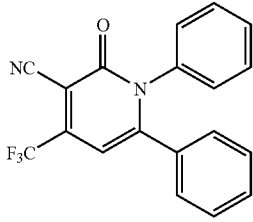

6.13

2-Oxo-1,6-diphenyl-4-trifluoromethyl-1,2-dihydro-
pyridine-3-carbonitrile $^1$H-NMR (CDCl$_3$): δ7.35-7.27 (m, 4H), 7.26-7.20 (m, 2H), 7.13-7.03 (m, 4H), 6.56 (s, 1H). MS(ES+): 341.1 (M+H)

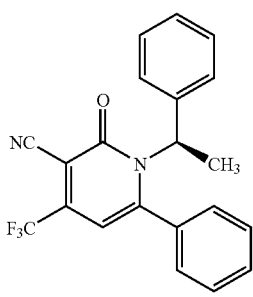

6.14

2-Oxo-6-phenyl-1-(1-phenyl-ethyl)-4-trifluorom-
ethyl-1,2-dihydro-pyridine-3-carbonitrile $^1$H-NMR (CDCl$_3$): δ7.6-7.39 (m, 5H), 7.34-7.20 (m, 3H), 7.15 (d, J=6.8 Hz, 2H), 6.37 (s, 1H), 5.60-5.49 (m, 1H), 1.95 (d, J=6.8 Hz, 3H).

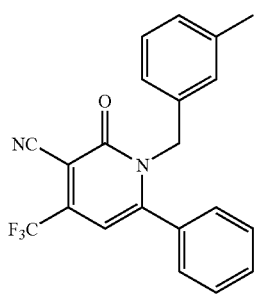

6.15

1-(3-Methyl-benzyl)-2-oxo-6-phenyl-4-trifluorom-
ethyl-1,2-dihydro-pyridine-3-carbonitrile

MS(ES+): 369.1 (M+H)

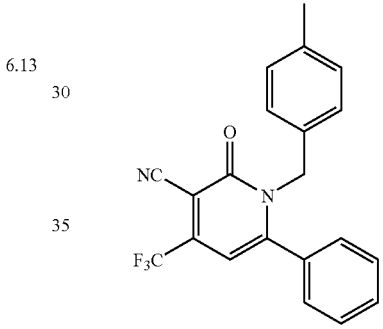

6.16

1-(4-Methyl-benzyl)-6-(1-methylene-but-2-enyl)-2-
oxo-4-trifluoromethyl-1,2-dihydro-pyridine-3-carbo-
nitrile $^1$H-NMR (CDCl$_3$): δ7.58-7.51 (m, 1H), 7.49-7.43 (m, 2H), 7.20 (d, J=7.3 Hz, 2H), 7.03 (d, J=8.1 Hz, 2H), 6.78 (d, J=7.8 Hz, 2H), 6.38 (s, 1H), 5.22 (s, 2H), 2.29 (s, 3H), 1.54 (s, 3H).

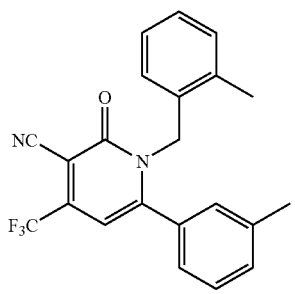

6.17

141

1-(2-Methyl-benzyl)-2-oxo-6-m-tolyl-4-trifluorom-
ethyl-1,2-dihydro-pyridine-3-carbonitrile

MS(ES+): 383.0 (M+H)

6.18

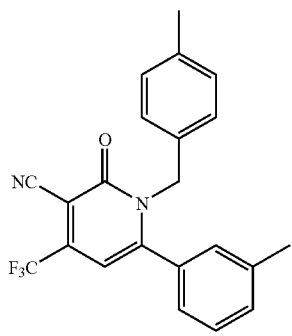

1-(4-Methyl-benzyl)-2-oxo-6-m-tolyl-4-trifluorom-
ethyl-1,2-dihydro-pyridine-3-carbonitrile $^1$H-NMR (CDCl$_3$): δ7.36-7.33 (m, 2H), 7.06-6.98 (m, 3H), 6.93 (bs, 1H), 6.79 (d, J=7.8 Hz, 2H), 6.37 (s, 1H), 5.20 (bs, 2H), 2.34 (s, 3H), 2.30 (s, 3H).

6.19

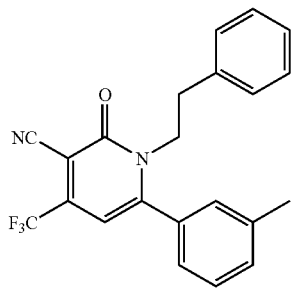

2-Oxo-1-phenethyl-6-m-tolyl-4-trifluoromethyl-1,2-
dihydro-pyridine-3-carbonitrile $^1$H-NMR (CDCl$_3$): δ7.40-7.33 (m, 2H), 7.23-7.18 (m, 3H), 6.97-6.93 (m, 1H), 6.89-6.83 (m, 3H), 6.31 (s, 1H), 4.23-4.16 (m, 2H), 2.97-2.90 (m, 2H), 2.40 (s, 3H).

6.20

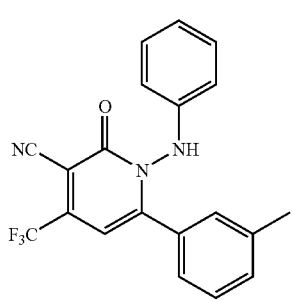

142

2-Oxo-1-phenylamino-6-m-tolyl-4-trifluoromethyl-
1,2-dihydro-pyridine-3-carbonitrile $^1$H-NMR (CDCl$_3$): δ7.91-7.84 (m, 1H), 7.47 (s, 1H), 7.38-7.32 (m, 2H), 7.18 (t, J=7.6 Hz, 2H), 6.97 (t, J=7.3 Hz, 1H), 6.62-6.56 (m, 3H), 2.35 (s, 3H).

6.21

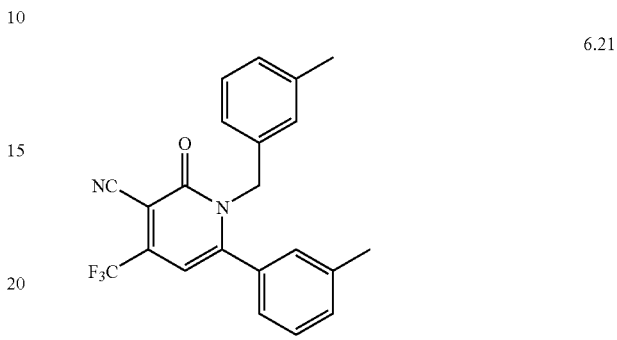

1-(3-Methyl-benzyl)-2-oxo-6-m-tolyl-4-trifluorom-
ethyl-1,2-dihydro-pyridine-3-carbonitrile

MS(ES+): 383.0 (M+H)

6.22

4-Methyl-1-(2-methyl-benzyl)-2-oxo-6-phenyl-1,2-
dihydro-pyridine-3-carbonitrile

MS(ES+): 315.0 (M+H)

6.23

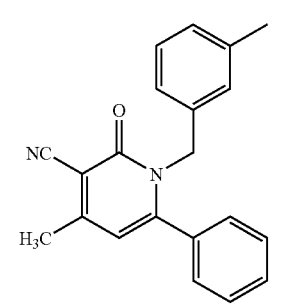

143

4-Methyl-1-(3-methyl-benzyl)-2-oxo-6-phenyl-1,2-dihydro-pyridine-3-carbonitrile

MS(ES+): 315.1 (M+H)

6.24

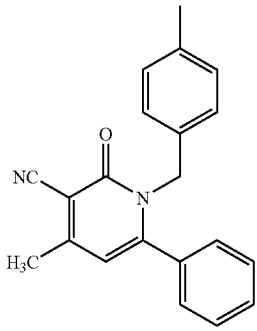

4-Methyl-1-(4-methyl-benzyl)-2-oxo-6-phenyl-1,2-dihydro-pyridine-3-carbonitrile

MS(ES+): 315.0 (M+H)

6.25

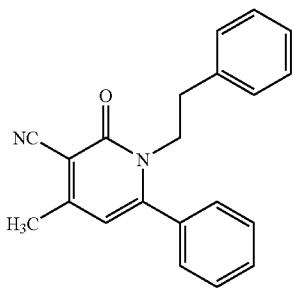

4-Methyl-2-oxo-1-phenethyl-6-phenyl-1,2-dihydro-pyridine-3-carbonitrile

MS(ES+): 315.2 (M+H)

6.26

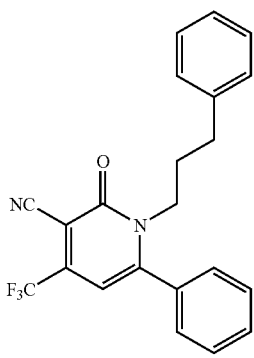

144

2-Oxo-6-phenyl-1-(3-phenyl-propyl)-4-trifluoromethyl-1,2-dihydro-pyridine-3-carbonitrile

MS(ES+): 383.3 (M+H)

6.27

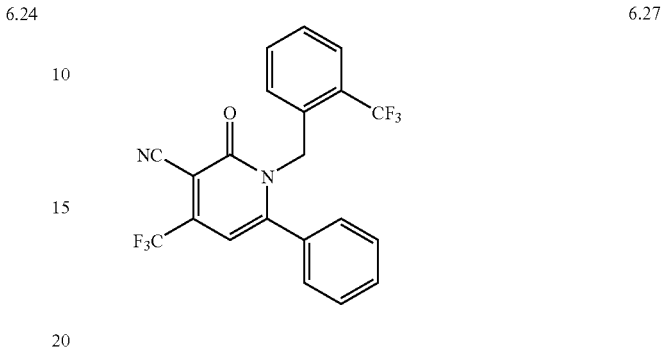

2-Oxo-6-phenyl-4-trifluoromethyl-1-(2-trifluoromethyl-benzyl)-1,2-dihydro-pyridine-3-carbonitrile $^1$H-NMR (CDCl$_3$): δ7.64-7.32 (m, 6H), 7.07 (d, J=6.8 Hz, 2H), 6.93 (d, J=7.8 Hz, 1H), 6.50 (s, 1H), 5.37 (s, 2H).

6.28

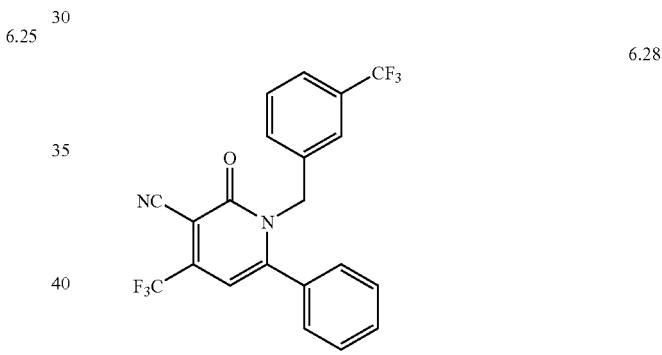

2-Oxo-6-phenyl-4-trifluoromethyl-1-(3-trifluoromethyl-benzyl)-1,2-dihydro-pyridine-3-carbonitrile

MS(ES+): 422.8 (M+H)

6.29

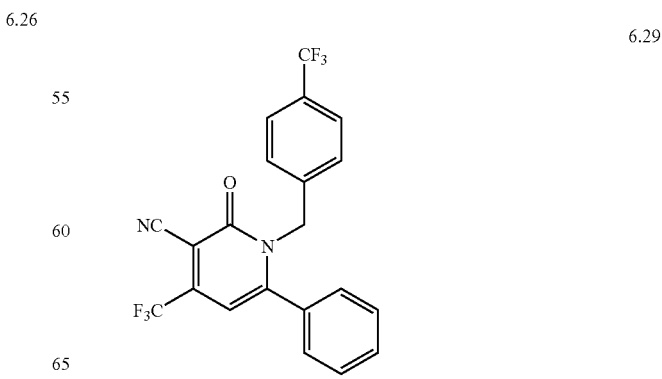

145

2-Oxo-6-phenyl-4-trifluoromethyl-1-(4-trifluoromethyl-benzyl)-1,2-dihydro-pyridine-3-carbonitrile

MS(ES+): 422.8 (M+H)

6.30

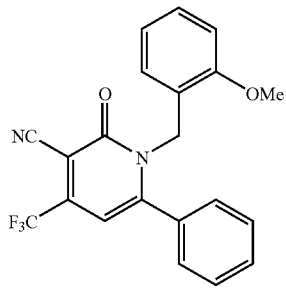

1-(2-Methoxy-benzyl)-2-oxo-6-phenyl-4-trifluoromethyl-1,2-dihydro-pyridine-3-carbonitrile

MS(ES+): 383.3 (M+H)

6.31

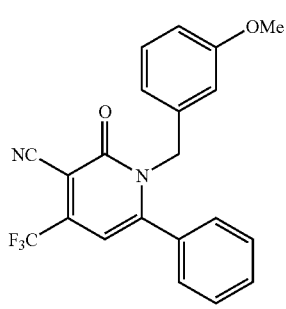

1-(3-Methoxy-benzyl)-2-oxo-6-phenyl-4-trifluoromethyl-1,2-dihydro-pyridine-3-carbonitrile

MS(ES+): 384.9 (M+H)

6.32

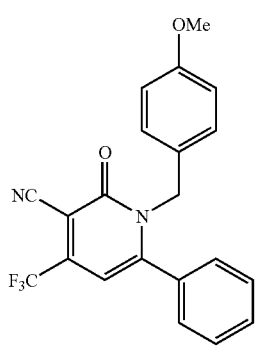

146

1-(4-Methoxy-benzyl)-2-oxo-6-phenyl-4-trifluoromethyl-1,2-dihydro-pyridine-3-carbonitrile

MS(ES+): 385.3 (M+H)

6.33

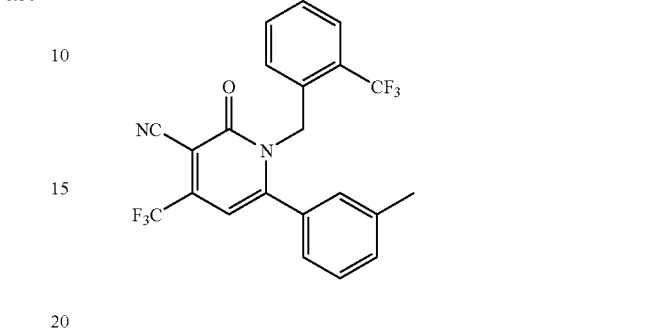

2-Oxo-6-m-tolyl-4-trifluoromethyl-1-(2-trifluoromethyl-benzyl)-1,2-dihydro-pyridine-3-carbonitrile MS(ES+): 459.2 (M+Na)

6.34

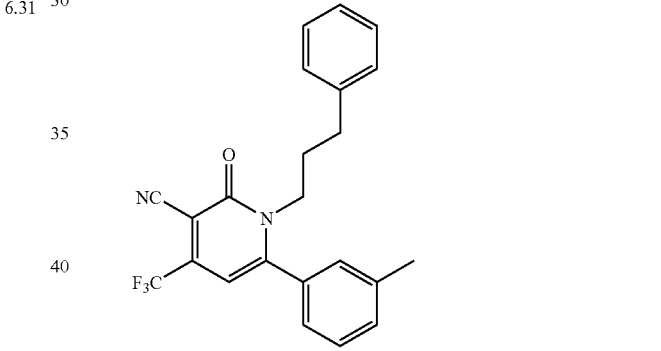

2-Oxo-1-(3-phenyl-propyl)-6-m-tolyl-4-trifluoromethyl-1,2-dihydro-pyridine-3-carbonitrile

MS(ES+): 397.0 (M+H)

6.35

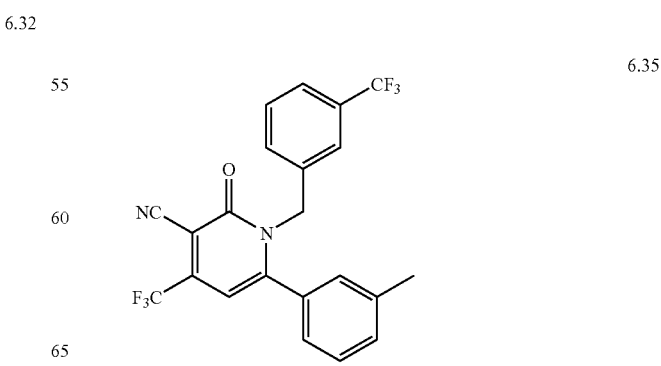

2-Oxo-6-m-tolyl-4-trifluoromethyl-1-(3-trifluoromethyl-benzyl)-1,2-dihydro-pyridine-3-carbonitrile

MS(ES+): 438.0 (M+H)

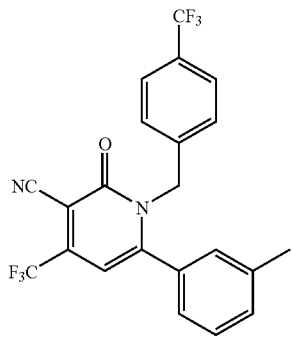

2-Oxo-6-m-tolyl-4-trifluoromethyl-1-(4-trifluoromethyl-benzyl)-1,2-dihydro-pyridine-3-carbonitrile

MS(ES+): 437.0 (M+H)

1-(2-Methoxy-benzyl)-2-oxo-6-m-tolyl-4-trifluoromethyl-1,2-dihydro-pyridine-3-carbonitrile MS(ES+): 420.8 (M+Na)

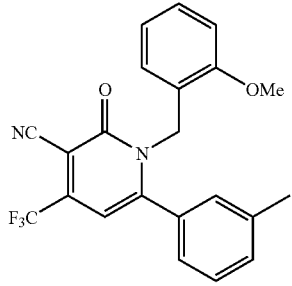

1-(3-Methoxy-benzyl)-2-oxo-6-m-tolyl-4-trifluoromethyl-1,2-dihydro-pyridine-3-carbonitrile

MS(ES+): 398.8 (M+H)

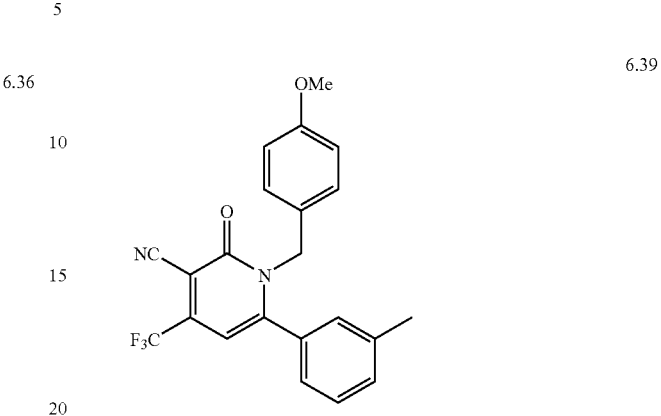

1-(4-Methoxy-benzyl)-2-oxo-6-m-tolyl-4-trifluoromethyl-1,2-dihydro-pyridine-3-carbonitrile MS(ES+): 421.0 (M+Na)

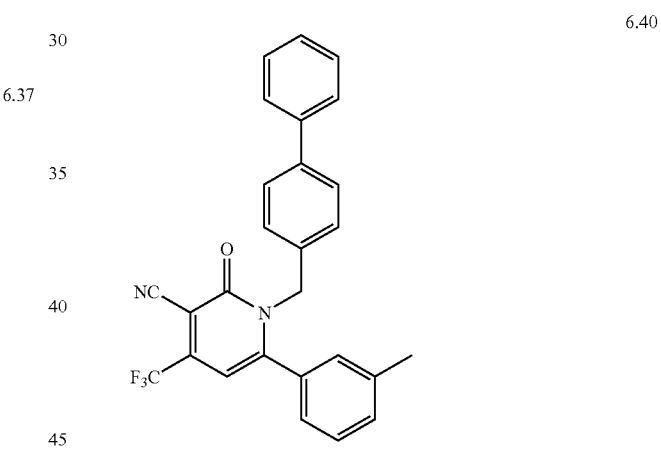

1-Biphenyl-4-ylmethyl-2-oxo-6-m-tolyl-4-trifluoromethyl-1,2-dihydro-pyridine-3-carbonitrile MS(ES+): 467.0 (M+Na)

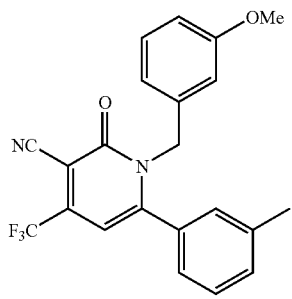

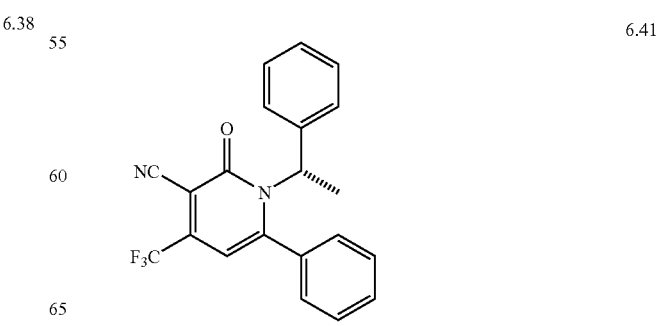

149

2-Oxo-6-phenyl-1-(1-phenyl-ethyl)-4-trifluoromethyl-1,2-dihydro-pyridine-3-carbonitrile

MS(ES+): 369.3 (M+H)

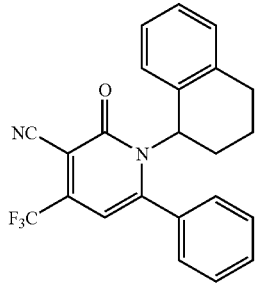

2-Oxo-6-phenyl-1-(1,2,3,4-tetrahydro-naphthalen-1-yl)-4-trifluoromethyl-1,2-dihydro-pyridine-3-carbonitrile

MS(ES+): 395.0 (M+H)

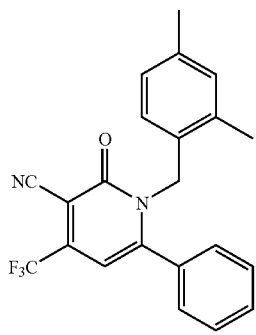

1-(2,4-Dimethyl-benzyl)-2-oxo-6-phenyl-4-trifluoromethyl-1,2-dihydro-pyridine-3-carbonitrile MS(ES+): 405.2 (M+Na)

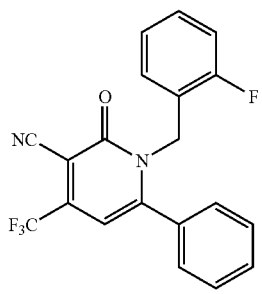

150

1-(2-Fluoro-benzyl)-2-oxo-6-phenyl-4-trifluoromethyl-1,2-dihydro-pyridine-3-carbonitrile

MS(ES+): 373.0 (M+H)

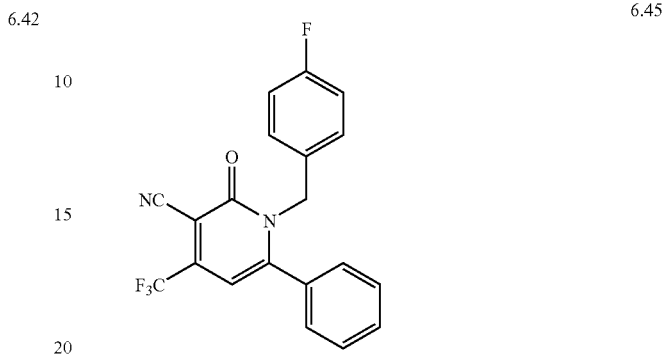

1-(4-Fluoro-benzyl)-2-oxo-6-phenyl-4-trifluoromethyl-1,2-dihydro-pyridine-3-carbonitrile

MS(ES+): 373.0 (M+H)

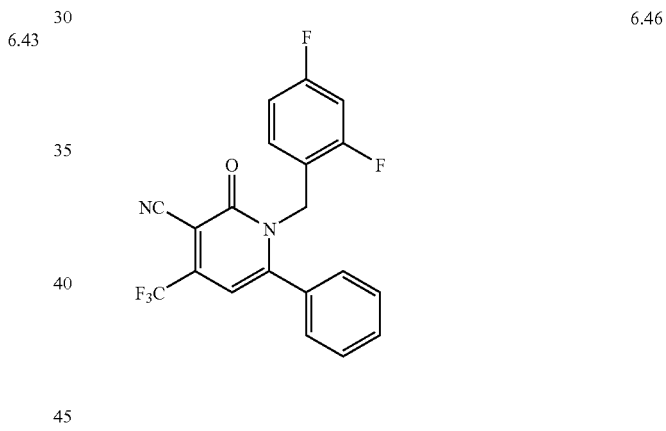

1-(2,4-Difluoro-benzyl)-2-oxo-6-phenyl-4-trifluoromethyl-1,2-dihydro-pyridine-3-carbonitrile

MS(ES+): 390.8 (M+H)

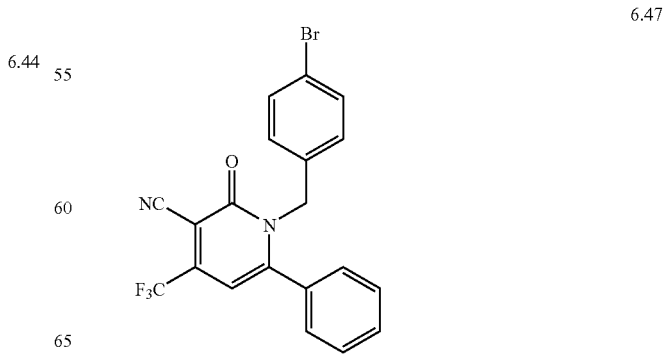

151

1-(4-Bromo-benzyl)-2-oxo-6-phenyl-4-trifluoromethyl-1,2-dihydro-pyridine-3-carbonitrile

MS(ES+): 435.0 (M+H)

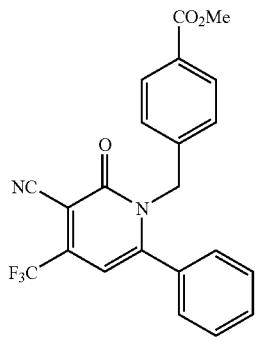

4-(3-Cyano-2-oxo-6-phenyl-4-trifluoromethyl-2H-pyridin-1-ylmethyl)-benzoic Acid Methyl Ester

MS(ES+): 413.2 (M+H)

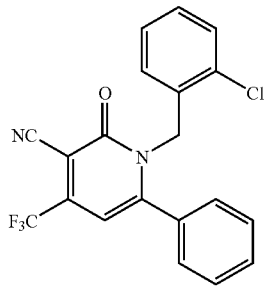

1-(2-Chloro-benzyl)-2-oxo-6-phenyl-4-trifluoromethyl-1,2-dihydro-pyridine-3-carbonitrile

MS(ES+): 389.0 (M+H)

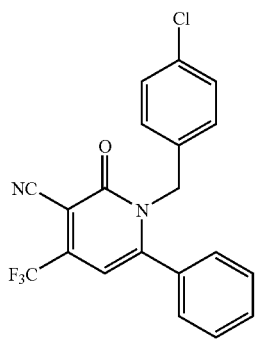

152

1-(4-Chloro-benzyl)-2-oxo-6-phenyl-4-trifluoromethyl-1,2-dihydro-pyridine-3-carbonitrile

MS(ES+): 389.0 (M+H)

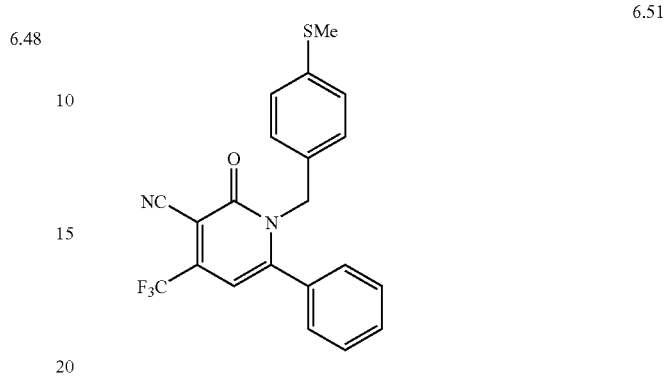

1-(4-Methylsulfanyl-benzyl)-2-oxo-6-phenyl-4-trifluoromethyl-1,2-dihydro-pyridine-3-carbonitrile MS(ES+): 423.0 (M+Na)

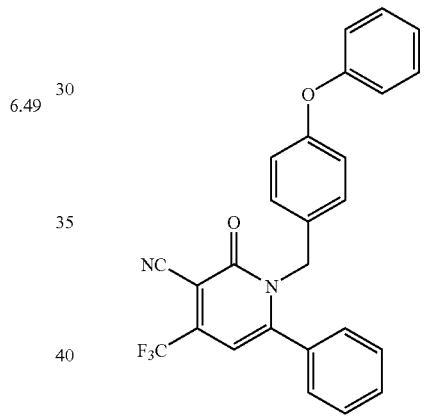

2-Oxo-1-(4-phenoxy-benzyl)-6-phenyl-4-trifluoromethyl-1,2-dihydro-pyridine-3-carbonitrile $^1$H-NMR (CDCl$_3$): δ7.59-7.53 (m, 1H), 7.48 (t, J=7.8 Hz, 2H), 7.37-7.30 (m, 2H), 7.25-7.20 (m, 2H), 7.15-7.09 (m, 1H), 7.00-6.95 (m, 2H), 6.88-6.81 (m, 4H), 6.39 (s, 1H), 5.24 (s, 2H).

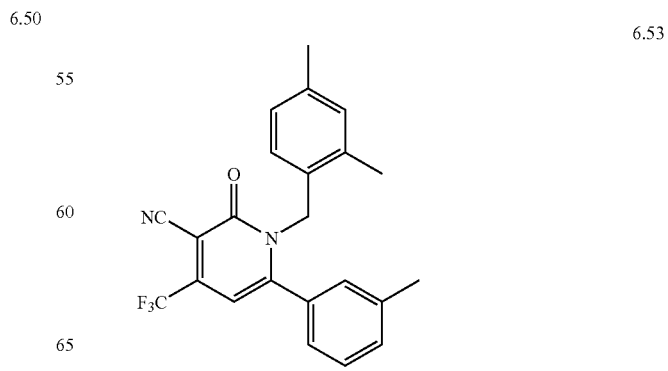

153

1-(2,4-Dimethyl-benzyl)-2-oxo-6-m-tolyl-4-trifluoromethyl-1,2-dihydro-pyridine-3-carbonitrile

MS(ES+): 397.0 (M+H)

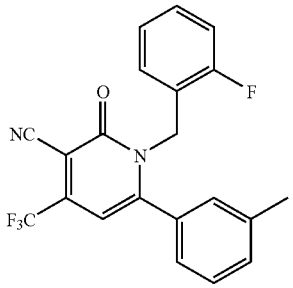

1-(2-Fluoro-benzyl)-2-oxo-6-m-tolyl-4-trifluoromethyl-1,2-dihydro-pyridine-3-carbonitrile

MS(ES+): 387.0 (M+H)

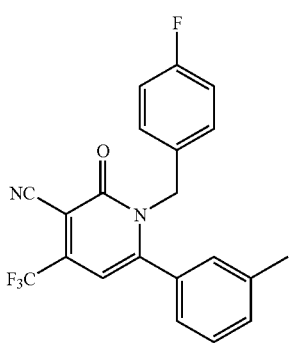

1-(4-Fluoro-benzyl)-2-oxo-6-m-tolyl-4-trifluoromethyl-1,2-dihydro-pyridine-3-carbonitrile

MS(ES+): 387.0 (M+H)

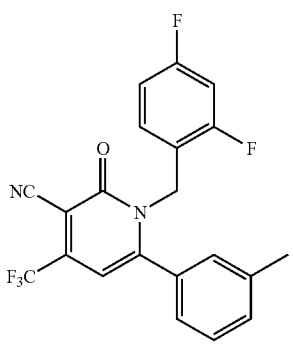

154

1-(2,4-Difluoro-benzyl)-2-oxo-6-m-tolyl-4-trifluoromethyl-1,2-dihydro-pyridine-3-carbonitrile

MS(ES+): 405.0 (M+H)

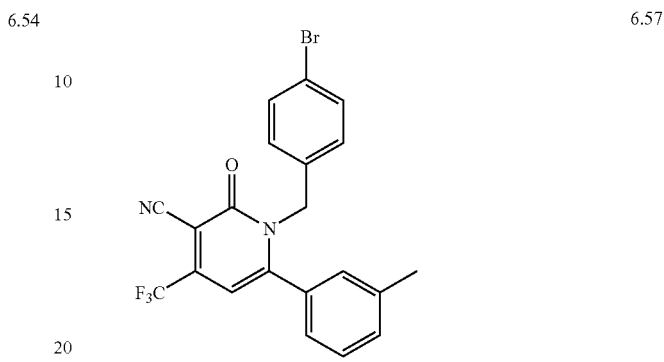

1-(4-Bromo-benzyl)-2-oxo-6-m-tolyl-4-trifluoromethyl-1,2-dihydro-pyridine-3-carbonitrile

MS(ES+): 449.0 (M+H)

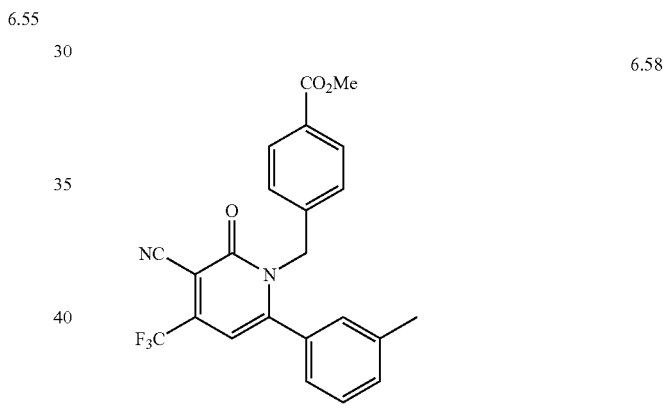

4-(3-Cyano-2-oxo-6-m-tolyl-4-trifluoromethyl-2H-pyridin-1-ylmethyl)-benzoic Acid Methyl Ester

MS(ES+): 427.2 (M+H)

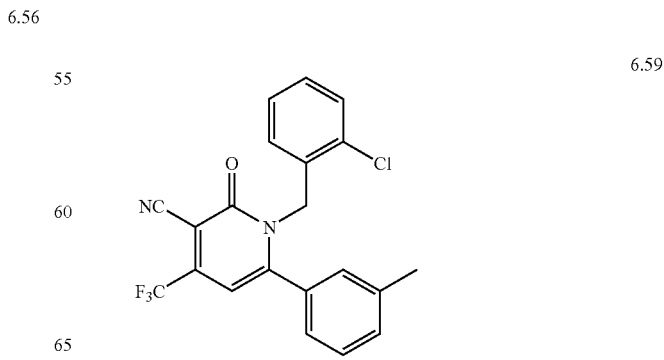

1-(2-Chloro-benzyl)-2-oxo-6-m-tolyl-4-trifluoromethyl-1,2-dihydro-pyridine-3-carbonitrile

MS(ES+): 403.0 (M+H)

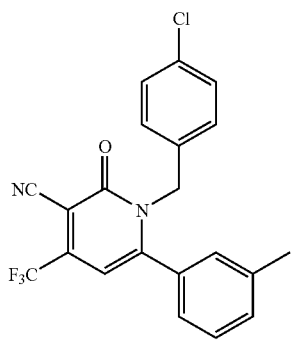

1-(4-Chloro-benzyl)-2-oxo-6-m-tolyl-4-trifluoromethyl-1,2-dihydro-pyridine-3-carbonitrile

MS(ES+): 402.8 (M+H)

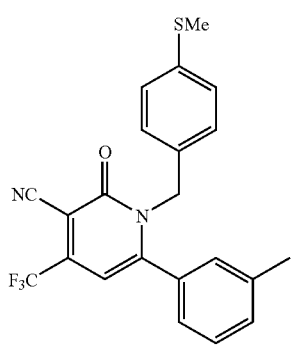

1-(4-Methylsulfanyl-benzyl)-2-oxo-6-m-tolyl-4-trifluoromethyl-1,2-dihydro-pyridine-3-carbonitrile MS(ES+): 437.2 (M+Na)

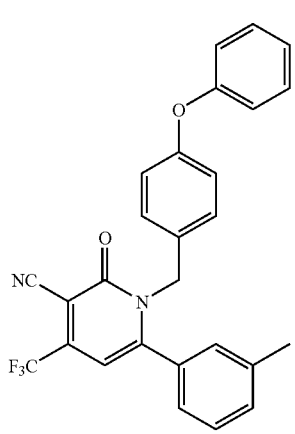

2-Oxo-1-(4-phenoxy-benzyl)-6-m-tolyl-4-trifluoromethyl-1,2-dihydro-pyridine-3-carbonitrile $^1$H-NMR (CDCl$_3$): δ7.40-7.30 (m, 4H), 7.14-7.09 (m, 1H), 7.05-6.94 (m, 4H), 6.90-6.83 (m, 4H), 6.39 (s, 1H), 5.22 (s, 2H), 2.36 (s, 3H).

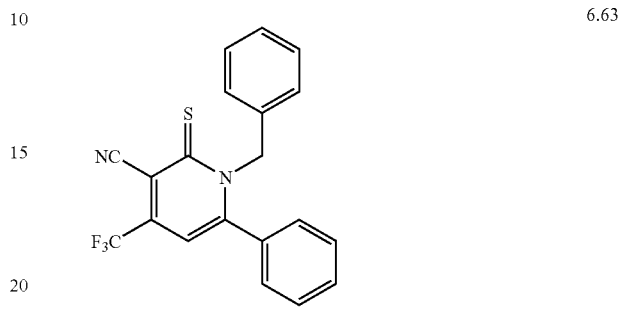

1-Benzyl-6-phenyl-2-thioxo-4-trifluoromethyl-1,2-dihydro-pyridine-3-carbonitrile

MS(ES+): 370.9 (M+H)

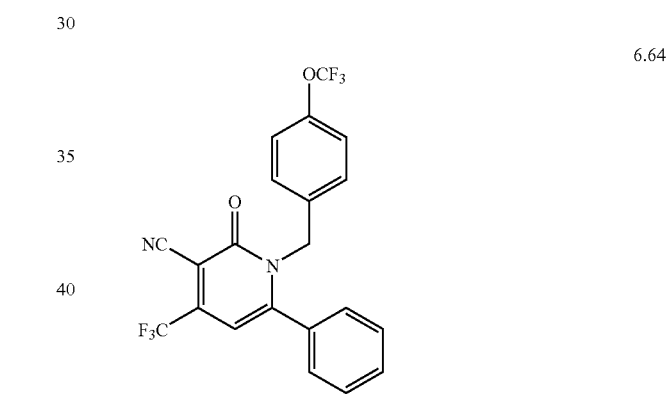

2-Oxo-6-phenyl-1-(4-trifluoromethoxy-benzyl)-4-trifluoromethyl-1,2-dihydro-pyridine-3-carbonitrile

MS(ES+): 439.2 (M+H)

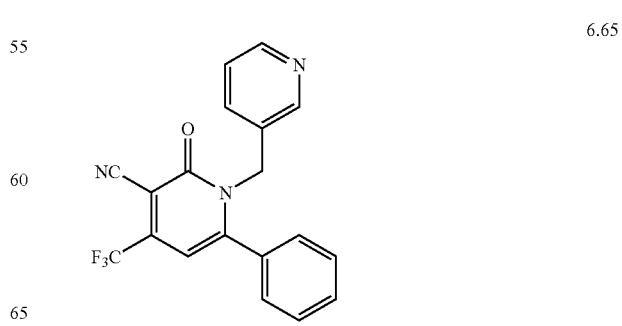

157

2-Oxo-6-phenyl-1-pyridin-3-ylmethyl-4-trifluoromethyl-1,2-dihydro-pyridine-3-carbonitrile

MS(ES+): 355.8 (M+H)

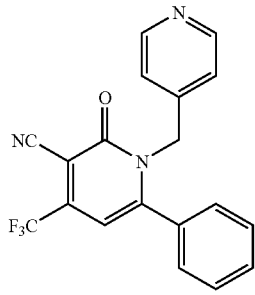

2-Oxo-6-phenyl-1-pyridin-4-ylmethyl-4-trifluoromethyl-1,2-dihydro-pyridine-3-carbonitrile

MS(ES+): 355.8 (M+H)

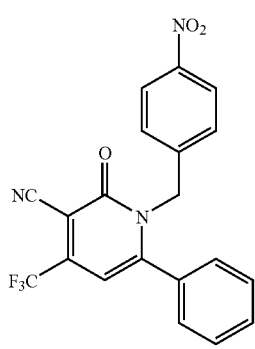

1-(4-Nitro-benzyl)-2-oxo-6-phenyl-4-trifluoromethyl-1,2-dihydro-pyridine-3-carbonitrile

MS(ES+): 400.0 (M+H)

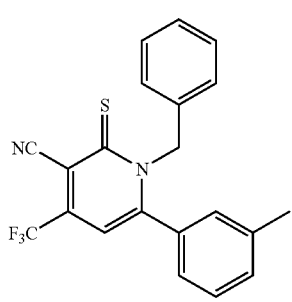

158

1-Benzyl-2-thioxo-6-m-tolyl-4-trifluoromethyl-1,2-dihydro-pyridine-3-carbonitrile

MS(ES+): 385.3 (M+H)

6.66

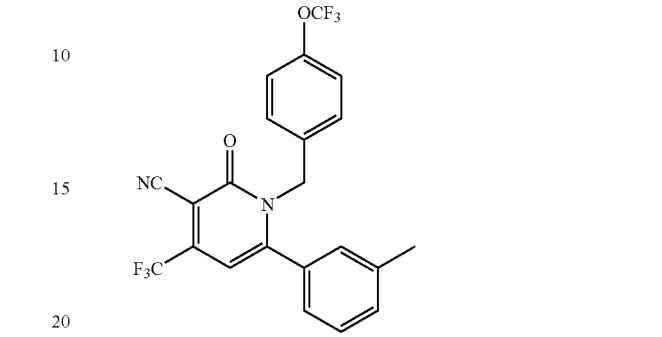

2-Oxo-6-m-tolyl-1-(4-trifluoromethoxy-benzyl)-4-trifluoromethyl-1,2-dihydro-pyridine-3-carbonitrile

MS(ES+): 453.0 (M+H)

6.69

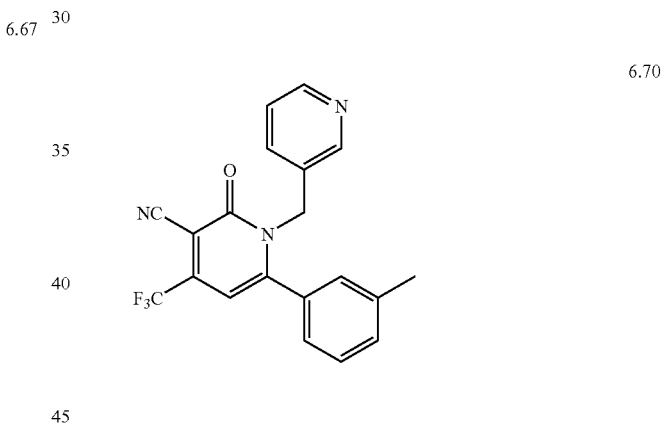

2-Oxo-1-pyridin-3-ylmethyl-6-m-tolyl-4-trifluoromethyl-1,2-dihydro-pyridine-3-carbonitrile

MS(ES+): 369.8 (M+H)

6.67

6.68

6.70

6.71

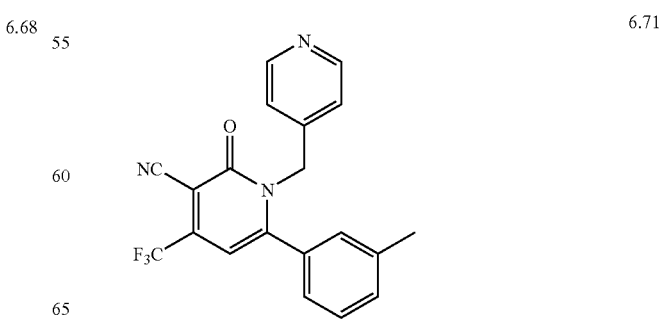

159

2-Oxo-1-pyridin-4-ylmethyl-6-m-tolyl-4-trifluoromethyl-1,2-dihydro-pyridine-3-carbonitrile

MS(ES+): 369.8 (M+H)

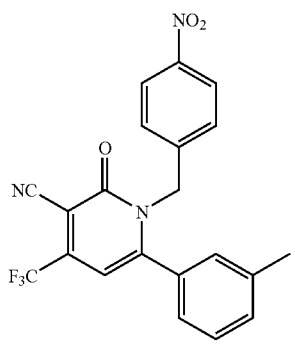

1-(4-Nitro-benzyl)-2-oxo-6-m-tolyl-4-trifluoromethyl-1,2-dihydro-pyridine-3-carbonitrile

MS(ES+): 414.0 (M+H)

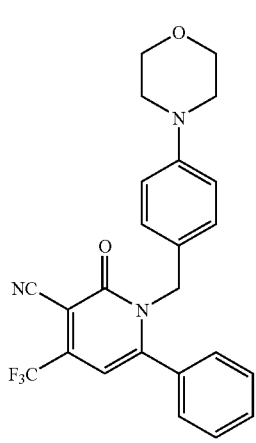

1-(4-Morpholin-4-yl-benzyl)-2-oxo-6-phenyl-4-trifluoromethyl-1,2-dihydro-pyridine-3-carbonitrile

MS(ES+): 440.2 (M+H)

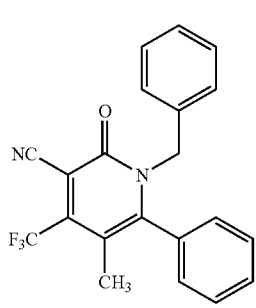

160

1-Benzyl-5-methyl-2-oxo-6-phenyl-4-trifluoromethyl-1,2-dihydro-pyridine-3-carbonitrile

MS(ES+): 369.0 (M+H)

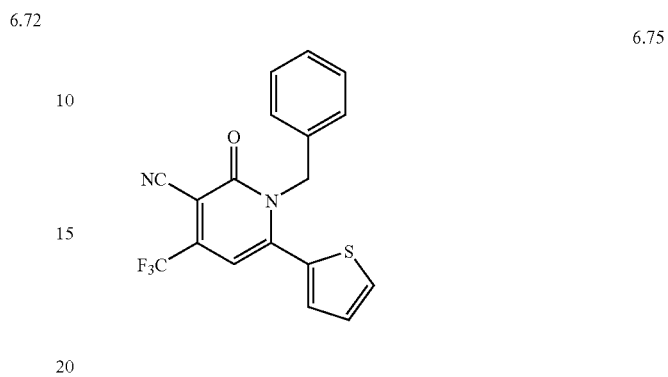

1-Benzyl-2-oxo-6-thiophen-2-yl-4-trifluoromethyl-1,2-dihydro-pyridine-3-carbonitrile MS(ES+): 383.0 (M+Na)

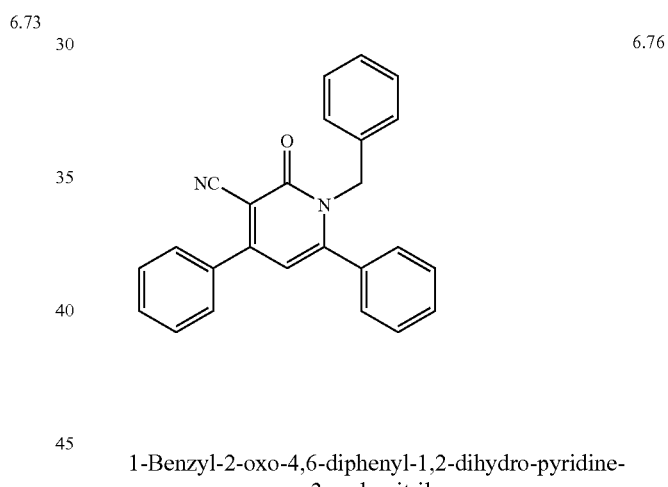

1-Benzyl-2-oxo-4,6-diphenyl-1,2-dihydro-pyridine-3-carbonitrile

MS(ES+): 385.2 (M+Na)

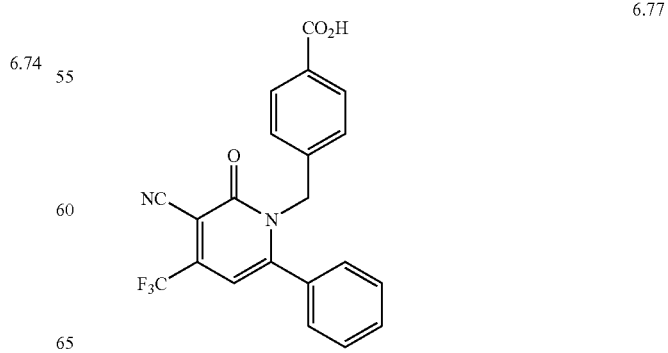

161

4-(3-Cyano-2-oxo-6-phenyl-4-trifluoromethyl-2H-pyridin-1-ylmethyl)-benzoic Acid

MS(ES+): 399.4 (M+H)

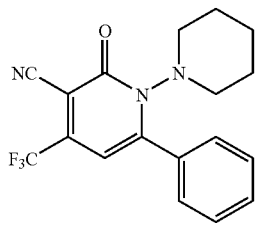

2-Oxo-6-phenyl-4-trifluoromethyl-3',4',5',6'-tetrahydro-2H, 2'H-[1,1']bipyridinyl-3-carbonitrile

MS(ES+): 348.0 (M+H)

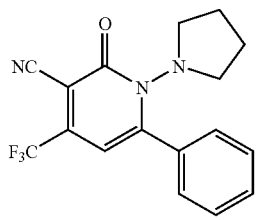

2-Oxo-6-phenyl-1-pyrrolidin-1-yl-4-trifluoromethyl-1,2-dihydro-pyridine-3-carbonitrile

MS(ES+): 334.0 (M+H)

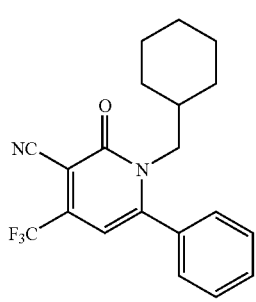

162

1-Cyclohexylmethyl-2-oxo-6-phenyl-4-trifluoromethyl-1,2-dihydro-pyridine-3-carbonitrile

MS(ES+): 361.0 (M+H)

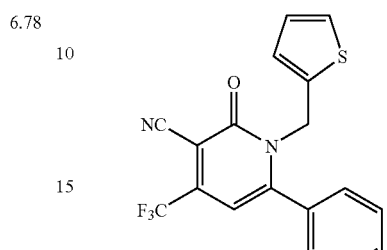

2-Oxo-6-phenyl-1-thiophen-2-ylmethyl-4-trifluoromethyl-1,2-dihydro-pyridine-3-carbonitrile

MS(ES+): 361.1 (M+H)

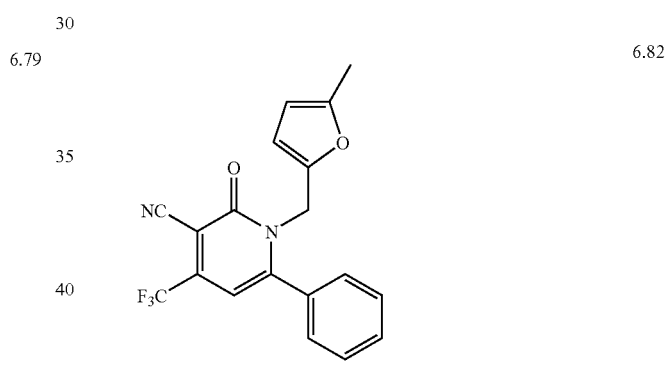

1-(5-Methyl-furan-2-ylmethyl)-2-oxo-6-phenyl-4-trifluoromethyl-1,2-dihydro-pyridine-3-carbonitrile MS(ES+): 381.0 (M+Na)

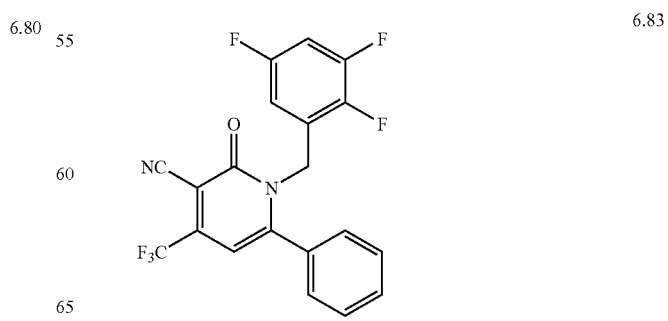

2-Oxo-6-phenyl-1-(2,3,5-trifluoro-benzyl)-4-trifluoromethyl-1,2-dihydro-pyridine-3-carbonitrile

MS(ES+): 409.2 (M+H)

6.84

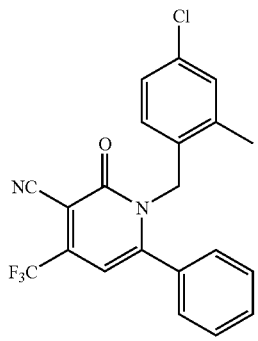

1-(4-Chloro-2-methyl-benzyl)-2-oxo-6-phenyl-4-trifluoromethyl-1,2-dihydro-pyridine-3-carbonitrile

MS(ES+): 403.0 (M+H)

6.85

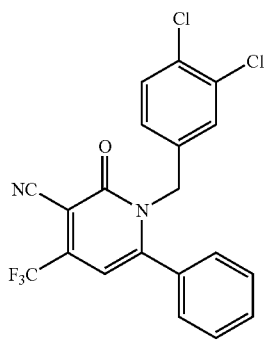

1-(3,4-Dichloro-benzyl)-2-oxo-6-phenyl-4-trifluoromethyl-1,2-dihydro-pyridine-3-carbonitrile

MS(ES+): 423.0 (M+H)

6.86

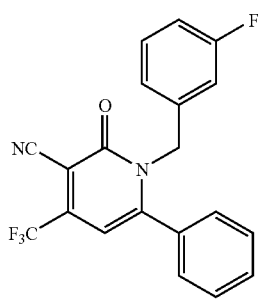

1-(3-Fluoro-benzyl)-2-oxo-6-phenyl-4-trifluoromethyl-1,2-dihydro-pyridine-3-carbonitrile

MS(ES+): 373.0 (M+H)

6.87

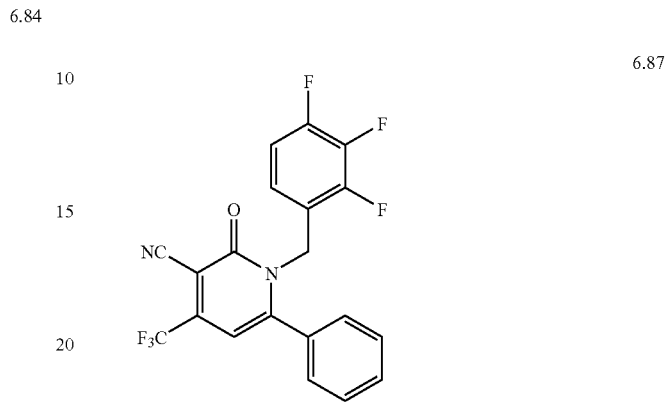

2-Oxo-6-phenyl-1-(2,3,4-trifluoro-benzyl)-4-trifluoromethyl-1,2-dihydro-pyridine-3-carbonitrile

MS(ES+): 409.2 (M+H)

6.88

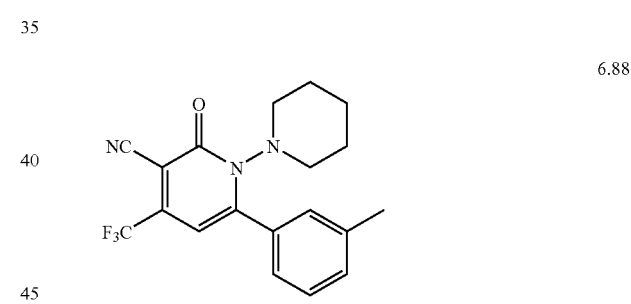

2-Oxo-6-m-tolyl-4-trifluoromethyl-3',4',5',6'-tetrahydro-2H,2'H-[1,1']bipyridinyl-3-carbonitrile

MS(ES+): 362.0 (M+H)

6.89

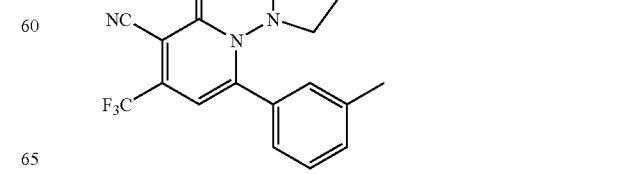

165

2-Oxo-1-pyrrolidin-1-yl-6-m-tolyl-4-trifluoromethyl-1,2-dihydro-pyridine-3-carbonitrile

MS(ES+): 348.0 (M+H)

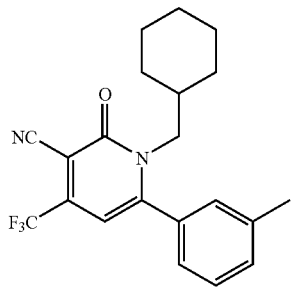

1-Cyclohexylmethyl-2-oxo-6-m-tolyl-4-trifluoromethyl-1,2-dihydro-pyridine-3-carbonitrile

MS(ES+): 375.0 (M+H)

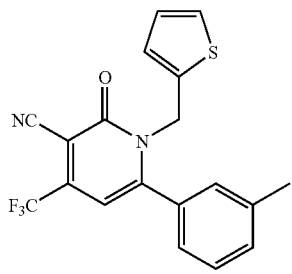

2-Oxo-1-thiophen-2-ylmethyl-6-m-tolyl-4-trifluoromethyl-1,2-dihydro-pyridine-3-carbonitrile

MS(ES+): 375.0 (M+H)

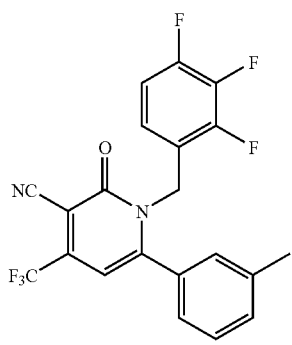

166

2-Oxo-6-m-tolyl-1-(2,3,4-trifluoro-benzyl)-4-trifluoromethyl-1,2-dihydro-pyridine-3-carbonitrile

MS(ES+): 423.0 (M+H)

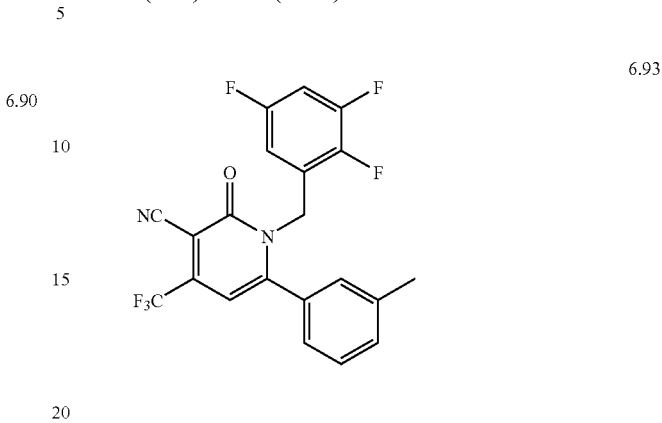

2-Oxo-6-m-tolyl-1-(2,3,5-trifluoro-benzyl)-4-trifluoromethyl-1,2-dihydro-pyridine-3-carbonitrile

MS(ES+): 423.0 (M+H)

1-(4-Chloro-2-methyl-benzyl)-2-oxo-6-m-tolyl-4-trifluoromethyl-1,2-dihydro-pyridine-3-carbonitrile

MS(ES+): 417.0 (M+H)

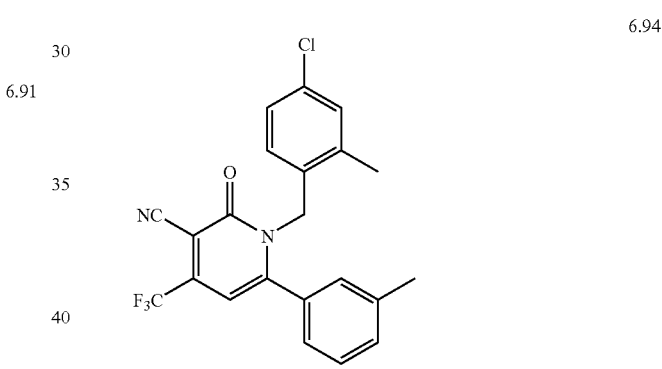

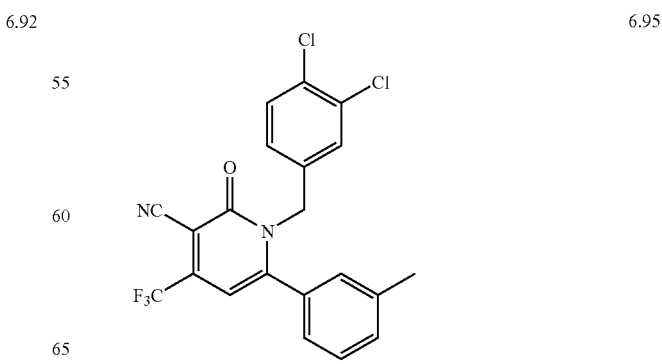

167

1-(3,4-Dichloro-benzyl)-2-oxo-6-m-tolyl-4-trifluoromethyl-1,2-dihydro-pyridine-3-carbonitrile

MS(ES+): 437.0 (M+H)

6.96

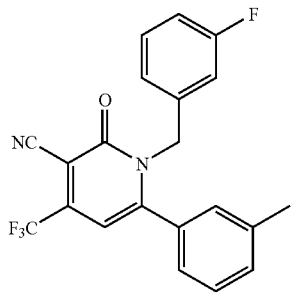

1-(3-Fluoro-benzyl)-2-oxo-6-m-tolyl-4-trifluoromethyl-1,2-dihydro-pyridine-3-carbonitrile

MS(ES+): 387.0 (M+H)

6.97

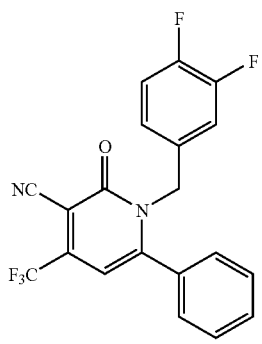

1-(3,4-Difluoro-benzyl)-2-oxo-6-phenyl-4-trifluoromethyl-1,2-dihydro-pyridine-3-carbonitrile

MS(ES+): 390.8 (M+H)

6.98

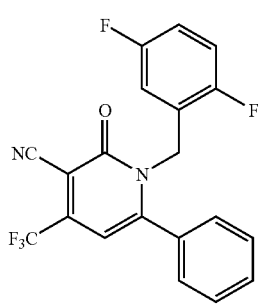

168

1-(2,5-Difluoro-benzyl)-2-oxo-6-phenyl-4-trifluoromethyl-1,2-dihydro-pyridine-3-carbonitrile

MS(ES+): 390.8 (M+H)

6.99

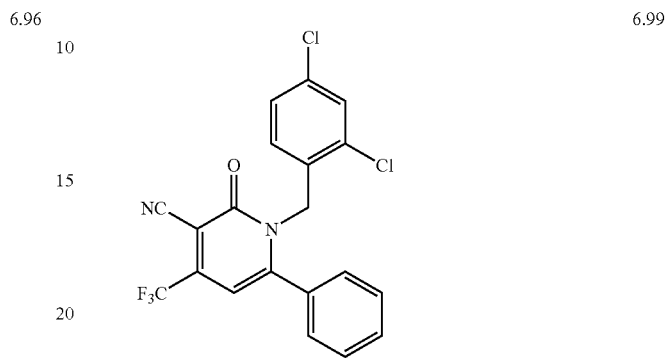

1-(2,4-Dichloro-benzyl)-2-oxo-6-phenyl-4-trifluoromethyl-1,2-dihydro-pyridine-3-carbonitrile

MS(ES+): 423.0 (M+H)

6.100

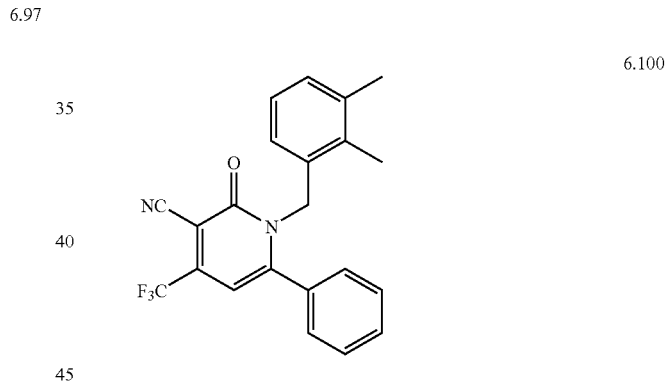

1-(2,3-Dimethyl-benzyl)-2-oxo-6-phenyl-4-trifluoromethyl-1,2-dihydro-pyridine-3-carbonitrile

MS(ES+): 383.2 (M+H)

6.101

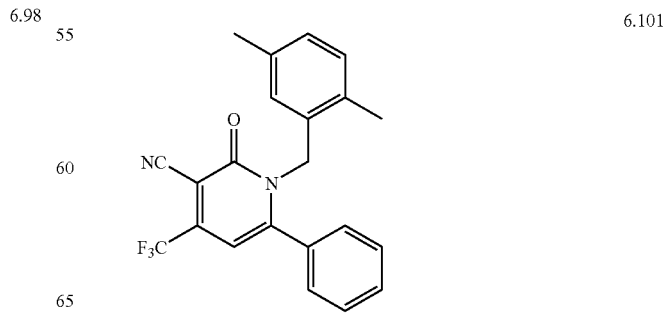

169

1-(2,5-Dimethyl-benzyl)-2-oxo-6-phenyl-4-trifluoromethyl-1,2-dihydro-pyridine-3-carbonitrile

MS(ES+): 383.0 (M+H)

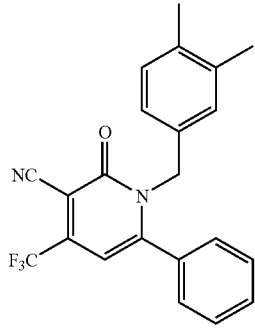

1-(3,4-Dimethyl-benzyl)-2-oxo-6-phenyl-4-trifluoromethyl-1,2-dihydro-pyridine-3-carbonitrile

MS(ES+): 383.2 (M+H)

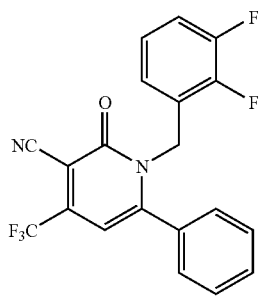

1-(2,3-Difluoro-benzyl)-2-oxo-6-phenyl-4-trifluoromethyl-1,2-dihydro-pyridine-3-carbonitrile

MS(ES+): 391.0 (M+H)

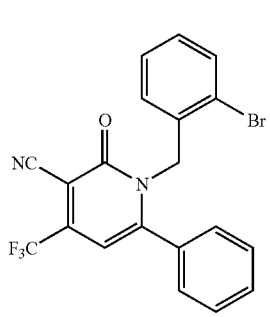

170

1-(2-Bromo-benzyl)-2-oxo-6-phenyl-4-trifluoromethyl-1,2-dihydro-pyridine-3-carbonitrile

MS(ES+): 433.0 (M+H)

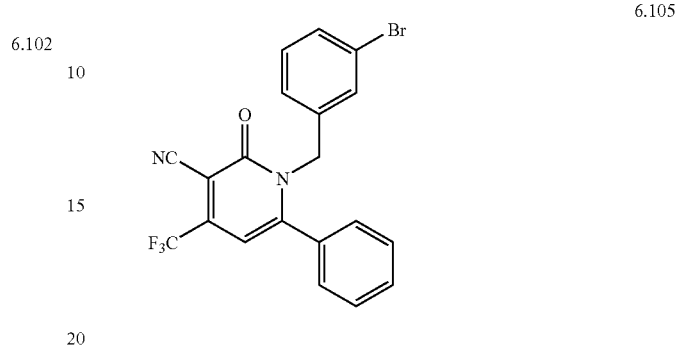

1-(3-Bromo-benzyl)-2-oxo-6-phenyl-4-trifluoromethyl-1,2-dihydro-pyridine-3-carbonitrile

MS(ES+): 435.0 (M+H)

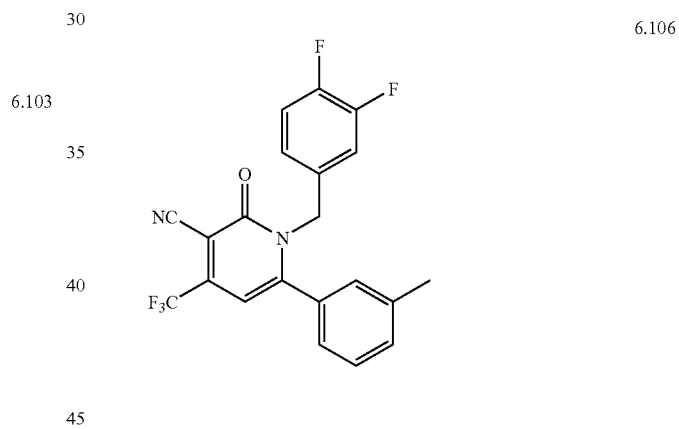

1-(3,4-Difluoro-benzyl)-2-oxo-6-m-tolyl-4-trifluoromethyl-1,2-dihydro-pyridine-3-carbonitrile

MS(ES+): 405.0 (M+H)

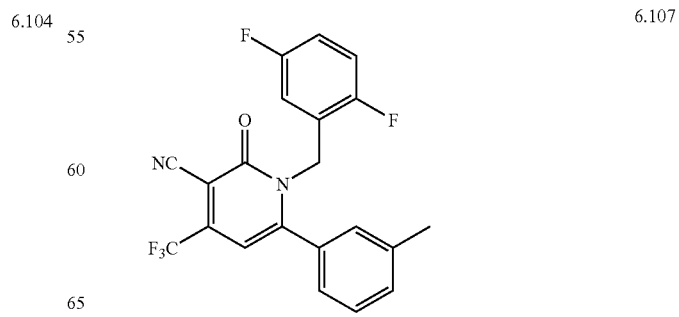

171

1-(2,5-Difluoro-benzyl)-2-oxo-6-m-tolyl-4-trifluoromethyl-1,2-dihydro-pyridine-3-carbonitrile

MS(ES+): 405.0 (M+H)

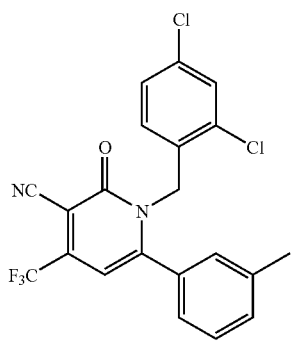

1-(2,4-Dichloro-benzyl)-2-oxo-6-m-tolyl-4-trifluoromethyl-1,2-dihydro-pyridine-3-carbonitrile

MS(ES+): 437.2 (M+H)

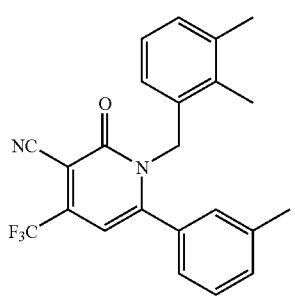

1-(2,3-Dimethyl-benzyl)-2-oxo-6-m-tolyl-4-trifluoromethyl-1,2-dihydro-pyridine-3-carbonitrile

MS(ES+): 397.0 (M+H)

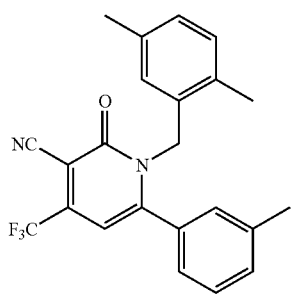

172

1-(2,5-Dimethyl-benzyl)-2-oxo-6-m-tolyl-4-trifluoromethyl-1,2-dihydro-pyridine-3-carbonitrile

MS(ES+): 397.0 (M+H)

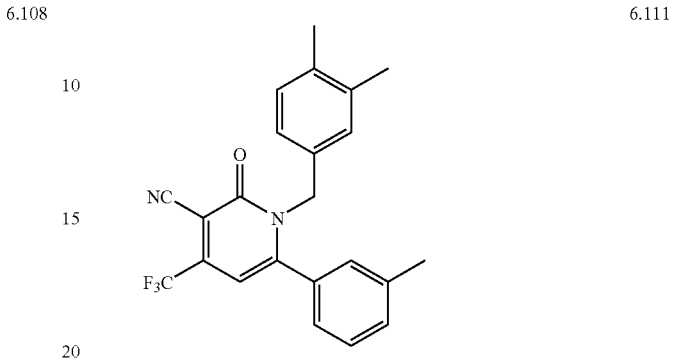

1-(3,4-Dimethyl-benzyl)-2-oxo-6-m-tolyl-4-trifluoromethyl-1,2-dihydro-pyridine-3-carbonitrile

MS(ES+): 397.0 (M+H)

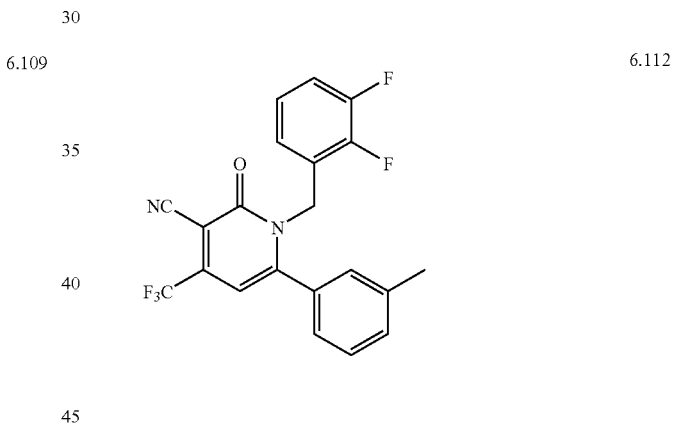

1-(2,3-Difluoro-benzyl)-2-oxo-6-m-tolyl-4-trifluoromethyl-1,2-dihydro-pyridine-3-carbonitrile

MS(ES+): 405.0 (M+H)

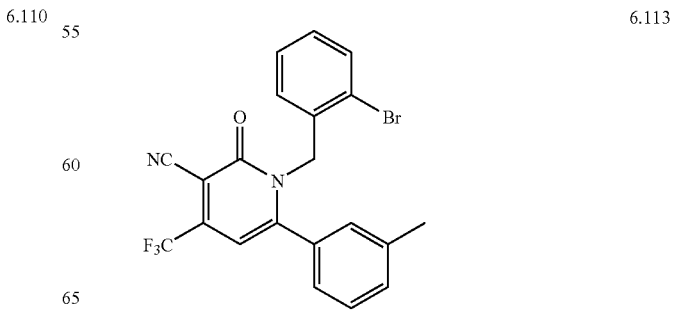

1-(2-Bromo-benzyl)-2-oxo-6-m-tolyl-4-trifluoromethyl-1,2-dihydro-pyridine-3-carbonitrile

MS(ES+): 449.1 (M+H)

1-Benzyl-2-oxo-4-pentafluoroethyl-6-phenyl-1,2-dihydro-pyridine-3-carbonitrile $^1$H-NMR (CDCl$_3$): δ7.58-7.52 (m, 1H), 7.45 (t, J=7.8 Hz, 2H), 7.26-7.16 (m, 5H), 6.92-6.86 (m, 2H), 6.32 (s, 1H), 5.26 (s, 2H).

6.114

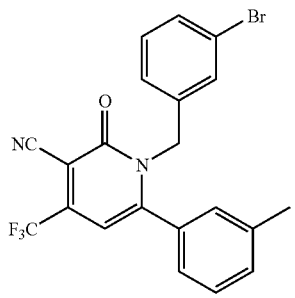

1-(3-Bromo-benzyl)-2-oxo-6-m-tolyl-4-trifluoromethyl-1,2-dihydro-pyridine-3-carbonitrile

MS(ES+): 447.0 (M+H)

6.117

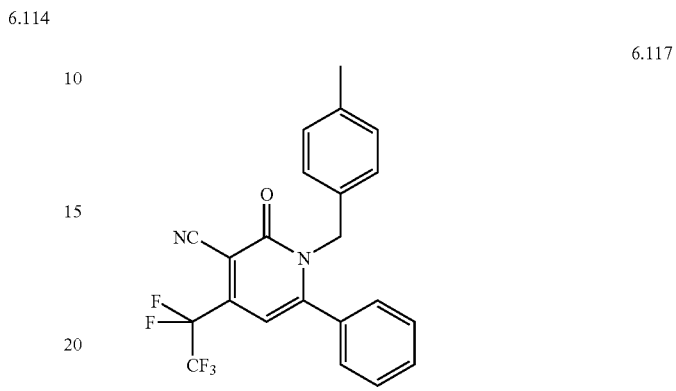

1-(4-Methyl-benzyl)-2-oxo-4-pentafluoroethyl-6-phenyl-1,2-dihydro-pyridine-3-carbonitrile

MS(ES+): 419.3 (M+H)

6.115

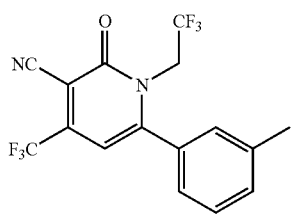

2-Oxo-6-m-tolyl-1-(2,2,2-trifluoro-ethyl)-4-trifluoromethyl-1,2-dihydro-pyridine-3-carbonitrile

MS(ES+): 347.0 (M+H)

6.118

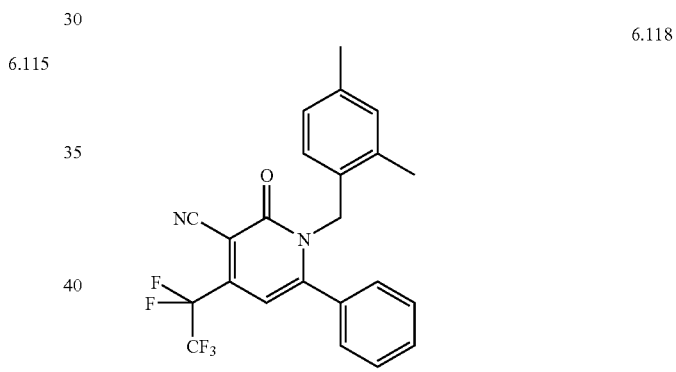

1-(2,4-Dimethyl-benzyl)-2-oxo-4-pentafluoroethyl-6-phenyl-1,2-dihydro-pyridine-3-carbonitrile

MS(ES+): 433.3 (M+H)

6.116

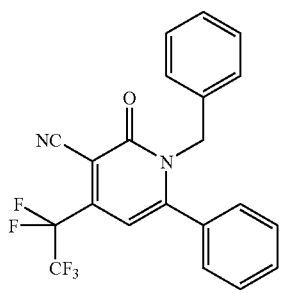

6.119

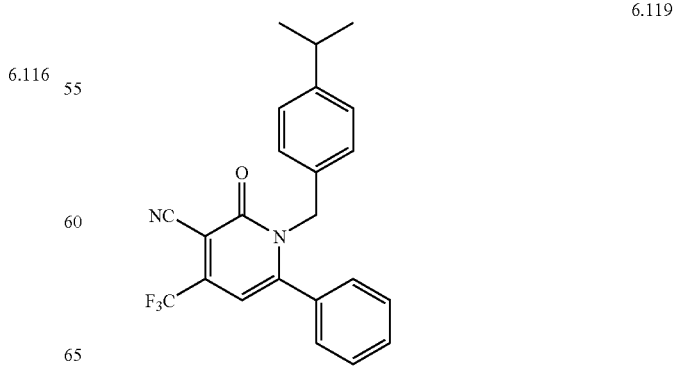

1-(4-Isopropyl-benzyl)-2-oxo-6-phenyl-4-trifluoromethyl-1,2-dihydro-pyridine-3-carbonitrile

MS(ES+): 397.1 (M+H)

6.120

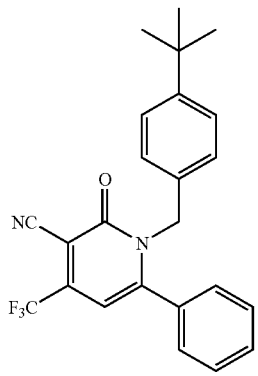

1-(4-tert-Butyl-benzyl)-2-oxo-6-phenyl-4-trifluoromethyl-1,2-dihydro-pyridine-3-carbonitrile

MS(ES+): 411.4 (M+H)

6.121

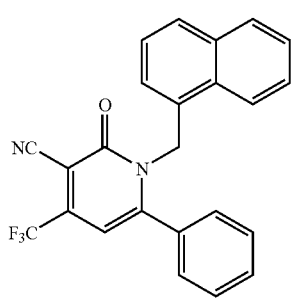

1-Naphthalen-1-ylmethyl-2-oxo-6-phenyl-4-trifluoromethyl-1,2-dihydro-pyridine-3-carbonitrile $^1$H-NMR (CDCl$_3$): δ7.86 (d, J=7.8 Hz, 1H), 7.79 (d, J=8.3 Hz, 1H), 7.58 (d, J=8.6 Hz, 1H), 7.52-7.35 (m, 4H), 7.16-7.14 (m, 2H), 6.87 (d, J=7.3 Hz, 1H), 6.49 (s, 1H), 5.68 (s, 2H).

6.122

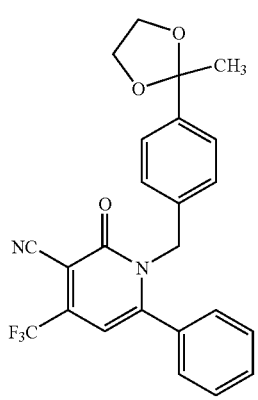

1-[4-(2-Methyl-[1,3]dioxolan-2-yl)-benzyl]-2-oxo-6-phenyl-4-trifluoromethyl-1,2-dihydro-pyridine-3-carbonitrile $^1$H-NMR (CDCl$_3$): δ7.59-7.52 (m, 1H), 7.46 (t, J=8.1 Hz, 2H), 7.34 (d, J=8.1 Hz, 2H), 7.23 (d, J=7.1 Hz, 2H), 6.88 (d, J=8.1 Hz, 2H), 6.41 (s, 1H), 5.25 (s, 2H), 4.05-3.99 (m, 2H), 3.75-3.70 (m, 2H), 1.60 (s, 3H).

6.123

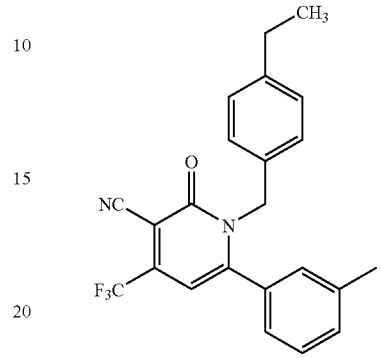

1-(4-Ethyl-benzyl)-2-oxo-6-m-tolyl-4-trifluoromethyl-1,2-dihydro-pyridine-3-carbonitrile $^1$H-NMR (CDCl$_3$): δ7.36-7.31 (m, 2H), 7.06 (d, J=8.1 Hz, 2H), 7.04-6.99 (m, 1H), 6.91 (bs, 1H), 6.81 (d, J=8.1 Hz, 2H), 6.37 (s, 1H), 5.21 (bs, 2H), 2.59 (q, J=7.6 Hz, 2H), 2.33 (s, 3H), 1.19 (t, J=7.3 Hz, 3H).

6.124

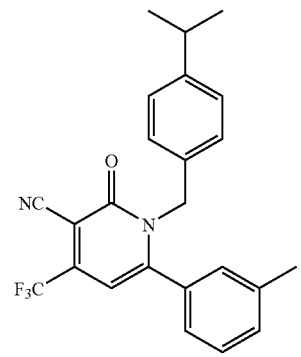

1-(4-Isopropyl-benzyl)-2-oxo-6-m-tolyl-4-trifluoromethyl-1,2-dihydro-pyridine-3-carbonitrile

MS(ES+): 411.4 (M+H)

6.125

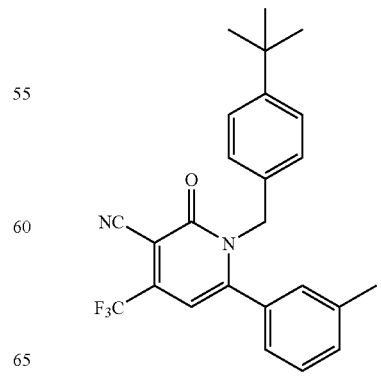

177

1-(4-tert-Butyl-benzyl)-2-oxo-6-m-tolyl-4-trifluoromethyl-1,2-dihydro-pyridine-3-carbonitrile

MS(ES+): 424.9 (M+H)

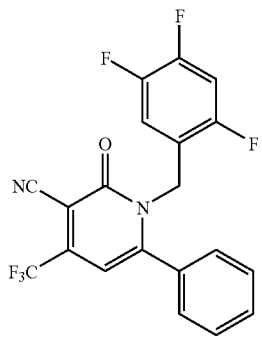

2-Oxo-6-phenyl-1-(2,4,5-trifluoro-benzyl)-4-trifluoromethyl-1,2-dihydro-pyridine-3-carbonitrile

MS(ES+): 409.2 (M+H)

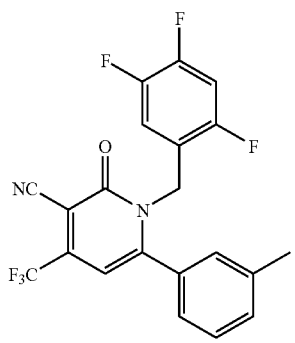

2-Oxo-6-m-tolyl-1-(2,4,5-trifluoro-benzyl)-4-trifluoromethyl-1,2-dihydro-pyridine-3-carbonitrile

MS(ES+): 423.1 (M+H)

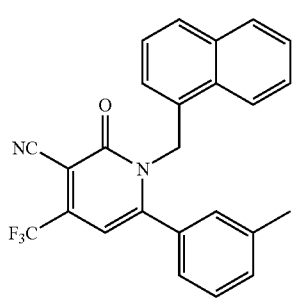

178

1-Naphthalen-1-ylmethyl-2-oxo-6-m-tolyl-4-trifluoromethyl-1,2-dihydro-pyridine-3-carbonitrile

MS(ES+): 419.2 (M+H)

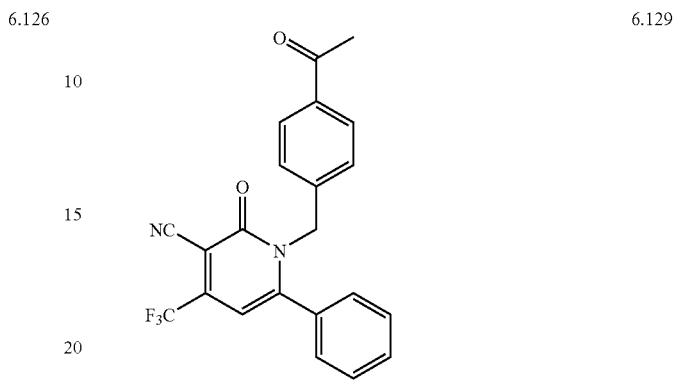

1-(4-Acetyl-benzyl)-2-oxo-6-phenyl-4-trifluoromethyl-1,2-dihydro-pyridine-3-carbonitrile

MS(ES+): 397.2 (M+H)

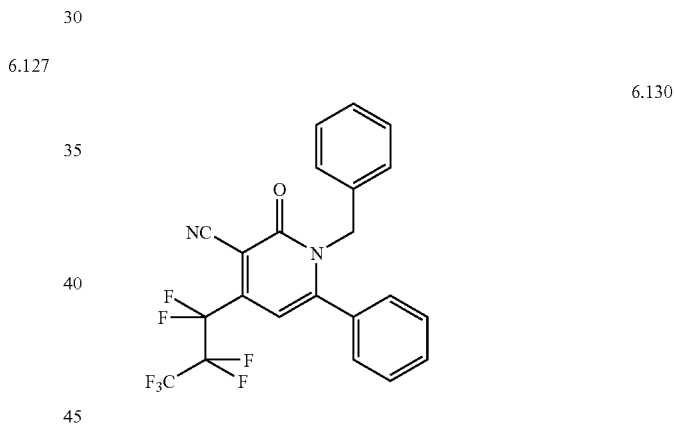

1-Benzyl-4-heptafluoropropyl-2-oxo-6-phenyl-1,2-dihydro-pyridine-3-carbonitrile

MS(ES+): 455.2 (M+H)

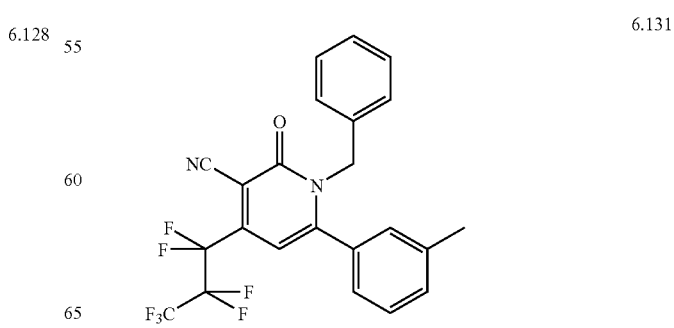

179

1-Benzyl-4-heptafluoropropyl-2-oxo-6-m-tolyl-1,2-dihydro-pyridine-3-carbonitrile

MS(ES+): 469.0 (M+H)

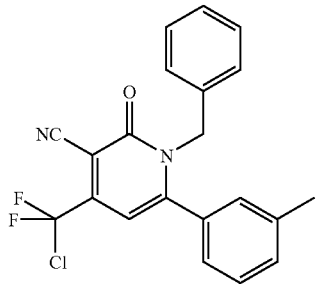

1-Benzyl-4-(chloro-difluoro-methyl)-2-oxo-6-m-tolyl-1,2-dihydro-pyridine-3-carbonitrile

MS(ES+): 385.2 (M+H)

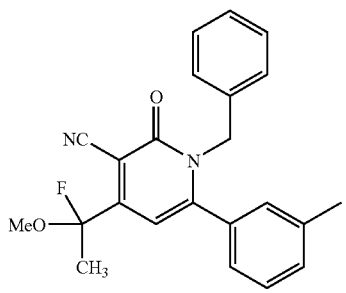

1-Benzyl-4-(1-fluoro-1-methoxy-ethyl)-2-oxo-6-m-tolyl-1,2-dihydro-pyridine-3-carbonitrile $^1$H-NMR (CDCl$_3$): δ7.34-7.31 (m, 2H), 7.26-7.22 (m, 2H), 7.02-6.88 (m, 4H), 6.35 (s, 1H), 5.23 (s, 2H), 3.66 (s, 3H), 2.32 (s, 3H).

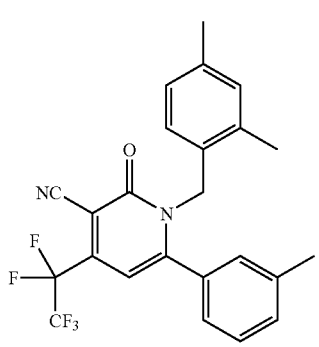

180

1-(2,4-Dimethyl-benzyl)-2-oxo-4-pentafluoroethyl-6-m-tolyl-1,2-dihydro-pyridine-3-carbonitrile

MS(ES+): 447.3 (M+H)

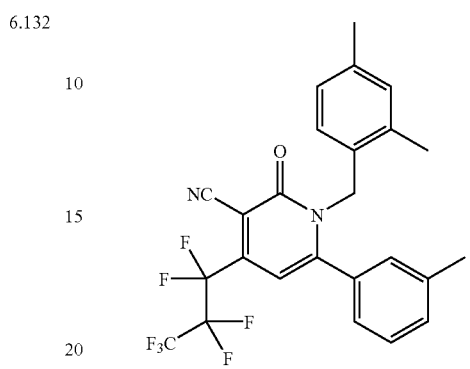

1-(2,4-Dimethyl-benzyl)-4-heptafluoropropyl-2-oxo-6-m-tolyl-1,2-dihydro-pyridine-3-carbonitrile

MS(ES+): 497.2 (M+H)

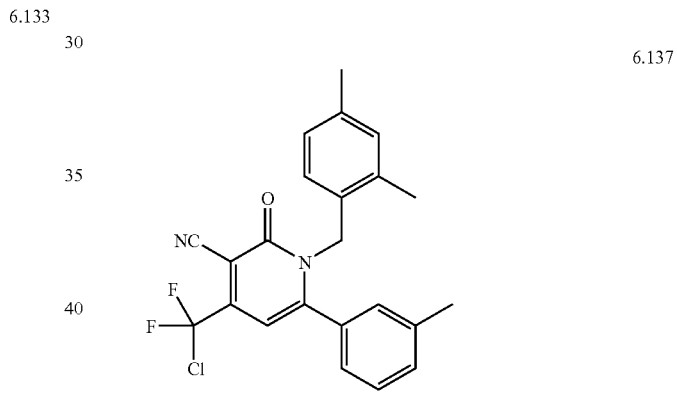

4-(Chloro-difluoro-methyl)-1-(2,4-dimethyl-benzyl)-2-oxo-6-m-tolyl-1,2-dihydro-pyridine-3-carbonitrile

MS(ES+): 413.1 (M+H)

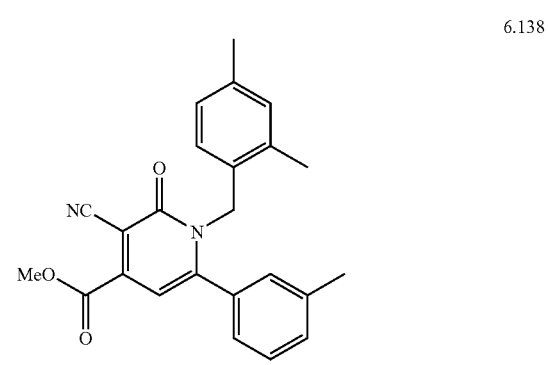

181

3-Cyano-1-(2,4-dimethyl-benzyl)-2-oxo-6-m-tolyl-1,2-dihydro-pyridine-4-carboxylic Acid Methyl Ester

MS(ES+): 387.1 (M+H)

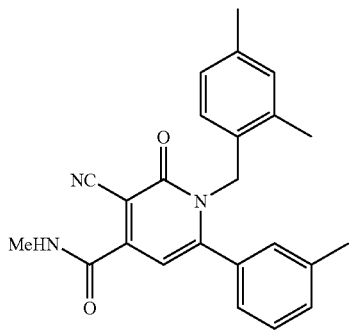

3-Cyano-1-(2,4-dimethyl-benzyl)-2-oxo-6-m-tolyl-1,2-dihydro-pyridine-4-carboxylic acid methylamide

MS(ES+): 386.1 (M+H)

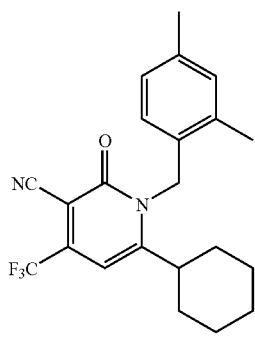

6-Cyclohexyl-1-(2,4-dimethyl-benzyl)-2-oxo-4-trifluoromethyl-1,2-dihydro-pyridine-3-carbonitrile

MS(ES+): 389.3 (M+H)

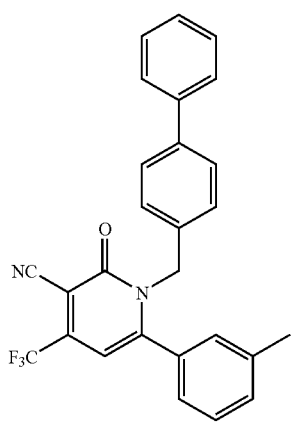

182

1-Biphenyl-3-yl-2-oxo-6-m-tolyl-4-trifluoromethyl-1,2-dihydro-pyridine-3-carbonitrile

MS(ES+): 431.0 (M+H)

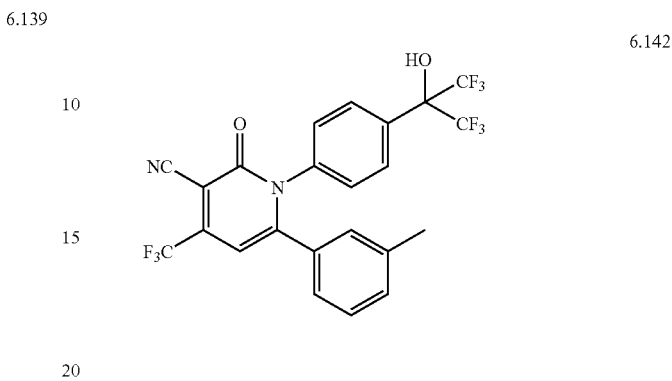

2-Oxo-6-m-tolyl-1-[4-(2,2,2-trifluoro-1-hydroxy-1-trifluoromethyl-ethyl)-phenyl]-4-trifluoromethyl-1,2-dihydro-pyridine-3-carbonitrile

MS(ES+): 521.2 (M+H)

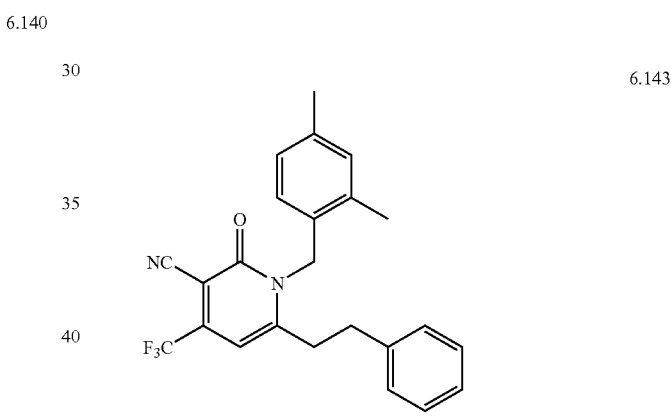

1-(2,4-Dimethyl-benzyl)-2-oxo-6-phenethyl-4-trifluoromethyl-1,2-dihydro-pyridine-3-carbonitrile

MS(ES+): 411.4 (M+H)

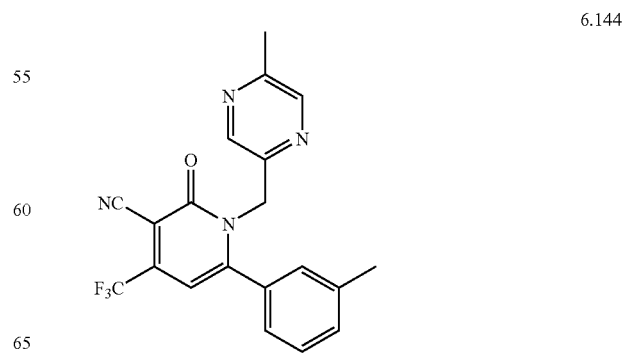

183

1-(5-Methyl-pyrazin-2-ylmethyl)-2-oxo-6-m-tolyl-4-trifluoromethyl-1,2-dihydro-pyridine-3-carbonitrile

MS(ES+): 385.1 (M+H)

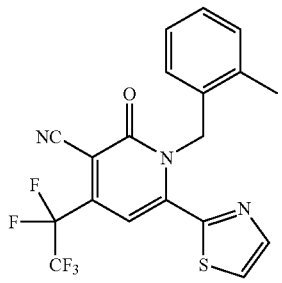

1-(2-Methyl-benzyl)-2-oxo-4-pentafluoroethyl-6-thiazol-2-yl-1,2-dihydro-pyridine-3-carbonitrile

MS(ES+): 426.0 (M+H)

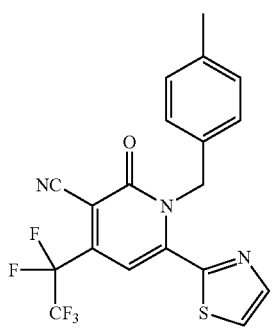

1-(4-Methyl-benzyl)-2-oxo-4-pentafluoroethyl-6-thiazol-2-yl-1,2-dihydro-pyridine-3-carbonitrile

MS(ES+): 426.1 (M+H)

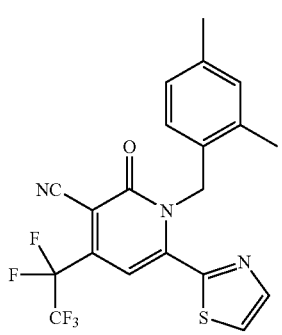

184

1-(2,4-Dimethyl-benzyl)-2-oxo-4-pentafluoroethyl-6-thiazol-2-yl-1,2-dihydro-pyridine-3-carbonitrile

MS(ES+): 440.2 (M+H)

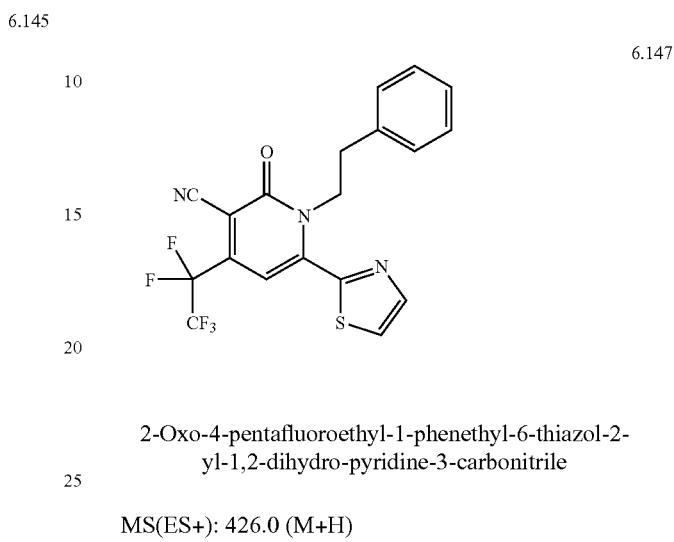

2-Oxo-4-pentafluoroethyl-1-phenethyl-6-thiazol-2-yl-1,2-dihydro-pyridine-3-carbonitrile

MS(ES+): 426.0 (M+H)

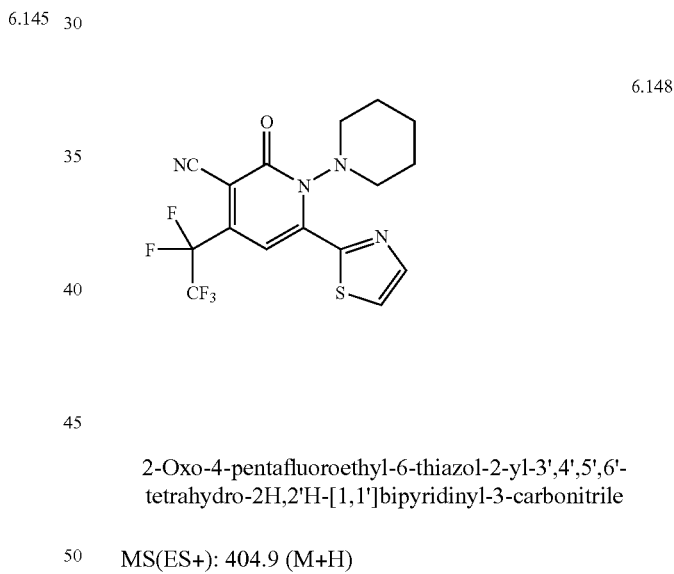

2-Oxo-4-pentafluoroethyl-6-thiazol-2-yl-3',4',5',6'-tetrahydro-2H,2'H-[1,1']bipyridinyl-3-carbonitrile

MS(ES+): 404.9 (M+H)

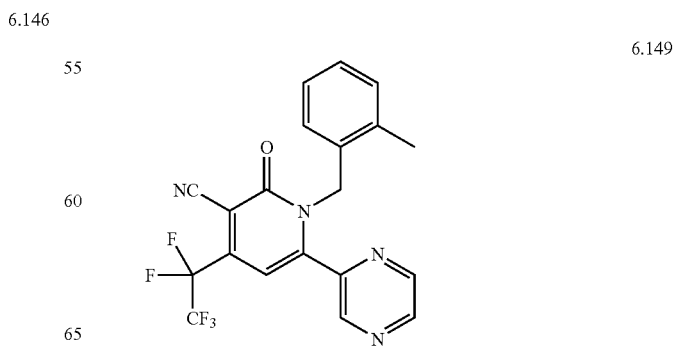

185

1-(2-Methyl-benzyl)-2-oxo-4-pentafluoroethyl-6-pyrazin-2-yl-1,2-dihydro-pyridine-3-carbonitrile

MS(ES+): 421.1 (M+H)

6.150

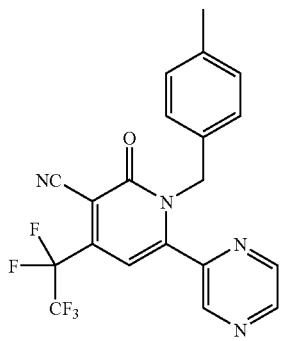

1-(4-Methyl-benzyl)-2-oxo-4-pentafluoroethyl-6-pyrazin-2-yl-1,2-dihydro-pyridine-3-carbonitrile

MS(ES+): 421.0 (M+H)

6.151

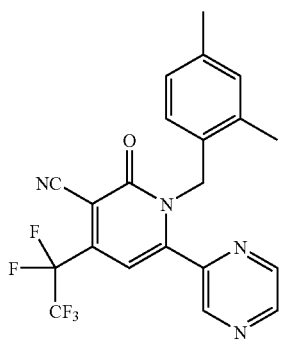

1-(2,4-Dimethyl-benzyl)-2-oxo-4-pentafluoroethyl-6-pyrazin-2-yl-1,2-dihydro-pyridine-3-carbonitrile

MS(ES+): 435.3 (M+H)

6.152

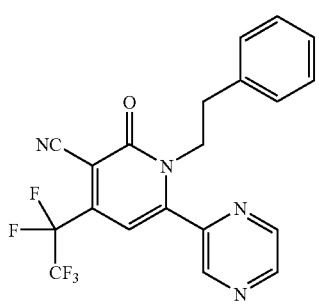

186

2-Oxo-4-pentafluoroethyl-1-phenethyl-6-pyrazin-2-yl-1,2-dihydro-pyridine-3-carbonitrile

MS(ES+): 421.1 (M+H)

6.153

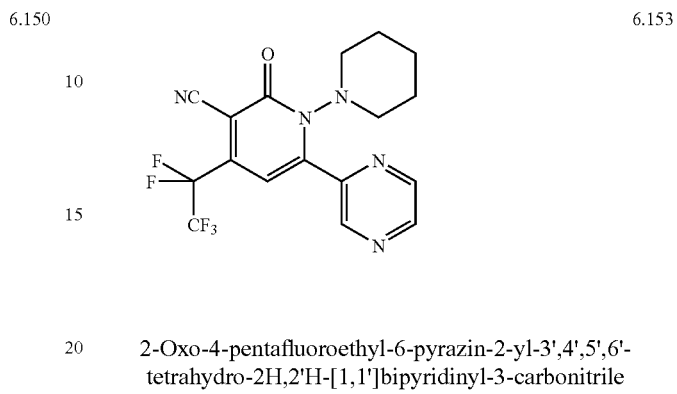

2-Oxo-4-pentafluoroethyl-6-pyrazin-2-yl-3',4',5',6'-tetrahydro-2H,2'H-[1,1']bipyridinyl-3-carbonitrile

MS(ES+): 400.3 (M+H)

6.154

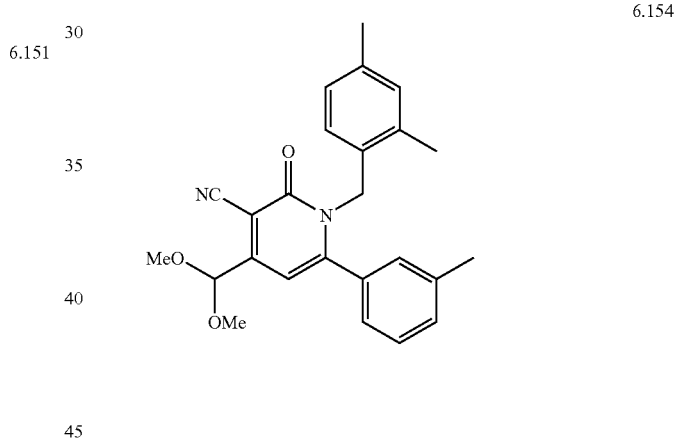

4-Dimethoxymethyl-1-(2,4-dimethyl-benzyl)-2-oxo-6-m-tolyl-1,2-dihydro-pyridine-3-carbonitrile

MS(ES+): 402.9 (M+H)

6.155

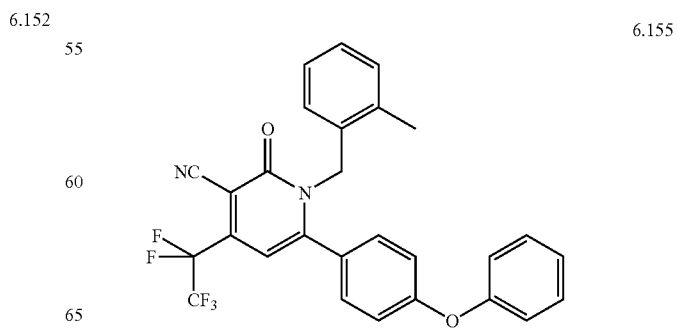

187

1-(2-Methyl-benzyl)-2-oxo-4-pentafluoroethyl-6-(4-phenoxy-phenyl)-1,2-dihydro-pyridine-3-carbonitrile

MS(ES+): 511.1 (M+H)

6.156

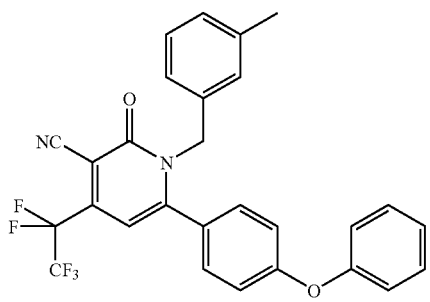

1-(3-Methyl-benzyl)-2-oxo-4-pentafluoroethyl-6-(4-phenoxy-phenyl)-1,2-dihydro-pyridine-3-carbonitrile

MS(ES+): 511.3 (M+H)

6.157

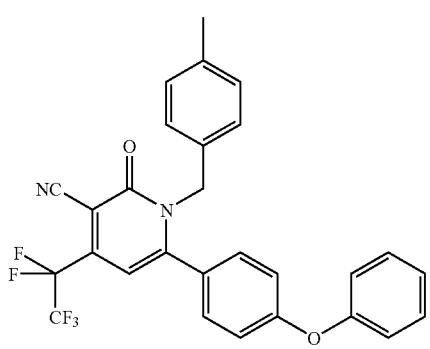

1-(4-Methyl-benzyl)-2-oxo-4-pentafluoroethyl-6-(4-phenoxy-phenyl)-1,2-dihydro-pyridine-3-carbonitrile

MS(ES+): 510.9 (M+H)

6.158

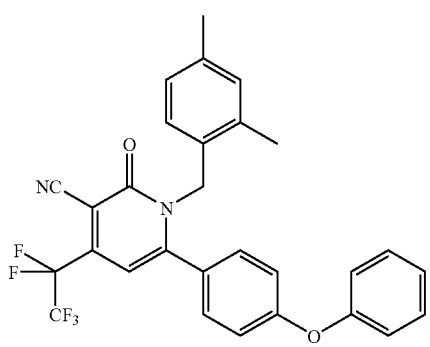

188

1-(2,4-Dimethyl-benzyl)-2-oxo-4-pentafluoroethyl-6-(4-phenoxy-phenyl)-1,2-dihydro-pyridine-3-carbonitrile

MS(ES+): 525.4 (M+H)

6.159

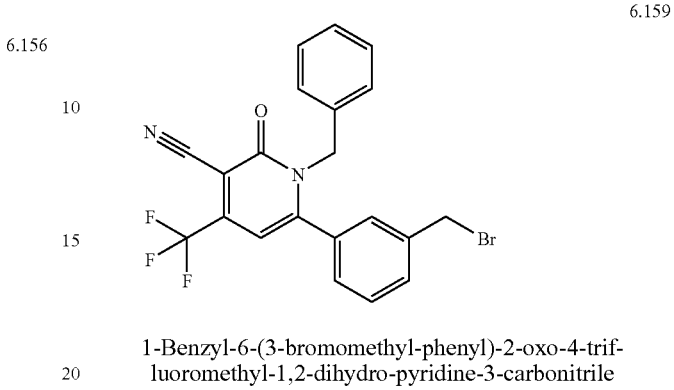

1-Benzyl-6-(3-bromomethyl-phenyl)-2-oxo-4-trifluoromethyl-1,2-dihydro-pyridine-3-carbonitrile $^1$H-NMR (CDCl$_3$): δ7.56 (m), 7.45 (m, 1H), 7.25 (m, 3H), 7.15 (m, 2H), 6.88 (m, 2H), 6.40 (s, 1H), 5.24 (s, 2H), 4.39 (s, 2H).

Example 7

This example illstrates the preparation of compound 7.

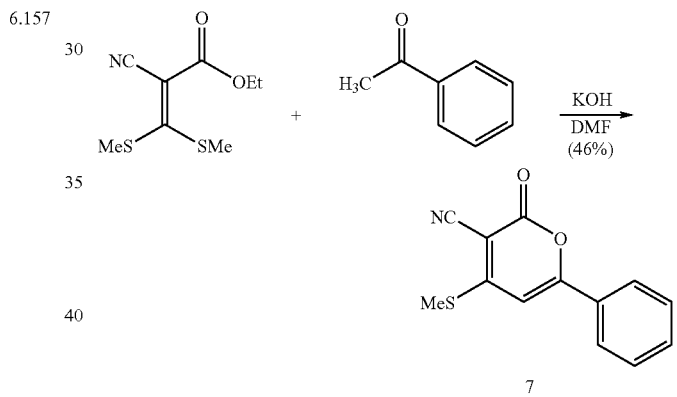

3,3-Bis(methylthio)-2-cyanoacrylic acid ethyl ester (2.0 g, 9.2 mmoles—TCI America) was combined with acetophenone (1.1 mL, 9.4 mmoles) in 100 mL of DMF within a round-bottom flask. To this stirring mixture at room temp was then added potassium hydroxide (1.0 g, 17.8 mmoles), and the reaction was stirring at this temp for 12 hours. After this period the reaction was combined with 150 mL of ice-water and the mixture was stirred for 2 hours. The resulting heterogeneous mixture was vacuum filtered, and the yellow filter cake was washed with water and dried to yield product 1.04 g (46% yield) as a yellow solid.

7

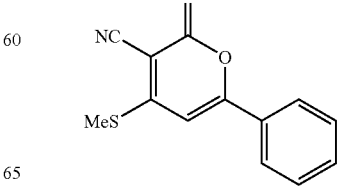

¹H-NMR (CDCl₃): δ7.88 (dt, J'=7.0 hz, J"=1.5 Hz, 2H), 7.6-7.49 (m, 3H), 6.72 (s, 1H), 2.73 (s, 3H).

Example 8

This example illustrates the preparation of compound 8.

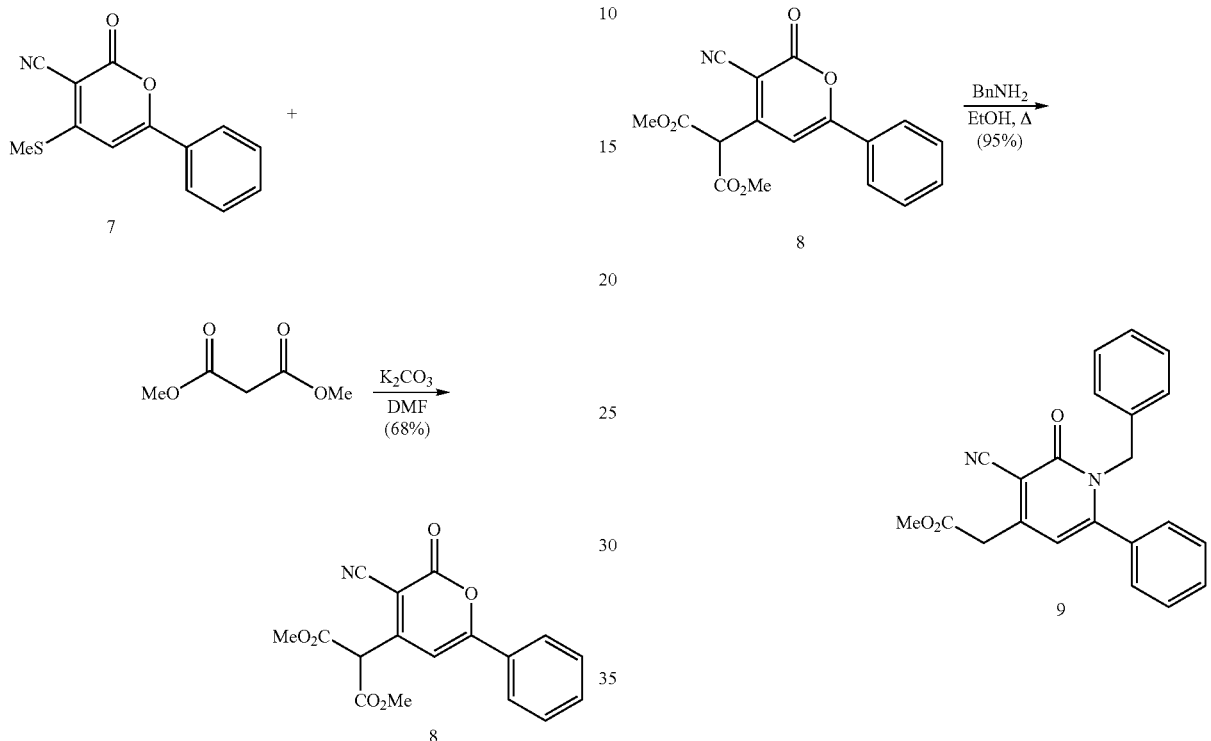

4-Methylsulfanyl-2-oxo-6-phenyl-2H-pyran-3-carbonitrile, 7 (0.11 g, 0.46 mmoles) was combined with dimethyl malonate (0.11 mL, 0.96 mmoles) and potassium carbonate (0.16 g, 1.2 mmoles) in 2.3 mL of anhydrous DMF. The reaction was stirred at room temp for 12 hours. After this period the mixture was combined with water and 1N HCl (to adjust pH <6) and was extracted with EtOAc (2×30 mL). The resulting organic layer was then washed with sat'd NaCl and was dried over anhydrous Na₂SO₄. The EtOAc layer was evaporated in vacuo to yield the crude product, which was purified using flash silica chromatography to yield product 0.103 g (68% yield) as a yellow solid.

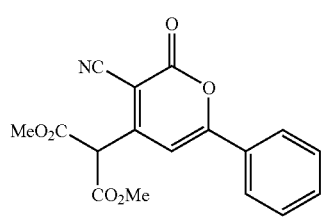

8

¹H-NMR (CDCl₃): δ7.90 (dt, J'=7.1 Hz, J"=1.8 Hz, 2H), 7.60-7.49 (m, 3H), 7.14 (s, 1H), 5.06 (s, 1H), 3.86 (s, 6H).

Example 9

This example illustrates the preparation of compound 9.

2-(3-Cyano-2-oxo-6-phenyl-2H-pyran-4-yl)-malonic acid dimethyl ester, 8 (26 mg, 0.079 mmoles) was combined with benzylamine (10 µL, 0.092 mmoles) and 1.0 mL of ethanol within a screw cap vial. The mixture was heated to 80° C. and was stirred at this temp for 2 hours. After this period the mixture was evaporated in vacuo and was purified directly by flash silica chromatography (0-50% EtOAc/Hexane) to yield product 27 mg (95% yield) as a beige solid.

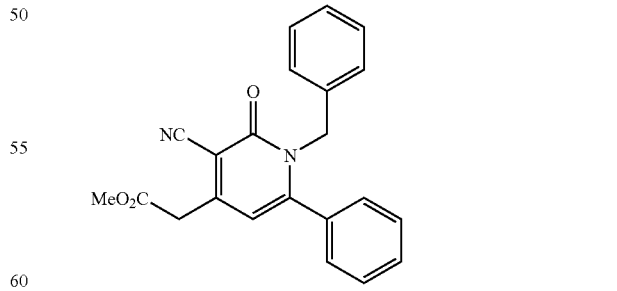

9

¹H-NMR (CDCl₃): δ7.5-7.44 (m, 1H), 7.38 (t, J=8.1 Hz, 2H), 7.22-7.17 (m, 3H), 7.15 (d, J=7.3 Hz, 2H), 6.91-6.85 (m, 2H), 6.31 (s, 1H), 5.19 (s, 2H), 3.96 (s, 3H), 3.86 (s, 2H). MS (ES+): 358.8 (M+H).

The following compounds were prepared in a manner similar to that described above.

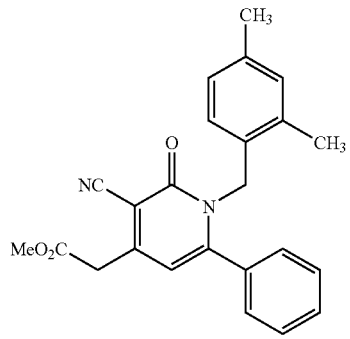

[3-Cyano-1-(2,4-dimethyl-benzyl)-2-oxo-6-phenyl-1,2-dihydro-pyridin-4-yl]-acetic Acid Methyl Ester $^1$H-NMR (CDCl$_3$): δ7.28-7.20 (m, 2H), 6.96-6.90 (m, 2H), 6.89-6.82 (m, 2H), 6.67 (s, 1H), 6.62 (d, J=7.8 Hz, 1H), 5.09 (s, 2H), 4.01 (s, 3H), 2.27 (s, 3H), 2.25 (s, 3H), 1.88 (s, 3H).

Example 10

This example illustrates the preparation of compound 10.1.

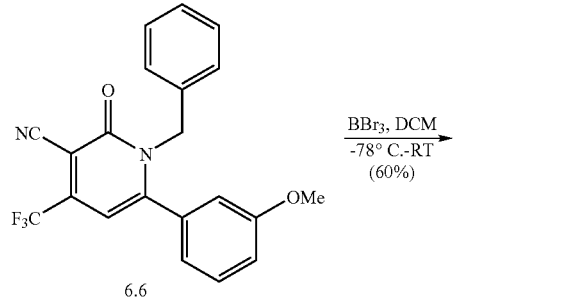

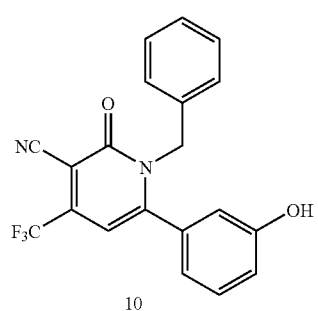

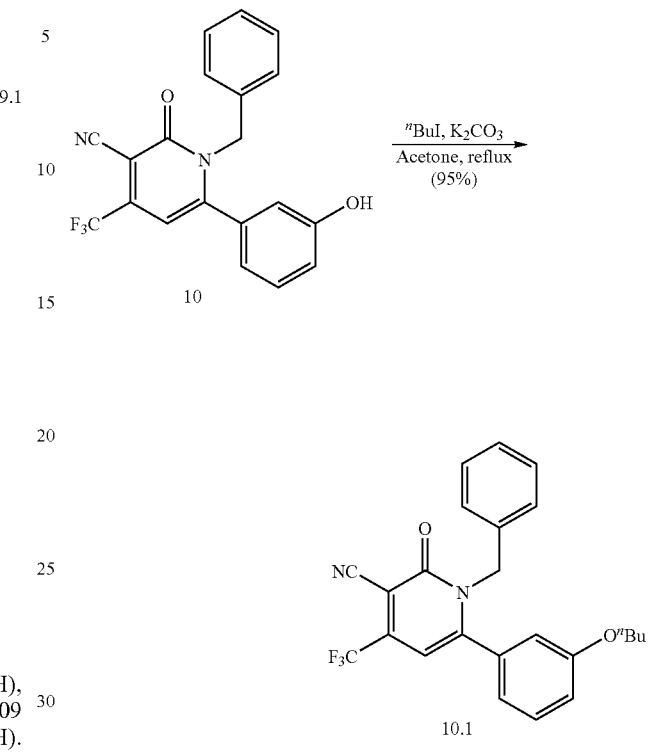

A solution of boron tribromide (4.5 mL, 47.9 mmol) in 10 mL anhydrous THF was slowly added to a solution of 1-benzyl-3-cyano-6-(3-methoxyphenyl)-4-trifluoromethyl-1H-pyridin-2-one (6.6) (8.37 g, 21.8 mmol) in 62 mL of anhydrous THF at −78° C. under nitrogen. The mixture was vigorously stirred and allowed to warm to ambient temperature overnight. The mixture was then cooled to 0° C. with an ice/water bath and to it was added 100 mL of MeOH in portion. The mixture was stirred at room temperature for 1 h and concentrated in vacuo. The residue was dissolved in dichloromethane and neutralized to pH 7 by adding 1 N NaOH. The organic layer was washed with water, separated and dried with anhydrous MgSO$_4$. The dichloromethane was concentrated in vacuo. The resulting crude product was purified by column chromatography (50% EtOAc/hexane), providing a bright yellow solid (10) (4.8 g, 60% yield). $^1$H-NMR (DMSO-d6): δ10.01 (s, 1H), 7.37 (m, 4H), 7.11 (m, 2H), 7.03 (m, 1H), 6.91 (m, 2H), 6.82 (s, 1H), 5.28 (s, 2H).

To a solution of 1-benzyl-3-cyano-6-(3-hydroxyphenyl)-4-trifluoromethyl-1H-pyridin-2-one (10) (98 mg, 0.27 mmol) in 4 mL of acetone was added 1-iodobutane (59 mg, 0.32 mmol) and K$_2$CO$_3$ (41 mg, 0.32 mmol). The mixture was stirred and heated to reflux overnight. The salt was removed by filtration and the solvent was concentrated in vacuo. The resulting crude product was purified by column chromatography (25% EtOAc/hexane), providing a yellow solid (10.1) (107 mg, 95% yield). $^1$H-NMR (CDCl$_3$): δ7.34 (m, 1H), 7.25 (m, 3H), 7.03 (m, 1H), 6.93 (m, 2H), 6.77 (m, 1H), 6.59 (m, 1H), 6.41 (s, 1H), 5.25 (s, 2H), 3.73 (m, 2H), 1.71 (m, 2H), 1.45 (m, 2H), 0.96 (t, J=7.3 Hz, 3H).

The following compounds were prepared in a manner similar to that described above.

10.2

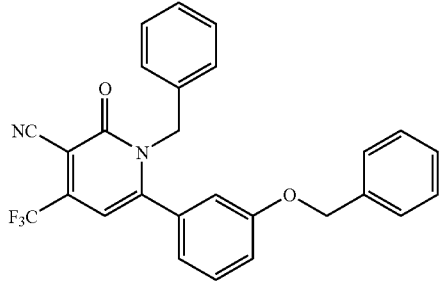

¹H-NMR (CDCl₃): δ7.44-7.33 (m, 6H), 7.26 (m, 3H), 7.12 (m, 1H), 6.90 (m, 2H), 6.79 (m, 1H), 6.68 (m, 1H), 6.40 (s, 1H), 5.21 (s, 2H), 4.68 (s, 2H).

10.3

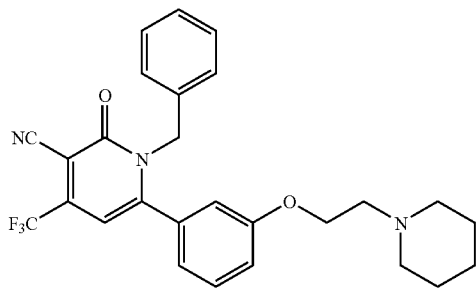

¹H-NMR (CDCl₃): δ7.34 (m, 1H), 7.24 (m, 3H), 7.06 (m, 1H), 6.92 (m, 2H), 6.77 (m, 1H), 6.64 (m, 1H), 6.40 (s, 1H), 5.25 (s, 2H), 3.91 (t, J=6.1 Hz, 2H), 2.72 (t, J=6.1 Hz, 2H), 2.48 (m, 4H), 1.61 (m, 4H), 1.45 (m, 2H).

10.4

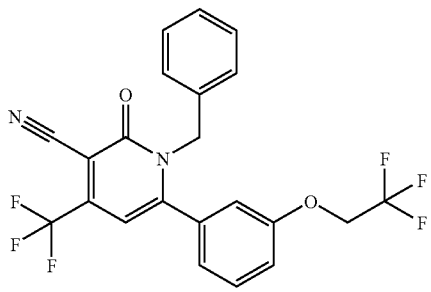

1-Benzyl-2-oxo-6-[3-(2,2,2-trifluoro-ethoxy)-phenyl]-4-trifluoromethyl-1,2-dihydro-pyridine-3-carbonitrile ¹H-NMR (CDCl₃): δ7.45 (m, 1H), 7.25 (m, 4H), 7.01 (m, 1H), 6.88 (m, 3 H), 6.40 (s, 1H), 5.33 (m, 2H), 5.26 (s, 2H).

10.5

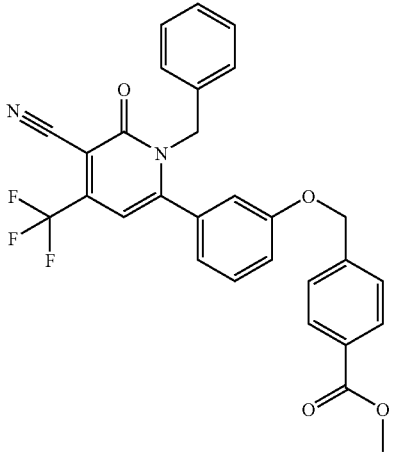

4-[3-(1-Benzyl-5-cyano-6-oxo-4-trifluoromethyl-1,6-dihydro-pyridin-2-yl)-phenoxymethyl]-benzoic Acid Methyl Ester ¹H-NMR (CDCl₃): δ8.06 (m, 2H), 7.42 (m, 2H), 7.36 (m, 1H), 7.26 (m, 4 H), 7.11 (m, 1H), 6.92 (m, 2H), 6.82 (m, 1H), 6.66 (m, 1H), 6.40 (s, 1H), 5.21 (s, 2H), 4.89 (s, 2H), 3.93 (s, 3H).

10.6

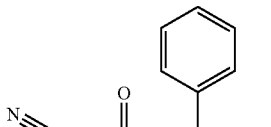
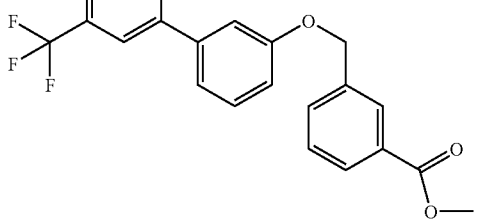

3-[3-(1-Benzyl-5-cyano-6-oxo-4-trifluoromethyl-1,6-dihydro-pyridin-2-yl)-phenoxymethyl]-benzoic Acid Methyl Ester ¹H-NMR (CDCl₃): δ8.03 (m, 2H), 7.56 (m, 1H), 7.48 (m, 1H), 7.37 (m, 1 H), 7.26 (m, 2H), 7.11 (m, 1H), 6.91 (m, 2H), 6.82 (m, 1H), 6.67 (m, 1H), 6.40 (s, 1H), 5.22 (s, 2H), 4.87 (s, 2H), 3.94 (s, 3H).

Example 11

This example illustrates the preparation of compound 11.1.

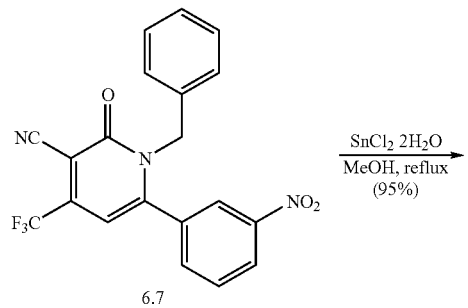

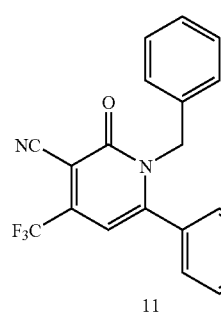

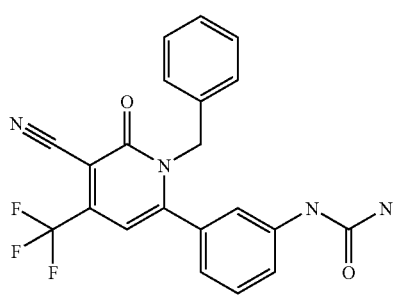

To a solution of 1-benzyl-3-cyano-6-(3-nitrophenyl)-4-trifluoromethyl-1H-pyridin-2-one (6.7) (200 mg, 0.50 mmol) in 5 mL of MeOH was added stannous (II) chloride dihydrate (565 mg, 2.5 mmol). The mixture was stirred and heated to reflux for 3 h. The mixture was then concentrated in vacuo. The residue was taken in a mixture of ethyl acetate and 5% aqueous NaHCO₃. The mixture was stirred for 1 h, and the organic layer was separated and the aqueous layer was extracted with ethyl acetate twice. The combined organic layer was dried with anhydrous MgSO₄ and concentrated in vacuo. The crude product (11) was relatively pure by analysis of its ¹H NMR spectrum and was used for the next reaction without further purification.

To a solution of 6-(3-aminophenyl)-1-benzyl-3-cyano-4-trifluoromethyl-1H-pyridin-2-one (11) (74 mg, 0.20 mmol) in 2 mL of dichloromethane was added acetyl chloride (48 mg, 0.6 mmol) and triethylamine (81 mg, 0.64 mmol). The mixture was refluxed overnight. The salt was removed by filtration and the solvent was concentrated in vacuo. The resulting crude product was purified by column chromatography (60% EtOAc/hexane), providing 11.1 as a yellow oil (69 mg, 84% yield). ¹H-NMR (CDCl₃): δ7.57 (m, 2H), 7.43 (s, 1H), 7.35 (m, 1H), 7.23 (m, 3H), 6.90 (m, 2H), 6.85 (m, 1H), 6.41 (s, 1H), 5.27 (s, 2H), 2.19 (s, 3H).

Example 12

This example illustrates the preparation of compound 12.

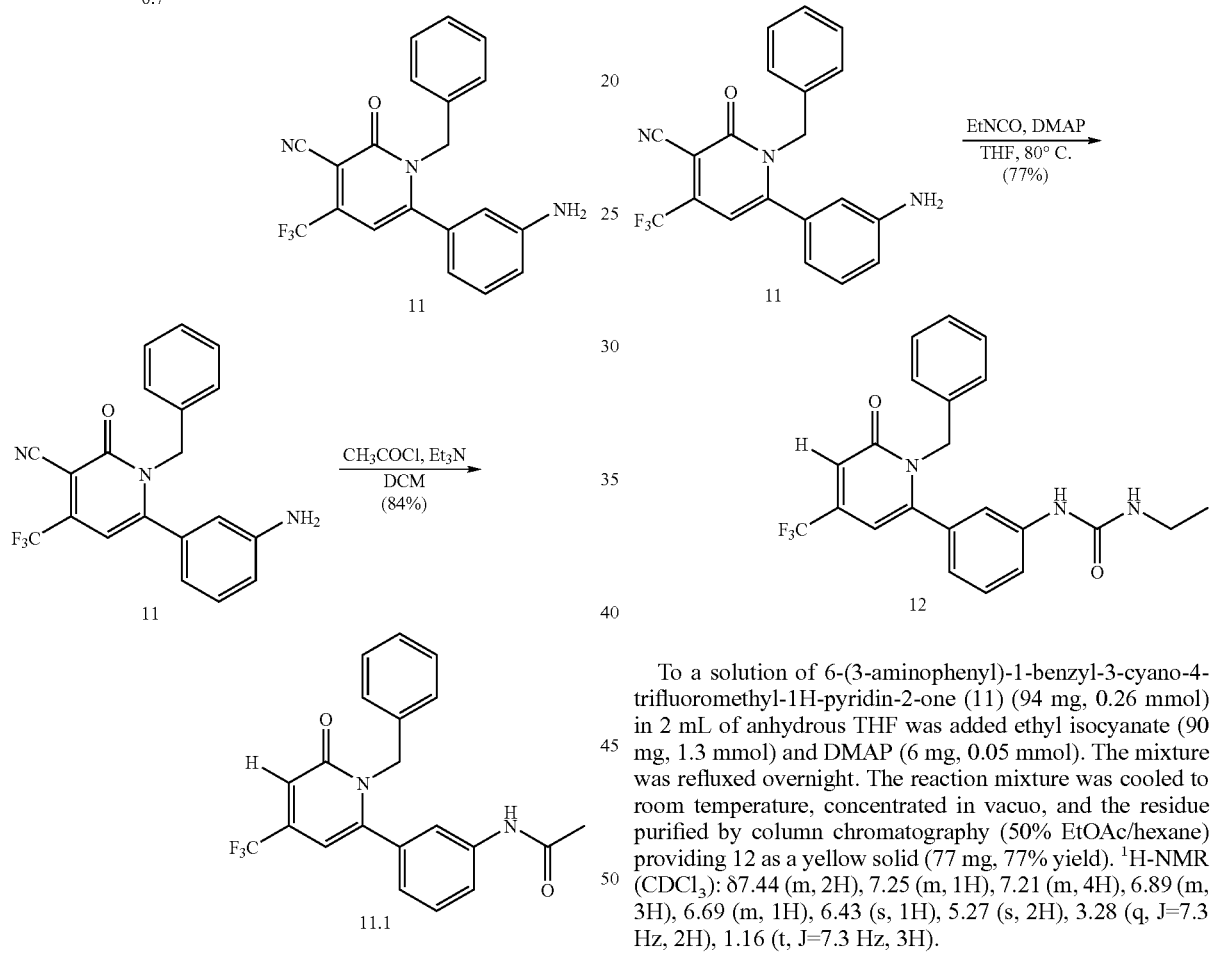

To a solution of 6-(3-aminophenyl)-1-benzyl-3-cyano-4-trifluoromethyl-1H-pyridin-2-one (11) (94 mg, 0.26 mmol) in 2 mL of anhydrous THF was added ethyl isocyanate (90 mg, 1.3 mmol) and DMAP (6 mg, 0.05 mmol). The mixture was refluxed overnight. The reaction mixture was cooled to room temperature, concentrated in vacuo, and the residue purified by column chromatography (50% EtOAc/hexane) providing 12 as a yellow solid (77 mg, 77% yield). ¹H-NMR (CDCl₃): δ7.44 (m, 2H), 7.25 (m, 1H), 7.21 (m, 4H), 6.89 (m, 3H), 6.69 (m, 1H), 6.43 (s, 1H), 5.27 (s, 2H), 3.28 (q, J=7.3 Hz, 2H), 1.16 (t, J=7.3 Hz, 3H).

[3-(1-Benzyl-5-cyano-6-oxo-4-trifluoromethyl-1,6-dihydro-pyridin-2-yl)-phenyl]-urea $^1$H-NMR (DMSO-d6): δ10.20 (s, 1H), 9.04 (s, 1H), 7.65 (m, 1H), 7.58 (m, 1 H), 7.43 (m, 1H), 7.29 (m, 3H), 7.07 (m, 1H), 7.02 (m, 2H), 6.80 (s, 1H), 5.23 (s, 2H).

Example 13

This example illustrates the preparation of compound 13.

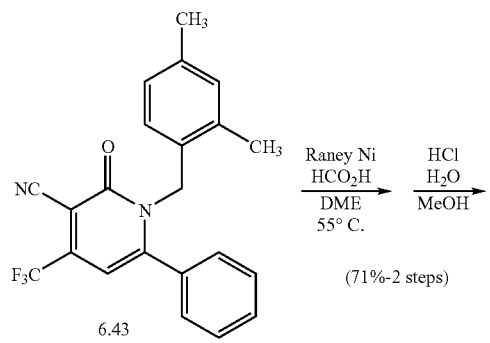

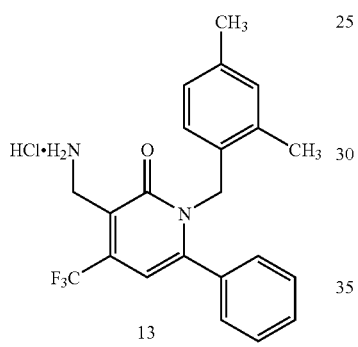

Within a 100 mL flask was placed Raney®-type Alloy (Aluminum-nickel catalyst, Aldrich, 2.0 g), a magnetic stir bar and 2N NaOH solution (20 mL). The flask was submerged into a water bath at ambient temperature and the mixture was vigorously stirred for 45 min (bubbling occurs). In a separate pear-shaped flask was placed 1-(2,4-Dimethyl-benzyl)-2-oxo-6-phenyl-4-trifluoromethyl-1,2-dihydro-pyridine-3-carbonitrile 6.43 (100 mg, 0.26 mmoles) and this was dissolved within formic acid (5 mL) and ethylene glycol dimethyl ether (DME, 1.0 mL). After Ra—Ni activation was complete the hydroxide mixture (heterogeneous) was carefully decanted, washed with water, and sequentially decanted to remove the residual sodium hydroxide. Excess water was removed from the activated Ra—Ni using a pipette. The nitrile solution was carefully added to the stirring Ra—Ni at room temperature, and mixture was heated to 55° C. for 3 hours. After this period the reaction mixture was filtered through Celite (with MeOH washings) and concentrated in vacuo. The residue was taken up in ethyl acetate and was washed with 50% v/v aqueous NH$_4$OH (3×20 mL) and brine. The resulting EtOAc solution was dried over anhydrous Na$_2$SO$_4$ and was concentrated in vacuo to yield crude product as a yellow residue. The crude product was purified using flash silica chromatography (0-10% MeOH/DCM) to yield the free base as a yellow residue. The free base was combined with 2N HCl/MeOH and evaporated to yield the hydrochloride salt. The salt was dissolved in deionized water and freeze-dried to yield 79 mg (71% yield) of product 13 as a yellowish powder.

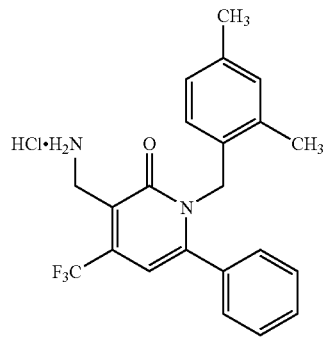

$^1$H-NMR (CDCl$_3$): δ(d6-DMSO) 8.38 (bs, 3H), 7.47 (t, J=7.5 Hz, 1H), 7.40 (t, J=7.6 Hz, 2H), 7.26 (d, J=7.6 Hz, 2H), 6.92-6.89 (m, 2H), 6.65 (d, J=7.6 Hz, 1H), 6.54 (s, 1H), 5.05 (s, 2H), 4.02 (bs, 2H), 2.21 (s, 3H), 1.87 (s, 3H). MS(ES+): 386.9 (M+H)

The following compound was prepared in a manner similar to that described above.

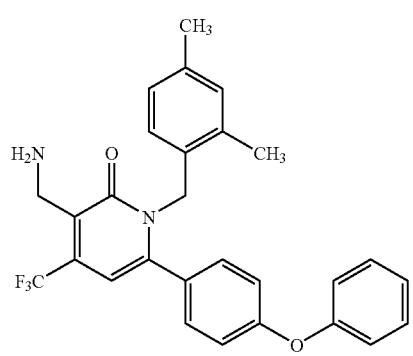

(3-Aminomethyl-1-(2,4-dimethyl-benzyl)-6-(4-phenoxy-phenyl)-4-trifluoromethyl-1H-pyridin-2-one)

$^1$H-NMR (CDCl$_3$): δ7.20-7.14 (m, 1H), 7.11-6.99 (m, 5H), 6.94-6.87 (m, 5H), 6.58 (d, J=7.3 Hz, 1H), 6.34 (s, 1H), 5.09 (s, 2H), 3.93 (s, 2H), 2.26 (s, 3H), 2.01 (s, 3H).

Example 14

This example illustrates the preparation of compound 14.

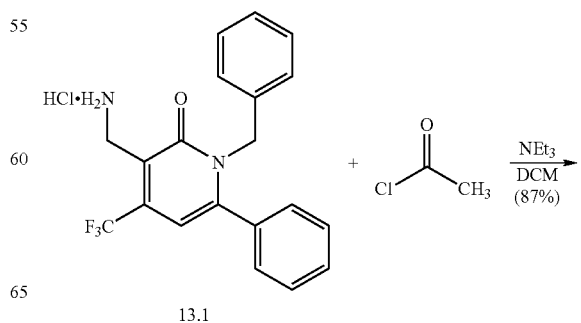

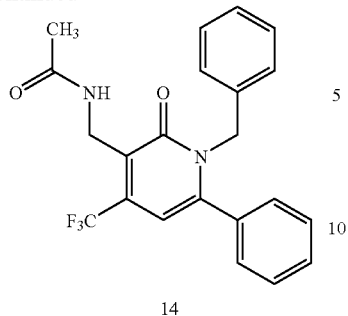

14

3-Aminomethyl-1-benzyl-6-phenyl-4-trifluoromethyl-1H-pyridin-2-one hydrochloride 13.1 (15 mg, 0.039 mmoles) was combined with acetyl chloride (5 μL, 0.070 mmoles) and triethylamine (12 μL, 0.086 mmoles) in 5 mL of anhydrous DCM within a round-bottom flask. The mixture was stirred at room temperature for 10 hours and was evaporated in vacuo to yield crude product as a yellow residue. The crude product was purified using flash silica chromatography (0-30% EtOAc/Hexane) to yield 15 mg (87% yield) of 14 as a white solid.

14

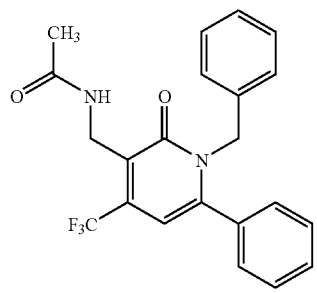

N-(1-Benzyl-2-oxo-6-phenyl-4-trifluoromethyl-1,2-dihydro-pyridin-3-ylmethyl)-acetamide $^1$H-NMR (CDCl$_3$): δ7.50-7.43 (m, 1H), 7.38 (t, J=7.8 Hz, 2H), 7.25-7.21 (m, 3H), 7.19-7.14 (m, 2H), 6.92-6.85 (m, 2H), 6.83-6.75 (m, 1H), 6.36 (s, 1H), 5.21 (bs, 2H), 4.62 (d, J=6.1 Hz, 2H), 1.97 (s, 3H).

MS(ES+): 401.2 (M+H)

The following compounds were prepared in a manner similar to that described above.

14.1

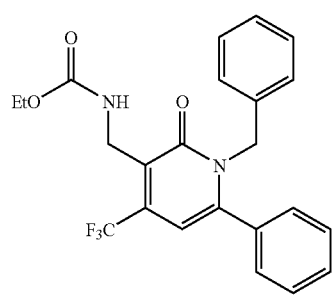

(1-Benzyl-2-oxo-6-phenyl-4-trifluoromethyl-1,2-dihydro-pyridin-3-ylmethyl)-carbamic Acid Ethyl Ester

MS(ES+): 431.1 (M+H)

14.2

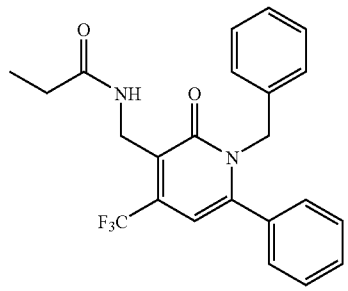

N-(1-Benzyl-2-oxo-6-phenyl-4-trifluoromethyl-1,2-dihydro-pyridin-3-ylmethyl)-propionamide

MS(ES+): 415.2 (M+H)

14.3

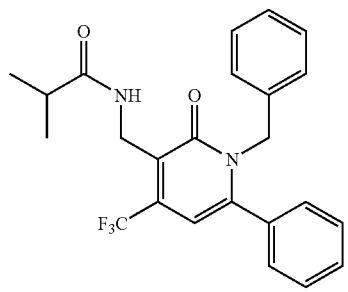

N-(1-Benzyl-2-oxo-6-phenyl-4-trifluoromethyl-1,2-dihydro-pyridin-3-ylmethyl)-isobutyramide

MS(ES+): 429.3 (M+H)

14.4

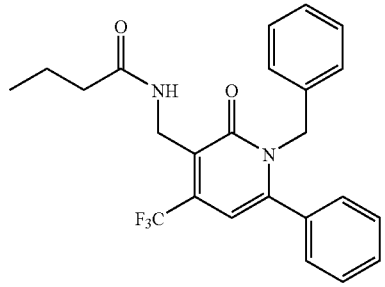

N-(1-Benzyl-2-oxo-6-phenyl-4-trifluoromethyl-1,2-dihydro-pyridin-3-ylmethyl)-butyramide

MS(ES+): 429.2 (M+H)

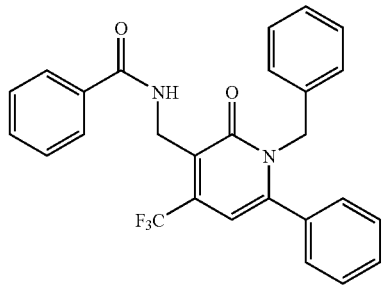

N-(1-Benzyl-2-oxo-6-phenyl-4-trifluoromethyl-1,2-dihydro-pyridin-3-ylmethyl)-benzamide

MS(ES+): 463.2 (M+H)

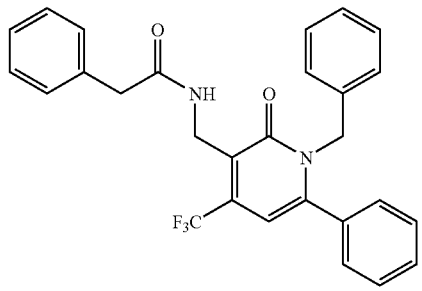

N-(1-Benzyl-2-oxo-6-phenyl-4-trifluoromethyl-1,2-dihydro-pyridin-3-ylmethyl)-2-phenyl-acetamide

MS(ES+): 477.1 (M+H)

Example 15

This example illustrates the preparation of compound 15.

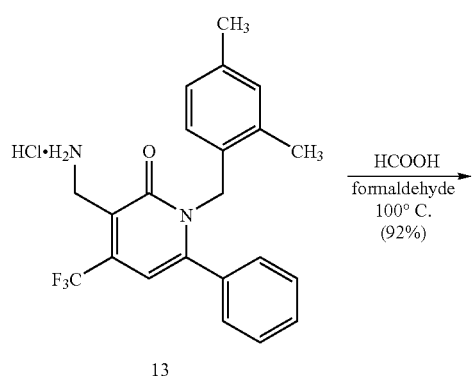

13

$\xrightarrow{\text{HCOOH, formaldehyde, 100° C. (92%)}}$

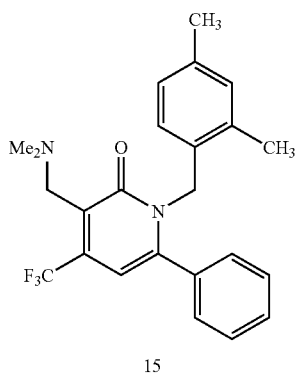

15

3-Aminomethyl-1-(2,4-dimethyl-benzyl)-6-phenyl-4-trifluoromethyl-1H-pyridin-2-one hydrochloride 13 (39 mg, 0.092 mmoles) was combined with formic acid (96%, 1.0 mL) in 3.0 mL of aqueous formaldehyde (37 wt. % solution in water), and the mixture was stirred at 100° C. for 16 hours. After this period the mixture was poured into a saturated NaHCO$_3$ solution (20 mL) which was extracted with copious Et$_2$O. The combined ether layer was washed with brine, dried over anhydrous Na$_2$SO$_4$, and was evaporated in vacuo to yield crude product as a yellowish residue. The crude product was purified using flash silica chromatography (0-10% MeOH/DCM w/0.1% diethylamine) to yield 35 mg (92% yield) of 15 as a yellowish residue.

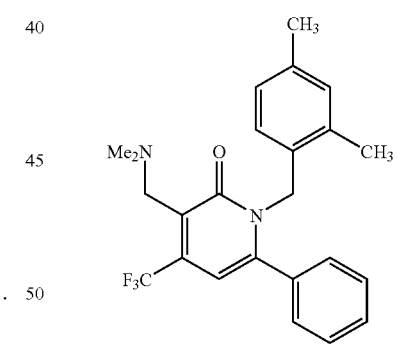

15

(3-Dimethylaminomethyl-1-(2,4-dimethyl-benzyl)-6-phenyl-4-trifluoromethyl-1H-pyridin-2-one)

$^1$H-NMR (CDCl$_3$): δ7.43-7.37 (m, 1H), 7.31 (t, J=7.8 Hz, 2H), 7.17-7.11 (m, 2H), 6.89 (bd, J=7.8 Hz, 1H), 6.85 (bs, 1H), 6.56 (d, J=7.8 Hz, 1H), 6.32 (s, 1H), 5.07 (s, 2H), 3.63-3.59 (m, 2H), 2.36 (s, 6H), 2.25 (s, 3H), 1.92 (s, 3H). MS(ES+): 415.4 (M+H)

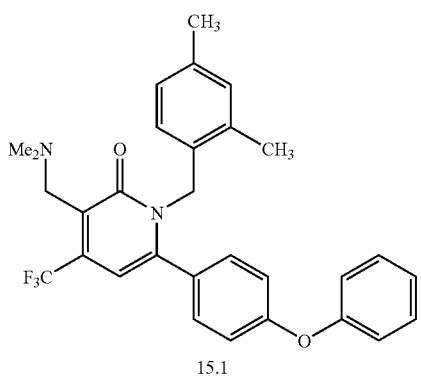

15.1

3-Dimethylaminomethyl-1-(2,4-dimethyl-benzyl)-6-(4-phenoxy-phenyl)-4-trifluoromethyl-1H-pyridin-2-one

MS(ES+): 507.2 (M+H)

Example 16

This example illustrates the preparation of compound 16.

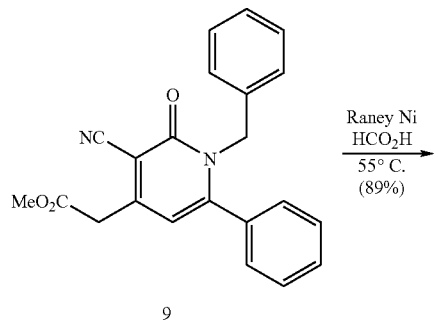

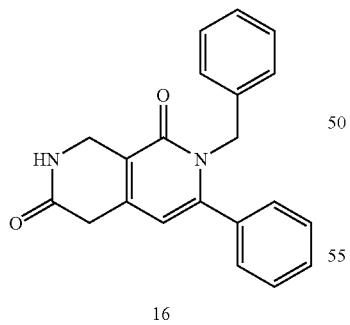

16

Within a 100 mL flask was placed Raney®-type Alloy (Aluminum-nickel catalyst, Aldrich, 4.0 g), a magnetic stir bar and 2N NaOH solution (50 mL). The flask was submerged into a water bath at ambient temperature and the mixture was vigorously stirred for 45 min (bubbling occurs). In a separate pear-shaped flask was placed [3-Cyano-1-(2,4-dimethyl-benzyl)-2-oxo-6-phenyl-1,2-dihydro-pyridin-4-yl]-acetic acid methyl ester 9 (183 mg, 0.46 mmoles) and this was dissolved within formic acid (8 mL). After Ra—Ni activation was complete the hydroxide mixture (heterogeneous) was carefully decanted, washed with water, and sequentially decanted to remove the residual sodium hydroxide. Excess water was removed from the activated Ra—Ni using a pipette. The nitrile solution was carefully added to the stirring Ra—Ni at room temperature, and mixture was heated to 55° C. for 90 min. After this period the reaction mixture was filtered through Celite (with MeOH washings) and concentrated in vacuo. The residue was taken up in EA and was washed with 50% v/v aqueous NH$_4$OH (3×20 mL) and brine. The resulting EA solution was dried over anhydrous Na$_2$SO$_4$ and was concentrated in vacuo to yield 0.151 g (89% yield) of 16 as a yellow residue.

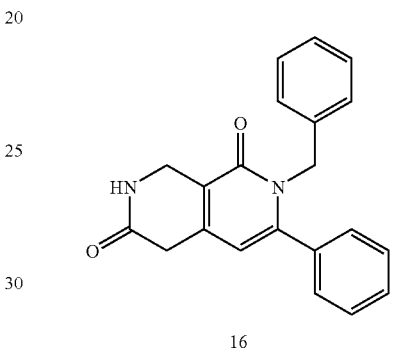

16

2-Benzyl-3-phenyl-7,8-dihydro-2H,5H-[2,7]naphthyridine-1,6-dione $^1$H-NMR (CDCl$_3$): δ7.48-7.41 (m, 1H), 7.40-7.33 (m, 2H), 7.20-7.09 (m, 5H), 6.95-6.89 (m, 2H), 5.95 (s, 1H), 5.84 (bs, 1H), 5.20 (bs, 2H), 3.55-3.47 (m, 2H), 2.81 (t, J=6.6 Hz, 2H). MS(ES+): 331.2 (M+H)

The following compound was prepared in a manner similar to that described above.

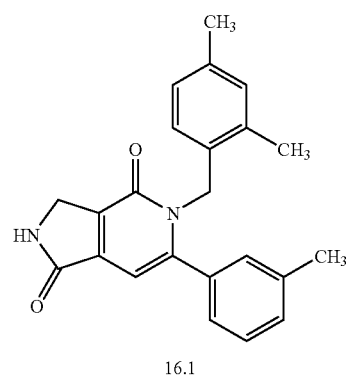

16.1

5-(2,4-Dimethyl-benzyl)-6-m-tolyl-3,5-dihydro-2H-pyrrolo[3,4-c]pyridine-1,4-dione

MS(ES+): 359.2 (M+H)

Example 17

This example illustrates the preparation of compound 17.

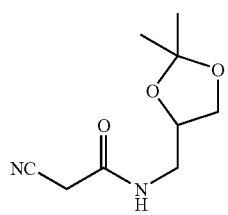

Methyl cyanoacetate (6.7 mL, 75.9 mmoles) was combined with 2,2-dimethyl-1,3-dioxolane-4-methanamine (4.6 g, 50.5 mmoles), 4-(N,N-dimethylamino)pyridine (20 mg, 0.16 mmoles) and 20 mL of Ethanol within a round-bottom flask. The mixture was then stirred at 80° C. for 16 hours. After this period reaction mixture was evaporated in vacuo and was purified using flash silica chromatography (0-60% EtOAc/hexane) to yield 7.33 g (96% yield) of 17 as a yellowish liquid.

17

2-Cyano-N-(2,2-dimethyl-[1,3]dioxolan-4-ylmethyl)-acetamide $^1$H-NMR (CDCl$_3$): δ6.43 (bs, 1H), 4.31-4.21 (m, 1H), 4.10-4.04 (m, 1H), 3.65 (dd, J'=8.3 Hz, J"=5.8 Hz, 1H), 3.59 (dq, J$^1$=13.9 Hz, J$^2$=5.6 Hz, J$^3$=3.5 Hz, 1H), 3.41 (s, 2H), 3.39-3.33 (m, 1H), 1.47 (s, 3H), 1.36 (s, 3H).

Example 18

This example illustrates the preparation of compound 18.

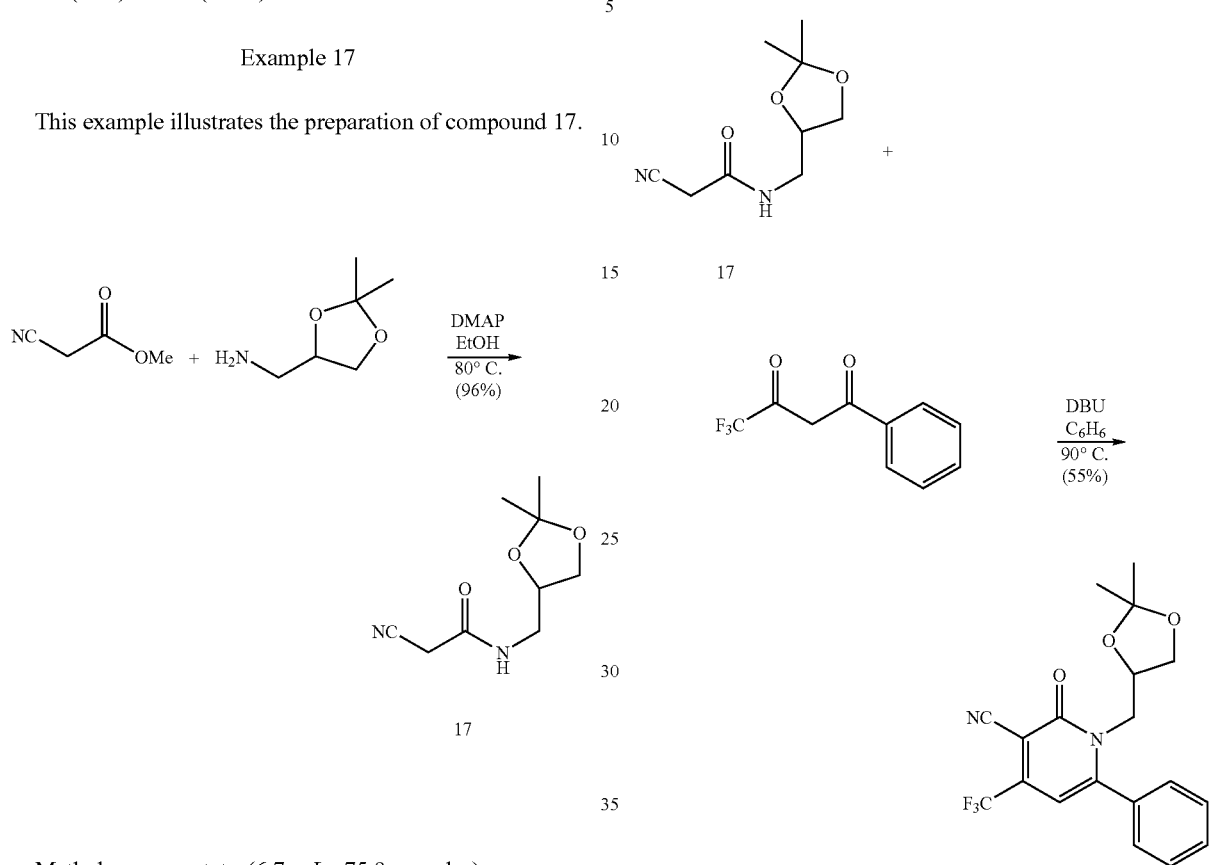

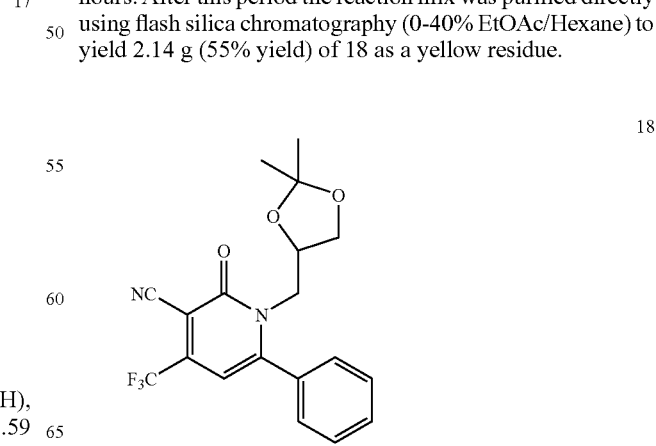

2-Cyano-N-(2,2-dimethyl-[1,3]dioxolan-4-ylmethyl)-acetamide 17 (2.05 g, 10.3 mmoles), 4,4,4-Trifluoro-1-phenyl-butane-1,3-dione (2.2 g, 10.3 mmoles) and DBU (0.77 mL, 5.1 mmoles) were combined with 20 mL of benzene within a round-bottom flask. The mixture was stirred at 90° C. for 16 hours. After this period the reaction mix was purified directly using flash silica chromatography (0-40% EtOAc/Hexane) to yield 2.14 g (55% yield) of 18 as a yellow residue.

18

1-(2,2-Dimethyl-[1,3]dioxolan-4-ylmethyl)-2-oxo-6-phenyl-4-trifluoromethyl-1,2-dihydro-pyridine-3-carbonitrile $^1$H-NMR (CDCl$_3$): δ7.60-7.49 (m, 3H), 7.48-7.37 (m, 2H), 6.42 (s, 1H), 4.59-4.52 (m, 1H), 4.33 (dd, J'=13.1 Hz, J"=2.5 Hz, 1H), 4.09 (dd, J'=8.8 Hz, J"=6.8 Hz, 1H), 4.02 (dd, J'=12.9 Hz, J"=8.6 Hz, 1H), 3.51 (dd, J'=8.6 Hz, J"=6.1 Hz, 1H), 1.24 (s, 3H), 1.10 (s, 3H). MS(ES+): 379.4 (M+H)

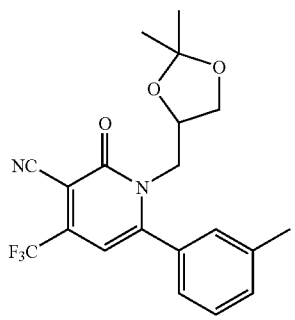

1-(2,2-Dimethyl-[1,3]dioxolan-4-ylmethyl)-2-oxo-6-m-tolyl-4-trifluoromethyl-1,2-dihydro-pyridine-3-carbonitrile $^1$H-NMR (CDCl$_3$): δ7.43-7.33 (m, 2H), 7.22 (bs, 2H), 6.41 (s, 1H), 4.59-4.51 (m, 1H), 4.34-4.30 (dd, J'=13.1 Hz, J"=2.8 Hz, 1H), 4.16-4.00 (m, 2H), 3.52 (dd, J'=8.8 Hz, J"=5.8 Hz, 1H), 2.43 (s, 6H), 1.11 (s, 3H).

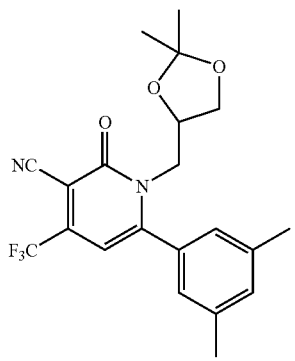

1-(2,2-Dimethyl-[1,3]dioxolan-4-ylmethyl)-6-(3,5-dimethyl-phenyl)-2-oxo-4-trifluoromethyl-1,2-dihydro-pyridine-3-carbonitrile $^1$H-NMR (CDCl$_3$): δ7.16 (s, 1H), 6.99 (bs, 2H), 6.40 (s, 1H), 4.59-4.52 (m, 1H), 4.34 (dd, J'=12.9 Hz, J"=2.5 Hz, 1H), 4.13-4.00 (m, 2H), 3.53 (dd, J'=8.6 Hz, J"=6.3 Hz, 1H), 2.38 (s, 6H), 1.24 (s, 3H), 1.12 (s, 3H).

Example 19

This example illustrates the preparation of compound 19.

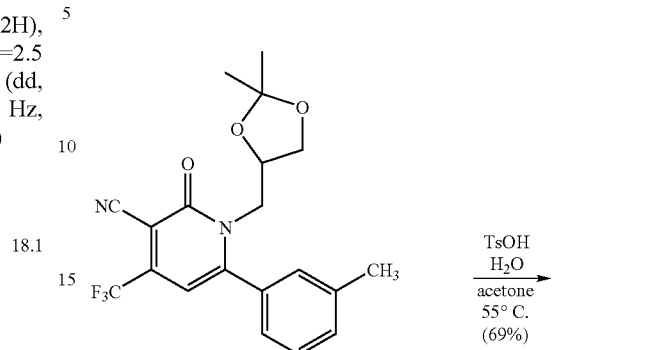

1-(2,2-Dimethyl-[1,3]dioxolan-4-ylmethyl)-6-(3,5-dimethyl-phenyl)-2-oxo-4-trifluoro-methyl-1,2-dihydro-pyridine-3-carbonitrile 18.2 (0.72 g, 1.78 moles) was combined with p-toluenesulfonic acid monohydrate (0.34 g, 1.78 mmoles), water (2 mL) and 30 mL of actone within a round-bottom flask equipped with a reflux condensor. The mixture was stirred at 55° C. for 3 hours. After this period the reaction mixture was evaporated in vacuo and was purified directly using flash silica chromatography (0-80% EtOAc/Hexane) to yield 0.45 g (69% yield) of 19 as a white solid.

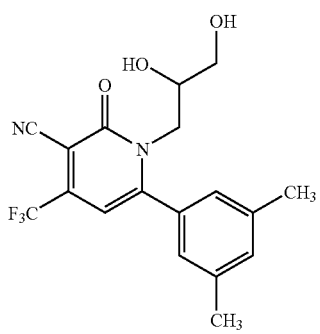

1-(2,3-Dihydroxy-propyl)-6-(3,5-dimethyl-phenyl)-2-oxo-4-trifluoromethyl-1,2-dihydro-pyridine-3-carbonitrile $^1$H-NMR (CDCl$_3$): δ7.19 (s, 1H), 6.95 (s, 2H), 6.46 (s, 1H), 4.24-4.12 (m, 2H), 3.94-3.86 (m, 1H), 3.63-3.55 (m, 1H), 3.43-3.36 (m, 1H), 3.21 (d, J=6.1 Hz, 1H), 2.39 (s, 6H).

The following compounds were prepared in a manner similar to that described above.

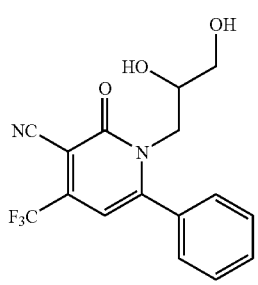

19.1

1-(2,3-Dihydroxy-propyl)-2-oxo-6-phenyl-4-trifluoromethyl-1,2-dihydro-pyridine-3-carbonitrile

MS(ES+): 339.1 (M+H)

19.2

1-(2,3-Dihydroxy-propyl)-2-oxo-6-m-tolyl-4-trifluoromethyl-1,2-dihydro-pyridine-3-carbonitrile $^1$H-NMR (CDCl$_3$): δ7.47-7.33 (m, 2H), 7.21 (bs, 2H), 6.48 (s, 1H), 4.24-4.09 (m, 2H), 4.04-3.97 (m, 1H), 3.56 (dd, J'=11.6 Hz, J''=4.0 Hz, 1H), 3.37 (dd, J'=11.9 Hz, J''=4.8 Hz, 1H), 2.82 (bs, 1H), 2.43 (s, 3H).

Example 20

This example illustrates the preparation of compound 20

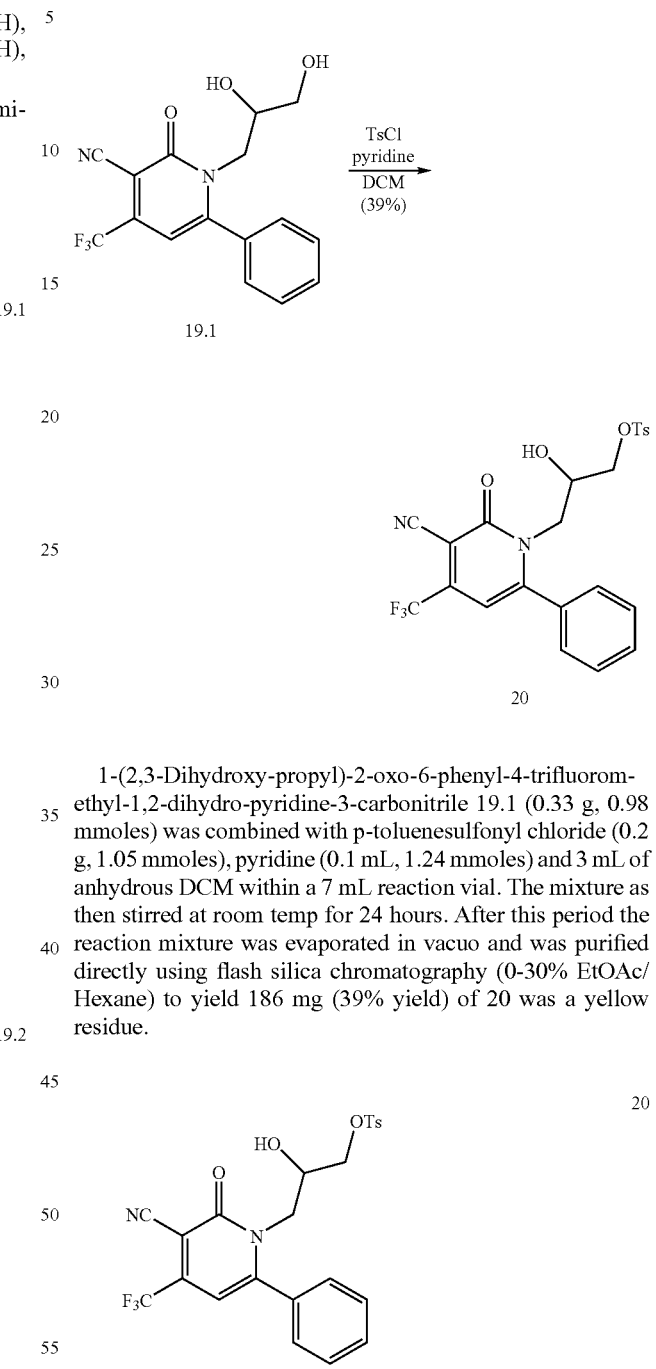

1-(2,3-Dihydroxy-propyl)-2-oxo-6-phenyl-4-trifluoromethyl-1,2-dihydro-pyridine-3-carbonitrile 19.1 (0.33 g, 0.98 mmoles) was combined with p-toluenesulfonyl chloride (0.2 g, 1.05 mmoles), pyridine (0.1 mL, 1.24 mmoles) and 3 mL of anhydrous DCM within a 7 mL reaction vial. The mixture as then stirred at room temp for 24 hours. After this period the reaction mixture was evaporated in vacuo and was purified directly using flash silica chromatography (0-30% EtOAc/Hexane) to yield 186 mg (39% yield) of 20 was a yellow residue.

Toluene-4-sulfonic acid 3-(3-cyano-2-oxo-6-phenyl-4-trifluoromethyl-2H-pyridin-1-yl)-2-hydroxy-propyl ester $^1$H-NMR (CDCl$_3$): δ7.66 (d, J=8.3 Hz, 2H), 7.62-7.52 (m, 3H), 7.44-7.38 (m, 2H), 7.33 (d, J=8.1 Hz, 2H), 6.46 (s, 1H), 4.30-4.21 (m, 1H), 4.17-4.07 (m, 2H), 3.97-3.87 (m, 2H), 3.38 (d, J=5.8 Hz, 1H), 2.45 (s, 3H).

The following compounds were prepared in a manner similar to that described above.

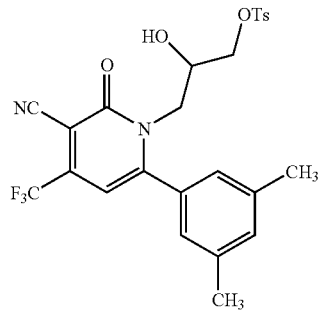

20.1

Toluene-4-sulfonic acid 3-[3-cyano-6-(3,5-dimethyl-phenyl)-2-oxo-4-trifluoromethyl-2H-pyridin-1-yl]-2-hydroxy-propyl Ester $^1$H-NMR (CDCl$_3$): δ7.67 (d, J=8.3 Hz, 2H), 7.33 (d, J=8.1 Hz, 2H), 7.20 (s, 1H), 6.97 (bs, 2H), 6.45 (s, 1H), 4.23-4.05 (m, 4H), 3.96-3.87 (m, 2H), 3.38-3.34 (m, 1H), 2.45 (s, 3H), 2.40 (s, 6H).

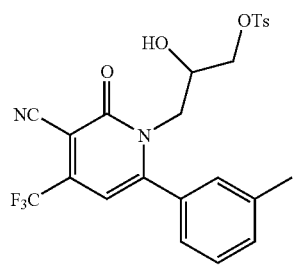

20.2

Toluene-4-sulfonic acid 3-(3-cyano-2-oxo-6-m-tolyl-4-trifluoromethyl-2H-pyridin-1-yl)-2-hydroxy-propyl Ester $^1$H-NMR (CDCl$_3$): δ7.66 d (J=8.3 Hz, 2H), 7.48-7.36 (m, 3H), 7.33 (d, J=8.3 Hz, 2H), 7.19 (bs, 2H), 6.45 (s, 1H), 4.25-4.05 (m, 3H), 3.96-3.86 (m, 2H), 3.45 (bs, 1H), 2.45 (s, 3H), 2.44 (s, 3H).

Example 21

This example illustrates the preparation of compound 21.

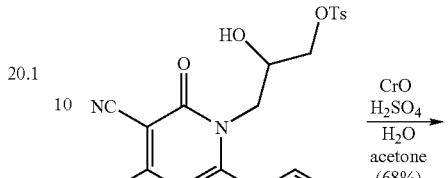

20

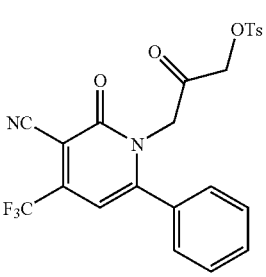

21

Toluene-4-sulfonic acid 3-(3-cyano-2-oxo-6-phenyl-4-trifluoromethyl-2H-pyridin-1-yl)-2-hydroxy-propyl ester 20 (46 mg, 0.093 mmoles) was dissolved into actone. To this solution at room temperature was added 2.67 M Jones Reagent (0.15 mL, 0.40 mmoles) and the resulting mixture was stirred at this temperature for 3 hours. After this period the reaction mixture was gravity filtered through paper, evaporated in vacuo and was purified directly using flash silica chromatography (0-30% EtOAc/Hexane) to yield 31 mg (68% yield) of 21 as a yellow residue.

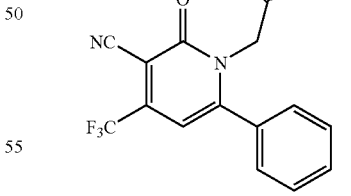

21

Toluene-4-sulfonic acid 3-(3-cyano-2-oxo-6-phenyl-4-trifluoromethyl-2H-pyridin-1-yl)-2-oxo-propyl Ester $^1$H-NMR (CDCl$_3$): δ7.76 (d, J=8.3 Hz, 2H), 7.63-7.52 (m, 3H), 7.40-7.32 (m, 4H), 6.50 (s, 1H), 4.84 (s, 2H), 4.59 (s, 2H), 2.47 (s, 3H).

The following compounds were prepared in a manner similar to that described above.

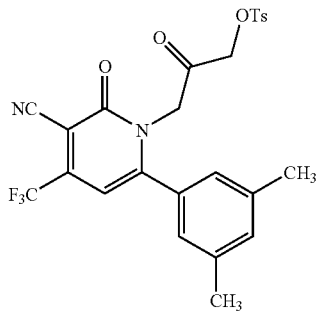

21.1

Toluene-4-sulfonic acid 3-[3-cyano-6-(3,5-dimethyl-phenyl)-2-oxo-4-trifluoromethyl-2H-pyridin-1-yl]-2-oxo-propyl Ester $^1$H-NMR (CDCl$_3$): δ7.76 (d, J=8.3 Hz, 2H), 7.38 (d, J=8.3 Hz, 2H), 7.21 (bs, 1H), 6.93 (s, 2H), 6.48 (s, 1H), 4.86 (s, 2H), 4.60 (s, 2H), 2.47 (s, 3H), 2.38 (s, 6H).

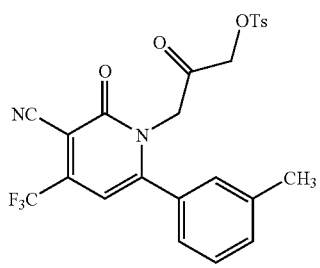

21.2

Toluene-4-sulfonic acid 3-(3-cyano-2-oxo-6-m-tolyl-4-trifluoromethyl-2H-pyridin-1-yl)-2-oxo-propyl Ester $^1$H-NMR (CDCl$_3$): δ7.76 (d, J=8.3 Hz, 2H), 7.45-7.35 (m, 4H), 7.17-7.10 (m, 2H), 6.49 (s, 1H), 4.85 (s, 2H), 4.59 (s, 2H), 2.47 (s, 3H), 2.43 (s, 3H).

Example 22

This example illustrates the preparation of compound 22.

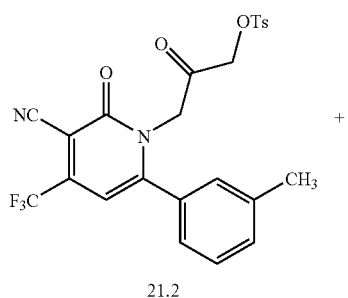

21.2

+

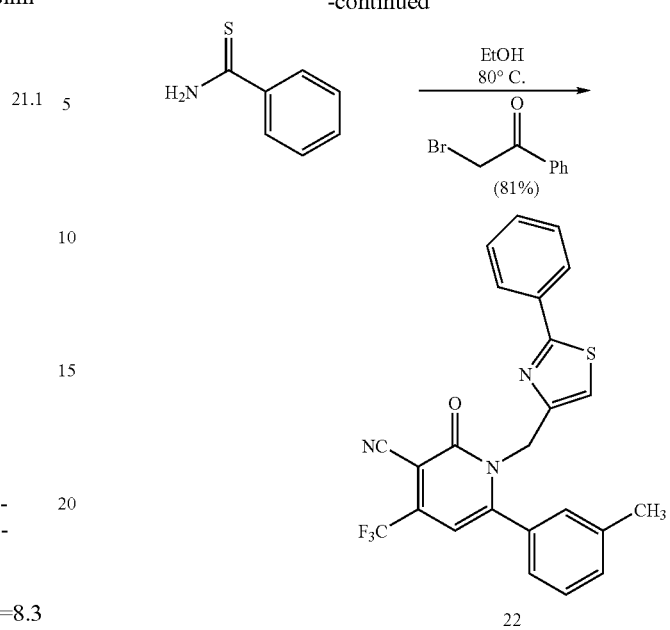

22

Toluene-4-sulfonic acid 3-(3-cyano-2-oxo-6-m-tolyl-4-trifluoromethyl-2H-pyridin-1-yl)-2-oxo-propyl ester 21.2 (11 mg, 0.022 mmoles) was combined with thiobenzamide (6 mg, 0.044 mmoles) and 1.0 mL of EtOH within a 7 mL reaction vial. This mixture was stirred at 80° C. for 16 hours. After this period 2-bromoacetophenone (7 mg, 0.035 mmoles) was added and the mixture was stirred at 80° C. for an additional 3 hours. After this period the reaction mixture was evaporated in vacuo and was purified using flash silica chromatography (0-20% EtOAc/Hexane) to yield 8 mg (81% yield) of 22 as a yellowish residue.

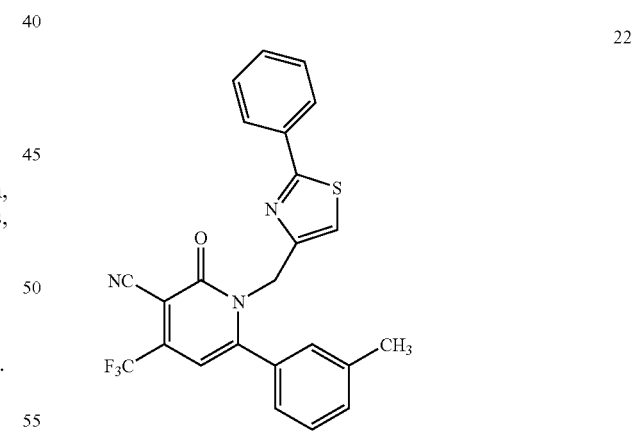

22

2-Oxo-1-(2-phenyl-thiazol-4-ylmethyl)-6-m-tolyl-4-trifluoromethyl-1,2-dihydro-pyridine-3-carbonitrile $^1$H-NMR (CDCl$_3$): δ7.89-7.82 (m, 2H), 7.46-7.34 (m, 7H), 7.30 (s, 1H), 6.44 (s, 1H), 5.28 (s, 2H), 2.41 (s, 3H). MS(ES+): 452.1 (M+H)

The following compounds were prepared in a manner similar to that described above.

215

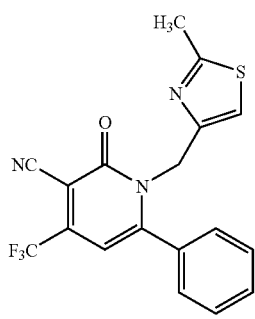

1-(2-Methyl-thiazol-4-ylmethyl)-2-oxo-6-phenyl-4-trifluoromethyl-1,2-dihyro-pyridine-3-carbonitrile MS(ES+): 398.0 (M+Na)

22.2

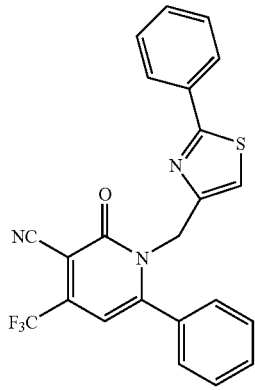

2-Oxo-6-phenyl-1-(2-phenyl-thiazol-4-ylmethyl)-4-trifluoromethyl-1,2-dihydro-pyridine-3-carbonitrile

MS(ES+): 438.2 (M+H)

22.3

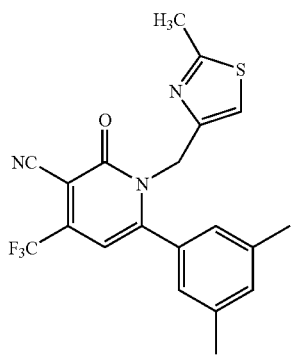

216

6-(3,5-Dimethyl-phenyl)-1-(2-methyl-thiazol-4-ylm-ethyl)-2-oxo-4-trifluoromethyl-1,2-dihydro-pyridine-3-carbonitrile

MS(ES+): 404.1 (M+H)

22.4

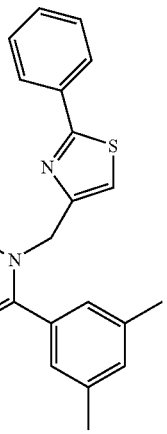

2-Oxo-1-(2-phenyl-thiazol-4-ylmethyl)-6-m-tolyl-4-trifluoromethyl-1,2-dihydro-pyridine-3-carbonitrile

MS(ES+): 466.2 (M+H)

22.5

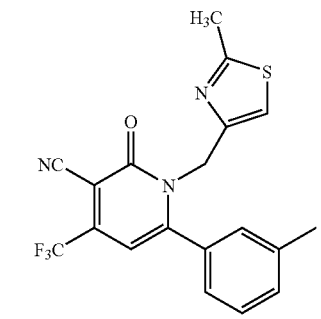

1-(2-Methyl-thiazol-4-ylmethyl)-2-oxo-6-m-tolyl-4-trifluoromethyl-1,2-dihydro-pyridine-3-carbonitrile

MS(ES+): 389.8 (M+H)

22.6

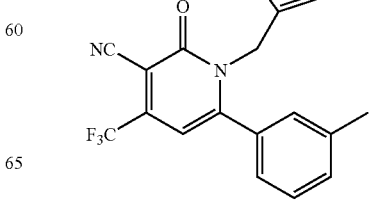

22.1

217

1-(2-Ethyl-thiazol-4-ylmethyl)-2-oxo-6-m-tolyl-4-trifluoromethyl-1,2-dihydro-pyridine-3-carbonitrile

MS(ES+): 404.0 (M+H)

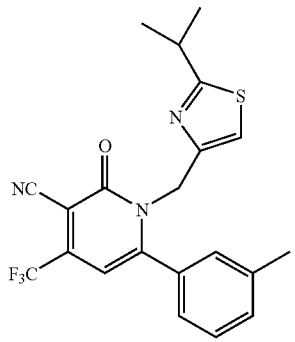

1-(2-Isopropyl-thiazol-4-ylmethyl)-2-oxo-6-m-tolyl-4-trifluoromethyl-1,2-dihydro-pyridine-3-carbonitrile $^1$H-NMR (CDCl$_3$): δ7.39-7.27 (m, 4H), 7.11 (s, 1H), 6.42 (s, 1H), 5.19 (s, 2H), 3.22 (m, J=6.8 Hz, 1H), 2.39 (s, 3H), 1.36 (d, J=6.8 Hz, 6H).

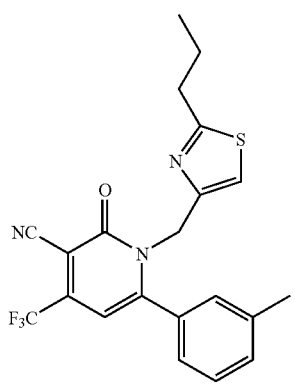

2-Oxo-1-(2-propyl-thiazol-4-ylmethyl)-6-m-tolyl-4-trifluoromethyl-1,2-dihydro-pyridine-3-carbonitrile

MS(ES+): 418.3 (M+H)

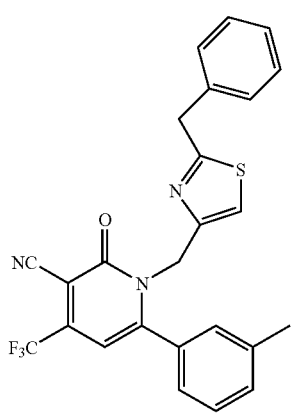

218

1-(2-Benzyl-thiazol-4-ylmethyl)-2-oxo-6-m-tolyl-4-trifluoromethyl-1,2-dihydro-pyridine-3-carbonitrile

MS(ES+): 466.2 (M+H)

Example 23

This example illustrates the preparation of compound 23.

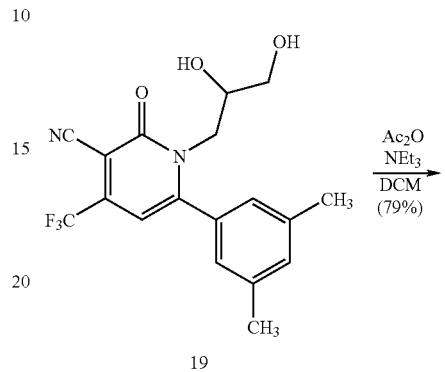

19

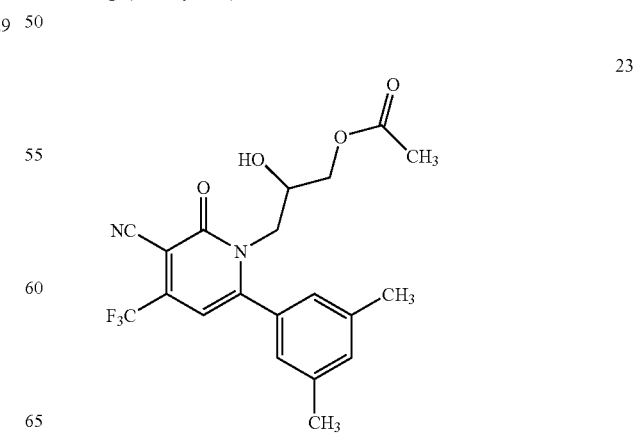

23

1-(2,3-Dihydroxy-propyl)-6-(3,5-dimethyl-phenyl)-2-oxo-4-trifluoromethyl-1,2-dihydro-pyridine-3-carbonitrile 19 (33 mg, 0.09 mmoles) was combined with acetic acid anhydride (9 μL, 0.095 mmoles), triethylamine (15 μL, 0.11 mmoles) and 2.0 mL of DCM within a 7 mL reaction vial. This mixture was stirred at room temperature for 24 hours. After this period the reaction mixture was purified directly by flash silica chromatography (0-40% EtOAc/Hexane) to yield 29 mg (79% yield) of 23 as a white solid.

23

Acetic acid 3-[3-cyano-6-(3,5-dimethyl-phenyl)-2-oxo-4-trifluoromethyl-2H-pyridin-1-yl]-2-hydroxy-propyl Ester $^1$H-NMR (CDCl$_3$): δ7.19 (bs, 1H), 6.98 (bs, 2H), 6.44 (s, 1H), 4.28-3.91 (m, 6H), 3.15 (bs, 1H), 2.39 (s, 6H), 1.94 (s, 3H).

The following compounds were prepared in a manner similar to that described above.

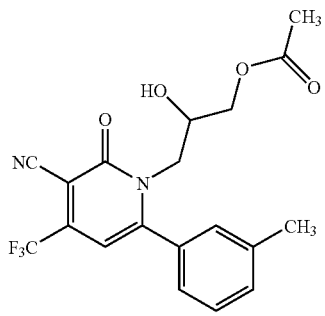

23.1

Acetic acid 3-(3-cyano-2-oxo-6-m-tolyl-4-trifluoromethyl-2H-pyridin-1-yl)-2-hydroxy-propyl Ester $^1$H-NMR (CDCl$_3$): δ7.45-7.35 (m, 2H), 7.19 (bs, 2H), 6.45 (s, 1H), 4.27-3.91 (m, 6H), 3.05 (bs, 1H), 2.44 (s, 3H), 1.93 (s, 3H).

Example 24

This example illustrates the preparation of compound 24.

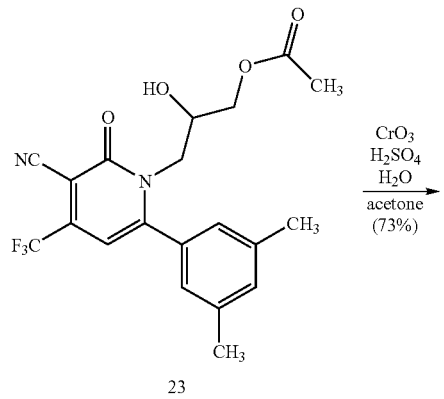

Acetic acid 3-[3-cyano-6-(3,5-dimethyl-phenyl)-2-oxo-4-trifluoromethyl-2H-pyridin-1-yl]-2-hydroxy-propyl ester 23 (29 mg, 0.071 mmoles) was dissolved into 3 mL of acetone within a 7 ml reaction vial. To this solution was added 2.67M Jones Reagent (53 mL, 0.142 mmoles) and the mixture was stirred at room temperature for 2 hours. After this period the reaction mixture was gravity filtered through paper and the resulting filtrate was evaporated in vacuo, and purified using flash silica chromatography (0-40% EtOAc/Hexane) to yield 21 mg (73% yield) of 24 as a white solid.

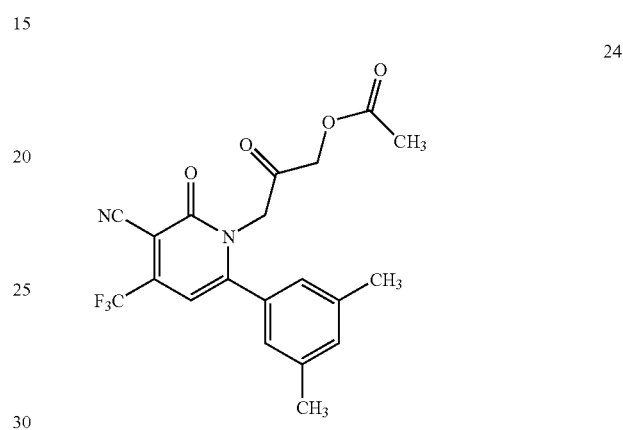

24

Acetic acid 3-[3-cyano-6-(3,5-dimethyl-phenyl)-2-oxo-4-trifluoromethyl-2H-pyridin-1-yl]-2-oxo-propyl Ester $^1$H-NMR (CDCl$_3$): δ7.19 (s, 1H), 6.93 (s, 2H), 6.48 (s, 1H), 4.73 (s, 2H), 4.72 (s, 2H), 2.37 (s, 6H), 2.14 (s, 3H).

Example 25

This example illustrates the preparation of compound 25.

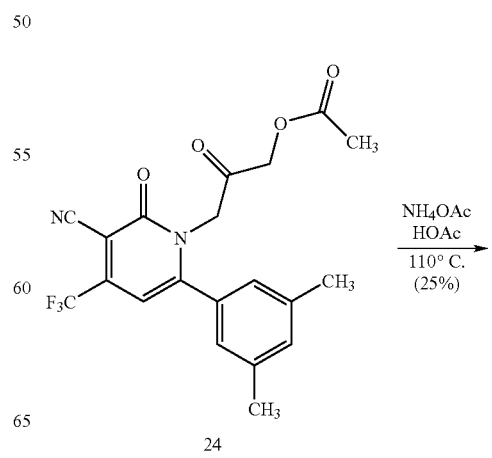

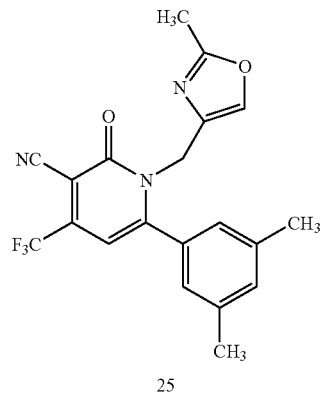

25

Acetic acid 3-[3-cyano-6-(3,5-dimethyl-phenyl)-2-oxo-4-trifluoromethyl-2H-pyridin-1-yl]-2-oxo-propyl ester 24 (21 mg, 0.052 mmoles) was combined with ammonium acetate (50 mg, 0.64 mmoles) and 1.0 mL of glacial acetic acid within a 7 mL reaction vial, and the mixture was stirred at 110° C. for 16 hours. After this period the reaction mixture was evaporated in vacuo and was purified using flash silica chromatography (0-40% EtOAc/Hexane) to yield 5 mg (25% yield) of 25 as a white solid.

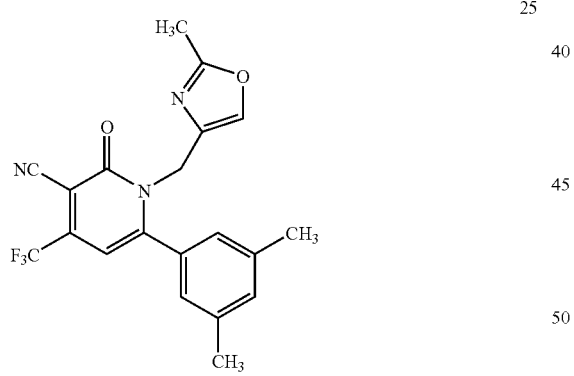

25

6-(3,5-Dimethyl-phenyl)-1-(2-methyl-oxazol-4-ylmethyl)-2-oxo-4-trifluoromethyl-1,2-dihydro-pyridine-3-carbonitrile $^1$H-NMR (CDCl$_3$): δ7.59 (s, 1H), 7.19 (bs, 1H), 7.15 (s, 2H), 6.41 (s, 1H), 4.98 (s, 2H), 2.41 (s, 3H), 2.38 (s, 6H).

The following compounds were prepared in a manner similar to that described above.

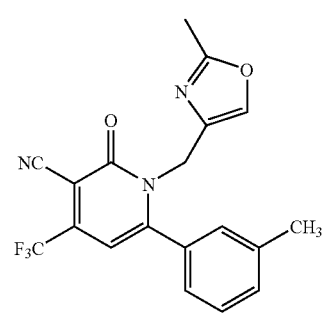

25.1

1-(2-Methyl-oxazol-4-ylmethyl)-2-oxo-6-m-tolyl-4-trifluoromethyl-1,2-dihydro-pyridine-3-carbonitrile

MS(ES+): 374.1 (M+H)

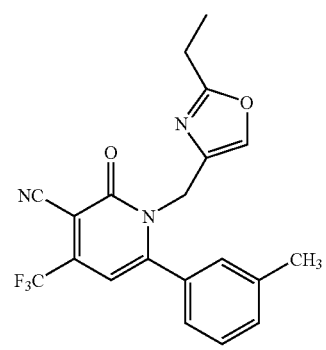

25.2

1-(2-Ethyl-oxazol-4-ylmethyl)-2-oxo-6-m-tolyl-4-trifluoromethyl-1,2-dihydro-pyridine-3-carbonitrile

MS(ES+): 388.0 (M+H)

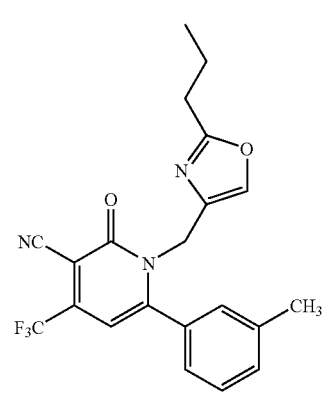

25.2

2-Oxo-1-(2-propyl-oxazol-4-ylmethyl)-6-m-tolyl-4-trifluoromethyl-1,2-dihydro-pyridine-3-carbonitrile

MS(ES+): 402.1 (M+H)

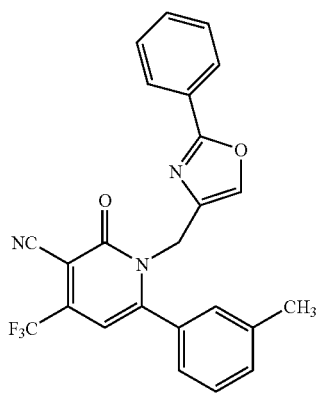

2-Oxo-1-(2-phenyl-oxazol-4-ylmethyl)-6-m-tolyl-4-trifluoromethyl-1,2-dihydro-pyridine-3-carbonitrile

MS(ES+): 436.3 (M+H)

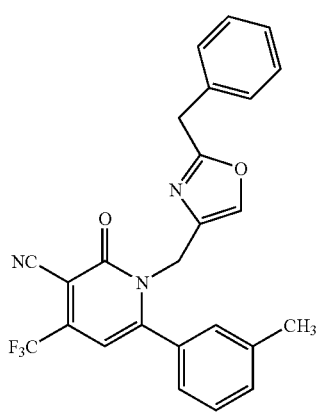

1-(2-Benzyl-oxazol-4-ylmethyl)-2-oxo-6-m-tolyl-4-trifluoromethyl-1,2-dihydro-pyridine-3-carbonitrile $^1$H-NMR (CDCl$_3$): δ7.64 (s, 1H), 7.37-7.24 (m, 9H), 6.4 (s, 1H), 4.98 (s, 2H), 4.06 (s, 2H), 2.36 (s, 3H). MS(ES+): 449.9 (M+H)

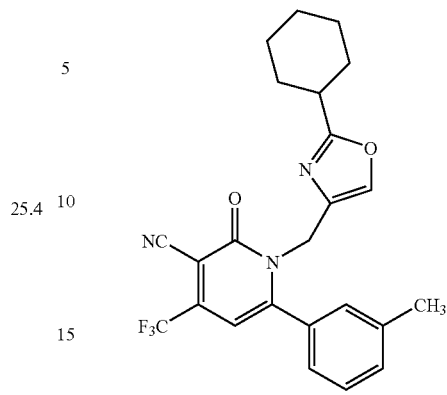

1-(2-Cyclohexyl-oxazol-4-ylmethyl)-2-oxo-6-m-tolyl-4-trifluoromethyl-1,2-dihydro-pyridine-3-carbonitrile

MS(ES+): 442.0 (M+H)

Example 26

This example illustrates the preparation of compound 26.

Pent-1-en-3-ol (5.0 mL, 48.7 mmoles), N,N-diisopropyl-ethylamine (10.2 mL, 58.6 mmoles) and MOMCl (4.4 mL, 57.9 mmoles) were dissolved in 10 mL of anhydrous DCM within a sealed-tube, and this mixture was stirred at 50° C. for 20 hours. After this period the reaction mixture was combined with Et$_2$O and the resulting precipitate was removed by gravity filtration. The filtrate was carefully evaporated (—Et$_2$O and DCM) and the resulting amber liquid was fractionally distilled to yield 5.4 g (85% yield) of 26 as a clear liquid. B.P. 126° C. @760 mmHg 3-Methoxymethoxy-pent-1-ene $^1$H-NMR (CDCl$_3$): δ5.72-5.61 (m, 1H), 5.23-5.16 (m, 2H), 4.71 (d, J=6.8 Hz, 1H), 4.55 (d, J=6.8 Hz, 1H), 3.91 (q, J=7.1 Hz, 1H), 3.38 (s, 3H), 1.70-1.48 (m, 2H), 0.93 (t, J=7.3 Hz, 3H).

The following compounds were prepared in a manner similar to that described above.

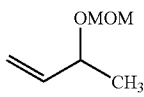

26.1

3-Methoxymethoxy-but-1-ene $^1$H-NMR (CDCl$_3$): δ5.80-5.70 (m, 1H), 5.24-5.11 (m, 2H), 4.69 (d, J=6.8 Hz, 1H), 4.58 (d, J=6.8 Hz, 1H), 4.21-4.09 (m, 1H), 3.38 (s, 3H), 1.27 (d, J=6.3 Hz, 3H).

Example 27

This example illustrates the preparation of compound 27.

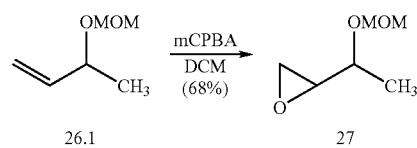

3-Methoxymethoxy-but-1-ene 26.1 (1.73 g, 14.9 mmoles) was dissolved into 100 mL of DCM and to this stirring mixture at 0° C. was added 3-chloroperoxybenzoic acid (77% max, 7.4 g, ~30 mmoles). This mixture was allowed to stir at room temperature for 20 hours. After this period the reaction mixture was combined with DCM and was washed with saturated Na$_2$S$_2$O$_3$ (2×20 mL) and 15 mL of saturated NaHCO$_3$. After drying the resulting DCM solution over anhydrous Na$_2$SO$_4$ the mixture was carefully evaporated in vacuo to yield crude product. The crude product was purified using flash silica chromatography (0-15% EtOAc/Hexane) to yield 1.34 g (68% yield) of 27 as yellowish liquid. Both $^1$H-NMR and TLC analysis show 27 to be a 1:1 mixture of diastereomers.

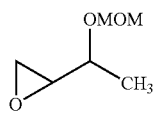

27

2-(1-Methoxymethoxy-ethyl)-oxirane $^1$H-NMR (CDCl$_3$): (diastereomers) δ4.81 (d, J=6.6 Hz, 1H), 4.72-4.67 (m, 2H), 4.64 (d, J=6.6 Hz, 1H), 3.65-3.57 (m, 1H), 3.53-3.44 (m, 1H), 3.40 (s, 3H), 3.37 (s, 3H), 3.02-2.98 (m, 1H), 2.95-2.91 (m, 1H), 2.81-2.76 (m, 2H), 2.73-2.70 (m, 1H), 2.57-2.54 (m, 1H).

Example 28

This example illustrates the preparaion of compound 28.

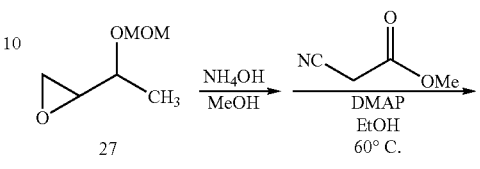

(65%-2 steps)

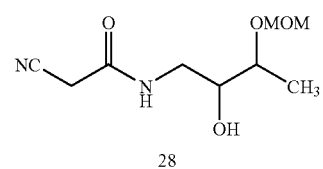

28

2-(1-Methoxymethoxy-ethyl)-oxirane 27 (1.89 g, 14.3 mmoles) was combined with NH$_4$OH (28% NH$_3$ in water, 5 mL) and 1 mL of MeOH within a sealed-tube and this mixture was vigorously stirred at room temperature for 48 hours. After this period the reaction mixture was evaporate in vacuo (—NH$_3$ and H$_2$O) to yield crude product as an amber liquid. This product was combined with methyl cyanoactate (3.0 mL, 34.0 mmoles), DMAP (10 mg) and 50 mL of anhydrous EtOH. This mixture was stirred at 60° C. for 48 hours. After this period the reaction mixture was evaporated in vacuo and was purified using flash silica chromatography (0-100% EtOAc/Hexane) to yield 2.02 g (65% yield) of 28 as an amber residue. Both $^1$H-NMR and TLC analysis show 28 to be a 1:1 mixture of diastereomers.

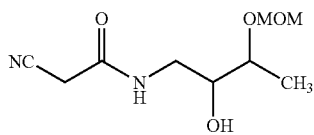

28

2-Cyano-N-(2-hydroxy-3-methoxymethoxy-butyl)-acetamide $^1$H-NMR (CDCl$_3$): (diastereomers) δ6.78 & 6.64 (bs, 1H—both peaks), 4.77-4.65 (m, 2H), 3.84-3.54 (m, 3H), 3.45-3.36 (m, 6H), 3.32-3.14 (m, 2H), 1.13 (d, J=6.3 Hz, 3H).

Example 29

This example illustrates the preparation of compound 29.

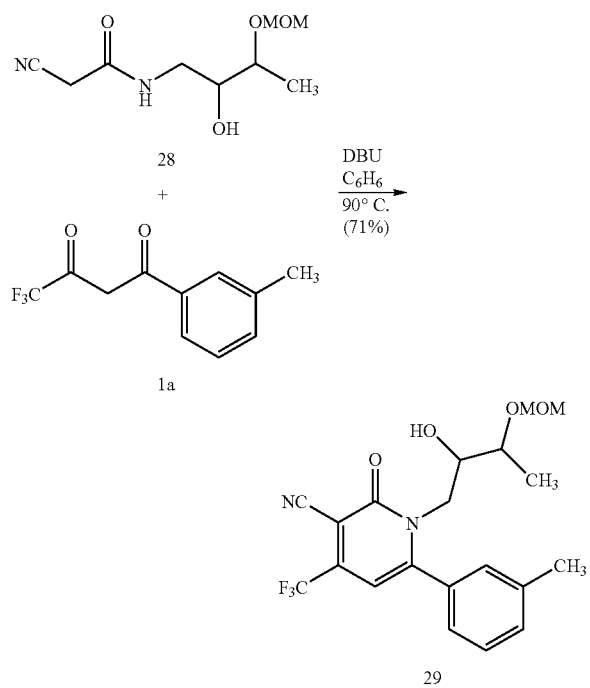

2-Cyano-N-(2-hydroxy-3-methoxymethoxy-butyl)-acetamide 28 (0.78 g, 3.6 mmoles) and 4,4,4-Trifluoro-1-m-tolyl-butane-1,3-dione 1a (0.83 g, 3.6 mmoles) were dissolved in 10 mL of $C_6H_6$ and this mixture was stirred at 90° C. for 16 hours. After this period the reaction mixture was purified directly using flash silica chromatography (0-40% EtOAc/Hexane) to yield 1.06 g (71% yield) of 29 as a yellow liquid. $^1$H-NMR analysis shows 29 to be a 1:1 mixture of diastereomers.

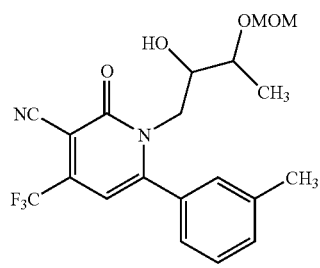

1-(2-Hydroxy-3-methoxymethoxy-butyl)-2-oxo-6-m-tolyl-4-trifluoromethyl-1,2-dihydro-pyridine-3-carbonitrile $^1$H-NMR (CDCl$_3$): (diastereomers) δ7.44-7.32 (m, 4H), 7.21 (bs, 4H), 6.40 (bs, 2H), 4.58-4.45 (m, 4H), 4.28-4.09 (m, 4H), 3.90-3.82 (m, 1H), 3.81-3.73 (m, 1H), 3.71-3.63 (m, 1H), 3.57-3.49 (m, 1H), 3.22 (s, 3H), 3.10 (s, 3H), 2.43 (s, 6H), 1.14 (d, J=6.3 Hz, 3H), 1.07 (d, J=6.6 Hz, 3H).

The following compounds were prepared in a manner similar to that described above.

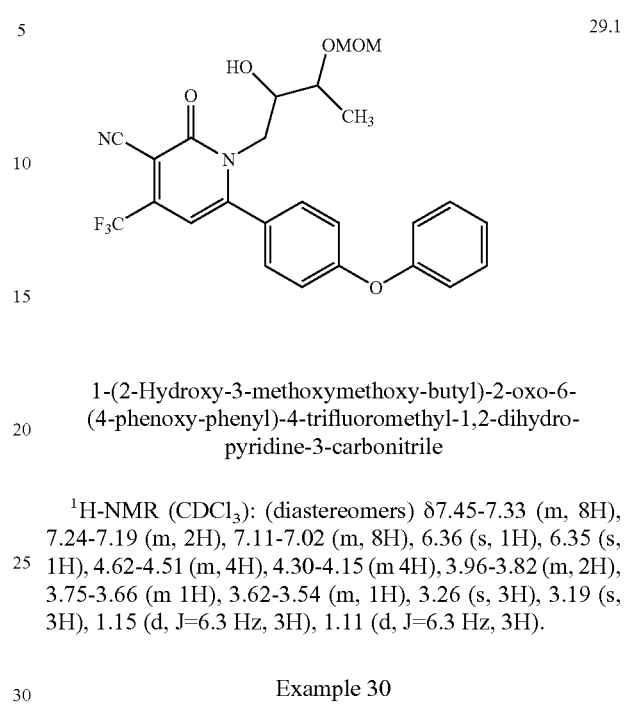

1-(2-Hydroxy-3-methoxymethoxy-butyl)-2-oxo-6-(4-phenoxy-phenyl)-4-trifluoromethyl-1,2-dihydro-pyridine-3-carbonitrile $^1$H-NMR (CDCl$_3$): (diastereomers) δ7.45-7.33 (m, 8H), 7.24-7.19 (m, 2H), 7.11-7.02 (m, 8H), 6.36 (s, 1H), 6.35 (s, 1H), 4.62-4.51 (m, 4H), 4.30-4.15 (m 4H), 3.96-3.82 (m, 2H), 3.75-3.66 (m 1H), 3.62-3.54 (m, 1H), 3.26 (s, 3H), 3.19 (s, 3H), 1.15 (d, J=6.3 Hz, 3H), 1.11 (d, J=6.3 Hz, 3H).

Example 30

This example illustrates the preparation of compound 30.

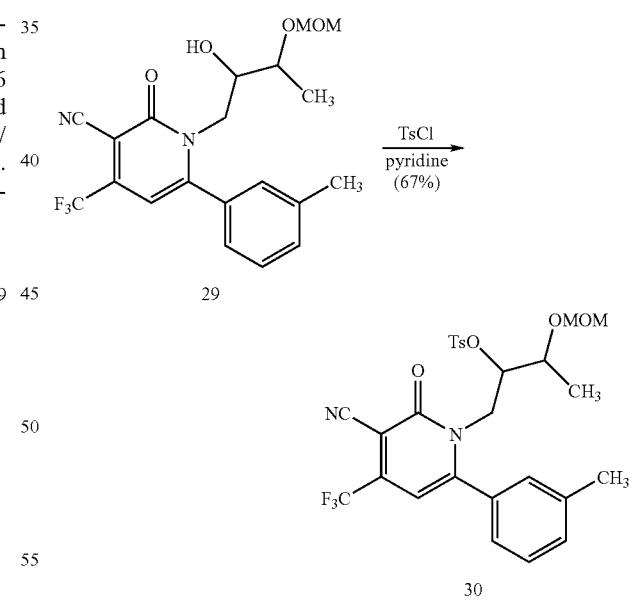

1-(2-Hydroxy-3-methoxymethoxy-butyl)-2-oxo-6-m-tolyl-4-trifluoromethyl-1,2-dihydro-pyridine-3-carbonitrile 29 (0.36 g, 0.87 mmoles) was combined with p-toluenesulfonyl chloride (0.33 g, 1.73 mmoles) in 2 mL of pyridine and this mixture was stirred at room temperature for 16 hours. After this period the mixture was evaporated and purified using flash silica chromatography (0-20% EtOAc/Hexane) to yield 0.33 g (67% yield) of 30 as a yellow residue. $^1$H-NMR analysis shows 30 to be a 1:1 mixture of diastereomers.

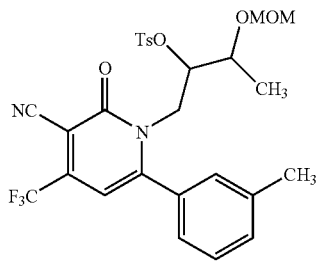

30

Toluene-4-sulfonic acid 1-(3-cyano-2-oxo-6-m-tolyl-4-trifluoromethyl-2H-pyridin-1-ylmethyl)-2-methoxymethoxy-propyl Ester ¹H-NMR (CDCl₃): (diastereomers) δ7.68-7.61 (m, 4H), 7.46-7.28 (m, 4H), 6.33 (s, 1H), 6.33 (s, 1H), 5.06-5.00 (m, 1H), 4.88-4.82 (m, 1H), 4.52-4.45 (m, 2H), 4.38 (q, J=6.8 Hz, 2H), 4.33-4.02 (m, 4H), 3.96-3.89 (m, 1H), 3.28 (s, 3H), 3.14 (s, 3H), 2.49 (s, 3H), 2.49 (s, 3H), 2.44 (s, 3H), 2.43 (s, 3H), 1.14 (d, J=6.8 Hz, 3H), 0.85 (d, J=6.6 Hz, 3H).

Example 31

This example illustrates the preparation of compound 31.

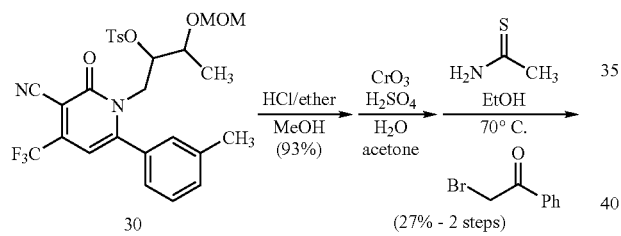

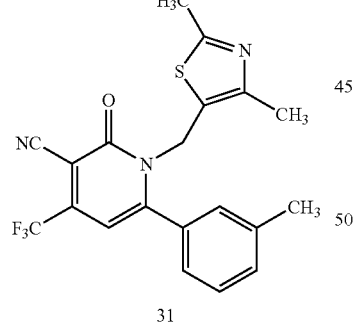

31

Toluene-4-sulfonic acid 1-(3-cyano-2-oxo-6-m-tolyl-4-trifluoromethyl-2H-pyridin-1-ylmethyl)-2-methoxymethoxy-propyl ester 30 (0.28 g, 0.50 mmoles) was dissolved into 7 mL of anhydrous MeOH and to this solution was added HCl (2.0 M solution in diethyl ether, 1.0 mL) and this mixture was stirred at room temperature for 2 hours. After this period the reaction mixture was evaporated in vacuo and was purified using flash silica chromatography (0-40% EtOAc/Hexane) to yield 0.24 g (93% yield) of 31 as a yellow residue. ¹H-NMR analysis shows 31 to be a 1:1 mixture of diastereomers.

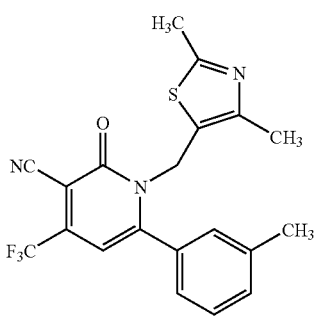

31

1-(2,4-Dimethyl-thiazol-5-ylmethyl)-2-oxo-6-m-tolyl-4-trifluoromethyl-1,2-dihydro-pyridine-3-carbonitrile ¹H-NMR (CDCl₃): δ7.47-7.38 (m, 2H), 7.13-7.06 (m, 2H), 6.37 (s, 1H), 5.28 (s, 2H), 2.58 (s, 3H), 2.43 (s, 3H). MS(ES+): 403.8 (M+H)

The following compounds were prepared in a manner similar to that described above.

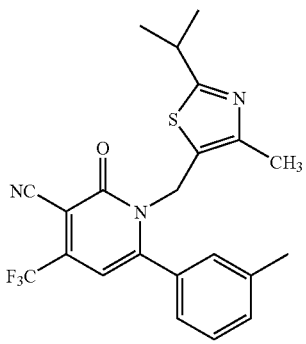

31.1

1-(2-Isopropyl-4-methyl-thiazol-5-ylmethyl)-2-oxo-6-m-tolyl-4-trifluoromethyl-1,2-dihydro-pyridine-3-carbonitrile

MS(ES+): 432.3 (M+H)

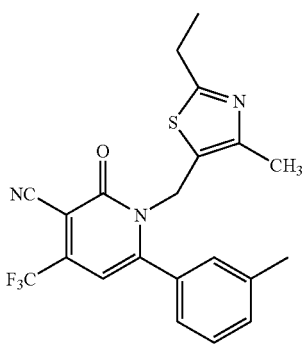

31.2

1-(2-Ethyl-4-methyl-thiazol-5-ylmethyl)-2-oxo-6-m-tolyl-4-trifluoromethyl-1,2-dihydro-pyridine-3-carbonitrile

MS(ES+): 418.2 (M+H)

Example 32

This example illustrates the preparation of compound 32.

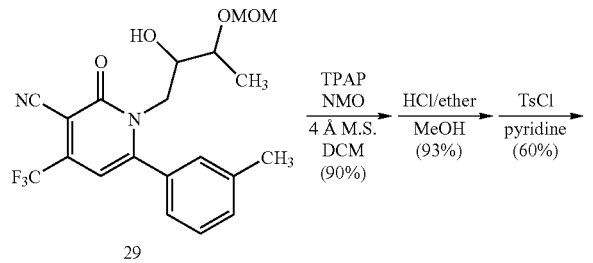

29

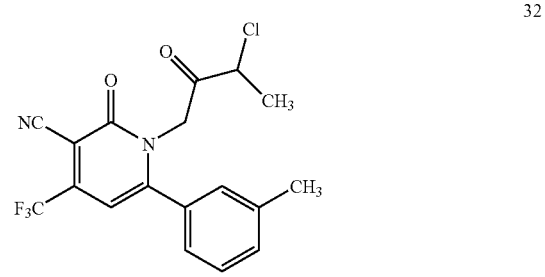

32

1-(2-Hydroxy-3-methoxymethoxy-butyl)-2-oxo-6-m-tolyl-4-trifluoromethyl-1,2-dihydro-pyridine-3-carbonitrile 29 (0.21 g, 0.52 mmoles) was combined with N-methylmorpholine N-oxide (NMO, 92 mg, 0.79 mmoles) and 4 Å molecular sieves (powder, 170 mg) in 5 mL of anhydrous DCM within a 7 mL reaction vial. The mixture was stirred at room temperature for 10 min. After this period tetrapropylammonium perruthenate (TPAP, 10 mg, 0.028 mmoles) was added and the mixture was stirred at room temperature for an additional 3 hours. After this period the reaction mixture was purified directly using flash silica chromatography (0-40% EtOAc/Hexane) to yield 0.191 g (90% yield) of 1-(3-Methoxymethoxy-2-oxo-butyl)-2-oxo-6-m-tolyl-4-trifluoromethyl-1,2-dihydro-pyridine-3-carbonitrile as a yellow residue.

$^1$H-NMR (CDCl$_3$): δ7.42-7.35 (m, 2H), 7.14-7.07 (m, 2H), 6.45 (s, 1H), 5.04-4.91 (m, 2H), 4.63-4.55 (m, 2H), 4.20 (q, J=6.8 Hz, 1H), 3.22 (s, 3H), 2.40 (s, 3H), 1.31 (d, J=7.1 Hz, 3H).

1-(3-Methoxymethoxy-2-oxo-butyl)-2-oxo-6-m-tolyl-4-trifluoromethyl-1,2-dihydro-pyridine-3-carbonitrile (0.191 g, 0.47 mmoles) was dissolved into 25 mL of anhydrous MeOH and to this solution was added HCl (2.0 M solution in diethyl ether, 5.0 mL). The mixture was then stirred at room temperature for 2 hours. After this period the reaction mixture was evaporated in vacuo and was purified using flash silica chromatography (0-60% EtOAc/Hexane) to yield 0.16 g (93% yield) of 1-(3-Hydroxy-2-oxo-butyl)-2-oxo-6-m-tolyl-4-trifluoromethyl-1,2-dihydro-pyridine-3-carbonitrile as a yellow residue. $^1$H-NMR (CDCl$_3$): δ7.42-7.35 (m, 2H), 7.14-7.08 (m, 2H), 6.50 (m, 1H), 5.06 (d, J=17.2 Hz, 1H), 4.92 (d, J=17.2 Hz, 1H), 4.39-4.31 (m, 1H), 3.48 (bs, 1H), 2.40 (s, 3H), 1.28 (d, J=6.8 Hz, 3H).

1-(3-Hydroxy-2-oxo-butyl)-2-oxo-6-m-tolyl-4-trifluoromethyl-1,2-dihydro-pyridine-3-carbonitrile (98 mg, 0.27 mmoles) was combined with p-toluenesulfonyl chloride (0.1 g, 0.52 mmoles) in 2.0 mL of pyridine. The mixture was stirred at room temperature for 16 hours. After this period the reaction mixture was evaporated in vacuo and was purified using flash silica chromatography (0-20% EtOAc/Hexane) to yield 62 mg (60% yield) of 32 as a yellow residue.

1-(3-Chloro-2-oxo-butyl)-2-oxo-6-m-tolyl-4-trifluoromethyl-1,2-dihydro-pyridine-3-carbonitrile $^1$H-NMR (CDCl$_3$): δ7.44-7.35 (m, 2H), 7.16-7.11 (m, 2H), 6.49 (s, 1H), 5.02-4.92 (m, 2H), 4.55 (q, J=6.8 Hz, 1H), 2.42 (s, 3H), 1.65 (d, J=6.8 Hz, 3H).

Example 33

This example illustrates the preparation of compound 33.

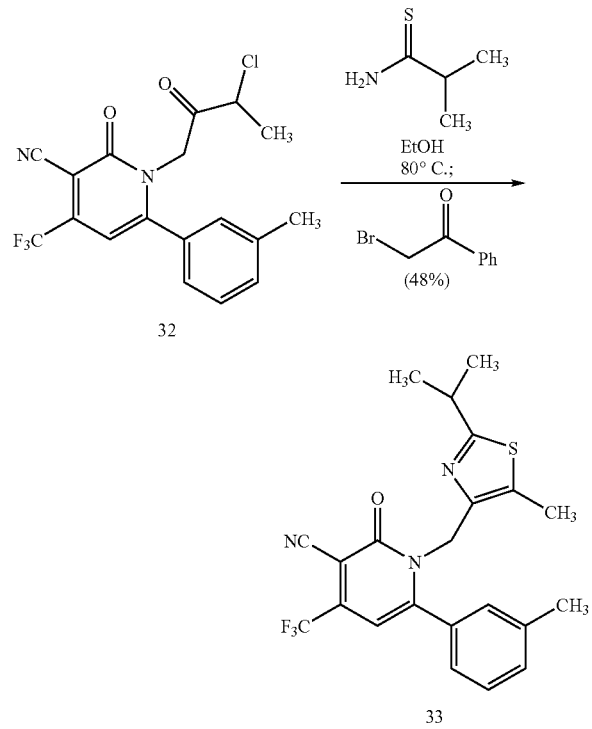

1-(3-Chloro-2-oxo-butyl)-2-oxo-6-m-tolyl-4-trifluoromethyl-1,2-dihydro-pyridine-3-carbonitrile 32 (41 mg, 0.11 mmoles) was combined with thioisobutyramide (22 mg, 0.22 mmoles) in 1.0 mL of anhydrous EtOH within a 7 mL reaction vial. This mixture was stirred at 80° C. for 16 hours. After this period 2-bromoacetophenone (33 mg, 0.17 mmoles) was added and the reaction was stirred at 80° C. for an additional 3 hours. After this period the reaction mixture was evaporated in vacuo and was purified using flash silica chromatography (0-40% EtOAc/Hexane) and normal-phase HPLC (YMC-Pack SIL, 250×50 mm I.D., S-5 μM: 4-20% EaOAc/Hexane over 30 minutes) to yield 22 mg (48% yield) of 33 as a yellow residue.

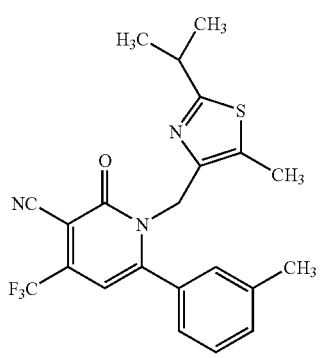

33

1-(2-Isopropyl-5-methyl-thiazol-4-ylmethyl)-2-oxo-6-m-tolyl-4-trifluoromethyl-1,2-dihydro-pyridine-3-carbonitrile $^1$H-NMR (CDCl$_3$): δ7.53-7.29 (4H), 6.40 (s, 1H), 5.03 (s, 2H), 3.13 (m, J=6.6 Hz, 1H), 2.40 (s, 3H), 2.38 (s, 3H), 1.32 (d, J=6.8 Hz, 6H). MS(ES+): 432.1 (M+H)

The following compounds were prepared in a manner similar to that described above.

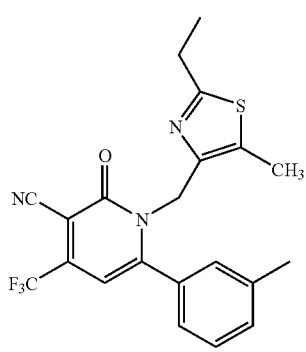

33.1

1-(2-Ethyl-5-methyl-thiazol-4-ylmethyl)-2-oxo-6-m-tolyl-4-trifluoromethyl-1,2-dihydro-pyridine-3-carbonitrile

MS(ES+): 417.9 (M+H)

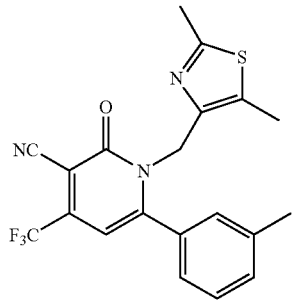

33.2

1-(2,5-Dimethyl-thiazol-4-ylmethyl)-2-oxo-6-m-tolyl-4-trifluoromethyl-1,2-dihydro-pyridine-3-carbo Nitrile

MS(ES+): 404.2 (M+H)

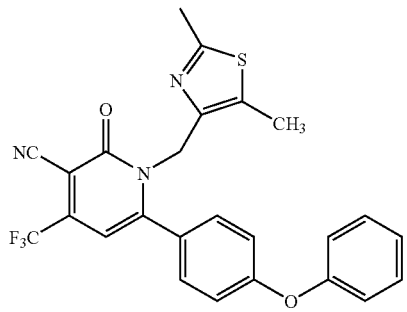

33.3

1-(2,5-Dimethyl-thiazol-4-ylmethyl)-2-oxo-6-(4-phenoxy-phenyl)-4-trifluoromethyl-1,2-dihydro-pyridine-3-carbonitrile

MS(ES+): 482.1 (M+H)

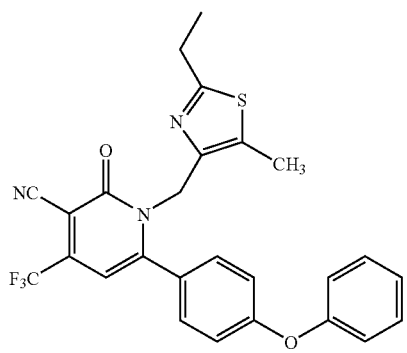

33.4

235

1-(2-Ethyl-5-methyl-thiazol-4-ylmethyl)-2-oxo-6-(4-phenoxy-phenyl)-4-trifluoromethyl-1,2-dihydro-pyridine-3-carbonitrile

MS(ES+): 496.2 (M+H)

33.5

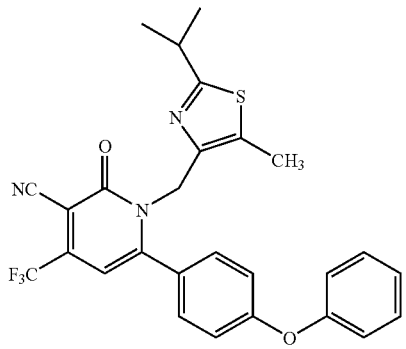

1-(2-Isopropyl-5-methyl-thiazol-4-ylmethyl)-2-oxo-6-(4-phenoxy-phenyl)-4-trifluoromethyl-1,2-dihydro-pyridine-3-carbonitrile

MS(ES+): 510.1 (M+H)

33.6

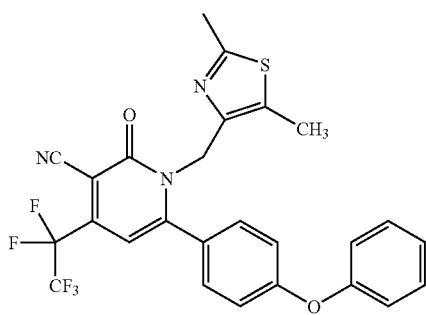

1-(2,5-Dimethyl-thiazol-4-ylmethyl)-2-oxo-4-pentafluoroethyl-6-(4-phenoxy-phenyl)-1,2-dihydro-pyridine-3-carbonitrile

MS(ES+): 532.0 (M+H)

33.7

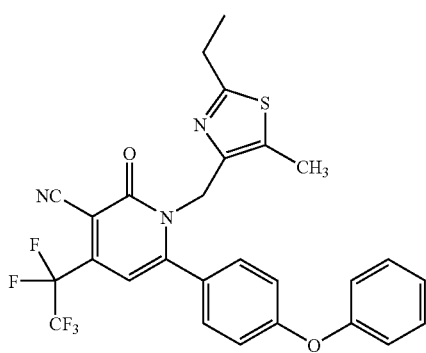

236

1-(2-Ethyl-5-methyl-thiazol-4-ylmethyl)-2-oxo-4-pentafluoroethyl-6-(4-phenoxy-phenyl)-1,2-dihydro-pyridine-3-carbonitrile

MS(ES+): 546.4 (M+H)

33.8

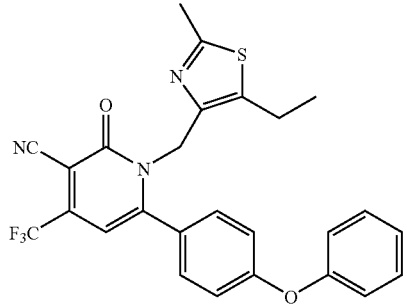

1-(5-Ethyl-2-methyl-thiazol-4-ylmethyl)-2-oxo-6-(4-phenoxy-phenyl)-4-trifluoromethyl-1,2-dihydro-pyridine-3-carbonitrile

MS(ES+): 496.1 (M+H)

33.9

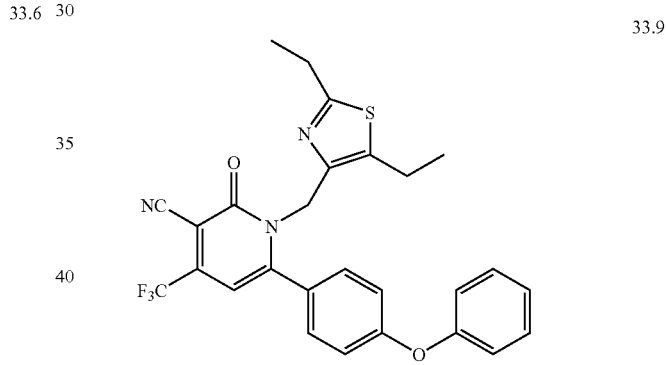

1-(2,5-Diethyl-thiazol-4-ylmethyl)-2-oxo-6-(4-phenoxy-phenyl)-4-trifluoromethyl-1,2-dihydro-pyridine-3-carbonitrile

MS(ES+): 510.1 (M+H)

Example 34

This example illustrates the preparation of compound 34.

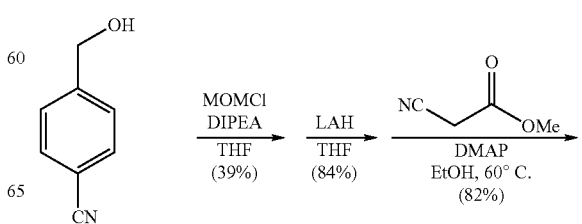

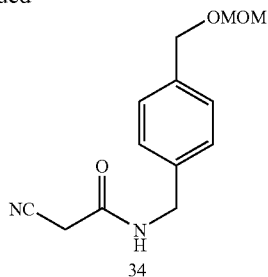

4-Hydroxymethyl-benzonitrile (3.1 g, 23.3 mmoles) was combined with N,N-diisopropylethylamine (4.9 mL, 28 mmoles) in 100 mL of anhydrous THF. To this solution was added MOMCl (3.5 mL, 46.1 mmoles) and the mixture was stirred at room temperature for 16 hours. After this period a solution of $NH_4OH/H_2O$ (1:1, 20 mL) was added (-MOMCl) and the solution was stirred for 15 minutes. After this period the reaction mixture was evaporated in vacuo (-THF) and the resulting mixture was extracted with DCM (3×30 mL). The combined DCM layer was dried over anhydrous $Na_2SO_4$, evaporated in vacuo, and the resulting crude product was purified using flash silica chromatography (0-20% EtOAc/Hexane) to yield 1.6 g (39% yield) of 4-Methoxymethoxymethylbenzonitrile as a colorless liquid.

4-Methoxymethoxymethylbenzonitrile (3.7 g, 20.9 mmoles) was dissolved into 100 mL of anhydrous THF and was placed under dry $N_2$ atmosphere. To this solution at 0° C. was added lithium aluminum hydride (LAH, 1.6 g, 42.2 mmoles, bubbling occurs) and this mixture (sealed under $N_2$) was gentle stirred at 75° C. for 12 hours. After this period the mixture was cooled down and placed into an ice bath under a dry $N_2$ atmosphere. To the vigorously stirring mixture at 0° C. was slowly and carefully sequentially added water (2 mL), 15% NaOH (2 mL) and water (4 mL). The resulting heterogenous mixture was vacuum filtered and the filtrate was evaporated in vacuo to yield 3.2 g (17.7 mmoles, 84% yield) of crude amine as a yellowish residue. The crude amine was combined with methyl cyanoacetate (3.1 mL, 35.1 mmoles) and DMAP (10 mg) in 50 mL of anhydrous EtOH. The mixture was then stirred at 60° C. for 16 hours. After this period the reaction mixture was evaporated in vacuo and was purified using flash silica chromatography (0-60% EtOAc/Hexane) to 3.6 g (82% yield) of 34 as a white powder.

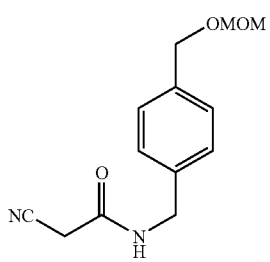

2-Cyano-N-(4-methoxymethoxymethyl-benzyl)-acetamide $^1$H-NMR (CDCl$_3$): δ7.36 (d, J=8.1 Hz, 2H), 7.28 (d, J=8.3 Hz, 2H), 6.34 (bs, 1H), 4.71 (s, 2H), 4.59 (s, 2H), 4.48 (d, J=5.6 Hz, 2H), 3.41 (s, 3H), 3.40 (s, 2H).

Example 35

This example illustrates the preparation of compound 35.

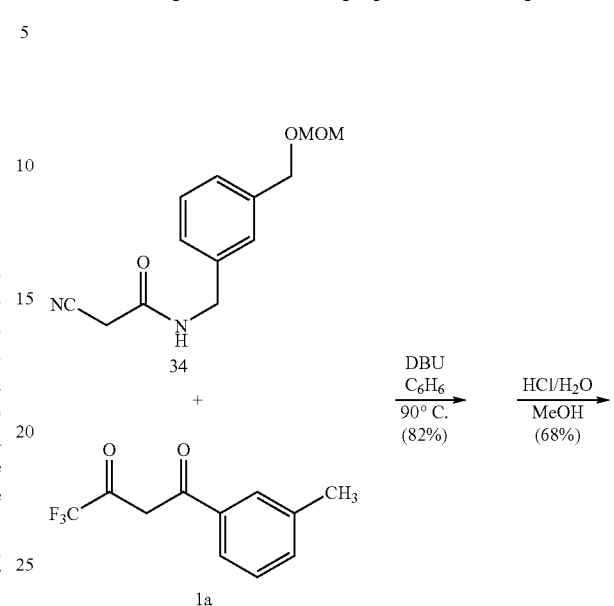

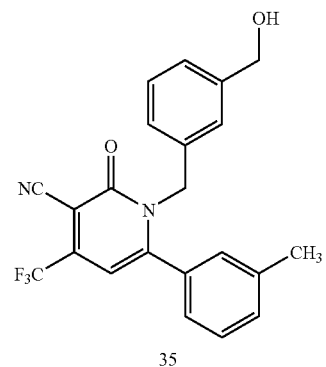

2-Cyano-N-(4-methoxymethoxymethyl-benzyl)-acetamide (0.84 g, 3.4 mmoles) was combined with 1a (0.78 g, 3.4 mmoles), DBU (0.25 mL, 1.7 mmoles) and 5 mL of $C_6H_6$ within a 7 mL reaction vial. The mixture was stirred at 90° C. for 16 hours. After this period the reaction mixture was purified directly using flash silica chromatography (0-20% EtOAc/Hexane) to yield 1.23 g (82% yield) of 35 as a yellow residue. $^1$H-NMR (CDCl$_3$): δ7.37-7.31 (m, 2H), 7.26-7.19 (m, 2H), 7.03-6.97 (m, 1H), 6.93 (bs, 1H), 6.89 (bs, 1H), 6.86-6.81 (m, 1H), 6.39 (s, 1H), 5.24 (bs, 2H), 4.67 (s, 2H), 4.50 (s, 2H), 3.39 (s, 3H), 2.33 (s, 3H). MS(ES+): 443.2 (M+H)

1-(3-Methoxymethoxymethyl-benzyl)-2-oxo-6-m-tolyl-4-trifluoromethyl-1,2-dihydro-pyridine-3-carbonitrile (0.65 g, 1.47 mmoles) was dissolved into 10 mL of MeOH and to this was added 12N HCl (100 μL). This mixture was then stirred at room temperature for 3 hours. After this period the reaction mixture was evaporated in vacuo and was purified using flash silica chromatography (0-40% EtOAc/Hexane) to yield 0.40 g (68% yield) of 35 as a yellow residue.

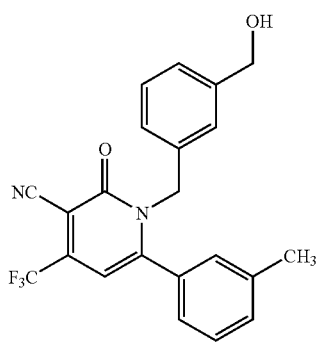

1-(3-Hydroxymethyl-benzyl)-2-oxo-6-m-tolyl-4-trifluoromethyl-1,2-dihydro-pyridine-3-carbonitrile ¹H-NMR (CDCl₃): δ7.36-7.32 (m, 2H), 7.26-7.19 (m, 2H), 7.02-6.97 (m, 1H), 6.92 (d, J=10 Hz, 2H), 6.82 (d, J=6.8 Hz, 1H), 6.39 (s, 1H), 5.24 (bs, 2H), 4.62 (s, 2H), 2.34 (s, 3H). MS(ES+): 398.8 (M+H)

The following compounds were prepared in a manner similar to that described above.

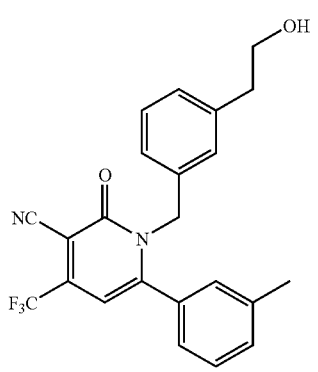

35.1

1-[3-(2-Hydroxy-ethyl)-benzyl]-2-oxo-6-m-tolyl-4-trifluoromethyl-1,2-dihydro-pyridine-3-carbonitrile ¹H-NMR (CDCl₃): δ7.36-7.33 (m, 2H), 7.11 (d, J=8.1 Hz, 2H), 7.04-7.00 (m, 1H), 6.95 (s, 1H), 6.87 (d, J=8.1 Hz, 2H), 6.39 (s, 1H), 5.22 (bs, 2H), 3.82 (q, J=5.8 Hz, 2H), 2.82 (t, J=6.8 Hz, 2H), 2.34 (s, 3H).

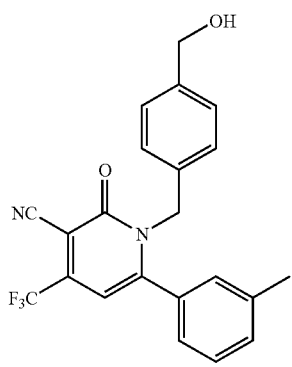

35.2

1-(4-Hydroxymethyl-benzyl)-2-oxo-6-m-tolyl-4-trifluoromethyl-1,2-dihydro-pyridine-3-carbonitrile

MS(ES+): 398.9 (M+H)

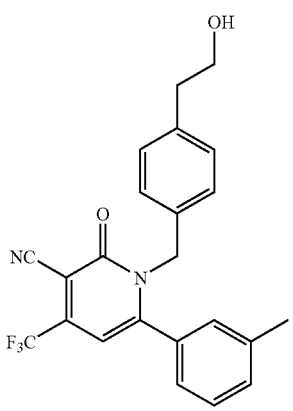

35.3

1-[4-(2-Hydroxy-ethyl)-benzyl]-2-oxo-6-m-tolyl-4-trifluoromethyl-1,2-dihydro-pyridine-3-carbonitrile

MS(ES+): 413.3 (M+H)

Example 36

This example illustrates the preparation of compound 36.

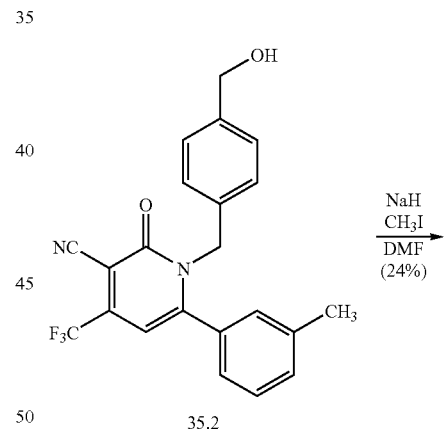

35.2

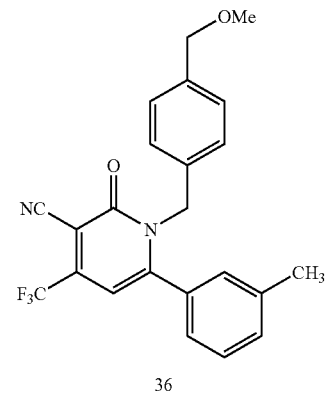

36

1-(4-Hydroxymethyl-benzyl)-2-oxo-6-m-tolyl-4-trifluoromethyl-1,2-dihydro-pyridine-3-carbonitrile 35.2 (41 mg, 0.10 mmoles) was dissolved into 1.0 mL of anhydrous N,N-dimethyl-formamide. To this solution was then added sodium hydride (60% dispersion in mineral oil, 5 mg, 0.125 mmoles) and the mixture was stirred (bubbling occurs) for 5 min. After this period iodomethane (15 μL, 0.24 mmoles) was added and the mixture was stirred at room temperature for 16 hours. After this period the reaction mixture was combined with 20 mL of water and was extracted with EtOAc (4×15 mL). The combined organic layer was washed with water (4×15 mL), 15 mL of brine, and was dried over $Na_2SO_4$. The EtOAc solution was evaporated in vacuo and purified using flash silica chromatography (0-20% EtOAc/Hexane) to yield 10 mg (24%) of 36 as a yellow residue.

36

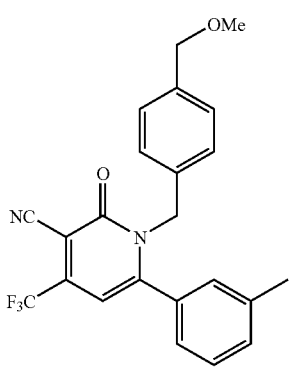

1-(4-Methoxymethyl-benzyl)-2-oxo-6-m-tolyl-4-trifluoromethyl-1,2-dihydro-pyridine-3-carbonitrile $^1$H-NMR (CDCl$_3$): δ7.36-7.32 (m, 2H), 7.21 (d, J=7.8 Hz, 2H), 7.02-6.96 (m, 1H), 6.93 (bs, 1H), 6.89 (d, J=7.6 Hz, 2H), 6.38 (s, 1H), 5.23 (bs, 2H), 4.41 (s, 3H), 3.37 (s, 3H), 2.33 (s, 3H). MS(ES+): 413.3 (M+H)

The following compounds were prepared in a manner similar to that described above.

36.1

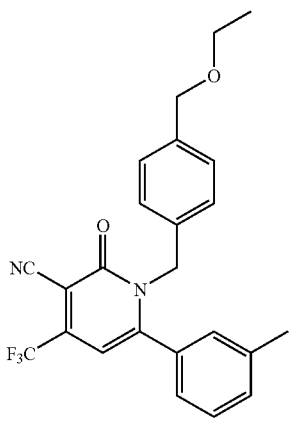

1-(4-Ethoxymethyl-benzyl)-2-oxo-6-m-tolyl-4-trifluoromethyl-1,2-dihydro-pyridine-3-carbonitrile

MS(ES+): 427.3 (M+H)

36.2

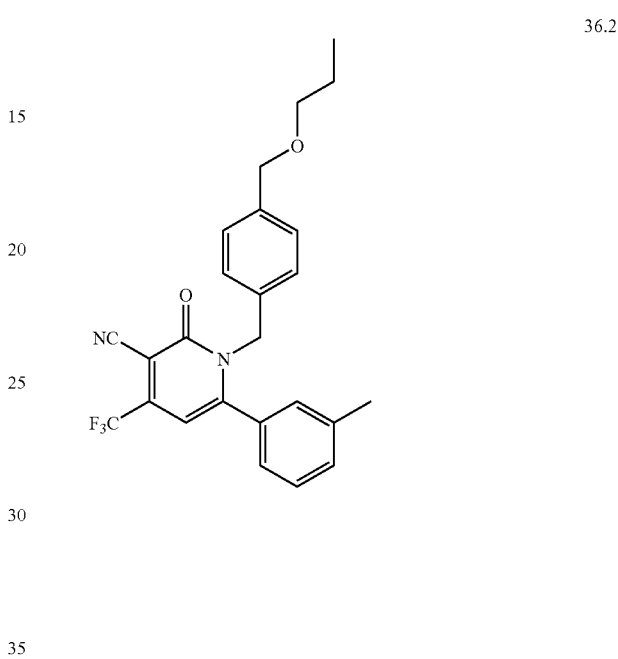

2-Oxo-1-(4-propoxymethyl-benzyl)-6-m-tolyl-4-trifluoromethyl-1,2-dihydro-pyridine-3-carbonitrile

MS(ES+): 441.2 (M+H)

36.3

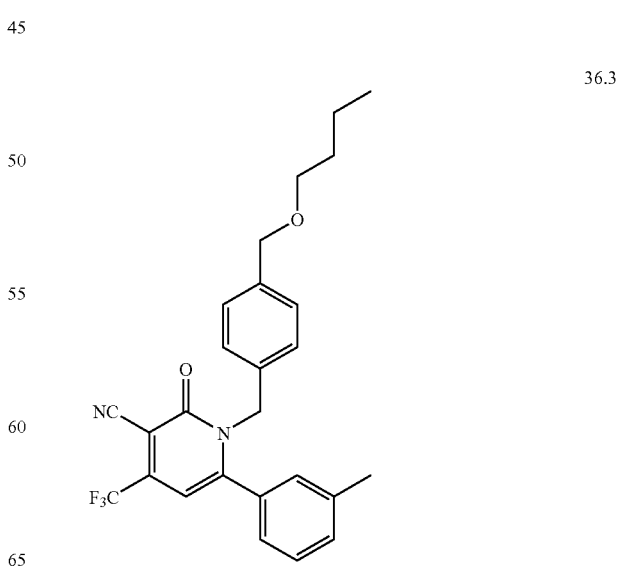

243

1-(4-Butoxymethyl-benzyl)-2-oxo-6-m-tolyl-4-trifluoromethyl-1,2-dihydro-pyridine-3-carbonitrile

MS(ES+): 455.2 (M+H)

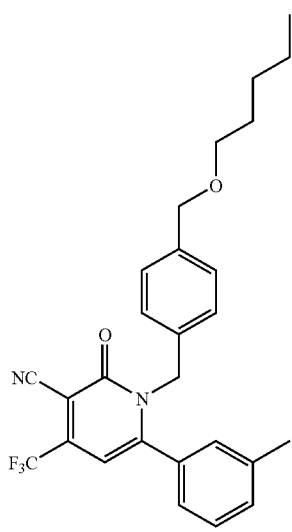

2-Oxo-1-(4-pentyloxymethyl-benzyl)-6-m-tolyl-4-trifluoromethyl-1,2-dihydro-pyridine-3-carbonitrile

MS(ES+): 469.2 (M+H)

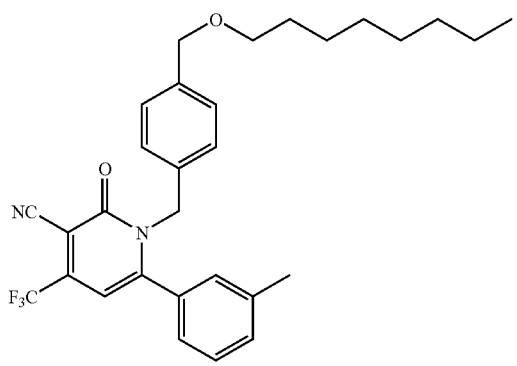

244

1-(4-Octyloxymethyl-benzyl)-2-oxo-6-m-tolyl-4-trifluoromethyl-1,2-dihydro-pyridine-3-carbonitrile

MS(ES+): 511.1 (M+H)

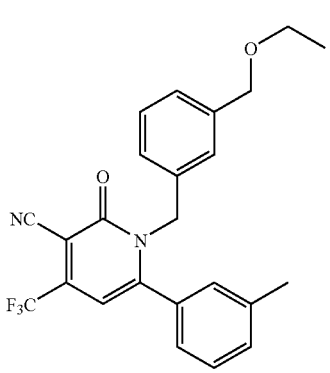

1-(3-Ethoxymethyl-benzyl)-2-oxo-6-m-tolyl-4-trifluoromethyl-1,2-dihydro-pyridine-3-carbonitrile

MS(ES+): 427.2 (M+H)

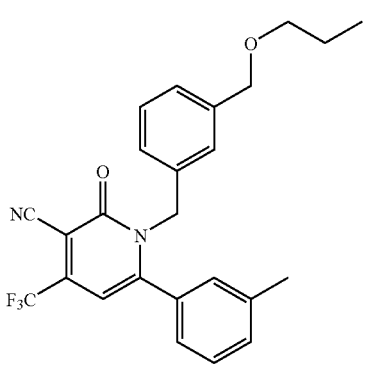

2-Oxo-1-(3-propoxymethyl-benzyl)-6-m-tolyl-4-trifluoromethyl-1,2-dihydro-pyridine-3-carbonitrile

MS(ES+): 441.1 (M+H)

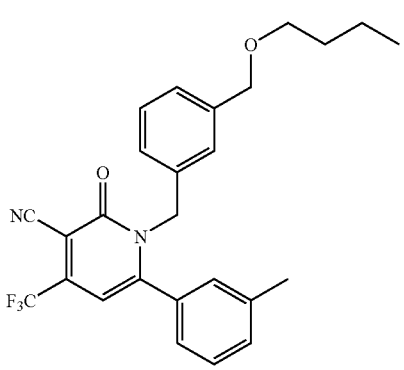

245

1-(3-Butoxymethyl-benzyl)-2-oxo-6-m-tolyl-4-trifluoromethyl-1,2-dihydro-pyridine-3-carbonitrile

MS(ES+): 455.2 (M+H)

36.10

1-(3-Hexyloxymethyl-benzyl)-6-(3-methyl-1-methylene-but-2-enyl)-2-oxo-4-trifluoromethyl-1,2-dihydro-pyridine-3-carbonitrile

MS(ES+): 483.1 (M+H)

36.11

246

1-(3-Octyloxymethyl-benzyl)-2-oxo-6-m-tolyl-4-trifluoromethyl-1,2-dihydro-pyridine-3-carbonitrile

MS(ES+): 511.0 (M+H)

Example 37

This example illustrates the preparation of compound 37.

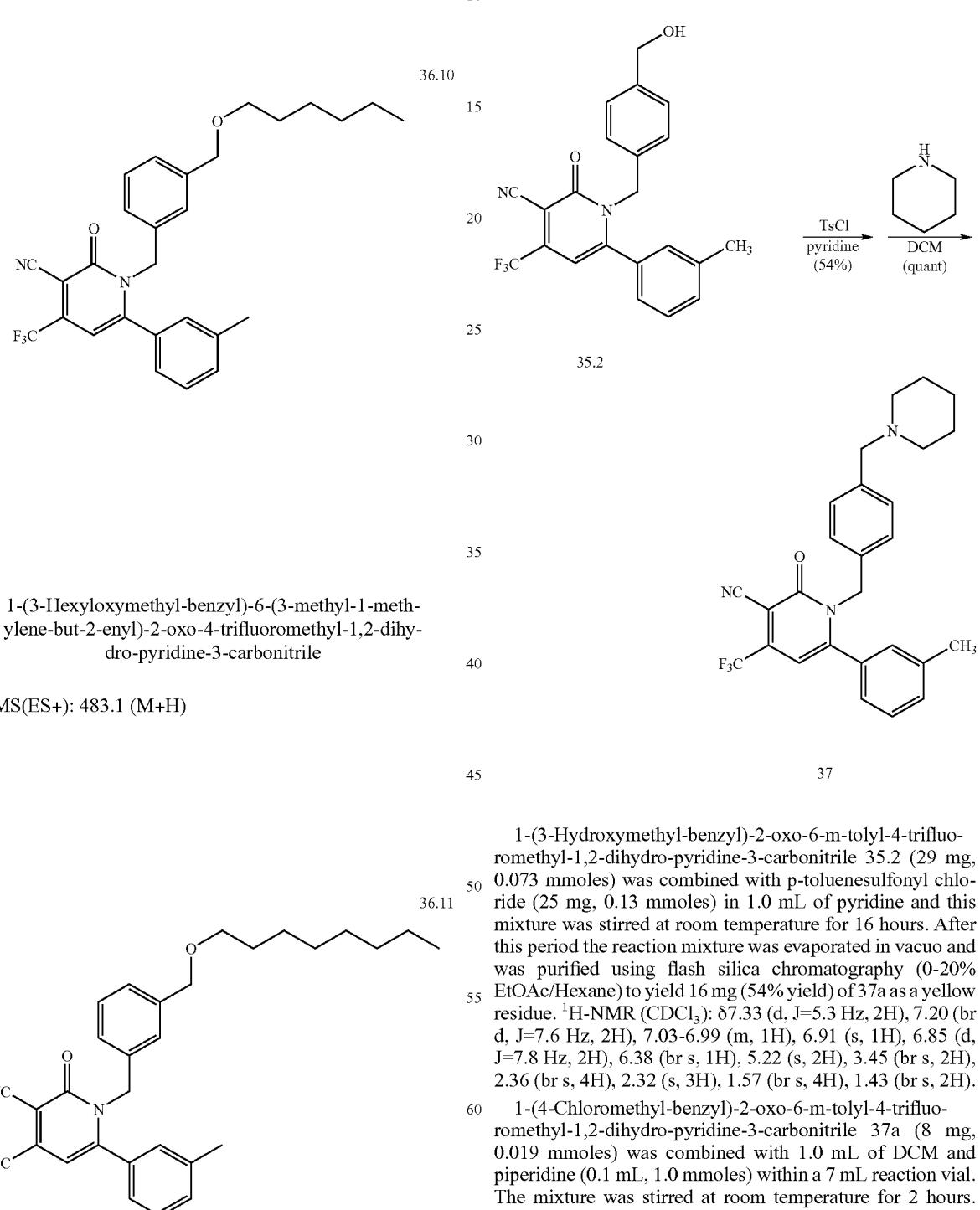

1-(3-Hydroxymethyl-benzyl)-2-oxo-6-m-tolyl-4-trifluoromethyl-1,2-dihydro-pyridine-3-carbonitrile 35.2 (29 mg, 0.073 mmoles) was combined with p-toluenesulfonyl chloride (25 mg, 0.13 mmoles) in 1.0 mL of pyridine and this mixture was stirred at room temperature for 16 hours. After this period the reaction mixture was evaporated in vacuo and was purified using flash silica chromatography (0-20% EtOAc/Hexane) to yield 16 mg (54% yield) of 37a as a yellow residue. $^1$H-NMR (CDCl$_3$): δ7.33 (d, J=5.3 Hz, 2H), 7.20 (br d, J=7.6 Hz, 2H), 7.03-6.99 (m, 1H), 6.91 (s, 1H), 6.85 (d, J=7.8 Hz, 2H), 6.38 (br s, 1H), 5.22 (s, 2H), 3.45 (br s, 2H), 2.36 (br s, 4H), 2.32 (s, 3H), 1.57 (br s, 4H), 1.43 (br s, 2H).

1-(4-Chloromethyl-benzyl)-2-oxo-6-m-tolyl-4-trifluoromethyl-1,2-dihydro-pyridine-3-carbonitrile 37a (8 mg, 0.019 mmoles) was combined with 1.0 mL of DCM and piperidine (0.1 mL, 1.0 mmoles) within a 7 mL reaction vial. The mixture was stirred at room temperature for 2 hours. After this period the reaction mixture was purified directly using flash silica chromatography (0-10% MeOH/DCM) to yield 9 mg (quantitative yield) of 37 as a yellow residue.

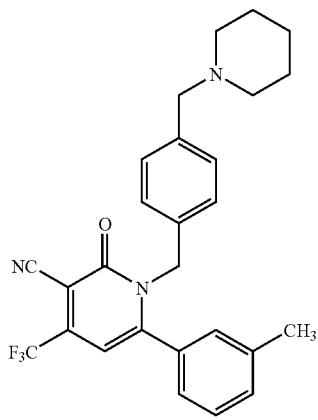

2-Oxo-1-(4-piperidin-1-ylmethyl-benzyl)-6-m-tolyl-4-trifluoromethyl-1,2-dihydro-pyridine-3-carbonitrile $^1$H-NMR (CDCl$_3$): δ7.33 (d, J=5.1 Hz, 2H), 7.20 (bd, J=7.3 Hz, 2H), 7.03-6.98 (m, 1H), 6.91 (m, 1H), 6.85 (d, J=7.8 Hz, 2H), 5.22 (bs, 2H) 3.45 (bs, 2H), 2.45-2.28 (m, 4H), 2.32 (s, 3H), 1.63-1.52 (m, 4H), 1.48-1.38 (m, 2H). MS(ES+): 466.2 (M+H)

Example 38

This example illustrates the preparation of compound 38.

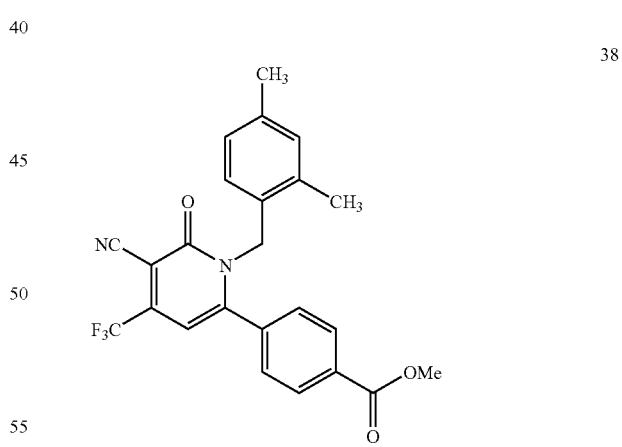

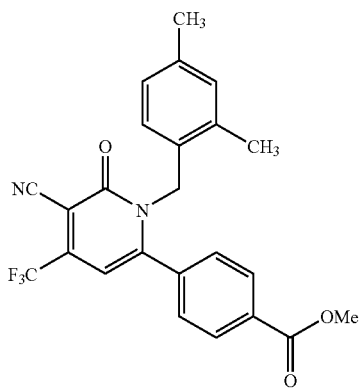

38

Within a Parr high-pressure apparatus were combined 6-(4-Bromo-phenyl)-1-(2,4-dimethyl-benzyl)-2-oxo-4-trifluoromethyl-1,2-dihydro-pyridine-3-carbonitrile 5a (0.51 g, 1.11 mmoles), Pd(OAc)$_2$ (15 mg, 0.067 mmoles), and 1,3-bis (diphenylphosphino)propane (30 mg, 0.073 mmoles). This mixture was dissolved into 15 mL of anhydrous MeOH, 5 mL of anhydrous DMSO and NEt$_3$ (0.6 mL, 4.3 mmoles), and was pressured to 100 psi with CO. The pressured and stirring reaction mixture was then heated to 90° C. for 48 hours. After this period the reaction mixture was cooled to ambient temperature, depressurized, and was combined with 100 mL of water. The aqueous mixture was extracted with EtOAc (4×25 mL) and the combined EtOAc layer was washed with water (4×25 mL) and brine. After drying over anhydrous Na$_2$SO$_4$ the crude product was purified using flash silica chromatography (0-30% EtOAc/Hexane) to yield 0.43 g (87% yield) of 38 as a yellow solid.

38

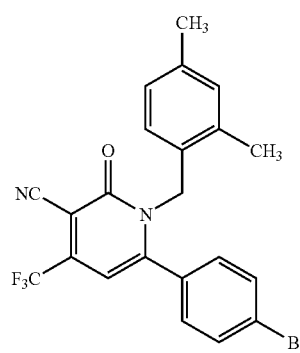

4-[5-Cyano-1-(2,4-dimethyl-benzyl)-6-oxo-4-trifluoromethyl-1,6-dihydro-pyridin-2-yl]-benzoic Acid Methyl Ester $^1$H-NMR (CDCl$_3$): δ8.03 (d, J=8.3 Hz, 2H), 7.23 (d, J=8.3 Hz, 2H), 6.95 (bd, J=7.8 Hz, 1H), 6.89 (bs, 1H), 6.58 (d, J=7.8 Hz, 1H), 6.42 (s, 1H), 5.09 (s, 2H), 3.95 (s, 3H), 2.28 (s, 3H), 1.88 (s, 3H).

Example 39

This example illustrates the preparation of compound 39.

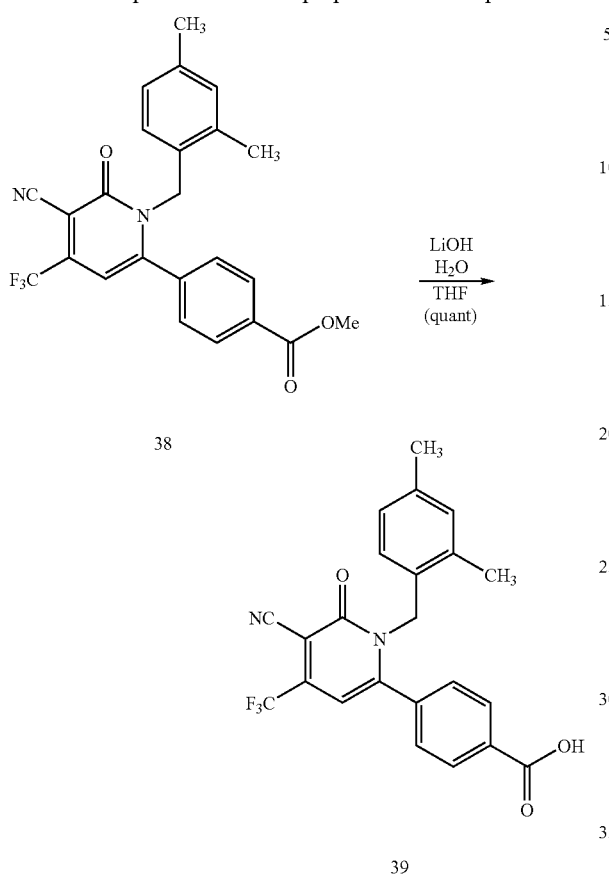

4-[5-Cyano-1-(2,4-dimethyl-benzyl)-6-oxo-4-trifluoromethyl-1,6-dihydro-pyridin-2-yl]-benzoic acid methyl ester 38 (0.105 g, 0.24 mmoles) was combined with LiOH (monohydrate, 22 mg, 0.52 mmoles) in 5 mL of THF and 1 mL of water. The mixture was stirred at room temperature for 90 minutes. After this period the reaction mixture was concentrated in vacuo (-THF) and the resulting aqueous mixture was combined with 10 mL of 1N HCl and salt (enough to affect saturation after mixing). The acidic aqueous layer was extracted with $Et_2O$ (3×20 mL) and the combined organic layer was washed with brine. The $Et_2O$ layer was dried over anhydrous $Na_2SO_4$ and evaporated in vacuo to yield 0.102 g (quantitative yield) as a yellowish solid.

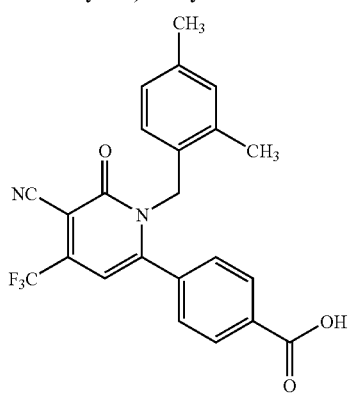

39

4-[5-Cyano-1-(2,4-dimethyl-benzyl)-6-oxo-4-trifluoromethyl-1,6-dihydro-pyridin-2-yl]-benzoic acid $^1$H-NMR ($CDCl_3$): δ8.09 (d, J=8.1 Hz, 2H), 7.29-7.25 (m, 2H), 6.95 (d, J=7.8 Hz, 1H), 6.90 (s, 1H), 6.59 (d, J=7.8 Hz, 1H), 6.43 (s, 1H), 5.10 (s, 2H), 2.29 (s, 3H), 1.89 (s, 3H). MS(ES+): 427.2 (M+H)

Example 40

This example illustrates the preparation of compound 40.

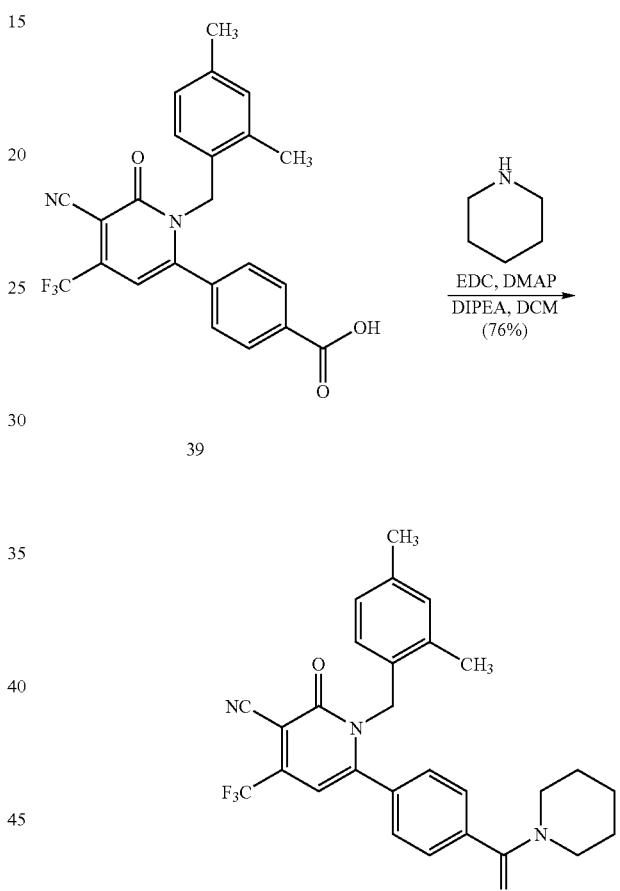

4-[5-Cyano-1-(2,4-dimethyl-benzyl)-6-oxo-4-trifluoromethyl-1,6-dihydro-pyridin-2-yl]-benzoic acid 39 (48 mg, 0.11 mmoles) was combined with 1-[3-(dimethylamino)propyl]-3-ethylcarbodiimide hydrochloride (EDC, 54 mg, 0.28 mmoles), 4-dimethylaminopyridine (DMAP, 2 mg, 0.016 mmoles) in 5 mL of anhydrous DCM. To this mixture was added diisopropylethylamine (DIPEA, 50 μL, 0.29 mmoles) and piperidine (28 μL, 0.28 mmoles). This mixture was then stirred at room temperature for 16 hours. After this period the reaction mixture was purified directly using flash silica chromatography (0-60% EtOAc/Hexane) to yield 41 mg (76% yield) of 40 as a yellow residue.

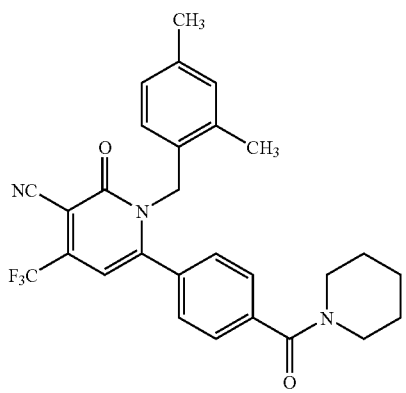

1-(2,4-Dimethyl-benzyl)-2-oxo-6-[4-(piperidine-1-carbonyl)-phenyl]-4-trifluoromethyl-1,2-dihydro-pyridine-3-carbonitrile ¹H-NMR (CDCl₃): δ7.39 (d, J=8.1 Hz, 2H), 7.19 (d, J=8.1 Hz, 2H), 6.94 (bd, J=8.1 Hz, 1H), 6.88 (bs, 1H), 6.59 (d, J=7.8 Hz, 1H), 6.42 (s, 1H), 5.11 (s, 2H), 3.75-3.66 (m, 2H), 3.34-3.24 (m, 2H), 2.28 (s, 3H), 1.93 (s, 3H), 1.75-1.63 (m, 4H), 1.56-1.48 (m, 2H). MS(ES+): 494.3 (M+H)

The following compounds were prepared in a manner similar to that described above.

40.1

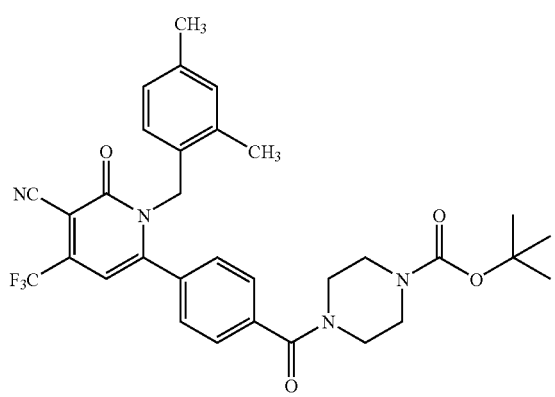

4-{4-[5-Cyano-1-(2,4-dimethyl-benzyl)-6-oxo-4-trifluoromethyl-1,6-dihydro-pyridin-2-yl]-benzoyl}-piperazine-1-carboxylic Acid Tert-butyl Ester

MS(ES+): 595.4 (M+H)

40.2

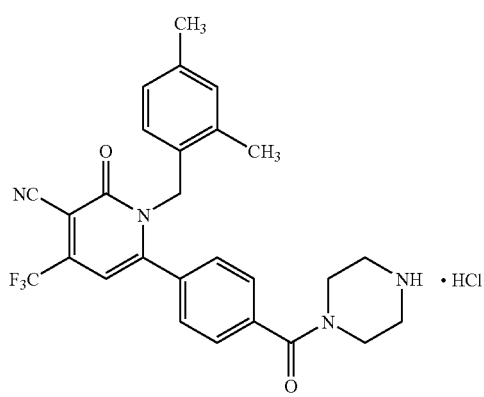

1-(2,4-Dimethyl-benzyl)-2-oxo-6-[4-(piperazine-1-carbonyl)-phenyl]-4-trifluoromethyl-1,2-dihydro-pyridine-3-carbonitrile Hydrochloride

MS(ES+): 495.2 (M+H)

40.3

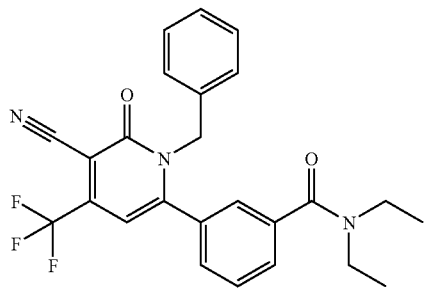

3-(1-Benzyl-5-cyano-6-oxo-4-trifluoromethyl-1,6-dihydro-pyridin-2-yl)-N,N-diethyl-benzamide ¹H-NMR (CDCl₃): δ7.54 (m, 1H), 7.48 (m, 1H), 7.23 (m, 5H), 6.89 (m, 2 H), 6.4 (s, 1H), 5.28 (s, 2H), 3.52 (br, 2H), 3.13 (br, 2H), 1.20 (br, 3H), 1.06 (br, 3H).

Example 41

This example illustrates the preparation of compound 41.

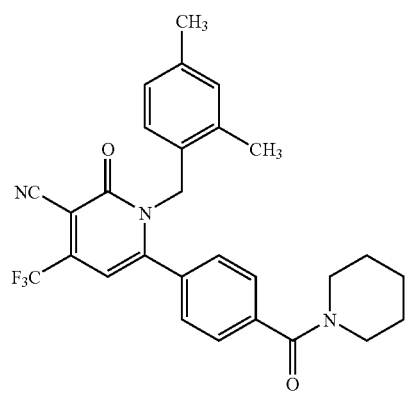

40

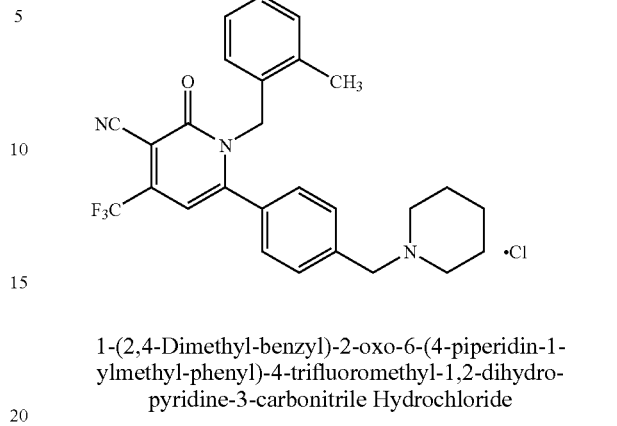

41

1-(2,4-Dimethyl-benzyl)-2-oxo-6-(4-piperidin-1-ylmethyl-phenyl)-4-trifluoromethyl-1,2-dihydro-pyridine-3-carbonitrile Hydrochloride $^1$H-NMR (D$_2$O—free base): δ7.31 (d, J=8.1 Hz, 2H), 7.21 (d, J=8.1 Hz, 2H), 6.86 (d, J=8.3 Hz, 1H), 6.82 (s, 1H), 6.51 (d, J=7.3 Hz, 1H), 5.09 (s, 2H), 4.14 (s, 2H), 3.27-3.17 (m, 2H), 2.84-2.70 (m, 2H), 2.10 (s, 3H), 1.87-1.24 (m, 6H), 2.10 (s, 3H), 1.75 (s, 3H). MS(ES+): 480.2 (M+H)

Example 42

This example illustrates the preparation of compound 42.

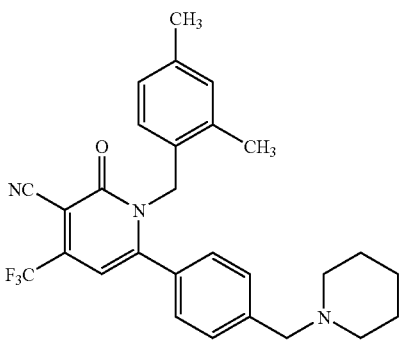

41

1-(2,4-Dimethyl-benzyl)-2-oxo-6-[4-(piperidine-1-carbonyl)-phenyl]-4-trifluoromethyl-1,2-dihydro-pyridine-3-carbonitrile 40 (20 mg, 0.041 mmoles) was dissolved into 2.0 mL of anhydrous THF within a 7 mL reaction vial. To this stirring mixture at room temperature was added diborane-THF (160 μL, 0.16 mmoles) and the mixture was stirred at room temperature for 16 hours. After this period the reaction was quenched by adding 3 mL of 25% NH$_4$Cl. This aqueous mixture was stirred for 30 min. After this period the resulting mixture was extracted with Et$_2$O (3×10 mL) and the resulting organic layer was washed with brine and dried over Na$_2$SO$_4$. The ether layer was evaporated in vacuo and the resulting crude product was purified using flash silica chromatography (0-5% MeOH/DCM w/0.1% NEt$_3$) to yield the free base. The free base was combined with 2N HCl/MeOH, evaporated, dissolved into deionized water and lyopholyzed to yield 12 mg (61% yield) of 41 as a white powder.

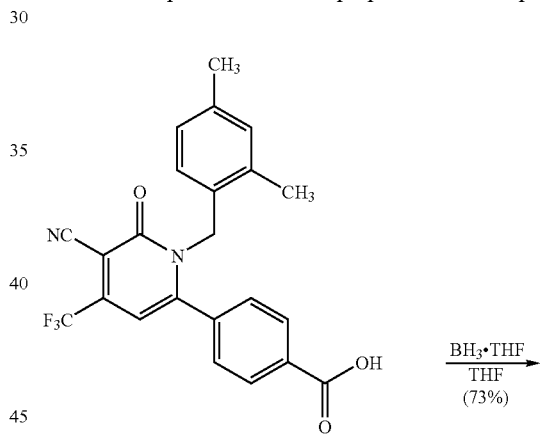

39

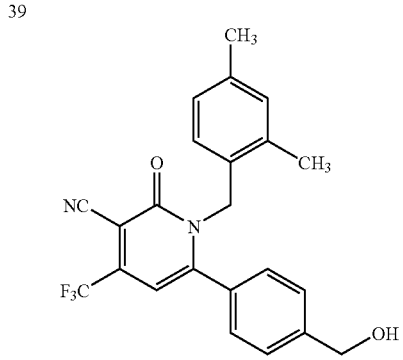

42

4-[5-Cyano-1-(2,4-dimethyl-benzyl)-6-oxo-4-trifluoromethyl-1,6-dihydro-pyridin-2-yl]-benzoic acid 39 (27 mg, 0.063 mmoles) was dissolved into 2.0 mL of anhydrous THF within a 7 mL reaction vial. To this stirring solution at 0° C. was added diborane-THF (0.11 mL, 0.11 mmoles). The reaction was then allowed to warm to room temperature and was stirred for 16 hours. After this period the reaction was quenched by adding 3 mL of 25% NH₄Cl, and this mixture was stirred for 30 min. The resulting aqueous mixture was evaporated in vacuo (-THF) and extracted with Et₂O (3×10 mL). The combined ether layer was washed with saturated NaHCO₃, dried over Na₂SO₄ and was evaporated in vacuo to yield the crude residue. The crude residue was purified using flash silica chromatography (0-60% EtOAc/Hexane) to yield 19 mg (73% yield) of 42 as a white solid.

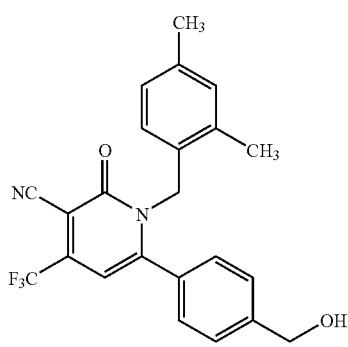

42

1-(2,4-Dimethyl-benzyl)-6-(4-hydroxymethyl-phenyl)-2-oxo-4-trifluoromethyl-1,2-dihydro-pyridine-3-carbonitrile ¹H-NMR (CDCl₃): δ7.39 (d, J=8.1 Hz, 2H), 7.17 (d, J=8.1 Hz, 2H), 6.95 (bd, J=7.8 Hz, 1H), 6.91 (bs, 1H), 6.60 (d, J=7.6 Hz, 1H), 6.43 (s, 1H), 5.10 (s, 2H), 4.76 (bd, 2H), 2.28 (s, 3H), 1.94 (s, 3H).

MS(ES+): 413.1 (M+H)

Example 43

This example illustrates the preparation of compound 43.

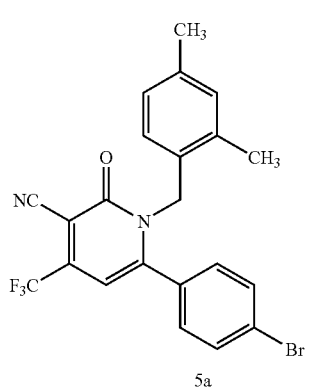

5a

+

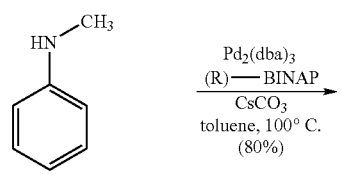

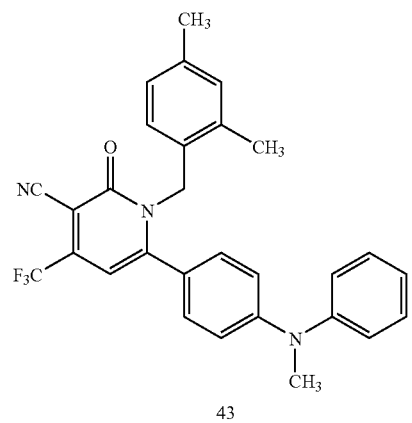

43

6-(4-Bromo-phenyl)-1-(2,4-dimethyl-benzyl)-2-oxo-4-trifluoromethyl-1,2-dihydro-pyridine-3-carbonitrile 5a (38 mg, 0.082 mmoles) was combined with N-methylaniline (11 μL, 0.10 mmoles) and 0.5 mL of anhydrous toluene within a 7 mL reaction vial. In a separate vial was added tris(dibenzylideneacetone) dipalladium (8 mg, 0.009 mmoles), (R)-BINAP (8 mg, 0.013 mmoles), cesium carbonate (38 mg, 0.12 mmoles) and 0.3 mL of anhydrous toluene. This "catalytic" mixture was stirred at room temperature for 5 min under dry-nitrogen. To the stirring "catalytic" solution under nitrogen was then added the "bromide" solution, and the resulting mixture was sealed under dry-nitrogen and was stirred at 100° C. for 16 hours. After this period the reaction mixture was purified directly using flash silica chromatography (0-20% EtOAc/Hexane) to provide 32 mg (80% yield) of 43 as an orange-red residue.

1-(2,4-Dimethyl-benzyl)-6-[4-(methyl-phenyl-amino)-phenyl]-2-oxo-4-trifluoromethyl-1,2-dihydro-pyridine-3-carbonitrile $^1$H-NMR (CDCl$_3$): δ7.44-7.34 (m, 2H), 7.25-7.14 (m, 3H), 7.07-7.02 (m, 2H), 6.97-6.92 (m, 2H), 6.72 (d, J=9.1 Hz, 2H), 6.63 (d, J=8.1 Hz, 1H), 6.46 (s, 1H), 5.18 (s, 2H), 3.33 (s, 3H), 2.28 (s, 3H), 2.10 (s, 3H). MS(E+): 488.4 (M+H)

The following compounds were prepared in a manner similar to that described above.

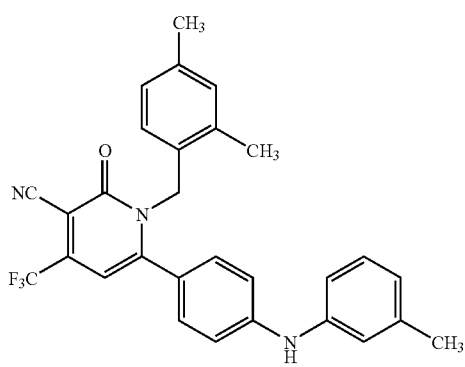

43.1

1-(2,4-Dimethyl-benzyl)-2-oxo-6-(4-m-tolylamino-phenyl)-4-trifluoromethyl-1,2-dihydro-pyridine-3-carbonitrile

MS(ES+): 488.4 (M+H)

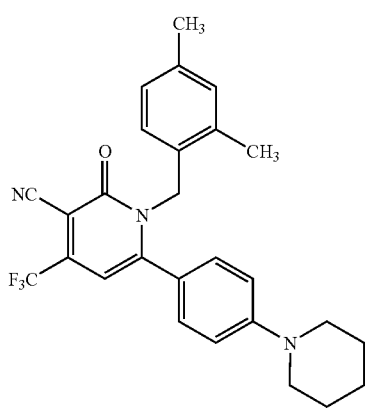

43.2

1-(2,4-Dimethyl-benzyl)-2-oxo-6-(4-piperidin-1-yl-phenyl)-4-trifluoromethyl-1,2-dihydro-pyridine-3-carbonitrile

MS(ES+): 466.4 (M+H)

39.3

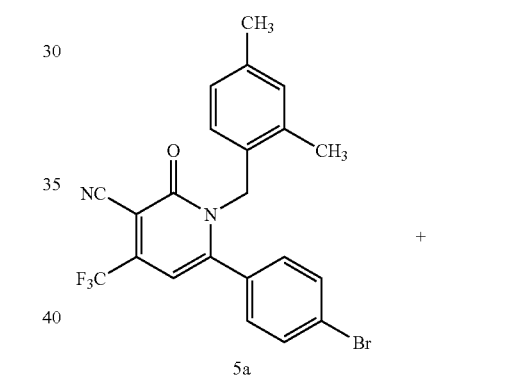

MS(ES+): 640.0 (M+H)

Example 44

This example illustrates the preparation of compound 44.

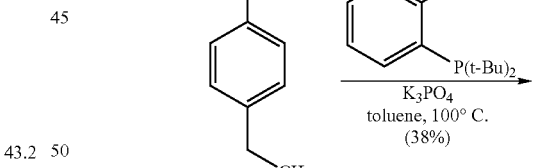

6-(4-Bromo-phenyl)-1-(2,4-dimethyl-benzyl)-2-oxo-4-trifluoromethyl-1,2-dihydro-pyridine-3-carbonitrile 5a (100 mg, 0.22 mmoles) was combined with 4-ethylphenol (32 mg, 0.26 mmoles), palladium acetate (5 mg, 0.022 mmoles), 2-(di-t-butylphosphino)biphenyl (12 mg, 0.040 mmoles), potassium phosphate (100 mg, 0.47 mmoles) and 1.0 mL of anhydrous toluene within an oven-dried 7 mL reaction vial. The mixture was sealed and stirred at 100° C. for 16 hours. After this period the mixture was purified directly using flash silica chromatography (0-20% EtOAc/Hexane) to yield 42 mg (38%) of 44 as a yellow residue.

44

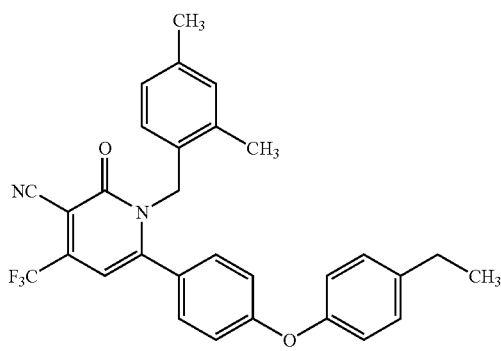

1-(2,4-Dimethyl-benzyl)-6-[4-(4-ethyl-phenoxy)-phenyl]-2-oxo-4-trifluoromethyl-1,2-dihydro-pyridine-3-carbonitrile $^1$H-NMR (CDCl$_3$): δ7.21 (d, J=8.3 Hz, 2H), 7.09 (d, J=8.3 Hz, 2H), 6.98-6.89 (m, 6H), 6.60 (d, J=7.8 Hz, 1H), 6.44 (s, 1H), 5.14 (s, 2H), 2.66 (q, J=7.6 Hz, 2H), 2.27 (s, 3H), 2.01 (s, 3H), 1.25 (t, J=7.6 Hz, 3H). MS(ES+): 503.2 (M+H)

The following compounds were prepared in a manner similar to that described above.

44.1

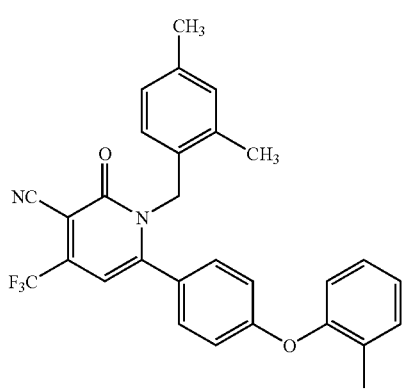

1-(2,4-Dimethyl-benzyl)-2-oxo-6-(4-o-tolyloxy-phenyl)-4-trifluoromethyl-1,2-dihydro-pyridine-3-carbonitrile

MS(ES+): 489.2 (M+H)

44.2

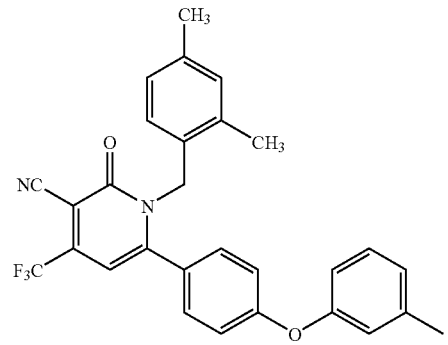

1-(2,4-Dimethyl-benzyl)-2-oxo-6-(4-m-tolyloxy-phenyl)-4-trifluoromethyl-1,2-dihydro-pyridine-3-carbonitrile

MS(ES+): 489.4 (M+H)

44.3

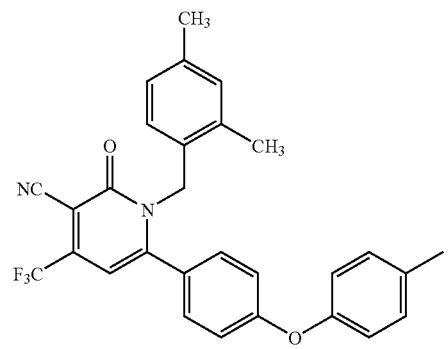

1-(2,4-Dimethyl-benzyl)-2-oxo-6-(4-p-tolyloxy-phenyl)-4-trifluoromethyl-1,2-dihydro-pyridine-3-carbonitrile

MS(ES+): 489.4 (M+H)

44.4

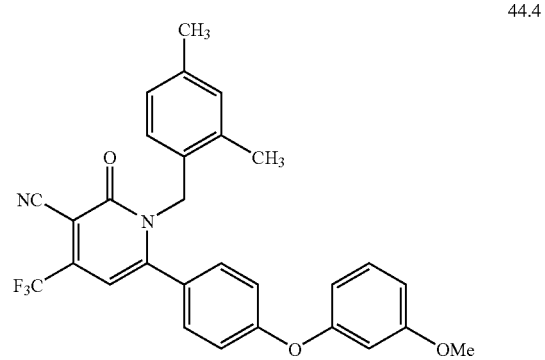

261

1-(2,4-Dimethyl-benzyl)-6-[4-(3-methoxy-phenoxy)-phenyl]-2-oxo-4-trifluoromethyl-1,2-dihydro-pyridine-3-carbonitrile

MS(ES+): 505.3 (M+H)

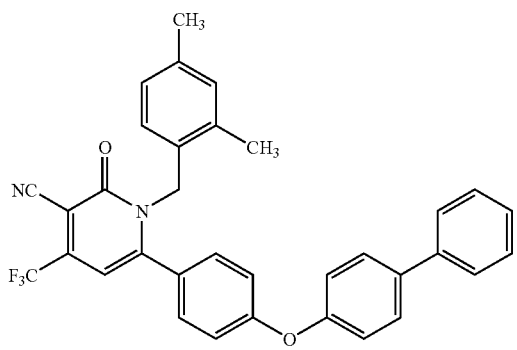

6-[4-(Biphenyl-4-yloxy)-phenyl]-1-(2,4-dimethyl-benzyl)-2-oxo-4-trifluoromethyl-1,2-dihydro-pyridine-3-carbonitrile $^1$H-NMR (CDCl$_3$): δ 7.64-7.54 (m, 4H), 7.48-7.42 (m, 2H), 7.40-7.33 (m, 1H), 7.16-7.08 (m, 4H), 7.02-6.87 (m, 4H), 6.61 (d, J=7.8 Hz, 1H), 6.46 (s, 1H), 5.15 (s, 2H), 2.28 (s, 3H), 2.02 (s, 3H).

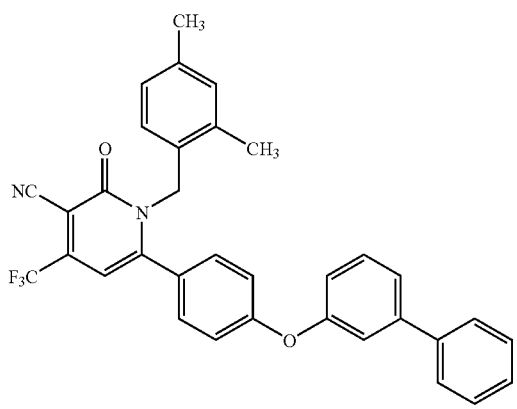

6-[4-(Biphenyl-3-yloxy)-phenyl]-1-(2,4-dimethyl-benzyl)-2-oxo-4-trifluoromethyl-1,2-dihydro-pyridine-3-carbonitrile $^1$H-NMR (CDCl$_3$): δ 7.59-7.53 (m, 2H), 7.49-7.35 (m, 4H), 7.15-7.09 (m, 2H), 7.05-6.88 (m, 5H), 6.61 (d, J=8.1 Hz, 1H), 6.45 (s, 1H), 5.14 (s, 2H), 2.26 (s, 3H), 2.00 (s, 3H).

262

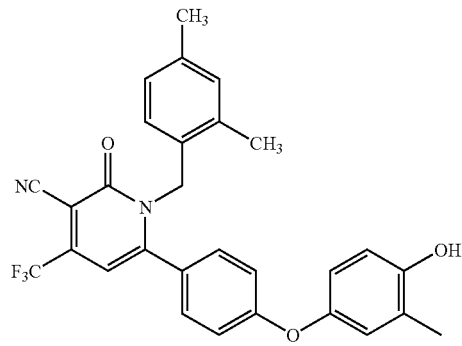

1-(2,4-Dimethyl-benzyl)-6-[4-(4-hydroxy-3-methyl-phenoxy)-phenyl]-2-oxo-4-trifluoromethyl-1,2-dihydro-pyridine-3-carbonitrile

MS(ES+): 505.1 (M+H)

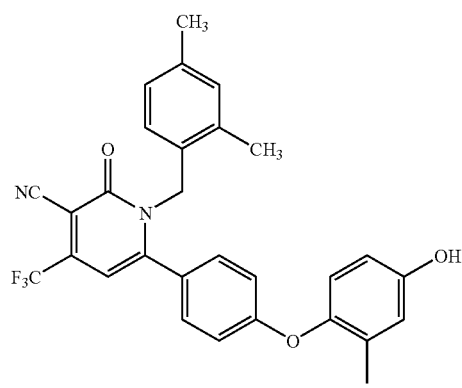

1-(2,4-Dimethyl-benzyl)-6-[4-(4-hydroxy-2-methyl-phenoxy)-phenyl]-2-oxo-4-trifluoromethyl-1,2-dihydro-pyridine-3-carbonitrile

MS(ES+): 505.4 (M+H)

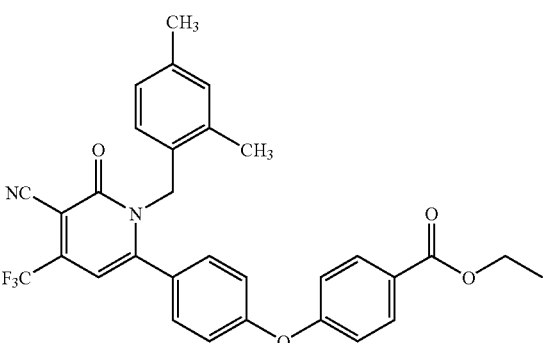

263

4-{4-[5-Cyano-1-(2,4-dimethyl-benzyl)-6-oxo-4-trifluoromethyl-1,6-dihydro-pyridin-2-yl]-phenoxy}-benzoic Acid Ethyl Ester

MS(ES+): 547.4 (M+H)

44.10

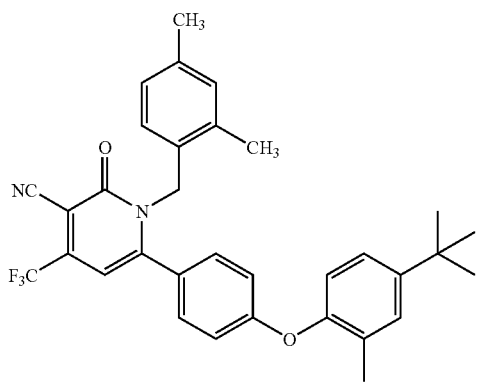

6-[4-(4-tert-Butyl-2-methyl-phenoxy)-phenyl]-1-(2,4-dimethyl-benzyl)-2-oxo-4-trifluoromethyl-1,2-dihydro-pyridine-3-carbonitrile

MS(ES+): 545.2 (M+H)

44.11

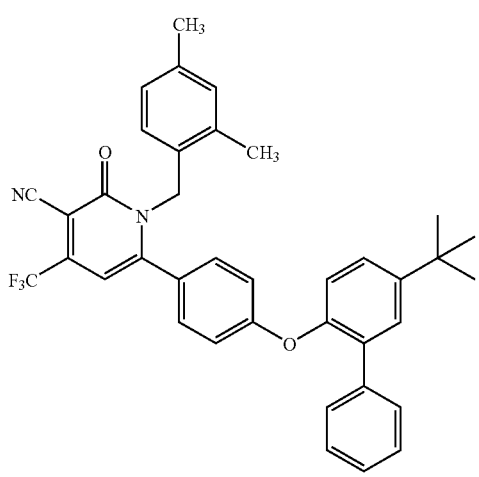

264

6-[4-(5-tert-Butyl-biphenyl-2-yloxy)-phenyl]-1-(2,4-dimethyl-benzyl)-2-oxo-4-trifluoromethyl-1,2-dihydro-pyridine-3-carbonitrile

MS(ES+): 607.6 (M+H)

44.12

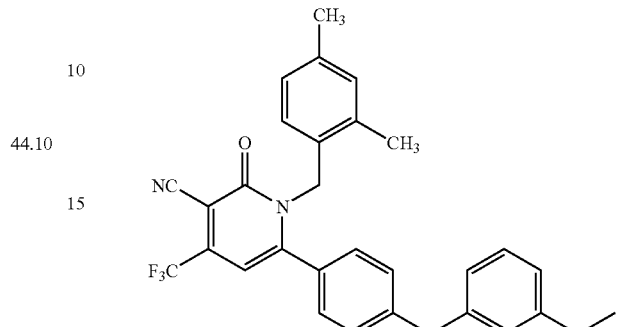

1-(2,4-Dimethyl-benzyl)-6-[4-(3-ethyl-phenoxy)-phenyl]-2-oxo-4-trifluoromethyl-1,2-dihydro-pyridine-3-carbonitrile

MS(ES+): 503.0 (M+H)

44.13

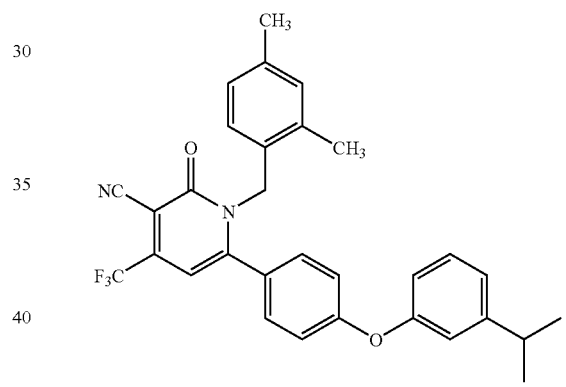

1-(2,4-Dimethyl-benzyl)-6-[4-(3-isopropyl-phenoxy)-phenyl]-2-oxo-4-trifluoromethyl-1,2-dihydro-pyridine-3-carbonitrile

MS(ES+): 517.4 (M+H)

44.14

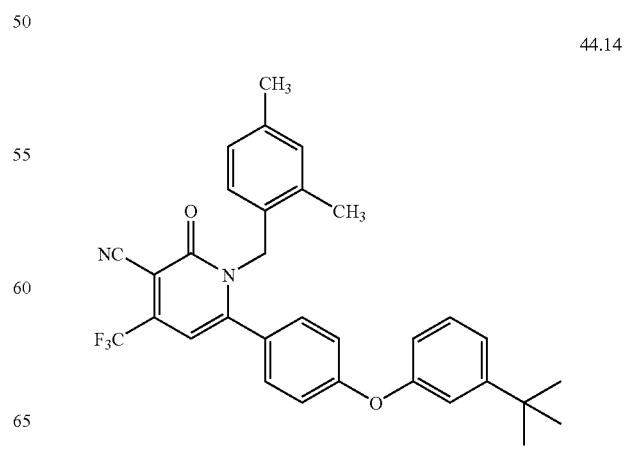

265

6-[4-(3-tert-Butyl-phenoxy)-phenyl]-1-(2,4-dimethyl-benzyl)-2-oxo-4-trifluoromethyl-1,2-dihydro-pyridine-3-carbonitrile

MS(ES+): 531.3 (M+H)

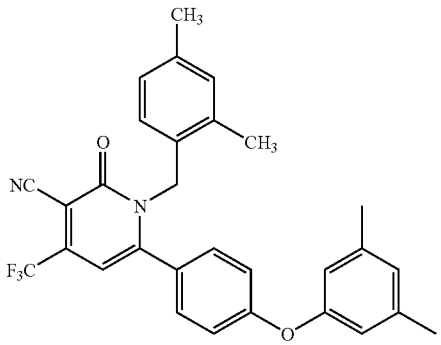

1-(2,4-Dimethyl-benzyl)-6-[4-(3,5-dimethyl-phenoxy)-phenyl]-2-oxo-4-trifluoromethyl-1,2-dihydro-pyridine-3-carbonitrile

MS(ES+): 503.3 (M+H)

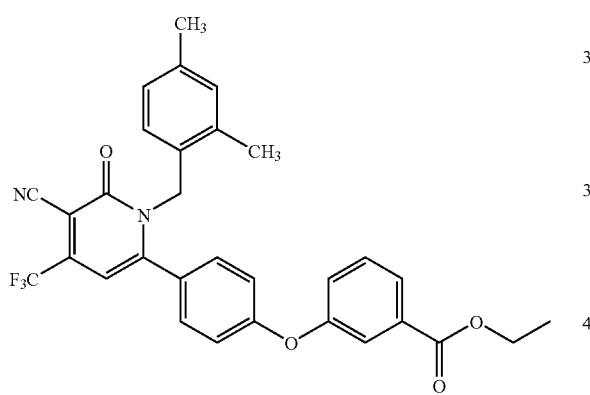

3-{4-[5-Cyano-1-(2,4-dimethyl-benzyl)-6-oxo-4-trifluoromethyl-1,6-dihydro-pyridin-2-yl]-phenoxy}-benzoic Acid Ethyl Ester

MS(ES+): 547.3 (M+H)

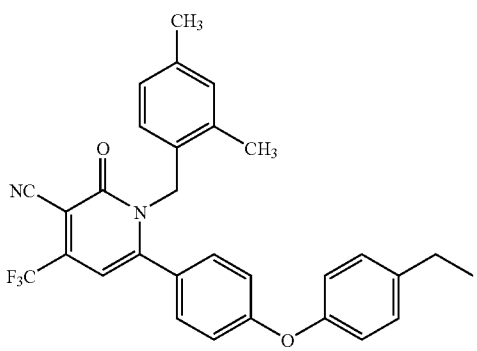

266

1-(2,4-Dimethyl-benzyl)-6-[4-(4-ethyl-phenoxy)-phenyl]-2-oxo-4-trifluoromethyl-1,2-dihydro-pyridine-3-carbonitrile $^1$H-NMR (CDCl$_3$): δ7.21 (d, J=8.6 Hz, 2H), 7.09 (d, J=8.6 Hz, 2H), 6.98-6.89 (m, 6H), 6.60 (d, J=7.8 Hz, 1H), 6.44 (s, 1H), 5.14 (s, 2H), 2.66 (q, J=7.6 Hz, 2H), 2.27 (s, 3H), 2.01 (s, 3H), 1.25 (t, J=7.6 Hz, 3H).

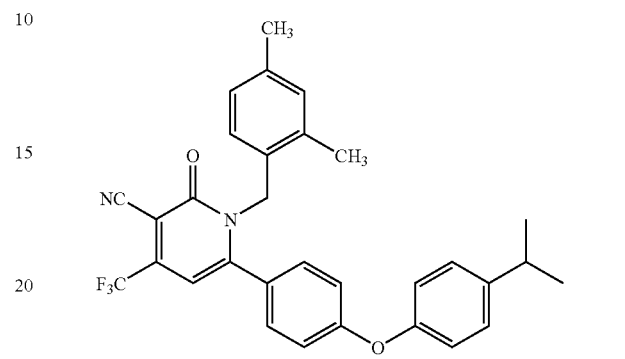

1-(2,4-Dimethyl-benzyl)-6-[4-(4-isopropyl-phenoxy)-phenyl]-2-oxo-4-trifluoromethyl-1,2-dihydro-pyridine-3-carbonitrile

MS(ES+): 517.4 (M+H)

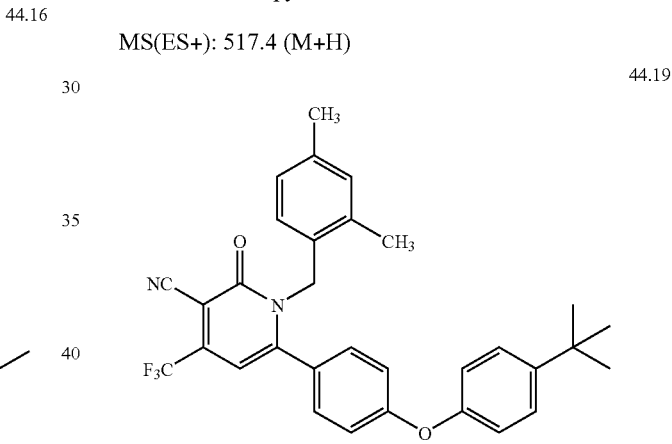

6-[4-(4-tert-Butyl-phenoxy)-phenyl]-1-(2,4-dimethyl-benzyl)-2-oxo-4-trifluoromethyl-1,2-dihydro-pyridine-3-carbonitrile

MS(ES+): 531.4 (M+H)

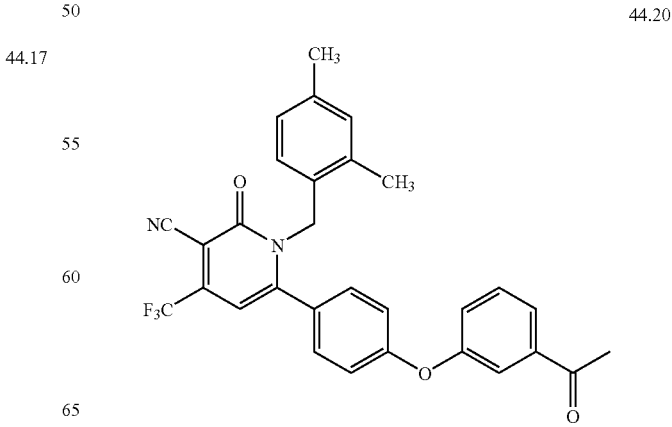

267

6-[4-(3-Acetyl-phenoxy)-phenyl]-1-(2,4-dimethyl-benzyl)-2-oxo-4-trifluoromethyl-1,2-dihydro-pyridine-3-carbonitrile

MS(ES+): 517.5 (M+H)

44.21

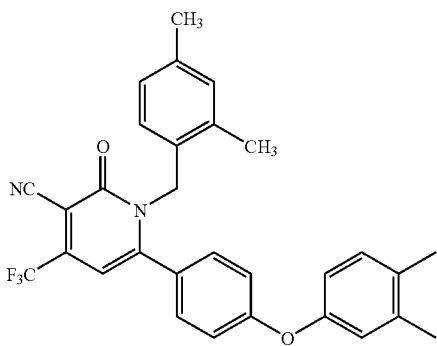

1-(2,4-Dimethyl-benzyl)-6-[4-(3,4-dimethyl-phenoxy)-phenyl]-2-oxo-4-trifluoromethyl-1,2-dihydro-pyridine-3-carbonitrile

MS(ES+): 503.1 (M+H)

44.22

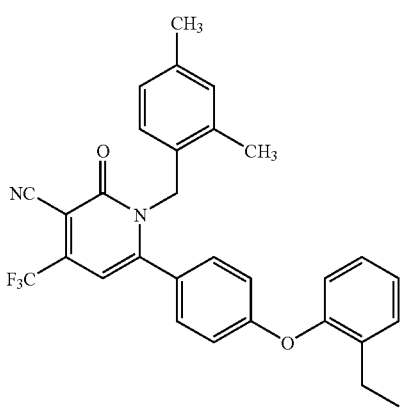

1-(2,4-Dimethyl-benzyl)-6-[4-(2-ethyl-phenoxy)-phenyl]-2-oxo-4-trifluoromethyl-1,2-dihydro-pyridine-3-carbonitrile

MS(ES+): 503.3 (M+H)

44.23

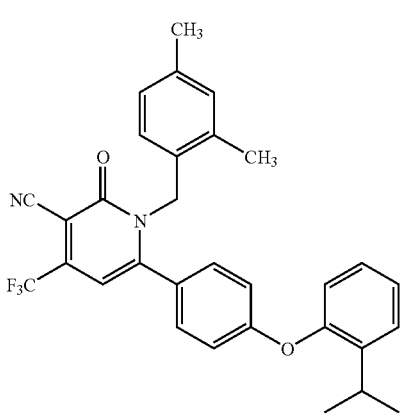

268

1-(2,4-Dimethyl-benzyl)-6-[4-(2-isopropyl-phenoxy)-phenyl]-2-oxo-4-trifluoromethyl-1,2-dihydro-pyridine-3-carbonitrile

MS(ES+): 517.5 (M+H)

44.24

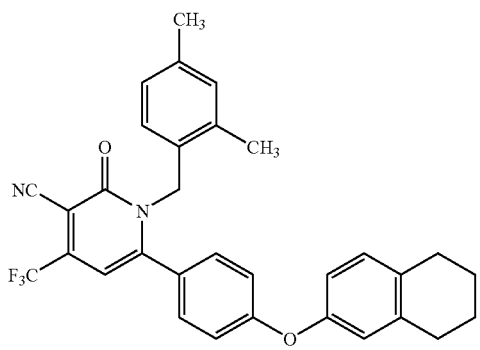

1-(2,4-Dimethyl-benzyl)-2-oxo-6-[4-(5,6,7,8-tetrahydro-naphthalen-2-yloxy)-phenyl]-4-trifluoromethyl-1,2-dihydro-pyridine-3-carbonitrile

MS(ES+): 529.3 (M+H)

44.25

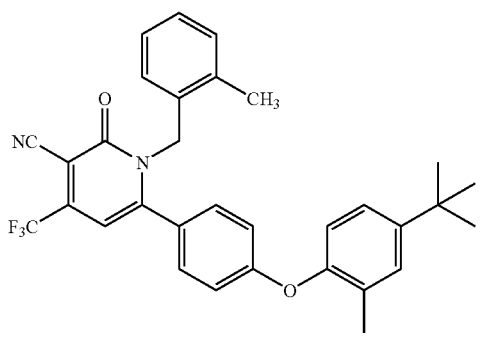

6-[4-(4-tert-Butyl-2-methyl-phenoxy)-phenyl]-1-(2-methyl-benzyl)-2-oxo-4-trifluoromethyl-1,2-dihydro-pyridine-3-carbonitrile

MS(ES+): 531.2 (M+H)

44.26

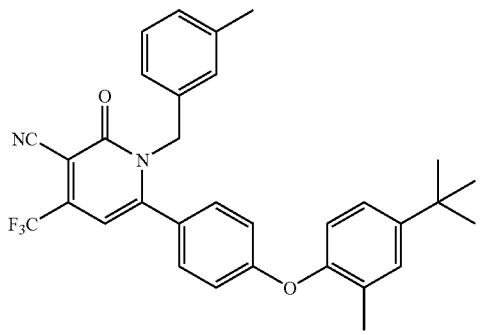

269

6-[4-(4-tert-Butyl-2-methyl-phenoxy)-phenyl]-1-(3-methyl-benzyl)-2-oxo-4-trifluoromethyl-1,2-dihydro-pyridine-3-carbonitrile

MS(ES+): 531.3 (M+H)

44.27

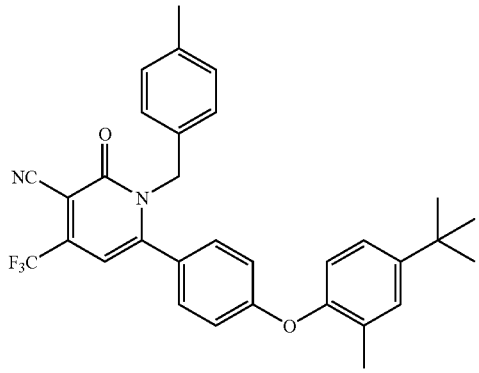

6-[4-(4-tert-Butyl-2-methyl-phenoxy)-phenyl]-1-(4-methyl-benzyl)-2-oxo-4-trifluoromethyl-1,2-dihydro-pyridine-3-carbonitrile

MS(ES+): 531.3 (M+H)

44.28

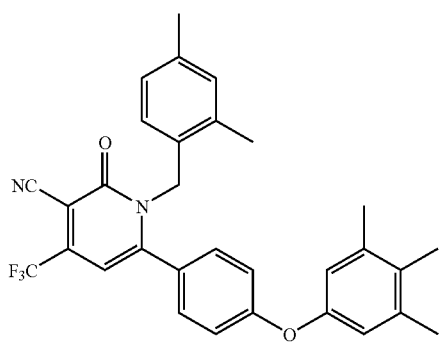

1-(2,4-Dimethyl-benzyl)-2-oxo-4-trifluoromethyl-6-[4-(3,4,5-trimethyl-phenoxy)-phenyl]-1,2-dihydro-pyridine-3-carbonitrile

MS(ES+): 517.4 (M+H)

44.29

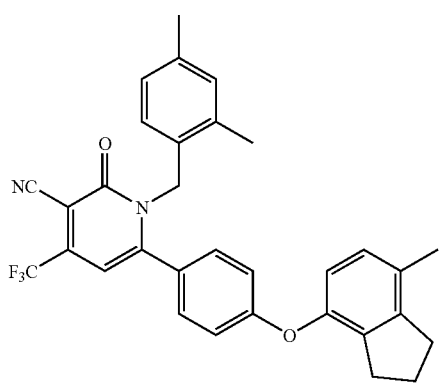

270

1-(2,4-Dimethyl-benzyl)-6-[4-(7-methyl-indan-4-yloxy)-phenyl]-2-oxo-4-trifluoromethyl-1,2-dihydro-pyridine-3-carbonitrile

MS(ES+): 529.4 (M+H)

44.30

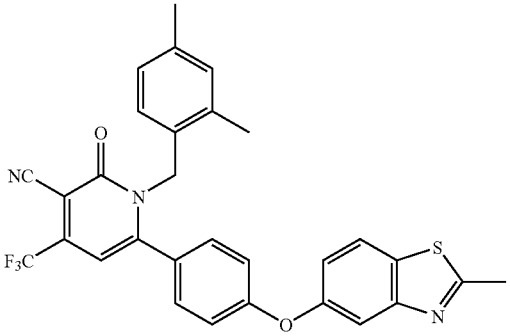

1-(2,4-Dimethyl-benzyl)-6-[4-(2-methyl-benzothiazol-5-yloxy)-phenyl]-2-oxo-4-trifluoromethyl-1,2-dihydro-pyridine-3-carbonitrile

MS(ES+): 546.5 (M+H)

44.31

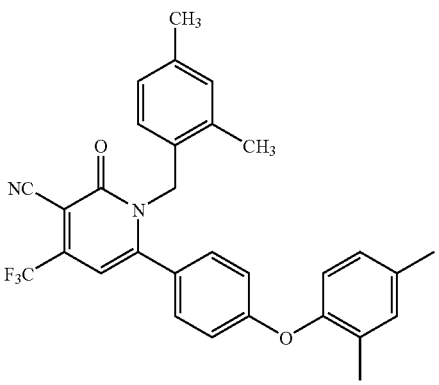

1-(2,4-Dimethyl-benzyl)-6-[4-(2,4-dimethyl-phenoxy)-phenyl]-2-oxo-4-trifluoromethyl-1,2-dihydro-pyridine-3-carbonitrile

MS(ES+): 503.2 (M+H)

44.32

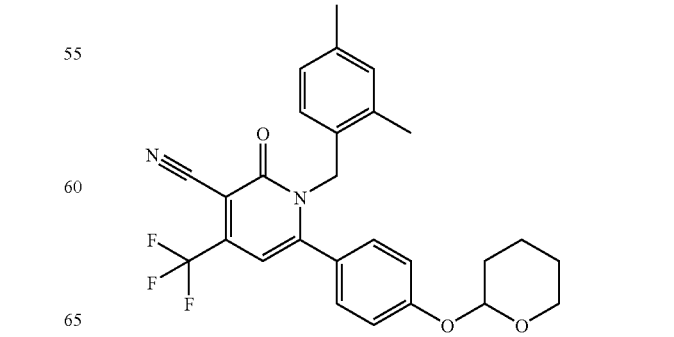

1-(2,4-Dimethyl-benzyl)-2-oxo-6-[4-(tetrahydro-pyran-2-yloxy)-phenyl]-4-trifluoromethyl-1,2-dihydro-pyridine-3-carbonitrile $^1$H-NMR (CDCl$_3$): δ7.10 (m, 2H), 7.02 (m, 2H), 6.94 (m, 2H), 6.61 (m, 1H), 6.44 (s, 1H), 5.45 (m, 1H), 5.13 (s, 2H), 3.83 (m, 1H), 3.61 (m, 1H), 2.28 (s, 3H), 2.00 (s, 3H), 1.87 (m, 2H), 1.87 (m, 2H), 1.68 (m, 4H).

44.33

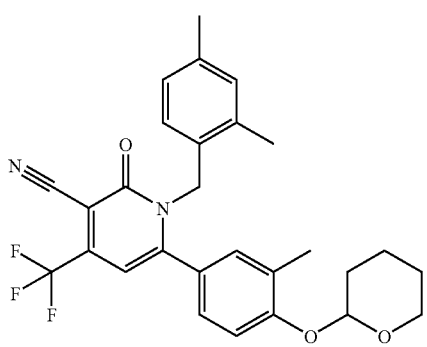

1-(2,4-Dimethyl-benzyl)-6-[3-methyl-4-(tetrahydro-pyran-2-yloxy)-phenyl]-2-oxo-4-trifluoromethyl-1,2-dihydro-pyridine-3-carbonitrile $^1$H-NMR (CDCl$_3$): δ7.03 (m, 1H), 6.95 (m, 2H), 6.91 (m, 1H), 6.86 (m, 1H), 6.63 (m, 1H), 6.42 (s, 1H), 5.46 (m, 1H), 5.11 (m, 2H), 3.79 (m, 1H), 3.60 (m, 1H), 2.27 (s, 3H), 2.14 (s, 3H), 2.01 (m, 1H), 1.97 (s, 3H), 1.89 (m, 2H), 1.68 (m, 2H), 1.60 (m, 1H).

Example 45

This example illustrates the preparation of compound 45.

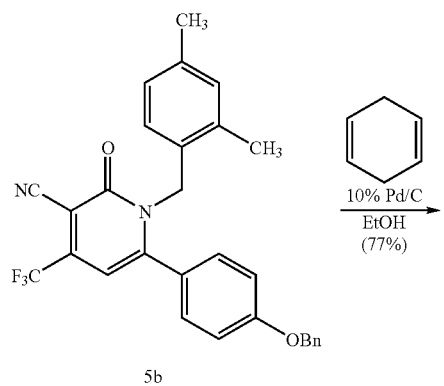

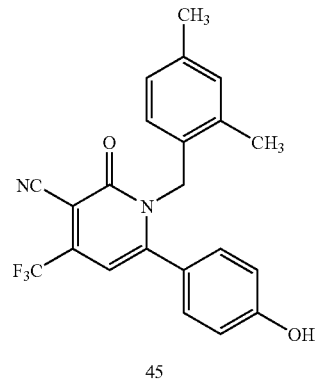

45

6-(4-Benzyloxy-phenyl)-1-(2,4-dimethyl-benzyl)-2-oxo-4-trifluoromethyl-1,2-dihydro-pyridine-3-carbonitrile 5b (0.55 g, 1.13 mmoles) was combined with cyclohexadiene (1.6 mL, 16.9 mmoles), 10% Pd/C (0.6 g) and 10 mL of anhydrous EtOH. This mixture was then stirred at room temperature for 24 hours. After this period the reaction mixture was vacuum filtered through. Celite and the resulting filtrate was evaporated in vacuo to yield 0.35 g (77%) of 45 as a yellowish/orange solid.

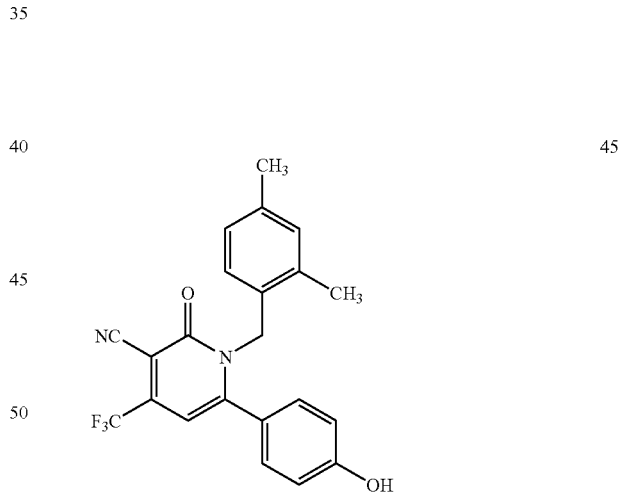

45

1-(2,4-Dimethyl-benzyl)-6-(4-hydroxy-phenyl)-2-oxo-4-trifluoromethyl-1,2-dihydropyridine-3-carbonitrile $^1$H-NMR (CDCl$_3$): δ7.04 (d, J=8.6 Hz, 2H), 6.95 (d, J=7.6 Hz, 1H), 6.92 (s, 1H), 6.80 (d, J=7.6 Hz, 2H), 6.60 (d, J=7.8 Hz, 1H), 6.43 (s, 1H), 5.47 (bs, 1H), 5.12 (s, 2H), 2.28 (s, 3H), 1.98 (s, 3H).

Following compounds were prepared in manner similar to that described above.

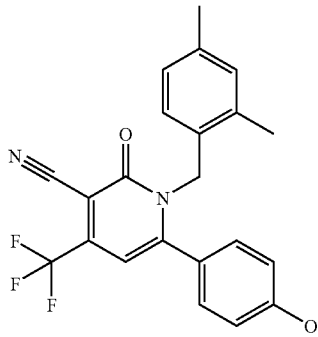

45.1

1-(2,4-Dimethyl-benzyl)-6-(4-hydroxy-phenyl)-2-oxo-4-trifluoromethyl-1,2-dihydro-pyridine-3-carbonitrile $^1$H-NMR (Acetone-d6): δ8.92 (s, 1H), 7.14 (m, 2H), 6.85 (m, 2H), 6.76 (m, 2H), 6.64 (m, 1H), 6.50 (s, 1H), 5.08 (s, 2H), 2.11 (s, 3H), 1.92 (s, 3H).

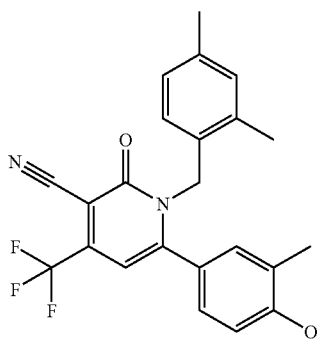

45.2

1-(2,4-Dimethyl-benzyl)-6-(4-hydroxy-3-methyl-phenyl)-2-oxo-4-trifluoromethyl-1,2-dihydro-pyridine-3-carbonitrile $^1$H-NMR (CDCl$_3$): δ6.91-6.78 (m, 4H), 6.66 (m, 1H), 6.56 (m, 1H), 6.35 (s, 1H), 5.05 (s, 2H), 2.22 (s, 3H), 2.07 (s, 3H), 1.90 (s, 3H).

Example 46

This example illustrates the preparation of compound 46.

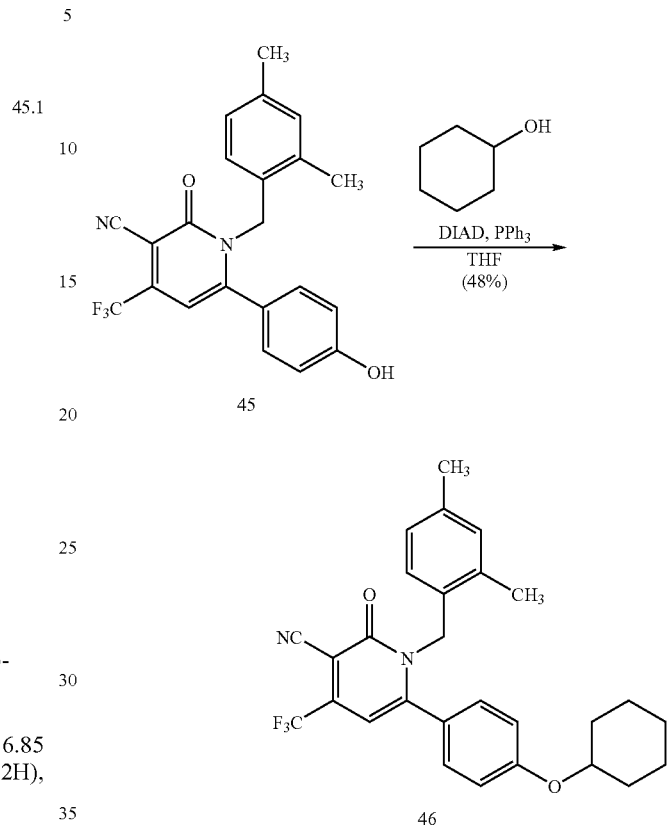

1-(2,4-Dimethyl-benzyl)-6-(4-hydroxy-phenyl)-2-oxo-4-trifluoromethyl-1,2-dihydro-pyridine-3-carbonitrile 45 (31 mg, 0.078 mmoles) was combined with triphenylphosphine (29 mg, 0.11 mmoles) in 1.0 mL of anhydrous THF. To this stirring mixture at room temperature was slowly added (over 1 hour using a syringe pump) a solution of cyclohexanol (12 μL, 0.11 mmoles) and diisopropyl azodicarboxylate (22 μL, 0.11 mmoles) in 1.0 mL of anhydrous THF. The mixture was then stirred at room temperature for 24 hours. After this period the reaction mixture was purified directly using flash silica chromatography (0-20% EtOAc/Hexane) to yield 18 mg (48%) of 46 as a yellow residue.

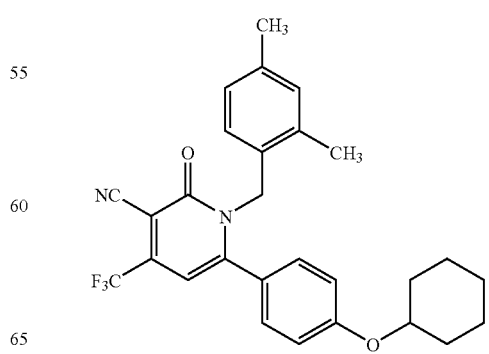

46

6-(4-Cyclohexyloxy-phenyl)-1-(2,4-dimethyl-benzyl)-2-oxo-4-trifluoromethyl-1,2-dihydro-pyridine-3-carbonitrile $^1$H-NMR (CDCl$_3$): δ 7.08 (d, J=8.6 Hz, 2H), 6.97-6.91 (m, 2H), 6.85 (d, J=8.6 Hz, 2H), 6.61 (d, J=7.8 Hz, 1H), 6.44 (s, 1H), 5.14 (s, 2H), 4.32-4.23 (m, 1H), 2.29 (s, 3H), 2.00 (s, 3H), 1.99-1.22 (m, 10H). MS(ES+): 481.4 (M+H)

The following compounds were prepared in a manner similar to that described above.

46.1

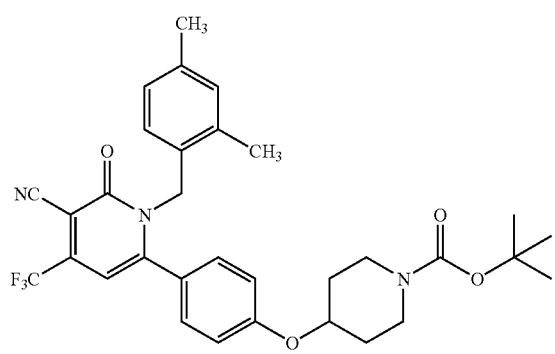

4-{4-[5-Cyano-1-(2,4-dimethyl-benzyl)-6-oxo-4-trifluoromethyl-1,6-dihydro-pyridin-2-yl]-phenoxy}-piperidine-1-carboxylic Acid Tert-butyl Ester

MS(ES+): 582.3 (M+H)

Example 47

This example illustrates the preparation of compound 47.

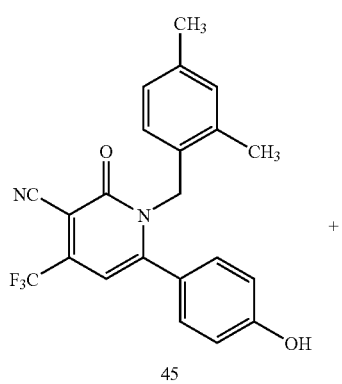

45

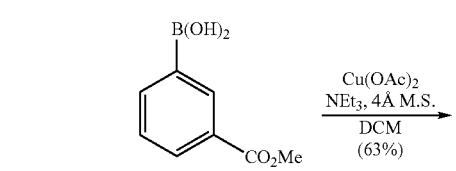

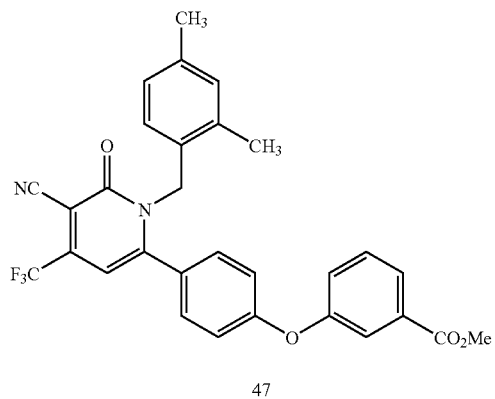

47

1-(2,4-Dimethyl-benzyl)-6-(4-hydroxy-phenyl)-2-oxo-4-trifluoromethyl-1,2-dihydro-pyridine-3-carbonitrile 45 (43 mg, 0.11 mmoles) was combined with (3-methoxycarbonylphenyl) boronic acid (62 mg, 0.34 mmoles), copper acetate (22 mg, 0.12 mmoles), 4 Å molecular sieves (0.18 g) and 1.0 mL of anhydrous DCM within an oven-dried reaction vial. The mixture was stirred at room temperature for 15 min. After this period triethylamine (75 µL, 0.54 mmoles) was added and the mixture was stirred at room temperature for 16 hours. After this period the reaction mixture was purified directly using flash silica chromatography (0-20% EtOAc/Hexane) to yield 38 mg (63%) of 47 as a yellow residue.

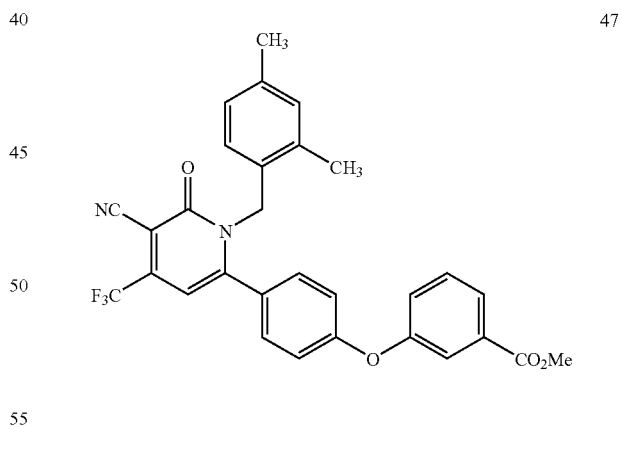

47

3-{4-[5-Cyano-1-(2,4-dimethyl-benzyl)-6-oxo-4-trifluoromethyl-1,6-dihydro-pyridin-2-yl]-phenoxy}-benzoic Acid Methyl Ester $^1$H-NMR (CDCl$_3$): δ 7.90-7.85 (m, 1H), 7.71-7.68 (m, 1H), 7.47 (t, J=7.8 Hz, 1H), 7.27-7.23 (m, 1H), 7.12 (d, J=8.8 Hz, 2H), 6.98-6.91 (m, 4H), 6.61 (d, J=7.8 Hz, 1H), 6.45 (s, 1H), 5.14 (s, 2H), 3.92 (s, 3H), 2.27 (s, 3H), 2.01 (s, 3H). MS(ES+): 533.2 (M+H)

The following compounds were prepared in a manner similar to that described above.

47.1

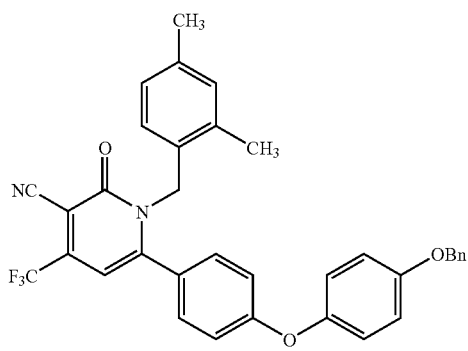

6-[4-(4-Benzyloxy-phenoxy)-phenyl]-1-(2,4-dimethyl-benzyl)-2-oxo-4-trifluoromethyl-1,2-dihydro-pyridine-3-carbonitrile

MS(ES+): 581.3 (M+H)

47.2

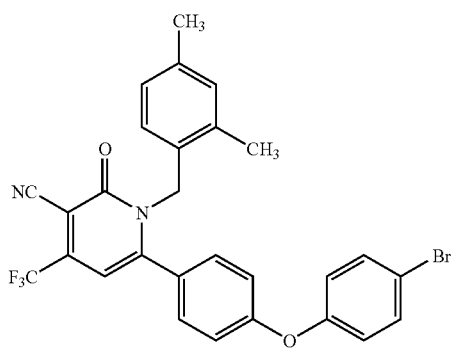

6-[4-(4-Bromo-phenoxy)-phenyl]-1-(2,4-dimethyl-benzyl)-2-oxo-4-trifluoromethyl-1,2-dihydro-pyridine-3-carbonitrile

MS(ES+): 555.2 (M+H)

47.3

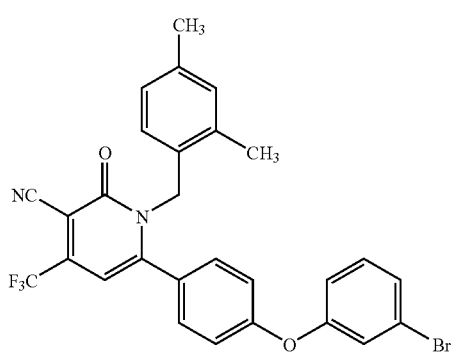

6-[4-(3-Bromo-phenoxy)-phenyl]-1-(2,4-dimethyl-benzyl)-2-oxo-4-trifluoromethyl-1,2-dihydro-pyridine-3-carbonitrile

MS(ES+): 555.3 (M+H)

47.4

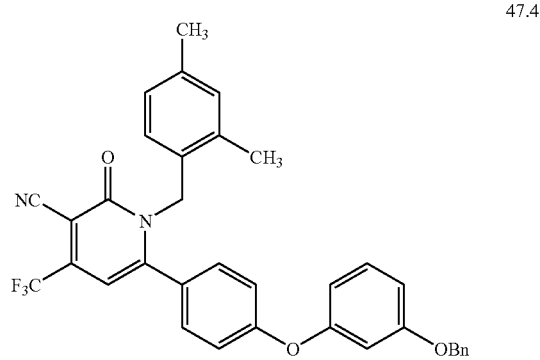

6-[4-(3-Benzyloxy-phenoxy)-phenyl]-1-(2,4-dimethyl-benzyl)-2-oxo-4-trifluoromethyl-1,2-dihydro-pyridine-3-carbonitrile

MS(ES+): 581.5 (M+H)

47.5

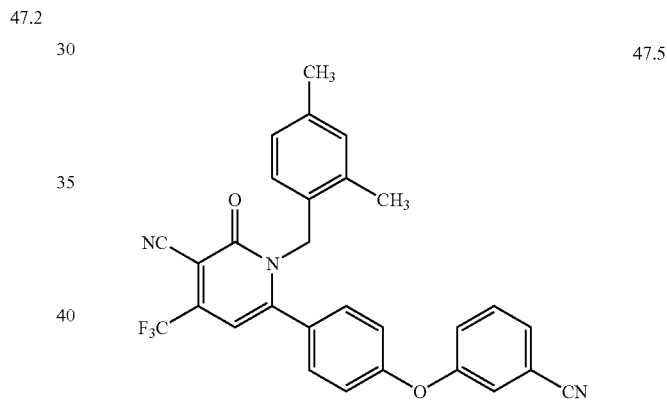

6-[4-(3-Cyano-phenoxy)-phenyl]-1-(2,4-dimethyl-benzyl)-2-oxo-4-trifluoromethyl-1,2-dihydro-pyridine-3-carbonitrile

MS(ES+): 500.4 (M+H)

47.6

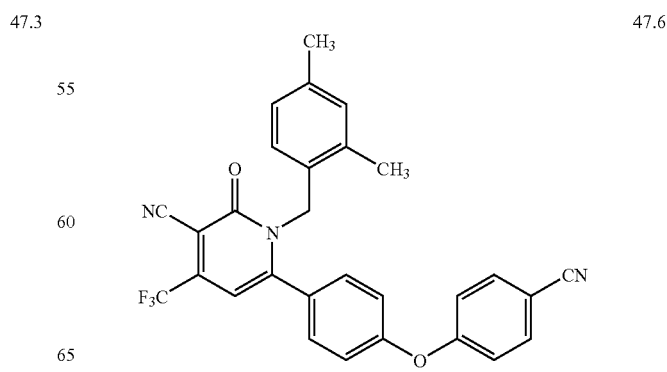

6-[4-(4-Cyano-phenoxy)-phenyl]-1-(2,4-dimethyl-benzyl)-2-oxo-4-trifluoromethyl-1,2-dihydro-pyridine-3-carbonitrile

MS(ES+): 500.4 (M+H)

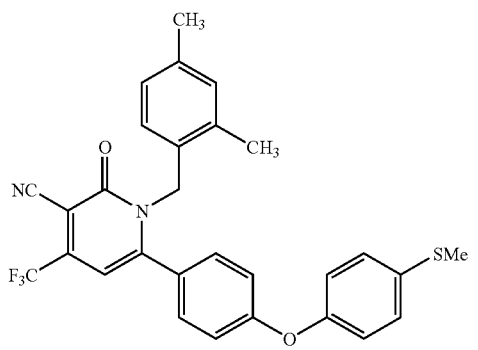

1-(2,4-Dimethyl-benzyl)-6-[4-(4-methylsulfanyl-phenoxy)-phenyl]-2-oxo-4-trifluoromethyl-1,2-dihydro-pyridine-3-carbonitrile

MS(ES+): 521.1 (M+H)

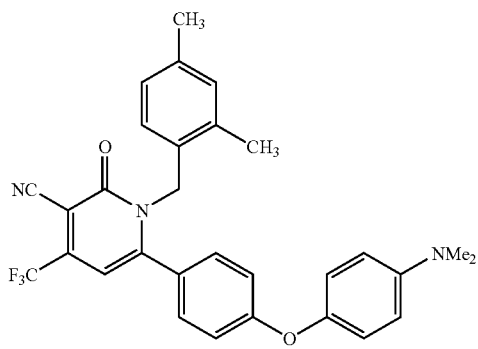

6-[4-(4-Dimethylamino-phenoxy)-phenyl]-1-(2,4-dimethyl-benzyl)-2-oxo-4-trifluoromethyl-1,2-dihydro-pyridine-3-carbonitrile

MS(ES+): 518.4 (M+H)

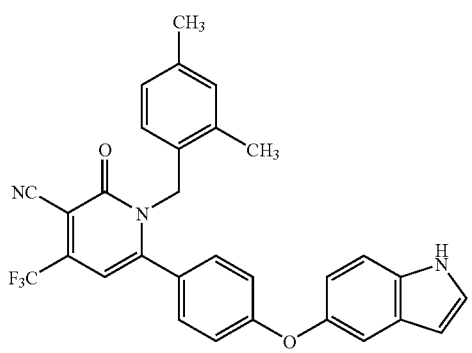

1-(2,4-Dimethyl-benzyl)-6-[4-(1H-indol-5-yloxy)-phenyl]-2-oxo-4-trifluoromethyl-1,2-dihydro-pyridine-3-carbonitrile

MS(ES+): 514.4 (M+H)

Example 48

This example illustrates the preparation of compound 48.

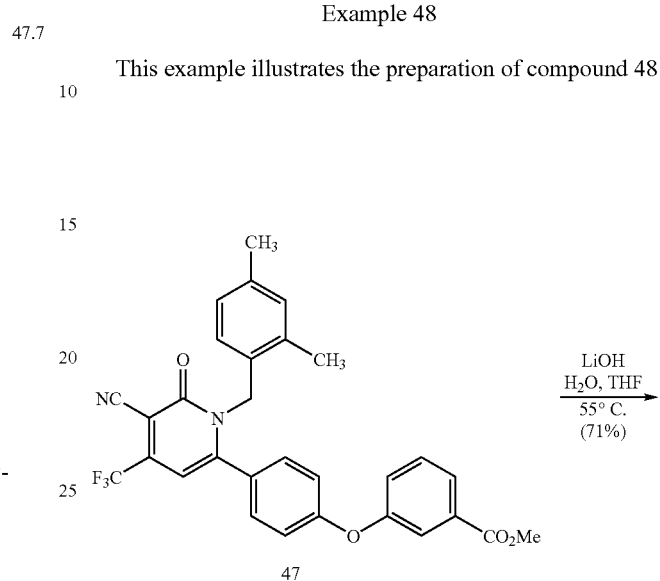

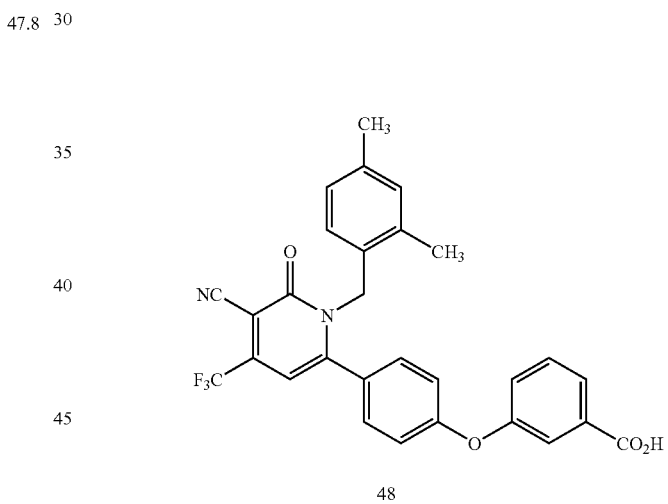

3-{4-[5-Cyano-1-(2,4-dimethyl-benzyl)-6-oxo-4-trifluoromethyl-1,6-dihydro-pyridin-2-yl]-phenoxy}-benzoic acid methyl ester 47 (0.55 g, 1.01 mmoles) was combined with lithium hydroxide (monohydrate, 93 mg, 2.22 mmoles) in 10 mL of THF/H$_2$O (4:1). This mixture was then heated at 55° C. for 12 hours. After this period the mixture was evaporated in vacuo (-THF) and was combined with 1N HCl (10 mL). The aqueous acidic mixture was combined with enough NaCl to affect saturation and was extracted with Et$_2$O (4×20 mL). The combined ether layer was washed with brine, dried over Na$_2$SO$_4$, and was evaporated in vacuo to yield crude product. The crude product was purified using flash silica chromatography (0-60% EtOAc/Hexane) to yield 0.37 g (71%) of product as a yellow residue.

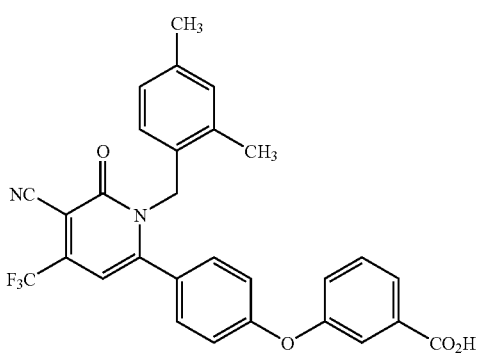

3-{4-[5-Cyano-1-(2,4-dimethyl-benzyl)-6-oxo-4-trifluoromethyl-1,6-dihydro-pyridin-2-yl]-phenoxy}-benzoic Acid ¹H-NMR (CDCl₃): δ7.95-7.91 (m, 1H), 7.74-7.71 (m, 1H), 7.51 (t, J=7.8 Hz, 1H), 7.33-7.28 (m, 1H), 7.15-7.10 (m, 2H), 7.00-6.91 (m, 4H), 6.61 (d, J=8.1 Hz, 1H), 6.46 (s, 1H), 5.14 (s, 2H), 2.27 (s, 3H), 2.00 (s, 3H). MS(ES+): 519.3 (M+H)

Example 49

This example illustrates the preparation of compound 49.

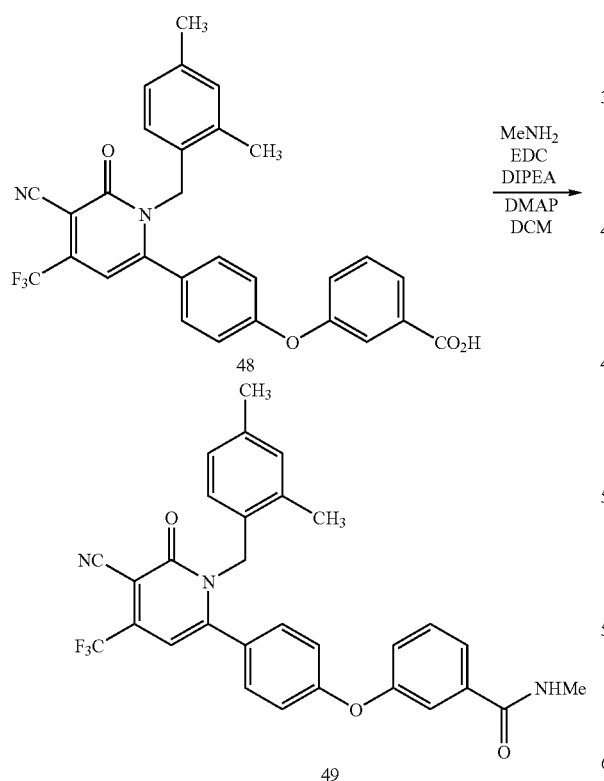

3-{4-[5-Cyano-1-(2,4-dimethyl-benzyl)-6-oxo-4-trifluoromethyl-1,6-dihydro-pyridin-2-yl]-phenoxy}-benzoic acid 48 (15 mg, 0.029 mmoles) was combined with 1-[3-(dimethylamino)propyl]-3-ethylcarbodiimide hydrochloride (EDC, 14 mg, 0.073 mmoles), 4-dimethylaminopyridine (DMAP, 2 mg, 0.016 mmoles) in 5 mL of anhydrous DCM. To this mixture was added diisopropylethylamine (DIPEA, 13 µL, 0.075 mmoles) and methylamine ([2.0 M] solution in THF, 36 µL, 0.72 mmoles). This mixture was then stirred at room temperature for 16 hours. After this period the reaction mixture was purified directly using flash silica chromatography (0-60% EtOAc/Hexane) to yield 13 mg (84% yield) of 49 as a yellow solid.

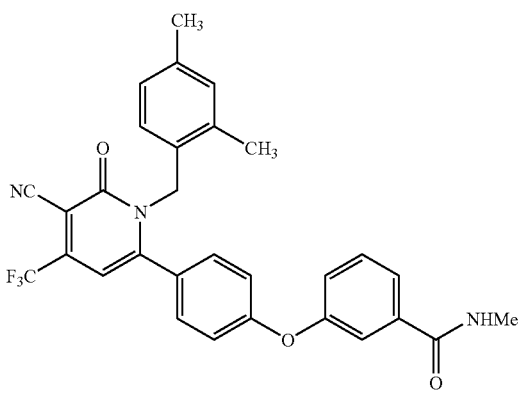

¹H-NMR (CDCl₃): δ7.52-7.41 (m, 3H), 7.19-7.10 (m, 3H), 6.98-6.91 (m, 4H), 6.61 (d, J=7.6 Hz, 1H), 6.45 (s, 1H), 6.09 (bs, 1H), 5.14 (s, 2H), 3.01 (d, J=5.1 Hz, 3H), 2.27 (s, 3H), 2.01 (s, 3H).

Example 50

This example illustrates the preparation of compound 50.

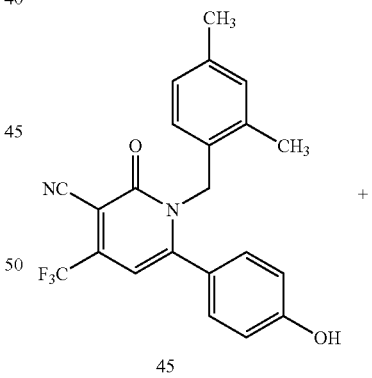

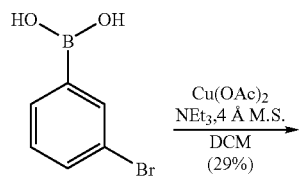

283

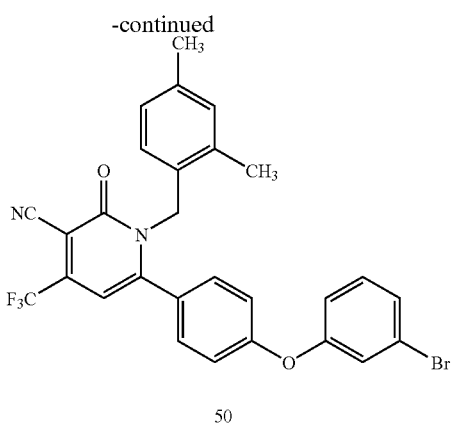

50

1-(2,4-Dimethyl-benzyl)-6-(4-hydroxy-phenyl)-2-oxo-4-trifluoromethyl-1,2-dihydro-pyridine-3-carbonitrile 45 (104 mg, 0.26 mmoles) was combined with (3-bromophenyl) boronic acid (157 mg, 0.78 mmoles), copper acetate (57 mg, 0.31 mmoles), 4 Å molecular sieves (0.20 g) and 1.0 mL of anhydrous DCM within an oven-dried reaction vial. The mixture was stirred at room temperature for 15 min. After this period triethylamine (182 µL, 1.31 mmoles) was added and the mixture was stirred at room temperature for 16 hours. After this period the reaction mixture was purified directly using flash silica chromatography (0-20% EtOAc/Hexane) to yield 41 mg (29%) of 50 as a yellow residue.

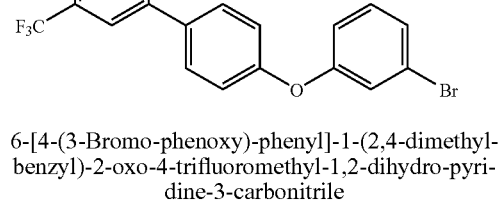

50

6-[4-(3-Bromo-phenoxy)-phenyl]-1-(2,4-dimethyl-benzyl)-2-oxo-4-trifluoromethyl-1,2-dihydro-pyridine-3-carbonitrile

MS(ES+): 555.3 (M+H)

The following compounds were prepared in a manner similar to that described above.

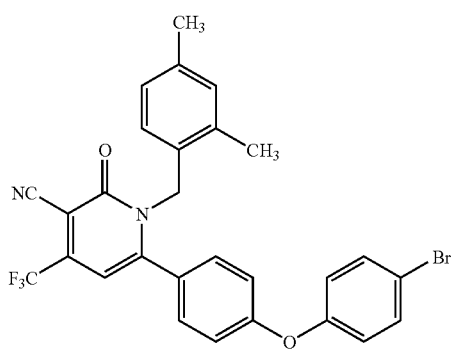

50.1

284

6-[4-(4-Bromo-phenoxy)-phenyl]-1-(2,4-dimethyl-benzyl)-2-oxo-4-trifluoromethyl-1,2-dihydro-pyridine-3-carbonitrile

MS(ES+): 555.2 (M+H)

Example 51

This example illustrates the preparation of compound 51.

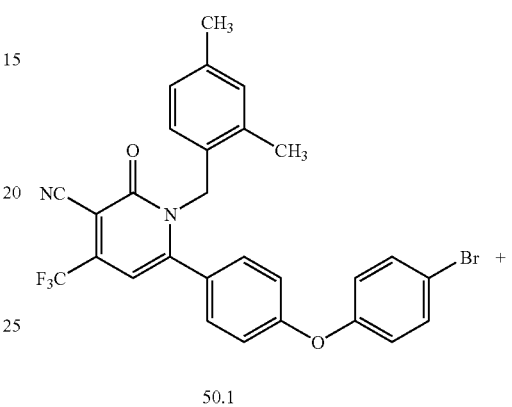

50.1

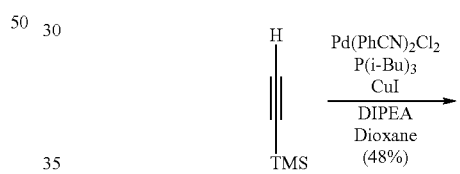

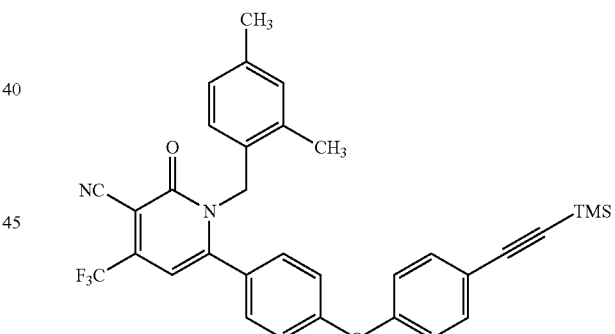

51

6-[4-(4-Bromo-phenoxy)-phenyl]-1-(2,4-dimethyl-benzyl)-2-oxo-4-trifluoromethyl-1,2-dihydro-pyridine-3-carbonitrile 50.1 (108 mg, 0.195 mmoles) was combined with dichlorobis(benzonitrile)palladium (II) (11 mg, 0.029 mmoles), tri-t-butylphosphine (33 mg, 0.065 mmoles), copper iodide (4 mg, 0.021 mmoles), diisopropylethylamine (33 µL, 0.24 mmoles) and trimethylsilylacetylene (33 µL, 0.23 mmoles) in 2.0 mL of anhydrous and thoroughly degassed dioxane. This mixture was then stirred at 50° C. for 24 hours. After this period the reaction mixture was evaporated and purified directly for flash silica chromatography (0-20% EtOAc/Hexane) to yield 53 mg (48% yield) of 51 as a yellow residue.

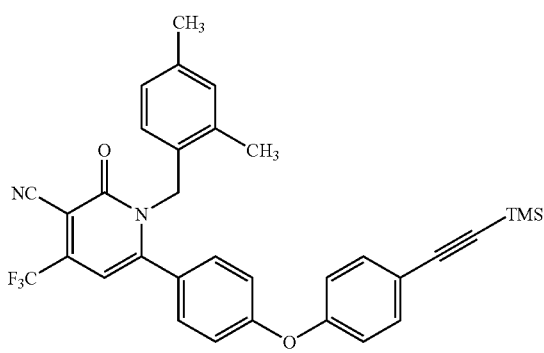

1-(2,4-Dimethyl-benzyl)-2-oxo-4-trifluoromethyl-6-[4-(4-trimethylsilanylethynyl-phenoxy)-phenyl]-1,2-dihydro-pyridine-3-carbonitrile $^1$H-NMR (CDCl$_3$): δ7.52-7.46 (m, 2H), 7.14-7.09 (m, 2H), 6.97-6.89 (m, 6H), 6.60 (d, J=8.1 Hz, 1H), 6.44 (s, 1H), 5.13 (s, 2H), 2.28 (s, 3H), 1.99 (s, 3H), 0.25 (s, 9H).

Example 52

This example illustrates the preparation of compound 52.

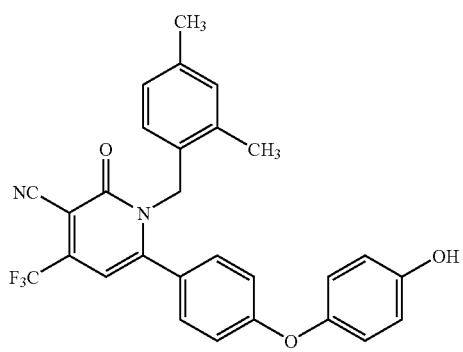

6-[4-(4-Benzyloxy-phenoxy)-phenyl]-1-(2,4-dimethyl-benzyl)-2-oxo-4-trifluoromethyl-1,2-dihydro-pyridine-3-carbonitrile 47.1 (29 mg, 0.05 mmoles) was combined with cyclohexadiene (0.1 mL, 1.05 mmoles), 10% Pd/C (50 mg) and 10 mL of anhydrous EtOH. This mixture was then stirred at room temperature for 24 hours. After this period the reaction mixture was vacuum filtered through Celite and the resulting filtrate was evaporated in vacuo to yield 13 mg (53%) of 52 as a yellow residue.

1-(2,4-Dimethyl-benzyl)-6-[4-(4-hydroxy-phenoxy)-phenyl]-2-oxo-4-trifluoromethyl-1,2-dihydro-pyridine-3-carbonitrile $^1$H-NMR (CDCl$_3$): δ7.12-7.06 (m, 2H), 6.97-6.82 (m, 8H), 6.59 (d, J=7.8 Hz, 1H), 6.44 (s, 1H), 5.13 (s, 2H), 4.84 (s, 1H), 2.28 (s, 3H), 2.01 (s, 3H). MS(ES+): 519.3 (M+H)

The following compounds were prepared in a manner similar to that described above.

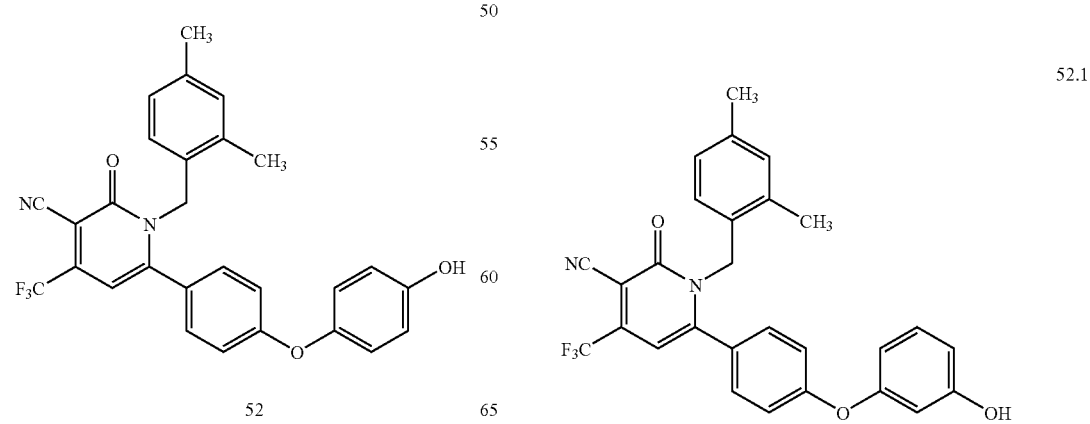

1-(2,4-Dimethyl-benzyl)-6-[4-(3-hydroxy-phenoxy)-phenyl]-2-oxo-4-trifluoromethyl-1,2-dihydro-pyridine-3-carbonitrile

MS(ES+): 519.3 (M+H)

Example 53

This example illustrates the preparation of compound 53.

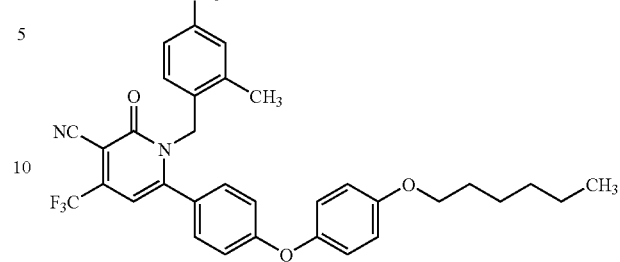

53

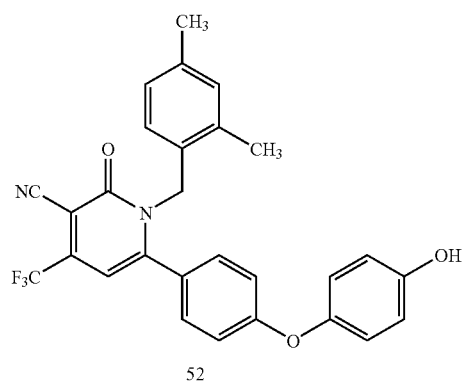

52

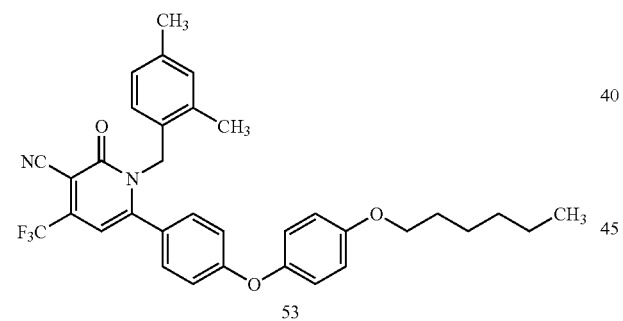

53

1-(2,4-Dimethyl-benzyl)-6-[4-(4-hydroxy-phenoxy)-phenyl]-2-oxo-4-trifluoromethyl-1,2-dihydro-pyridine-3-carbonitrile 52 (16 mg, 0.033 mmoles) was combined with potassium carbonate (23 mg, 0.166 mmoles) and hexyl bromide (20 µL, 0.142 mmoles) in 2.0 mL of anhydrous DMF. This mixture was stirred at room temperature for 24 hours. After this period the reaction mixture was combined with 50 mL of water and was extracted with EtOAc (4×15 mL). The combined EtOAc layer was washed with water (4×15 mL) and 15 mL of brine. The resulting EtOAc later was dried over anhydrous $Na_2SO_4$ and was evaporated in vacuo to yield the crude product. The crude product was purified using flash silica chromatography (0-20% EtOAc/Hexane) to yield 14 mg (84%) of 53 as a yellow residue.

$^1$H-NMR (CDCl$_3$): δ7.05 (d, J=8.8 Hz, 2H), 6.97-6.81 (m, 8H), 6.57 (d, J=7.3 Hz, 1H), 6.40 (s, 1H), 5.10 (s, 2H), 3.92 (t, J=6.6 Hz, 2H), 2.24 (s, 3H), 1.98 (s, 3H), 1.81-1.71 (m, 2H), 1.49-1.39 (m, 2H), 1.35-1.28 (m, 4H), 0.91-0.84 (m, 3H). MS(ES+): 575.5 (M+H)

53.1

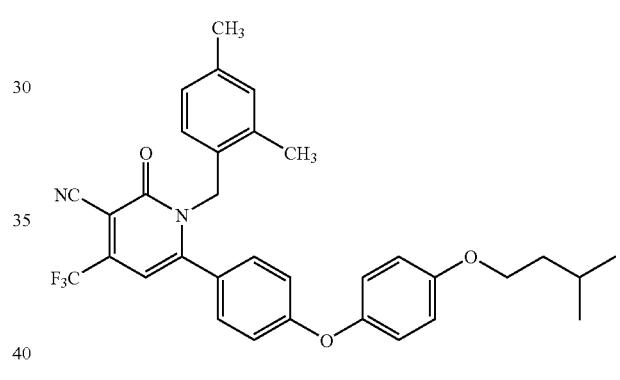

MS(ES+): 561.3 (M+H)

Example 54

This example illustrates the preparation of compound 54.

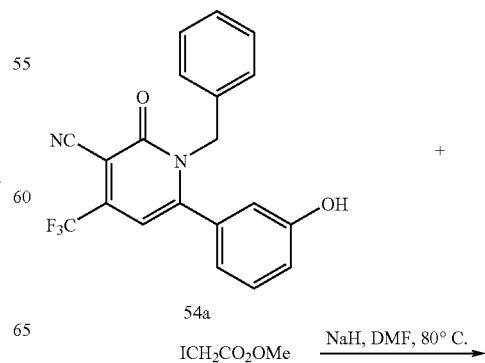

54a

ICH$_2$CO$_2$Me  $\xrightarrow{\text{NaH, DMF, 80° C.}}$

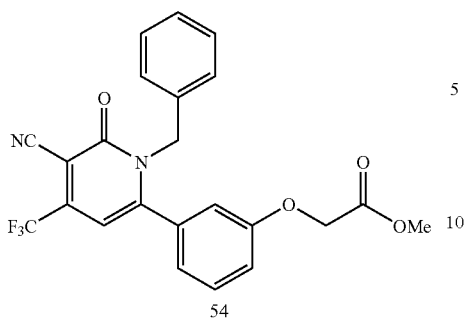

Sodium hydride (18 mg, 0.43 mmol) was added to a solution of 54a (80 mg, 0.22 mmol) and methyl 2-iodoacetate (82 μL, 0.86 mmol) in anhydrous DMF (2 mL). The reaction mixture was stirred under nitrogen atmosphere at 80° C. overnight. After the reaction mixture was cooled off, it was poured into 20 mL of water and extract with ethyl acetate (3×30 mL). The combined organic layer was washed with brine and water and concentrated in vacuo. The crude product was purified by column chromatography (40% ethyl acetate in hexane), providing product 54 (67 mg, 70% yield). ¹H-NMR (CDCl₃): δ7.37 (m, 1H), 7.26 (m, 4H), 7.06 (m, 1H), 6.91 (m, 1H), 6.82 (m, 1H), 6.62 (m, 1H), 6.40 (s, 1H), 5.24 (s, 2H), 4.46 (s, 2H), 3.80 (s, 2H).

Example 55

This example illustrates the preparation of compound 55.

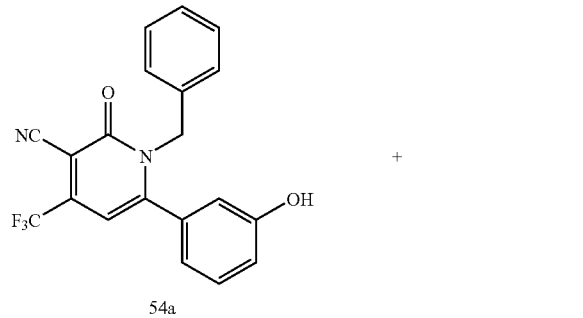

To a solution of 54a (80 mg, 0.22 mmol) and triethylamine (60 μL, 0.43 mmol) in anhydrous THF (2 mL) was added ethyl isocyanate (43 μL, 0.54 mmol). The reaction mixture was stirred at 65° C. under nitrogen atmosphere for overnight. The reaction mixture was then cooled off and concentrated in vacuo. The crude product was purified by column chromatography (40% ethyl acetate in hexane) to yield product 55 (91 mg, 95% yield). ¹H-NMR (CDCl₃): δ 7.39 (m, 1H), 7.29 (m, 1H), 7.24-7.20 (m, 3H), 7.04 (m, 1H), 6.91 (m, 3 H), 6.41 (s, 1H), 5.29 (s, 2H), 5.05 (s, 1H), 3.33 (m, 2H), 1.24 (t, 7.1 Hz, 3H).

Example 56

This example illustrates the preparation of compound 56.

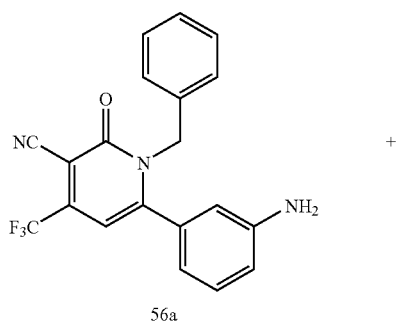

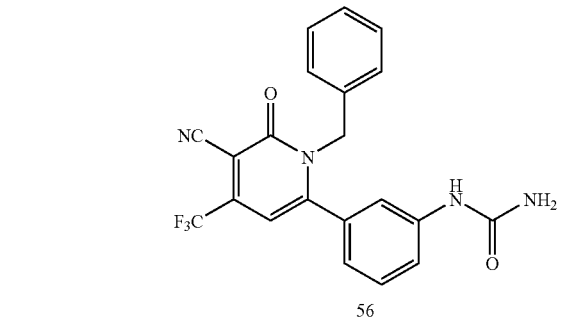

To a solution of 56a (117 mg, 0.32 mmol) in anhydrous THF (4 mL) was added trimethylsilyl isocyanate (0.24 mL, 1.6 mmol) and 4-dimethylaminopyridine (4 mg, 0.03 mmol). The reaction mixture was stirred at 65° C. under nitrogen atmosphere overnight. The mixture was concentrated in vacuo. The resulting residue was dissolved in anhydrous THF (4 mL), and to it was added tetrabutylammonium fluoride (0.7 mL, 1.0 M) in THF. The reaction mixture was stirred at room temperature overnight. The crude product was purified by column chromatography (60% ethyl acetate in hexane) to yield product 56 (95 mg, 72% over two steps). ¹H-NMR (DMSO-d6): δ10.20 (s, 1 H), 9.04 (s, 1H), 7.65 (m, 1H), 7.58 (m, 1H), 7.43 (m, 1H), 7.29 (m, 3H), 7.07 (m, 1H), 7.02 (m, 2H), 6.80 (s, 1H), 5.23 (s, 2H).

Example 57

This example illustrates the preparation of compound 57.

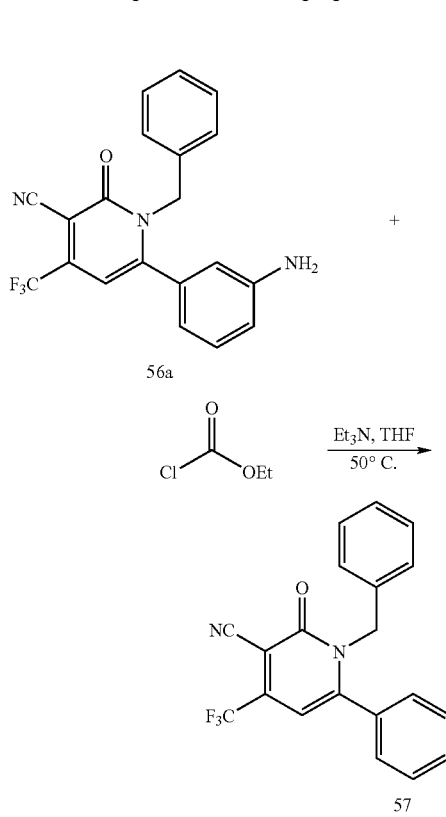

To a solution of 56a (80 mg, 0.22 mmol) and triethyl amine (76 µL, 0.54 mmol) in anhydrous methylene chloride (2 mL) was added ethyl chloroformate (41 µL, 0.54 mmol). The reaction mixture was sealed in a vial and stirred at 50° C. overnight. The mixture was cooled off and concentrated in vacuo. The product was purified by column chromatography (40% ethyl acetate in hexane) to yield 57 (40 mg, 42% yield).
$^1$H-NMR (CDCl$_3$): δ7.41 (m, 2H), 7.34 (m, 1H), 7.25-7.21 (m, 3H), 6.91 (m, 2H), 6.81 (m, 1H), 6.64 (s, 1H), 6.40 (s, 1H), 5.27 (s, 2H), 4.24 (q, 7.1 Hz, 2H), 1.32 (t, 7.1 Hz, 3H).

Example 58

This example illustrates the preparation of compound 58.

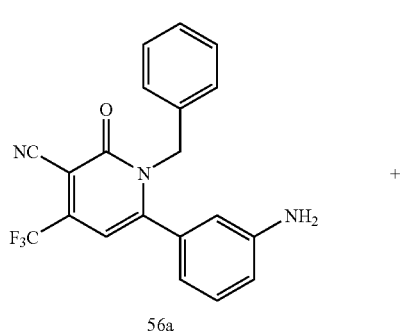

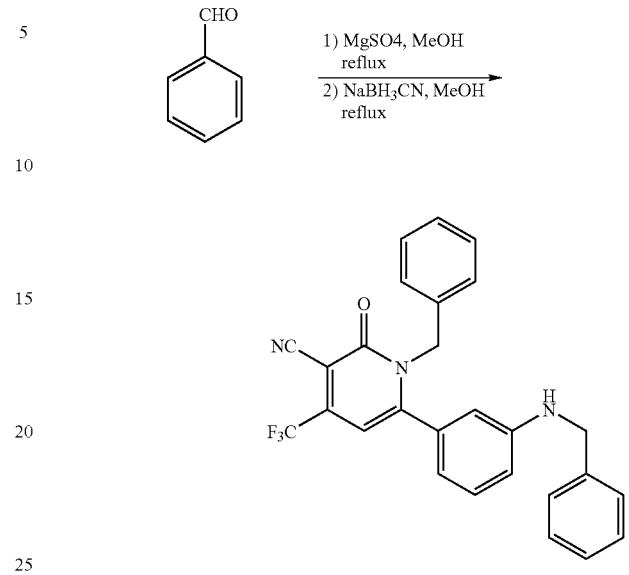

To a solution of 56a (100 mg, 0.27 mmol) in methanol (15 mL) was added benzaldehyde (41 µL, 0.41 mmol) and anhydrous magnesium sulfate (500 mg). The reaction mixture was heated to reflux overnight. Sodium cyanoborohydride (85 mg, 1.36 mmol) was added to the mixture, which was heated to reflux overnight. The reaction mixture was concentrated in vacuo and the crude mixture was partitioned between ethyl acetate and saturated sodium bicarbonate solution. The combined ethyl acetate was concentrated in vacuo. The crude product was purified by column chromatography (30% ethyl acetate in hexane) to yield compound 58 (24 mg, 19% yield).
$^1$H-NMR (CDCl$_3$): δ7.38-7.19 (br, 10H), 6.93 (m, 2H), 6.75 (m, 1H), 6.50 (m, 1H), 6.38 (s, 1H), 6.27 (s, 1H), 5.19 (s, 2H), 4.17 (s, 2H).

Example 59

This example illustrates the preparation of compound 59.

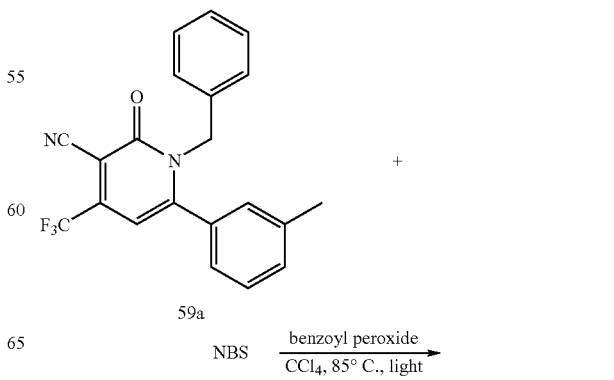

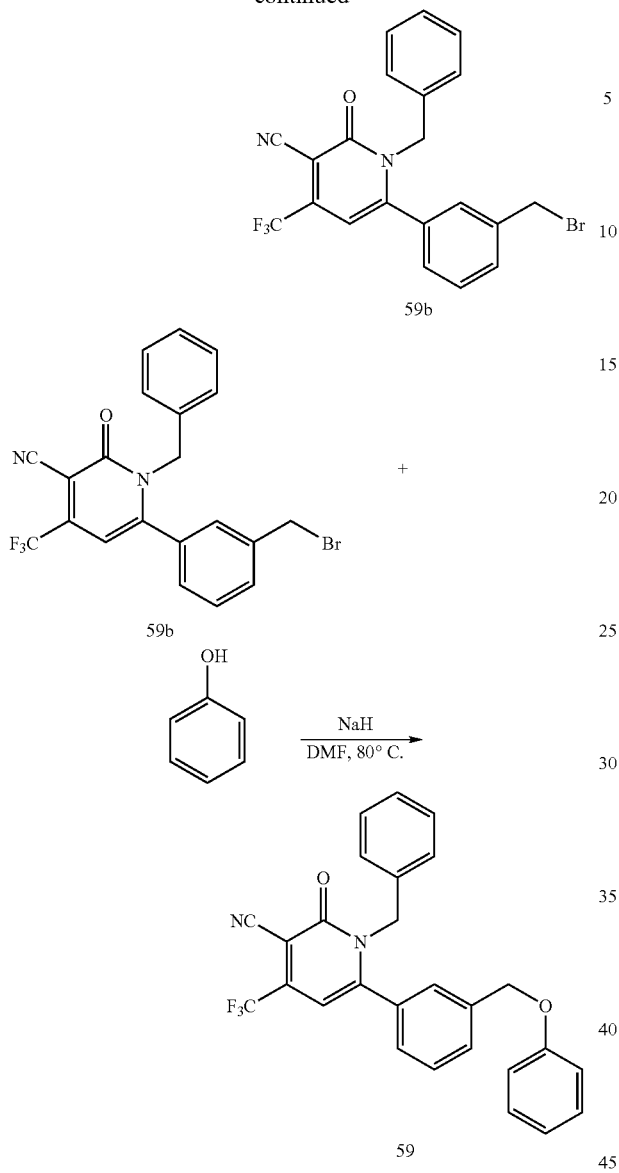

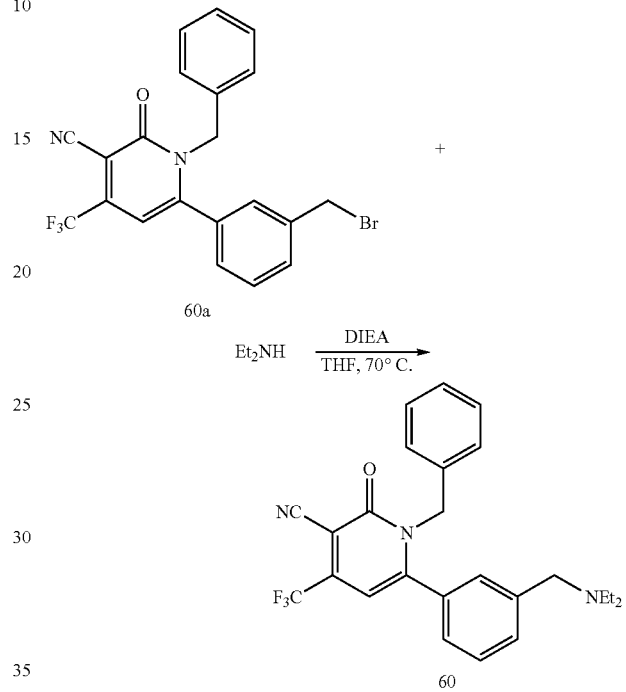

A solution of 59a (0.96 g, 2.61 mmol) in carbon tetrachloride (50 mL) was treated with N-bromosuccinimide (557 mg, 3.13 mmol) and catalytic amount of benzoyl peroxide. The reaction mixture was heated to reflux and irradiated with a 500 W floodlamp for 24 h. It was then cooled off and the white precipitate was filtered off. The solvent was evaporated to dryness, and the residue was purified by column chromatography (40% ethyl acetate in hexane) to yield 59b (0.79 g, 65% yield). $^1$H-NMR (CDCl$_3$): δ 7.56 (m, 1H), 7.43 (m, 1H), 7.25 (m, 3H), 7.13 (m, 2H), 6.88 (m, 2H), 6.39 (s, 1H), 5.24 (s, 2H), 4.38 (s, 2H).

To a solution of 59b (151 mg, 0.34 mmol) and phenol (127 mg, 1.35 mmol) in anhydrous DMF was added sodium hydride (54 mg, 60%, 1.35 mmol). The reaction mixture was stirred and heated to 80° C. for overnight. It was cooled off and poured into water and extracted with ether. The ether layer was dried with anhydrous sodium sulfate and concentrated in vacuo. The crude product was purified by column chromatography (15-30% ethyl acetate in hexane) to yield product 59 (66 mg, 42% yield). $^1$H-NMR (CDCl$_3$): δ7.60 (m, 1H), 7.46 (m, 1H), 7.30 (m, 2H), 7.24-7.20 (br, 4H), 7.12 (m, 1 H), 7.00 (m, 1H), 6.92 (m, 2H), 6.86 (m, 2H), 6.40 (s, 1H), 5.22 (s, 1H), 5.03 (s, 2H).

Example 60

This example illustrates the preparation of compound 60.

To a solution of 60a (152 mg, 0.34 mmol) and diisopropylethyl amine (89 µL, 0.51 mmol) in THF (2 mL) was added diethyl amine (53 µL, 0.51 mmol). The reaction mixture was heated to 70° C. for overnight. The solvent was evaporated in vacuo and the crude product was purified by column chromatography (50% ethyl acetate in hexane) to yield product 60 (82 mg, 55%). $^1$H-NMR (CDCl$_3$): δ7.51 (m, 1H), 7.38 (m, 1H), 7.24-7.17 (m, 4H), 7.07 (m, 1H), 6.88 (m, 2H), 6.41 (s, 1H), 5.27 (s, 2H), 3.52 (m, 2H), 2.48 (m, 4H), 1.01 (m, 6H).

Example 61

This example illustrates the preparation of compound 61.

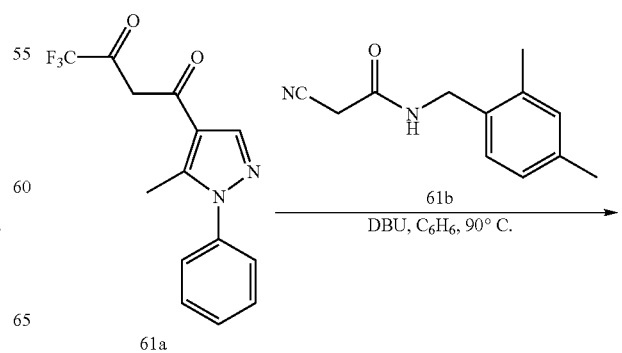

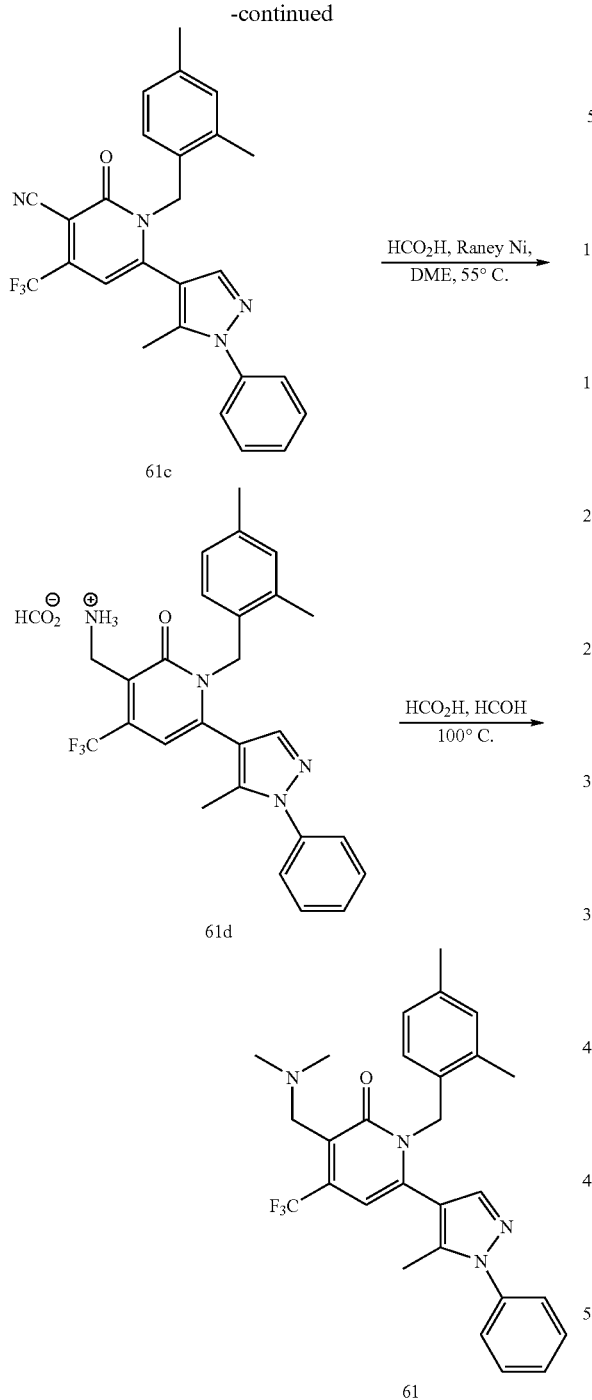

mixture was stirred for 45 min. The solution was decanted, while the solid Ni catalyst was kept washing with water 8 times until it became clear solution. The water was removed as much as possible, using a pipet. To a solution of 61c (48 mg, 0.10 mmol) in 5 mL of DME was added 5 mL of formic acid. The reaction mixture was stirred at 55° C. for 4 h under a slow stream of nitrogen. The reaction mixture was filtered through a short pad of celite, and the celite was washed with MeOH. The filtrate was concentrated in vacuo. The residue was purified by column chromatography (10% MeOH in DCM containing 0.1% triethyl amine) to provide product 61d (26 mg, 50% yield).

The resulting product 61d (21 mg, 0.04 mmol) was dissolved in a mixture of formic acid (2 mL, 96%) and formaldehyde (6 mL, 37% in water). The reaction mixture was heated at 100° C. for 16 h and then cooled off. The reaction mixture was neutralized by 10% aq NaOH with ice to weekly basic and then extracted with ether (3×20 mL). The combined ether was concentrated in vacuo. This crude product was purified by HPLC with 30% $CH_3CN$ in water to yield 61 (12 mg, 80% yield) as trifluoroacetic acid salt. $^1$H-NMR ($CDCl_3$): δ 7.50 (m, 2H), 7.45 (m, 1H), 7.36 (m, 3H), 6.97 (s, 1H), 6.91 (m, 1H), 6.56 (m, 1H), 6.49 (s, 1H), 5.23 (s, 2H), 4.34 (s, 2H), 3.00 (s, 6H), 2.27 (s, 3H), 2.11 (s, 6H). MS (ES+): 495.2 (M+H)

Example 62

This example illustrates the preparation of compound 62.

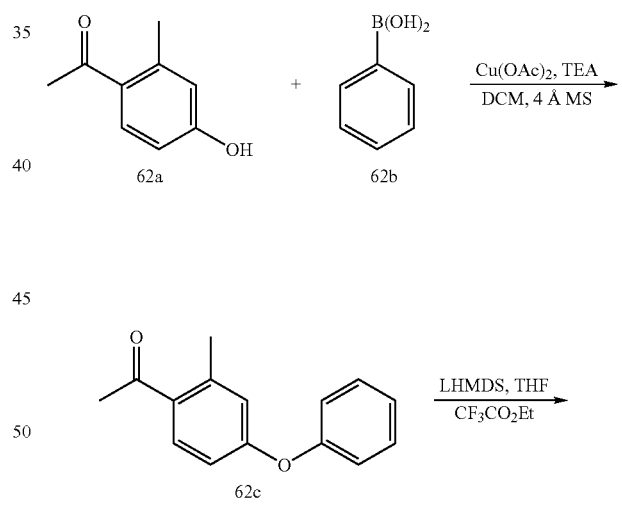

2,4-dimethylbenzyl cyanoacetamide 61a (103 mg, 0.59 mmol) and diketone 61b (175 mg, 0.59 mmol) were suspended in 2 mL of benzene. To the above reaction mixture was added DBU (45 μL, 0.3 mmol). The mixture was sealed in a vial and stirred at 90° C. for overnight. The reaction mixture was concentrated in vacuo and the resulting residue was purified by column chromatography (35% ethyl acetate in hexane) to yield 61c (50 mg, 18%). $^1$H-NMR ($CDCl_3$): δ 7.54-7.45 (m, 3H), 7.34 (m, 3H), 6.95 (m, 2H), 6.61 (m, 1H), 6.44 (s, 1H), 5.28 (m, 2H), 2.28 (s, 3H), 2.08 (s, 3H), 2.03 (s, 3H).

1.0 g of aluminum-nickel catalyst was placed in 10 mL of 2 N aq NaOH and stirred in a flask cooled with ice water. The

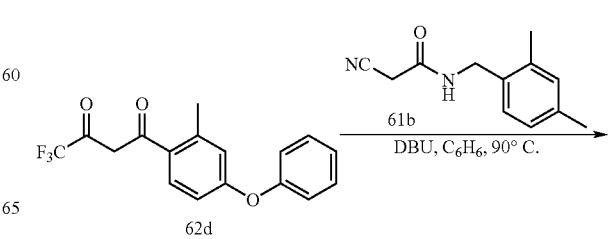

Example 63

This example illustrates the preparation of compound 63.

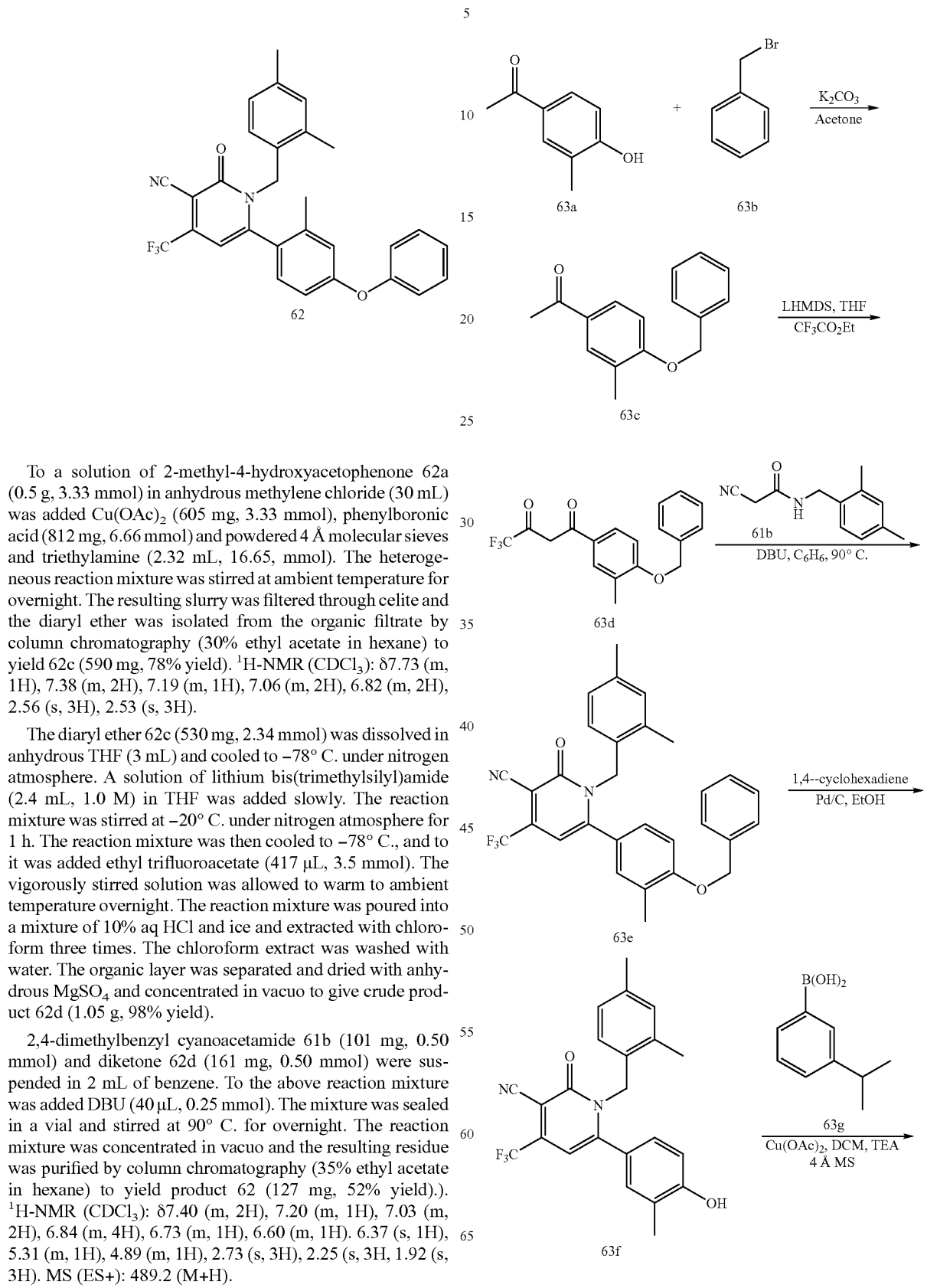

To a solution of 2-methyl-4-hydroxyacetophenone 62a (0.5 g, 3.33 mmol) in anhydrous methylene chloride (30 mL) was added Cu(OAc)$_2$ (605 mg, 3.33 mmol), phenylboronic acid (812 mg, 6.66 mmol) and powdered 4 Å molecular sieves and triethylamine (2.32 mL, 16.65, mmol). The heterogeneous reaction mixture was stirred at ambient temperature for overnight. The resulting slurry was filtered through celite and the diaryl ether was isolated from the organic filtrate by column chromatography (30% ethyl acetate in hexane) to yield 62c (590 mg, 78% yield). $^1$H-NMR (CDCl$_3$): δ7.73 (m, 1H), 7.38 (m, 2H), 7.19 (m, 1H), 7.06 (m, 2H), 6.82 (m, 2H), 2.56 (s, 3H), 2.53 (s, 3H).

The diaryl ether 62c (530 mg, 2.34 mmol) was dissolved in anhydrous THF (3 mL) and cooled to −78° C. under nitrogen atmosphere. A solution of lithium bis(trimethylsilyl)amide (2.4 mL, 1.0 M) in THF was added slowly. The reaction mixture was stirred at −20° C. under nitrogen atmosphere for 1 h. The reaction mixture was then cooled to −78° C., and to it was added ethyl trifluoroacetate (417 µL, 3.5 mmol). The vigorously stirred solution was allowed to warm to ambient temperature overnight. The reaction mixture was poured into a mixture of 10% aq HCl and ice and extracted with chloroform three times. The chloroform extract was washed with water. The organic layer was separated and dried with anhydrous MgSO$_4$ and concentrated in vacuo to give crude product 62d (1.05 g, 98% yield).

2,4-dimethylbenzyl cyanoacetamide 61b (101 mg, 0.50 mmol) and diketone 62d (161 mg, 0.50 mmol) were suspended in 2 mL of benzene. To the above reaction mixture was added DBU (40 µL, 0.25 mmol). The mixture was sealed in a vial and stirred at 90° C. for overnight. The reaction mixture was concentrated in vacuo and the resulting residue was purified by column chromatography (35% ethyl acetate in hexane) to yield product 62 (127 mg, 52% yield).). $^1$H-NMR (CDCl$_3$): δ7.40 (m, 2H), 7.20 (m, 1H), 7.03 (m, 2H), 6.84 (m, 4H), 6.73 (m, 1H), 6.60 (m, 1H). 6.37 (s, 1H), 5.31 (m, 1H), 4.89 (m, 1H), 2.73 (s, 3H), 2.25 (s, 3H, 1.92 (s, 3H). MS (ES+): 489.2 (M+H).

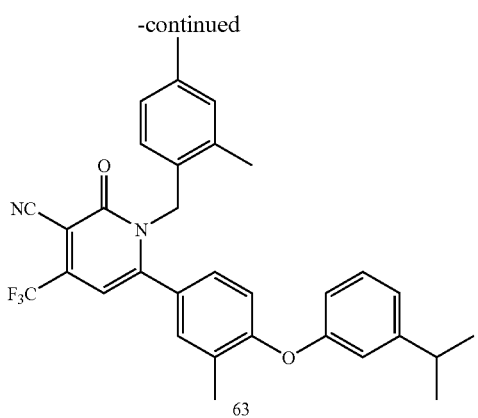

To a solution of 3-methyl-4-hydroxyacetophenone 63a (9.01 g, 60 mmol) and benzyl bromide 63b (7.49 mL, 63 mmol) in acetone (120 mL) was added potassium carbonate (8.71 g, 63 mmol). The reaction mixture was stirred at ambient temperature under nitrogen atmosphere for overnight. The white solid was filtered off and the solvent was concentrated in vacuo to yield product 63c (14.13 g, 98% yield). The product was used for the next reaction without further purification.

The aryl benzyl ether 63c (14.13 g, 59.3 mmol) was dissolved in anhydrous THF (150 mL) and cooled to −78° C. under nitrogen atmosphere. A solution of lithium bis(trimethylsilyl)amide (59.3 mL, 1.0 M) in THF was added slowly. The reaction mixture was stirred at −20° C. under nitrogen atmosphere for 2 h. The reaction mixture was then cooled to −78° C., and to it was added ethyl trifluoroacetate (10.58 mL, 89 mmol). The vigorously stirred solution was allowed to warm to ambient temperature overnight. The reaction mixture was poured into a mixture of 10% aq HCl and ice and extracted with chloroform three times. The chloroform extract was washed with water. The organic layer was separated and dried with anhydrous MgSO$_4$ and concentrated in vacuo to give crude product 63d (19.5 g, 98% yield). The product was used for the next reaction without purification.

2,4-dimethylbenzyl cyanoacetamide 61b (3.01 g, 14.88 mmol) and diketone 63d (5.0 g, 14.87 mmol) were suspended in 50 mL of benzene. To the above reaction mixture was added DBU (1.11 mL, 7.43 mmol). The mixture was heated to reflux under nitrogen atmosphere for overnight. The reaction mixture was concentrated in vacuo and the resulting residue was purified by column chromatography (20% ethyl acetate in hexane) to yield product 63e (3.90 g, 45% yield).

To a solution of 63e (3.71 g, 7.38 mmol) in anhydrous ethanol (74 mL) was added 2.85 g of 10% Pd/C and 1,4-cyclohexadiene (6.98 mL, 73.8 mmol). The mixture was stirred under nitrogen atmosphere for overnight. The solution was filtered through a pad of celite and the solvent was concentrated in vacuo to yield product 63f (2.96 g, 97%).

To a solution of 63f (103 mg, 0.25 mmol) in anhydrous methylene chloride (3 mL) was added Cu(OAc)$_2$ (91 mg, 0.5 mmol), 3-isopropylphenylboronic acid (82 mg, 0.5 mmol) and powdered 4 Å molecular sieves and triethylamine (174 μL, 1.25 mmol). The heterogeneous reaction mixture was stirred at ambient temperature for overnight. The resulting slurry was filtered through celite and the diaryl ether was isolated from the organic filtrate by column chromatography (20% ethyl acetate in hexane) to yield 63 (63 mg, 47% yield).). $^1$H-NMR (CDCl$_3$): δ7.27 (m, 1H), 7.03 (m, 1H), 6.98-6.85 (m, 5H), 6.74 (m, 2H), 6.64 (m, 1H). 6.46 (s, 1H), 5.15 (s, 2H), 2.90 (hep, J=7.0 Hz, 1H), 2.27 (s, 3H), 2.21 (s, 3H), 1.99 (s, 3H), 1.25 (d, J=7.0 Hz, 6H). MS (ES+): 531.3 (M+H).

Example 64

This example illustrates the preparation of compound 64.

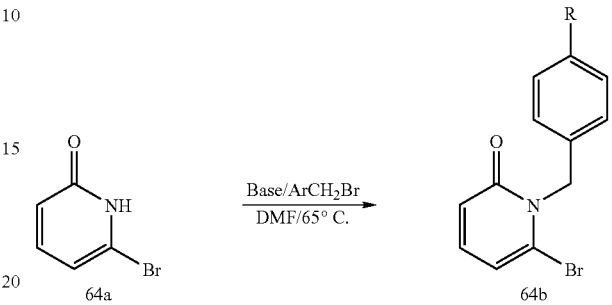

Method A (R=Me): To a solution of bromopyridone 64a (2.12 g, 12.2 mmols) in 60 mL of DMF at room temperature was added LiH (145.0 mg, 18.3 mmols). After stirring for 1 hour at 65° C., 4-methylbenzyl bromide (2.7 g, 14.6 mmols) was added and heating continued for 12 h. The solution was cooled to room temperature and concentrated under reduced pressure. Pyridone 64b (R═Me) was isolated from the residue by column chromatography on silica gel (0 to 20% EtOAC/hexanes) as a colorless oil (1.6 g, 47%). $^1$H NMR (CDCl$_3$) δ: 7.34 (t, J=7.8 Hz, 1H), 7.28 (d, J=8.0 Hz, 2H), 7.12 (d, J=8.0 Hz, 2H), 6.98 (d, J=7.6 Hz, 1H), 6.64 (d, J=8.0 Hz, 1H), 5.24 (s, 2H), 2.29 (s, 3H).

Method B (R═H): To a solution of bromopyridone (405.0 mg, 2.3 mmols) in 6.0 mL of DME:DMF (10:1, v/v) at 0° C. was added NaH (92.0 mg, 2.3 mmols, 60% dispersion in mineral oil). After 10 minutes LiBr (800.0 mg, 9.2 mmols) was added and the mixture warmed to room temperature over 15 minutes and then benzyl bromide (786.6 mg, 4.6 mmols) was added. The resulting solution was heated to 65° C. for 12 h, cooled to room temperature, diluted with saturated aqueous sodium chloride solution, and extracted with EtOAc. The combined organic layers were dried over MgSO$_4$ and concentrated under reduced pressure. Pyridone (R═H) was isolated from the residue by column chromatography on silica gel (0 to 20% EtOAC/hexanes) as a colorless oil (533 mg, 88%). $^1$H NMR (CDCl$_3$) δ: 7.40-4.24 (m, 6H), 7.00 (d, J=7.2 Hz, 1H), 6.66 (d, J=7.6 Hz, 1H), 5.28 (s, 2H).

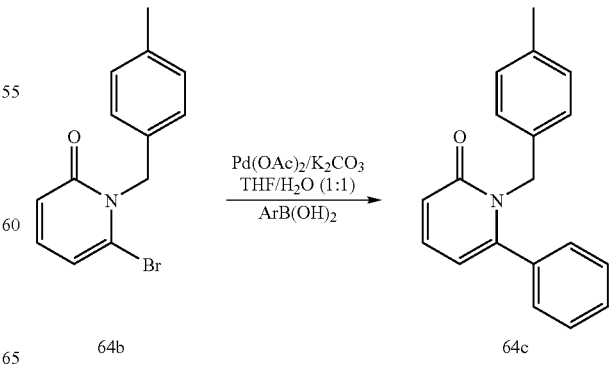

A degassed solution of bromopyridone 64b (100 mg, 0.4 mmol) and phenylboronic acid (44 mg, 0.4 mmol) in 0.9 mL THF was added Pd(OAc)$_2$ (4 mg, 0.02 mmol). A degassed solution of Na$_2$CO$_3$ (95 mg, 0.9 mmol) in 0.9 mL H$_2$O was added and the resulting mixture heated to reflux for 12 h. The mixture was cooled to room temperature, diluted with H$_2$O, and extracted with EtOAc. The combined organic layers were dried over NaSO$_4$ before being concentrated under reduced pressure. The product 64C (91 mg, 97%) was isolated as a colorless solid from the residual oil by column chromatography on silica (0 to 20% EtOAc/hexanes). $^1$H NMR (CDCl$_3$) δ: 7.52 (dd, J=8.6, 1.6 Hz, 1H), 7.39-7.26 (7H), 7.11 (d, J=8.0 Hz, 2H), 6.98 (d, J=7.2 Hz, 1H), 6.64 (d, J=8.1 Hz, 1H), 5.24 (s, 2H), 2.29 (s, 3H).

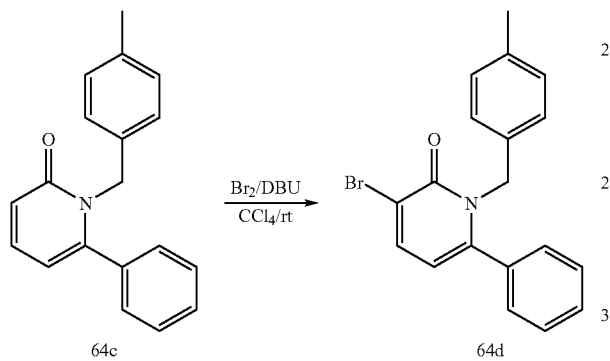

To a solution of pyridone 64c (70 mg, 0.3 mmol) in 0.54 mL CCl$_4$ at 0° C. in the dark (foil wrapped flask) was added Br$_2$ (62 mg, 0.4 mmol) and DBU (61 mg, 0.4 mmol). The resulting solution was allowed to warm to slowly room temperature and stir for 12 h. The solution was diluted with CH$_2$Cl$_2$ (25 mL) and washed with 1N aqueous HCl, saturated aqueous NaHCO$_3$, and dried over Na$_2$SO$_4$ before being concentrated under reduced pressure. The product 64d (71 mg, 75%) was isolated from the residual oil as a colorless solid by column chromatography on silica (0 to 5% EtOAc/hexanes). $^1$H NMR (CDCl$_3$) δ: 7.92 (m, 2H), 7.78 (d, J=8.0 Hz, 1H), 7.37 (m, 5H), 7.17 (d, J=8.0 Hz, 1H), 7.12 (d, J 8.0 Hz, 2H), 5.48 (s, 2H), 2.28 (s, 3H).

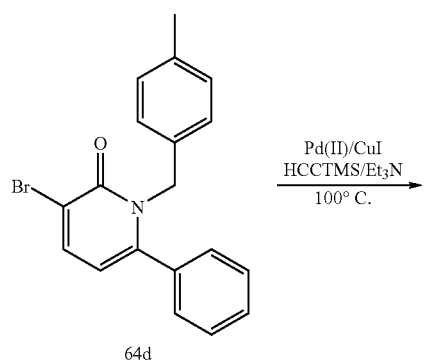

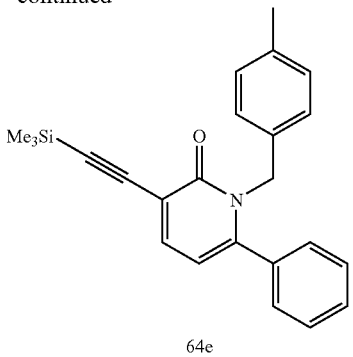

To a solution of bromide 64d (12 mg, 0.03 mmol) in 0.3 mL Et$_3$N was added CuI (2 mg, 0.01 mmol), dichloro(bis-triphenylphosphine)palladium (II) (4 mg, 0.005 mmol), and 1,3-(bis-diphenylphosphino)propane (2 mg, 0.005). The system was purged with N$_2$, trimethylsilylacetylene (59 mg, 0.6 mmol) added and the resulting mixture heated to 100° C. for 17 h. Upon cooling to room temperature the mixture was concentrated under reduced pressure and product 64e (8 mg, 73%) was isolated from the residual oil as a yellow oil by column chromatography on silica (0 to 5% EtOAc/hexanes). $^1$H NMR (CDCl$_3$) δ: 8.09 (d, J=7.2 Hz, 1H), 7.82 (d, J=7.6 Hz, 1H), 7.70-7.37 (m, 5H), 7.39 (d, J=7.6 Hz, 2H), 7.34 (d, J=8.0 Hz, 2H), 5.62 (s, 2H), 2.42 (s, 3H), 0.34 (s, 9H).

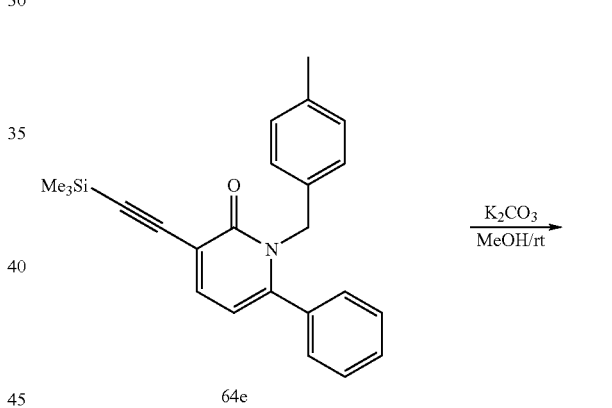

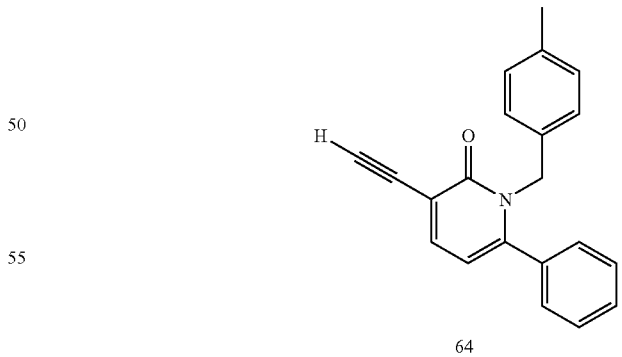

Alkyne 64e (2 mg, 0.005 mmol) was combined with K$_2$CO$_3$ (3 mg, 0.025 mmol) in 0.1 mL of MeOH and stirred overnight at room temperature. The mixture was concentrated under reduced pressure and product 64f (1 mg) was isolated from the residual oil as a yellow oil by column chromatography on silica (0 to 5% EtOAc/hexanes). $^1$H NMR (CDCl$_3$) δ: 7.95 (d, J=8.4 Hz, 1H), 7.72 (d, J=8.0 Hz, 1H), 7.39 (m, 5H), 7.26 (d, J=8.0 Hz, 2H), 7.10 (d, J=8.0 Hz, 2H), 5.51 (s, 2H), 3.30 (s, 1H), 2.28 (s, 3H).

Example 65

This example illustrates the preparation of compound 65.

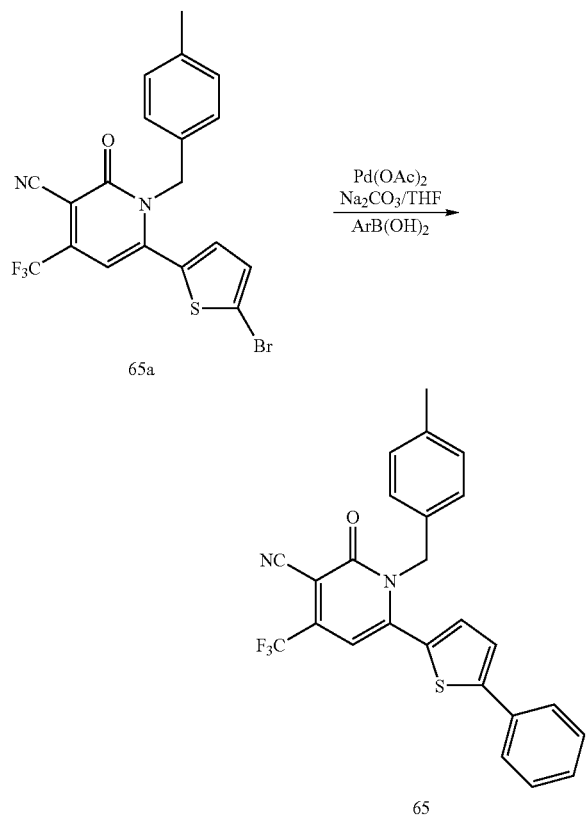

To a degassed solution of thienylbromide 65a (50 mg, 0.11 mmol) and phenylboronic acid (13 mg, 0.11 mmol) in 0.6 mL THF was added Pd(OAc)₂ (1 mg, 0.006 mmol). A degassed solution of Na₂CO₃ (30 mg, 0.3 mmol) in 0.6 mL H₂O was added and the resulting mixture heated to reflux for 12 h. The mixture was cooled to room temperature, diluted with H₂O and extracted with EtOAc. The combined organic layers were dried over NaSO₄ before being concentrated under reduced pressure. The product 65 (28 mg, 55%) was isolated as a colorless solid from the residual oil by column chromatography on silica (10 to 20% EtOAc/hexanes). $^1$H NMR (CDCl₃) δ: 7.51 (d, J=8.0 Hz, 2H), 7.35 (m, 5H), 7.35 (d, J=7.3 Hz, 1H), 7.01 (d, J=3.8 Hz, 1H), 6.88 (d, J=8.1 Hz, 2H), 6.56 (s, 1H), 5.38 (s, 2H), 2.25 (s, 3H).

Example 66

This example illustrates the preparation of compound 66.

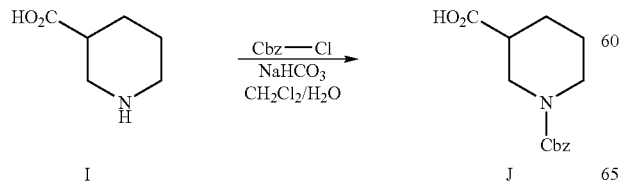

To a solution of acid I (2.0 g, 15.5 mmols) in 8.0 mL of dioxane was added benzyl chloroformate (3.1 g, 18.6 mmols) at room temperature followed by the addition of 8 mL of saturated aqueous NaHCO₃. The resulting mixture was vigorously stirred for 4 hours, the dioxane removed under reduced pressure, and the resulting solution diluted with H₂O. Extraction with CH₂Cl₂ was followed by drying the combined fractions over Na₂SO₄ and concentration under reduced pressure. The product J (3.3 g, 81%) was isolated as a colorless oil from the residual oil by column chromatography on silica (5-10% MeOH/CH₂Cl₂). $^1$H NMR (CDCl₃) δ: 7.36 (m, 5H), 5.13 (m, 2H), 4.19 (bm, 1H), 3.97 (m, 1H), 3.13 (bm, 1H), 2.94 (ddd, J=3.0, 10.6, 13.6 Hz, 1H), 2.53 (bm, 1H), 2.09 (m, 1H), 1.72 (m, 2H), 1.51 (bm, 1H).

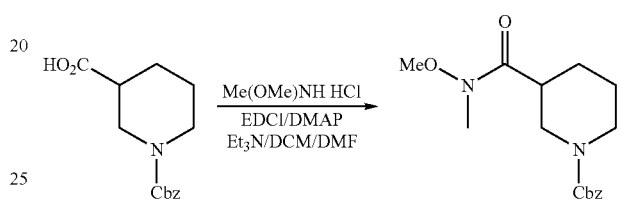

To a solution of acid J (3.3 g, 12.6 mmols) in 120 mL CH₂Cl₂:DMF (4:1, v/v) was added 1-(3-dimethylaminopropyl)-3-ethylcarbodiimide hydrochloride (EDCl) (4.8 g, 25.2 mmols) and 4-N,N-dimethylaminopyridine (77 mg, 0.6 mmol). After stirring for 30 minutes N,O-dimethylhydroxylamine hydrochloride (1.2 g, 12.6 mmols) followed by triethylamine (1.3 g, 12.6 mmols). After stirring for 12 hours the solution was concentrated under reduced pressure and the residue dissolved in CH₂Cl₂ (200 mL). The solution was then washed with H₂O and 1N aqueous HCl before being dried over Na₂SO₄ and concentrated under reduced pressure. The product K (3.2 g, 81%) was isolated as a pale yellow oil from the residual oil by column chromatography on silica (5-10% MeOH/CH₂Cl₂). $^1$H NMR (CDCl₃) δ: 7.35 (m, 5H), 5.13 (M, 2H), 4.20 (bm, 1H), 4.11 (m, 1H), 3.72 (s, 3H), 3.59, (s, 3H), 2.92 (m, 1H), 2.81 (m, 1H), 2.19 (m, 1H), 1.94 (m, 1H), 1.70 (m, 2H), 1.51 (m, 1H).

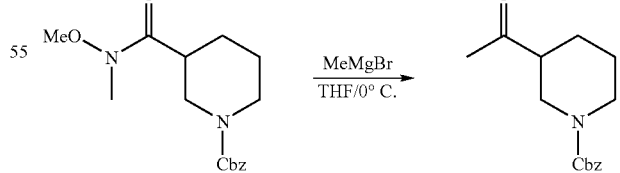

To a solution of amide K (600 mg, 2.0 mmols) in THF (20 mL) at 0° C. was added MeMgBr (1.2 mL, 2.2 mmols, 1.4 M in THF). After stirring for 1 hour, the reaction was quenched at 0° C. by the addition of 1N HCl in EtOH. The solution was diluted with CH₂Cl₂:Et₂O (100 ml, v/v) and washed with saturated aqueous NaCl before being dried (Na₂SO₄) and concentrated under reduced pressure. The product L (257 mg, 50%) was isolated as a colorless oil from the residual oil by column chromatography on silica (10-50% EtOAc/hexanes). ¹H NMR (CDCl₃) δ: 7.37 (m, 5H), 5.15 (m, 2H), 4.22 (bm, 1H), 4.04 (bm, 1H), 3.02 (m, 1H), 2.88 (bm, 1H), 2.54 (bm, 1H), 2.19 (s, 3H), 2.04 (bm, 1H), 1.76 (m, 1H), 1.55 (m, 2H).

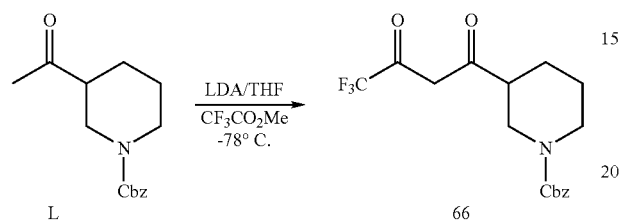

To a solution of ketone L (237 mg, 0.9 mmol) in 3.0 mL THF at −78° C. was added a solution of lithium diisopropylamide (0.45 mL, 0.9 mmol, 2.0M in THF). After stirring for 5 minutes ethyl trifluoromethylacetate (155 mg, 1.1 mmols) was added. Stirring for 2 hours at −78° C. was followed by warming to room temperature and the addition of EtOAc (50 mL). The resulting solution was washed with 10% aqueous H₂SO₄ and H₂O before being dried with Na₂SO₄ and concentrated under reduced pressure. The product 66 (50 mg, 16%) was isolated from the residual oil by column chromatography on silica (10-50% EtOAc/hexanes). ¹H NMR (CDCl₃) δ: 7.34 (m, 5H), 5.96 (s, 1H), 5.14 (m, 2H), 4.18 (bm, 1H), 4.07 (m, 1H), 3.01 (m, 1H), 2.89 (m, 1H), 2.68 (m, 1H), 2.52 (bm, 1H), 2.28 (m, 1H), 1.73 (m, 2H).

Example 67

This example illustrates the preparation of compound 67.

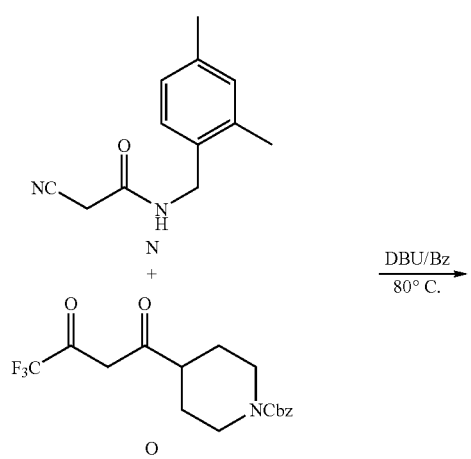

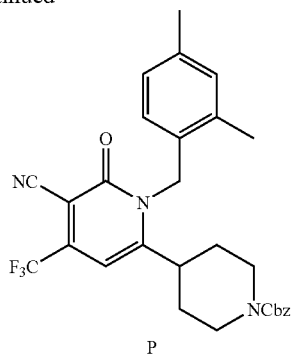

A solution of amide N (81 mg, 0.4 mmol), diketone O (150 mg, 0.4 mmol), and DBU (30.4 mg, 0.2 mmol) in 2.0 mL benzene was heated to reflux for 12 hours. The solution was cooled to room temperature and concentrated under reduced pressure. The product P (118 mg, 58%) was isolated as a pale yellow solid from the residue by column chromatography on silica (10-50% EtOAc/hexanes). ¹H NMR (CDCl₃) δ: 7.34 (m, 5H), 7.10 (d, J=8.1 Hz, 1H), 7.01 (t, J=13.4 Hz), 6.93 (d, J=8.0 Hz), 6.35 (s, 1H), 5.35 (s, 2H), 5.10 (s, 2H), 4.27 (bm, 2H), 2.68 (m, 1H), 2.60 (bm, 2H), 2.30 (s, 3H), 2.28 (s, 3H), 1.63 (m, 2H), 1.57 (m, 2H).

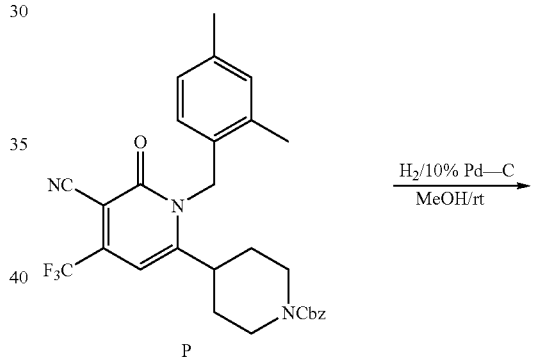

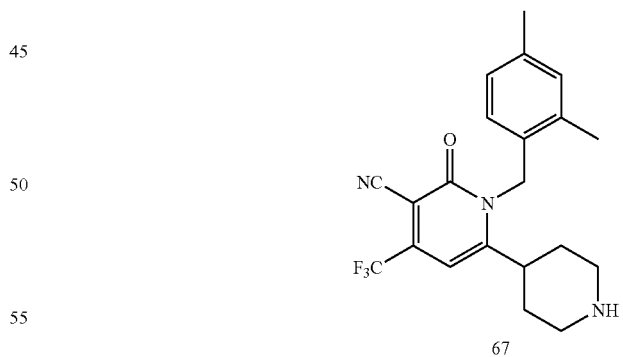

To a solution of pyridone P (50 mg, 0.1 mmol) in 0.5 mL MeOH was added 10% Pd-C (5 mg, 10 wt %). The mixture was then stirred under H₂ (1 atm) at room temperature for 30 minutes. The flask was purged with N₂ and the mixture filtered through a pad of Celite using an EtOAc wash. The filtrate was concentrated under reduced pressure and the product 67 (20 mg, 51%) was isolated from the residual oil by column chromatography on silica (5-20% MeOH/CH₂Cl₂). ¹H NMR (CDCl₃) δ: 7.10 (d, J=7.6 Hz, 1H), 7.01 (t, J=14.6

Hz, 1H), 6.93 (d, J=7.3 Hz, 1H), 6.35 (s, 1H), 5.34 (m, 2H), 4.26 (bm, 2H), 2.65 (m, 1H), 2.51 (m, 2H), 2.30 (s, 3H), 2.28 (s, 3H), 1.66 (m, 2H).

Example 68

This example illustrates the preparation of compound 68.

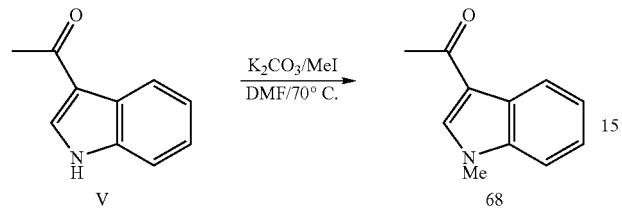

To a solution of indole V (0.5 g, 3.1 mmols) in 10 mL DMF was added MeI (483 mg, 3.4 mmols) and $K_2CO_3$ (1.3 g, 9.3 mmols). The resulting mixture was heated to 70° C. for 15 hours, cooled to room temperature, and concentrated under reduced pressure. The product 68 (569 mg, 99%) was isolated as an off-white solid from the residual oil by column chromatography on silica (5-10% $MeOH/CH_2Cl_2$). $^1H$ NMR $(CDCl_3)$ δ: 8.12 (m, 1H), 7.27 (s, 1H), 7.05-6.92 (m, 3H), 3.38 (s, 3H), 2.16 (s, 3H).

Example 69

This example illustrates the preparation of compound 69.

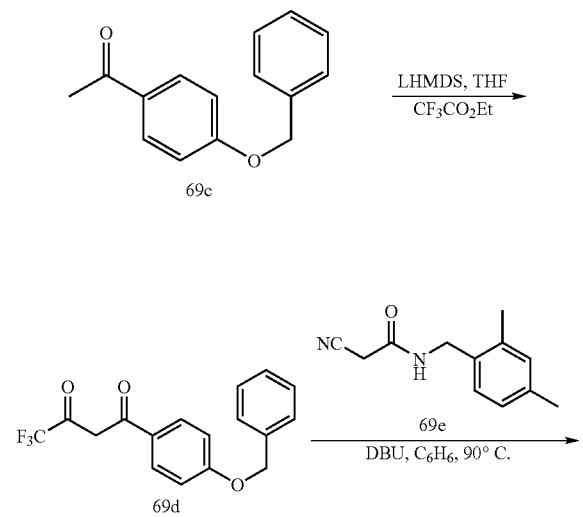

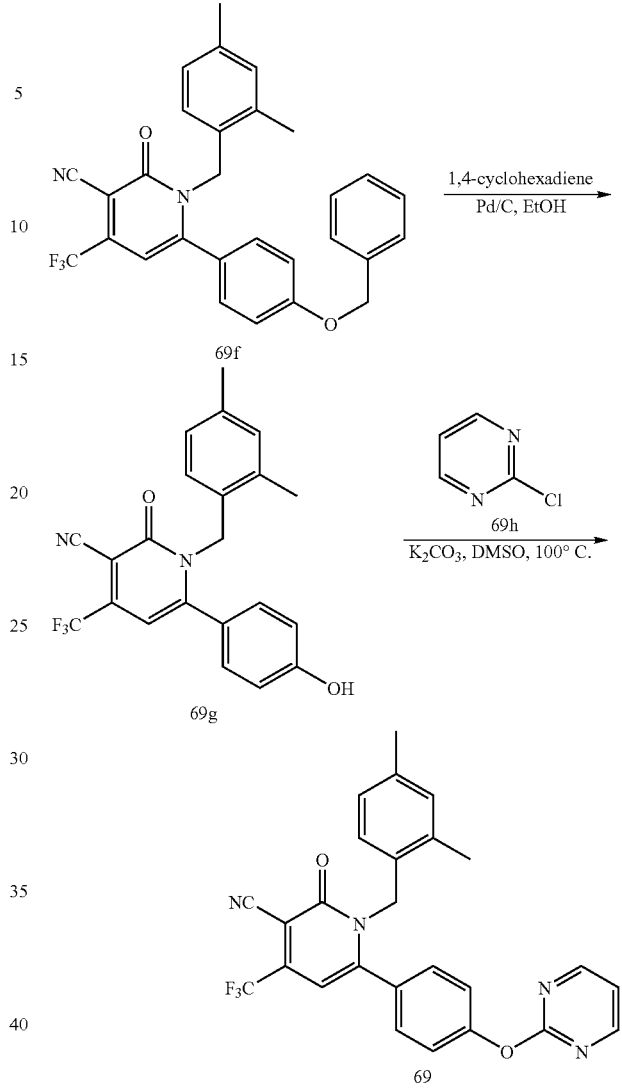

To a solution of 4-hydroxyacetophenone 30 (6.81 g, 50 mmol) and benzyl bromide 23 (5.95 mL, 50 mmol) in acetone (100 mL) was added potassium carbonate (7.6 g, 55 mmol). The reaction mixture was stirred at ambient temperature under nitrogen atmosphere for overnight. The white solid was filtered off and the solvent was concentrated in vacuo to yield product 31 (11.8 g, 98% yield). The product was used for the next reaction without further purification.

The aryl benzyl ether 31 (11.14 g, 49.2 mmol) was dissolved in anhydrous THF (70 mL) and cooled to −78° C. under nitrogen atmosphere. A solution of lithium bis(trimethylsilyl)amide (49.2 mL, 1.0 M) in THF was added slowly. The reaction mixture was stirred at −20° C. under nitrogen atmosphere for 2 h. The reaction mixture was then cooled to −78° C., and to it was added ethyl trifluoroacetate (8.78 mL, 73.8 mmol). The vigorously stirred solution was allowed to warm to ambient temperature overnight. The reaction mixture was poured into a mixture of 10% aq HCl and ice and extracted with chloroform three times. The chloroform extract was washed with water. The organic layer was separated and dried with anhydrous $MgSO_4$ and concentrated in vacuo to give crude product 32 (15.5 g, 98% yield). The product was used for the next reaction without purification.

2,4-dimethylbenzyl cyanoacetamide 13 (2.02 g, 10 mmol) and diketone 32 (3.22 g, 10 mmol) were suspended in 25 mL of benzene. To the above reaction mixture was added DBU (0.75 mL, 5.0 mmol). The mixture was heated to reflux under nitrogen atmosphere for overnight. The reaction mixture was concentrated in vacuo and the resulting residue was purified by column chromatography (20% ethyl acetate in hexane) to yield product 33 (3.2 g, 66% yield).

To a solution of 33 (2.84 g, 5.81 mmol) in anhydrous ethanol (90 mL) was added 2.85 g of 10% Pd/C and 1,4-cyclohexadiene (5.5 mL, 58.1 mmol). The mixture was stirred under nitrogen atmosphere for overnight. The solution was filtered through a pad of celite and the solvent was concentrated in vacuo to yield product 34 (2.20 g, 95%).

To a solution of 34 (100 mg, 0.25 mmol) and 2-chloropyrimidine 35 (29 mg, 0.25 mmol) in DMSO (2 mL) was added potassium carbonate (52 mg, 0.38 mmol). The reaction mixture in a sealed vial was stirred and heated to 100° C. overnight. After cooling off, the mixture was poured into water and extracted with chloroform. The chloroform extract was dried with anhydrous MgSO$_4$ and concentrated in vacuo. The crude product was purified by column chromatography (30-60% EtOAc in hexane) to yield the product 36 (65 mg, 55% yield). $^1$H-NMR (CDCl$_3$): δ 8.58 (d, J=4.8 Hz, 2H), 7.21 (m, 3H), 7.12 (m, 1H), 6.95 (m, 1H), 6.91 (m, 1H), 6.63 (m, 1H), 6.50 (s, 1H), 5.15 (s, 2 H), 2.27 (s, 3H), 1.97 (s, 3H). MS (ES+): 477.1 (M+H).

Example 70

This example illustrates the preparation of compound 70.

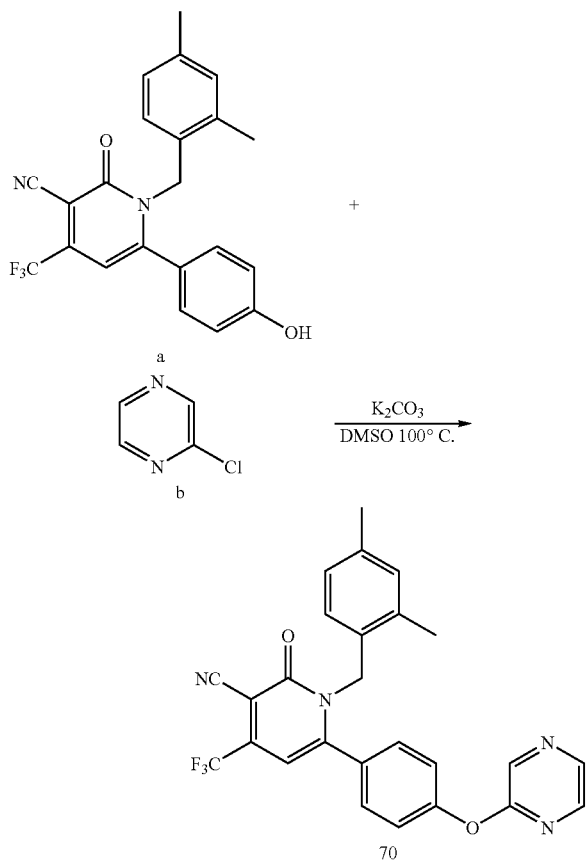

To a solution of a (71 mg, 0.18 mmol) and 2-chloropyrazine b (20 mg, 0.18 mmol) in DMSO (2 mL) was added potassium carbonate (37 mg, 0.27 mmol). The reaction mixture in a sealed vial was stirred and heated to 100° C. overnight. After cooling off, the mixture was poured into water and extracted with chloroform. The chloroform extract was dried with anhydrous MgSO$_4$ and concentrated in vacuo. The crude product was purified by column chromatography (25-50% EtOAc in hexane) to yield the product 70 (48 mg, 57% yield). $^1$H-NMR (CDCl$_3$): δ8.49 (m, 1H), 8.34 (m, 1H), 8.11 (m, 1H), 7.19 (m, 4H), 6.95 (m, 1H), 6.92 (m, 1H), 6.63 (m, 1H), 6.49 (s, 1H), 5.15 (s, 2H), 2.28 (s, 3H), 1.98 (s, 3H). MS (ES+): 477.2 (M+H).

Example 71

FRET Coactivator Assay

The FRET coactivator assay measures the ability of LXR ligands to promote protein-protein interactions between the ligand binding domain (LBD) of LXR and transcriptional coactivator proteins. The assay involves the use a recombinant Glutathione-S-transferase (GST)-nuclear receptor ligand binding domain (LBD) fusion protein and a synthetic biotinylated peptide sequence derived from the receptor interacting domain of a co-activator peptide such as the steroid receptor coactivator 1 (SRC-1). Typically GST-LBD is labeled with a europium chelate (donor) via a europium-tagged anti-GST antibody, and the coactivator peptide is labeled with allophycocyanin via a streptavidin-biotin linkage.

In the presence of an agonist for the nuclear receptor, the peptide is recruited to the GST-LBD bringing europium and allophycocyanin into close proximity to enable energy transfer from the europium chelate to the allophycocyanin. Upon excitation of the complex with light at 340 nm excitation energy absorbed by the europium chelate is transmitted to the allophycocyanin moiety resulting in emission at 665 nm. If the europium chelate is not brought in to close proximity to the allophycocyanin moiety there is little or no energy transfer and excitation of the europium chelate results in emission at 615 nm. Thus the intensity of light emitted at 665 nm gives an indication of the strength of the protein-protein interaction.

A. Required Materials
1. Partially purified recombinant protein comprising glutathione-S-transferase fused in frame to the LXR-ligand binding domain (comprising amino acids 188-447 of human LXR α, or amino acids 198-461 of human LXR β).
2. Biotinylated peptide containing a SRC-1 LXXLL receptor interaction motif (B-SRC-1)
3. Anti-GST antibody conjugated to an Europium chelate (αGST-K) (From Wallac/PE Life Sciences Cat# AD0064)
4. Streptavidin linked allophycocyanin (SA-APC) (From Wallac/PE Life Sciences CAT# AD0059A)
5. 1×FRET Buffer: (20 mM KH$_2$PO$_4$/K$_2$HPO$_4$ pH 7.3, 150 mM NaCl, 2.5 mM CHAPS, 2 mM EDTA, 1 mM DTT (add fresh))
6. 96 well or 384 well black multiwell plates (from LJL)

Stock Solutions
0.5M KH$_2$PO$_4$/K$_2$HPO$_4$: pH 7.3
5M NaCl
80 mM (5%) CHAPS
0.5M EDTA pH 8.0
1M DTT (keep at −20° C.)

B. Preparation of Screening Reagents
Prepare reaction mixture for the appropriate number of wells by combining the following reagents 5 nM/well GSThLXRαLBD, 5 nM/well GST-hLXR βLBD, 5 nM/well Anti-GST antibody (Eu), 12 nM/well biotin-SRC-1 peptide, 12 nM/well APC-SA adjust the volume to 10 uL/well with 1x-FRET buffer.

C. Procedure

Add 0.5 ul of a 1 mM stock compound (for approx. 10 uM final concentration) or solvent to each well in a 96 well or 384 well black plate (LJL).

1. Add 10 ul reaction mixture (prepared above) to each well of the multiwell plate.
2. Incubate covered or in the dark (the APC is light sensitive) at room temperature for 1-4 hr. After this time if reactions are not read they can be stored at 4 degrees for several more hours without too much loss of signal.
3. Read the plate using an LJL Analyst, or similar instrument, using the following conditions:

Channel 1: Excitation is 330 nm and emission is 615. This is for Eu chelate

Channel 2: Excitation is 330 nm and emission is 665. This is for APC

For channel 1: Flashes per well=100; Integration time=1000 μs; interval between flashes=1×10 ms; Delay after flash=200 μs For channel 2: Flashes per well=100; Integration time=100 μs; interval between flashes=1×10 ms; Delay after flashes=65 μs Example 72

Scintillation Proximity Assay (SPA)

The SPA assay measures the radioactive signal generated by the binding of $^3$H-24, 25-epoxycholesterol to LXRα or LXRβ. The basis of the assay is the use of SPA beads containing a scintillant, such that when binding to the receptor brings the labeled ligand into proximity with the bead, the energy from the label stimulates the scintillant to emit light. The light is measured using a standard microplate scintillation reader. The ability of a ligand to bind to a receptor can be measured by assessing the degree to which the compound can compete off a radiolabelled ligand with known affinity for the receptor.

A. Required Materials
1. Label: $^3$H-24, 25-epoxy-cholesterol (Amersham)
2. LXRα lysate: Baculovirus expressed LXRα/RXR heterodimer with RXR having a 6-HIS tag produced as a crude lysate
3. LXRβ lysate: Baculovirus expressed LXRβ/RXR heterodimer with RXR having a 6-HIS tag produced as a crude lysate
4. SPA beads: Ysi copper His-tag SPA beads (Amersham)
5. Plates: Non-binding surface 96-well plate (Corning)
6. Protein lysate dilution buffer: (20 mM Tris-HCl pH 7.9, 500 mM NaCl, 5 mM Imidazole).
7. 2×SPA Buffer: (40 mM $K_2HPO_4/KH_2PO_4$ pH7.3, 100 mM NaCl, 0.05% Tween 20, 20% Glycerol, 4mM EDTA)
8. 2×SPA Buffer w/o EDTA: (40 mM $K_2HPO_4/KH_2PO_4$ pH7.3, 100 mM NaCl, 0.05% Tween 20, 20% Glycerol)

A. Stock Solutions
0.5M $K_2HPO_4/KH_2PO_4$ pH 7.3
0.5M EDTA pH 8.0
5M NaCl
10% Tween-20
Glycerol B. Preparation of Screening Reagents
1. [$^3$H]24,25 Epoxycholesterol (EC) solution. For a single 384-well plate (or 400 wells), add 21 μl [$^3$H] EC (specific activity 76.5Ci/mmol, concentration 3.2mCi/ml) in 4.4 ml of 2×SPA buffer to a final concentration of 200nM. For each additional 384-well plate, add 19.1 μl additional [$^3$H] EC and 4.0 ml additional 2×SPA buffer. The final concentration of [$^3$H] EC in the well will be 50 nM.
2. Dilute LXRα lysate with protein lysate dilution buffer. Make 1400 μl of diluted LXRα lysate for a 384-well plate, (or 200 wells) and 1120 μl of diluted LXRα lysate for each additional 384-well plate.
3. Diluted LXRβ lysate with protein lysate dilution buffer. Make 1400 μl of diluted LXRβ lysate for 1 a 384-well plate, (or 200 wells) and 1120 μl of diluted LXRβ lysate for each additional 384-well plate.
4. SPA bead solution. For 1 a 384-well plate (or 400 wells), mix 3.75 ml of 2× SPA buffer w/o EDTA, 2.25 ml of $H_2O$, and 1.5 ml of Ysi His-tag SPA beads (Vortex well before taking). For each addition 384-well plate, mix additional 3.5 ml of 2×SPA buffer w/o EDTA, 2.1 ml of $H_2O$, and 1.4 ml of Ysi His-tag SPA beads to the SPA bead solution.

C. Procedure:
1. Prepare appropriate dilutions of each compound and pipette into the appropriate wells of a multiwell plate.
2. Add 9.1 μl of [$^3$H] EC to each well of column 2-23 of the multiwell plate.
3. Add 5 μl of diluted LXRα lysate to each well of column 2-23 on odd rows of the multiwell plate.
Add 5 μl of diluted LXRβ lysate to each well of column 2-23 on even rows of the multiwell plate.
4. Add 17.5 μl of SPA bead solution to each well of column 2-23 of the multiwell plate.
5. Cover the plates with clear sealer. Place the plates in the MicroBeta. Incubate at room temperature for 1 hr.
6. Count using program n ABASE 3H__384DPM. The setting for n ABASE 3H__384DPM is:

Counting Mode: DPM
Sample Type: SPA
ParaLux Mode: low background
Count time: 30 sec.

Assays for LXRα and LXRβ were performed in the identical manner. The determined Ki represents the average of at least two independent dose response experiments. The binding affinity for each compound may be determined by non-linear regression analysis using the one site competition formula to determine the IC50 where:

$$Y = \text{Bottom} + \frac{(\text{Top} - \text{Bottom})}{1 + 10^{X - \text{Log} IC50}}$$

The Ki is than calculated using the Cheng and Prusoff equation where:

$$Ki = \frac{IC50}{1 + [\text{Ligand}]/Kd}$$

Ligand=50 nM EC and Kd=200 nM as determined by saturation binding

Example 73

Co-Transfection Assay

To measure the ability of compounds to activate or inhibit the transcriptional activity of LXR, in a cell based assay, the cotransfection assay may be used. It has been shown that LXR functions as a heterodimer with RXR. For the co-transfection assay, expression plasmids for LXR and RXR are introduced via transient transfection into mammalian cells along with a luciferase reporter plasmid that contains one copy of a DNA sequence that is bound by LXR-RXR heterodimers (LXRE; Willy, P. et al. 1995). Treatment of transfected cells with an LXR agonist increases the transcriptional activity of LXR, which is measured by an increase in luciferase activity. Similarly, LXR antagonist activity can be measured by determining the ability of a compound to competitively inhibit the activity of a LXR agonist.

A. Required Materials
1. CV-1 African Green Monkey Kidney Cells
2. Co-transfection Expression plasmids, CMX-hLXR, or CMX-hLXR, CMX-RXR, reporter (LXREx1-Tk-Luciferase), and control (CMX-Galactosidase expression vector).
3. Transfection reagent such as FuGENE6 (Roche).
4. 1× Cell lysis buffer (1% Triton X 100 (JT Baker X200-07), 10% Glycerol (JT Baker M778-07), 5 mM Ditriotreitol (Quantum Bioprobe DTT03; add fresh before lysing), 1 mM EGTA (Ethylene Glycol-bis (B-Amino ethyl ether)-N,N,N',N'-Tetracetic Acid) (Sigma E-4378), 25 mM Tricine (ICN 807420) pH 7.8
5. 1× Luciferase assay buffer (pH at 7.8) (0.73 mM ATP, 22.3 mM Tricine, 0.11 mM EDTA 33.3 mM DTT)
6. 1× Luciferrin/CoA (11 mM Luciferin, 3.05 mM Coenzyme A, 10 mM HEPES B. Preparation of Screening Reagents
1. CV-1 cells are prepared 24 hours prior to the experiment by plating them into T-175 flasks or 500 cm² dishes in order to achieve 70-80% confluency on the day of the transfection. The number of cells to be transfected is determined by the number of plates to be screened. Each 384 well plate requires $1.92 \times 10^6$ cells or 5000 cells per well.
2. DNA Transfection Reagent is prepared by mixing the required plasmid DNAs with a cationic lipid transfection reagent such as DOTAP or FuGENE6 by following the instructions provided with the reagents. Optimal DNA amounts need to be determined empirically per cell line and size of vessel to be transfected.
3. Add 10-12 mls media to the DNA Transfection Reagent and add this mixture to the cells after aspirating media from a T175 cm² flask.
4. Incubate at least 5 hours at 37 degrees to prepare screening cells.
5. Luciferase assay reagent is prepared by combining before use (per 10 ml):
10 ml 1× Luciferase assay buffer
0.54 mls of 1× Luciferrin/CoA
0.54 mls of 0.2 M Magnesium sulfate
1. C. Procedure
1. Prepare assay plates by dispensing 0.5 ul of 1 mM compound per well of a 384 well plate to achieve final compound concentration of 10 uM and 1% DMSO.
2. Remove media from the screening cells, trypsinize, harvest cells by centrifugation, count the cells, and plate at 5000 cells per well in the 384 well assay plate prepared above in a volume of about 45 ul.
3. Incubate assay plates containing both compounds and screening cells for 20 hours at 37 C. degrees.
4. Carefully aspirate media from cells and ensure that cells are not lifted off.
5. Add lysis buffer (30 ul/well) and incubate at least 30 minutes room temp.
6. Add luciferase assay buffer (30 ul/well) and read assay plates on luminometer (PE Biosystems Northstar reader with on-board injectors, or equivalent).
7. Read plates immediately after addition of luciferase assay reagent.

The LXR/LXRE co-transfection assay can be used to establish the $EC_{50}/IC_{50}$ values for potency and percent activity or inhibition for efficacy. Efficacy defines the activity of a compound relative to a high control ((N-(3-((4-fluorophenyl)-(naphthalene-2-sulfonyl)-amino)propyl)-2,2-dimethyl-propionamide)) or a low control (DMSO/vehicle). The dose response curves are generated from an 8 point curve with concentrations differing by ½ LOG units. Each point represents the average of 4 wells of data from a 384 well plate. The curve for the data is generated by using the equation:

$$Y=\text{Bottom}+(\text{Top-Bottom})/(1+10\hat{}((\text{LogEC50-X})*\text{HillSlope}))$$

The $EC_{50}/IC_{50}$ is therefore defined as the concentration at which an agonist or antagonist elicits a response that is half way between the Top (maximum) and Bottom (baseline) values. The $EC_{50}/IC_{50}$ values represented are the averages of at least 3 independent experiments. The determination of the relative efficacy or % control for an agonist is by comparison to the maximum response achieved by ((N-(3-((4-fluorophen-yl)-(naphthalene-2-sulfonyl)-amino)propyl)-2,2-dimethylpropionamide) that is measured individually in each dose response experiment.

For the antagonist assay, a LXR agonist can be added to each well of a 384 well plate to elicit a response. The % inhibition for each antagonist is therefore a measurement of the inhibition of the activity of the agonist. In this example 100% inhibition would indicate that the activity of a specific concentration of LXR agonist has been reduced to baseline levels, defined as the activity of the assay in the presence of DMSO only.

Example 74

In Vivo Studies

In order to evaluate direct regulation of key target genes by the compounds of the invention, animals are administered a single oral dose of the test compound and tissues collected at six or fifteen hours after dose. Male C57BL/6 mice (n=8) are dosed by oral gavage with vehicle or compound. At six and fifteen hours after the dose, animals are bled via the retro orbital sinus for plasma collection. Animals are then euthanized and tissues, such as liver and intestinal mucosa are collected and snap frozen for further analysis. Plasma is analyzed for lipid parameters, such as total cholesterol, HDL cholesterol and triglyceride levels. RNA is extracted for frozen tissues and can be analyzed by quantitative real time PCR for regulation of key target genes. To identify specificity of target gene regulation by LXR subtypes, LXR deficient mice ($LXR\alpha^{-/-}$ or $LXR\beta^{-/-}$) and C57BL/6 wild-type controls are used in this same protocol.

Plasma Lipid Evaluation

To compare the effects of compounds on plasma cholesterol and triglycerides, animals are dosed with compound for one week and plasma lipid levels are monitored throughout the study. Male C57BL/6 mice (n=8) are dosed daily by oral gavage with vehicle or compound. Plasma samples are taken on day-1 (in order to group animals), day 1, 3, and 7. Samples are collected three hours after the daily dose. On day 7 of the study, following plasma collection, animals are euthanized and tissues, such as liver and intestinal mucosa are collected and snap frozen for further analysis. Plasma is analyzed for lipid parameters, such as total cholesterol, HDL cholesterol and triglyceride levels. RNA is extracted for frozen tissues and can be analyzed by quantitative real time PCR for regulation of key target genes. To identify specificity of target gene regulation by LXR subtypes, LXR deficient mice (LXRα$^{-/-}$ or LXRβ$^{-/-}$) and C57BL/6 wild-type controls are used in this same protocol.

Cholesterol Absorption

Evaluation of compounds to inhibit cholesterol absorption is done via measurement of labeled cholesterol in feces. Male A129 mice (n=7) are dosed daily by oral gavage with vehicle or compound for 7 days. On day 7 of the study, animals are administered [$^{14}$C]-cholesterol and [$^3$H]-sitostanol by oral gavage. Animals are individually housed on wire racks for the next 24 hours in order to collect feces. Feces are then dried and ground to a fine powder. Labeled cholesterol and sitostanol are extracted from the feces and ratios of the two are counted on a liquid scintillation counter in order to evaluate the amount of cholesterol absorbed by the individual animal.

Results of Examples 71, 72 and 73

Most of the compounds disclosed herein and tested exhibited activity in at least one of the above assays (EC$_{50}$ or IC$_{50}$ less than 10 μM). Most showed activity at below 1 μM. Some showed activity below 100 nM. Representative data is shown in the Tables below. Ki's are determined in a scintillation proximity binding assay (Example 70). EC$_{50}$ and % efficacy are determined in a co-transfection assay (Example 71).

| Compound | Ki(α) μM | Ki(β) μM | LXRα/LXRE EC$_{50}$ (μM) |
|---|---|---|---|
| 1-Cyclohexylideneamino-2-oxo-6-phenyl-4-trifluoromethyl-1,2-dihydropyridine-3-carbonitrile | 0.69 | 0.45 | 3.4 |
| 1-benzyl-3-cyano-6-(3-methoxyphenyl)-4-trifluoromethyl-1H-pyridin-2-one | 0.51 | 0.12 | 1.2 |
| 1-Benzyl-2-oxo-6-thiophen-2-yl-4-trifluoromethyl-1,2-dihydro-pyridine-3-carbonitrile | 1.4 | 0.58 | 1.6 |
| 1-(5-Methyl-furan-2-ylmethyl)-2-oxo-6-phenyl-4-trifluoromethyl-1,2-dihydro-pyridine-3-carbonitrile | 0.36 | 0.23 | 0.58 |

| Compound | LXRα/LXRE Eff (%) | LXRβ/LXRE EC$_{50}$ (μM) | LXRβ/LXRE Eff (%) |
|---|---|---|---|
| 1-Cyclohexylidene-amino-2-oxo-6-phenyl-4-trifluoromethyl-1,2-dihydropyridine-3-carbonitrile | 90 | 4.3 | 72 |
| 1-benzyl-3-cyano-6-(3-methoxyphenyl)-4-trifluoromethyl-1H-pyridin-2-one | 78 | 0.84 | 79 |

| Compound | LXRα/LXRE Eff (%) | LXRβ/LXRE EC$_{50}$ (μM) | LXRβ/LXRE Eff (%) |
|---|---|---|---|
| 1-Benzyl-2-oxo-6-thiophen-2-yl-4-trifluoromethyl-1,2-dihydro-pyridine-3-carbonitrile | 56 | 1.8 | 82 |
| 1-(5-Methyl-furan-2-ylmethyl)-2-oxo-6-phenyl-4-trifluoromethyl-1,2-dihydro-pyridine-3-carbonitrile | 91 | 0.81 | 93 |

Since modifications will be apparent to those of skill in this art, it is intended that this invention be limited only by the scope of the appended claims.

What is claimed is:

1. A compound of formula I:

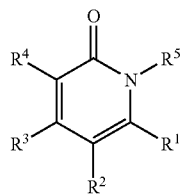

or a pharmaceutically acceptable salt thereof, wherein $R^1$ is selected from substituted or unsubstituted alkenyl, substituted or unsubstituted alkynyl, substituted or unsubstituted aryl, substituted or unsubstituted heteroaryl, substituted or unsubstituted aralkyl, substituted or unsubstituted heteroaralkyl, substituted or unsubstituted cyclohexyl, substituted or unsubstituted cyclopentenyl, substituted or unsubstituted cycloalkenyl, substituted or unsubstituted cycloalkynyl, substituted or unsubstituted heterocyclyl, substituted or unsubstituted cycloallylalkyl and substituted or unsubstituted heterocyclylalkyl;

$R^2$ is hydrogen, substituted or unsubstituted alkyl, substituted or unsubstituted alkenyl, substituted or unsubstituted alkynyl; wherein unsubstituted alkyl is selected from the group consisting of propyl, isopropyl, isobutyl, n-butyl, sec-butyl, tert-butyl, isopentyl, neopentyl, isopentyl, neopentyl, tert-pentyl, and isohexyl;

$R^3$ and $R^4$ are selected from (i) or (ii) as follows:

(i) $R^3$ is substituted or unsubstituted alkyl, substituted or unsubstituted alkenyl, substituted or unsubstituted alkynyl, substituted or unsubstituted alkylaminocarbonyl or $C(J)OR^{30}$; and $R^4$ is hydrogen, substituted or unsubstituted alkyl, unsubstituted alkenyl, substituted or unsubstituted alkynyl, halide, cyanide, cyanate, thiocyanate, selenocyanate, trifluoromethoxy, azide, hydroxycarbonyl, $C(J)R^{30}$, $C(J)NR^{31}R^{32}$, $CH_2NR^{31}R^{32}$; and (ii) $R^3$ and $R^4$, together with the atoms to which they are attached, form a substituted or unsubstituted heterocyclic ring, with the proviso that the heterocyclic ring has one oxo substituent;

$R^5$ is substituted alkyl or unsubstituted $C_2$-$C_6$alkyl, substituted or unsubstituted N or S-containing heterocyclyl, unsubstituted O-containing heterocyclyl, substituted aryl, substituted or unsubstituted aralkyl, substituted or unsubstituted heterocyclylalkyl, substituted or unsubstituted heteroaryl, substituted or unsubstituted heteroaralkyl, $-N=CR^6R^7$ or $-NR^9R^{10}$; wherein substituted or unsubstituted heteroaralkyl is selected from the group consisting of substituted or unsubstituted 3-pyridylmethyl, substituted or unsubstituted 4-pyridylmethyl, substituted or unsubstituted thiazolylmethyl, and substituted or unsubstituted oxazolylmethyl, and wherein the $R^5$ substituents are selected from alkyl, haloalkyl, halohydroxyalkyl, alkoxy, alkoxyalkoxyalkyl, alkoxyalkyl, aryl, halo, alkylthio, aryloxy, haloalkoxy, aralkyl, heteroaryl, hydroxyalkyl, heterocyclyl, heterocyclylalkyl, alkylcarbonyl, arylcarbonyl, alkylalkelenedioxy and dialkylalkelenedioxy;

$R^6$ and $R^7$ are each independently hydrogen, substituted or unsubstituted alkyl, substituted or unsubstituted alkynyl, substituted or unsubstituted cycloalkyl, substituted or unsubstituted heterocyclyl, substituted or unsubstituted heteroaryl, substituted or unsubstituted aralkyl, or substituted or unsubstituted heteroaralkyl; or together form substituted or unsubstituted alkylene, substituted or unsubstituted alkenylene, substituted or unsubstituted alkynylene, or $-(CH_2)_xX(CH_2)_y-$ where x and y are each independently 1, 2 or 3, and X is O, S or $NR^8$;

$R^8$ is substituted or unsubstituted alkyl, substituted or unsubstituted alkenyl, substituted or unsubstituted alkynyl, substituted or unsubstituted alkylcarbonyl, substituted or unsubstituted arylcarbonyl, or substituted or unsubstituted heteroarylcarbonyl;

$R^9$ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted aralkyl, or substituted or unsubstituted heteroaralkyl;

$R^{10}$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted aralkyl, or substituted or unsubstituted heteroaralkyl;

or $R^9$ and $R^{10}$ together form substituted or unsubstituted alkylene, substituted or unsubstituted alkenylene, substituted or unsubstituted alkynylene, or —$(CH_2)_x X (CH_2)_y$— where x and y are each independently 1, 2 or 3, and X is O, S or $NR^8$;

$R^{30}$ is hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, or substituted or unsubstituted heteroaralkyl;

$R^{31}$ and $R^{32}$ are each independently hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, or $C(J)R^{35}$;

or $R^{31}$ and $R^{32}$, together with the atoms to which they are attached, form substituted or unsubstituted cycloalkyl ring, a substituted or unsubstituted heterocyclic ring or a substituted or unsubstituted heteroaryl ring;

J is O, S or $NR^{40}$;

$R^{35}$ is hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted aryl, substituted or unsubstituted heteroaryl, substituted or unsubstituted alkoxy, substituted or unsubstituted aralkoky, substituted or unsubstituted alkylamino, substituted or unsubstituted dialkylamino, substituted or unsubstituted arylalkylamino, or substituted or unsubstituted diarylamino;

$R^{40}$ is hydrogen, substituted or unsubstituted alkyl, substituted or unsubstituted aryl, or substituted or unsubstituted heteroaryl;

where the alkyl, alkenyl, alkynyl, cycloalkyl, heterocyclyl, alkylene, alkenylene, alkynylene, aryl, heteroaryl, aralkyl, aralkenyl, aralkynyl, heteroaralkyl, heteroaralkenyl and heteroaralkynyl moieties of $R^1$, $R^2$, $R^3$, $R^4$, $R^6$, $R^7$, $R^8$, $R^9$ and $R^{10}$ are unsubstituted or substituted with one or more substituents, each independently selected from $Q^1$, where $Q^1$ is halo, cyanide, cyanate, thiocyanate, selenocyanate, trifluoromethoxy, azide, hydroxy, nitrile, nitro, formyl, mercapto, amino, hydroxyalkyl, hydroxyalkylaryloxy, hydroxyaryl, hydroxyalkylaryl, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, diaryl, hydroxyaryl, alkylaryl, heteroaryl, aralkyl, aralkenyl, aralkynyl, alkylaralkyl, heteroarylalkyl, trialkylsilyl, dialkylarylsilyl, alkyldiarylsilyl, triarylsilyl, alkylidene, arylalkylidene, alkylcarbonyl, alkylarylcarbonyl, arylcarbonyl, heterocyclylcarbonyl, heteroarylcarbonyl, alkoxycarbonyl, alkoxycarbonylalkyl, alkoxycarbonylaryloxy, aryloxycarbonyl, aryloxycarbonylalkyl, heterocyclylcarbonylalkylaryl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, haloalkoxy, alkoxyaryloxy, alkylaryloxy, diaryloxy, alkylaryloxyalkyl, alkyldiaryloxy, perfluoroalkoxy, alkenyloxy, alkynyloxy, aryloxyalkoxy, aralkoxyaryloxy, alkylarylcycloalkyloxy, heterocyclyloxy, alkoxyalkyl, alkoxyalkoxyalkyl, alkylheteroaryloxy, alkylcycloalkoxy, cycloalkyloxy, heterocyclyloxy, aralkoxy, haloaryloxy, heteroaryloxy, alkylheteroaryloxy, alkoxycarbonylheterocyclyloxy, alkylcarbonylaryloxy, alkylcarbonyloxy, arylcarbonyloxy, aralkylcarbonyloxy, alkoxycarbonyloxy, aryloxycarbonyloxy, alkoxyaryloxy, aralkoxycarbonyloxy, ureido, alkylureido, arylureido, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, haloalkylarylamino, arylamino, diarylamino, alkylarylamino, aralkylamino, alkylcarbonylamino, aralkylcarbonylamino, haloalkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylenedioxyalkyl, dialkylalkylenedioxyalkyl, alkylsulfonylamino, arylsulfonylamino, azido, dialkylphosphonyl, alkylarylphosphonyl, diarylphosphonyl, alkylthio, arylthio, perfluoroalkylthio, hydroxycarbonylalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl, arylaminosulfonyl, diarylaminosulfonyl or alkylarylaminosulfonyl; or two $Q^1$ groups, which substitute atoms in a 1,2 or 1,3 arrangement, together faun alkylenedioxy, thioalkyleneoxy or alkylenedithioxy; and each $Q^1$ is independently unsubstituted or substituted with one or more substituents, each independently selected from $Q^2$, where $Q^2$ is halo, cyanide, cyanate, thiocyanate, selenocyanate, trifluoromethoxy, azide, hydroxy, oxo, nitrile, nitro, formyl, mercapto, amino, hydroxyalkyl, hydroxyaryl, hydroxycarbonyl, alkyl, haloalkyl, polyhaloalkyl, aminoalkyl, diaminoalkyl, alkenyl containing 1 to 2 double bonds, alkynyl containing 1 to 2 triple bonds, cycloalkyl, heterocyclyl, aryl, heteroaryl, aralkyl, aralkenyl, aralkynyl, alkoxycarbonyl, aryloxycarbonyl, aralkoxycarbonyl, arylcarbonylalkyl, aminocarbonyl, alkoxy, aryloxy, aralkoxy, alkylenedioxy, amino, aminoalkyl, dialkylamino, arylamino, diarylamino, alkylamino, dialkylamino, haloalkylamino, arylamino, diarylamino, alkylarylamino, aralkylamino, alkoxycarbonylamino, arylcarbonylamino, alkylthio or arylthio.

2. The compound of claim 1, wherein $R^1$ is substituted or unsubstituted aryl.

3. The compound of claim 1, wherein $R^1$ is substituted or unsubstituted heteroaryl.

4. The compound of claim 1, wherein $R^1$ is substituted or unsubstituted heterocyclyl.

5. The compound of claim 1, wherein $R^1$ is substituted or unsubstituted cyclohexyl, substituted or unsubstituted cyclopentenyl, substituted or unsubstituted phenyl, substituted or unsubstituted benzyl, substituted or unsubstituted naphthyl, substituted or unsubstituted furyl, substituted or unsubstituted thienyl, substituted or unsubstituted pyrrolyl, substituted or unsubstituted pyrazolyl, substituted or unsubstituted thiazolyl, substituted or unsubstituted piperidinyl, substituted or unsubstituted pyridinyl, substituted or unsubstituted pyrazinyl, substituted or unsubstituted indanyl, substituted or unsubstituted benzofuryl, substituted or unsubstituted benzothiophenyl or substituted or unsubstituted indolyl, where the substituents are each independently selected from one or more $Q^1$.

6. The compound of claim 1, wherein $R^1$ is substituted or unsubstituted phenyl.

7. The compound of claim 1, wherein $R^1$ is substituted or unsubstituted furyl, substituted or unsubstituted thienyl, substituted or unsubstituted pyrrolyl, substituted or unsubstituted pyrazolyl, substituted or unsubstituted thiazolyl, substituted or unsubstituted piperidinyl, substituted or unsubstituted pyridinyl, substituted or unsubstituted pyrazinyl, substituted or unsubstituted benzofuryl, substituted or unsubstituted benzothiophenyl or substituted or unsubstituted indolyl, where the substituents are each independently selected from one or more $Q^1$.

8. The compound of claim 1, wherein $R^1$ is substituted or unsubstituted thienyl.

9. The compound of claim 8, wherein $R^1$ is thienyl.

10. The compound of claim 1, wherein $R^1$ is substituted with one to five substituents each independently selected from $Q^1$, where $Q^1$ is halo, cyanide, cyanate, thiocyanate, selenocyanate, trifluoromethoxy, azide, nitro, hydroxy, amino, hydroxyalkyl, hydroxyalkylaryloxy, hydroxyaryl, hydroxyalkylaryl, hydroxycarbonyl, haloalkyl, alkyl, heterocyclyl, heterocyclylalkyl, aryl, heteroaryl, aralkyl, heteroaralkyl, alkylaralkyl, alkylarylcarbonyl, heterocyclylcarbonyl, alkoxycarbonyl, alkoxycarbonylaryloxy, aryloxycarbonyl, heterocyclylcarbonylalkylaryl, aralkoxycarbonyl, alkoxy, aryloxy, heteroaryloxy, aralkoxy, alkylaryloxy, alkylaryloxyalkyl, alkyldiaryloxy, aryloxyalkoxy, aralkoxyaryloxy, alkylarylcycloalkyloxy, alkylheteroaryloxy, cycloalkyloxy, heterocyclylalkoxy, heterocyclyloxy, haloaryloxy, alkylcarbonylaryloxy, arylamino, alkylarylamino, aralkylamino, alkylcarbonylamino, alkylaminocarbonyl, haloalkylcarbonylamino, or arylthio; and each $Q^1$ is unsubstituted or further substituted with $Q^2$, which is alkyl, aryl, alkoxy, hydroxycarbonyl, alkoxycarbonyl, pseudohalidecyanide, cyanate, thiocyanate, selenocyanate, trifluoromethoxy, azide, halo, aryloxy, aralkoxy, haloalkyl, alkylthio, alkylamino, dialkylamino or hydroxy.

11. The compound of claim 1, wherein $R^1$ is substituted with $Q^1$, which is selected from alkoxycarbonylaryloxy, aryloxy, alkylaryloxy, alkylaryloxyalkyl, alkyldiaryloxy, aryloxyalkoxy, aralkoxyaryloxy, alkylarylcycloallyloxy, alkylheteroaryloxy, cycloalkyloxy, heterocyclylalkoxy, heterocyclyloxy, heteroaryloxy, haloaryloxy, alkoxycarbonylheterocycloxy, alkylcarbonylaryloxy, dialkylaminoaryloxy, alkoxyaryloxy, cyanoaryloxy, aryloxyaryloxy, dialkylaryloxy, haloalkylaryloxy, alkylthioaryloxy, alkylarylamino, hydroxyaryloxy, arylamino, alkylamino, aralkylamino and arylthio.

12. The compound of claim 1, wherein $R^1$ is substituted with $Q^1$, which is selected from methyl, ethyl, trifluoromethyl, nitro, hydroxy, n-butyloxy, 3-(2-piperidinyl)ethoxy, methylcarbonylamino, ethylaminocarbonylamino, chloro, bromo, benzylamino, methylphenoxymethyl, trifluoromethylcarbonylamino, methoxycarbonyl, phenoxy, cyano, n-butoxy, benzoxy, 1-piperidinyl, methoxy, hydroxycarbonyl, tert-butoxycarbonylpiperazinylcarbonyl, hydroxymethyl, 1-piperidinylcarbonyl, phenyl, methylphenyl, dimethylamino, methylcarbonylamino, methoxyphenoxy, methylphenoxy, piperidinylmethyl, biphenoxy, benzoxycarbonyl, piperazinylcarbonyl, benzyl, phenylthio, chlorophenoxy, methylbenzyl, hydroxymethylphenoxy, ethoxycarbonylphenoxy, tert-butylmethylphenoxy, tert-butylbiphenoxy, ethylphenoxy, isopropylphenoxy, tert-butylphenoxy, N,N-dimethylphenoxy, N,N-phenylmethylamino, 3-methylphenyl-1-amino, trifluoromethylphenoxy, ethylphenoxy, methylcarbonylphenoxy, tetrahydropyranyloxy, tetrahydronaphthoxy, hydroxycarbonylphenoxy, benzoxyphenoxy, cyclohexyloxy, indanyloxy, methoxycarbonylphenoxy, isopropylphenoxy, tert-butylphenoxy, N,N-dimethylaminophenoxy, methoxyphenoxy, methoxycarbonylphenoxy, cyanophenoxy, fluorophenoxy, benzoxyphenoxy, trifluoromethylphenoxy, bromophenoxy, 3,5-di(trifluoromethyl)phenoxy, methylthiophenoxy, indolyl, tert-butoxycarbonyl-piperidinyloxy, hydroxyphenoxy, pyrimidinoxy and pyrazinoxy.

13. A compound of formula I,

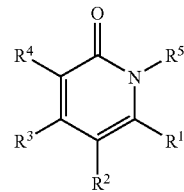

or a pharmaceutically acceptable salt thereof, wherein
wherein $R^1$ has formula IA:

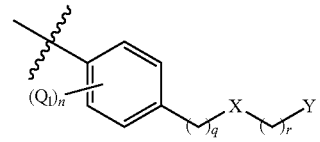

where, q and r are each independently an integer from 0 to 5;
n is an integer from 0 to 4;
X is O, S or NR', where R' is alkyl, aryl or hydrogen;
Y is substituted or unsubstituted alkyl, substituted or unsubstituted aryl, substituted or unsubstituted heteroaryl, substituted or unsubstituted heterocyclyl or substituted or unsubstituted cycloalkyl, where the substituents, when present are each independently selected from one or more $Q^1$,
$R^2$ is hydrogen, substituted or unsubstituted alkyl, substituted or unsubstituted alkenyl, substituted or unsubstituted alkynyl; wherein unsubstituted alkyl is selected from the group consisting of propyl, isopropyl, isobutyl, n-butyl, sec-butyl, tert-butyl, isopentyl, neopentyl, isopentyl, neopentyl, tert-pentyl, and isohexyl;

$R^3$ and $R^4$ are selected from (i) or (ii) as follows:
(i) $R^3$ is substituted or unsubstituted alkyl, substituted or unsubstituted alkenyl, substituted or unsubstituted alkynyl, substituted or unsubstituted alkylaminocarbonyl or $C(J)OR^{30}$; and $R^4$ is hydrogen, substituted or unsubstituted alkyl, substituted or unsubstituted alkenyl, substituted or unsubstituted alkynyl, halide, cyanide, cyanate, thiocyanate, selenocyanate, trifluoromethoxy, azide, hydroxycarbonyl, $C(J)R^{30}$, $C(J)NR^{31}R^{32}$, $CH_2NR^{31}R^{32}$, $CH_2OR^{31}$, $CR^{30}=CR^{31}R^{32}$, $NO_2$ or $NR^{31}R^{32}$; and (ii) $R^3$ and $R^4$, together with the atoms to which they are attached, form a substituted or unsubstituted heterocyclic ring, with the proviso that the heterocyclic ring has one oxo substituent;

$R^5$ is substituted alkyl or unsubstituted $C_2$-$C_6$alkyl, substituted or unsubstituted N or S-containing heterocyclyl, unsubstituted O-containing heterocyclyl, substituted aryl, substituted or unsubstituted aralkyl, substituted or unsubstituted heterocyclylalkyl, substituted or unsubstituted heteroaryl, substituted or unsubstituted heteroaralkyl, $-N=CR^6R^7$ or $-NR^9R^{10}$; wherein substituted or unsubstituted heteroaralkyl is selected from the group consisting of substituted or unsubstituted 3-pyridylmethyl, substituted or unsubstituted 4-pyridylmethyl, substituted or unsubstituted thiazolylmethyl, and substituted or unsubstituted oxazolylmethyl, and wherein the $R^5$ substituents are selected from alkyl, haloalkyl, halohydroxyalkyl, alkoxy, alkoxyalkoxyalkyl, alkoxyalkyl, aryl, halo, alkylthio, aryloxy, haloalkoxy, aralkyl, heteroaryl, hydroxyalkyl, heterocyclyl, heterocyclylalkyl, alkylcarbonyl, arylcarbonyl, alkylalkelenedioxy and dialkylalkelenedioxy;

$R^6$ and $R^7$ are each independently hydrogen, substituted or unsubstituted alkyl, substituted or unsubstituted alkenyl, substituted or unsubstituted alkynyl, substituted or unsubstituted cycloalkyl, substituted or unsubstituted aryl, substituted or unsubstituted heterocyclyl, substituted or unsubstituted heteroaryl, substituted or unsubstituted aralkyl, or substituted or unsubstituted heteroaralkyl; or together form substituted or unsubstituted alkylene, substituted or unsubstituted alkenylene, substituted or unsubstituted alkynylene, or $-(CH_2)_xX(CH_2)_y-$ where x and y are each independently 1, 2 or 3, and X is o, S or $NR^8$;

$R^8$ is substituted or unsubstituted alkyl, substituted or unsubstituted alkenyl, substituted or unsubstituted alkynyl, substituted or unsubstituted alkylcarbonyl, substituted or unsubstituted arylcarbonyl, or substituted or unsubstituted heteroarylcarbonyl;

$R^9$ and $R^{10}$ are each independently hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted aralkyl, or substituted or unsubstituted heteroaralkyl; or together faun substituted or unsubstituted alkylene, substituted or unsubstituted alkenylene, substituted or unsubstituted alkynylene, or $-(CH_2)_xX'(CH_2)_y-$ where x and y are each independently 1, 2 or 3, and X' is O, S or $NR^8$;

$R^{30}$ is hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, or substituted or unsubstituted heteroaralkyl;

$R^{31}$ and $R^{32}$ are each independently hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, or $C(J)R^{35}$; or $R^{31}$ and $R^{32}$, together with the atoms to which they are attached, form substituted or unsubstituted cycloalkyl ring, a substituted or unsubstituted heterocyclic ring or a substituted or unsubstituted heteroaryl ring;

J is O, S or $NR^{40}$;

$R^{35}$ is hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted aryl, substituted or unsubstituted heteroaryl, substituted or unsubstituted alkoxy, substituted or unsubstituted aralkoxy, substituted or unsubstituted alkylamino, substituted or unsubstituted dialkylamino, substituted or unsubstituted arylalkylamino, or substituted or unsubstituted diarylamino;

$R^{40}$ is hydrogen, substituted or unsubstituted alkyl, substituted or unsubstituted aryl, or substituted or unsubstituted heteroaryl;

where the alkyl, alkenyl, alkynyl, cycloalkyl, heterocyclyl, alkylene, alkenylene, alkynylene, aryl, heteroaryl, aralkyl, aralkenyl, aralkynyl, heteroaralkyl, heteroaralkenyl and heteroaralkynyl moieties of $R^1$, $R^2$, $R^3$, $R^4$, $R^6$, $R^7$, $R^8$, $R^9$ and $R^{10}$ are unsubstituted or substituted with one or more substituents, each independently selected from $Q^1$, where $Q^1$ is halo, cyanide, cyanate, thiocyanate, selenocyanate, trifluoromethoxy, azide, hydroxy, nitrile, nitro, formyl, mercapto, amino, hydroxyalkyl, hydroxyalkylaryloxy, hydroxyaryl, hydroxyalkylaryl, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, diaryl, hydroxyaryl, alkylaryl, heteroaryl, aralkyl, aralkenyl, aralkynyl, alkylaralkyl, heteroarylalkyl, trialkylsilyl, dialkylarylsilyl, alkyldiarylsilyl, triarylsilyl, alkylidene, arylalkylidene, alkylcarbonyl, alkylarylcarbonyl, arylcarbonyl, heterocyclylcarbonyl, heteroarylcarbonyl, alkoxycarbonyl, alkoxycarbonylalkyl, alkoxycarbonylaryloxy, aryloxycarbonyl, aryloxycarbonylalkyl, heterocyclylcarbonylalkylaryl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, haloalkoxy, alkoxyaryloxy, alkylaryloxy, diaryloxy, alkylaryloxyalkyl, alkyldiaryloxy, perfluoroalkoxy, alkenyloxy, alkynyloxy, aryloxyalkaoxy, aralkoxyaryloxy, alkylarylcycloalkyloxy, heterocycloxy, alkoxyalkyl, alkoxyalkoxyalkyl, alkylheteroaryloxy, alkylcycloalkoxy, cycloalkyloxy, heterocyclyloxy, aralkoxy, haloaryloxy, heteroaryloxy, alkylheteroaryloxy, alkoxycarbonylheterocycloxy, alkylcarbonylaryloxy, alkylcarbonyloxy, arylcarbonyloxy, aralkylcarbonyloxy, alkoxycarbonyloxy, aryloxycarbonyloxy, alkoxyaryloxy, aralkoxycarbonyloxy, ureido, alkylureido, arylureido, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, haloalkylarylamino, arylamino, diarylamino, alkylarylamino, aralkylamino, alkylcarbonylamino, aralkylcarbonylamino, haloalkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylenedioxyalkyl, dialkylalkylenedioxyalkyl, alkylsulfonylamino, arylsulfonylamino, azido, dialkylphosphonyl, alkylarylphosphonyl, diarylphosphonyl, alkylthio, arylthio, perfluoroalkylthio, hydroxycarbonylalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl, arylaminosulfonyl, diarylaminosulfonyl or alkylarylaminosulfonyl; or two $Q^1$ groups, which substitute atoms in a 1,2 or 1,3 arrangement, together foam alkylenedioxy, thioalkyleneoxy or alkylenedithioxy; and each $Q^1$ is independently unsubstituted or substituted with one or more substituents, each independently selected from $Q^2$, where $Q^2$ is halo, cyanide, cyanate, thiocyanate, selenocyanate, trifluoromethoxy, azide, hydroxy, oxo, nitrile, nitro, formyl, mercapto, amino, hydroxyalkyl, hydroxyaryl, hydroxycarbonyl, alkyl, haloalkyl, polyhaloalkyl, aminoalkyl, diaminoalkyl, alkenyl containing 1 to 2 double bonds, alkynyl containing 1 to 2 triple bonds, cycloalkyl, heterocyclyl, aryl, heteroaryl, aralkyl, aralkenyl, aralkynyl, alkoxycarbonyl, aryloxycarbonyl, aralkoxycarbonyl, arylcarbonylalkyl, aminocarbonyl, alkoxy, aryloxy, aralkoxy, alkylenedioxy, amino, aminoalkyl, dialkylamino, arylamino, diarylamino, alkylamino, dialkylamino, haloalkylamino, arylamino, diarylamino, alkylarylamino, aralkylamino, alkoxycarbonylamino, arylcarbonylamino, alkylthio or arylthio.

14. The compound of claim 13, wherein q and r are each independently an integer from 0 to 3.

15. The compound of claim 13, wherein q and r are each independently 0 or 1.

16. The compound of claim 13, wherein n is 1 to 3.

17. The compound of claim 13, wherein n is 1.

18. The compound of claim 13, wherein X is O.

19. The compound of claim 13, wherein X is S.

20. The compound of claim 13, wherein X is NR'.

21. The compound of claim 20, wherein R' is alkyl or hydrogen.

22. The compound of claim 21, wherein R' is lower alkyl or hydrogen.

23. The compound of claim 22, wherein R' is hydrogen.

24. The compound of claim 13, wherein Y is substituted or unsubstituted heteroaryl, where the substituents, when present are each independently selected from one or more $Q^1$.

25. The compound of claim 13, wherein Y is substituted or unsubstituted heterocyclyl, where the substituents, when present are each independently selected from one or more $Q^1$.

26. The compound of claim 13, wherein Y is substituted or unsubstituted aryl, where the substituents, when present are each independently selected from one or more $Q^1$.

27. The compound of claim 13, wherein Y is substituted or unsubstituted phenyl, where the substituents, when present are each independently selected from one or more $Q^1$.

28. The compound of claim 13, wherein Y is substituted with $Q^1$, which is selected from halo, hydroxy, alkyl, alkoxy, alkoxycarbonyl, haloalkyl, alkylcarbonyl, hydroxycarbonyl, hydroxyhaloalkyl, aryl, aralkoxy, alkylaryl, alkylheteroaryl and heteroaryl.

29. The compound of claim 1, wherein $R^1$ is substituted or unsubstituted phenyl, substituted or unsubstituted naphthyl, substituted or unsubstituted furyl, substituted or unsubstituted thienyl, or substituted or unsubstituted pyrrolyl, where the substituents are selected from one or more $Q^1$.

30. The compound of claim 1, wherein $R^1$ is cyclohexyl, 1-cyclopentenyl, indanyl, phenyl, 1-naphthyl, 2-naphthyl, 3-methylphenyl, 2-chlorophenyl, 4-chlorophenyl, 3-ethylphenyl, 3-trifluoromethylphenyl, 3-nitrophenyl, 3-hydroxyphenyl, 3-n-butoxyphenyl, 3-benzyloxyphenyl, 3-(2-piperidinyl)ethoxyphenyl, 3-methylcarbonylaminophenyl, 3-ethylaminocarbonylaminophenyl, 2-methylphenyl, 2-methoxyphenyl, 4-methylphenyl, 3-methoxyphenyl, 4-methoxyphenyl, 3-chlorophenyl, 4-chlorophenyl, 3-benzylaminophenyl, 3-(3-methyl)phenoxymethylphenyl, benzyl, 3-trifluoromethylcarbonylaminophenyl, 3,5-dimethylphenyl, 2-chloro-3-methylphenyl, phenylethyl, 4-butoxyphenyl, 4-methoxycarbonylphenyl, 4-phenoxyphenyl, 4-cyanophenyl, 4-benzoxyphenyl, 4-(1-piperidinyl)phenyl, 4-hydroxycarbonylphenyl, 4-(4-tert-butoxycarbonylpiperazin-1-ylcarbonyl)phenyl, 4-hydroxymethylphenyl, 4-(1-piperidinylcarbonyl)phenyl, 4-dimethylaminophenyl, 4-methylcarbonylaminophenyl, 4-nitrophenyl, 6-(1,2,3,4-tetrahydro)naphthyl, 4-(4-methoxyphenoxy)phenyl, 4-(2-methylphenoxy)phenyl, 4-(3-methylphenoxy)phenyl, 4-(4-methylphenoxy)phenyl, 4-(3-methoxyphenoxy)phenyl, 4-(1-piperidinylmethyl)phenyl, 4-(4-biphenoxy)phenyl, 3-(1-benzoxycarbonyl)-piperidinyl, 4-(1-piperazinylcarbonyl)phenyl, 5-(2-methyl-2,3-dihydro)benzofuryl, 4-benzylphenyl, 4-phenylthiophenyl, 4-(4-chlorophenoxy)-2-chlorophenyl, 4-(3-biphenoxy)phenyl, 4-(1-benzoxycarbonyl)-piperidinyl, 4-piperidinyl, 4-(1-(3-methylbenzyl))-piperidinyl, 4-(3-methyl-4-hydroxyphen-1-oxy)phenyl, 4-(2-methyl-4-hydroxyphenoxy)phenyl, 4-(4-ethoxycarbonylphenoxy)phenyl, 4-(2-methyl-4-tert-butylphenoxy)phenyl, 4-(2-phenyl-4-tert-butylphenoxy)phenyl, 4-(3-ethylphenoxy)phenyl, 4-(3-isopropylphenoxy)phenyl, 4-(3-tert-butylphenoxy)phenyl, 4-(3,5-dimethylphenoxy)phenyl, 4-phenoxy-2-methylphenyl, 4-(2-methylphenoxy)-2-methylphenyl, 4-(2-methylphenoxy)-3-methylphenyl, 4-N-methyl-N-phenylaminophenyl, 4-(3-trifluoromethylphenoxy)phenyl, 4-(4-ethylphenoxy)phenyl, 4-(4-isopropylphenoxy)phenyl, 4-(4-tert-butylphenoxy)phenyl, 4-(3-methylcarbonylphenoxy)phenyl, 4-(3,4-dimethylphenoxy)phenyl, 4-(2-tetrahydropyranyloxy)phenyl, 4-(2-tetrahydropyranyloxy)-3-methylphenyl, 4-hydroxyphenyl, 3-methyl-4-hydroxyphenyl, 4-(4-methylphenoxy)-3-methylphenyl, 4-(2-ethylphenoxy)phenyl, 4-(2-isopropylphenoxy)phenyl, 4-(5,6,7,8-tetrahydronaphthyloxy)phenyl, 4-(3-hydroxycarbonylphenoxy)phenyl, 2-methyl-4-hydroxyphenyl, 4-phenoxy-2-hydroxyphenyl, 3-phenoxyphenyl 4-(2,3,4-trimethylphenoxy)phenyl, 4-(4-benzyloxyphenoxy)phenyl, 4-(3-(methyl-3-indanyloxy)phenyl, 4-(2-methyl-5-benzothiazoloxy)phenyl, 4-cyclohexyloxyphenyl, 4-(3-methoxycarbonylphenoxy)phenyl, 4-(3-isopropylphenoxy)-3-methylphenyl, 4-tert-butyl-phenoxy-3-methylphenyl, 4-N,N-dimethylaminophenoxy-3-methylphenyl, 4-methoxyphenoxy-3-methylphenyl, 3-methoxy-phenoxy-3-methylphenyl, 4-(3-methoxycarbonyl-phenoxy)-3-methylphenyl, 4-(3-cyanophenoxy)-3-methylphenyl, 4-(4-fluorophenoxy)-3-methylphenyl, 4-(4-benzoxy-phenoxy)-3-methylphenyl, 4-(3-benzoxy-phenoxy)-3-methylphenyl, dimethylphenoxy)-3-methylphenyl, 4-(2-chlorophenoxy)-3-methylphenyl, 4-(3-chlorophenoxy)-3-methylphenyl, 4-(2- trifluoromethylphenoxy)-3-methylphenyl, 4-(3-trifluoromethylphenoxy)-2-methylphenyl, 4-(3-bromophenoxy)-phenyl, 4-(4-bromophenoxy)-phenyl, 4-(3-benzyloxyphenoxy)-phenyl, 4-(3-cyanophenoxy)-phenyl, 4-(4-cyanophenoxy)phenyl, 4-(2,4-dimethylphenoxy)-phenyl, 4-(3,5-trifluoromethylphenoxy)phenyl, 4-(4-methylthiophenoxy)-phenyl, 4-(4-N,N-dimethylamino-phenoxy)-phenyl, 5-indolyloxyphenyl, 4-(1-tert-butoxycarbonyl-piperidin-4-oxy)-phenyl, 4-(4-hydroxyphenoxy)-phenyl, 4-(2-pyrimidinoxy)-phenyl, 4-(2-pyrazinoxy)-phenyl, 2-thienyl, 2-(5-chloro)thienyl, 2-(5-bromo)thienyl, 2-(5-phenyl)thienyl, 3-benzothiophenyl, 3-methyl-2-benzothiophenyl, 2-(5-(3-methylphenyl))-thienyl, 3-pyridinyl, 2-pyrazinyl, 4-(1-phenyl-5-methyl)pyrazolyl, 2-(1-methyl)pyrrolyl, 3-(1-methyl)indolyl, 3-(1-benzyloxycarbonyl)-piperidinyl, 4-(1-benzyloxyarbonyl)-piperidinyl, 4-piperidinyl, 4-(1-(3-methylbenzyl)-piperidinyl, 2-furyl, 2-(5-methyl)-furyl, 3-(2,5-dimethyl)-furyl, benzofuryl, 3-(2,4-dimethyl)uryl, 2-thiazolyl, or 5-(2,4-dimethyl)-1,3-thiazolyl.

31. The compound of claim 1, wherein $R^1$ is phenyl, 1-naphthyl, 2-naphthyl, 3-methylphenyl, 2-chlorophenyl, 3-ethylphenyl, 3-trifluoromethylphenyl, 3-nitrophenyl, 3-hydroxyphenyl, 3-n-butoxyphenyl, 3-benzyloxyphenyl, 3-(2-piperidinyl)ethoxyphenyl, 3-methylcarbonylaminophenyl, 3-ethylaminocarbonylaminophenyl, 2-methylphenyl, 2-methoxyphenyl, 4-methylphenyl, 3-methoxyphenyl, 4-methoxyphenyl, 3-chlorophenyl or 4-chlorophenyl.

32. The compound of claim 1, wherein $R^1$ is 3-(3-methyl)phenoxymethylphenyl, 4-phenoxyphenyl, 4-benzoxyphenyl, 4-(4-methoxyphenoxy)phenyl, 4-(2-methylphenoxy)phenyl, 4-(3-methylphenoxy)phenyl, 4-(4-methylphenoxy)phenyl, 4-(3-methoxyphenoxy)phenyl, 4-(4-biphenoxy)phenyl, 4-(4-chlorophenoxy)-2-chlorophenyl, 4-(3-biphenoxy)phenyl, 4-(3-methyl-4-hydroxyphenoxy)phenyl, 4-(2-methyl-4-hydroxyphenoxy)phenyl, 4-(4-ethoxycarbonylphenoxy)phenyl, 4-(2-methyl-4-tert-butylphenoxy)phenyl, 4-(2-phenyl-4-tert-butylphenoxy)phenyl, 4-(3-ethylphenoxy)phenyl, 4-(3-isopropylphenoxy)phenyl, 4-(3-tert-butylphenoxy)phenyl, 4-(3,5-dimethylphenoxy)phenyl, 4-phenoxy-2-methylphenyl, 4-(4-methylphenoxy)-2-methylphenyl, 4-(2-methylphenoxy)-3-methylphenyl, 4-(3-trifluoromethylphenoxy)phenyl, 4-(4-ethylphenoxy)phenyl, 4-(4-isopropylphenoxy)phenyl, 4-(4-tert-butylphenoxy)phenyl, 4-(3-methylcarbonylphenoxy)phenyl, 4-(3,4-dimethylphenoxy)phenyl, 4-(4-methylphenoxy)-3-methylphenyl, 4-(2-ethylphenoxy)phenyl, 4-(2-isopropylphenoxy)phenyl, 4-(5,6,7,8-tetrahydronaphthyloxy)phenyl, 4-(3-hydroxycarbonylphenoxy)phenyl, 2-methyl-4-hydroxyphenyl, 4-phenoxy-2-hydroxyphenyl, 3-phenoxyphenyl, 4-(2,3,4-trimethylphenoxy)phenyl, 4-(4-benzyloxyphenoxy)phenyl, 4-(3-methoxycarbonylphenoxy)phenyl, 4-(3-isopropylphenoxy)-3-methylphenyl, 4-tert-butyl-phenoxy-3-methylphenyl, 4-N,N-dimethylaminophenoxy-3-methylphenyl, 4-methoxyphenoxy-3-methylphenyl, 3-methoxy-phenoxy-3-methylphenyl, 4-(3-methoxycarbonyl-phenoxy)-3-methylphenyl, 4-(3-cyanophenoxy)-3-methylphenyl, 4-(4-fluorophenoxy)-3-methylphenyl, 4-(4-benzoxy-phenoxy)-3-methylphenyl, 4-(3-benzoxy-phenoxy)-3-methylphenyl, 4-(2,5-dimethylphenoxy)-3-methylphenyl, 4-(2-chlorophenoxy)-3-methylphenyl, 4-(3-chlorophenoxy)-3-methylphenyl, 4-(2-trifluoromethylphenoxy)-3-methylphenyl, 4-(3-trifluoromethylphenoxy)-2-methylphenyl, 4-(3-bromophenoxy)-phenyl, 4-(4-bromophenoxy)-phenyl, 4-(3-benzyloxy-phenoxy)-phenyl, 4-(3-cyanophenoxy)-phenyl, 4-(4-cyanophenoxy)phenyl, 4-(2,4-dimethylphenoxy)-phenyl, 4-(3,5-trifluoromethylphenoxy)phenyl, 4-(4-methylthio-phenoxy)-phenyl or 4-(4-N,N-dimethylamino-phenoxy)-phenyl.

33. The compound of claim 1, wherein $R^1$ is 4-N-methyl-N-phenylaminophenyl, or 4-phenylthiophenyl.

34. The compound of claim 1, wherein $R^1$ is 2-thienyl, 2-(5-chloro)thienyl, 2-(5-bromo)thienyl, 2-(5-phenyl)thienyl, 3-benzothiophenyl, 3-methyl-2-benzothiophenyl or 2-(5-(3-methylphenyl p-thienyl.

35. The compound of claim 34, wherein $R^1$ is 2-thienyl.

36. The compound of claim 1, wherein $R^1$ is 3-pyridinyl, 2-pyrazinyl, 4-(1-phenyl-5-methyl)pyrazolyl, 2-(1-methyl)pyrrolyl, 3-(1-methyl)indolyl, 3-(1-benzyloxycarbonyl)-piperidinyl, 4-(1-benzyloxycarbonyl)-piperidinyl, 4-piperidinyl or 4-(1-(3-methylbenzyl)-piperidinyl.

37. The compound of claim 1, wherein $R^1$ is 2-furyl, 2-(5-methyl)-furyl, 3-(2,5-dimethyl)-furyl, benzofuryl or 3-(2,4-dimethyl)-furyl.

38. The compound of claim 1, wherein $R^1$ is 2-thiazolyl or 5-(2,4-dimethyl)thiazolyl.

39. The compound of claim 1, wherein $R^1$ is substituted or unsubstituted phenyl, substituted or unsubstituted naphthyl, substituted or unsubstituted furyl, substituted or unsubstituted thienyl, or substituted or unsubstituted pyrrolyl, where the substituents are selected from one or more $Q^1$.

40. The compound of claim 1, wherein $R^1$ is substituted or unsubstituted phenyl, substituted or unsubstituted naphthyl, or substituted or unsubstituted thienyl, where the substituents are selected from one or more $Q^1$.

41. The compound of claim 1, wherein $R^1$ is substituted with $Q^1$, which is selected from alkyl, alkoxy, halo, cyanide, cyanate, thiocyanate, selenocyanate, trifluoromethoxy, azide, haloalkyl, nitro, hydroxy, alkoxy, aralkoxy, heterocyclylalkoxy, alkylcarbonylamino and alkylaminocarbonylamino.

42. The compound of claim 1, wherein $R^1$ is substituted with $Q^1$, which is selected from methyl, methoxy, chloro, ethyl, trifluoromethyl, nitro, hydroxy, n-butoxy, 3-(2-piperidinyl)ethoxy, methylcarbonylamino or ethylaminocarbonylamino.

43. The compound of claim 1, wherein $R^2$ is alkyl or hydrogen, wherein the alkyl selected from the group consisting of propyl, isopropyl, isobutyl, n-butyl, sec-butyl, tert-butyl, isopentyl, neopentyl, isopentyl, neopentyl, tert-pentyl, and isohexyl.

44. The compound of claim 1, wherein $R^2$ is hydrogen.

45. The compound of claim 1, wherein $R^3$ is substituted or unsubstituted alkyl, substituted or unsubstituted alkoxycarbonyl or substituted or unsubstituted alkylaminocarbonyl, where the substitutents are each independently selected from one or more $Q^1$.

46. The compound of claim 1, wherein $R^3$ is substituted or unsubstituted alkoxycarbonyl, where the substitutents are each independently selected from one or more $Q^1$.

47. The compound of claim 1, wherein $R^3$ is haloalkyl.

48. The compound of claim 1, wherein $R^3$ is substituted with $Q^1$, which are selected from halo, cyanide, cyanate, thiocyanate, selenocyanate, trifluoromethoxy, azide, alkyl, alkoxy, alkoxycarbonyl and aryloxycarbonyl.

49. The compound of claim 1, wherein $R^3$ is substituted with one or more $Q^1$, which are selected from halo.

50. The compound of claim 1, wherein $R^3$ is substituted with one or more $Q^1$, which are selected from fluoro, chloro, phenyl, methyl, methoxy and methylamino.

51. The compound of claim 1, wherein $R^3$ is perfluoroalkyl.

52. The compound of claim 1, wherein $R^3$ is methyl, trifluoromethyl, pentafluoroethyl, heptafluoropropyl, chlorodifluoromethyl, 1-(1-methoxy-1-fluoro)ethyl, methoxycarbonyl, ethoxycarbonyl, methylaminocarbonyl, dimethoxymethyl, or methoxycarbonylmethyl.

53. The compound of claim 1, wherein $R^3$ is trifluoromethyl or pentafluoroethyl.

54. The compound of claim 1, wherein $R^3$ is trifluoromethyl.

55. The compound of claim 1, wherein $R^4$ is hydrogen, substituted or unsubstituted alkyl, substituted or unsubstituted alkynyl, cyanide, cyanate, thiocyanate, selenocyanate, trifluoromethoxy, azide, $C(J)R^{30}$, $CH_2NR^{31}R^{32}$ or $NO_2$, where the substituents are each independently selected from one or more $Q^1$.

56. The compound of claim 1, wherein $R^4$ is substituted or unsubstituted methyl, substituted or unsubstituted acetyl or cyano, where the substituents are each independently selected from one or more $Q^1$.

57. The compound of claim 1, wherein $R^4$ is substituted or unsubstituted methyl, where the substituents are each independently selected from one or more $Q^1$.

58. The compound of claim 1, wherein $R^4$ is substituted or unsubstituted acetyl, where the substitutent is trialkylsilyl.

59. The compound of claim 1, wherein $R^4$ is substituted with $Q^1$, which is selected from trialkylsilyl, alkylcarbonylamino, arylcarbonylamino, aralkylcarbonylamino, alkoxycarbonylamino, dialkylamino, alkylamino and amino.

60. The compound of claim 1, wherein $R^4$ is alkylcarbonylaminoalkyl, alkoxycarbonylaminoalkyl, aralkoxycarbonylaminoalkyl or aryloxycarbonylaminoalkyl.

61. The compound of claim 1, wherein $R^4$ is hydrogen, cyano, nitro, hydroxycarbonyl, trimethylsilylacetyl, acetyl, methylcarbonylaminomethyl, ethylcarbonylaminomethyl, n-propylcarbonylaminomethyl, isopropylcarbonylaminomethyl, n-octylcarbonylaminomethyl, phenylcarbonylaminomethyl, benzylcarbonylaminomethyl, phenylethylcarbonylaminomethyl, ethoxycabonylaminomethyl dimethylaminomethyl or aminomethyl.

62. The compound of claim 1, wherein $R^4$ is cyano.

63. The compound of claim 1, wherein $R^3$ and $R^4$, together with the atoms to which they are attached, form a substituted or unsubstituted heterocyclic ring, with the proviso that the heterocyclic ring has one oxo substitutent.

64. The compound of claim 1, wherein $R^3$ and $R^4$ together with the atoms to which they are attached form 2-oxo-tetrahydropyridine or 2-oxo-pyrrole.

65. The compound of claim 1, wherein $R^5$ is substituted or unsubstituted $C_2$-$C_6$-alkyl, substituted or unsubstituted aralkyl, substituted aryl, unsubstituted N, O, or S-containing heterocyclyl, substituted or unsubstituted heterocyclylalkyl, substituted or unsubstituted heteroaryl, substituted or unsubstituted heteroaralkyl, $—N=CR^6R^7$ or $—NR^9R^{10}$, wherein substituted or unsubstituted heteroaralkyl is selected from the group consisting of substituted or unsubstituted 3-pyridylmethyl, substituted or unsubstituted 4-pyridylmethyl, substituted or unsubstituted thiazolylmethyl, and substituted or unsubstituted oxazolylmethyl, and wherein the $R^5$ substituents are selected from alkyl, haloalkyl, halohydroxyalkyl, alkoxy, alkoxyalkoxyalkyl, alkoxyalkyl, aryl, halo, alkylthio, aryloxy, haloalkoxy, aralkyl, heteroaryl, hydroxyalkyl, heterocyclyl, heterocyclylalkyl, alkylcarbonyl, arylcarbonyl, alkylalkelenedioxy and dialkylalkelenedioxy.

66. The compound of claim 1, wherein $R^5$ is substituted or unsubstituted aralkyl, wherein the substituents are selected from alkyl, haloalkyl, halohydroxyalkyl, alkoxy, alkoxyalkoxyalkyl, alkoxyalkyl, aryl, halo, alkylthio, aryloxy, haloalkoxy, aralkyl, heteroaryl, hydroxyalkyl, heterocyclyl, heterocyclylalkyl, alkylcarbonyl, arylcarbonyl, alkylalkelenedioxy and dialkylalkelenedioxy.

67. The compound of claim 1, wherein $R^5$ is substituted or unsubstituted heteroaralkyl, wherein substituted or unsubstituted heteroaralkyl is selected from the group consisting of substituted or unsubstituted 3-pyridylmethyl, substituted or unsubstituted 4-pyridylmethyl, substituted or unsubstituted thiazolylmethyl, and substituted or unsubstituted oxazolylmethyl, and wherein the $R^5$ substituents are selected from alkyl, haloalkyl, halohydroxyalkyl, alkoxy, alkoxyalkoxyalkyl, alkoxyalkyl, aryl, halo, alkylthio, aryloxy, haloalkoxy, aralkyl, heteroaryl, hydroxyalkyl, heterocyclyl, heterocyclylalkyl, alkylcarbonyl, arylcarbonyl, alkylalkelenedioxy and dialkylalkelenedioxy.

68. The compound of claim 1, wherein $R^5$ is unsubstituted heterocyclylalkyl.

69. The compound of claim 1, wherein $R^5$ is substituted or unsubstituted N-heterocyclyl, wherein the substituents are selected from alkyl, haloalkyl, halohydroxyalkyl, alkoxy, alkoxyalkoxyalkyl, alkoxyalkyl, aryl, halo, alkoxycarbonyl, alkylthio, aryloxy, haloalkoxy, aralkyl, heteroaryl, hydroxy, hydroxyalkyl, heterocyclyl, heterocyclylalkyl, alkylcarbonyl, arylcarbonyl, alkylalkelenedioxy and dialkylalkelenedioxy.

70. The compound of claim 1, wherein $R^5$ is $—N=CR^6R^7$.

71. The compound of claim 1, wherein $R^5$ is substituted or unsubstituted ethyl, substituted or unsubstituted propyl, substituted phenyl, substituted or unsubstituted piperidinyl, substituted or unsubstituted benzyl, substituted or unsubstituted 2-phenethyl, substituted or unsubstituted 1-phenethyl, substituted or unsubstituted 3-phenylpropyl, substituted or unsubstituted 1,2,3,4-tetrahydro-1-naphthyl, substituted or unsubstituted 3-pyridylmethyl, substituted or unsubstituted 4-pyridylmethyl, substituted or unsubstituted 2-pyrazinyl, substituted or unsubstituted thiazolylmethyl, substituted or unsubstituted oxazolylmethyl.

72. The compound of claim 1, wherein $R^5$ is substituted or unsubstituted piperidinyl, substituted or unsubstituted 3-pyridylmethyl, substituted or unsubstituted 4-pyridylmethyl, substituted or unsubstituted 2-pyrazinyl, substituted or unsubstituted thiazolylmethyl, or substituted or unsubstituted oxazolylmethyl.

73. The compound of claim 1, wherein $R^5$ is substituted phenyl, substituted or unsubstituted benzyl, substituted or unsubstituted 2-phenethyl, substituted or unsubstituted 1-phenethyl, substituted or unsubstituted 3-phenylpropyl, or $—N=CR^6R^7$.

74. The compound of claim 1, wherein $R^5$ is substituted or unsubstituted benzyl, or $—N=CR^6R^7$.

75. The compound of claim 1, $R^5$ is substituted with alkyl, haloalkyl, alkoxy, aryl, halo, alkylthio, aryloxy, haloalkoxy, aralkyl, heteroaryl, alkylcarbonyl or arylcarbonyl.

76. The compound of claim 1, $R^5$ is substituted with methyl, isopropyl, trifluoromethyl, methoxy, fluoro, bromo, methoxycarbonyl, chloro, methylthio, phenoxy, trifluoromethoxy, 3-pyridyl, 4-pyridyl, 2-pyridyl, ethyl, n-propyl, n-propyloxymethyl, n-pentyloxymethyl, n-octyloxymethyl, ethoxymethyl, n-butoxymethyl, n-hexyloxymethyl, n-octyloxymethyl, tert-butyl, methylcarbonyl, phenyl, benzyl, n-butyl, ethoxy, phenylcarbonyl, 2-(2-methyl)-methylenedioxy, 1-piperidinyl, (5-(2,2-dimethyl-1,3-dioxolanyl)methyl), methoxymethoxymethyl, hydroxymethyl, hydroxyethyl, methoxymethyl, 1-piperidinylmethyl or 1,1,1,3,3,3-hexafluoro-2-hydroxypropyl.

77. The compound of claim 1, $R^5$ is substituted with methyl, trifluoromethyl, methoxy, fluoro, bromo, chloro, methylthio, phenoxy, trifluoromethoxy, 3-pyridyl, 4-pyridyl, 2-pyridyl, ethyl, tert-butyl, methylcarbonyl, phenyl, benzyl, n-butyl, ethoxy or phenylcarbonyl.

78. The compound of claim 1, wherein R⁵ is 2,4-dimethylbenzyl, 4-isopropylbenzyl, 4-tert-butylbenzyl, 2,4,5-trifluorobenzyl, 1-naphthylmethyl, 4-(2-methyl-[1,3]dioxolan-2-yl)benzyl, 4-methylbenzyl, 4-ethylbenzyl, 1-piperidinyl, 4-methylcarbonylbenzyl, (5-(2,2-dimethyl-1,3-dioxolanyl) methyl), 1,2-dihydroxypropanyl, benzyl, 4-(2-methyl)-thiazolylmethyl, 4-(2-phenyl)thiazolylmethyl, 3-methoxymethoxymethylbenzyl, 3-hydroxymethylbenzyl, 4-hydroxymethylbenzyl, 4-hydroxyethylbenzyl, 4-methoxymethylbenzyl, 4-(1-piperidinylmethyl)benzyl, 3-biphenylyl, 4-biphenylyl, 4-(1,1,1,3,3,3-hexafluoro-2-hydroxypropyl)phenyl, 4-(2-ethyl)thiazolylmethyl, 4-(2-isopropyl) thiazolylmethyl, 4-(2-propyl)thiazolylmethyl, 4-(2-benzyl) thiazolylmethyl, 4-(2-methyl)oxazolylmethyl, 4-(2-ethyl) oxazolylmethyl, 4-(2-propyl)oxazolylmethyl, 4-(2-phenyl) oxazolylmethyl, 4-(2-benzyl)oxazolylmethyl, 4-(2-cyclohexyl)oxazolylmethyl, 4-n-propyloxymethylbenzyl, 2-(5-methyl)pyrazinylmethyl, 4-n-pentyloxymethylbenzyl, 4-n-octyloxymethylbenzyl, 3-ethoxymethylbenzyl, 3-n-butoxymethylbenzyl, 3-n-hexyloxymethylbenzyl, 3-n-octyloxymethylbenzyl, 2-methylbenzyl, 4-methylbenzyl, 3-methylbenzyl, phenylethyl, 4-(2,5-dimethyl)thiazolylmethyl, 4-(2-isopropyl-5-methyl)thiazolylmethyl, 4-(2-ethyl-5-methyl)thiazolylmethyl, 4-(2-methyl-5-ethyl)thiazolylmethyl, 4-(2,5-diethyl)thiazolylmethyl, phenyl, 2-phenylethyl, 3-phenylpropyl, benzyl, 3-methylbenzyl, 2-trifluoromethylbenzyl, 3-trifluoromethylbenzyl, 4-trifluoromethylbenzyl, 2-methoxybenzyl, 3-methoxybenzyl, 4-methoxybenzyl, 4-phenylbenzyl, 1-phenylethyl, 1,2,3,4-tetrahydro-1-naphthyl, 2-fluorobenzyl, 4-fluorobenzyl, 2,4-difluorobenzyl, 4-bromobenzyl, 4-methoxycarbonylbenzyl, 2-chlorobenzyl, 4-chlorobenzyl, 4-methylthiobenzyl, 4-phenoxybenzyl, 4-trifluoromethoxybenzyl, 3-pyridylmethyl or 4-pyridylmethyl.

79. The compound of claim 1, wherein R⁵ is 4-(2-methyl-[1,3]dioxolan-2-yl)benzyl, 1-piperidinyl, (5-(2,2-dimethyl-1,3-dioxolanyl)methyl), 4-(2-methyl)-thiazolylmethyl, 4-(2-phenyl)thiazolylmethyl, 4-(1-piperidinylmethyl)benzyl, 4-(2-ethyl)thiazolylmethyl, 4-(2-isopropyl)thiazolylmethyl, 4-(2-propyl)thiazolylmethyl, 4-(2-benzyl)thiazolylmethyl, 4-(2-methyl)oxazolylmethyl, 4-(2-ethyl)oxazolylmethyl, 4-(2-propyl)oxazolylmethyl, 4-(2-phenyl)oxazolylmethyl, 4-(2-benzyl)oxazolylmethyl, 4-(2-cyclohexyl)oxazolylmethyl, 2-(5-methyl)pyrazinylmethyl, 4-(2,5-dimethyl)thiazolylmethyl, 4-(2-isopropyl-5-methyl)thiazolylmethyl, 4-(2-ethyl-5-methyl)thiazolylmethyl, 4-(2-methyl-5-ethyl) thiazolylmethyl, 4-(2,5-diethyl)thiazolylmethyl, 3-pyridylmethyl or 4-pyridylmethyl.

80. The compound of claim 1, wherein R⁵ is 2-phenylethyl, 3-phenylpropyl, benzyl, 2-methylbenzyl, 3-methylbenzyl, 4-methylbenzyl, 2-trifluoromethylbenzyl, 3-trifluoromethylbenzyl, 4-trifluoromethylbenzyl, 2-methoxybenzyl, 3-methoxybenzyl, 4-methoxybenzyl, 4-phenylbenzyl, 1-phenylethyl, 2,4-dimethylbenzyl, 2-fluorobenzyl, 4-fluorobenzyl, 2,4-difluorobenzyl, 4-bromobenzyl, 4-methoxycarbonylbenzyl, 2-chlorobenzyl, 4-chorobenzyl, 4-methylthiobenzyl, 4-phenoxybenzyl or 4-trifluoromethoxybenzyl.

81. The compound of claim 1, wherein R⁵ is —N═CR⁶R⁷ where R⁶ and R⁷ are each independently hydrogen, substituted or unsubstituted methyl, substituted or unsubstituted ethyl, substituted or unsubstituted n-propyl, substituted or unsubstituted i-propyl, substituted or unsubstituted i-butyl, substituted or unsubstituted tert-butyl, substituted or unsubstituted s-butyl, or substituted or unsubstituted 3-pentyl; where the substituents are selected from one or more Q¹, with the proviso that R⁶ and R⁷ are not both methyl.

82. The compound of claim 81, wherein R⁶ and R⁷ are unsubstituted or substituted with one or more Q¹ groups, where Q¹ is hydroxy, halo, alkyl or alkoxy.

83. The compound of claim 81, wherein R⁶ and R⁷ are unsubstituted or substituted with one or more Q¹ groups, where Q¹ is hydroxy, chloro, bromo, methyl or methoxy.

84. The compound of claim 81, wherein R⁶ and R⁷ are each independently hydrogen, methyl, ethyl, isopropyl, n-propyl, s-butyl, 3-pentyl, isobutyl or t-butyl, with the proviso that R⁶ and R⁷ are not both methyl.

85. A compound of formula III:

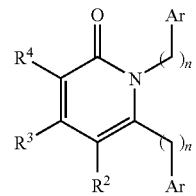

or a pharmaceutically acceptable salt thereof, wherein:
each Ar is independently substituted or unsubstituted aryl, substituted or unsubstituted cyclohexyl, substituted or unsubstituted cyclopentenyl; substituted or unsubstituted heteroaryl, or substituted or unsubstituted N or S-containing heterocyclyl, unsubstituted O-containing heterocyclyl, where there are 0 to 5 substituents each independently selected from Q¹; and
each n is independently an integer from 0 to 6, and with the proviso that for the —(CH₂)ₙAr group on the nitrogen atom, when n=0 then Ar is not unsubstituted phenyl;
R² is hydrogen, substituted or unsubstituted alkyl, substituted or unsubstituted alkenyl, substituted or unsubstituted alkynyl; wherein unsubstituted alkyl is selected from the group consisting of propyl, isopropyl, isobutyl, n-butyl, sec-butyl, tert-butyl, isopentyl, neopentyl, isopentyl, neopentyl, tert-pentyl, and isohexyl;
R³ and R⁴ are selected from (i) or (ii) as follows:
(i) R³ is substituted or unsubstituted alkyl, substituted or unsubstituted alkenyl, substituted or unsubstituted alkynyl, substituted or unsubstituted alkylaminocarbonyl or C(J)OR³⁰; and R⁴ is hydrogen, substituted or unsubstituted alkyl, substituted or unsubstituted alkenyl, substituted or unsubstituted alkynyl, halide, cyanide, cyanate, thiocyanate, selenocyanate, trifluoromethoxy, azide, hydroxycarbonyl, C(J)R³⁰, C(J)NR³¹R³², CH₂NR³¹R³², CH₂OR³¹, CR³⁰═CR³¹R³², NO₂ or NR³¹R³²; and
(ii) R³ and R⁴, together with the atoms to which they are attached, form a substituted or unsubstituted heterocyclic ring, with the proviso that the heterocyclic ring has one oxo substituent;
R³⁰ is hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, or substituted or unsubstituted heteroaralkyl;
R³¹ and R³² are each independently hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, or C(J)R$^{35}$; or R$^{31}$ and R$^{32}$, together with the atoms to which they are attached, form substituted or unsubstituted cycloalkyl ring, a substituted or unsubstituted heterocyclic ring or a substituted or unsubstituted heteroaryl ring;

J is O, S or NR$^{40}$;

R$^{35}$ is hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted aryl, substituted or unsubstituted heteroaryl, substituted or unsubstituted alkoxy, substituted or unsubstituted aralkoxy, substituted or unsubstituted alkylamino, substituted or unsubstituted dialkylamino, substituted or unsubstituted arylalkylamino, or substituted or unsubstituted diarylamino;

R$^{40}$ is hydrogen, substituted or unsubstituted alkyl, substituted or unsubstituted aryl, or substituted or unsubstituted heteroaryl;

where the alkyl, alkenyl, alkynyl, cycloalkyl, heterocyclyl, alkylene, alkenylene, alkynylene, aryl, heteroaryl, aralkyl, aralkenyl, aralkynyl, heteroaralkyl, heteroaralkenyl and heteroaralkynyl moieties of R$^2$, R$^3$, and R$^4$ are unsubstituted or substituted with one or more substituents, each independently selected from Q$^1$, where Q$^1$ is halo, cyanide, cyanate, thiocyanate, selenocyanate, trifluoromethoxy, azide, hydroxy, oxo, thia, nitrile, nitro, formyl, mercapto, amino, hydroxyalkyl, hydroxyalkylaryloxy, hydroxyaryl, hydroxyalkylaryl, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, diaryl, hydroxyaryl, alkylaryl, heteroaryl, aralkyl, aralkenyl, aralkynyl, alkylaralkyl, heteroaralkyl, trialkylsilyl, dialkylarylsilyl, alkyldiarylsilyl, triarylsilyl, alkylidene, arylalkylidene, alkylcarbonyl, alkylarylcarbonyl, arylcarbonyl, heterocyclylcarbonyl, heteroarylcarbonyl, alkoxycarbonyl, alkoxycarbonylalkyl, alkoxycarbonylaryloxy, aryloxycarbonyl, aryloxycarbonylalkyl, heterocyclylcarbonylalkylaryl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, haloalkoxy, alkoxyaryloxy, alkylaryloxy, diaryloxy, alkylaryloxyalkyl, alkyldiaryloxy, perfluoroalkoxy, alkenyloxy, alkynyloxy, aryloxyalkaoxy, aralkoxyaryloxy, alkylarylcycloalkyloxy, heterocycloxy, alkoxyalkyl, alkoxyalkoxyalkyl, alkylheteroaryloxy, alkylcycloalkoxy, cycloalkyloxy, heterocyclyloxy, aralkoxy, haloaryloxy, heteroaryloxy, alkylheteroaryloxy, alkoxycarbonylheterocycloxy, alkylcarbonylaryloxy, alkylcarbonyloxy, arylcarbonyloxy, aralkylcarbonyloxy, alkoxycarbonyloxy, aryloxycarbonyloxy, alkoxyaryloxy, aralkoxycarbonyloxy, ureido, alkylureido, arylureido, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, haloalkylarylamino, arylamino, diarylamino, alkylarylamino, aralkylamino, arylcarbonylamino, aralkylcarbonylamino, haloalkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylenedioxyalkyl, dialkylalkylenedioxyalkyl, alkylsulfonylamino, arylsulfonylamino, azido, dialkylphosphonyl, alkylarylphosphonyl, diarylphosphonyl, alkylthio, arylthio, perfluoroalkylthio, hydroxycarbonylalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl, arylaminosulfonyl, diarylaminosulfonyl or alkylarylaminosulfonyl; or two Q$^1$ groups, which substitute atoms in a 1,2 or 1,3 arrangement, together form alkylenedioxy, thioalkyleneoxy or alkylenedithioxy; and each Q$^1$ is independently unsubstituted or substituted with one or more substituents, each independently selected from Q$^2$, where Q$^2$ is halo, cyanide, cyanate, thiocyanate, selenocyanate, trifluoromethoxy, azide, hydroxy, oxo, thia, nitrile, nitro, formyl, mercapto, amino, hydroxyalkyl, hydroxyaryl, hydroxycarbonyl, alkyl, haloalkyl, polyhaloalkyl, aminoalkyl, diaminoalkyl, alkenyl containing 1 to 2 double bonds, alkynyl containing 1 to 2 triple bonds, cycloalkyl, heterocyclyl, aryl, heteroaryl, aralkyl, aralkenyl, aralkynyl, alkoxycarbonyl, aryloxycarbonyl, aralkoxycarbonyl, arylcarbonylalkyl, aminocarbonyl, alkoxy, aryloxy, aralkoxy, alkylenedioxy, amino, aminoalkyl, dialkylamino, arylamino, diarylamino, alkylamino, dialkylamino, haloalkylamino, arylamino, diarylamino, alkylarylamino, aralkylamino, alkoxycarbonylamino, arylcarbonylamino, alkylthio or arylthio.

86. The compound of claim 85 that has formula IV:

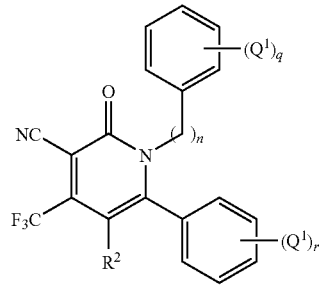

wherein q and r are each independently an integer from 0 to 5.

87. The compound of claim 85 that has formula V:

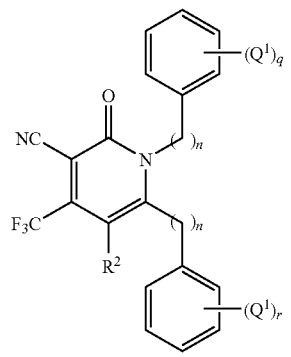

wherein q and r are each independently an integer from 0 to 5.

88. The compound of claim 85 that has formula VI:

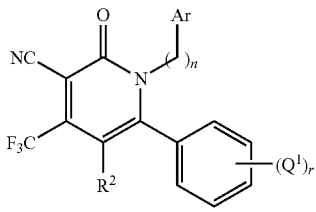

wherein r is an integer from 0 to 5.

89. The compound of claim 85 that has formula VII:

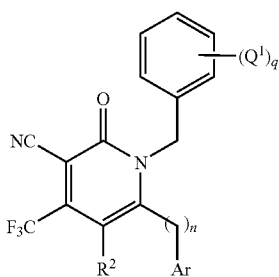

wherein q is an integer from 0 to 5.

90. The compound of claim 85 that has formula VIII:

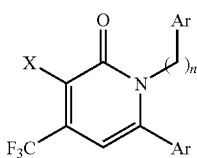

wherein X is cyano, nitro or $NR^{31}R^{32}$.

91. The compound of claim 85 that has formula IX:

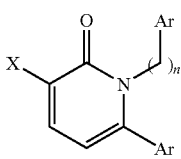

wherein X is bromo, CHO, $COOR^{30}$ or $CONR^{31}R^{32}$.

92. The compound of claim 1 that has formula X:

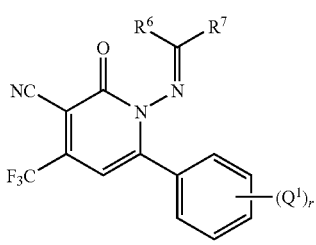

wherein r is an integer from 0 to 5.

93. The compound of claim 85 that has formula XI:

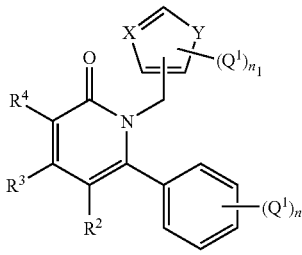

wherein n is an integer from 0 to 5; $n_1$ is an integer from 0 to 2; Y is selected from —CH=CH—, —C($Q^1$)=CH—, —C($Q^1$)=C($Q^1$)—, —CH=N—, —C($Q^1$)=N—, O, S and $NR^1$, where R' is hydrogen, alkyl or aryl and X is N or CH.

94. The compound of claim 85 that has formula XII:

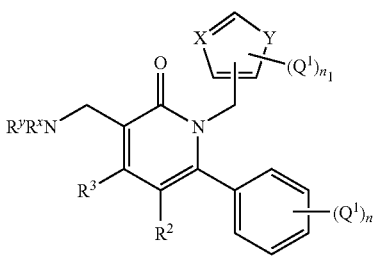

wherein n is an integer from 0 to 5; $n_1$ is an integer from 0 to 2; Y is selected from —CH=CH—, —C($Q^1$)=CH—, —C($Q^1$)=C($Q^1$)—, —CH=N—, —C($Q^1$)=N—, O, S and NR', where R' is hydrogen, alkyl or aryl and X is N or CH; $R^x$ and $R^y$ are each independently selected from hydrogen, alkyl, alkylcarbonyl, aryl, arylcarbonyl, aralkylcarbonyl, alkoxycarbonyl, aryloxycarbonyl and aralkoxycarbonyl.

95. The compound of claim 85 that has formula XIII:

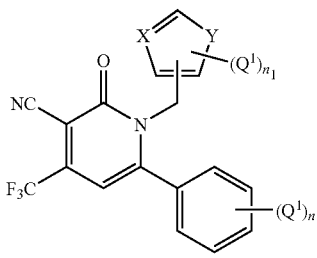

wherein n is an integer from 0 to 5; $n_1$ is an integer from 0 to 2; Y is selected from —CH=CH—, —C($Q^1$)=CH—, —C($Q^1$)=C($Q^1$)—, —CH=N—, —C($Q^1$)=N—, O, S and NR', where R' is hydrogen, alkyl or aryl and X is N or CH.

96. The compound of claim 85 that has formula XIV:

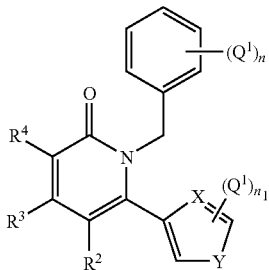

wherein n is an integer from 0 to 5; $n_1$ is an integer from 0 to 2; Y is selected from —CH=CH—, —C($Q^1$)=CH—, —C($Q^1$)=C($Q^1$)—, —CH=N—, —C($Q^1$)=N—, O, S and NR', where R' is hydrogen, alkyl or aryl and X is N.

97. The compound of claim 85 that has formula XV:

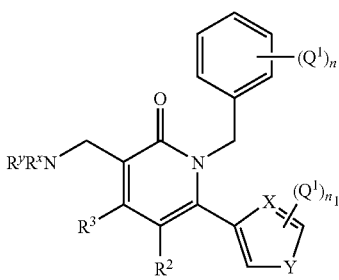

wherein n is an integer from 0 to 5; $n_1$ is an integer from 0 to 2; Y is selected from —CH=CH—, —C($Q^1$)=CH—, —C($Q^1$)=C($Q^1$)—, —CH=N—, —C($Q^1$)=N—, O, S and NR', where R' is hydrogen, alkyl or aryl and X is N; $R^x$ and $R^y$ are each independently selected from hydrogen, alkyl, alkylcarbonyl, aryl, arylcarbonyl, aralkylcarbonyl, alkoxycarbonyl, aryloxycarbonyl and aralkoxycarbonyl.

98. The compound of claim 85 that has formula XVI:

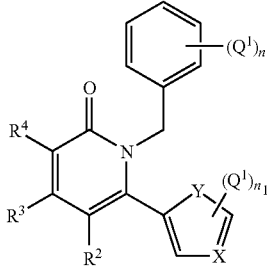

wherein n is an integer from 0 to 5; $n_1$ is an integer from 0 to 2; Y is selected from —CH=CH—, —C($Q^1$)=CH—, —C($Q^1$)=C($Q^1$)—, —CH=N—, —C($Q^1$)=N—, O, S and NR', where R' is hydrogen, alkyl or aryl and X is N.

99. The compound of claim 85 that has formula XVII:

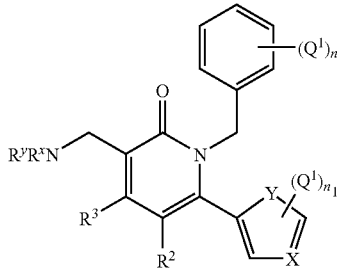

wherein n is an integer from 0 to 5; $n_1$ is an integer from 0 to 2; Y is selected from —CH=CH—, —C($Q^1$)=CH—, —C($Q^1$)=C($Q^1$)—, —CH=N—, —C($Q^1$)=N—, O, S and NR', where R' is hydrogen, alkyl or aryl and X is N; $R^x$ and $R^y$ are each independently selected from hydrogen, alkyl, alkylcarbonyl, aryl, arylcarbonyl, aralkylcarbonyl, alkoxycarbonyl, aryloxycarbonyl and aralkoxycarbonyl.

100. The compound of claim 85 that has formula XVII:

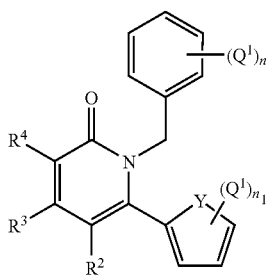

wherein n is an integer from 0 to 5; $n^1$ is an integer from 0 to 2; Y is selected from O, S and NR', where R' is hydrogen, alkyl or aryl.

101. The compound of claim 85 that has formula XVIII:

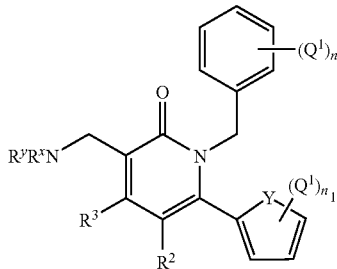

wherein n is an integer from 0 to 5; $n_1$ is an integer from 0 to 2; Y is selected from O, S and NR', where R' is hydrogen, alkyl or aryl; $R^x$ and $R^y$ are each independently selected from hydrogen, alkyl, alkylcarbonyl, aryl, arylcarbonyl, aralkylcarbonyl, alkoxycarbonyl, aryloxycarbonyl and aralkoxycarbonyl.

102. The compound of claim 85 that has formula XIX:

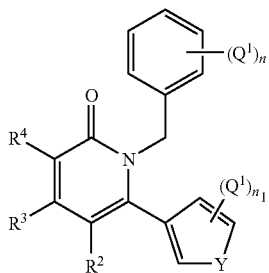

wherein n is an integer from 0 to 5; $n^1$ is an integer from 0 to 2; Y is selected from O, S and NR', where R' is hydrogen, alkyl or aryl.

103. The compound of claim 85 that has formula XX:

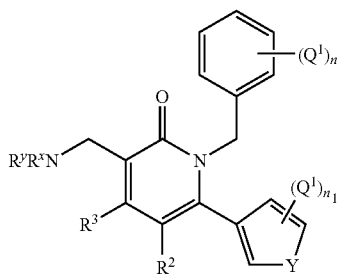

wherein n is an integer from 0 to 5; $n_1$ is an integer from 0 to 2; Y is selected from O, S and NR', where R' is hydrogen, alkyl or aryl and $R^x$ and $R^y$ are each independently selected from hydrogen, alkyl, alkylcarbonyl, aryl, arylcarbonyl, aralkylcarbonyl, alkoxycarbonyl, aryloxycarbonyl and aralkoxycarbonyl.

104. A compound selected from FIG. 1.

105. A pharmaceutical composition, comprising the compound of claim 1, or a pharmaceutically acceptable salt thereof, in a pharmaceutically acceptable carrier.

106. The pharmaceutical composition of claim 105 formulated for single dosage administration.

107. A method of reducing cholesterol levels in a subject in need thereof, comprising administering an effective amount of a compound of claim 1, or a pharmaceutically acceptable salt thereof.

108. A method of treating or ameliorating a symptom of a disease or disorder which is affected by cholesterol, triglyceride, or bile acid levels, comprising administering to a subject in need thereof an effective amount of a compound of claim 1, or a pharmaceutically acceptable salt thereof, wherein the disease or disorder is selected from hypercholesterolemia, hyperlipoproteinemia, hypertriglyceridemia, lipodystrophy, hyperglycemia, diabetes mellitus, dyslipidemia, atherosclerosis, gallstone disease, acne vulgaris, acneiform skin conditions, diabetes, lipid disorders, and obesity.

109. A method of enhancing cholesterol metabolism, comprising administering an effective amount of a compound of claim 1, or a pharmaceutically acceptable salt thereof.

110. A method of treating, preventing or ameiliorating a symptom of hypocholesterolemia in a subject in need thereof, comprising administering an effective amount of a compound of claim 1, or a pharmaceutically acceptable salt thereof.

111. An in vitro method for altering liver X receptor (LXRα or LXRβ) activity, comprising contacting the nuclear receptor with a compound of claim 1, or a pharmaceutically acceptable salt thereof.

112. A method of reducing cholesterol levels in a subject in need thereof, comprising administering an effective amount of a compound of formula I:

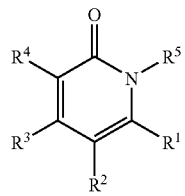

or a pharmaceutically acceptable salt thereof, wherein:
$R^1$ is selected from substituted or unsubstituted alkenyl, substituted or unsubstituted alkynyl, substituted or unsubstituted aryl, substituted or unsubstituted heteroaryl, substituted or unsubstituted aralkyl, substituted or unsubstituted heteroaralkyl, substituted or unsubstituted cycloalkyl, substituted or unsubstituted cycloalkenyl, substituted or unsubstituted cycloalkynyl, substituted or unsubstituted heterocyclyl, substituted or unsubstituted cycloalkylalkyl and substituted or unsubstituted heterocyclylalkyl;

$R^2$ is hydrogen, substituted or unsubstituted alkyl, substituted or unsubstituted alkenyl, substituted or unsubstituted alkynyl, substituted or unsubstituted aryl;

$R^3$ and $R^4$ are selected from (i) and (ii) as follows:
(i) $R^3$ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted alkylaminocarbonyl or $C(J)OR^{30}$; and $R^4$ is hydrogen, substituted or unsubstituted alkyl, substituted or unsubstituted alkenyl, substituted or unsubstituted alkynyl, halide, pseudohalidecyanide, cyanate, thiocyanate, selenocyanate, trifluoromethoxy, azide, hydroxycarbonyl, $C(J)R^{30}$, $C(J)NR^{31}R^{32}$, $CH_2NR^{31}R^{32}$, $CH_2OR^{31}$, $CR^{30}=CR^{31}R^{32}$, $NO_2$ or $NR^{31}R^{32}$; and (ii) $R^3$ and $R^4$, together with the atoms to which they are attached, form a substituted or unsubstituted heterocyclic ring, with the proviso that the heterocyclic ring has one oxo substituent;

$R^5$ is substituted or unsubstituted alkyl, substituted or unsubstituted alkenyl, substituted or unsubstituted alkynyl, substituted or unsubstituted heterocyclyl, substituted or unsubstituted aryl, substituted or unsubstituted heteroaryl, substituted or unsubstituted aralkyl, substituted or unsubstituted aralkenyl, substituted or unsubstituted aralkynyl, substituted or unsubstituted heteroaralkyl, substituted or unsubstituted heteroaralkenyl, substituted or unsubstituted heteroaralkynyl, —N=CR$^6$R$^7$ or —NR$^9$R$^{19}$;

$R^6$ and $R^7$ are each independently hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted aryl, substituted or unsubstituted heteroaryl, substituted or unsubstituted aralkyl, or substituted or unsubstituted heteroaralkyl; or together form substituted or unsubstituted alkylene, substituted or unsubstituted alkenylene, substituted or unsubstituted alkynylene, or —(CH$_2$)$_x$X(CH$_2$)$_y$— where x and y are each independently 1, 2 or 3, and X is O, S or NR$^8$;

R$^8$ is substituted or unsubstituted alkyl, substituted or unsubstituted alkenyl, substituted or unsubstituted alkynyl, substituted or unsubstituted alkylcarbonyl, substituted or unsubstituted arylcarbonyl, or substituted or unsubstituted heteroarylcarbonyl;

R$^9$ and R$^{10}$ are each independently hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted aralkyl, or substituted or unsubstituted heteroaralkyl;

R$^{30}$ is hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, or substituted or unsubstituted heteroaralkyl;

R$^{31}$ and R$^{32}$ are each independently hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, or C(J)R$^{35}$; or R$^{31}$ and R$^{32}$, together with the atoms to which they are attached, form substituted or unsubstituted cycloalkyl ring, a substituted or unsubstituted heterocyclic ring or a substituted or unsubstituted heteroaryl ring;

J is O, S or NR$^{40}$;

R$^{35}$ is hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted aryl, substituted or unsubstituted heteroaryl, substituted or unsubstituted alkoxy, substituted or unsubstituted aralkoxy, substituted or unsubstituted alkylamino, substituted or unsubstituted dialkylamino, substituted or unsubstituted arylalkylamino, or substituted or unsubstituted diarylamino;

R$^{40}$ is hydrogen, substituted or unsubstituted alkyl, substituted or unsubstituted aryl, or substituted or unsubstituted heteroaryl;

where the alkyl, alkenyl, alkynyl, cycloalkyl, heterocyclyl, alkylene, alkenylene, alkynylene, aryl, heteroaryl, aralkyl, aralkenyl, aralkynyl, heteroaralkyl, heteroaralkenyl and heteroaralkynyl moieties of R$^1$, R$^2$, R$^3$, R$^4$, R$^5$, R$^6$, R$^7$, R$^8$, R$^9$ and R$^{10}$ are unsubstituted or substituted with one or more substituents, each independently selected from Q$^1$, where Q$^1$ is halo, cyanide, cyanate, thiocyanate, selenocyanate, trifluoromethoxy, azide, hydroxy, oxo, thia, nitrile, nitro, formyl, mercapto, amino, hydroxyalkyl, hydroxyalkylaryloxy, hydroxyaryl, hydroxyalkylaryl, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, diaryl, hydroxyaryl, alkylaryl, heteroaryl, aralkyl, aralkenyl, aralkynyl, alkylaralkyl, heteroaralkyl, trialkylsilyl, dialkylarylsilyl, alkyldiarylsilyl, triarylsilyl, alkylidene, arylalkylidene, alkylcarbonyl, alkylarylcarbonyl, arylcarbonyl, heterocyclylcarbonyl, heteroarylcarbonyl, alkoxycarbonyl, alkoxycarbonylalkyl, alkoxycarbonylaryloxy, aryloxycarbonyl, aryloxycarbonylalkyl, heterocyclylcarbonylalkylaryl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, haloalkoxy, alkoxyaryloxy, alkylaryloxy, diaryloxy, alkylaryloxyalkyl, alkyldiaryloxy, perfluoroalkoxy, alkenyloxy, alkynyloxy, aryloxyalkaoxy, aralkoxyaryloxy, alkylarylcycloalkyloxy, heterocycloxy, alkoxyalkyl, alkoxyalkoxyalkyl, alkylheteroaryloxy, alkylcycloalkoxy, cycloalkyloxy, heterocyclyloxy, aralkoxy, haloaryloxy, heteroaryloxy, alkylheteroaryloxy, alkoxycarbonylheterocycloxy, alkylcarbonylaryloxy, alkylcarbonyloxy, arylcarbonyloxy, aralkylcarbonyloxy, alkoxycarbonyloxy, aryloxycarbonyloxy, alkoxyaryloxy, aralkoxycarbonyloxy, ureido, alkylureido, arylureido, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, haloalkylarylamino, arylamino, diarylamino, alkylarylamino, aralkylamino, alkylcarbonylamino, aralkylcarbonylamino, haloalkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylenedioxyalkyl, dialkylalkylenedioxyalkyl, alkylsulfonylamino, arylsulfonylamino, azido, dialkylphosphonyl, alkylarylphosphonyl, diarylphosphonyl, alkylthio, arylthio, perfluoroalkylthio, hydroxycarbonylalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl, arylaminosulfonyl, diarylaminosulfonyl or alkylarylaminosulfonyl; or two Q$^1$ groups, which substitute atoms in a 1,2 or 1,3 arrangement, together form alkylenedioxy, thioalkylenoxy or alkylenedithioxy; and each Q$^1$ is independently unsubstituted or substituted with one or more substituents, each independently selected from Q$^2$, where Q$^2$ is halo, cyanide, cyanate, thiocyanate, selenocyanate, trifluoromethoxy, azide, hydroxy, oxo, thia, nitrile, nitro, formyl, mercapto, amino, hydroxyalkyl, hydroxyaryl, hydroxycarbonyl, alkyl, haloalkyl, polyhaloalkyl, aminoalkyl, diaminoalkyl, alkenyl containing 1 to 2 double bonds, alkynyl containing 1 to 2 triple bonds, cycloalkyl, heterocyclyl, aryl, heteroaryl, aralkyl, aralkenyl, aralkynyl, alkoxycarbonyl, aryloxycarbonyl, aralkoxycarbonyl, arylcarbonylalkyl, aminocarbonyl, alkoxy, aryloxy, aralkoxy, alkylenedioxy, amino, aminoalkyl, dialkylamino, arylamino, diarylamino, alkylamino, dialkylamino, haloalkylamino, arylamino, diarylamino, alkylarylamino, aralkylamino, alkoxycarbonylamino, arylcarbonylamino, alkylthio or arylthio.

113. A method of treating or ameliorating hypercholesterolemia, hyperlipoproteinemia, hypertriglyceridemia, lipodystrophy, hyperglycemia, diabetes mellitus, dyslipidemia, atherosclerosis, gallstone disease, acne vulgaris, acneiform skin conditions, diabetes, lipid disorders, or obesity comprising administering to a subject in need thereof an effective amount of a compound of formula I:

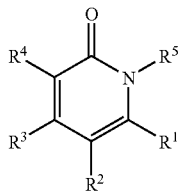

or a pharmaceutically acceptable derivative thereof, wherein:

$R^1$ is selected from substituted or unsubstituted alkyl, substituted or unsubstituted alkenyl, substituted or unsubstituted alkynyl, substituted or unsubstituted aryl, substituted or unsubstituted heteroaryl, substituted or unsubstituted aralkyl, substituted or unsubstituted heteroaralkyl, substituted or unsubstituted cycloalkyl, substituted or unsubstituted cycloalkenyl, substituted or unsubstituted cycloalkynyl, substituted or unsubstituted heterocyclyl, substituted or unsubstituted cycloalkylalkyl and substituted or unsubstituted heterocyclylalkyl;

$R^2$ is hydrogen, substituted or unsubstituted alkyl, substituted or unsubstituted alkenyl, substituted or unsubstituted alkynyl, substituted or unsubstituted aryl;

$R^3$ and $R^4$ are selected from (i) and (ii) as follows:

(i) $R^3$ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted alkylaminocarbonyl or $C(J)OR^{30}$; and $R^4$ is hydrogen, substituted or unsubstituted alkyl, substituted or unsubstituted alkenyl, substituted or unsubstituted alkynyl, halide, pseudohalidecyanide, cyanate, thiocyanate, selenocyanate, trifluoromethoxy, azide, hydroxycarbonyl, $C(J)R^{30}$, $C(J)NR^{31}R^{32}$, $CH_2NR^{31}R^{32}$, $CH_2OR^{31}$, $CR^{30}=CR^{31}R^{32}$, $NO_2$ or $NR^{31}R^{32}$; and (ii) $R^3$ and $R^4$, together with the atoms to which they are attached, form a substituted or unsubstituted heterocyclic ring with the proviso that the heterocyclic ring has one oxo substituent;

$R^5$ is substituted or unsubstituted alkyl, substituted or unsubstituted alkenyl, substituted or unsubstituted alkynyl, substituted or unsubstituted heterocyclyl, substituted or unsubstituted aryl, substituted or unsubstituted heteroaryl, substituted or unsubstituted aralkyl, substituted or unsubstituted aralkenyl, substituted or unsubstituted aralkynyl, substituted or unsubstituted heteroaralkyl, substituted or unsubstituted heteroaralkenyl, substituted or unsubstituted heteroaralkynyl, —N=$CR^6R^7$ or —$NR^9R^{10}$;

$R^6$ and $R^7$ are each independently hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted aryl, substituted or unsubstituted heteroaryl, substituted or unsubstituted aralkyl, or substituted or unsubstituted heteroaralkyl; or together faun substituted or unsubstituted alkylene, substituted or unsubstituted alkenylene, substituted or unsubstituted alkynylene, or —$(CH_2)_xX(CH_2)_y$— where x and y are each independently 1, 2 or 3, and X is O, S or $NR^8$;

$R^8$ is substituted or unsubstituted alkyl, substituted or unsubstituted alkenyl, substituted or unsubstituted alkynyl, substituted or unsubstituted alkylcarbonyl, substituted or unsubstituted arylcarbonyl, or substituted or unsubstituted heteroarylcarbonyl;

$R^9$ and $R^{10}$ are each independently hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted aralkyl, or substituted or unsubstituted heteroaralkyl;

$R^{30}$ is hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, or substituted or unsubstituted heteroaralkyl;

$R^{31}$ and $R^{32}$ are each independently hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, or $C(J)R^{35}$; or $R^{31}$ and $R^{32}$, together with the atoms to which they are attached, form substituted or unsubstituted cycloalkyl ring, a substituted or unsubstituted heterocyclic ring or a substituted or unsubstituted heteroaryl ring;

J is O, S or $NR^{40}$;

$R^{35}$ is hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted aryl, substituted or unsubstituted heteroaryl, substituted or unsubstituted alkoxy, substituted or unsubstituted aralkoxy, substituted or unsubstituted alkylamino, substituted or unsubstituted dialkylamino, substituted or unsubstituted arylalkylamino, or substituted or unsubstituted diarylamino;

$R^{40}$ is hydrogen, substituted or unsubstituted alkyl, substituted or unsubstituted aryl, or substituted or unsubstituted heteroaryl;

where the alkyl, alkenyl, alkynyl, cycloalkyl, heterocyclyl, alkylene, alkenylene, alkynylene, aryl, heteroaryl, aralkyl, aralkenyl, aralkynyl, heteroaralkyl, heteroaralkenyl and heteroaralkynyl moieties of $R^1$, $R^2$, $R^3$, $R^4$, $R^5$, $R^6$, $R^7$, $R^8$, $R^9$ and $R^{10}$ are unsubstituted or substituted with one or more substituents, each independently selected from $Q^1$, where $Q^1$ is halo, cyanide, cyanate, thiocyanate, selenocyanate, trifluoromethoxy, azide, hydroxy, oxo, thia, nitrile, nitro, formyl, mercapto, amino, hydroxyalkyl, hydroxyalkylaryloxy, hydroxyaryl, hydroxyalkylaryl, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, diaryl, hydroxyaryl, alkylaryl, heteroaryl, aralkyl, aralkenyl, aralkynyl, alkylaralkyl, heteroaralkyl, trialkylsilyl, dialkylarylsilyl, alkyldiarylsilyl, triarylsilyl, alkylidene, arylalkylidene, alkylcarbonyl, alkylarylcarbonyl, arylcarbonyl, heterocyclylcarbonyl, heteroarylcarbonyl, alkoxycarbonyl, alkoxycarbonylalkyl, alkoxycarbonylaryloxy, aryloxycarbonyl, aryloxycarbonylalkyl, heterocyclylcarbonylalkylaryl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, haloalkoxy, alkoxyaryloxy, alkylaryloxy, diaryloxy, alkylaryloxyalkyl, alkyldiaryloxy, perfluoroalkoxy, alkenyloxy, alkynyloxy, aryloxyalkaoxy, aralkoxyaryloxy, alkylarylcycloalkyloxy, heterocycloxy, alkoxyalkyl, alkoxyalkoxyalkyl, alkylheteroaryloxy, alkylcycloalkoxy, cycloalkyloxy, heterocyclyloxy, aralkoxy, haloaryloxy, heteroaryloxy, alkylheteroaryloxy, alkoxycarbonylheterocycloxy, alkylcarbonylaryloxy, alkylcarbonyloxy, arylcarbonyloxy, aralkylcarbonyloxy, alkoxycarbonyloxy, aryloxycarbonyloxy, alkoxyaryloxy, aralkoxycarbonyloxy, ureido, alkylureido, arylureido, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, haloalkylarylamino, arylamino, diarylamino, alkylarylamino, aralkylamino, alkylcarbonylamino, aralkylcarbonylamino, haloalkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylenedioxyalkyl, dialkylalkylenedioxyalkyl, alkylsulfonylamino, arylsulfonylamino, azido, dialkylphosphonyl, alkylarylphosphonyl, diarylphosphonyl, alkylthio, arylthio, perfluoroalkylthio, hydroxycarbonylalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl, arylaminosulfonyl, diarylaminosulfonyl or alkylarylaminosulfonyl; or two $Q^1$ groups, which substitute atoms in a 1,2 or 1,3 arrangement, together faun alkylenedioxy, thioalkylenoxy or alkylenedithioxy; and each $Q^1$ is independently unsubstituted or substituted with one or more substituents, each independently selected from $Q^2$, where $Q^2$ is halo, cyanide, cyanate, thiocyanate, selenocyanate, trifluoromethoxy, azide, hydroxy, oxo, thia, nitrile, nitro, formyl, mercapto, amino, hydroxyalkyl, hydroxyaryl, hydroxycarbonyl, alkyl, haloalkyl, polyhaloalkyl, aminoalkyl, diaminoalkyl, alkenyl containing 1 to 2 double bonds, alkynyl containing 1 to 2 triple bonds, cycloalkyl, heterocyclyl, aryl, heteroaryl, aralkyl, aralkenyl, aralkynyl, alkoxycarbonyl, aryloxycarbonyl, aralkoxycarbonyl, arylcarbonylalkyl, aminocarbonyl, alkoxy, aryloxy, aralkoxy, alkylenedioxy, amino, aminoalkyl, dialkylamino, arylamino, diarylamino, alkylamino, dialkylamino, haloalkylamino, arylamino, diarylamino, alkylarylamino, aralkylamino, alkoxycarbonylamino, arylcarbonylamino, alkylthio or arylthio.

114. A method of enhancing cholesterol metabolism, comprising administering an effective amount of a compound of formula I:

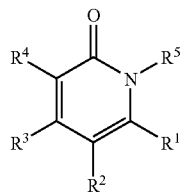

or a pharmaceutically acceptable salt thereof, wherein:

$R^1$ is selected from, substituted or unsubstituted alkenyl, substituted or unsubstituted alkynyl, substituted or unsubstituted aryl, substituted or unsubstituted heteroaryl, substituted or unsubstituted aralkyl, substituted or unsubstituted heteroaralkyl, substituted or unsubstituted cycloalkyl, substituted or unsubstituted cycloalkenyl, substituted or unsubstituted cycloalkynyl, substituted or unsubstituted heterocyclyl, substituted or unsubstituted cycloalkylalkyl and substituted or unsubstituted heterocyclylalkyl;

$R^2$ is hydrogen, substituted or unsubstituted alkyl, substituted or unsubstituted alkenyl, substituted or unsubstituted alkynyl, substituted or unsubstituted aryl;

$R^3$ and $R^4$ are selected from (i) and (ii) as follows:

(i) $R^3$ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted alkylaminocarbonyl or $C(J)OR^{30}$; and $R^4$ is hydrogen, substituted or unsubstituted alkyl, substituted or unsubstituted alkenyl, substituted or unsubstituted alkynyl, halide, pseudohalidecyanide, cyanate, thiocyanate, selenocyanate, trifluoromethoxy, azide, hydroxycarbonyl, $C(J)R^{30}$, $C(J)NR^{31}R^{32}$, $CH_2NR^{31}R^{32}$, $CH_2OR^{31}$, $CR^{30}=CR^{31}R^{32}$, $NO_2$ or $NR^{31}R^{32}$; and (ii) $R^3$ and $R^4$, together with the atoms to which they are attached, form a substituted or unsubstituted heterocyclic ring with the proviso that the heterocyclic ring has one oxo substituent;

$R^5$ is substituted or unsubstituted alkyl, substituted or unsubstituted alkenyl, substituted or unsubstituted alkynyl, substituted or unsubstituted heterocyclyl, substituted or unsubstituted aryl, substituted or unsubstituted heteroaryl, substituted or unsubstituted aralkyl, substituted or unsubstituted aralkenyl, substituted or unsubstituted aralkynyl, substituted or unsubstituted heteroaralkyl, substituted or unsubstituted heteroaralkenyl, substituted or unsubstituted heteroaralkynyl, —N=$CR^6R^7$ or —$NR^9R^{10}$;

$R^6$ and $R^7$ are each independently hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted aryl, substituted or unsubstituted heteroaryl, substituted or unsubstituted aralkyl, or substituted or unsubstituted heteroaralkyl; or together form substituted or unsubstituted alkylene, substituted or unsubstituted alkenylene, substituted or unsubstituted alkynylene, or —$(CH_2)_xX(CH_2)_y$— where x and y are each independently 1, 2 or 3, and X is O, S or $NR^B$;

$R^8$ is substituted or unsubstituted alkyl, substituted or unsubstituted alkenyl, substituted or unsubstituted alkynyl, substituted or unsubstituted alkylcarbonyl, substituted or unsubstituted arylcarbonyl, or substituted or unsubstituted heteroarylcarbonyl;

$R^9$ and $R^{10}$ are each independently hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted aralkyl, or substituted or unsubstituted heteroaralkyl;

$R^{30}$ is hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, or substituted or unsubstituted heteroaralkyl;

$R^{31}$ and $R^{32}$ are each independently hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, or $C(J)R^{35}$; or $R^{31}$ and $R^{32}$, together with the atoms to which they are attached, form substituted or unsubstituted cycloalkyl ring, a substituted or unsubstituted heterocyclic ring or a substituted or unsubstituted heteroaryl ring;

J is P, S or $NR^{40}$;

$R^{35}$ is hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted aryl, substituted or unsubstituted heteroaryl, substituted or unsubstituted alkoxy, substituted or unsubstituted aralkoxy, substituted or unsubstituted alkylamino, substituted or unsubstituted dialkylamino, substituted or unsubstituted arylalkylamino, or substituted or unsubstituted diarylamino;

$R^{40}$ is hydrogen, substituted or unsubstituted alkyl, substituted or unsubstituted aryl, or substituted or unsubstituted heteroaryl;

where the alkyl, alkenyl, alkynyl, cycloalkyl, heterocyclyl, alkylene, alkenylene, alkynylene, aryl, heteroaryl, aralkyl, aralkenyl, aralkynyl, heteroaralkyl, heteroaralkenyl and heteroaralkynyl moieties of $R^1$, $R^2$, $R^3$, $R^4$, $R^5$, $R^6$, $R^7$, $R^8$, $R^9$ and $R^{10}$ are unsubstituted or substituted with one or more substituents, each independently selected from $Q^1$, where $Q^1$ is halo, cyanide, cyanate, thiocyanate, selenocyanate, trifluoromethoxy, azide, hydroxy, oxo, thia, nitrile, nitro, formyl, mercapto, amino, hydroxyalkyl, hydroxyalkylaryloxy, hydroxyaryl, hydroxyalkylaryl, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, diaryl, hydroxyaryl, alkylaryl, heteroaryl, aralkyl, aralkenyl, aralkynyl, alkylaralkyl, heteroarylalkyl, trialkylsilyl, dialkylarylsilyl, alkyldiarylsilyl, triarylsilyl, alkylidene, arylalkylidene, alkylcarbonyl, alkylarylcarbonyl, arylcarbonyl, heterocyclylcarbonyl, heteroarylcarbonyl, alkoxycarbonyl, alkoxycarbonylalkyl, alkoxycarbonylaryloxy, aryloxycarbonyl, aryloxycarbonylalkyl, heterocyclylcarbonylalkylaryl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, haloalkoxy, alkoxyaryloxy, alkylaryloxy, diaryloxy, alkylaryloxyalkyl, alkyldiaryloxy, perfluoroalkoxy, alkenyloxy, alkynyloxy, aryloxyalkaoxy, aralkoxyaryloxy, alkylarylcycloalkyloxy, heterocycloxy, alkoxyalkyl, alkoxyalkoxyalkyl, alkylheteroaryloxy, alkylcycloalkoxy, cycloalkyloxy, heterocyclyloxy, aralkoxy, haloaryloxy, heteroaryloxy, alkylheteroaryloxy, alkoxycarbonylheterocycloxy, alkylcarbonylaryloxy, alkylcarbonyloxy, arylcarbonyloxy, aralkylcarbonyloxy, alkoxycarbonyloxy, aryloxycarbonyloxy, alkoxyaryloxy, aralkoxycarbonyloxy, ureido, alkylureido, arylureido, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, haloalkylarylamino, arylamino, diarylamino, alkylarylamino, aralkylamino, alkylcarbonylamino, aralkylcarbonylamino, haloalkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylenedioxyalkyl, dialkylalkylenedioxyalkyl, alkylsulfonylamino, arylsulfonylamino, azido, dialkylphosphonyl, alkylarylphosphonyl, diarylphosphonyl, alkylthio, arylthio, perfluoroalkylthio, hydroxycarbonylalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl, arylaminosulfonyl, diarylaminosulfonyl or alkylarylaminosulfonyl; or two $Q^1$ groups, which substitute atoms in a 1,2 or 1,3 arrangement, together form alkylenedioxy, thioalkylenoxy or alkylenedithioxy; and each $Q^1$ is independently unsubstituted or substituted with one or more substituents, each independently selected from $Q^2$, where $Q^2$ is halo, cyanide, cyanate, thiocyanate, selenocyanate, trifluoromethoxy, azide, hydroxy, oxo, thia, nitrile, nitro, formyl, mercapto, amino, hydroxyalkyl, hydroxyaryl, hydroxycarbonyl, alkyl, haloalkyl, polyhaloalkyl, aminoalkyl, diaminoalkyl, alkenyl containing 1 to 2 double bonds, alkynyl containing 1 to 2 triple bonds, cycloalkyl, heterocyclyl, aryl, heteroaryl, aralkyl, aralkenyl, aralkynyl, alkoxycarbonyl, aryloxycarbonyl, aralkoxycarbonyl, arylcarbonylalkyl, aminocarbonyl, alkoxy, aryloxy, aralkoxy, alkylenedioxy, amino, aminoalkyl, dialkylamino, arylamino, diarylamino, alkylamino, dialkylamino, haloalkylamino, arylamino, diarylamino, alkylarylamino, aralkylamino, alkoxycarbonylamino, arylcarbonylamino, alkylthio or arylthio.

115. A method of treating, preventing or ameliorating hypocholesterolemia in a subject in need thereof, comprising administering an effective amount of a compound of formula I:

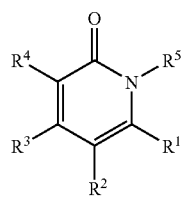

or a pharmaceutically acceptable derivative thereof, wherein:

$R^1$ is selected from substituted or unsubstituted alkenyl, substituted or unsubstituted alkynyl, substituted or unsubstituted aryl, substituted or unsubstituted heteroaryl, substituted or unsubstituted aralkyl, substituted or unsubstituted heteroaralkyl, substituted or unsubstituted cycloalkyl, substituted or unsubstituted cycloalkenyl, substituted or unsubstituted cycloalkynyl, substituted or unsubstituted heterocyclyl, substituted or unsubstituted cycloalkylalkyl and substituted or unsubstituted heterocyclylalkyl;

$R^2$ is hydrogen, substituted or unsubstituted alkyl, substituted or unsubstituted alkenyl, substituted or unsubstituted alkynyl, substituted or unsubstituted aryl;

$R^3$ and $R^4$ are selected from (i) and (ii) as follows:

(i) $R^3$ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted alkylaminocarbonyl or $C(J)OR^{30}$; and $R^4$ is hydrogen, substituted or unsubstituted alkyl, substituted or unsubstituted alkenyl, substituted or unsubstituted alkynyl, halide, pseudohalidecyanide, cyanate, thiocyanate, selenocyanate, trifluoromethoxy, azide, hydroxycarbonyl, $C(J)R^{30}$, $C(J)NR^{31}R^{32}$, $CH_2NR^{31}R^{32}$, $CH_2OR^{31}$, $CR^{30}=CR^{31}R^{32}$, $NO_2$ or $NR^{31}R^{32}$; and (ii) $R^3$ and $R^4$, together with the atoms to which they are attached, form a substituted or unsubstituted heterocyclic ring with the proviso that the heterocyclic ring has one oxo substituent;

$R^5$ is substituted or unsubstituted alkyl, substituted or unsubstituted alkenyl, substituted or unsubstituted alkynyl, substituted or unsubstituted heterocyclyl, substituted or unsubstituted aryl, substituted or unsubstituted heteroaryl, substituted or unsubstituted aralkyl, substituted or unsubstituted aralkenyl, substituted or unsubstituted aralkynyl, substituted or unsubstituted heteroaralkyl, substituted or unsubstituted heteroaralkenyl, substituted or unsubstituted heteroaralkynyl, $-N=CR^6R^7$ or $-NR^9R^{10}$;

$R^6$ and $R^7$ are each independently hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted aryl, substituted or unsubstituted heteroaryl, substituted or unsubstituted aralkyl, or substituted or unsubstituted heteroaralkyl; or together form substituted or unsubstituted alkylene, substituted or unsubstituted alkenylene, substituted or unsubstituted alkynylene, or $-(CH_2)_xX(CH_2)_y-$ where x and y are each independently 1, 2 or 3, and X is O, S or $NR^8$;

$R^8$ is substituted or unsubstituted alkyl, substituted or unsubstituted alkenyl, substituted or unsubstituted alkynyl, substituted or unsubstituted alkylcarbonyl, substituted or unsubstituted arylcarbonyl, or substituted or unsubstituted heteroarylcarbonyl;

$R^9$ and $R^{10}$ are each independently hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted aralkyl, or substituted or unsubstituted heteroaralkyl;

$R^{30}$ is hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, or substituted or unsubstituted heteroaralkyl;

$R^{31}$ and $R^{32}$ are each independently hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, or $C(J)R^{35}$; or $R^{31}$ and $R^{32}$, together with the atoms to which they are attached, form substituted or unsubstituted cycloalkyl ring, a substituted or unsubstituted heterocyclic ring or a substituted or unsubstituted heteroaryl ring;

J is P, S or $NR^{40}$;

$R^{35}$ is hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted aryl, substituted or unsubstituted heteroaryl, substituted or unsubstituted alkoxy, substituted or unsubstituted aralkoxy, substituted or unsubstituted alkylamino, substituted or unsubstituted dialkylamino, substituted or unsubstituted arylalkylamino, or substituted or unsubstituted diarylamino;

$R^{40}$ is hydrogen, substituted or unsubstituted alkyl, substituted or unsubstituted aryl, or substituted or unsubstituted heteroaryl;

where the alkyl, alkenyl, allynyl, cycloalkyl, heterocyclyl, alkylene, alkenylene, alkynylene, aryl, heteroaryl, aralkyl, aralkenyl, aralkynyl, heteroaralkyl, heteroaralkenyl and heteroaralkynyl moieties of $R^1$, $R^2$, $R^3$, $R^4$, $R^5$, $R^6$, $R^7$, $R^8$, $R^9$ and $R^{10}$ are unsubstituted or substituted with one or more substituents, each independently selected from $Q^1$, where $Q^1$ is halo, cyanide, cyanate, thiocyanate, selenocyanate, trifluoromethoxy, azide, hydroxy, oxo, thia, nitrile, nitro, formyl, mercapto, amino, hydroxyalkyl, hydroxyalkylaryloxy, hydroxyaryl, hydroxyalkylaryl, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocylyalkyl, aryl, diaryl, hydroxyaryl, alkylaryl, heteroaryl, aralkyl, aralkenyl, aralkynyl, alkylaralkyl, heteroaralkyl, trialkylsilyl, dialkylarylsilyl, alkyldiarylsilyl, triarylsilyl, alkylidene, arylalkylidene, alkylcarbonyl, alkylarylcarbonyl, arylcarbonyl, heterocyclylcarbonyl, heteroarylcarbonyl, alkoxycarbonyl, alkoxycarbonylalkyl, alkoxycarbonylaryloxy, aryloxycarbonyl, aryloxycarbonylalkyl, heterocyclylcarbonylalkylaryl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, haloalkoxy, alkoxyaryloxy, alkylaryloxy, diaryloxy, alkylaryloxyalkyl, alkyldiaryloxy, perfluoroalkoxy, alkenyloxy, alkynyloxy, aryloxyalkaoxy, aralkoxyaryloxy, alkylarylcycloalkyloxy, heterocycloxy, alkoxyalkyl, alkoxyalkoxyalkyl, alkylheteroaryloxy, alkylcycloalkoxy, cycloalkyloxy, heterocyclyloxy, aralkoxy, haloaryloxy, heteroaryloxy, alkylheteroaryloxy, alkoxycarbonylheterocycloxy, alkylcarbonylaryloxy, alkylcarbonyloxy, arylcarbonyloxy, aralkylcarbonyloxy, alkoxycarbonyloxy, aryloxycarbonyloxy, alkoxyaryloxy, aralkoxycarbonyloxy, ureido, alkylureido, arylureido, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, haloalkylarylamino, arylamino, diarylamino, alkylarylamino, aralkylamino, alkylcarbonylamino, aralkylcarbonylamino, haloalkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylenedioxyalkyl, dialkylalkylenedioxyalkyl, alkylsulfonylamino, arylsulfonylamino, azido, dialkylphosphonyl, alkylarylphosphonyl, diarylphosphonyl, alkylthio, arylthio, perfluoroalkylthio, hydroxycarbonylalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl, arylaminosulfonyl, diarylaminosulfonyl or alkylarylaminosulfonyl; or two $Q^1$ groups, which substitute atoms in a 1,2 or 1,3 arrangement, together form alkylenedioxy, thioalkylenoxy or alkylenedithioxy; and each $Q^1$ is independently unsubstituted or substituted with one or more substituents, each independently selected from $Q^2$, where $Q^2$ is halo, cyanide, cyanate, thiocyanate, selenocyanate, trifluoromethoxy, azide, hydroxy, oxo, thia, nitrile, nitro, formyl, mercapto, amino, hydroxyalkyl, hydroxyaryl, hydroxycarbonyl, alkyl, haloalkyl, polyhaloalkyl, aminoalkyl, diaminoalkyl, alkenyl containing 1 to 2 double bonds, alkynyl containing 1 to 2 triple bonds, cycloalkyl, heterocyclyl, aryl, heteroaryl, aralkyl, aralkenyl, aralkynyl, alkoxycarbonyl, aryloxycarbonyl, aralkoxycarbonyl, arylcarbonylalkyl, aminocarbonyl, alkoxy, aryloxy, aralkoxy, alkylenedioxy, amino, aminoalkyl, dialkylamino, arylamino, diarylamino, alkylamino, dialkylamino, haloalkylamino, arylamino, diarylamino, alkylarylamino, aralkylamino, alkoxycarbonylamino, arylcarbonylamino, alkylthio or arylthio.

116. An in vitro method for altering liver X receptor (LXRα or LXRβ) activity, comprising contacting the nuclear receptor with a compound of formula I:

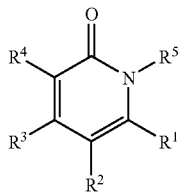

or a pharmaceutically acceptable salt thereof, wherein:
$R^1$ is selected from substituted or unsubstituted alkenyl, substituted or unsubstituted alkynyl, substituted or unsubstituted aryl, substituted or unsubstituted heteroaryl, substituted or unsubstituted aralkyl, substituted or unsubstituted heteroaralkyl, substituted or unsubstituted cycloalkyl, substituted or unsubstituted cycloalkenyl, substituted or unsubstituted cycloalkynyl, substituted or unsubstituted heterocyclyl, substituted or unsubstituted cycloalkylalkyl and substituted or unsubstituted heterocyclylalkyl;
$R^2$ is hydrogen, substituted or unsubstituted alkyl, substituted or unsubstituted alkenyl, substituted or unsubstituted alkynyl, substituted or unsubstituted aryl;
$R^3$ and $R^4$ are selected from (i) and (ii) as follows:
(i) $R^3$ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted alkylaminocarbonyl or C(J)OR$^{30}$; and $R^4$ is hydrogen, substituted or unsubstituted alkyl, substituted or unsubstituted alkenyl, substituted or unsubstituted alkynyl, halide, pseudohalidecyanide, cyanate, thiocyanate, selenocyanate, trifluoromethoxy, azide, hydroxycarbonyl, C(J)R$^{30}$, C(J)NR$^{31}$R$^{32}$, CH$_2$NR$^{31}$R$^{32}$, CH$_2$OR$^{31}$, CR$^{30}$=CR$^{31}$R$^{32}$, NO$_2$ or NR$^{31}$R$^{32}$; and
(ii) $R^3$ and $R^4$, together with the atoms to which they are attached, form a substituted or unsubstituted heterocyclic ring with the proviso that the heterocyclic ring has one oxo substituent;
$R^5$ is substituted or unsubstituted alkyl, substituted or unsubstituted alkenyl, substituted or unsubstituted alkynyl, substituted or unsubstituted heterocyclyl, substituted or unsubstituted aryl, substituted or unsubstituted heteroaryl, substituted or unsubstituted aralkyl, substituted or unsubstituted aralkenyl, substituted or unsubstituted aralkynyl, substituted or unsubstituted heteroaralkyl, substituted or unsubstituted heteroaralkenyl, substituted or unsubstituted heteroaralkynyl, —N=CR$^6$R$^7$ or —NR$^9$R$^{10}$;
$R^6$ and $R^7$ are each independently hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted aryl, substituted or unsubstituted heteroaryl, substituted or unsubstituted aralkyl, or substituted or unsubstituted heteroaralkyl; or together form substituted or unsubstituted alkylene, substituted or unsubstituted alkenylene, substituted or unsubstituted alkynylene, or —(CH$_2$)$_x$X(CH$_2$)$_y$— where x and y are each independently 1, 2 or 3, and X is O, S or NR$^8$;
$R^8$ is substituted or unsubstituted alkyl, substituted or unsubstituted alkenyl, substituted or unsubstituted alkynyl, substituted or unsubstituted alkylcarbonyl, substituted or unsubstituted arylcarbonyl, or substituted or unsubstituted heteroarylcarbonyl;
$R^9$ and $R^{19}$ are each independently hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted aralkyl, or substituted or unsubstituted heteroaralkyl;
$R^{30}$ hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, or substituted or unsubstituted heteroaralkyl;
$R^{31}$ and $R^{32}$ are each independently hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, or C(J)R$^{35}$; or $R^{31}$ and $R^{32}$, together with the atoms to which they are attached, form substituted or unsubstituted cycloalkyl ring, a substituted or unsubstituted heterocyclic ring or a substituted or unsubstituted heteroaryl ring;
J is P, S or NR$^{40}$;
$R^{35}$ is hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted aryl, substituted or unsubstituted heteroaryl, substituted or unsubstituted alkoxy, substituted or unsubstituted aralkoxy, substituted or unsubstituted alkylamino, substituted or unsubstituted dialkylamino, substituted or unsubstituted arylalkylamino, or substituted or unsubstituted diarylamino;

$R^{40}$ is hydrogen, substituted or unsubstituted alkyl, substituted or unsubstituted aryl, or substituted or unsubstituted heteroaryl;

where the alkyl, alkenyl, alkynyl, cycloalkyl, heterocyclyl, alkylene, alkenylene, alkynylene, aryl, heteroaryl, aralkyl, aralkenyl, aralkynyl, heteroaralkyl, heteroaralkenyl and heteroaralkynyl moieties of $R^1$, $R^2$, $R^3$, $R^4$, $R^5$, $R^6$, $R^7$, $R^8$, $R^9$ and $R^{10}$ are unsubstituted or substituted with one or more substituents, each independently selected from $Q^1$, where $Q^1$ is halo, cyanide, cyanate, thiocyanate, selenocyanate, trifluoromethoxy, azide, hydroxy, oxo, thia, nitrile, nitro, formyl, mercapto, amino, hydroxyalkyl, hydroxyalkylaryloxy, hydroxyaryl, hydroxyalkylaryl, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, diaryl, hydroxyaryl, alkylaryl, heteroaryl, aralkyl, aralkenyl, aralkynyl, alkylaralkyl, heteroaralkyl, trialkylsilyl, dialkylarylsilyl, alkyldiarylsilyl, triarylsilyl, alkylidene, arylalkylidene, alkylcarbonyl, alkylarylcarbonyl, arylcarbonyl, heterocyclylcarbonyl, heteroarylcarbonyl, alkoxycarbonyl, alkoxycarbonylalkyl, alkoxycarbonylaryloxy, aryloxycarbonyl, aryloxycarbonylalkyl, heterocyclylcarbonylalkylaryl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, haloalkoxy, alkoxyaryloxy, alkylaryloxy, diaryloxy, alkylaryloxyalkyl, alkyldiaryloxy, perfluoroalkoxy, alkenyloxy, alkynyloxy, aryloxyalkaoxy, aralkoxyaryloxy, alkylarylcycloalkyloxy, heterocycloxy, alkoxyalkyl, alkoxyalkoxyalkyl, alkylheteroaryloxy, alkylcycloalkoxy, cycloalkyloxy, heterocyclyloxy, aralkoxy, haloaryloxy, heteroaryloxy, alkylheteroaryloxy, alkoxycarbonylheterocycloxy, alkylcarbonylaryloxy, alkylcarbonyloxy, arylcarbonyloxy, aralkylcarbonyloxy, alkoxycarbonyloxy, aryloxycarbonyloxy, alkoxyaryloxy, aralkoxycarbonyloxy, ureido, alkylureido, arylureido, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, haloalkylarylamino, arylamino, diarylamino, alkylarylamino, aralkylamino, alkylcarbonylamino, aralkylcarbonylamino, haloalkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylenedioxyalkyl, dialkylalkylenedioxyalkyl, alkylsulfonylamino, arylsulfonylamino, azido, dialkylphosphonyl, alkylarylphosphonyl, diarylphosphonyl, alkylthio, arylthio, perfluoroalkylthio, hydroxycarbonylalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl, arylaminosulfonyl, diarylaminosulfonyl or alkylarylaminosulfonyl; or two $Q^1$ groups, which substitute atoms in a 1,2 or 1,3 arrangement, together form alkylenedioxy, thioalkylenoxy or alkylenedithioxy; and each $Q^1$ is independently unsubstituted or substituted with one or more substituents, each independently selected from $Q^2$, where $Q^2$ is halo, cyanide, cyanate, thiocyanate, selenocyanate, trifluoromethoxy, azide, hydroxy, oxo, thia, nitrile, nitro, formyl, mercapto, amino, hydroxyalkyl, hydroxyaryl, hydroxycarbonyl, alkyl, haloalkyl, polyhaloalkyl, aminoalkyl, diaminoalkyl, alkenyl containing 1 to 2 double bonds, alkynyl containing 1 to 2 triple bonds, cycloalkyl, heterocyclyl, aryl, heteroaryl, aralkyl, aralkenyl, aralkynyl, alkoxycarbonyl, aryloxycarbonyl, aralkoxycarbonyl, arylcarbonylalkyl, aminocarbonyl, alkoxy, aryloxy, aralkoxy, alkylenedioxy, amino, aminoalkyl, dialkylamino, arylamino, diarylamino, alkylamino, dialkylamino, haloalkylamino, arylamino, diarylamino, alkylarylamino, aralkylamino, alkoxycarbonylamino, arylcarbonylamino, alkylthio or arylthio.

117. The compound of claim 1 that has formula II:

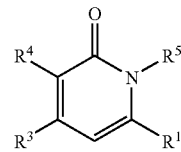

or a pharmaceutically acceptable salt thereof.

118. The compound of claim 85, wherein each Ar is independently substituted or unsubstituted heteroaryl.

119. A compound having formula I:

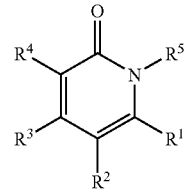

or a pharmaceutically acceptable salt thereof, wherein
$R^1$ is selected from substituted or unsubstituted alkenyl, substituted or unsubstituted alkynyl, substituted or unsubstituted aryl, substituted or unsubstituted heteroaryl, substituted or unsubstituted aralkyl, substituted or unsubstituted heteroaralkyl, substituted or unsubstituted cyclohexyl, substituted or unsubstituted cyclopentenyl, substituted or unsubstituted cycloalkenyl, substituted or unsubstituted cycloalkynyl, substituted or unsubstituted heterocyclyl, substituted or unsubstituted cycloalkylalkyl and substituted or unsubstituted heterocyclylalkyl;

$R^2$ is hydrogen, substituted or unsubstituted alkyl, substituted or unsubstituted alkenyl, substituted or unsubstituted alkynyl; wherein unsubstituted alkyl is selected from the group consisting of propyl, isopropyl, isobutyl, n-butyl, sec-butyl, tert-butyl, isopentyl, neopentyl, isopentyl, neopentyl, tert-pentyl, and isohexyl;

$R^3$ and $R^4$ are selected from (i) or (ii) as follows:
(i) $R^3$ is substituted or unsubstituted alkyl, substituted or unsubstituted alkenyl, substituted or unsubstituted alkynyl, substituted or unsubstituted alkylaminocarbonyl or C(J)OR$^{30}$; and R$^4$ is hydrogen, substituted or unsubstituted alkyl, unsubstituted alkenyl, substituted or unsubstituted alkynyl, halide, cyanide, cyanate, thiocyanate, selenocyanate, trifluoromethoxy, azide, hydroxycarbonyl, C(J)R$^{30}$, C(J)NR$^{31}$R$^{32}$, CH$_2$NR$^{31}$R$^{32}$, CH$_2$OR$^{31}$, CR$^{30}$=CR$^{31}$R$^{32}$, NO$_2$ or NR$^{31}$R$^{32}$; and (ii) R$^3$ and R$^4$, together with the atoms to which they are attached, form a substituted or unsubstituted heterocyclic ring, with the proviso that the heterocyclic ring has one oxo substituent;

R$^5$ is substituted or unsubstituted aralkyl, substituted or unsubstituted heterocyclylalkyl, wherein the substituents are selected from alkyl, haloalkyl, halohydroxyalkyl, alkoxy, alkoxyalkoxyalkyl, alkoxyalkyl, aryl, halo, alkoxycarbonyl, alkylthio, aryloxy, haloalkoxy, aralkyl, heteroaryl, hydroxy, hydroxyalkyl, heterocyclyl, heterocyclylalkyl, alkylcarbonyl, arylcarbonyl, alkylalkelenedioxy and dialkylalkelenedioxy;

R$^{30}$ is hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, or substituted or unsubstituted heteroaralkyl;

R$^{31}$ and R$^{32}$ are each independently hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted cycloalkylalkyl, substituted or unsubstituted heterocyclylalkyl, substituted or unsubstituted aryl, substituted or unsubstituted heteroaryl, substituted or unsubstituted aralkyl, substituted or unsubstituted heteroaralkyl, or C(J)R$^{35}$; or R$^{31}$ and R$^{32}$, together with the atoms to which they are attached, form substituted or unsubstituted cycloalkyl ring, a substituted or unsubstituted heterocyclic ring or a substituted or unsubstituted heteroaryl ring;

J is O, S or NR$^{40}$;

R$^{35}$ is hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted aryl, substituted or unsubstituted heteroaryl, substituted or unsubstituted alkoxy, substituted or unsubstituted aralkoxy, substituted or unsubstituted alkylamino, substituted or unsubstituted dialkylamino, substituted or unsubstituted arylalkylamino, or substituted or unsubstituted diarylamino;

R$^{40}$ is hydrogen, substituted or unsubstituted alkyl, substituted or unsubstituted aryl, or substituted or unsubstituted heteroaryl;

where the alkyl, alkenyl, alkynyl, cycloalkyl, heterocyclyl, alkylene, alkenylene, alkynylene, aryl, heteroaryl, aralkyl, aralkenyl, aralkynyl, heteroaralkyl, heteroaralkenyl and heteroaralkynyl moieties of R$^1$, R$^2$, R$^3$, R$^4$, R$^6$, R$^7$, R$^8$, R$^9$ and R$^{10}$ are unsubstituted or substituted with one or more substituents, each independently selected from Q$^1$, where Q$^1$ is halo, cyanide, cyanate, thiocyanate, selenocyanate, trifluoromethoxy, azide, hydroxy, oxo, thia, nitrile, nitro, formyl, mercapto, amino, hydroxyalkyl, hydroxyalkylaryloxy, hydroxyaryl, hydroxyalkylaryl, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, diaryl, hydroxyaryl, alkylaryl, heteroaryl, aralkyl, aralkenyl, aralkynyl, alkylaralkyl, heteroarylalkyl, trialkylsilyl, dialkylarylsilyl, alkyldiarylsilyl, triarylsilyl, alkylidene, arylalkylidene, alkylcarbonyl, alkylarylcarbonyl, arylcarbonyl, heterocyclylcarbonyl, heteroarylcarbonyl, alkoxycarbonyl, alkoxycarbonylalkyl, alkoxycarbonylaryloxy, aryloxycarbonyl, aryloxycarbonylalkyl, heterocyclylcarbonylalkylaryl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, haloalkoxy, alkoxyaryloxy, alkylaryloxy, diaryloxy, alkylaryloxyalkyl, alkyldiaryloxy, perfluoroalkoxy, alkenyloxy, alkynyloxy, aryloxyalkoxy, aralkoxyaryloxy, alkylarylcycloalkyloxy, heterocyclyloxy, alkoxyalkyl, alkoxyalkoxyalkyl, alkylheteroaryloxy, alkylcycloalkoxy, cycloalkyloxy, heterocyclyloxy, aralkoxy, haloaryloxy, heteroaryloxy, alkylheteroaryloxy, alkoxycarbonylheterocyclyloxy, alkylcarbonylaryloxy, alkylcarbonyloxy, arylcarbonyloxy, aralkylcarbonyloxy, alkoxycarbonyloxy, aryloxycarbonyloxy, alkoxyaryloxy, aralkoxycarbonyloxy, ureido, alkylureido, arylureido, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, haloalkylarylamino, arylamino, diarylamino, alkylarylamino, aralkylamino, alkylcarbonylamino, aralkylcarbonylamino, haloalkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylenedioxyalkyl, dialkylalkylenedioxyalkyl, alkylsulfonylamino, arylsulfonylamino, azido, dialkylphosphonyl, alkylarylphosphonyl, diarylphosphonyl, alkylthio, arylthio, perfluoroalkylthio, hydroxycarbonylalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl, arylaminosulfonyl, diarylaminosulfonyl or alkylarylaminosulfonyl; or two Q$^1$ groups, which substitute atoms in a 1,2 or 1,3 arrangement, together form alkylenedioxy, thioalkyleneoxy or alkylenedithioxy; and each Q$^1$ is independently unsubstituted or substituted with one or more substituents, each independently selected from Q$^2$, where Q$^2$ is halo, cyanide, cyanate, thiocyanate, selenocyanate, trifluoromethoxy, azide, hydroxy, oxo, thia, nitrile, nitro, formyl, mercapto, amino, hydroxyalkyl, hydroxyaryl, hydroxycarbonyl, alkyl, haloalkyl, polyhaloalkyl, aminoalkyl, diaminoalkyl, alkenyl containing 1 to 2 double bonds, alkynyl containing 1 to 2 triple bonds, cycloalkyl, heterocyclyl, aryl, heteroaryl, aralkyl, aralkenyl, aralkynyl, alkoxycarbonyl, aryloxycarbonyl, aralkoxycarbonyl, arylcarbonylalkyl, aminocarbonyl, alkoxy, aryloxy, aralkoxy, alkylenedioxy, amino, aminoalkyl, dialkylamino, arylamino, diarylamino, alkylamino, dialkylamino, haloalkylamino, acylamino, diarylamino, alkylarylamino, aralkylamino, alkoxycarbonylamino, arylcarbonylamino, alkylthio or arylthio.

* * * * *